(12) United States Patent
Balsitis et al.

(10) Patent No.: US 12,364,751 B2
(45) Date of Patent: *Jul. 22, 2025

(54) HBV VACCINES AND METHODS TREATING HBV

(71) Applicant: Gilead Sciences, Inc., Foster City, CA (US)

(72) Inventors: Scott J. Balsitis, Moss Beach, CA (US); Sarah M. Ahmadi-Erber, Vienna (AT); Timo Schippers, Vienna (AT); Sarah Schmidt, Vienna (AT)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/335,810

(22) Filed: Jun. 15, 2023

(65) Prior Publication Data

US 2024/0066117 A1     Feb. 29, 2024

Related U.S. Application Data

(63) Continuation of application No. 17/937,567, filed on Oct. 3, 2022, now Pat. No. 11,730,808, which is a continuation of application No. 17/034,706, filed on Sep. 28, 2020, now Pat. No. 11,497,808.

(60) Provisional application No. 62/908,494, filed on Sep. 30, 2019.

(51) Int. Cl.
| | |
|---|---|
| A61K 39/29 | (2006.01) |
| A61K 39/00 | (2006.01) |
| A61P 37/04 | (2006.01) |
| C12N 9/12 | (2006.01) |

(52) U.S. Cl.
CPC ............ *A61K 39/292* (2013.01); *A61P 37/04* (2018.01); *C12N 9/1252* (2013.01); *C12Y 207/07007* (2013.01); *A61K 2039/5256* (2013.01); *C12N 2730/10122* (2013.01); *C12N 2730/10134* (2013.01); *C12N 2760/10034* (2013.01); *C12N 2760/10043* (2013.01)

(58) Field of Classification Search
CPC .......... A61K 39/292; A61K 2039/5256; A61K 2039/545; A61K 39/12; A61K 38/00; A61K 45/06; A61P 37/04; A61P 31/20; C12N 9/1252; C12N 2730/10122; C12N 2730/10134; C12N 2760/10034; C12N 2760/10043; C12N 15/86; C12Y 207/07007; Y02A 50/30

See application file for complete search history.

(56) References Cited

U.S. PATENT DOCUMENTS

| | | | |
|---|---|---|---|
| 4,428,941 A | 1/1984 | Galibert et al. | |
| 5,196,194 A | 3/1993 | Rutter et al. | |
| 5,593,825 A | 1/1997 | Carman et al. | |
| 5,856,084 A | 1/1999 | Karayiannis et al. | |
| 6,060,595 A | 5/2000 | Scaglioni et al. | |
| 6,072,049 A | 6/2000 | Thoma | |
| 6,096,879 A | 8/2000 | Tiollais et al. | |
| 6,110,706 A | 8/2000 | Thoma | |
| 6,172,193 B1 | 1/2001 | Primi et al. | |
| 6,232,099 B1 | 5/2001 | Chapman et al. | |
| 6,268,122 B1 | 7/2001 | Murray | |
| 6,270,955 B1 | 8/2001 | Murray | |
| 6,297,048 B1 | 10/2001 | Jolly et al. | |
| 6,558,675 B1 | 5/2003 | Oon et al. | |
| 6,787,142 B2 | 9/2004 | Oon et al. | |
| 7,038,035 B1 | 5/2006 | Oon et al. | |
| 7,067,247 B2 | 6/2006 | Zheng | |
| 7,105,165 B2 | 9/2006 | Oon et al. | |
| 7,141,242 B2 | 11/2006 | Coleman et al. | |
| 7,202,354 B2 | 4/2007 | Coleman et al. | |
| 7,313,357 B2 | 12/2007 | Stuyver et al. | |
| 7,732,423 B2 | 6/2010 | Michel et al. | |
| 8,138,318 B2 | 3/2012 | Coleman et al. | |
| 8,216,589 B2 | 7/2012 | Yum et al. | |
| 8,729,231 B2 | 5/2014 | Bussfeld et al. | |
| 8,945,876 B2 | 2/2015 | Su et al. | |
| 9,017,695 B2 | 4/2015 | de los Rios et al. | |
| 9,238,679 B2 | 1/2016 | Weiner et al. | |
| 9,353,158 B2 | 5/2016 | Whalen et al. | |
| 9,403,879 B2 | 8/2016 | Weiner et al. | |
| 9,428,556 B2 | 8/2016 | Apelian et al. | |
| 9,512,412 B2 | 12/2016 | Martin et al. | |
| 9,512,443 B2 | 12/2016 | Richmond et al. | |

(Continued)

FOREIGN PATENT DOCUMENTS

| | | |
|---|---|---|
| EP | 1294893 B1 | 3/2006 |
| EP | 1572234 B1 | 2/2012 |

(Continued)

OTHER PUBLICATIONS

Boni C et al. (2019), "Combined GS-4774 and Tenofovir Therapy Can Improve HBV-Specific T-Cell Responses in Patients With Chronic Hepatitis", Gastroenterology, vol. 157, No. 1, pp. 227-241.
Bénéchet A P et al. (2019), "Dynamics and genomic landscape of CD8+ T cells undergoing hepatic priming", Nature, vol. 574.
Chinnakannan S K et al. (2020), "The Design and Development of a Multi-HBV Antigen Encoded in Chimpanzee Adenoviral and Modified Vaccinia Ankara Viral Vectors; A Novel Therapeutic Vaccine Strategy against HBV", Vaccines, vol. 8, No. 2, 184.
Clark D N et al. (2017), "Mapping of Functional Subdomains in the Terminal Protein Domain of Hepatitis B Virus Polymerase", Journal of Virology, vol. 91, Issue 3, e01785-16.
Examination Report dated Oct. 13, 2021 for GCC Appl. No. 40546.
Examination Report dated May 5, 2023 for Canadian Appl. No. 3149557.

(Continued)

*Primary Examiner* — Rachel B Gill

(57) ABSTRACT

Provided are HBV immunogenic polypeptides, polynucleotides encoding such polypeptides, vectors expressing such immunogenic polypeptides for use in eliciting an immune response against HBV; pharmaceutical and immunogenic compositions and kits comprising such polypeptides, polynucleotides or vectors, and methods of use in treating and/or preventing HBV.

53 Claims, 49 Drawing Sheets

Specification includes a Sequence Listing.

(56) References Cited

U.S. PATENT DOCUMENTS

| | | | |
|---|---|---|---|
| 9,675,690 B2 | 6/2017 | Weiner et al. | |
| 9,751,914 B2 | 9/2017 | Yuan et al. | |
| 9,878,035 B2 | 1/2018 | Du et al. | |
| 10,076,570 B2 | 9/2018 | Martin et al. | |
| 10,190,105 B2 | 1/2019 | Martin et al. | |
| 10,195,268 B2 | 2/2019 | Weiner et al. | |
| 10,369,204 B2 | 8/2019 | Schøller et al. | |
| 10,695,421 B2 | 6/2020 | Weiner et al. | |
| 11,020,476 B2 | 6/2021 | Boden et al. | |
| 11,497,808 B2 | 11/2022 | Balsitis et al. | |
| 11,730,808 B2 | 8/2023 | Balsitis et al. | |
| 2006/0051746 A1* | 3/2006 | Chisari | A61K 39/464838 435/5 |
| 2011/0027183 A1 | 2/2011 | Mier et al. | |
| 2012/0251569 A1 | 10/2012 | Martin et al. | |
| 2013/0011435 A1 | 1/2013 | Martin et al. | |
| 2013/0243805 A1 | 9/2013 | Apelian et al. | |
| 2016/0206724 A1 | 7/2016 | de la Torre et al. | |
| 2017/0056493 A1 | 3/2017 | Robek et al. | |
| 2017/0072047 A1 | 3/2017 | Martin et al. | |
| 2017/0196964 A1 | 7/2017 | Martinez-Sobrido et al. | |
| 2019/0185828 A1 | 6/2019 | Boden et al. | |
| 2021/0154290 A1 | 5/2021 | Ammendola et al. | |

FOREIGN PATENT DOCUMENTS

| | | |
|---|---|---|
| EP | 2057268 B1 | 8/2014 |
| EP | 3269390 B1 | 2/2021 |
| GB | 1721069.1 | 1/2018 |
| TW | I555531 B | 11/2016 |
| WO | WO-93/03753 A1 | 3/1993 |
| WO | WO-97/00698 A1 | 1/1997 |
| WO | WO-2009/083210 A1 | 7/2009 |
| WO | WO-2010/037083 A1 | 4/2010 |
| WO | WO-2011/000929 A1 | 1/2011 |
| WO | WO-2011/015656 A2 | 2/2011 |
| WO | WO-2013/007772 A1 | 1/2013 |
| WO | WO-2013/083847 A2 | 6/2013 |
| WO | WO-2014/168821 A1 | 10/2014 |
| WO | WO-2016/075250 A1 | 5/2016 |
| WO | WO-2016/090470 A1 | 6/2016 |
| WO | WO-2016/128542 A1 | 8/2016 |
| WO | WO-2016/191545 A1 | 12/2016 |
| WO | WO-2017/040815 A1 | 3/2017 |
| WO | WO-2017/076988 A1 | 5/2017 |
| WO | WO-2017/132332 A1 | 8/2017 |
| WO | WO-2017/198726 A1 | 11/2017 |
| WO | WO-2018/189522 A1 | 10/2018 |
| WO | WO-2019/115816 A1 | 6/2019 |
| WO | WO-2019/115817 A2 | 6/2019 |
| WO | WO-2020/255023 A1 | 12/2020 |
| WO | WO-2021/045969 A1 | 3/2021 |

OTHER PUBLICATIONS

Examination Report dated May 15, 2023 for European Appl. No. 20792808.6.
Intl. Preliminary Report on Patentability—Written Opinion dated Apr. 14, 2022 for Intl. Appl. No. PCT/US2020/053060.
Intl. Search Report—Written Opinion dated Jan. 25, 2021 for Intl. Appl. No. PCT/US2020/053060.
Jones S A et al. (2014), "Comparative Analysis of Hepatitis B Virus Polymerase Sequences Required for Viral RNA Binding, RNA Packaging, and Protein Priming", Journal of Virology, vol. 88, No. 3, pp. 1564-1572.
Kosinska A D et al. (2017), "Therapeutic vaccination for chronic hepatitis B", Current Opinion in Virology, vol. 23, pp. 75-81.
Kwon T K et al. (2002), "Intramuscular co-injection of naked DNA encoding HBV core antigen and Flt3 ligand suppresses anti-HBc antibody response", Immunology Letters 81(3): 229-234.
Lanford R E et al. (1999), "Mapping of the Hepatitis B Virus Reverse Transcriptase TP and RT Domains by Transcomplementation for Nucleotide Priming and by Protein-Protein Interaction", Journal of Virology, vol. 73, No. 3, p. 1885-1893.
Li et al. Hepatitis B virus isolate CX003C(e204), complete genome. GenBank Acc. No. KJ173341, Dep. Jan. 22, 2014. (Year: 2014).
McNaughton A L et al. (2018), "Insights From Deep Sequencing of the HBV Genome—Unique, Tiny, and Misunderstood", Gastroenterology, Elsevier Inc, US, vol. 156, No. 2, pp. 384-399.
Non-Final Office Action dated Jan. 7, 2022 for U.S. Appl. No. 17/034,706.
Non-Final Office Action dated Feb. 2, 2023 for U.S. Appl. No. 17/937,567.
Notice of Allowance dated Jul. 7, 2022 for U.S. Appl. No. 17/034,706.
Notice of Allowance dated May 22, 2023 for U.S. Appl. No. 17/937,567.
Notice of Allowance dated Jun. 8, 2023 for U.S. Appl. No. 17/937,567.
Office Action and Search Report dated Oct. 15, 2021 for Taiwanese Appl. No. 109133810.
Office Action dated Apr. 11, 2022 for Panamanian Appl. No. 93895-01.
Office Action dated Jan. 24, 2023 for Eurasian Appl. No. 202290638.
Office Action dated Mar. 20, 2023 for Japanese Appl. No. 2022-519697.
Office Action dated Jun. 8, 2023 for Eurasian Appl. No. 202290638.
Office Action dated Aug. 25, 2023 for Japanese Appl. No. 2022-519697.
Radoshitzky S R et al. (2015), "Past, present, and future of arenavirus taxonomy", Arch Virol 160:1851-1874.
Radziwill G et al. (1990), "Mutational analysis of the hepatitis B virus P gene product: domain structure and RNase H activity", Journal of Virology, vol. 64, No. 2, pp. 613-620.
Stahl S J et al. (1989), "Immunogenicity of peptide fusions to hepatitis B virus core antigen", Proc Natl Acad Sci USA, 86(16):6283-7.
Vörös J et al. (2014), "Large-Scale Production and Structural and Biophysical Characterizations of the Human Hepatitis B Virus Polymerase", Journal of Virology, vol. 88, No. 5, p. 2584-2599.
Office Action and Search Report dated Aug. 30, 2023 for Chinese Appl. No. 202080068039.0.
Huang C J et al. (2013), "Hepatitis B virus isolate EP0445 polymerase (pol) gene, partial cds", GenBank Acc. No. KC793092.1, Aug. 20, 2013.
Gallagher J R et al. (2017), "Characterization of the disassembly and reassembly of the HBV glycoprotein surface antigen, a pliable nanoparticle vaccine platform", Virology 502:176-187.
Examination Report dated Oct. 13, 2023 for European Appl. No. 20792808.6.
Notice of Allowance dated Dec. 1, 2023 for Japanese Appl. No. 2022-519697.
Office Action dated Oct. 17, 2023 for Egyptian Appl. No. 355/2022.
Office Action dated Dec. 1, 2023 for Dominican Republic Appl. No. P2022-0067.
Schmidt S et al. (2023), "Alternating Arenavirus Vector Immunization Generates Robust Polyfunctional Genotype Cross-Reactive Hepatitis B Virus-Specific CD8 T-Cell Responses and High Anti-Hepatitis B Surface Antigen Titers", The Journal of Infectious Diseases, pp. 1-11.
Search Report dated Dec. 7, 2023 for Eurasian Appl. No. 202391164.
Search Report dated Dec. 7, 2023 for Eurasian Appl. No. 202391166.
Office Action dated Mar. 29, 2024 for Vietnamese Appl. No. 1-2022-01504.
Office Action dated May 9, 2024 for Dominican Republic Appl. No. P2022-0067.
Office Action dated May 24, 2024 for Chinese Appl. No. 202080068039.0.
Office Action and Search Report dated May 30, 2024 for Taiwanese Appl. No. 111144984.
Office Action dated Jan. 8, 2024 for Eurasian Appl. No. 202290638.
Rule 71(3) EPC Communication dated Apr. 11, 2024 for European Appl. No. 20792808.6.
Office Action and Search Report dated Apr. 16, 2024 for Chilean Appl. No. 202200774.
Office Action and Search Report dated Oct. 24, 2024 for Chilean Appl. No. 202200774.

(56) References Cited

OTHER PUBLICATIONS

Office Action dated Oct. 21, 2024 for Dominican Republic Appl. No. P2022-0067.
Examination Report dated Sep. 23, 2024 for Canadian Appl. No. 3149557.
Examination Report dated May 24, 2024 for Australian Appl. No. 2020357502.
Notice of Allowance dated Jun. 5, 2024 for Eurasian Appl. No. 202290638.
Office Action dated May 28, 2024 for Egyptian Appl. No. 355/2022.
Office Action dated Aug. 2, 2024 for Japanese Appl. No. 2023-166294.
Rejection Decision dated Jul. 16, 2024 for Chinese Appl. No. 2020800680390.
Examination Report dated Oct. 24, 2024 for New Zealand Appl. No. 787659.
Examination Report dated Apr. 17, 2025 for New Zealand Appl. No. 787659.
Cargill T et al. (2021), "Therapeutic vaccination for treatment of chronic hepatitis B", Clinical and Experimental Immunology, 205(2): 106-118.
Extended European Search Report dated Jan. 10, 2025 for European Appl. No. 24200377.0.
Notice of Acceptance dated Jan. 13, 2015 for Australian Appl. No. 2020357502.
Notice of Allowance dated Dec. 30, 2024 for Vietnamese Appl. No. 1-2022-01504.
Notice of Allowance and Search Report dated Jan. 15, 2015 for Malaysian Appl. No. PI2022001413.
Office Action dated Dec. 5, 2024 for Ukranian Appl. No. a 2022 00978.
Office Action dated Jan. 10, 2025 for South Korean Appl. No. 10-2022-7014322.
Office Action dated Jan. 14, 2015 for Japanese Appl. No. 2023-166294.
Office Action dated Feb. 25, 2025 for Colombian Appl. No. NC2022/0003702.
Rejection Decision dated Feb. 21, 2025 for Taiwanese Appl. No. 111144984.
Office Action dated Mar. 30, 2025 for Eurasian Appl. No. 202391164.
Office Action dated Mar. 30, 2025 for Eurasian Appl. No. 202391166.

* cited by examiner

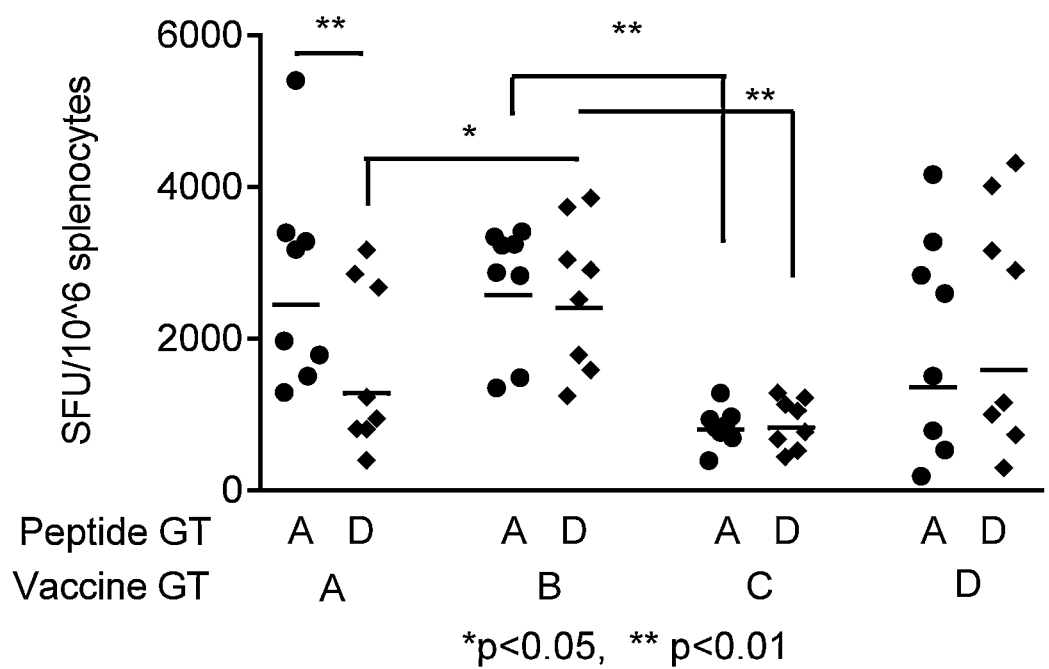
*Fig. 4A*
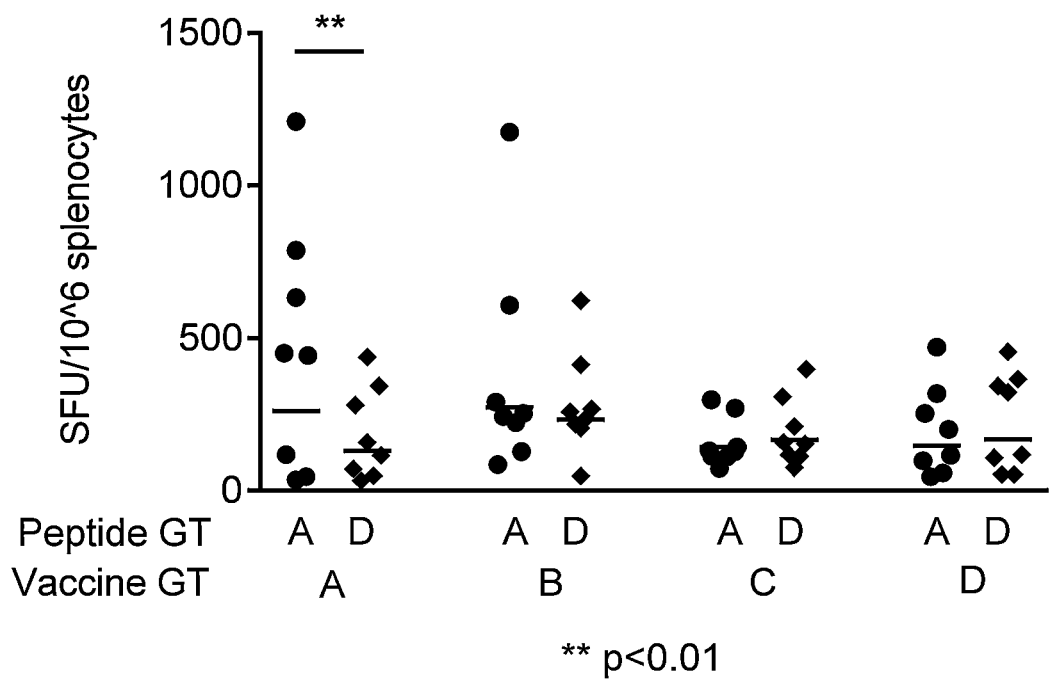
*Fig. 4B*
Figs. 4A-4B

Fig. 9B
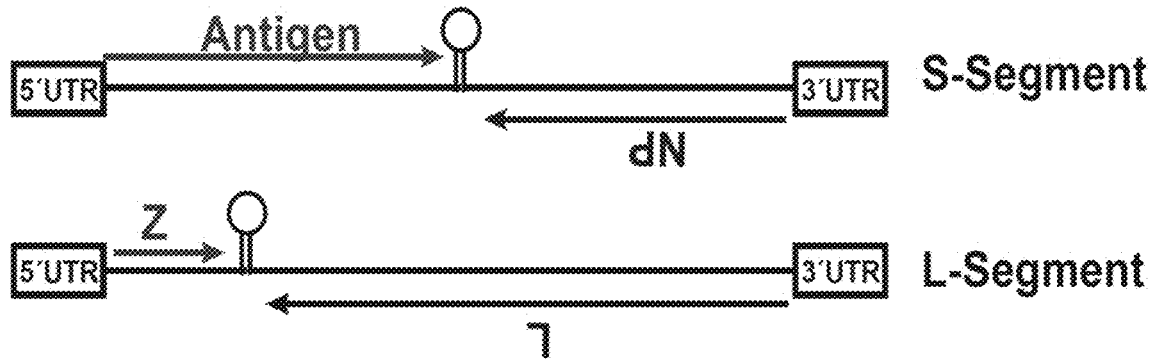
+ viral GP is delivered in trans
Fig. 9C
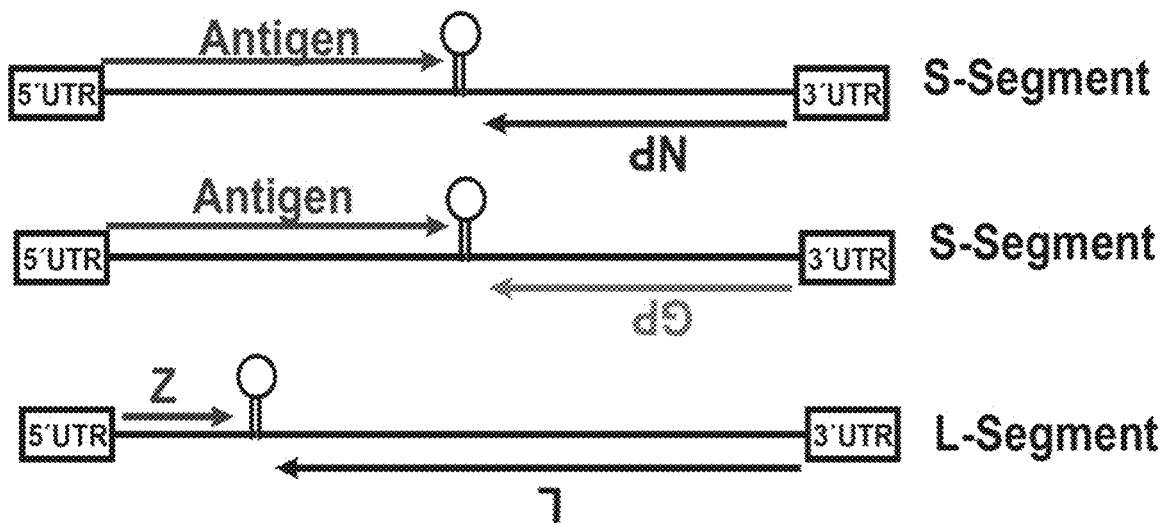
Figs. 9B-9C

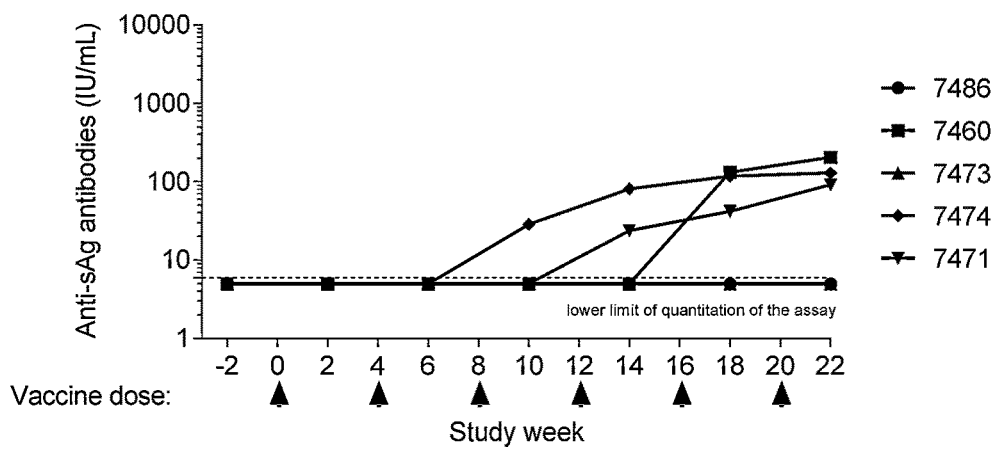
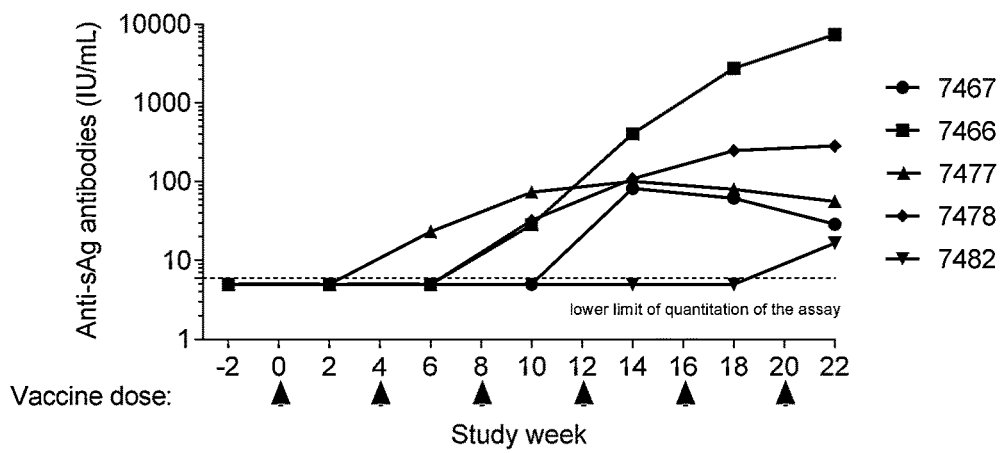
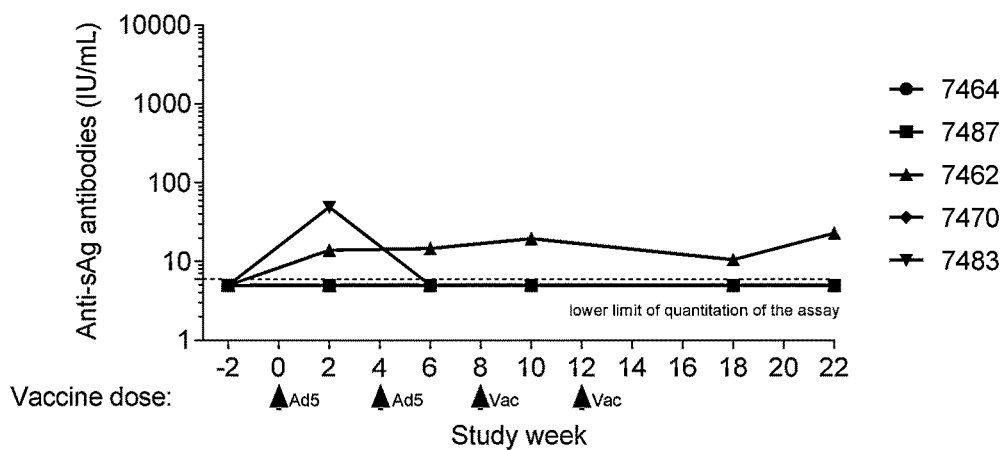
Figs. 22A-C

HBV VACCINES AND METHODS TREATING HBV

CROSS-REFERENCE TO RELATED APPLICATIONS

This application is a continuation of U.S. application Ser. No. 17/937,567 filed on Oct. 3, 2022 and issued as U.S. Pat. No. 11,730,808 on Aug. 22, 2023, which is a continuation of U.S. application Ser. No. 17/034,706 filed on Sep. 28, 2020 and issued as U.S. Pat. No. 11,497,808 on Nov. 15, 2022, which claims the benefit under 35 U.S.C. § 119(e) of U.S. provisional application No. 62/908,494, filed on Sep. 30, 2019, which are hereby incorporated herein by reference in their entireties for all purposes.

SEQUENCE LISTING

The instant application contains a Sequence Listing which has been submitted electronically in XML format and is hereby incorporated by reference in its entirety. Said XML copy, created on Jun. 15, 2023 is named 1324-US-CNT2_2022-09-30_Sequence-Listing.xml and is 193,982 bytes in size.

BACKGROUND

There have been many attempts to use vaccination to treat patients with chronic hepatitis B virus (HBV) infection to improve rates of HBV surface antigen (sAg) loss, the primary marker of functional cure. Such attempts have included vaccination with recombinant proteins (Dikici, et al., *J Gastroenterol Hepatol.* (2003) 18(2):218-22; Pol, et al., *J Hepatol.* (2001) 34(6):917-21; Vandepapeliere, et al., *Vaccine* (2007) 25(51):8585-97; Yalcin, et al., *J Clin Gastroenterol.* (2003) 37(4):330-5; Al-Mahtab, *Hepatol Int.* (2013) 7(4):981-9; Hoa, et al., *Antimicrob Agents Chemother.* (2009) 53(12):5134-40; and Yalcin, et al., *Infection.* (2003) 31(4):221-5), recombinant DNA (Mancini-Bourgine, et al., *Hepatology.* (2004) 40(4):874-82; Yang, et al., *World J Gastroenterol.* (2017) 23(2):306-17; Yang, et al., *J Viral Hepat.* (2012) 19(8):581-93; Yoon, et al., *Liver Int.* (2015) 35(3):805-15; Cavenaugh, et al., *PLoS One.* (2011) 6(2):e14626; and Godon, et al., *Mol Ther.* (2014) 22(3):675-84), dendritic cells (Luo, et al., *Vaccine.* (2010) 28(13):2497-504; and Wei, et al., *Int Immunopharmacol.* (2015) 27(2):238-43), a yeast vector (Gane. et al., *J Hepatol.* (2019) Epub 2019/07/16. doi: 10.1016/j.jhep.2019.06.028. PubMed PMID: 31306680), and some viral vectors (Cavenaugh, et al., supra; and Zoulim, et al., *Hum Vaccin Immunother.* (2019) Epub 2019/08/03. doi: 10.1080/21645515.2019.1651141. PubMed PMID: 31373537). Despite these many attempts, to date no therapeutic vaccination approach has shown consistent benefit in chronic HBV infection (CHB). Deficits in previous vaccine approaches may explain the failures of previous vaccine approaches.

Such deficits include limitations in the antigen designs and in the vaccine technologies used. An optimal antigen will contain highly conserved portions of HBV proteins and exclude poorly conserved regions, because highly conserved regions can induce responses against epitopes that are identical in the vaccine antigen and in the virus present in the treated patient, while poorly conserved regions may elicit immunodominant T cell responses against epitopes that are not present in the patient's infecting virus strain (Swadling, et al., *Vaccines* (Basel). (2016) 4(3). Epub 2016/08/05. doi: 10.3390/vaccines4030027. PubMed PMID: 27490575). However, some prior vaccines used antigen designs that do not meet these criteria (Yalcin, et al., *J Clin Gastroenterol.* (2003) 37(4):330-5; Hoa, et al., supra; Yalcin, et al., *Infection.* (2003) 31(4):221-5; Mancini-Bourgine, et al., supra; Yang, et al., *J Viral Hepat.* (2012) 19(8):581-93; Cavenaugh, et al., supra; Godon, et al., supra; Gane. et al., supra; and Obeng-Adjei, et al., *Cancer Gene Ther.* (2013) 20(12):652-62). Additionally, many prior vaccines have failed to induce a full combination of virus-specific CD4$^+$ T cells, CD8$^+$ T cells, and antibody responses (Dikici, et al., supra; Pol, et al., supra; Vandepapeliere, et al., supra; Yalcin, et al., *J Clin Gastroenterol.* (2003) 37(4):330-5; Al-Mahtab, supra; Hoa, et al., supra; Yalcin, et al., *Infection.* (2003) 31(4):221-5; Mancini-Bourgine, et al., supra; Yang, et al., *J Viral Hepat.* (2012) 19(8):581-93; Gane. et al., supra; and Zoulim, et al., supra). These immune components are particularly important for curing chronic HBV infection as CD8$^+$ T cells have been shown to be the main effector cells responsible for viral clearance during acute HBV infection in chimpanzees (Thimme, et al., *J Virol.* (2003) 77(1):68-76). In addition, antibodies that bind to HBV surface antigen (HBsAg) facilitate HBsAg clearance and prevent spread of residual HBV. Moreover, a high magnitude of immune response is likely necessary to achieve a therapeutic effect, but many prior CHB vaccines have failed to induce such a robust response (Mancini-Bourgine, et al., supra; Yang, et al., *J Viral Hepat.* (2012) 19(8):581-93; Cavenaugh, et al., supra; Gane. et al., supra; and Zoulim, et al., supra). Lastly, some prior CHB vaccine antigens have not been sufficiently stable in the delivery vectors to enable commercial-scale vaccine manufacture.

SUMMARY

In one aspect, provided are truncated hepatitis B virus (HBV) polymerase polypeptides, e.g., capable of inducing or eliciting an immune response in a human upon administration. In some embodiments, the truncated HBV polymerase polypeptide comprises an inactivated reverse transcriptase domain and an inactivated RNase H, and does not comprise all of the terminal protein (TP) domain and all or part of the Spacer domain. In some embodiments, the polypeptide is no longer than 600 amino acids in length, e.g., no longer than 595, 590, 585, 580, 575, 570, 565, 560, 555, 550, 545, 540 or 535 amino acids in length. In some embodiments, the reverse transcriptase domain does not comprise a YMDD motif (SEQ ID NO: 97) and the RNase H domain does not comprise an AELL motif (SEQ ID NO: 98). In some embodiments, the YMDD motif (SEQ ID NO: 97) in the reverse transcriptase domain is mutated to YMHD (SEQ ID NO: 99) and wherein the AELL motif (SEQ ID NO: 98) in the RNase H domain is mutated to AHLL (SEQ ID NO: 100). In some embodiments, the polypeptide is from an HBV genotype A, B, C or D. In some embodiments, (a) the polypeptide is from HBV genotype B and does not comprise a polypeptide sequence (e.g., the sequence is removed or deleted or not included) of SEQ ID NO: 50, or a sequence that is at least 90%, 91%, 92%, 93%, 94%, 95%, 96%, 97%, 98% or 99% identical to any one of SEQ ID NO: 50; or (b) the polypeptide is from HBV genotype D and does not comprise a polypeptide sequence of SEQ ID NO: 51, or a sequence that is at least 90%, 91%, 92%, 93%, 94%, 95%, 96%, 97%, 98% or 99% identical to any one of SEQ ID NO: 51. In some embodiments, the truncated HBV polymerase polypeptide comprises or consists of an amino acid sequence of any one of SEQ ID NOs: 13-14, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 13-14.

In another aspect, provided are HBV polymerase deletion mutant polypeptides. In some embodiments, the HBV polymerase deletion mutant polypeptide comprises in sequential order from the N-terminus to the C-terminus, a terminal protein (TP) domain, an inactivated reverse transcriptase domain, and an inactivated RNase H, wherein the mutant polypeptide does not comprise all or part of a Spacer domain. In some embodiments, the polypeptide is no longer than 800 amino acids in length, e.g., no longer than 795, 790, 785, 780, 775, 770, 765, 760, 755, 750, 745, 740, 735, 730, 725, 720, 715, 710 or 705 amino acids in length. In some embodiments, the reverse transcriptase domain does not comprise a YMDD motif (SEQ ID NO: 97) and the RNase H domain does not comprise an AELL motif (SEQ ID NO: 98). In some embodiments, the YMDD motif (SEQ ID NO: 97) in the reverse transcriptase domain is mutated to YMHD (SEQ ID NO: 99) and wherein the AELL motif (SEQ ID NO: 98) in the RNase H domain is mutated to AHLL (SEQ ID NO: 100). In some embodiments, the polypeptide is from an HBV genotype A, B, C or D. In some embodiments, (a) the polypeptide is from HBV genotype A and does not comprise a polypeptide of SEQ ID NO: 42 or 46, or a sequence that is at least 90%, 91%, 92%, 93%, 94%, 95%, 96%, 97%, 98% or 99% identical to any one of SEQ ID NO: 42 or 46; (b) the polypeptide is from HBV genotype B and does not comprise a polypeptide of SEQ ID NO: 43 or 47, or a sequence that is at least 90%, 91%, 92%, 93%, 94%, 95%, 96%, 97%, 98% or 99% identical to any one of SEQ ID NO: 43 or 47; (c) the polypeptide is from HBV genotype C and does not comprise a polypeptide of SEQ ID NO: 44 or 48, or a sequence that is at least 90%, 91%, 92%, 93%, 94%, 95%, 96%, 97%, 98% or 99% identical to any one of SEQ ID NO: 44 or 48; or (d) the polypeptide is from HBV genotype D and does not comprise a polypeptide of SEQ ID NO: 45 or 49, or a sequence that is at least 90%, 91%, 92%, 93%, 94%, 95%, 96%, 97%, 98% or 99% identical to any one of SEQ ID NO: 45 or 49. In some embodiments, the HBV polymerase deletion mutant polypeptide comprises or consists of an amino acid sequence of any one of SEQ ID NOs: 5-12, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 5-12. In some embodiments, HBV polymerase deletion mutant polypeptide further comprises (e.g., is a fusion protein including) an HBV core polypeptide. In some embodiments, the HBV polymerase deletion mutant polypeptide comprises in sequential order from the N-terminus to the C-terminus, an HBV core polypeptide and the HBV polymerase deletion mutant polypeptide, as described herein. In some embodiments, the HBV polymerase deletion mutant polypeptide comprises or consists of an amino acid sequence of any one of SEQ ID NOs: 19-26, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 19-26.

In a further aspect, provided is an HBV core-sAg fusion protein. In some embodiments, the core-sAg fusion protein comprises in sequential order from the N-terminus to the C-terminus, an HBV core polypeptide and an HBV small surface antigen (sAg) polypeptide. In various embodiments, the core polypeptide is from an HBV genotype B or C and the sAg polypeptide is from an HBV genotype C. In some embodiments, the core polypeptide is from an HBV genotype D and the sAg polypeptide is from an HBV genotype D. In some embodiments, the core-sAg fusion protein comprises: (a) a core polypeptide comprising or consisting of an amino acid sequence of SEQ ID NO: 65, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 65, and a sAg polypeptide comprising or consisting of an amino acid sequence of SEQ ID NO: 3, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical SEQ ID NO: 3; or (b) a core polypeptide comprising or consisting of an amino acid sequence of SEQ ID NO: 66, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 66, and a sAg polypeptide comprising or consisting of an amino acid sequence of SEQ ID NO: 4, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical SEQ ID NO: 4. In some embodiments, the core polypeptide comprises a serine (S) residue at the amino acid position corresponding to position 12, and an asparagine (N) residue at the amino acid position corresponding to position 67, wherein the position numbers are with reference to SEQ ID NO:65 or SEQ ID NO:66. In some embodiments, the sAg polypeptide comprises an isoleucine (I) residue at the amino acid position corresponding to position 68, wherein the position numbers are with reference to SEQ ID NO:3 or SEQ ID NO:4. In some embodiments, the sAg polypeptide comprises one or more of a serine (S) residue at the amino acid position corresponding to position 53, an isoleucine (I) residue at the amino acid position corresponding to position 68, a threonine (T) residue at the amino acid position corresponding to position 125, a proline (P) residue at the amino acid position corresponding to position 127, an phenylalanine (F) residue at the amino acid position corresponding to position 161, a tyrosine (Y) residue at the amino acid position corresponding to position 200, a serine (S) residue at the amino acid position corresponding to position 210, and a leucine (L) residue at the amino acid position corresponding to position 213, wherein the position numbers are with reference to SEQ ID NO:3 or SEQ ID NO:4. In various embodiments, the sAg polypeptide does not comprise a pre-S1 polypeptide. In various embodiments, the sAg polypeptide does not comprise a pre-S2 polypeptide. In some embodiments, the sAg polypeptide does not comprise an HBV pre-S2 polypeptide comprising or consisting of an amino acid sequence of any one of SEQ ID NOs: 79-83, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 79-83. In some embodiments, the sAg polypeptide does not comprise both of an HBV pre-S1 polypeptide and an HBV pre-S2 polypeptide. In some embodiments, the sAg polypeptide does not comprise an HBV pre-S1-pre-S2 polypeptide comprising or consisting of an amino acid sequence of any one of SEQ ID NO: 84-88, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84-88. In various embodiments, the core-sAg fusion protein comprises a cleavable linker operably linked to and positioned between the HBV core polypeptide and the HBV sAg polypeptide. In some embodiments, the cleavable linker is a 2A cleavable peptide. In some embodiments, the cleavable linker is a 2A cleavable peptide selected from foot-and-mouth disease virus (F2A), equine rhinitis A virus (E2A), porcine teschovirus-1 (P2A) and Thosea asigna virus (T2A). In some embodiments, the cleavable linker is a porcine teschovirus-1 (P2A) linker. In some embodiments, the cleavable linker comprises or consists of an amino acid sequence of ATNFSLLKQAGDVEENPGP (SEQ ID NO: 56), APVKQTLNFDLLKLAGDVESNPGP (SEQ ID NO: 57), QCTNYALLKLAGDVESNPGP (SEQ ID NO: 58), or EGRGSLLTCGDVEENPGP (SEQ ID NO: 59), or an amino acid sequence that is at least 90%, 91%, 92%, 93%, 94%, 95%, 96%, 97%, 98% or at least 99% identical to ATNFSLLKQAGDVEENPGP (SEQ ID NO: 56), APVKQTLNFDLLKLAGDVESNPGP (SEQ ID NO: 57), QCTNYALLKLAGDVESNPGP (SEQ ID NO: 58), or EGRGSLLTCGDVEENPGP (SEQ ID NO: 59). In some embodiments, the cleavable linker comprises or consists of an amino acid sequence of ATNFSLLKQAGDVEENPGP (SEQ ID NO: 56), or an amino acid sequence that is at least 90%, 91%, 92%, 93%, 94%, 95%, 96%, 97%, 98% or at least 99% identical to ATNFSLLKQAGDVEENPGP (SEQ ID NO: 56). In some embodiments, the core-sAg fusion protein comprises a flexible linker and/or a furin recognition/cleavage site operably linked to and positioned N-terminal to the cleavable linker and C-terminal to the HBV core polypeptide. In some embodiments, the furin recognition/cleavage site comprises or consists of an amino acid sequence selected from RAKR (SEQ ID NO: 60), REKR (SEQ ID NO: 61) and RRKR (SEQ ID NO: 62). In some embodiments, the flexible linker comprises a polyglycine or polyalanine sequence. In some embodiments, the flexible linker comprises or consists of a polyglycine or polyalanine sequence selected from AA, AAA, AAY, GG, GGG, GGS, GSG and GGGS (SEQ ID NO: 63). In some embodiments, the core-sAg fusion protein is no longer than 450 amino acids in length, e.g., no longer than 445, 440, 435, 430, 425, 420, 415 or 410 amino acids in length. In some embodiments, the core-sAg fusion protein comprises or consists of an amino acid sequence of any one of SEQ ID NOs: 38-41, e.g., SEQ ID NO: 41, or a sequence that is at least 90%, 91%, 92%, 93%, 94%, 95%, 96%, 97%, 98% or 99% identical to any one of SEQ ID NOs: 38-41, e.g., SEQ ID NO:41. In some embodiments, the fusion polypeptide comprises one or more of a serine (S) residue at the amino acid position corresponding to position 12, an asparagine (N) residue at the amino acid position corresponding to position 67, a valine (V) residue at the amino acid position corresponding to position 74, a phenylalanine (F) residue at the amino acid position corresponding to position 97, a threonine (T) residue at the amino acid position corresponding to position 249, a threonine (T) residue at the amino acid position corresponding to position 250, a serine (S) residue at the amino acid position corresponding to position 317, a serine (S) residue at the amino acid position corresponding to position 318, an arginine (R) residue at the amino acid position corresponding to position 326, a tyrosine (Y) residue at the amino acid position corresponding to position 338, a glycine (G) residue at the amino acid position corresponding to position 363, and an alanine (A) residue at the amino acid position corresponding to position 372, wherein the position numbers are with reference to SEQ ID NO:41. In various embodiments, the core-sAg fusion polypeptide does not comprise an amino sequence or fragment thereof from an HBV protein selected from the group consisting of X, pre-core, pre-S1 and pre-S2.

With respect to the immunogenic HBV polypeptides, in some embodiments, the truncated HBV polymerase polypeptide, the HBV polymerase deletion mutant polypeptide, or the core-sAg fusion protein, as described herein, further comprise an N-terminal signal peptide or leader sequence. In various embodiments, the signal peptide or leader sequence is from a source protein selected from a serum protein, a cytokine, a chemokine, a chaperone protein, an invariant protein, and a protein that directs proteins to the lysosomal compartment. In various embodiments, the signal peptide or leader sequence is from a source protein selected from colony stimulating factor 2 (CSF2, GM-CSF), tissue type plasminogen activator (PLAT, t-PA), C-C motif chemokine ligand 7 (CCL7, MCP-3), C-X-C motif chemokine ligand 10 (CXCL10, IP-10), catenin beta 1 (CTNNB1), CD74 (p33; DHLAG; HLADG; Ia-GAMMA, invariant chain), serum albumin (ALB), polyubiquitin B/C (UBB/UBC), calreticulin (CALR), vesicular stomatitis virus G protein (VSV-G), lysosomal associated membrane protein 1 (LAMP-1) and lysosomal associated membrane protein 2 (LAMP-2). In some embodiments, the signal peptide or leader sequence is selected from an amino acid sequence of any one of SEQ ID NOs: 67-78, or a sequence that is at least 95%, 96%, 97%, 98%, or 99% identical to any one of SEQ ID NOs: 67-78. In various embodiments, the truncated HBV polymerase polypeptide, the HBV polymerase deletion mutant polypeptide, and/or the core-sAg fusion protein, as described herein, can be recombinantly produced or chemically synthesized. In various embodiments, the truncated HBV polymerase polypeptide, the HBV polymerase deletion mutant polypeptide, and/or the core-sAg fusion protein, as described herein, are capable of inducing, promoting or stimulating an immune response (e.g., expansion and/or activation of CD8+ and/or CD4+ T cells; production of antibodies that bind to and/or neutralize one or more of HBV polymerase, HBV core and HBV sAg) in a human. In various embodiments, the truncated HBV polymerase polypeptide, the HBV polymerase deletion mutant polypeptide, and/or the core-sAg fusion protein, as described herein, are capable of inducing, promoting or stimulating an immune response against HBV (e.g., that prevents, delays progression of, inhibits and/or reverses HBV infection) in a human. In various embodiments, the truncated HBV polymerase polypeptide, the HBV polymerase deletion mutant polypeptide, and/or the core-sAg fusion protein, as described herein, are capable of inducing, promoting or stimulating proliferation and/or activation of one or more cell types selected from monocyte-derived dendritic cells (DCs), CD8+ T cells and CD4+ T cells.

In a further aspect, provided are polynucleotides encoding the immunogenic HBV polypeptides, as described herein. For example, provided are polynucleotides encoding one or more of the truncated HBV polymerase polypeptides, the HBV polymerase deletion mutant polypeptide, or the core-sAg fusion protein, as described herein. In some embodiments, the polynucleotide comprises cDNA, mRNA, self-amplifying RNA (SAM), self-replicating RNA, or self-amplifying replicon RNA (RepRNA). In some embodiments, polynucleotide comprises self-replicating or self-amplifying alphavirus replicons. In some embodiments, the polynucleotide comprises or consists of a nucleic acid sequence of any one of SEQ ID NOs: 27-37, e.g., SEQ ID NOs: 37 and 89-94, e.g., SEQ ID NOs: 29, 89, 90 or 92, or that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 27-37, e.g., SEQ ID NO:37 and 89-94, e.g., SEQ ID NOs: 29, 89, 90 or 92.

In another aspect, provided is a lipid nanoparticle (LNP) comprising one or more of the polynucleotides encoding an immunogenic HBV polypeptide, as described herein.

In another aspect, provided are expression cassettes comprising one or more of the polynucleotides encoding an immunogenic HBV polypeptide, as described herein, operably linked to one or more regulatory sequences. In some embodiments, the polynucleotide is operably linked to and under the control of a constitutive promoter. In some embodiments, the promoter is selected from cytomegalovirus major immediate-early (CMV), the CMV enhancer fused to the chicken beta-actin promoter (CAG), human elongation factor-1α (HEF-1α), mouse cytomegalovirus (mouse CMV), Chinese hamster elongation factor-la (CHEF-la), and phosphoglycerate kinase (PGK).

In another aspect, provided are comprising one or more of the polynucleotides encoding an immunogenic HBV polypeptide, as described herein, or one or more expression cassettes comprising such polynucleotides. In various embodiments, the vector is a plasmid vector, a bacterial vector or a viral vector. In some embodiments, the vector is a viral vector. In various embodiments, the viral vector is a DNA virus or an RNA virus. In some embodiments, the viral vector is from a virus selected from adenovirus, adeno-associated virus, arenavirus, alphavirus, poxvirus, cytomegalovirus, rhabdovirus, vesicular stomatitis virus, flavivirus, maraba virus and vaccinia virus. In some embodiments, the viral vector is from a virus from a taxonomic family selected from Adenoviridae, Arenaviridae, Herpesviridae (e.g. Cytomegalovirus), Poxviridae (e.g. Vaccinia virus, e.g. modified vaccinia Ankara (MVA)), Flaviviridae (e.g. Yellow fever virus), Rhabdoviridae (e.g. Vesiculovirus, e.g. Maraba vesiculovirus), Togaviridae (e.g., Alphavirus). In some embodiments, the viral vector is an arenavirus vector selected from Lymphocytic choriomeningitis mammarenavirus (LCMV), Cali mammarenavirus (a.k.a., Pichinde mammarenavirus or Pichinde arenavirus (PICV)), Guanarito virus (GTOV), Junin virus (JUNV), Lassa virus (LASV), Lujo virus (LUJV), Machupo virus (MACV), Sabia virus (SABV), and Whitewater Arroyo virus (WWAV). In some embodiments, the viral vector is an arenavirus vector selected from Lymphocytic choriomeningitis mammarenavirus (LCMV) or Cali mammarenavirus (a.k.a., Pichinde mammarenavirus or Pichinde arenavirus (PICV)). In some embodiments, the viral vector is a human adenovirus or a simian adenovirus (e.g., a chimpanzee adenovirus, a gorilla adenovirus or a rhesus adenovirus). In some embodiments, the viral vector is an adenovirus vector selected from adenovirus serotype 5 (Ad5), adenovirus serotype 26 (Ad26), adenovirus serotype 34 (Ad34), adenovirus serotype 35 (Ad35), adenovirus serotype 48 (Ad48), chimpanzee adenovirus (e.g. ChAdOx1, ChAdOx2, ChAd3 (AdC3), ChAd5 (AdC5), ChAd6 (AdC6), ChAd7 (AdC7), ChAd8 (AdC8), ChAd9 (AdC9), ChAd10 (AdC10), ChAd11 (AdC11), ChAd17 (AdC17), ChAd16 (AdC16), ChAd19 (AdC19), ChAd20 (AdC20), ChAd22 (AdC22), ChAd24 (AdC24), ChAdY25, ChAd26 (AdC26), ChAd28 (AdC28), ChAd30 (AdC30), ChAd31 (AdC31), ChAd37 (AdC37), ChAd38 (AdC38), ChAd43 (AdC43), ChAd44 (AdC44), ChAd55 (AdC55), ChAd63 (AdC63), ChAdV63, ChAd68 (AdC68), ChAd73 (AdC73), ChAd82 (AdC82), ChAd83 (AdC83), ChAd143 (AdC143), ChAd144 (AdC144), ChAd145 (AdC145), ChAd147 (AdC147)), gorilla adenovirus (e.g. GC44, GC45, GC46) and rhesus adenovirus (e.g., RhAd51, RhAd52, RhAd53, RhAd54, RhAd55, RhAd56, RhAd57, RhAd58, RhAd59, RhAd60, RhAd61, RhAd62, RhAd63, RhAd64, RhAd65, RhAd66).

In some embodiments, the viral vector is replication-defective, replication-deficient, replication-attenuated or replication-competent. In some embodiments, the viral vector is a replication-defective arenavirus having a bi-segmented genome. In some embodiments, the viral vector is a replication-attenuated arenavirus having a tri-segmented genome.

In a further aspect, provided are arenavirus vectors. In one embodiment, provided is an arenavirus vector comprising a polynucleotide encoding an HBV core-sAg fusion polypeptide comprising or consisting of an amino acid sequence of any one of SEQ ID NOs: 38-41, e.g., SEQ ID NO:41, or a sequence that is at least 90%, 91%, 92%, 93%, 94%, 95%, 96%, 97%, 98% or 99% identical to any one of SEQ ID NOs: 38-41, e.g., SEQ ID NO:41, and wherein the sAg polypeptide does not comprise an HBV pre-S1 polypeptide and/or an HBV pre-S2 polypeptide. In some embodiments, the core polypeptide comprises a serine (S) residue at the amino acid position corresponding to position 12, and an asparagine (N) residue at the amino acid position corresponding to position 67, wherein the position numbers are with reference to SEQ ID NO:65 or SEQ ID NO:66. In some embodiments, the sAg polypeptide comprises an isoleucine (I) residue at the amino acid position corresponding to position 68, wherein the position numbers are with reference to SEQ ID NO:3 or SEQ ID NO:4. In some embodiments, the sAg polypeptide comprises one or more of a serine (S) residue at the amino acid position corresponding to position 53, an isoleucine (I) residue at the amino acid position corresponding to position 68, a threonine (T) residue at the amino acid position corresponding to position 125, a proline (P) residue at the amino acid position corresponding to position 127, an phenylalanine (F) residue at the amino acid position corresponding to position 161, a tyrosine (Y) residue at the amino acid position corresponding to position 200, a serine (S) residue at the amino acid position corresponding to position 210, and a leucine (L) residue at the amino acid position corresponding to position 213, wherein the position numbers are with reference to SEQ ID NO:3 or SEQ ID NO:4. In some embodiments, the core-sAg fusion polypeptide comprises one or more of a serine (S) residue at the amino acid position corresponding to position 12, an asparagine (N) residue at the amino acid position corresponding to position 67, a valine (V) residue at the amino acid position corresponding to position 74, a phenylalanine (F) residue at the amino acid position corresponding to position 97, a threonine (T) residue at the amino acid position corresponding to position 249, a threonine (T) residue at the amino acid position corresponding to position 250, a serine (S) residue at the amino acid position corresponding to position 317, a serine (S) residue at the amino acid position corresponding to position 318, an arginine (R) residue at the amino acid position corresponding to position 326, a tyrosine (Y) residue at the amino acid position corresponding to position 338, a glycine (G) residue at the amino acid position corresponding to position 363, and an alanine (A) residue at the amino acid position corresponding to position 372, wherein the position numbers are with reference to SEQ ID NO:41. In some embodiments, the polynucleotide comprises or consists of a nucleic acid sequence of any one of SEQ ID NOs: 33-37, or that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 33-37. In some embodiments, the polynucleotide comprises or consists of a nucleic acid sequence of SEQ ID NO: 37, or that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 37. In some embodiments, the arenavirus vector has a bisegmented genome and further comprises a polynucleotide encoding a truncated HBV polymerase comprising or consisting of an amino acid sequence of any one of SEQ ID NOs: 13-14, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 13-14, and wherein the truncated HBV polymerase does not comprise all of an HBV polymerase terminal protein (TP) domain and does not comprise all or part of an HBV polymerase Spacer domain. In some embodiments, the truncated HBV polymerase does not comprise a polypeptide sequence of SEQ ID NO: 50 or SEQ ID NO:51, or a sequence that is at least 90%, 91%, 92%, 93%, 94%, 95%, 96%, 97%, 98% or 99% identical to any one of SEQ ID NO: 50 or SEQ ID NO: 51. In some embodiments, the polynucleotide comprises or consists of a nucleic acid sequence of any one of SEQ ID NOs: 29 and 89-94, e.g., SEQ ID NOs: 29, 89, 90 or 92, or that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 29 and 89-94, e.g., SEQ ID NOs: 29, 89, 90 or 92. In some embodiments, the arenavirus vector is a Lymphocytic choriomeningitis mammarenavirus (LCMV) vector and the polynucleotide comprises or consists of a nucleic acid sequence of SEQ ID NO: 29, or that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NO: 29. In some embodiments, the arenavirus vector is a Cali mammarenavirus (a.k.a., Pichinde mammarenavirus or Pichinde arenavirus (PICV)) vector and the polynucleotide comprises or consists of a nucleic acid sequence of SEQ ID NO: 90, or that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 90.

Further provided is an arenavirus vector comprising a polynucleotide encoding a truncated HBV polymerase comprising or consisting of an amino acid sequence of any one of SEQ ID NOs: 13-14, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 13-14, and wherein the truncated HBV polymerase does not comprise all of an HBV polymerase terminal protein (TP) domain and does not comprise all or part of an HBV polymerase Spacer domain. In some embodiments, the truncated HBV polymerase does not comprise a polypeptide sequence of SEQ ID NO: 50 or SEQ ID NO:51, or a sequence that is at least 90%, 91%, 92%, 93%, 94%, 95%, 96%, 97%, 98% or 99% identical to any one of SEQ ID NO: 50 or SEQ ID NO: 51. In some embodiments, the polynucleotide comprises or consists of a nucleic acid sequence of any one of SEQ ID NOs: 29 and 89-94, e.g., SEQ ID NOs: 29, 89, 90 or 92, or that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 29 and 89-94, e.g., SEQ ID NOs: 29, 89, 90 or 92. In some embodiments, the arenavirus vector is a Lymphocytic choriomeningitis mammarenavirus (LCMV) vector and the polynucleotide comprises or consists of a nucleic acid sequence of SEQ ID NO: 29, or that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NO: 29. In some embodiments, the arenavirus vector is a Cali mammarenavirus vector and the polynucleotide comprises or consists of a nucleic acid sequence of SEQ ID NO: 90, or that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 90. In some embodiments, the arenavirus vector is replication-defective, replication-deficient, or replication-incompetent.

In a further aspect, provided are host cells comprising one or more polynucleotides encoding one or more immunogenic HBV polypeptides, as described herein, or one or more vectors comprising such polynucleotides. In some embodiments, the one or more polynucleotides encoding one or more immunogenic HBV polypeptides, as described herein, are not integrated into the host cell genome, e.g., are episomal. In some embodiments, the one or more polynucleotides are integrated into the host cell genome. In some embodiments, the host cell is a mammalian cell, e.g., a human cell. In various embodiments, the host cell can be in vitro or in vivo.

In another aspect, provided are immunogenic compositions comprising one or more of the immunogenic HBV polypeptides, as described herein. In some embodiments, the immunogenic composition comprises one or more, e.g., two or more, of the truncated HBV polymerase polypeptides, one or more, e.g., two or more, of the HBV polymerase deletion mutant polypeptides, and/or one or more, e.g., two or more, of the core-sAg fusion protein, as described herein. In some embodiments, the immunogenic composition comprises one or more, e.g., two or more, polynucleotides encoding one or more, e.g., two or more, of the truncated HBV polymerase polypeptides, one or more, e.g., two or more, of the HBV polymerase deletion mutant polypeptides, and/or one or more, e.g., two or more, of the core-sAg fusion protein, as described herein. In some embodiments, the immunogenic composition comprises one or more, e.g., two or more, one or more, e.g., two or more, vectors comprising one or more, e.g., two or more, polynucleotides encoding one or more, e.g., two or more, of the truncated HBV polymerase polypeptides, one or more, e.g., two or more, of the HBV polymerase deletion mutant polypeptides, and/or one or more, e.g., two or more, of the core-sAg fusion protein, as described herein. The immunogenic compositions further comprise a pharmaceutically acceptable carrier. In some embodiments, the immunogenic composition comprises one or more polynucleotides in the form of DNA, cDNA, mRNA, or self-replicating RNA. In various embodiments, the immunogenic composition comprises a first viral expression vector and a second viral expression vector, wherein: (a) the first viral expression vector comprises a polynucleotide encoding a truncated HBV polymerase polypeptide or an HBV polymerase deletion mutant polypeptide, as described herein; and (b) the second viral expression vector comprises a polynucleotide encoding the core-sAg fusion protein, as described. In some embodiments, the immunogenic composition comprises a first viral expression vector and a second viral expression vector, wherein: (a) the first viral expression vector comprises a polynucleotide encoding an HBV polymerase polypeptide mutant comprising or consisting of an amino acid sequence of any one of SEQ ID NOs: 5-14, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 5-14; and (b) the second viral expression vector comprises a polynucleotide encoding the core-sAg fusion protein comprising or consisting of an amino acid sequence of any one of SEQ ID NOs: 38-41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 38-41. In some embodiments, the immunogenic composition comprises a first viral expression vector and a second viral expression vector, wherein: (a) the first viral expression vector comprises a polynucleotide encoding an HBV polymerase polypeptide mutant comprising or consisting of an amino acid sequence of any one of SEQ ID NOs: 13-14, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 13-14; and (b) the second viral expression vector comprises a polynucleotide encoding the core-sAg fusion protein comprising or consisting of an amino acid sequence of any one of SEQ ID NOs: 38-41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 38-41. In some embodiments, the immunogenic compositions comprise a first viral expression vector and a second viral expression vector, wherein: (a) the first viral expression vector comprises a polynucleotide encoding an HBV polymerase polypeptide mutant comprising or consisting of an amino acid sequence of SEQ ID NO: 13, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 13; and (b) the second viral expression vector comprises a polynucleotide encoding the core-sAg fusion protein comprising or consisting of an amino acid sequence of SEQ ID NO: 41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 41. In some embodiments, the core polypeptide comprises a serine (S) residue at the amino acid position corresponding to position 12, and an asparagine (N) residue at the amino acid position corresponding to position 67, wherein the position numbers are with reference to SEQ ID NO:65 or SEQ ID NO:66. In some embodiments, the sAg polypeptide comprises an isoleucine (I) residue at the amino acid position corresponding to position 68, wherein the position numbers are with reference to SEQ ID NO:3 or SEQ ID NO:4. In some embodiments, the sAg polypeptide comprises one or more of a serine (S) residue at the amino acid position corresponding to position 53, an isoleucine (I) residue at the amino acid position corresponding to position 68, a threonine (T) residue at the amino acid position corresponding to position 125, a proline (P) residue at the amino acid position corresponding to position 127, an phenylalanine (F) residue at the amino acid position corresponding to position 161, a tyrosine (Y) residue at the amino acid position corresponding to position 200, a serine (S) residue at the amino acid position corresponding to position 210, and a leucine (L) residue at the amino acid position corresponding to position 213, wherein the position numbers are with reference to SEQ ID NO:3 or SEQ ID NO:4. In some embodiments, the core-sAg fusion polypeptide comprises one or more of a serine (S) residue at the amino acid position corresponding to position 12, an asparagine (N) residue at the amino acid position corresponding to position 67, a valine (V) residue at the amino acid position corresponding to position 74, a phenylalanine (F) residue at the amino acid position corresponding to position 97, a threonine (T) residue at the amino acid position corresponding to position 249, a threonine (T) residue at the amino acid position corresponding to position 250, a serine (S) residue at the amino acid position corresponding to position 317, a serine (S) residue at the amino acid position corresponding to position 318, an arginine (R) residue at the amino acid position corresponding to position 326, a tyrosine (Y) residue at the amino acid position corresponding to position 338, a glycine (G) residue at the amino acid position corresponding to position 363, and an alanine (A) residue at the amino acid position corresponding to position 372, wherein the position numbers are with reference to SEQ ID NO:41. In some embodiments, the immunogenic compositions comprise a first viral expression vector and a second viral expression vector, wherein: (a) the first viral expression vector comprises a polynucleotide comprising or consisting of a nucleic acid sequence of any one of SEQ ID NOs: 27-32 and 89-94 e.g., SEQ ID NOs: 29, 89, 90 or 92, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 27-32 and 89-94 e.g., SEQ ID NOs: 29, 89, 90 or 92; and (b) the second viral expression vector comprises a polynucleotide comprising or consisting of a nucleic acid sequence of any one of SEQ ID NOs: 33-37 or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 33-37. In some embodiments, the immunogenic composition comprises a first viral expression vector and a second viral expression vector, wherein: (a) the first viral expression vector comprises a polynucleotide comprising or consisting of a nucleic acid sequence of SEQ ID NO: 29 or 90, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 29 or 90; and (b) the second viral expression vector comprises a polynucleotide comprising or consisting of a nucleic acid sequence of SEQ ID NO: 37 or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NO: 37. In various embodiments, the first viral expression vector and the second viral expression vector are independently from a taxonomic family selected from Adenoviridae, Arenaviridae, Herpesviridae (e.g. Cytomegalovirus), Poxviridae (e.g. Vaccinia virus, e.g. modified vaccinia Ankara (MVA)), Flaviviridae (e.g. Yellow fever virus), Rhabdoviridae (e.g. Vesiculovirus, e.g. Maraba vesiculovirus), Togaviridae (e.g., Alphavirus). In various embodiments, the first viral expression vector and the second viral expression vector in the immunogenic composition can be from the same taxonomic family or different taxonomic families. In some embodiments, the first viral expression vector and the second viral expression vector in the immunogenic composition are from Arenaviridae. In some embodiments, the first viral expression vector and the second viral expression vector in the immunogenic composition are independently from an arenavirus vector selected from Lymphocytic choriomeningitis mammarenavirus (LCMV), Cali mammarenavirus (a.k.a., Pichinde mammarenavirus or Pichinde arenavirus (PICV)), Guanarito virus (GTOV), Junin virus (JUNV), Lassa virus (LASV), Lujo virus (LUJV), Machupo virus (MACV), Sabia virus (SABV), and Whitewater Arroyo virus (WWAV). In some embodiments, the first viral expression vector and the second viral expression vector are independently from an arenavirus vector selected from Lymphocytic choriomeningitis mammarenavirus (LCMV) or Cali mammarenavirus (a.k.a., Pichinde mammarenavirus or Pichinde arenavirus (PICV)). In some embodiments, the first viral expression vector and the second viral expression vector are replication-defective or replication-deficient. In some embodiments, the first viral expression vector and the second viral expression vector are replication-attenuated. In some embodiments, the immunogenic composition comprises a first LCMV arenavirus expression vector and a second LCMV arenavirus expression vector, wherein: (a) the first LCMV arenavirus expression vector comprises a polynucleotide comprising or consisting of a nucleic acid sequence of SEQ ID NO: 29, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 29; and (b) the second LCMV arenavirus expression vector comprises a polynucleotide comprising or consisting of a nucleic acid sequence of SEQ ID NO: 37 or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NO: 37. In some embodiments, the immunogenic composition comprises a first Pichinde arenavirus expression vector and a second Pichinde arenavirus expression vector, wherein: (a) the first Pichinde arenavirus expression vector comprises a polynucleotide comprising or consisting of a nucleic acid sequence of SEQ ID NO: 90, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 90; and (b) the second Pichinde arenavirus expression vector comprises a polynucleotide comprising or consisting of a nucleic acid sequence of SEQ ID NO: 37 or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NO: 37. In various embodiments, the first viral expression vector and the second viral expression vector are provided in the immunogenic composition in a ratio in the range of from 1:10 to 10:1, e.g., 1:9 to 9:1, 1:8 to 8:1, 1:7 to 7:1, 1:6 to 6:1, 1:5 to 5:1, 1:4 to 4:1, 1:3 to 3:1, 1:2 to 2:1 or 1:1. In some embodiments, the immunogenic composition comprises in the range of about $10^3$ to about $10^{12}$ viral focus forming units (FFU) or plaque forming units (PFU) or infectious units (IU) or viral particles (vp) per milliliter, e.g. from about $10^4$ to about $10^7$ viral FFU or PFU or IU or vp per milliliter, e.g. from about $10^3$ to about $10^4$, $10^5$, $10^6$, $10^7$, $10^8$, $10^9$, $10^{10}$, $10^{11}$ or $10^{12}$ viral FFU or PFU or IU or vp per milliliter, of each of the first viral expression vector and the second viral expression vector. In some embodiments, the immunogenic composition further comprises one or more of an adjuvant, a detergent, a micelle-forming agent, and an oil. In various embodiments, the immunogenic composition is formulated for administration via a route selected from intravenous, intramuscular, intradermal, subcutaneous and mucosal (e.g. buccal, intranasal, intrarectal, intravaginal). In some embodiments, the immunogenic composition is an aqueous solution or suspension, e.g., is formulated as a liquid. In some embodiments, the immunogenic composition is lyophilized.

In a further aspect, provided are kits. In various embodiments, the kit comprises one or more, e.g., two or more, unitary doses of one or more, e.g., two or more, of a truncated HBV polymerase polypeptide, one or more, e.g., two or more, of an HBV polymerase deletion mutant polypeptide and/or one or more, e.g., two or more, of a core-sAg fusion protein, as described herein. In some embodiments, the kit comprises one or more, e.g., two or more, unitary doses of one or more, e.g., two or more, polynucleotides encoding one or more, e.g., two or more, of a truncated HBV polymerase polypeptide, one or more, e.g., two or more, of an HBV polymerase deletion mutant polypeptide and/or one or more, e.g., two or more, of a core-sAg fusion protein, as described herein. In some embodiments, the kit comprises one or more, e.g., two or more, unitary doses of one or more, e.g., two or more, vectors comprising one or more, e.g., two or more, polynucleotides encoding one or more, e.g., two or more, of a truncated HBV polymerase polypeptide, one or more, e.g., two or more, of an HBV polymerase deletion mutant polypeptide and/or one or more, e.g., two or more, of a core-sAg fusion protein, as described herein. In various embodiments, the kit comprises one or more, e.g., two or more, unitary doses of one or more, e.g., two or more, immunogenic compositions, as described herein. In some embodiments, the one or more unitary doses in the kit are in a single container. In some embodiments, the one or more unitary doses in the kit are in two or more separate containers. In some embodiments, the kit comprises one or more containers selected from vials, ampules and pre-loaded syringes. In some embodiments, the kit comprises one or more containers comprising the one or more polypeptides, one or more polynucleotides, one or more vectors or one or more immunogenic compositions in an aqueous solution or suspension, or as a lyophilized preparation. In various embodiments, the one or more unitary doses can be the same or different. In some embodiments, the kit comprises one or more unitary doses of one or more viral vectors, as described herein, wherein the unitary doses are in the range of about $10^3$ to about $10^{12}$ viral focus forming units (FFU) or plaque forming units (PFU) or infectious units (IU) or viral particles (vp), e.g. from about $10^4$ to about $10^7$ viral FFU or PFU or IU or vp, e.g. from about $10^3$ to about $10^4$, $10^5$, $10^6$, $10^7$, $10^8$, $10^9$, $10^{10}$, $10^{11}$ or $10^{12}$ viral FFU or PFU or IU or vp. In some embodiments, the kit comprises one or more polynucleotides encoding, or one or more vectors expressing, or an immunogenic composition comprising, at least two immunogenic polypeptides, the immunogenic polypeptides comprising: (a) an HBV polymerase polypeptide mutant comprising or consisting of an amino acid sequence of any one of SEQ ID NOs: 5-14, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 5-14; and (b) an HBV core-sAg fusion protein comprising or consisting of an amino acid sequence of any one of SEQ ID NOs: 38-41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 38-41. In some embodiments, the kit comprises one or more polynucleotides encoding, or one or more vectors expressing, or an immunogenic composition comprising, at least two immunogenic polypeptides, the immunogenic polypeptides comprising: (a) an HBV polymerase polypeptide mutant comprising or consisting of an amino acid sequence of any one of SEQ ID NOs: 13-14, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 13-14; and (b) an HBV core-sAg fusion protein comprising or consisting of an amino acid sequence of any one of SEQ ID NOs: 38-41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 38-41. In some embodiments, the kit comprises one or more polynucleotides encoding, or one or more vectors expressing, or an immunogenic composition comprising, at least two immunogenic polypeptides, the immunogenic polypeptides comprising: (a) an HBV polymerase polypeptide mutant comprising or consisting of an amino acid sequence of SEQ ID NO: 13, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 13; and (b) an HBV core-sAg fusion protein comprising or consisting of an amino acid sequence of SEQ ID NO: 41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 41. In some embodiments, the core polypeptide comprises a serine (S) residue at the amino acid position corresponding to position 12, and an asparagine (N) residue at the amino acid position corresponding to position 67, wherein the position numbers are with reference to SEQ ID NO:65 or SEQ ID NO:66. In some embodiments, the sAg polypeptide comprises an isoleucine (I) residue at the amino acid position corresponding to position 68, wherein the position numbers are with reference to SEQ ID NO:3 or SEQ ID NO:4. In some embodiments, the sAg polypeptide comprises one or more of a serine (S) residue at the amino acid position corresponding to position 53, an isoleucine (I) residue at the amino acid position corresponding to position 68, a threonine (T) residue at the amino acid position corresponding to position 125, a proline (P) residue at the amino acid position corresponding to position 127, an phenylalanine (F) residue at the amino acid position corresponding to position 161, a tyrosine (Y) residue at the amino acid position corresponding to position 200, a serine (S) residue at the amino acid position corresponding to position 210, and a leucine (L) residue at the amino acid position corresponding to position 213, wherein the position numbers are with reference to SEQ ID NO:3 or SEQ ID NO:4. In some embodiments, the core-sAg fusion polypeptide comprises one or more of a serine (S) residue at the amino acid position corresponding to position 12, an asparagine (N) residue at the amino acid position corresponding to position 67, a valine (V) residue at the amino acid position corresponding to position 74, a phenylalanine (F) residue at the amino acid position corresponding to position 97, a threonine (T) residue at the amino acid position corresponding to position 249, a threonine (T) residue at the amino acid position corresponding to position 250, a serine (S) residue at the amino acid position corresponding to position 317, a serine (S) residue at the amino acid position corresponding to position 318, an arginine (R) residue at the amino acid position corresponding to position 326, a tyrosine (Y) residue at the amino acid position corresponding to position 338, a glycine (G) residue at the amino acid position corresponding to position 363, and an alanine (A) residue at the amino acid position corresponding to position 372, wherein the position numbers are with reference to SEQ ID NO:41. In some embodiments, the kit comprises first and second vectors encoding first and second immunogenic polypeptides, respectively, the first and second immunogenic polypeptides comprising, respectively: (a) an HBV polymerase polypeptide mutant comprising or consisting of an amino acid sequence of SEQ ID NO: 13, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 13; and (b) an HBV core-sAg fusion protein comprising or consisting of an amino acid sequence of SEQ ID NO: 41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 41. In some embodiments, the kit comprises a first viral expression vector and a second viral expression vector, wherein: (a) the first viral expression vector comprises a polynucleotide comprising or consisting of a nucleic acid sequence of any one of SEQ ID NOs: 27-32 and 89-94, e.g., SEQ ID NOs: 29, 89, 90 or 92, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 27-32 and 89-94, e.g., SEQ ID NOs: 29, 89, 90 or 92; and (b) the second viral expression vector comprises a polynucleotide comprising or consisting of a nucleic acid sequence of any one of SEQ ID NOs: 33-37, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 33-37. In some embodiments, the kit comprises a first viral expression vector and a second viral expression vector, wherein: (a) the first viral expression vector comprises a polynucleotide comprising or consisting of a nucleic acid sequence of SEQ ID NO: 29 or 90, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 29 or 90; and (b) the second viral expression vector comprises a polynucleotide comprising or consisting of a nucleic acid sequence of SEQ ID NO: 37, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 37. In some embodiments, the kit comprises one or more unitary doses of an immunogenic composition comprising first and second viral expression vectors, as described herein, wherein the first and second viral expression vectors comprise a replication-deficient or replication-defective Cali mammarenavirus (a.k.a., Pichinde mammarenavirus or Pichinde arenavirus (PICV)). In some embodiments, the kit comprises one or more unitary doses of an immunogenic composition comprising first and second viral expression vectors, as described herein, wherein the first and second viral expression vectors comprise a replication-deficient or replication-defective Lymphocytic choriomeningitis mammarenavirus (LCMV). In some embodiments, the kit comprises (a) one or more unitary doses of an immunogenic composition, as described herein, wherein the first and second viral expression vectors are from Adenoviridae; and (b) one or more unitary doses of an immunogenic composition, as described herein, wherein the first and second viral expression vectors are from Poxviridae (e.g., Vaccinia virus, e.g., modified vaccinia Ankara (MVA)). In some embodiments, the kit comprises (a) one or more unitary doses of an immunogenic composition, as described herein, wherein the first and second viral expression vectors are from Arenaviridae; and (b) one or more unitary doses of an immunogenic composition, as described herein, wherein the first and second viral expression vectors are from Adenoviridae. In some embodiments, the kit comprises a first LCMV arenavirus expression vector and a second LCMV arenavirus expression vector, wherein: (a) the first LCMV arenavirus expression vector comprises a polynucleotide comprising or consisting of a nucleic acid sequence of SEQ ID NO: 29, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 29; and (b) the second LCMV arenavirus expression vector comprises a polynucleotide comprising or consisting of a nucleic acid sequence of SEQ ID NO: 37, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 37. In some embodiments, the kit comprises a first Pichinde arenavirus expression vector and a second Pichinde arenavirus expression vector, wherein: (a) the first Pichinde arenavirus expression vector comprises a polynucleotide comprising or consisting of a nucleic acid sequence of SEQ ID NO: 90, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 90; and (b) the second Pichinde arenavirus expression vector comprises a polynucleotide comprising or consisting of a nucleic acid sequence of SEQ ID NO: 37, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 37. In various embodiment, the kit further comprises one or more unitary doses of one or more additional therapeutic agents. In some embodiments, the kit further comprises one or more agonists or activators of one or more toll-like receptors (TLRs). In some embodiments, the kit further comprises one or more TLR agonists or activators selected from a TLR2 agonist, a TLR3 agonist, a TLR4 agonist, a TLR5 agonist, a TLR7 agonist, a TLR8 agonist and a TLR9 agonist. In some embodiments, the kit further comprises a TLR7 agonist selected from GS 9620 (vesatolimod), R848 (Resiquimod), DS-0509, LHC-165 and TMX-101 (imiquimod). In some embodiments, the kit further comprises a TLR8 agonist selected from GS-9688, R848 (Resiquimod) and NKTR-262 (dual TLR7/TLR8 agonist). In some embodiments, the kit further comprises one or more interleukin receptor agonists of an interleukin receptor selected from IL-2, IL-7, IL-12 and IL-15. In some embodiments, the kit further comprises one or more cytokines selected from IL-2, IL-7, IL-12, IL-15, and variants thereof. In some embodiments, the kit further comprises one or more innate immune activators. In some embodiments, the kit further comprises one or more innate immune activators comprising an agonist of a receptor selected from fins related tyrosine kinase 3 (FLT3), stimulator of interferon genes (STING) receptor, DExD/H-box helicase 58 (DDX58; a.k.a., RIG-I), nucleotide binding oligomerization domain containing 2 (NOD2). In some embodiments, the kit further comprises one or more unitary doses of GS-3583 and/or GS-9992. In some embodiments, the kit further comprises one or more antagonists or inhibitors of an inhibitory immune checkpoint protein or receptor and/or one or more activators or agonists of a stimulatory immune checkpoint protein or receptor. In some embodiments, the kit further comprises one or more immune checkpoint proteins or receptors selected from CD27, CD70; CD40, CD40LG; CD47, CD48 (SLAMF2), transmembrane and immunoglobulin domain containing 2 (TMIGD2, CD28H), CD84 (LY9B, SLAMF5), CD96, CD160, MS4A1 (CD20), CD244 (SLAMF4); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); natural killer cell cytotoxicity receptor 3 ligand 1 (NCR3LG1, B7H6); HERV-H LTR-associating 2 (HHLA2, B7H7); inducible T cell co-stimulator (ICOS, CD278); inducible T cell co-stimulator ligand (ICOSLG, B7H2); TNF receptor superfamily member 4 (TNFRSF4, OX40); TNF superfamily member 4 (TNFSF4, OX40L); TNFRSF8 (CD30), TNFSF8 (CD30L); TNFRSF10A (CD261, DR4, TRAILR1), TNFRSF9 (CD137), TNFSF9 (CD137L); TNFRSF10B (CD262, DR5, TRAILR2), TNFRSF10 (TRAIL); TNFRSF14 (HVEM, CD270), TNFSF14 (HVEML); CD272 (B and T lymphocyte associated (BTLA)); TNFRSF17 (BCMA, CD269), TNFSF13B (BAFF); TNFRSF18 (GITR), TNFSF18 (GITRL); MHC class I polypeptide-related sequence A (MICA); MHC class I polypeptide-related sequence B (MICB); CD274 (CD274, PDL1, PD-L1); programmed cell death 1 (PDCD1, PD1, PD-1); cytotoxic T-lymphocyte associated protein 4 (CTLA4, CD152); CD80 (B7-1), CD28; nectin cell adhesion molecule 2 (NECTIN2, CD112); CD226 (DNAM-1); Poliovirus receptor (PVR) cell adhesion molecule (PVR, CD155); PVR related immunoglobulin domain containing (PVRIG, CD112R); T cell immunoreceptor with Ig and ITIM domains (TIGIT); T cell immunoglobulin and mucin domain containing 4 (TIMD4; TIM4); hepatitis A virus cellular receptor 2 (HAVCR2, TIMD3, TIM3); galectin 9 (LGALS9); lymphocyte activating 3 (LAG3, CD223); signaling lymphocytic activation molecule family member 1 (SLAMF1, SLAM, CD150); lymphocyte antigen 9 (LY9, CD229, SLAMF3); SLAM family member 6 (SLAMF6, CD352); SLAM family member 7 (SLAMF7, CD319); UL16 binding protein 1 (ULBP1); UL16 binding protein 2 (ULBP2); UL16 binding protein 3 (ULBP3); retinoic acid early transcript 1E (RAET1E; ULBP4); retinoic acid early transcript 1G (RAET1G; ULBP5); retinoic acid early transcript 1L (RAET1L; ULBP6); lymphocyte activating 3 (CD223); killer cell immunoglobulin like receptor, three Ig domains and long cytoplasmic tail 1 (KIR, CD158E1); killer cell lectin like receptor C1 (KLRC1, NKG2A, CD159A); killer cell lectin like receptor K1 (KLRK1, NKG2D, CD314); killer cell lectin like receptor C2 (KLRC2, CD159c, NKG2C); killer cell lectin like receptor C3 (KLRC3, NKG2E); killer cell lectin like receptor C4 (KLRC4, NKG2F); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor D1 (KLRD1); and SLAM family member 7 (SLAMF7). In some embodiments, the kit further comprises one or more blockers or inhibitors of one or more T-cell inhibitory immune checkpoint proteins or receptors. In some embodiments, the kit further comprises one or more T-cell inhibitory immune checkpoint proteins or receptors selected from CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In some embodiments, the kit further comprises one or more agonists or activators of one or more T-cell stimulatory immune checkpoint proteins or receptors. In some embodiments, the kit further comprises one or more T-cell stimulatory immune checkpoint proteins or receptors selected from CD27, CD70; CD40, CD40LG; inducible T cell co-stimulator (ICOS, CD278); inducible T cell co-stimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); Poliovirus receptor (PVR) cell adhesion molecule (PVR, CD155). In some embodiments, the kit further comprises one or more unitary doses of AGEN-2373 and/or AGEN-1223. In some embodiments, the kit further comprises one or more blockers or inhibitors of one or more NK-cell inhibitory immune checkpoint proteins or receptors. In some embodiments, the kit further comprises one or more NK-cell inhibitory immune checkpoint proteins or receptors selected from killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); and killer cell lectin like receptor D1 (KLRD1, CD94). In some embodiments, the kit further comprises one or more agonists or activators of one or more NK-cell stimulatory immune checkpoint proteins or receptors. In some embodiments, the kit further comprises one or more NK-cell stimulatory immune checkpoint proteins or receptors selected from CD16, CD226 (DNAM-1); killer cell lectin like receptor K1 (KLRK1, NKG2D, CD314); and SLAM family member 7 (SLAMF7). In some embodiments, the kit further comprises one or more proteinaceous inhibitors of PD-L1 (CD274), PD-1 (PDCD1) and/or CTLA4. In some embodiments, the kit further comprises one or more proteinaceous inhibitors of CTLA4 selected from ipilimumab, tremelimumab, BMS-986218, AGEN1181, AGEN1884, BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4) and AK-104 (CTLA4/PD-1). In some embodiments, the kit further comprises one or more proteinaceous inhibitors of PD-L1 (CD274) or PD-1 (PDCD1) selected from zimberelimab (AB122), pembrolizumab, nivolumab, cemiplimab, pidilizumab, AMP-224, MEDIO680 (AMP-514), spartalizumab, atezolizumab, avelumab, ASC22, durvalumab, BMS-936559, CK-301, PF-06801591, BGB-A317 (tislelizumab), GLS-010 (WBP-3055), AK-103 (HX-008), AK-105, CS-1003, HLX-10, MGA-012, BI-754091, AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181, PD1-PIK, BAT-1306, (MSB0010718C), CX-072, CBT-502, TSR-042 (dostarlimab), MSB-2311, JTX-4014, BGB-A333, SHR-1316, CS-1001 (WBP-3155, KN-035, IBI-308 (sintilimab), HLX-20, KL-A167, STI-A1014, STI-A1015 (IMC-001), BCD-135, FAZ-053, TQB-2450, MDX1105-01, FPT-155 (CTLA4/PD-L1/CD28), PF-06936308 (PD-1/CTLA4), MGD-013 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/TIM-3), XmAb-20717 (PD-1/CTLA4), AK-104 (CTLA4/PD-1), M7824 (PD-L1/TGFβ-EC domain), CA-170 (PD-L1/VISTA), CDX-527 (CD27/PD-L1), LY-3415244 (TIM3/PDL1), and INBRX-105 (4-1BB/PDL1). In some embodiments, the kit further comprises one or more small molecule inhibitors of CD274 (PDL1, PD-L1), programmed cell death 1 (PDCD1, PD1, PD-1) and/or CTLA4. In some embodiments, the kit further comprises one or more small molecule inhibitors of CD274 or PDCD1 selected from GS-4224, GS-4416, INCB086550 and MAX10181. In some embodiments, the kit further comprises the small molecule inhibitor of CTLA4, BPI-002. In some embodiments, the kit further comprises one or more one or more anti-viral agents. In some embodiments, the kit further comprises one or more antiviral agents selected from lamivudine (LAM), adefovir dipivoxil (ADV), entecavir (ETV), telbivudine (LdT), tenofovir disoproxil fumarate (TDF), tenofovir alafenamide (TAF or VEMLIDY®) and ledipasvir+sofosbuvir (HARVONI®). In some embodiments, the kit further comprises one or more therapeutic agents selected from HBV antigen inhibitors (e.g., HBV core antigen (HBcAg) inhibitors, HBV surface antigen (HBsAg) inhibitors, HBx inhibitors, HBV E antigen inhibitors), anti-HBV antigen antibodies, inhibitory nucleic acids targeting HBV (e.g., antisense oligonucleotide, short interfering RNA (siRNA), DNA-directed RNA interference (ddRNAi)), gene editors targeting HBV (e.g., CRISPR-Cas (e.g., Cas9, Cas12, Cascade, Cas13), zinc finger nucleases, homing endonucleases, homing meganucleases (e.g., ARCUS), synthetic nucleases, TALENs), covalently closed circular DNA (cccDNA) inhibitors and HBsAg secretion or assembly inhibitors and HBV viral entry inhibitors.

In a further aspect, provided are methods for eliciting an immune response to human hepatitis B virus (HBV) in a subject in need thereof. Also provided are methods of treating or preventing human hepatitis B virus (HBV) in a subject in need thereof. In some embodiments, the methods comprise administering to the subject a therapeutically effective amount of one or more immunogenic compositions, as described herein. In some embodiments, the methods entail administering one or more immunogenic compositions comprising a mixture comprising a first viral expression vector and a second viral expression vector, wherein: (a) the first viral expression vector comprises a polynucleotide encoding a truncated HBV polymerase polypeptide or a HBV polymerase deletion mutant polypeptide, as described herein; and (b) the second viral expression vector comprises a polynucleotide encoding the core-sAg fusion protein, as described herein. In some embodiments, the methods entail administering to the subject a therapeutically effective amount of one or more immunogenic compositions comprising a mixture comprising a first viral expression vector and a second viral expression vector, wherein: (a) the first viral expression vector comprises a polynucleotide encoding an HBV polymerase polypeptide mutant comprising or consisting of an amino acid sequence of any one of SEQ ID NOs: 5-14, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 5-14; and (b) the second viral expression vector comprises a polynucleotide encoding the core-sAg fusion protein comprising or consisting of an amino acid sequence of any one of SEQ ID NOs: 38-41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 38-41. In some embodiments, the methods entail administering to the subject a therapeutically effective amount of one or more immunogenic compositions comprising a mixture comprising a first viral expression vector and a second viral expression vector, wherein: (a) the first viral expression vector comprises a polynucleotide encoding an HBV polymerase polypeptide mutant comprising or consisting of an amino acid sequence of any one of SEQ ID NOs: 13-14, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 13-14; and (b) the second viral expression vector comprises a polynucleotide encoding the core-sAg fusion protein comprising or consisting of an amino acid sequence of any one of SEQ ID NOs: 38-41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 38-41. In some embodiments, the methods entail administering to the subject a therapeutically effective amount of one or more immunogenic compositions comprising a mixture comprising a first viral expression vector and a second viral expression vector, wherein: (a) the first viral expression vector comprises a polynucleotide encoding an HBV polymerase polypeptide mutant comprising or consisting of an amino acid sequence of SEQ ID NO: 13, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 13; and (b) the second viral expression vector comprises a polynucleotide encoding the core-sAg fusion protein comprising or consisting of an amino acid sequence of SEQ ID NO: 41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 41. In some embodiments, the core polypeptide comprises a serine (S) residue at the amino acid position corresponding to position 12, and an asparagine (N) residue at the amino acid position corresponding to position 67, wherein the position numbers are with reference to SEQ ID NO:65 or SEQ ID NO:66. In some embodiments, the sAg polypeptide comprises an isoleucine (I) residue at the amino acid position corresponding to position 68, wherein the position numbers are with reference to SEQ ID NO:3 or SEQ ID NO:4. In some embodiments, the sAg polypeptide comprises one or more of a serine (S) residue at the amino acid position corresponding to position 53, an isoleucine (I) residue at the amino acid position corresponding to position 68, a threonine (T) residue at the amino acid position corresponding to position 125, a proline (P) residue at the amino acid position corresponding to position 127, an phenylalanine (F) residue at the amino acid position corresponding to position 161, a tyrosine (Y) residue at the amino acid position corresponding to position 200, a serine (S) residue at the amino acid position corresponding to position 210, and a leucine (L) residue at the amino acid position corresponding to position 213, wherein the position numbers are with reference to SEQ ID NO:3 or SEQ ID NO:4. In some embodiments, the core-sAg fusion polypeptide comprises one or more of a serine (S) residue at the amino acid position corresponding to position 12, an asparagine (N) residue at the amino acid position corresponding to position 67, a valine (V) residue at the amino acid position corresponding to position 74, a phenylalanine (F) residue at the amino acid position corresponding to position 97, a threonine (T) residue at the amino acid position corresponding to position 249, a threonine (T) residue at the amino acid position corresponding to position 250, a serine (S) residue at the amino acid position corresponding to position 317, a serine (S) residue at the amino acid position corresponding to position 318, an arginine (R) residue at the amino acid position corresponding to position 326, a tyrosine (Y) residue at the amino acid position corresponding to position 338, a glycine (G) residue at the amino acid position corresponding to position 363, and an alanine (A) residue at the amino acid position corresponding to position 372, wherein the position numbers are with reference to SEQ ID NO:41. In some embodiments, the methods entail administering to the subject a therapeutically effective amount of one or more immunogenic compositions comprising a mixture comprising a first viral expression vector and a second viral expression vector, wherein: (a) the first viral expression vector comprises a polynucleotide comprising or consisting of a nucleic sequence of any one of SEQ ID NOs: 27-32 and 89-94, e.g., SEQ ID NOs: 29, 89, 90 or 92, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 27-32 and 89-94, e.g., SEQ ID NOs: 29, 89, 90 or 92; and (b) the second viral expression vector comprises a polynucleotide comprising or consisting of a nucleic acid sequence of any one of SEQ ID NOs: 33-37, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 33-37. In some embodiments, the methods comprise administering to the subject a therapeutically effective amount of one or more immunogenic compositions comprising a mixture comprising a first viral expression vector and a second viral expression vector, wherein: (a) the first viral expression vector comprises a polynucleotide comprising or consisting of a nucleic sequence of SEQ ID NO: 29 or 90, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 29 or 90; and (b) the second viral expression vector comprises a polynucleotide comprising or consisting of a nucleic acid sequence of SEQ ID NO: 37, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 37. In some embodiments of the methods, the first viral expression vector and the second viral expression vector are from Arenaviridae. In some embodiments of the methods, the first viral expression vector and the second viral expression vector are from an arenavirus vector selected from Lymphocytic choriomeningitis mammarenavirus (LCMV), Cali mammarenavirus (a.k.a., Pichinde mammarenavirus or Pichinde arenavirus (PICV)), Guanarito virus (GTOV), Junin virus (JUNV), Lassa virus (LASV), Lujo virus (LUJV), Machupo virus (MACV), Sabia virus (SABV), and Whitewater Arroyo virus (WWAV). In some embodiments of the methods, the first viral expression vector and the second viral expression vector are from an arenavirus vector selected from Lymphocytic choriomeningitis mammarenavirus (LCMV) or Cali mammarenavirus (a.k.a., Pichinde mammarenavirus or Pichinde arenavirus (PICV)). In some embodiments of the methods, the first viral expression vector and the second viral expression vector are replication-defective or replication-deficient. In some embodiments of the methods, the first viral expression vector and the second viral expression vector are replication-attenuated. In some embodiments, the methods comprise administering to the subject a therapeutically effective amount of one or more immunogenic compositions comprising a mixture comprising a first LCMV arenavirus expression vector and a second LCMV arenavirus expression vector, wherein: (a) the first LCMV arenavirus expression vector comprises a polynucleotide comprising or consisting of a nucleic sequence of SEQ ID NO: 29, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 29; and (b) the second LCMV arenavirus expression vector comprises a polynucleotide comprising or consisting of a nucleic acid sequence of SEQ ID NO: 37, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 37. In some embodiments, the methods comprise administering to the subject a therapeutically effective amount of one or more immunogenic compositions comprising a mixture comprising a first Pichinde arenavirus expression vector and a second Pichinde arenavirus expression vector, wherein: (a) the first Pichinde arenavirus expression vector comprises a polynucleotide comprising or consisting of a nucleic sequence of SEQ ID NO: 90, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 90; and (b) the second Pichinde arenavirus expression vector comprises a polynucleotide comprising or consisting of a nucleic acid sequence of SEQ ID NO: 37, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 37. In some embodiments of the methods, the subject is infected with HBV, is suspected of being infected with HBV, or is at risk of being infected with HBV. In some embodiments of the methods, the subject is asymptomatic. In some embodiments of the methods, the subject is chronically infected with HBV. In some embodiments of the methods, the subject is exhibiting or experiencing one or more symptoms selected from hepatic failure, hepatic cancer, hepatic fibrosis and hepatic cirrhosis. In some embodiments of the methods, the subject is acutely infected with HBV. In some embodiments of the methods, the subject is exhibiting or experiencing one or more symptoms selected from jaundice, visible webs of swollen blood vessels in the skin, dark-colored (e.g., orange or brown) urine, light-colored feces, fever, persistent fatigue, malaise, abdominal pain, abdominal fluid, loss of appetite, nausea, and vomiting. In some embodiments of the methods, the subject is co-infected with hepatitis D virus (HDV). In some embodiments of the methods, the composition is administered via a route selected from intravenous, intramuscular, intradermal, subcutaneous and mucosal (e.g. buccal, intranasal, intrarectal, intravaginal). In some embodiments, the methods entail administering to the subject from about $10^3$ to about $10^{12}$ viral focus forming units (FFU) or plaque forming units (PFU) or infectious units (IU) or viral particles (vp), e.g. from about $10^4$ to about $10^7$ viral FFU or PFU or IU or vp, e.g. from about $10^3$ to about $10^4$, $10^5$, $10^6$, $10^7$, $10^8$, $10^9$, $10^{10}$, $10^{11}$ or $10^{12}$ viral FFU or PFU or IU or vp, per administration. In some embodiments of the methods, the one or more compositions are administered multiple times. In some embodiments, the methods entail administering intravenously or intramuscularly from about $10^6$ to about $10^8$ viral FFU or PFU or IU or vp per administration every other week (Q2W) or monthly (Q4W). In some embodiments, the methods entail multiple administrations of the one or more immunogenic compositions over a time period of at least about 2 weeks, 3 weeks, 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, or longer, or until sAg is not detectable in the serum or plasma of the subject. In some embodiments, the methods comprise a prime-boost regimen comprising administering a priming composition at a first time point and administering one or more boosting compositions at one or more subsequent time points. As appropriate, the methods can entail repeating the prime-boost regimen one or more iterations. In some embodiments of the methods, the administrations of the priming composition and the one or more boosting compositions are spaced at least 1 week and up to at least 2 weeks, 3 weeks, 1 month, 2 months, 3 months, 4 months, 5 months or 6 months apart. In some embodiments of the methods, the priming composition and the boosting composition can comprise the same immunogenic composition or can comprise different immunogenic compositions. In some embodiments of the methods, the priming composition and the boosting composition comprise the same one or more polypeptides and same viral expression vector. In some embodiments of the methods, the priming composition and the boosting composition comprise different polypeptides and/or different viral expression vectors. In some embodiments, the methods entail priming with a priming composition comprising one or more (e.g., first and second) viral expression vectors, and boosting with a boosting composition comprising one or more (e.g., third and fourth) viral expression vectors. In various embodiments, the prime-boost regimen comprises: (a) Priming with a priming composition comprising one or more viral expression vectors and boosting with a boosting composition comprising one or more polynucleotides, wherein the one or more polynucleotides comprise DNA, cDNA, mRNA or self-replicating RNA; (b) Priming with a priming composition comprising one or more polynucleotides, wherein the one or more polynucleotides comprise DNA, cDNA, mRNA or self-replicating RNA, and boosting with a boosting composition comprising one or more viral expression vectors; (c) Priming with a priming composition comprising one or more viral expression vectors, and boosting with a boosting composition comprising one or more viral expression vectors, wherein the one or more viral expression vectors in the priming composition and the one or more viral expression vectors in the boosting composition are from identical, related or unrelated taxonomical families; (d) Priming with a priming composition comprising one or more replication-deficient viral expression vectors and boosting with a boosting composition comprising one or more replication-deficient viral expression vectors, wherein the one or more replication-deficient viral expression vectors in the priming composition and the one or more replication-deficient viral expression vectors in the boosting composition are from identical, related or unrelated taxonomical families; (e) Priming with a priming composition comprising one or more replication-attenuated viral expression vectors and boosting with a boosting composition comprising one or more replication-attenuated viral expression vectors, wherein the one or more replication-attenuated viral expression vectors in the priming composition and the one or more replication-attenuated viral expression vectors in the boosting composition are from identical, related or unrelated taxonomical families; (f) Priming with a priming composition comprising one or more replication-deficient viral expression vectors and boosting with a boosting composition comprising one or more replication-attenuated viral expression vectors; (g) Priming with a priming composition comprising one or more replication-attenuated viral expression vectors and boosting with a boosting composition comprising one or more replication-deficient viral expression vectors; (h) Priming with a priming composition comprising one or more Lymphocytic choriomeningitis mammarenavirus (LCMV) viral expression vectors and boosting with a boosting composition comprising one or more Pichinde mammarenavirus (PICV) viral expression vectors; (i) Priming with a priming composition comprising one or more Pichinde mammarenavirus (PICV) viral expression vectors and boosting with a boosting composition comprising one or more Lymphocytic choriomeningitis mammarenavirus (LCMV) viral expression vectors; (j) Priming with a priming composition comprising one or more replication deficient Pichinde mammarenavirus (PICV) viral expression vectors and boosting with a boosting composition comprising one or more replication deficient Lymphocytic choriomeningitis mammarenavirus (LCMV) viral expression vectors; (k) Priming with a priming composition comprising one or more replication deficient Lymphocytic choriomeningitis mammarenavirus (LCMV) viral expression vectors and boosting with a boosting composition comprising one or more replication deficient Pichinde mammarenavirus (PICV) viral expression vectors; (l) Priming with a priming composition comprising one or more arenavirus viral expression vectors and boosting with a boosting composition comprising one or more adenovirus viral expression vectors; (m) Priming with a priming composition comprising one or more adenovirus viral expression vectors and boosting with boosting composition comprising one or more arenavirus viral expression vectors; (n) Priming with a priming composition comprising one or more poxvirus viral expression vectors and boosting with a boosting composition comprising one or more arenavirus viral expression vectors; (o) Priming with a priming composition comprising one or more arenavirus viral expression vectors and boosting with boosting composition comprising one or more poxvirus viral expression vectors; (p) Priming with a priming composition comprising one or more poxvirus viral expression vectors and boosting with a boosting composition comprising one or more adenovirus viral expression vectors; or (q) Priming with a priming composition comprising one or more adenovirus viral expression vectors and boosting with boosting composition comprising one or more poxvirus viral expression vectors. In some embodiments, the methods entail a prime-boost regimen that comprises: (a) Priming with a priming composition comprising one or more Lymphocytic choriomeningitis mammarenavirus (LCMV) viral expression vectors and boosting with a boosting composition comprising one or more Pichinde mammarenavirus (PICV) viral expression vectors; (b) Priming with a priming composition comprising one or more Pichinde mammarenavirus (PICV) viral expression vectors and boosting with a boosting composition comprising one or more Lymphocytic choriomeningitis mammarenavirus (LCMV) viral expression vectors; (c) Priming with a priming composition comprising one or more replication deficient Pichinde mammarenavirus (PICV) viral expression vectors and boosting with a boosting composition comprising one or more replication deficient Lymphocytic choriomeningitis mammarenavirus (LCMV) viral expression vectors; or (d) Priming with a priming composition comprising one or more replication deficient Lymphocytic choriomeningitis mammarenavirus (LCMV) viral expression vectors and boosting with a boosting composition comprising one or more replication deficient Pichinde mammarenavirus (PICV) viral expression vectors. In some embodiments, the priming composition and the boosting composition comprise an immunogenic composition as described herein. In some embodiments, the subject is not receiving antiviral therapy or antiviral therapy is discontinued prior to administration of the one or more immunogenic compositions. In some embodiments of the methods, antiviral therapy is discontinued after one or more administrations of the one or more immunogenic compositions. In some embodiments, the methods further comprise administering to the subject one or more additional therapeutic agents, e.g. two, three, four, or more additional therapeutic agents. In some embodiments, the methods comprise co-administering one or more agonists or activators of one or more toll-like receptors (TLRs). In some embodiments, the methods comprise co-administering one or more TLR agonists or activators selected from a TLR2 agonist, a TLR3 agonist, a TLR4 agonist, a TLR5 agonist, a TLR7 agonist, a TLR8 agonist and a TLR9 agonist. In some embodiments, the methods entail co-administering a TLR7 agonist selected from GS-9620 (vesatolimod), R848 (Resiquimod), DS-0509, LHC-165 and TMX-101 (imiquimod). In some embodiments, the methods entail co-administering a TLR8 agonist selected from GS-9688, R848 (Resiquimod) and NKTR-262 (dual TLR7/TLR8 agonist). In some embodiments, the methods entail co-administering one or more interleukin receptor agonists of an interleukin receptor selected from IL-2, IL-7, IL-12 and IL-15. In some embodiments, the methods entail co-administering one or more cytokines selected from IL-2, IL-7, IL-12, IL-15, and variants thereof. In some embodiments, the methods entail co-administering one or more innate immune activators. In some embodiments, the methods entail co-administering one or more innate immune activators comprising an agonist of a receptor selected from fms related tyrosine kinase 3 (FLT3), stimulator of interferon genes (STING) receptor, DExD/H-box helicase 58 (DDX58; a.k.a., RIG-I), nucleotide binding oligomerization domain containing 2 (NOD2). In some embodiments, the methods entail co-administering GS-3583 and/or GS-9992. In some embodiments, the methods entail co-administering one or more antagonists or inhibitors of an inhibitory immune checkpoint protein or receptor and/or one or more activators or agonists of a stimulatory immune checkpoint protein or receptor. In some embodiments, the methods entail co-administering one or more immune checkpoint proteins or receptors selected from: CD27, CD70; CD40, CD40LG; CD47, CD48 (SLAMF2), transmembrane and immunoglobulin domain containing 2 (TMIGD2, CD28H), CD84 (LY9B, SLAMF5), CD96, CD160, MS4A1 (CD20), CD244 (SLAMF4); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); natural killer cell cytotoxicity receptor 3 ligand 1 (NCR3LG1, B7H6); HERV-H LTR-associating 2 (HHLA2, B7H7); inducible T cell co-stimulator (ICOS, CD278); inducible T cell co-stimulator ligand (ICOSLG, B7H2); TNF receptor superfamily member 4 (TNFRSF4, OX40); TNF superfamily member 4 (TNFSF4, OX40L); TNFRSF8 (CD30), TNFSF8 (CD30L); TNFRSF10A (CD261, DR4, TRAILR1), TNFRSF9 (CD137), TNFSF9 (CD137L); TNFRSF10B (CD262, DR5, TRAILR2), TNFRSF10 (TRAIL); TNFRSF14 (HVEM, CD270), TNFSF14 (HVEML); CD272 (B and T lymphocyte associated (BTLA)); TNFRSF17 (BCMA, CD269), TNFSF13B (BAFF); TNFRSF18 (GITR), TNFSF18 (GITRL); MHC class I polypeptide-related sequence A (MICA); MHC class I polypeptide-related sequence B (MICB); CD274 (CD274, PDL1, PD-L1); programmed cell death 1 (PDCD1, PD1, PD-1); cytotoxic T-lymphocyte associated protein 4 (CTLA4, CD152); CD80 (B7-1), CD28; nectin cell adhesion molecule 2 (NECTIN2, CD112);

CD226 (DNAM-1); Poliovirus receptor (PVR) cell adhesion molecule (PVR, CD155); PVR related immunoglobulin domain containing (PVRIG, CD112R); T cell immunoreceptor with Ig and ITIM domains (TIGIT); T cell immunoglobulin and mucin domain containing 4 (TIMD4; TIM4); hepatitis A virus cellular receptor 2 (HAVCR2, TIMD3, TIM3); galectin 9 (LGALS9); lymphocyte activating 3 (LAG3, CD223); signaling lymphocytic activation molecule family member 1 (SLAMF1, SLAM, CD150); lymphocyte antigen 9 (LY9, CD229, SLAMF3); SLAM family member 6 (SLAMF6, CD352); SLAM family member 7 (SLAMF7, CD319); UL16 binding protein 1 (ULBP1); UL16 binding protein 2 (ULBP2); UL16 binding protein 3 (ULBP3); retinoic acid early transcript 1E (RAET1E; ULBP4); retinoic acid early transcript 1G (RAET1G; ULBP5); retinoic acid early transcript 1L (RAET1L; ULBP6); lymphocyte activating 3 (CD223); killer cell immunoglobulin like receptor, three Ig domains and long cytoplasmic tail 1 (KIR, CD158E1); killer cell lectin like receptor C1 (KLRC1, NKG2A, CD159A); killer cell lectin like receptor K1 (KLRK1, NKG2D, CD314); killer cell lectin like receptor C2 (KLRC2, CD159c, NKG2C); killer cell lectin like receptor C3 (KLRC3, NKG2E); killer cell lectin like receptor C4 (KLRC4, NKG2F); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor D1 (KLRD1); and SLAM family member 7 (SLAMF7). In some embodiments, the methods entail co-administering one or more blockers or inhibitors of one or more T-cell inhibitory immune checkpoint proteins or receptors. In some embodiments, the methods entail co-administering one or more T-cell inhibitory immune checkpoint proteins or receptors selected from CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In some embodiments, the methods entail co-administering one or more agonists or activators of one or more T-cell stimulatory immune checkpoint proteins or receptors. In some embodiments, the methods entail co-administering one or more T-cell stimulatory immune checkpoint proteins or receptors selected from CD27, CD70; CD40, CD40LG; inducible T cell co-stimulator (ICOS, CD278); inducible T cell co-stimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); Poliovirus receptor (PVR) cell adhesion molecule (PVR, CD155). In some embodiments, the methods entail co-administering AGEN-2373 and/or AGEN-1223. In some embodiments, the methods entail co-administering one or more blockers or inhibitors of one or more NK-cell inhibitory immune checkpoint proteins or receptors. In some embodiments, the methods entail co-administering one or more NK-cell inhibitory immune checkpoint proteins or receptors selected from killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); and killer cell lectin like receptor D1 (KLRD1, CD94). In some embodiments, the methods entail co-administering one or more agonists or activators of one or more NK-cell stimulatory immune checkpoint proteins or receptors. In some embodiments, the methods entail co-administering one or more NK-cell stimulatory immune checkpoint proteins or receptors are selected from CD16, CD226 (DNAM-1); killer cell lectin like receptor K1 (KLRK1, NKG2D, CD314); and SLAM family member 7 (SLAMF7). In some embodiments, the methods entail co-administering one or more proteinaceous inhibitors of PD-L1 (CD274), PD-1 (PDCD1) or CTLA4. In some embodiments, the methods entail co-administering one or more proteinaceous inhibitors of CTLA4 selected from ipilimumab, tremelimumab, BMS-986218, AGEN1181, AGEN1884, BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4) and AK-104 (CTLA4/PD-1). In some embodiments, the methods entail co-administering one or more proteinaceous inhibitors of PD-L1 (CD274) or PD-1 (PDCD1) selected from zimberelimab (AB122), pembrolizumab, nivolumab, cemiplimab, pidilizumab, AMP-224, MEDI0680 (AMP-514), spartalizumab, atezolizumab, avelumab, ASC22, durvalumab, BMS-936559, CK-301, PF-06801591, BGB-A317 (tislelizumab), GLS-010 (WBP-3055), AK-103 (HX-008), AK-105, CS-1003, HLX-10, MGA-012, BI-754091, AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181, PD1-PIK, BAT-1306, (MSB0010718C), CX-072, CBT-502, TSR-042 (dostarlimab), MSB-2311, JTX-4014, BGB-A333, SHR-1316, CS-1001 (WBP-3155, KN-035, IBI-308 (sintilimab), HLX-20, KL-A167, STI-A1014, STI-A1015 (IMC-001), BCD-135, FAZ-053, TQB-2450, MDX1105-01, FPT-155 (CTLA4/PD-L1/CD28), PF-06936308 (PD-1/CTLA4), MGD-013 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/TIM-3), XmAb-20717 (PD-1/CTLA4), AK-104 (CTLA4/PD-1), M7824 (PD-L1/TGFβ-EC domain), CA-170 (PD-L1/

VISTA), CDX-527 (CD27/PD-L1), LY-3415244 (TIM3/PDL1), and INBRX-105 (4-1BB/PDL1). In some embodiments, the methods entail co-administering one or more small molecule inhibitors of CD274 (PDL1, PD-L1), programmed cell death 1 (PDCD1, PD1, PD-1) or CTLA4. In some embodiments, the methods entail co-administering one or more small molecule inhibitors of CD274 or PDCD1 selected from GS-4224, GS-4416, INCB086550 and MAX10181. In some embodiments, the methods entail co-administering BPI-002 (a small molecule inhibitor of CTLA4). In some embodiments, the methods comprise co-administering to the subject one or more antiviral agents. In some embodiments, the methods comprise co-administering one or more antiviral agents selected from lamivudine (LAM), adefovir dipivoxil (ADV), entecavir (ETV), telbivudine (LdT), tenofovir disoproxil fumarate (TDF), tenofovir alafenamide (TAF or VEMLIDY®) and ledipasvir+sofosbuvir (HARVONI®). In some embodiments, the methods comprise co-administering to the subject one or more therapeutic agents selected from HBV antigen inhibitors (e.g., HBV core antigen (HBcAg) inhibitors, HBV surface antigen (HBsAg) inhibitors, HBx inhibitors, HBV E antigen inhibitors), anti-HBV antigen antibodies, inhibitory nucleic acids targeting HBV (e.g., antisense oligonucleotide, short interfering RNA (siRNA), DNA-directed RNA interference (ddRNAi)), gene editors targeting HBV (e.g., CRISPR-Cas (e.g., Cas9, Cas12, Cascade, Cas13), zinc finger nucleases, homing endonucleases, homing meganucleases (e.g., ARCUS), synthetic nucleases, TALENs), covalently closed circular DNA (cccDNA) inhibitors and HBsAg secretion or assembly inhibitors and HBV viral entry inhibitors. In some embodiments, the method activates in the subject CD8+ T cells and/or CD4+ T cells targeting one or more HBV polypeptide epitopes. In some embodiments, the method elicits in the subject production of antibodies that bind one or more HBV polypeptides.

BRIEF DESCRIPTION OF THE DRAWINGS

FIGS. 4A-4B illustrate the immunogenicity of Core-Pol fusion protein-expressing adenovirus vectors in DO mice. Five- to seven-week-old DO mice (n=8 per group) were injected intramuscularly with $1\times10^8$ viral particles (vp) of adenovirus encoding GT-A core-Pol$^{Δ3}$ or GT-B, C, or D core-Pol$^{Δ1}$. On day 14 after injection, splenocytes were harvested and T cell responses evaluated by IFN-γ ELISPOT (BD mouse IFN-γ ELISPOT kit, catalog #551083) responses to overlapping peptide pools corresponding to GT-A and D core and Pol. Statistical comparisons between responses to peptides of different genotypes within mice receiving the same vaccine were assessed with Wilcoxon signed-rank tests. Statistical comparisons between mice receiving different vaccines were assessed with Mann-Whitney tests. (A) Responses to Pol peptides. (B) Responses to Core peptides. SFU, spot forming units.

FIGS. 9A-9C illustrate an overview of the arenavirus vector platforms demonstrated in the examples provided herein. (A) Schematic of a phylogenetic tree of the arenavirus family (Arenaviridae). In the examples provided herein, Lymphocytic choriomeningitis mammarenavirus (LCMV) (NCBI:txid11623) from the Old World (OW) clade and Cali mammarenavirus (a.k.a., Pichinde mammarenavirus or Pichinde arenavirus (PICV)) (NCBI:txid2169993) from the New World (NW) clade were selected for generation of HBV antigen encoding vectors. See, e.g., Buchmeier et al., 2001, "Arenaviridae: The Viruses and Their Replication," Fields Virology Vol 2, 1635-1668. Arenavirus taxonomy is more recently reviewed in, e.g., Radoshitzky, et al., *Arch Virol.* (2015) 160(7):1851-74. Phylogenetic information for Arenaviridae is also available at the Virus Pathogen Resource website, located at viprbrc.org. (B) Schematic of replication-defective arenavirus vectors having a bi-segmented genome, described in WO2009083210, and (C) replication-attenuated arenavirus vectors having a tri-segmented genome, described in WO2016075250 and WO2017198726. Replication-defective arenavirus vectors having a bi-segmented genome, described in WO2009083210 and used in the examples provided herein, encode three of the four viral proteins (L, Z and NP) and an open reading frame for insertion of a heterologous polynucleotide, e.g., encoding an antigen. The replication-defective arenavirus vectors having a bi-segmented genome can only propagate when viral GP is delivered in trans. Replication-attenuated arenavirus vectors having a tri-segmented genome, described in WO2016075250 and WO2017198726, have an artificial duplication of the genomic S-segment, encode all four viral proteins (L, Z, NP & GP) and have two open reading frames for insertion of one or two heterologous polynucleotides, e.g., encoding one or two antigens.

Figure 1:
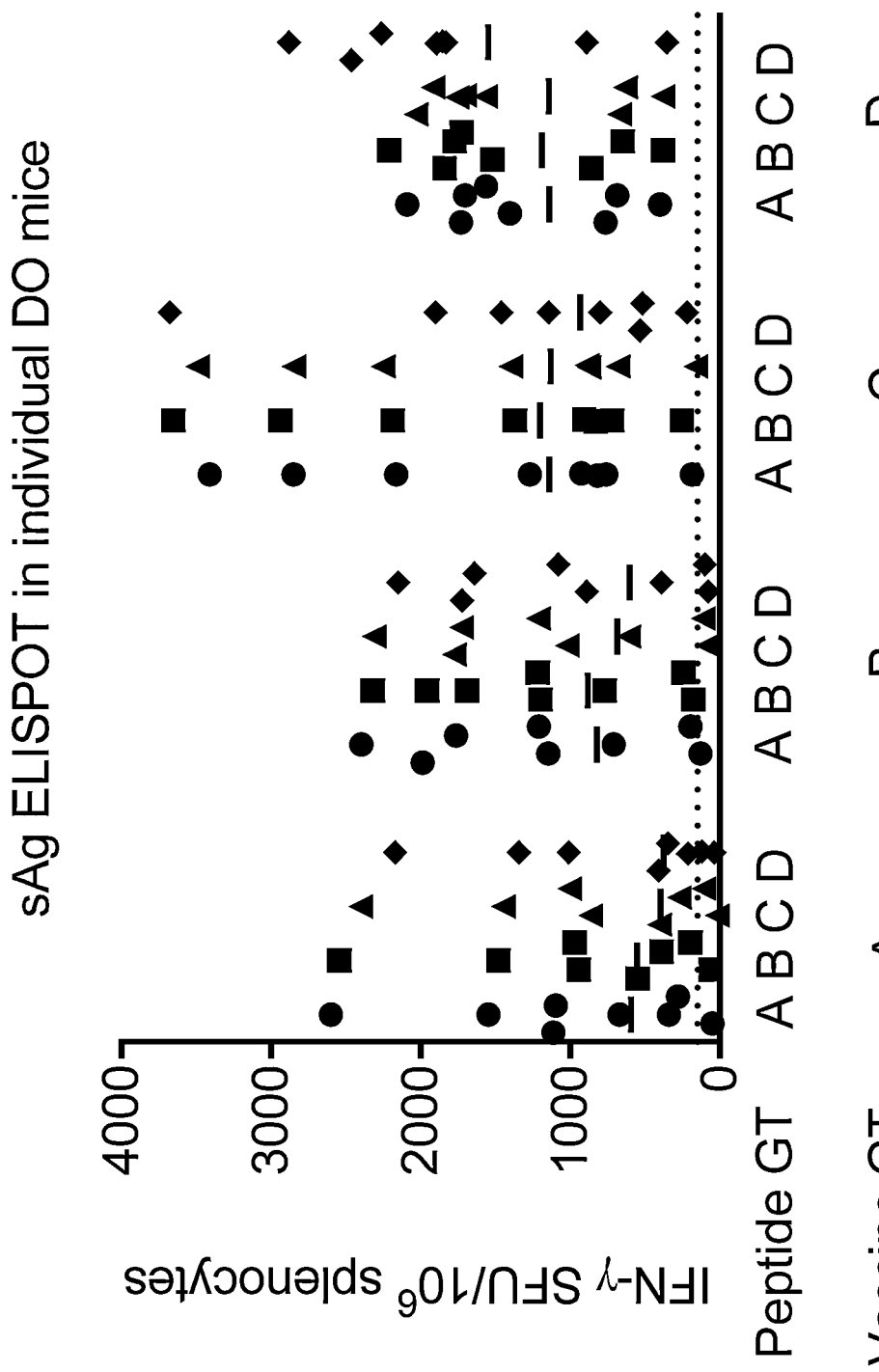
FIG. 1 illustrates the immunogenicity of HBsAg-expressing adenovirus vectors from genotypes (GT) A, B, C and D in DO mice. Five- to seven-week-old Diversity Outbred (DO) mice (n=8 per group) were injected intramuscularly with $1\times10^8$ viral particles (vp) of adenovirus encoding HBsAg consensus sequences of HBV genotypes (GT)-A, B, C, D (SEQ ID NOs: 1-4, respectively). On day 14 after injection, splenocytes were harvested and T cell responses were evaluated by interferon (IFN)-γ ELISPOT (BD mouse IFN-γ ELISPOT kit, catalog #551083). Each symbol corresponds to an individual mouse which was assessed for responses to overlapping peptide pools corresponding to GT-A, B, C, and D HBsAg.

ELISPOT values obtained after stimulation with sAg, core and polymerase peptide pools.

FIGS. 18A-18F illustrate the immunogenicity of repeat vaccinations with replication-incompetent LCMV vectors encoding GT-D iCore-P2A-sAg and GT-B Pol$^{300}$ in cynomolgus macaques as described in FIG. 17 and Table 11. FIGS. 18A-18F focus on IFN-γ ELISPOT obtained after stimulation with core peptide pools. 18A: Group 1; 18B: Group 2; 18C: Group 3; 18D; Group 4; 18E: Group 5; 18F: Group 6.

FIGS. 19A-19F illustrate the immunogenicity of repeat vaccinations with replication-incompetent LCMV vectors encoding GT-D iCore-P2A-sAg and GT-B Pol$^{300}$ in cynomolgus macaques as described in FIG. 17 and Table 11. FIGS. 19A-19F focus on IFN-γ ELISPOT obtained after stimulation with sAg peptide pools. 19A: Group 1; 19B: Group 2; 19C: Group 3; 19D; Group 4; 19E: Group 5; 19F: Group 6.

FIGS. 20A-20F illustrate the immunogenicity of repeat vaccinations with replication-incompetent LCMV vectors encoding GT-D iCore-P2A-sAg and GT-B Pol300 in cynomolgus macaques as described in FIG. 17 and Table 11. FIGS. 20A-20F focus on IFN-γ ELISPOT obtained after stimulation with Pol peptide pools. 20A: Group 1; 20B: Group 2; 20C: Group 3; 20D; Group 4; 20E: Group 5; 20F: Group 6.

FIGS. 21A-21B illustrate the frequency of peripheral HBV-specific IFN-γ CD8+ T cells (A) and CD4+ T cells (B) at week 14 cynomolgus macaques from group 1, 2 and 6 as described in Table 11. Data are obtained from PBMCs harvested at week 14 and re-stimulated with HBV sAg, core and polymerase peptide pools. CD4+ and CD8+T subsets were then analyzed for intracellular IFN-γ by flow cytometry.

FIGS. 22A-22C illustrate the antibody response to HBsAg in cynomolgus macaques from group 1 (22A), group 2 (22B) and group 6 (22C) as described in Table 11. Serum samples were collected at the indicated timepoints and quantified for anti-HBsAg antibody by ELISA. Dashed line indicates the lower limit of quantitation of the assay (5 mIU/mL).

FIG. 23 illustrates the study design assessing the immunogenicity of replication-incompetent LCMV vectors encoding GT-D iCore-P2A-sAg and GT-B Pol$^{300}$ (HBV vaccine) alone or in combination with the immunomodulators anti-PD1, anti-CTLA4, anti-CD137 and FLT3L-Fc fusion in the AAV-HBV mouse model. Six- to ten-week-old C57BL/6 mice were transduced with $10^{11}$ genome copies of AAV-HBV on day −35. Mice were randomized to treatment groups based on serum HBsAg levels at day −11. Replication-incompetent LCMV vectors encoding GT-D iCore-P2A-sAg and GT-B Pol300 were administered intravenously (i.v.) in 200 μl on day 0, day 21 and day 42. Mice were given intraperitoneally 200 μl of i) saline solution at day 0, 7, 14, 21, 28, 35, 42, 49 and 56; ii) anti-PD-1 monoclonal antibody RMP1-14 at day 42, 46, 49, 53, 56 and 60; iii) anti-CTLA-4 monoclonal antibody clone 9D9 at day 0, 4, 7, 11, 14, 18, 21, 25, 28, 32, 35, 39, 42, 46, 49 and 53; iv) anti-CD137 monoclonal antibody clone mAb8 (IgG2b) at day 0, 21 and 42; v) FLT3L-Fc fusion protein at day −7, 14 and 35. Asterisks depict doses of each immunomodulator. Splenocytes were harvested on day 105 and assessed for IFN-γ ELISPOT using sAg, core and Pol peptide pools. A group of C57BL/6 mice that did not receive the AAV-HBV but was administrated the replication-incompetent LCMV vectors alone was used as a positive control for IFN-γ ELISPOT.

FIGS. 24A-24C illustrates the immunogenicity of repeat vaccinations with replication-incompetent LCMV vectors encoding GT-D iCore-P2A-sAg and GT-B Pol300 in AAV-HBV mice as described in Table 12 and FIG. 23. Splenocytes were harvested on day 105 and assessed for IFN-γ ELISPOT using sAg (24A), core (24B) and polymerase (24C) peptide pools. Statistical analyses were performed with Mann-Whitney tests. ns: not statistically significant; *p<0.0332, p<0.0021, *p<0.0002, ****p<0.0001.

FIG. 25 illustrates the immunogenicity of prime-boost vaccination with replication-incompetent PICV (VV2) vectors encoding GT-B Pol$^{300}$ ori or GT-B Pol$^{300}$ dint in C57BL/6 mice. Animals were administered with 2 doses of vaccine at day 0 and day 21. Splenocytes were harvested at day 28 and HBV Polymerase-specific T cell responses were measured by IFN-γ ELISPOT using Pol peptide pools. Data are expressed as background (no peptide)-subtracted values. Statistical analyses were performed with Mann-Whitney tests. **p<0.0021.

FIGS. 26A-26C illustrate the immunogenicity of homologous and heterologous prime/boost vaccination with replication-incompetent LCMV (VV1) and PICV (VV2) vectors encoding GT-D iCore-P2A-sAg or GT-B Pol$^{300}$ in C57BL/6 mice. Animals were administered with 2 doses of vector at day 0 and day 21 as described in Table 15. Splenocytes were harvested at day 28 and HBV-specific T cell responses were measured by IFN-γ ELISPOT using sAg (26A), core (26B) and polymerase (26C) peptide pools. Data are expressed as background (no peptide)-subtracted values.

FIG. 27 illustrates the antibody response to HBsAg in C57BL/6 mice administered with replication-incompetent LCMV and PICV vectors encoding GT-D iCore-P2A-sAg using homologous (VV1/VV1) or heterologous (VV2/VV1) prime/boost vaccination at day 0 and day 21. Serum samples were collected at day 28 and quantified for anti-HBsAg antibody by ELISA. Dashed line indicates the lower limit of quantitation of the assay (20 mIU/mL). Statistical analyses were performed with Mann-Whitney tests. **p<0.0021.

FIGS. 28A-28C illustrate the immunogenicity of homologous and heterologous prime/boost vaccination with replication-attenuated LCMV (TT1) and PICV (TT2) vectors encoding GT-D core-P2A-sAg and GT-B Pol300 in C57BL/6 mice. Animals were administered with 2 doses of the vectors at day 0 and day 21 as described in Table 16. Splenocytes were harvested at day 28 and HBV-specific T cell responses were measured by IFN-γ ELISPOT using sAg (28A), core (28B) and polymerase (28C) peptide pools.

FIG. 29 illustrates the immunogenicity of homologous and heterologous prime/boost vaccination with replication-deficient LCMV (VV1) and PICV (VV2) vectors encoding GT-D core-P2A-sAg and GT-B Pol$^{300}$ in cynomolgus macaques. Animals were administered with 2 doses of the vectors, one at week 0 and one at week 4. PBMCs were harvested at week 6 and HBV-specific T cell responses were measured by IFN-γ ELISPOT using sAg, core and polymerase peptide pools. Data are expressed at total HBV-specific T cell responses defined as the sum of IFN-γ ELISPOT values obtained after stimulation with sAg, core and polymerase peptide pools. The lower limit of quantitation (LLOQ) ELISPOT (dashed line) was defined as 200 IFN-γ+ SFU/$10^6$ PBMC. Statistical analysis was performed with Mann-Whitney test.

FIG. 30 illustrates the immunogenicity of homologous and heterologous prime/boost vaccination with replication-deficient LCMV (VV1) and PICV (VV2) vectors encoding GT-D core-P2A-sAg and GT-B Pol$^{300}$ administered every week in cynomolgus macaques. Animals were administered 4 doses of the vectors at week 0, 1, 2 and 3. PBMCs were harvested at week 4 and HBV-specific T cell responses were measured by IFN-γ ELISPOT using sAg, core and polymerase peptide pools. Data are expressed at total HBV-specific T cell responses defined as the sum of IFN-γ ELISPOT values obtained after stimulation with sAg, core and polymerase peptide pools. The lower limit of quantitation (LLOQ) ELISPOT (dashed line) was defined as 200 IFN-γ+ SFU/$10^6$ PBMC.

DETAILED DESCRIPTION

1. Introduction

Provided are polypeptides useful to elicit a protective immune response against one or more hepatitis B virus (HBV) antigens in a human. The immunogenic polypeptides described herein are capable of eliciting preventative and/or therapeutic immune responses in a human against one or more hepatitis B virus (HBV) antigens. Generally, the immunogenic polypeptides described herein contain highly conserved portions of HBV proteins in order to induce responses against epitopes that are identical in the vaccine antigen and in the infecting HBV present in the patient, while also excluding poorly conserved regions, thereby avoiding eliciting immunodominant T cell responses targeting epitopes that are not present in the patient's infecting HBV strain. The herein described immunogenic polypeptides furthermore induce both CD4+ and CD8+ T cell responses to facilitate infected cell elimination, and additionally anti-sAg antibody responses that facilitate sAg clearance, thereby reducing or eliminating spread of residual virus if sterilizing viral clearance is not completely achieved. Moreover, the herein described immunogenic polypeptides are demonstrated to be immunogenic when delivered using vaccine technologies capable of inducing the desired responses in humans, and stable in the delivery vectors through sufficient rounds of vector replication to enable commercial-scale vaccine manufacture. The immunogenic polypeptides can be used in various vector systems known to induce CD4+ and CD8+ T cell, and antibody responses in humans and other non-human primates. In certain embodiments, the immunogenic polypeptides are expressed from arenavirus vectors that can be repeatedly dosed without inducing anti-vector antibodies, thereby overcoming a limitation of many previous viral vector technologies and providing the possibility of enhancing therapeutic benefit with repeated dosing.

2. Polypeptides Useful to Promote Immune Response Against Hepatitis B Virus (HBV)

Provided are immunogenic polypeptides useful to promote, induce and/or elicit an immunogenic response against one or more hepatitis B virus (HBV) antigens. In various embodiments, the immunogenic polypeptides comprise variants and/or fragments of polypeptides encoded by an HBV polymerase (Pol) gene and fusion polypeptides having in sequential order, from the N-terminus to the C-terminus, a variant and/or fragment of a polypeptide encoded by an HBV core gene and a variant and/or fragment of a polypeptide encoded by the surface antigen (sAg) gene. The immunogenic polypeptides can contain amino acid sequences based on consensus or near-consensus sequences from HBV A, B, C or D genotypes, and combinations thereof. Generally, the immunogenic polypeptides described herein do not comprise sequences of HBV X protein (HBx), pre-core, pre-S1, pre-S2, or fragments thereof.

In various embodiments, immunogenic polypeptides described herein, and/or the polynucleotides encoding such polypeptides, are provided in isolated form. This means that such the polypeptide or polynucleotide is at least 50% w/w pure of interfering proteins, cellular and other contaminants arising from its production or purification but does not exclude the possibility that the agent is combined with an excess of pharmaceutical acceptable carrier(s) or other vehicle intended to facilitate its use. The term "isolated," when applied to a polypeptide or polynucleotide, as described herein, denotes that the polypeptide or polynucleotide is essentially free of cellular components with which it is associated in the natural state. It can be, for example, in a homogeneous state and may be in either a dry or aqueous solution. Purity and homogeneity can be determined using known methods, e.g., analytical chemistry techniques such as polyacrylamide gel electrophoresis, column chromatography, thin layer chromatography, or high-performance liquid chromatography (HPLC) analysis. A protein that is the predominant species present in a preparation is substantially purified. An "isolated" or "purified" polypeptide or polynucleotide is substantially free of other cellular material, or culture medium when produced by recombinant techniques, or chemical precursors or other chemicals when chemically synthesized. In various embodiments, purified polypeptides and/or polynucleotides are at least 60%, 70%, 75%, 80%, 85%, 90%, 91%, 92%, 93%, 94%, 95%, 96%, 97%, 98%, 99%, or 100% (w/w), separated from, purified of, or free of interfering proteins and contaminants from production or purification. Often an agent is the predominant macromolecular species remaining after its purification.

HBV Polymerase Polypeptide Variants

In various embodiments, provided are truncated and/or internal deletion mutant hepatitis B virus (HBV) polymerase polypeptides.

Wild-type HBV polymerase has four domains, arranged in tandem in a single polypeptide from N-terminus to C-terminus: the terminal protein (TP) domain conserved across the hepadnaviridae (amino acid residues 1 to 177), the Spacer region (amino acid residues 178 to 335), linking TP to the reverse transcriptase (RT) domain (amino acid residues 336 to 678; comprising NCBI conserved domain pfam00078 or cd01645) and the C-terminal RNase H (RH) domain (amino acid residues 679 to 832). See, e.g., Lanford, et al., *J. Virol.* (1999) 73(3): 1885-93; V6r6s, et al., *J Virol.* (2014) 88(5):2584-99 and Jones, et al., *J Virol.* (2014) 88(3):1564-72. In the HBV polymerase variants described herein, all or part of the Spacer region has been deleted or removed. In the HBV polymerase truncation mutants, the entire TP domain has been deleted or removed.

Generally, the enzymatic domains, i.e., the reverse transcriptase and RNase H domains, are inactivated in the HBV polymerase protein mutants described herein. In various embodiments, the reverse transcriptase domain does not comprise a YMDD motif (SEQ ID NO: 97). In some embodiments, the YMDD motif (SEQ ID NO: 97) in the reverse transcriptase domain is changed to YMHD (SEQ ID NO: 99). In some embodiments, the RNase H domain does not comprise an AELL motif (SEQ ID NO: 98). In some embodiments, the AELL motif (SEQ ID NO: 98) in the RNase H domain is changed to AHLL (SEQ ID NO: 100).

Truncated Polymerase Mutants

In some embodiments, the truncated HBV polymerase polypeptides comprise an inactivated reverse transcriptase domain and an inactivated RNase H, wherein the polypeptide does not comprise all of the terminal protein (TP) domain and does not comprise all or part of the Spacer domain (i.e., the terminal protein (TP) domain and all or part of the Spacer domain is removed, excised or excluded). In the truncated HBV polymerase polypeptides described herein, all of the TP domain and all or part of the Spacer domain or region is deleted or removed. For example, in some embodiments, the N-terminal 300 amino acids of a native or wild-type HBV polymerase are deleted or removed from the truncated HBV polymerase polypeptides described herein. In various embodiments, the inactivated reverse transcriptase domain and the inactivated RNase H can be directly fused or operably linked or connected via a linker, as described herein. In some embodiments, the truncated HBV polymerase polypeptide is no longer than 600 amino acids in length, e.g., no longer than 595, 590, 585, 580, 575, 570, 565, 560, 555, 550, 545, 540 or 535 amino acids in length. In some embodiments, the truncated HBV polymerase polypeptides comprise the C-terminal 528, 529, 530, 531, 532, 533, 534 or 535 amino acids of a native or wild-type HBV polymerase.

In some embodiments, the truncated HBV polymerase polypeptides comprise an amino acid sequence corresponding to amino acid residues 300-832, 301-832, 302-832, 303-832, 304-832, 305-832, 306-832, 307-832, 308-832, 309-832, 310-832, 311-832, 312-832, 313-832, 314-832, 315-832, 316-832, 317-832, 318-832, 319-832, 320-832, 325-832, 326-832, 327-832, 328-832, 329-832, 330-832, 331-832, 332-832, 333-832, 334-832, 335-832 or 336-832 of a native or wild-type HBV polymerase. As used herein, numbering of a given amino acid polymer or nucleic acid polymer "corresponds to", is "corresponding to" or is "relative to" the numbering of a selected or reference amino acid polymer or nucleic acid polymer when the position of any given polymer component (e.g., amino acid, nucleotide, also referred to generically as a "residue") is designated by reference to the same or to an equivalent position (e.g., based on an optimal alignment or a consensus sequence) in the selected amino acid or nucleic acid polymer, rather than by the actual numerical position of the component in the given polymer. In various embodiments, the truncated HBV polymerase polypeptides comprise an amino acid sequence corresponding to amino acid residues 300-832. In such embodiments, the N-terminus corresponds to amino acid position 300 of the prototype genotype D pol protein. The N-terminal 6 amino acid residues of this sequence is SARSQS (SEQ ID NO: 95) in the genotype D Pol antigen, and SSRSQS (SEQ ID NO: 96) in the genotype B Pol antigen. Literature reports have indicated that this N-terminal start site allows for function of the RT domain (see, e.g., Lanford, et al., supra) and expression of the truncated protein in vitro (see, e.g., Vörös, et al., supra).

In some embodiments, the truncated HBV polymerase polypeptide is from HBV genotype B and comprises or consists of an amino acid sequence of SEQ ID NO: 13, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 13. In some embodiments, the truncated HBV polymerase polypeptide is from HBV genotype B and does not comprise a polypeptide sequence (i.e., the sequence is excluded, excised or removed; the sequence is not included) of SEQ ID NO: 50, or a sequence that is at least 90%, 91%, 92%, 93%, 94%, 95%, 96%, 97%, 98% or 99% identical to any one of SEQ ID NO: 50.

In some embodiments, the truncated HBV polymerase polypeptide is from HBV genotype D and comprises or consists of an amino acid sequence of SEQ ID NO: 14, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 14. In some embodiments, the truncated HBV polymerase polypeptide is from HBV genotype D and does not comprise a polypeptide sequence of SEQ ID NO: 51, or a sequence that is at least 90%, 91%, 92%, 93%, 94%, 95%, 96%, 97%, 98% or 99% identical to any one of SEQ ID NO: 51.

Modifications may be made in the structure of the polypeptides and polynucleotides encoding such polypeptides, described herein, and still obtain a functional molecule that encodes a variant or derivative polypeptide with desirable (e.g., immunogenic) characteristics. When it is desired to alter the amino acid sequence of a polypeptide to create an equivalent, or even an improved, variant or portion of a polypeptide described herein, one skilled in the art will typically change one or more of the codons of the encoding DNA sequence.

For example, certain amino acids may be substituted for other amino acids in a protein structure without appreciable loss of its ability to bind other polypeptides (e.g., antigens) or cells. Since it is the binding capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the polypeptide sequences of the disclosed polypeptides, or corresponding DNA sequences that encode such polypeptides without appreciable loss of their biological utility or activity.

A "substitution," as used herein, denotes the replacement of one or more amino acids or nucleotides by different amino acids or nucleotides, respectively.

In many instances, a polypeptide variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged.

As used herein, "identity" means the percentage of identical nucleotide or amino acid residues at corresponding positions in two or more sequences when the sequences are aligned to maximize sequence matching, i.e., taking into account gaps and insertions. Sequences are generally aligned for maximum correspondence over a designated region, e.g., a region at least 20, 25, 30, 35, 40, 45, 50, 55, 60, 65 or more amino acids or nucleotides in length, and can be up to the full length of the reference polypeptide or polynucleotide sequence. For sequence comparison, typically one sequence acts as a reference sequence, to which test sequences are compared. When using a sequence comparison algorithm, test and reference sequences are input into a computer program, subsequence coordinates are designated, if necessary, and sequence algorithm program parameters are designated. Otherwise, standard parameters can be used. The sequence comparison algorithm then calculates the percent sequence identity for the test sequence (s) relative to the reference sequence, based on the designated program parameters.

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, or over the full length of a sequence, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, WI), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington DC Vol. 5, Suppl. 3, pp. 345-358; Hein J. (1990) Unified Approach to Alignment and Phylogenes pp. 626-645 Methods in Enzymology vol. 183, Academic Press, Inc., San Diego, CA; Higgins, D. G. and Sharp, P. M. (1989) CABIOS 5: 151-153; Myers, E. W. and Muller W. (1988) CABIOS 4:11-17; Robinson, E. D. (1971) Comb. Theor 77: 105; Santou, N. Nes, M. (1987) Mol. Biol. Evol. 4:406-425; Sneath, P. H. A. and Sokal, R. R. (1973) Numerical Taxonomy—the Principles and Practice of Numerical Taxonomy, Freeman Press, San Francisco, CA; Wilbur, W. J. and Lipman, D. J. (1983) Proc. Natl. Acad., Sci. USA 80:726-730.

Alternatively, optimal alignment of sequences for comparison may be conducted by the local identity algorithm of Smith and Waterman (1981) Add. APL. Math 2:482, by the identity alignment algorithm of Needleman and Wunsch (1970) J. Mol. Biol. 48:443, by the search for similarity methods of Pearson and Lipman (1988) Proc. Natl. Acad. Sci. USA 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, WI), or by inspection.

One example of algorithms that are suitable for determining percent sequence identity and sequence similarity are the BLAST and BLAST 2.0 algorithms, which are described in Altschul et al. (1977) Nucl. Acids Res. 25:3389-3402 and Altschul et al. (1990) J. Mol. Biol. 215:403-410, respectively. BLAST and BLAST 2.0 can be used, for example with the parameters described herein, to determine percent sequence identity for the polynucleotides and polypeptides described herein. Software for performing BLAST analyses is publicly available through the National Center for Biotechnology Information (blast.ncbi.nlm.nih.gov/Blast.cgi).

In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a word length (W) of 11, and expectation (E) of 10, and the BLOSUM62 scoring matrix (see Henikoff and Henikoff (1989) Proc. Natl. Acad. Sci. USA 89: 10915) alignments, (B) of 50, expectation (E) of 10, M=5, N=-4 and a comparison of both strands.

For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one approach, the "percentage of sequence identity" is determined by comparing two optimally aligned sequences over a window of comparison of at least 20 positions, e.g., at least 50 positions, at least 100 positions, or over the full length of a reference sequence, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

A "polypeptide variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences described herein and evaluating one or more biological activities of the polypeptide as described herein and/or using any of a number of techniques well known in the art. The term "variant" may also refer to any naturally occurring or engineered molecule comprising one or more nucleotide or amino acid mutations.

Illustrative HBV polymerase truncation mutants for use in promoting, inducing or eliciting an immunogenic response, e.g., against a polymerase antigen expressed by HBV, are provided in Table A. Illustrative N-terminal sequence segments deleted or removed from, and therefore not contained in, the HBV polymerase truncation mutants described herein are provided in Table B.

TABLE A

Pol$^{300}$ mutants - Motifs containing inactivating mutations are underlined (YMDD mutated to YMHD, AELL mutated to AHLL).

| SEQ ID NO: | HBV genotype | Length (# amino acids) | Polypeptide sequence |
|---|---|---|---|
| 13 | B | 534 | MSSRSQSQGPVLSCWWLQFRNSEPCSEYCLCHIVNLIEDWGPCTE HGEHRIRTPRTPARVTGGVFLVDKNPHNTTESRLVVDFSQFSRGN TRVSWPKFAVPNLQSLTNLLSSNLSWLSLDVSAAFYHLPLHPAAM PHLLVGSSGLSRYVARLSSNSRIINNQHRTMQNLHDSCSRNLYVS LMLLYKTYGRKLHLYSHPIILGFRKIPMGVGLSPFLLAQFTSAIC SVVRRAFPHCLAFSYMHDVVLGAKSVQHLESLYAAVTNFLLSLGI HLNPHKTKRWGYSLNFMGYVIGSWGTLPQEHIVQKIKMCFRKLPV NRPIDWKVCQRIVGLLGFAAPFTQCGYPALMPLYACIQAKQAFTF SPTYKAFLSKQYLHLYPVARQRPGLCQVFADATPTGWGLAIGHQR MRGAFVSPLPIHTAHLLAACFARSRSGAKLIGTDNSVVLSRKYTS FPWLLGCAANWILRGTSFVYVPSALNPADDPSRGRLGLYRPLLRL LYRPTTGRTSLYADSPSVPSHLPDRVHFASPLHVAWRPP |

TABLE A-continued

Pol300 mutants - Motifs containing inactivating mutations are underlined (YMDD mutated to YMHD, AELL mutated to AHLL).

| SEQ ID NO: | HBV geno-type | Length (# amino acids) | Polypeptide sequence |
|---|---|---|---|
| 14 | D | 534 | MSARSQSERPVFPCWWLQFRNSKPCSDYCLSHIVNLLEDWGPCAE HGEHHIRIPRTPARVTGGVFLVDKNPHNTAESRLVVDFSQFSRGN YRVSWPKFAVPNLQSLTNLLSSNLSWLSLDVSAAFYHLPLHPAAM PHLLVGSSGLSRYVARLSSNSRIFNYQHGTMQNLHDSCSRNLYVS LMLLYQTFGRKLHLYSHPIILGFRKIPMGVGLSPFLLAQFTSAIC SVVRRAFPHCLAFS<u>YMHD</u>VVLGAKSVQHLESLFTAVTNFLLSLGI HLNPNKTKRWGYSL<u>HF</u>MGYVIGCYGSLPQDHIIQKIKECFRKLPV NRPIDWKVCQRIVGLLGFAAPFTQCGYPALMPLYACIQSKQAFTF SPTYKAFLCKQYLNLYPVARQRPGLCQVFADATPTGWGLVMGHQR MRGTFKAPLPIHT<u>AHLL</u>AACFARSRSGANILGTDNSVVLSRKYTS FPWLLGCAANWIL<u>RGTS</u>FVYVPSALNPADDPSRGRLGLYRPLLRL PFRPTTGRTSLYADSPSVPSHLPDRVHFASPLHVAWRPP |

TABLE B

N-terminal polypeptide sequence removed from Pol300 truncated mutants

| SEQ ID NO: | HBV geno-type | Polypeptide sequence |
|---|---|---|
| 50 | B | PLSYQHFRKLLLLDDEAGPLEEELPRLADEGLNRRVAEDLNLGNLNVSIPWTHKV GNFTGLYSSTVPVFNPEWQTPSFPHIHLQEDIINRCQQYVGPLTVNEKRRLKLIM PARFYPNLTKYLPLDKGIKPYYPEHVVNHYFQTRHYLHTLWKAGILYKRESTRSA SFCGSPYSWEQDLQHGRLVFQTSKRHGDKSFCPQSPGILPRSSVGPCIQNQLRKS RLGPQPAQGQLAGRQQGGSGSIRARVHPSPWGTVGVEPSGSGHIHNCASNSSSCL HQSAVRKAAYSHISTSKGHSSSGHAVELHHFPPS |
| 51 | D | PLSYQHFRRLLLLDDEAGPLEEELPRLADEGLNRRVAEDLNLGNLNVSIPWTHKV GNFTGLYSSTVPVFNPHWKTPSFPNIHLHQDIIKKCEQFVGPLTVNEKRRLQLIM PARFYPNVTKYLPLDKGIKPYYPEHLVNHYFQTRHYLHTLWKAGILYKRETTHSA SFCGSPYSWEQELQHGAESFHQQSSGILSRPPVGSSLQSKHRKSRLGLQSQQGHL ARRQQGRGWSIRAGIHPTARRPFGVEPSGSGHTANLASKSASCLYQSAVRKAAYP VVSTFKKHSSSGHAVELHNLPPN |

In some embodiments, the truncated polymerase polypeptide does not comprise an amino sequence or fragment thereof from another HBV protein. In some embodiments, truncated HBV polymerase polypeptide does not comprise an amino sequence or fragment thereof from an HBV protein selected from the group consisting of pre-core, core, X and envelope (e.g., small, medium or large surface antigen (sAg)).

Internal Deletion Polymerase Mutants

Further provided are HBV polymerase internal deletion mutant polypeptides. In various embodiments, the HBV polymerase internal deletion mutant polypeptides comprise in sequential order, from the N-terminus to C-terminus, a terminal protein (TP) domain, an inactivated reverse transcriptase domain, an inactivated RNase H, wherein the mutant polypeptide does not comprise all or part of a Spacer domain (i.e., all or part of the Spacer domain or region is deleted or removed). In various embodiments, the HBV polymerase deletion mutant polypeptide is no longer than 800 amino acids in length, e.g., no longer than 795, 790, 785, 780, 775, 770, 765, 760, 755, 750, 745, 740, 735, 730, 725, 720, 715, 710 or 705 amino acids in length. In some embodiments, the HBV polymerase internal deletion mutant polypeptides comprise in sequential order, from the N-terminus to C-terminus, a terminal protein (TP) domain, and an amino acid sequence corresponding to amino acid residues 300-832, 301-832, 302-832, 303-832, 304-832, 305-832, 306-832, 307-832, 308-832, 309-832, 310-832, 311-832, 312-832, 313-832, 314-832, 315-832, 316-832, 317-832, 318-832, 319-832, 320-832, 325-832, 326-832, 327-832, 328-832, 329-832, 330-832, 331-832, 332-832, 333-832, 334-832, 335-832 or 336-832 of a native or wild-type HBV polymerase. In various embodiments, the terminal protein (TP) domain, the inactivated reverse transcriptase domain, and the inactivated RNase H independently can be directly fused or operably linked or connected via a linker, e.g., as described herein, e.g., as provided in Table J.

In some embodiments, the HBV polymerase internal deletion mutant polypeptide is from HBV genotype A and comprises or consists of an amino acid sequence of any one of SEQ ID NOs: 5 and 9, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 5 and 9. In some embodiments, the HBV polymerase internal deletion mutant polypeptide is from HBV genotype A and does not comprise a polypeptide of SEQ ID NO: 42 or 46, or a sequence that is at least 90%, 91%, 92%, 93%, 94%, 95%, 96%, 97%, 98% or 99% identical to any one of SEQ ID NO: 42 or 46.

In some embodiments, the HBV polymerase internal deletion mutant polypeptide is from HBV genotype B and comprises or consists of an amino acid sequence of any one of SEQ ID NOs: 6 and 10, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 6 and 10. In some embodiments, the HBV polymerase internal deletion mutant polypeptide is from HBV genotype B and does not comprise a polypeptide of SEQ ID NO: 43 or 47, or a sequence that is at least 90%, 91%, 92%, 93%, 94%, 95%, 96%, 97%, 98% or 99% identical to any one of SEQ ID NO: 43 or 47.

In some embodiments, the HBV polymerase internal deletion mutant polypeptide is from HBV genotype C and comprises or consists of an amino acid sequence of any one of SEQ ID NOs: 8 and 11, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 8 and 11. In some embodiments, the HBV polymerase internal deletion mutant polypeptide is from HBV genotype C and does not comprise a polypeptide of SEQ ID NO: 44 or 48, or a sequence that is at least 90%, 91%, 92%, 93%, 94%, 95%, 96%, 97%, 98% or 99% identical to any one of SEQ ID NO: 44 or 48.

In some embodiments, the HBV polymerase internal deletion mutant polypeptide is from HBV genotype D and comprises or consists of an amino acid sequence of any one of SEQ ID NOs: 9 and 12, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 9 and 12. In some embodiments, the HBV polymerase internal deletion mutant polypeptide is from HBV genotype D and does not comprise a polypeptide of SEQ ID NO: 45 or 49, or a sequence that is at least 90%, 91%, 92%, 93%, 94%, 95%, 96%, 97%, 98% or 99% identical to any one of SEQ ID NO: 45 or 49.

In some embodiments, the HBV polymerase internal deletion mutant polypeptide does not comprise an amino sequence or fragment thereof from another HBV protein. In some embodiments, HBV polymerase internal deletion mutant polypeptide does not comprise an amino sequence or fragment thereof from an HBV protein selected from the group consisting of pre-core, core, X and envelope (e.g., small, medium or large surface antigen (sAg)).

Illustrative HBV polymerase internal deletion mutants for use in promoting, inducing or eliciting an immunogenic response, e.g., against a polymerase antigen expressed by HBV, are provided in Tables C and E. Illustrative internal amino acid sequence segments deleted or removed from, and therefore not contained in, the HBV polymerase internal deletion mutants described herein, e.g., corresponding to all or part of an HBV polymerase Spacer region, are provided in Tables D and F.

Core-Polymerase Fusion Polypeptides

In various embodiments, the truncated and internal deletion HBV polymerase polypeptide variants described herein are fused to an HBV core polypeptide. The core polypeptide can be positioned either N-terminal or C-terminal to the HBV polymerase. Further provided are fusion polypeptides comprising in sequential order from the N-terminus to the C-terminus, an HBV core polypeptide and a truncated or internal deletion HBV polymerase polypeptide mutant, as described herein. In some embodiments, the core-Pol fusion polypeptide comprises the HBV polymerase deletion mutant polypeptide, described herein, comprises in sequential order from the N-terminus to the C-terminus, an HBV core polypeptide and an internal deletion HBV polymerase polypeptide mutant, as described herein.

In some embodiments, the core-Pol fusion polypeptide comprises or consists of an amino acid sequence of any one of SEQ ID NOs: 19-26, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 19-26.

In some embodiments, the HBV core-polymerase internal deletion mutant fusion protein does not comprise an amino sequence or fragment thereof from an HBV protein selected from the group consisting of X, pre-core, and envelope (e.g., small, medium or large surface antigen (sAg)).

Illustrative core-polymerase fusion proteins for use in promoting, inducing or eliciting an immunogenic response, e.g., against a core and/or polymerase antigen expressed by HBV, are provided in Table G.

TABLE C

Pol$^{AI}$ mutants: Motifs containing inactivating mutations are underlined (YMDD mutated to YMHD, AELL mutated to AHLL). Amino acids in bold + underline + italic mark the site of deletion (last amino acid prior to the deleted region, and the first amino acid after the deleted region).

| SEQ ID NO: | HBV geno- type | Length (# amino acids) | Polypeptide sequence |
|---|---|---|---|
| 5 | A | 755 | MPLSYQHFRKLLLLDDETEAGPLEEELPRLADEDLNRRVAEDLNLGNLNVSIPWTHKVGNFTGLYSSTVP IFNPEWQTPSFPKIHLHEDIANRCQQPVGPLTVNEKRRLRLIMPARFYPNSTKYLPLDKGIKPYYPDHVV NHYFQTRHYLHTLWKAGILYKRETTRSASFCGSPYSWEQELHHGRLVIKTSQRHGDEPPFCSQPSGILSRS SVGPE FHSFPPSSARSQSQGPVFSCWWLQFRNTQPCSKYCLSHLVNLLEDWGPCDEHGEHHIRIPRTPAR VTGGVFLVDKNPHNTAESRLVVDFSQFSRGITRVSWPKFAVPNLQSLTNLLSSNLSWLSLDVSAAFYHIP LHPAAMPHLLVGSSGLSRYVARLSSNSRIHNNQHGTLQNLHDSCSRQLYVSLMLLYKTYGRKLHLYSHPI ILGFRKIPMGVGLSPFLLAQFTSAICSVVRRAFPHCLAFSYMHDVVLGAKSVQHLESLYTAVTNFLLSLG IHLNPNKTKRWGYSLNFMGYVIGSWGTLPQDHIVQKIKHCFRKLPINRPIDWKVCQRIVGLLGFTWPFTQ CGYPALMPLYACIQAKQAFTFSPTYKAFLSKQYLNLYPVARQRPGLCQVFADATPTGWGLAIGHQRMRGT FVAPLPIHTAHLLAACFARSRSGAKLIGTDNSVVLSRKYTSFPWLLGCTANWILRGTSFVYVPSALNPAD DPSRGRLGLYRPLLRLPYRPTTGRTSLYAVSPSVPSHLPVRVHFASPLHVAWRPP |
| 6 | B | 749 | MPLSYQHFRKLLLLDDEAGPLEEELPRLADEGLNRRVAEDLNLGNLNVSIPWTHKVGNFTGLYSSTVPVF NPEWQTPSFPHIHLQEDIINRCQQYVGPLTVNEKRRLKLIMPARFYPNLTKYLPLDKGIKPYYPEHVVNH YFQTRHYLHTLWKAGILYKRESTRSASFCGSPYSWEQDLQHGRLVFQTSKRHGDKSFCPQSPGILPRSE L HHFPPSSSRSQSQGPVLSCWWLQFRNSEPCSEYCLCHIVNLIEDWGPCTEHGEHRIRTPRTPARVTGGVF LVDKNPHNTTESRLVVDFSQFSRGNTRVSWPKFAVPNLQSLTNLLSSNLSWLSLDVSAAFYHLPLHPAAM PHLLVGSSGLSRYVARLSSNSRIINNQHRTMQNLHDSCSRNLYVSLMLLYKTYGRKLHLYSHPIILGFRK IPMGVGLSPFLLAQFTSAICSVVRRAFPHCLAFSYMHDVVLGAKSVQHLESLYAAVTNFLLSLGIHLNPH KTKRWGYSLNFMGYVIGSWGTLPQEHIVQKIKMCFRKLPVNRPIDWKVCQRIVGLLGFAAPFTQCGYPAL MPLYACIQAKQAFTFSPTYKAFLSKQYLHLYPVARQRPGLCQVFADATPTGWGLAIGHQRMRGAFVSPLP IHTAHLLAACFARSRSGAKLIGTDNSVVLSRKYTSFPWLLGCAANWILRGTSFVYVPSALNPADDPSRGR LGLYRPLLRLLYRPTTGRTSLYADSPSVPSHLPDRVHFASPLHVAWRPP |
| 7 | C | 753 | MPLSYQHFRKLLLLDDEAGPLEEELPRLADEDLNRRVAEDLNLGNLNVSIPWTHKVGNFTGLYSSTVPVF NPEWQTPSFPHIHLQEDIINRCQQYVGPLTVNEKRRLKLIMPARFYPNLTKYLPLDKGIKPYYPEHVVNH YFKTRHYLHTLWKAGILYKRETTRSASFCGSPYSWEQELQHGRLVFQTSTRHGDESFCSQSSGILSRSPV |

TABLE C-continued

Pol$^{A1}$ mutants: Motifs containing inactivating mutations are underlined (YMDD mutated to YMHD, AELL mutated to AHLL). Amino acids in bold + underline + italic mark the site of deletion (last amino acid prior to the deleted region, and the first amino acid after the deleted region).

| SEQ ID NO: | HBV genotype | Length (# amino acids) | Polypeptide sequence |
|---|---|---|---|
| | | | G_PE_ LHNFPPSSARSQSEGPLLSCWWLQFRNSKPCSDYCLSHIVNLLEDWGPCTEHGEHNIRIPRTPARVT GGVFLVDKNPHNTTESRLVVDFSQFSRGSTHVSWPKFAVPNLQSLTNLLSSNLSWLSLDVSAAFYHLPLH PAAMPHLLVGSSGLSRYVARLSSTSRNINYQHGAMQDLHDSCSRNLYVSLLLLYKTFGRKLHLYSHPIIL GFRKIPMGVGLSPFLLAQFTSAICSVVRRAFPHCLAFS<u>YMHD</u>VVLGAKSVQHLESLFTAVTNFLLSLGIH LNPNKTKRWGYSLNFMGYVIGSWGTLPQEHIVLKIKQC<u>FRKL</u>PVNRPIDWKVCQRIVGLLGFAAPFTQCG YPALMPLYACIQAKQAFTFSPTYKAFLCKQYLNLYPVARQRSGLCQVFADATPTGWGLAVGHQRMRGTFV SPLPIHT<u>AHLL</u>AACFARSRSGAKLIGTDNSVVLSRKYTSFPWLLGCAANWILRGTSFVYVPSALNPADDP SRGRLGL<u>YRPL</u>LRLPFRPTTGRTSLYAVSPSVPSHLPVRVHFASPLHVAWRPP |
| 8 | D | 742 | MPLSYQHFRRLLLLLDDEAGPLEEELPRLADEGLNRRVAEDLNLGNLNVSIPWTHKVGNFTGLYSSTVPVF NPHWKTPSFPNIHLHQDIIKKCEQFVGPLTVNEKRRLQLIMPARFYPNVTKYLPLDKGIKPYYPEHLVNH YFQTRHYLHTLWKAGILYKRETTHSASFCGSPYSWEQELQHGAESFHQQSSGILSRPPVG_SE_ LHNLPPNS ARSQSERPVFPCWWLQFRNSKPCSDYCLSHIVNLLEDWGPCAEHGEHHIRIPRTPARVTGGVFLVDKNPH NTAESRLVVDFSQFSRGNYRVSWPKFAVPNLQSLTNLLSSNLSWLSLDVSAAFYHLPLHPAAMPHLLVGS SGLSRYVARLSSNSRIFNYQHGTMQNLHDSCSRNLYVSLMLLYQTFGRKLHLYSHPIILGFRKIPMGVGL SPFLLAQFTSAICSVVRRAFPHCLAFS<u>YMHD</u>VVLGAKSVQHLESLFTAVTNFLLSLGIHLNPNKTKRWGY SLHFMGYVIGCYGSLPQDHIIQKIKEC<u>FRKL</u>PVNRPIDWKVCQRIVGLLGFAAPFTQCGYPALMPLYACI QSKQAFTFSPTYKAFLCKQYLNLYPVARQRPGLCQVFADATPTGWGLVMGHQRMRGTFKAPLPIHTAHLL AACFARSRSGANILGTDNSVVLSRKYTSFPWLLGCAANWILRGTSFVYVPSALNPADDPSRGRLGL<u>YRPL</u> LRLPFRPTTGRTSLYADSPSVPSHLPDRVHFASPLHVAWRPP |

TABLE D

Internal Spacer polypeptide sequences removed from Pol$^{A1}$ mutants and Core-Pol$^{A1}$ fusion proteins

| SEQ ID NO: | HBV genotype | Polypeptide sequence |
|---|---|---|
| 42 | A | CIRSQFKQSRLGLQPHQGPLATSQSGRSGSIRARVH SPTRRCFGVEPSGSGHIGHSASSSSSCLHQSAVRKA AYSHLSTSKRQSSSGHAV |
| 43 | B | SVGPCIQNQLRKSRLGPQPAQGQLAGRQQGGSGSIR ARVHPSPWGTVGVEPSGSGHIHNCASNSSSCLHQSA VRKAAYSHISTSKGHSSSGHAV |
| 44 | C | CIRSQLKQSRLGLQPQQGSLARSKSGRSGSIRARVH PTTRQSFGVEPSGSGHIDNSASSASSCLHQSAVRKT AYSHLSTSKRQSSSGHAV |
| 45 | D | SLQSKHRKSRLGLQSQQGHLARRQQGRGWSIRAGIH PTARRPFGVEPSGSGHTANLASKSASCLYQSAVRKA AYPVVSTFKKHSSSGHAV |

TABLE E

Pol$^{A3}$ mutants - Motifs containing inactivating mutations are underlined (YMDD mutated to YMHD, AELL mutated to AHLL). Amino acids in bold + underline + italic mark the site of deletion (last amino acid prior to the deleted region, and the first amino acid after the deleted region).

| SEQ ID NO: | HBV genotype | Length (# amino acids) | Polypeptide sequence |
|---|---|---|---|
| 9 | A | 705 | MPLSYQHFRKLLLLDDETEAGPLEEELPRLADEDLNRRVAEDLNLGNLNVSIPWTHKVGNFTGLYSSTVPIFNPEWQTPSFP KIHLHEDIANRCQQFVGPLTVNEKRRLRLIMPARFYPNSTKYLPLDKGIKPYYPDHVVNHYFQTRHYLHTLWKAGILYKRET TRSASFCGSPYSWEQELHH _GC_WWLQFRNTQPCSKYCLSHLVNLLEDWGPCDEHGEHHIRIPRTPARVTGGVFLVDKNPHNTA ESRLVVDFSQFSRGITRVSWPKFAVPNLQSLTNLLSSNLSWLSLDVSAAFYHIPLHPAAMPHLLVGSSGLSRYVARLSSNSR IHNNQHGTLQNLHDSCSRQLYVSLMLLYKTYGRKLHLYSHPIILGFRKIPMGVGLSPFLLAQFTSAICSVVRRAFPHCLAFS <u>YMHD</u>VVLGAKSVQHLESLYTAVTNFLLSLGIHLNPNKTKRWGYSLNFMGYVIGSWGTLPQDHIVQKIKHCFRKLPINRPIDW KVCQRIVGLLGFAAPFTQCGYPALMPLYACIQAKQAFTFSPTYKAFLSKQYLNLYPVARQRPGLCQVFADATPTGWGLAIGH QRMRGTFVAPLPIHT<u>AHLL</u>AACFARSRSGAKLIGTDNSVVLSRKYTSFPWLLGCTANWILRGTSFVYVPSALNPADDPSRGR LGLYRPLLRLPYRPTTGRTSLYAVSPSVPSHLPVRVHFASPLHVAWRPP |
| 10 | B | 703 | MPLSYQHFRKLLLLDDEAGPLEEELPRLADEGLNRRVAEDLNLGNLNVSIPWTHKVGNFTGLYSSTVPVFNPEWQTPSFPHI HLQEDIINRCQQYVGPLTVNEKRRLKLIMPARFYPNLTKYLPLDKGIKPYYPEHVVNHYFQTRHYLHTLWKAGILYKRESTR SASFCGSPYSWEQDLQH _GC_WWLQFRNSEPCSEYCLCHIVNLIEDWGPCTEHGEHRIRTPRTPARVTGGVFLVDKNPHNTTES RLVVDFSQFSRGNTRVSWPKFAVPNLQSLTNLLSSNLSWLSLDVSAAFYHLPLHPAAMPHLLVGSSGLSRYVARLSSNSRII NNQHRTMQNLHDSCSRNLYVSLMLLYKTYGRKLHLYSHPIILGFRKIPMGVGLSPFLLAQFTSAICSVVRRAFPHCLAFS<u>YM HD</u>VVLGAKSVQHLESLYAAVTNFLLSLGIHLNPHKTKRWGYSLNFMGYVIGSWGTLPQEHIVQKIKMCFRKLPVNRPIDWKV CQRIVGLLGFAAPFTQCGYPALMPLYACIQAKQAFTFSPTYKAFLSKQYLHLYPVARQRPGLCQVFADATPTGWGLAIGHQR |

TABLE E-continued

Pol^A3 mutants - Motifs containing inactivating mutations are underlined (YMDD mutated to YMHD, AELL mutated to AHLL). Amino acids in bold + underline + italic mark the site of deletion (last amino acid prior to the deleted region, and the first amino acid after the deleted region).

| SEQ ID NO: | HBV geno-type | Length (# amino acids) | Polypeptide sequence |
|---|---|---|---|
| | | | MRGAFVSPLPIHTAHLLAACFARSRSGAKLIGTDNSVVLSRKYTSFPWLLGCAANWILRGTSFVYVPSALNPADDPSRGRLG LYRPLLRLLYRPTTGRTSLYADSPSVPSHLPDRVHFASPLHVAWRPP |
| 11 | C | 703 | MPLSYQHFRKLLLLLDDEAGPLEEELPRLADEDLNRRVAEDLNLGNLNVSIPWTHKVGNFTGLYSSTVPVFNPEWQTPSFPHI HLQEDIINRCQQYVGPLTVNEKRRLKLIMPARFYPNLTKYLPLDKGIKPYYPEHTVNHYFKTRHYLHTLWKAGILYKRETTR SASFCGSPYSWEQELQH GCWWLQFRNSKPCSDYCLSHIVNLLEDWGPCTEHGEHNIRIPRTPARVTGGVFLVDKNPHNTTES RLVVDFSQFSRGSTHVSWPKFAVPNLQSLTNLLSSNLSWLSLDVSAAFYHLPLHPAAMPHLLVGSSGLSRYVARLSSTSRNI NYQHGAMQDLHDSCSRNLYVSLLLLYKTFGRKLHLYSHPIILGFRKIPMGVGLSPFLLAQFTSAICSVVRRAFPHCLAFSYM HDVVLGAKSVQHLESLFTAVTNFLLSLGIHLNPNKTKRWGYVIGSWGTLPQEHIVLKIKQCFRKLPVNRPIDWKV CQRIVGLLGFAAPFTQCGYPALMPLYACIQAKQAFTFSPTYKAFLCKQYLNLYPVARQRSGLCQVFADATPTGWGLAVGHQR MRGTFVSPLPIHTAHLLAACFARSRSGAKLIGTDNSVVLSRKYTSFPWLLGCAANWILRGTSFVYVPSALNPADDPSRGRLG LYRPLLRLPFRPTTGRTSLYAVSPSVPSHLPVRVHFASPLHVAWRPP |
| 12 | D | 703 | MPLSYQHFRRLLLLLDDEAGPLEEELPRLADEGLNRRVAEDLNLGNLNVSIPWTHKVGNFTGLYSSTVPVFNPHWKTPSFPNI HLHQDIIKKCEQFVGPLTVNEKRRLQLIMPARFYPNVTKYLPLDKGIKPYYPEHLVNHYFQTRHYLHTLWKAGILYKRETTH SASFCGSPYSWEQELQH GCWWLQFRNSKPCSDYCLSHIVNLLEDWGPCAEHGEHHIRIPRTPARVTGGVFLVDKNPHNTAES RLVVDFSQFSRGNYRVSWPKFAVPNLQSLTNLLSSNLSWLSLDVSAAFYHLPLHPAAMPHLLVGSSGLSRYVARLSSNSRIF NYQHGTMQNLHDSCSRNLYVSLMLLYQTFGRKLHLYSHPIILGFRKIPMGVGLSPFLLAQFTSAICSVVRRAFPHCLAFSYM HDVVLGAKSVQHLESLFTAVTNFLLSLGIHLNPNKTKRWGYSLHFMGYVIGCYGSLPQDHIIQKIKECFRKLPVNRPIDWKV CQRIVGLLGFAAPFTQCGYPALMPLYACIQSKQAFTFSPTYKAFLCKQYLNLYPVARQRPGLCQVFADATPTGWGLVMGHQR MRGTFKAPLPIHTAHLLAACFARSRSGANILGTDNSVVLSRKYTSFPWLLGCAANWILRGTSFVYVPSALNPADDPSRGRLG LYRPLLRLPFRPTTGRTSLYADSPSVPSHLPDRVHFASPLHVAWRPP |

TABLE F

Internal Spacer polypeptide sequences removed from Pol^A3 mutants and Core-Pol^A3 fusion proteins

| SEQ ID NO: | HBV geno-type | Polypeptide sequence |
|---|---|---|
| 46 | A | RLVIKTSQRHGDEPFCSQPSGILSRSSVGPCIRSQFKQSR LGLQPHQGPLATSQSGRSGSIRARVHSPTRRCFGVEPSGS GHIGHSASSSSSCLHQSAVRKAAYSHLSTSKRQSSSGHAV EFHSFPPSSARSQSQGPVFS |
| 47 | B | RLVFQTSKRHGDKSFCPQSPGILPRSSVGPCIQNQLRKSR LGPQPAQGQLAGRQQGGSGSIRARVHSPWGTVGVEPSGS GHIHNCASNSSSCLHQSAVRKAAYSHISTSKGHSSSGHAV ELHHFPPSSSRSQSQGPVLS |
| 48 | C | RLVFQTSTRHGDESFCSQSSGILSRSPVGPCIRSQLKQSR LGLQPQQGSLARSKSGRSGSIRARVHPTTRQSFGVEPSGS GHIDNSASSASSCLHQSAVRKTAYSHLSTSKRQSSSGHAV ELHNFPPSSARSQSEGPLLS |
| 49 | D | AESFHQQSSGILSRPPVGSSLQSKHRKSRLGLQSQQGHLA RRQQGRGWSIRAGIHPTARRPFGVEPSGSGHTANLASKSA SCLYQSAVRKAAYPVVSTFKKHSSSGHAVELHNLPPNSAR SQSERPVFP |

TABLE G

Core-Pol fusion proteins

| SEQ ID NO: | HBV geno-type | Length (# amino acids) | Polypeptide sequence |
|---|---|---|---|

Core-Pol^mut fusion proteins - Core sequences are indicated with bold + underline. Motifs containing inactivating mutations in Pol are underlined (YMDD mutated to YMHD, AELL mutated to AHLL).

| SEQ ID NO: | HBV geno-type | Length (# amino acids) | Polypeptide sequence |
|---|---|---|---|
| 15 | A | 1030 | MDIDPYKEFGASVELLSFLPSDFFPSVRDLLDTASALYEREALESPEHCSPHHTALRQAILCWGELMTLATWVGNNLEDPASR DLVVNYVNTNMGLKIRQLLWFHISCLTFGRETVLEYLVSFGVWIRTPPAYRPPNAPILSTLPETTVVRRRDRGRSPRRRTPS PRRRSQSPRRRRSQSRESQCMPLSYQHFRKLLLLLDDETEAGPLEEELPRLADEDLNRRVAEDLNLGNLNVSIPWTHKVGNF TGLYSSTVPIFNPEWQTPSFPKIHLHEDIANRCQQFVGPLTVNEKRRLRLIMPARFYPNSTKYLPLDKGIKPYYPDHVVNHY FQTRHYLHTLWKAGILYKRETTRSASFCGSPYSWEQELHHGRLVIKTSQRHGDEPFCSQPSGILSRSSVGPCIRSQFKQSRL GLQPHQGPLATSQSGRSGSIRARVHSPTRRCFGVEPSGSGHIGHSASSSSSCLHQSAVRKAAYSHLSTSKRQSSSGHAVEFH SFPPSSARSQSQGPVFSCWWLQFRNTQPCSKYCLSHLVNLLEDWGPCDEHGEHHIRIPRTPARVTGGVFLVDKNPHNTAESR LVVDFSQFSRGITRVSWPKFAVPNLQSLTNLLSSNLSWLSLDVSAAFYHIPLHPAAMPHLLVGSSGLSRYVARLSSNSRIHN NQHGTLQNLHDSCSRQLYVSLMLLYKTYGRKLHLYSHPIILGFRKIPMGVGLSPFLLAQFTSAICSVVRRAFPHCLAFSYMH DVVLGAKSVQHLESLYTAVTNFLLSLGIHLNPNKTKRWGYSLNFMGYVIGSWGTLPQDHIVQKIKHCFRKLPINRPIDWKVC QRIVGLLGFAAPFTQCGYPALMPLYACIQAKQAFTFSPTYKAFLSKQYLNLYPVARQRPGLCQVFADATPTGWGLAIGHQRM RGTFVAPLPIHTAHLLAACFARSRSGAKLIGTDNSVVLSRKYTSFPWLLGCTANWILRGTSFVYVPSALNPADDPSRGRLGL YRPLLRLPYRPTTGRTSLYAVSPSVPSHLPVRVHFASPLHVAWRPP |

TABLE G-continued

Core-Pol fusion proteins

| SEQ ID NO: | HBV geno- type | Length (# amino acids) | Polypeptide sequence |
|---|---|---|---|
| 16 | B | 1026 | MDIDPYKEFGASVELLSFLPSDFFPSVRDLLDTASALYREALESPEHCSPHHTALRQAILCWGELMNLATWVGSNLEDPASR ELVVSYVNVNMGLKIRQLLWFHISCLTFGRETVLEYLVSFGVWIRTPPAYRPPNAPILSTLPETTVVRRRGRSPRRRTPSPR RRRSQSPRRRRSQSRESQCMPLSYQHFRKLLLLDDEAGPLEEELPRLADEGLNRRVAEDLNLGNLNVSIPWTHKVGNFTGLY SSTVPVFNPEWQTPSFPHIHLQEDIINRCQQYVGPLTVNEKRRLKLIMPARFYPNLTKYLPLDKGIKPYYPEHVVNHYFQTR HYLHTLWKAGILYKRESTRSASFCGSPYSWEQDLQHGRLVFQTSKRHGDKSFCPQSPGILPRSSVGPCIQNQLRKSRLGPQP AQGQLAGRQQGSGSIRARVHPSPWGTVGVEPSGSGHIHNCASNSSSCLHQSAVRKAAYSHISTSKGHSSSGHAVELHHFPP SSSRSQSQGPVLSCWWLQFRNSEPCSEYCLCHIVNLIEDWGPCTEHGEHRIRTPRTPARVTGGVFLVDKNPHNTTESRLVVD FSQFSRGNTRVSWPKFAVPNLQSLTNLLSSNLSWLSLDVSAAFYHLPLHPAAMPHLLVGSSGLSRYVARLSSNSRIINNQHR TMQNLHDSCSRNLYVSLMLLYKTYGRKLHLYSHPIILGFRKIPMGVGLSPFLLAQFTSAICSVVRRAFPHCLAFSYMHDVVL GAKSVQHLESLYAAVTNFLLSLGIHLNPHKTKRWGYSLNFMGYVIGSWGTLPQEHIVQKIKMCFRKLPVNRPIDWKVCQRIV GLLGFAAPFTQCGYPALMPLYACIQAKQAFTFSPTYKAFLHLYPVARQRPGLCQVFADATPTGWGLAIGHQRMRGAF VSPLPIHT<u>AHLL</u>AACFARSRSGAKLIGTDNSVVLSRKYTSFPWLLGCAANWILRGTSFVYVPSALNPADDPSRGRLGLYRPL LRLLYRPTTGRTSLYADSPSVPSHLPDRVHFASPLHVAWRPP |
| 17 | C | 1026 | MDIDPYKEFGASVELLSFLPSDFFPSVRDLLDTASALYREALESPEHCSPHHTALRQAILCWGELMNLATWVGSNLEDPASR ELVVSYVNVNMGLKIRQLLWFHISCLTFGRETVLEYLVSFGVWIRTPPAYRPPNAPILSTLPETTVVRRRGRSPRRRTPSPR RRRSQSPRRRRSQSRESQCMPLSYQHFRKLLLLDDEAGPLEEELPRLADEDLNRRVAEDLNLGNLNVSIPWTHKVGNFTGLY SSTVPVFNPEWQTPSFPHIHLQEDIINRCQQYVGPLTVNEKRRLKLIMPARFYPNLTKYLPLDKGIKPYYPEHTVNHYFKTR HYLHTLWKAGILYKRETTRSASFCGSPYSWEQLQHGRLVFQTSTRHGDESFCSQSSGILSRSPVGPCIRSQLKQSRLGLQP QQGSLARSKSGRSGSIRARVHPTTRQSFGVEPSGSGHIDNSASSASSCLHQSAVRKTAYSHLSTSKRQSSSGHAVELHNFPP SSARSQSEGPLLSCWWLQFRNSKPCSDYCLSHIVNLLEDWGPCTEHGEHNIRIPRTPARVTGGVFLVDKNPHNTTESRLVVD FSQFSRGSTHVSWPKFAVPNLQSLTNLLSSNLSWLSLDVSAAFYHLPLHPAAMPHLLVGSSGLSRYVARLSSTSRNINYQHG AMQDLHDSCSRNLYVSLLLLYKTFGRKLHLYSHPIILGFRKIPMGVGLSPFLLAQFTSAICSVVRRAFPHCLAFSYMHDVVL GAKSVQHLESLFTAVTNFLLSLGIHLNPNKTKRWGYSLNFMGYVIGSWGTLPQEHIVLKIKQCFRKLPVNRPIDWKVCQRIV GLLGFAAPFTQCGYPALMPLYACIQAKQAFTFSPTYKAFLCKQYLNLYPVARQRSGLCQVFADATPTGWGLAVGHQRMRGTF VSPLPIHT<u>AHLL</u>AACFARSRSGAKLIGTDNSVVLSRKYTSFPWLLGCAANWILRGTSFVYVPSALNPADDPSRGRLGLYRPL LRLPFRPTTGRTSLYAVSPSVPSHLPVRVHFASPLHVAWRPP |
| 18 | D | 1015 | MDIDPYKEFGASVELLSFLPSDFFPSVRDLLDTASALYREALESPEHCSPHHTALRQAILCWGELMNLATWVGVNLEDPASR DLVVSYVNTNMGLKFRQLLWFHISCLTFGRETVLEYLVSFGVWIRTPPAYRPPNAPILSTLPETTVVRRRGRSPRRRTPSPR RRRSQSPRRRRSQSRESQCMPLSYQHFRRLLLLDDEAGPLEEELPRLADEGLNRRVAEDLNLGNLNVSIPWTHKVGNFTGLY SSTVPVFNPHWKTPSFPNIHLHQDIIKKCEQFVGPLTVNEKRRLQIMPARFYPNVTKYLPLDKGIKPYYPEHLVNHYFQTR HYLHTLWKAGILYKRETTHSASFCGSPYSWEQELQHGAESFHQQSSGILSRPPVGSSLQSKHRKSRLGLQSQQGHLARRQQG RGWSIRAGIHPTARRPPGVEPSGSGHTANLASKSASCLYQSAVRKAAYPVVSTFKKHSSSGHAVELHNLPPNSARSQSERPV FPCWWLQFRNSKPCSDYCLSHIVNLLEDWGPCAEHGEHHIRIPRTPARVTGGVFLVDKNPHNTAESRLVVDFSQFSRGNYRV SWPKFAVPNLQSLTNLLSSNLSWLSLDVSAAFYHLPLHPAAMPHLLVGSSGLSRYVARLSSNSRIFNYQHGTMQNLHDSCSR NLYVSLMLLYQTFGRKLHLYSHPIILGFRKIPMGVGLSPFLLAQFTSAICSVVRRAFPHCLAFS<u>YMHD</u>VVLGAKSVQHLESL FTAVTNFLLSLGIHLNPNKTKRWGYSHFMGYVIGCGYSLPQDHIIQKIKECFRKLPVNRPIDWKVCQRIVGLLGFAAPFTQ CGYPALMPLYACIQSKQAFTFSPTYKAFLCKQYLNLYPVARQRPGLCQVFADATPTGWGLVMGHQRMRGTFKAPLPIHTAHL LAACFARSRSGANILGTDNSVVLSRKYTSFPWLLGCAANWILRGTSFVYVPSALNPADDPSRGRLGLYRPLLRLPFRPTTGR TSLYADSPSVPSHLPDRVHFASPLHVAWRPP |

Core-Pol<sup>Δ1</sup> fusion proteins - Core sequences are indicated with bold + underline. Motifs containing inactivating mutations in Pol are underlined (YMDD mutated to YMHD, AELL mutated to AHLL). Amino acids in bold + italic mark the site of deletion (last amino acid prior to the deleted region, and the first amino acid after the deleted region).

| 19 | A | 940 | MDIDPYKEFGASVELLSFLPSDFFPSVRDLLDTASALYREALESPEHCSPHHTALRQAILCWGELMTLATWVGNNLEDPASR DLVVNYVNTNMGLKIRQLLWFHISCLTFGRETVLEYLVSFGVWIRTPPAYRPPNAPILSTLPETTVVRRRDRGRSPRRRTPS PRRRRSQSPRRRRSQSRESQCMPLSYQHFRKLLLLDDETEAGPLEEELPRLADEDLNRRVAEDLNLGNLNVSIPWTHKVGNF TGLYSSTVPIFNPEWQTPSFPKIHLHEDIANRCQQFVGPLTVNEKRRLRLIMPARFYPNSTKYLPLDKGIKPYYPDHVVNHY FQTRHYLHTLWKAGILYKRETTRSASFCGSPYSWEQELHHGRLVIKTSQRHGDEPFCSQPSGILSRSSVG*PE* FHSFPPSSAR SQSQGPVFSCWWLQFRNTQPCSKYCLSHLVNLLEDWGPCDEHGEHHIRIPRTPARVTGGVFLVDKNPHNTAESRLVVDFSQF SRGITRVSWPKFAVPNLQSLTNLLSSNLSWLSLDVSAAFYHIPLHPAAMPHLLVGSSGLSRYVARLSSNSRIHNNQHGTLQN LHDSCSRQLYVSLMLLYKTYGRKLHLYSHPIILGFRKIPMGVGLSPFLLAQFTSAICSVVRRAFPHCLAFS<u>YMHD</u>VVLGAKS VQHLESLYTAVTNFLLSLGIHLNPNKTKRWGYSLNFMGYVIGSWGTLPQDHIVQKIKHCFRKLPINRPIDWKVCQRIVGLLG FAAPFTQCGYPALMPLYACIQAKQAFTFSPTYKAFLSKQYLNLYPVARQRPGLCQVFADATPTGWGLAIGHQRMRGTFVAPL PIHT<u>AHLL</u>AACFARSRSGAKLIGTDNSVVLSRKYTSFPWLLGCTANWILRGTSFVYVPSALNPADDPSRGRLGLYRPLLRLP YRPTTGRTSLYAVSPSVPSHLPVRVHFASPLHVAWRPP |
| 20 | B | 932 | MDIDPYKEFGASVELLSFLPSDFFPSVRDLLDTASALYREALESPEHCSPHHTALRQAILCWGELMNLATWVGSNLEDPASR ELVVSYVNVNMGLKIRQLLWFHISCLTFGRETVLEYLVSFGVWIRTPPAYRPPNAPILSTLPETTVVRRRGRSPRRRTPSPR RRRSQSPRRRRSQSRESQCMPLSYQHFRKLLLLDDEAGPLEEELPRLADEGLNRRVAEDLNLGNLNVSIPWTHKVGNFTGLY SSTVPVFNPEWQTPSFPHIHLQEDIINRCQQYVGPLTVNEKRRLKLIMPARFYPNLTKYLPLDKGIKPYYPEHVVNHYFQTR HYLHTLWKAGILYKRESTRSASFCGSPYSWEQDLQHGRLVFQTSKRHGDKSFCPQSPGILPR*SE* LHHFPPSSSRSQSQGPVL SCWWLQFRNSEPCSEYCLCHIVNLIEDWGPCTEHGEHRIRTPRTPARVTGGVFLVDKNPHNTTESRLVVDFSQFSRGNTRVS WPKFAVPNLQSLTNLLSSNLSWLSLDVSAAFYHLPLHPAAMPHLLVGSSGLSRYVARLSSNSRIINNQHRTMQNLHDSCSRN LYVSLMLLYKTYGRKLHLYSHPIILGFRKIPMGVGLSPFLLAQFTSAICSVVRRAFPHCLAFS<u>YMHD</u>VVLGAKSVQHLESLY AAVTNFLLSLGIHLNPHKTKRWGYSLNFMGYVIGSWGTLPQEHIVQKIKMCFRKLPVNRPIDWKVCQRIVGLLGFAAPFTQC GYPALMPLYACIQAKQAFTFSPTYKAFLSKQYLHLYPVARQRPGLCQVFADATPTGWGLAIGHQRMRGAFVSPLPIHT<u>AHLL</u> AACFARSRSGAKLIGTDNSVVLSRKYTSFPWLLGCAANWILRGTSFVYVPSALNPADDPSRGRLGLYRPLLRLLYRPTTGRT SLYADSPSVPSHLPDRVHFASPLHVAWRPP |

TABLE G-continued

Core-Pol fusion proteins

| SEQ ID NO: | HBV geno-type | Length (# amino acids) | Polypeptide sequence |
|---|---|---|---|
| 21 | C | 936 | MDIDPYKEFGASVELLSFLPSDFFPSVRDLLDTASALYREALESPEHCSPHHTALRQAILCWGELMNLATWVGSNLEDPASR ELVVSYVNVNMGLKIRQLLWFHISCLTFGRETVLEYLVSFGVWIRTPPAYRPPNAPILSTLPETTVVRRRGRSPRRRTPSPR RRRSQSPRRRRSQSRES<u>QC</u>MPLSYQHFRKLLLLDDEAGPLEEELPRLADEDLNRRVAEDLNLGNLNVSIPWTHKVGNFTGLY SSTVPVFNPEWQTPSFPHIHLQEDIINRCQQYVGPLTVNEKRRLKLIMPARFYPNLTKYLPLDKGIKPYYPEHTVNHYFKTR HYLHTLWKAGILYKRETTRSASFCGSPYSWEQELQHGRLVFQTSTRHGDESFCSQSSGILSRSPVG<u>PE</u> LHNFPPSSARSQSE GPLLSCWWLQFRNSKPCSDYCLSHIVNLLEDWGPCTEHGEHNIRIPRTPARVTGGVFLVDKNPHNTTESRLVVDFSQFSRGS THVSWPKFAVPNLQSLTNLLSSNLSWLSLDVSAAFYHLPLHPAAMPHLLVGSSGLSRYVARLSSTSRNINYQHGAMQDLHDS CSRNLYVSLLLLYKTFGRKLHLYSHPIILGFRKIPMGVGLSPFLLAQFTSAICSVVRRAFPHCLAFSYMHDVVLGAKSVQHL ESLFTAVTNFLLSLGIHLNPNKTKRWGYSLNFMGYVIGSWGTLPQEHIVLKIKQCFRKLPVNRPIDW<u>KV</u>CQRIVGLLGFAAP FTQCGYPALMPLYACIQAKQAFTFSPTYKAFLCKQYLNLYPVARQRSGLCQVFADATPTGWGLAVGHQRMRGTFVSPLPIHT <u>AHLL</u>AACFARSRSGAKLIGTDNSVVLSRKYTSFPWLLGCAANWILRGTSFVYVPSALNPADDPSRGRLGLYRPLLRLPFRPT TGRTSLYAVSPSVPSHLPVRVHFASPLHVAWRPP |
| 22 | D | 925 | MDIDPYKEFGASVELLSFLPSDFFPSVRDLLDTASALYREALESPEHCSPHHTALRQAILCWGELMNLATWVGVNLEDPASR DLVVSYVNTNMGLKFRQLLWFHISCLTFGRETVLEYLVSFGVWIRTPPAYRPPNAPILSTLPETTVVRRRGRSPRRRTPSPR RRRSQSPRRRRSQSRES<u>QC</u>MPLSYQHFRRLLLLDDEAGPLEEELPRLADEGLNRRVAEDLNLGNLNVSIPWTHKVGNFTGLY SSTVPVFNPHWKTPSFPNIHLQDIIKKCEQFVGPLTVNEKRRLQLIMPARFYPNVTKYLPLDKGIKPYYPEHLVNHYFQTR HYLHTLWKAGILYKRETTHSASFCGSPYSWEQELQHGAESFHQQSSGILSRPPVG<u>SE</u> LHNLPPNSARSQSERPVFPCWWLQF RNSKPCDYCLSHIVNLLEDWGPCAEHGEHHIRIPRTPARVTGGVFLVDKNPHNTAESRLVVDFSQFSRGNYRVSWPKFAVP NLQSLTNLLSSNLSWLSLDVSAAFYHLPLHPAAMPHLLVGSSGLSRYVARLSSNSRIFNYQHGTMQNLHDSCSRNLYVSLML LYQTFGRKLHLYSHPIILGFRKIPMGVGLSPFFLAQFTSAICSVVRRAFPHCLAFSYMHDVVLGAKSVQHLESLFTAVTNFL LSLGIHLNPNKTKRWGYSLHFMGYVIGCYGSLPQDHIIQKIKECFRKLPVNRPIDW<u>KV</u>CQRIVGLLGFAAPFTQCGYPALMP LYACIQSKQAFTSPTYKAFLCKQYLNLYPVARQRPGLCQVFADATPTGWGLVMGHQRMRGTFKAPLPIHT<u>AHLL</u>AACFARS RSGANILGTDNSVVLSRKYTSFPWLLGCAANWILRGTSFVYVPSALNPADDPSRGRLGLYRPLLRLPFRPTTGRTSLYADSP SVPSHLPDRVHFASPLHVAWRPP |

Core-Pol<sup>Δ3</sup> fusion proteins - Core sequences are indicated with bold + underline. Motifs containing inactivating mutations in Pol are underlined (YMDD mutated to YMHD, AELL mutated to AHLL). Amino acids in bold + underline + italic mark the site of deletion (last amino acid prior to the deleted region, and the first amino acid after the deleted region).

| 23 | A | 890 | MDIDPYKEFGASVELLSFLPSDFFPSVRDLLDTASALYREALESPEHCSPHHTALRQAILCWGELMTLATWVGNNLEDPASR DLVVNYVNTNMGLKIRQLLWFHISCLTFGRETVLEYLVSFGVWIRTPPAYRPPNAPILSTLPETTVVRRRDRGRSPRRRTPS PRRRRSQSPRRRRSQSRES<u>QC</u>MPLSYQHFRKLLLLDDETEAGPLEEELPRLADEDLNRRVAEDLNLGNLNVSIPWTHKVGNF TGLYSSTVPIFNPEWQTPSFPKIHLHEDIANRCQQFVGPLTVNEKRRLRLIMPARFYPNSTKYLPLDKGIKPYYPDHVVNHY FQTRHYLHTLWKAGILYKRETTRSASFCGSPYSWEQELHH<u>GC</u> WWLQFRNTQPCSKYCLSHIVNLLEDWGPCDEHGEHHIRIP RTPARVTGGVFLVDKNPHNTAESRLVVDFSQFSRGITRVSWPKFAVPNLQSLTNLLSSNLSWLSLDVSAAFYPLPLHPAAMP HLLVGSSGLSRYVARLSSNSRIHNNQHGTLQNLHDSCSRQLYVSLMLLYKTYGRKLHLYSHPIILGFRKIPMGVGLSPFLLA QFTSAICSVVRRAFPHCLAFS<u>YMHD</u>VVLGAKSVQHLESLYTAVTNFLLSLGIHLNPNKTKRWGYSLNFMGYVIGSWGTLPQD HIVQKIKHCFRKLPINRPIDWKVCQRIVGLLGFAAPFTQCGYPALMPLYACIQAKQAFTFSPTYKAFLSKQYLNLYPVARQR PGLCQVFADATPTGWGLAIGHQRMRGTFVAPLPIHT<u>AHLL</u>AACFARSRSGAKLIGTDNSVVLSRKYTSFPWLLGCTANWILR GTSFVYVPSALNPADDPSRGRLGLYRPLLRLPYRPTTGRTSLYAVSPSVPSHLPVRVHFASPLHVAWRPP |
| 24 | B | 886 | MDIDPYKEFGASVELLSFLPSDFFPSVRDLLDTASALYREALESPEHCSPHHTALRQAILCWGELMNLATWVGSNLEDPASR ELVVSYVNVNMGLKIRQLLWFHISCLTFGRETVLEYLVSFGVWIRTPPAYRPPNAPILSTLPETTVVRRRGRSPRRRTPSPR RRRSQSPRRRRSQSRES<u>QC</u>MPLSYQHFRKLLLLDDEAGPLEEELPRLADEGLNRRVAEDLNLGNLNVSIPWTHKVGNFTGLY SSTVPVFNPEWQTPSFPHIHLQEDIINRCQQYVGPLTVNEKRRLKLIMPARFYPNLTKYLPLDKGIKPYYPEHVVNHYFQTR HYLHTLWKAGILYKRETTRSASFCGSPYSWEQDLQH<u>GC</u> WWLQFRNSEPCSEYCLCHIVNLLEDWGPCTEHGEHRIRTPRTPA RVTGGVFLVDKNPHNTTESRLVVDFSQFSRGNTRVSWPKFAVPNLQSLTNLLSSNLSWLSLDVSAAFYHLPLHPAAMPHLLV GSSGLSRYVARLSSNSRIINNQHRTMQNLHDSCSRNLYVSLMLLYKTYGRKLHLYSHPIILGFRKIPMGVGLSPFLLAQFTS AICSVVRRAFPHCLAFS<u>YMHD</u>VVLGAKSVQHLESLYAAVTNFLLSLGIHLNPHKTKRWGYSLNFMGYVIGSWGTLPQEHIVQ KIKMCFRKLPVNRPIDW<u>KV</u>CQRIVGLLGFAAPFTQCGYPALMPLYACIQAKQAFTFSPTYKAFLSKQYLHLYPVARQRPGLC QVFADATPTGWGLAIGHQRMRGAFVSPLPIHT<u>AHLL</u>AACFARSRSGAKLIGTDNSVVLSRKYTSFPWLLGCAANWILRGTSF VYVPSALNPADDPSRGRLGLYRPLLRLLYRPTTGRTSLYADSPSVPSHLPDRVHFASPLHVAWRPP |
| 25 | C | 886 | MDIDPYKEFGASVELLSFLPSDFFPSVRDLLDTASALYREALESPEHCSPHHTALRQAILCWGELMNLATWVGSNLEDPASR ELVVSYVNVNMGLKIRQLLWFHISCLTFGRETVLEYLVSFGVWIRTPPAYRPPNAPILSTLPETTVVRRRGRSPRRRTPSPR RRRSQSPRRRRSQSRES<u>QC</u>MPLSYQHFRKLLLLDDEAGPLEEELPRLADEDLNRRVAEDLNLGNLNVSIPWTHKVGNFTGLY SSTVPVFNPEWQTPSFPHIHLQEDIINRCQQYVGPLTVNEKRRLKLIMPARFYPNLTKYLPLDKGIKPYYPEHTVNHYFKTR HYLHTLWKAGILYKRETTRSASFCGSPYSWEQELQH<u>GC</u> WWLQFRNSKPCSDYCLSHIVNLLEDWGPCTEHGEHNIRIPRTPA RVTGGVFLVDKNPHNTTESRLVVDFSQFSRGSTHVSWPKFAVPNLQSLTNLLSSNLSWLSLDVSAAFYHLPLHPAAMPHLLV GSSGLSRYVARLSSTSRNINYQHGAMQDLHDSCSRNLYVSLLLLYKTFGRKLHLYSHPIILGFRKIPMGVGLSPFLLAQFTS AICSVVRRAFPHCLAFS<u>YMHD</u>VVLGAKSVQHLESLFTAVTNFLLSLGIHLNPNKTKRWGYSLNFMGYVIGSWGTLPQEHIVL KIKQCFRKLPVNRPIDW<u>KV</u>CQRIVGLLGFAAPFTQCGYPALMPLYACIQAKQAFTFSPTYKAFLCKQYLNLYPVARQRSGLC QVFADATPTGWGLAVGHQRMRGTFVSPLPIHT<u>AHLL</u>AACFARSRSGAKLIGTDNSVVLSRKYTSFPWLLGCAANWILRGTSF VYVPSALNPADDPSRGRLGLYRPLLRLPFRPTTGRTSLYAVSPSVPSHLPVRVHFASPLHVAWRPP |
| 26 | D | 886 | MDIDPYKEFGASVELLSFLPSDFFPSVRDLLDTASALYREALESPEHCSPHHTALRQAILCWGELMNLATWVGVNLEDPASR DLVVSYVNTNMGLKFRQLLWFHISCLTFGRETVLEYLVSFGVWIRTPPAYRPPNAPILSTLPETTVVRRRGRSPRRRTPSPR RRRSQSPRRRRSQSRES<u>QC</u>MPLSYQHFRRLLLLDDEAGPLEEELPRLADEGLNRRVAEDLNLGNLNVSIPWTHKVGNFTGLY SSTVPVFNPHWKTPSFPNIHLQDIIKKCEQFVGPLTVNEKRRLQLIMPARFYPNVTKYLPLDKGIKPYYPEHLVNHYFQTR HYLHTLWKAGILYKRETTHSASFCGSPYSWEQELQH<u>GC</u> WWLQFRNSKPCSDYCLSHIVNLLEDWGPCAEHGEHHIRIPRTPA RVTGGVFLVDKNPHNTAESRLVVDFSQFSRGNYRVSWPKFAVPNLQSLTNLLSSNLSWLSLDVSAAFYHLPLHPAAMPHLLV GSSGLSRYVARLSSNSRIFNYQHGTMQNLHDSCSRNLYVSLMLLYQTFGRKLHLYSHPIILGFRKIPMGVGLSPFLLAQFTS |

TABLE G-continued

Core-Pol fusion proteins

| SEQ ID NO: | HBV geno-type | Length (# amino acids) | Polypeptide sequence |
|---|---|---|---|
| | | | AICSVVRRAFPHCLAFSYMHDVVLGAKSVQHLESLFTAVTNFLLSLGIHLNPNKTKRWGYSLHFMGYVIGCYGSLPQDHIIQ KIKECFRKLPVNRPIDWKVCQRIVGLLGFAAPFTQCGYPALMPLYACIQSKQAFTFSPTYKAFLCKQYLNLYPVARQRPGLC QVFADATPTGWGLVMGHQRMRGTFKAPLPIHTAHLLAACFARSRSGANILGTDNSVVLSRKYTSFPWLLGCAANWILRGTSF VYVPSALNPADDPSRGRLGLYRPLLRLPFRPTTGRTSLYADSPSVPSHLPDRVHFASPLHVAWRPP |

Core-sAg Fusion Proteins

Further provided are fusion proteins composed of an N-terminal portion comprising an HBV core polypeptide, or an immunogenic fragment thereof, and a C-terminal portion comprising an HBV small surface antigen, or an immunogenic fragment thereof. In various embodiments, the HBV core polypeptide or fragment thereof and the HBV small surface antigen (sAg), or fragment thereof, are directly fused or abutted. In some embodiments, the HBV core polypeptide or fragment thereof and the HBV small surface antigen, or fragment thereof, are connected via a linker.

HBV Core Polypeptide, or an Immunogenic Fragment Thereof

In various embodiments, the HBV core polypeptide, or immunogenic fragment thereof, of the core-sAg fusion protein independently can be from an HBV genotype A, B/C or D. Illustrative HBV core polypeptide amino acid sequences that can be used in the herein described core-sAg fusion proteins are provided in Table H.

TABLE H

Illustrative HBV core polypeptide sequences

| SEQ ID NO: | HBV geno-type | Polypeptide sequence |
|---|---|---|
| 64 | A | MDIDPYKEFGASVELLSFLPSDFFPSVRDLLDTASALYRE ALESPEHCSPHHTALRQAILCWGELMTLATWVGNNLEDPA SRDLVVNYVNTNMGLKIRQLLWFHISCLTFGRETVLEYLV SFGVWIRTPPAYRPPNAPILSTLPETTVVRRRDRGRSPRR RTPSPRRRRSQSPRRRRSQSRESQC |
| 65 | B/C | MDIDPYKEFGASVELLSFLPSDFFPSVRDLLDTASALYRE ALESPEHCSPHHTALRQAILCWGELMNLATWVGSNLEDPA SRELVVSYVNVNMGLKIRQLLWFHISCLTFGRETVLEYLV SFGVWIRTPPAYRPPNAPILSTLPETTVVRRRGRSPRRRT PSPRRRRSQSPRRRRSQSRESQC |
| 66 | D | MDIDPYKEFGASVELLSFLPSDFFPSVRDLLDTASALYRE ALESPEHCSPHHTALRQAILCWGELMNLATWVGVNLEDPA SRDLVVSYVNTNMGLKFRQLLWFHISCLTFGRETVLEYLV SFGVWIRTPPAYRPPNAPILSTLPETTVVRRRGRSPRRRT PSPRRRRSQSPRRRRSQSRESQC |

In some embodiments, the core polypeptide in the core-sAg fusion polypeptide comprises or consists of an amino acid sequence of any one of SEQ ID NOs: 64-66, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 64-66. In some embodiments, the core polypeptide comprises a serine (S) residue at the amino acid position corresponding to position 12, and an asparagine (N) residue at the amino acid position corresponding to position 67, wherein the position numbers are with reference to SEQ ID NO:65 or SEQ ID NO:66.

HBV Small Surface Antigen, or an Immunogenic Fragment Thereof

In various embodiments, the HBV sAg polypeptide, or immunogenic fragment thereof, of the core-sAg fusion protein independently can be from an HBV genotype A, B, C or D. Illustrative HBV sAg polypeptide amino acid sequences that can be used in the herein described core-sAg fusion proteins are provided in Table 1, in Example 1 below.

In some embodiments, the sAg polypeptide in the core-sAg fusion polypeptide comprises or consists of an amino acid sequence of any one of SEQ ID NOs: 1-4, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 1-4, e.g., comprising one or more of a serine (S) residue at the amino acid position corresponding to position 53, an isoleucine (I) residue at the amino acid position corresponding to position 68, a threonine (T) residue at the amino acid position corresponding to position 125, a proline (P) residue at the amino acid position corresponding to position 127, an phenylalanine (F) residue at the amino acid position corresponding to position 161, a tyrosine (Y) residue at the amino acid position corresponding to position 200, a serine (S) residue at the amino acid position corresponding to position 210, and a leucine (L) residue at the amino acid position corresponding to position 213.

With respect to the core-sAg fusion proteins, the HBV core polypeptide and the HBV sAg polypeptide can be from the same or different HBV genotypes. In some embodiments, the core-sAg fusion protein comprises in sequential order, from the N-terminus to the C-terminus, an HBV core polypeptide and an HBV small surface antigen (sAg) polypeptide, wherein:
  the core polypeptide is from an HBV genotype A and the sAg polypeptide is from an HBV genotype A;
  the core polypeptide is from an HBV genotype B or C and the sAg polypeptide is from an HBV genotype B;
  the core polypeptide is from an HBV genotype B or C and the sAg polypeptide is from an HBV genotype C;
  the core polypeptide is from an HBV genotype D and the sAg polypeptide is from an HBV genotype D;
  the core polypeptide is from an HBV genotype A and the sAg polypeptide is from an HBV genotype B;
  the core polypeptide is from an HBV genotype A and the sAg polypeptide is from an HBV genotype C;
  the core polypeptide is from an HBV genotype A and the sAg polypeptide is from an HBV genotype D;
  the core polypeptide is from an HBV genotype B or C and the sAg polypeptide is from an HBV genotype A;
  the core polypeptide is from an HBV genotype B or C and the sAg polypeptide is from an HBV genotype D;
  the core polypeptide is from an HBV genotype D and the sAg polypeptide is from an HBV genotype A;

the core polypeptide is from an HBV genotype D and the sAg polypeptide is from an HBV genotype B; or the core polypeptide is from an HBV genotype D and the sAg polypeptide is from an HBV genotype C.

In some embodiments, the core-sAg fusion protein comprises in sequential order, from the N-terminus to the C-terminus, an HBV core polypeptide and an HBV small surface antigen (sAg) polypeptide, wherein:

the core polypeptide is from an HBV genotype B or C and the sAg polypeptide is from an HBV genotype C; or the core polypeptide is from an HBV genotype D and the sAg polypeptide is from an HBV genotype D.

In some embodiments, the core-sAg fusion protein comprises in sequential order, from the N-terminus to the C-terminus, (i) an HBV core polypeptide comprising or consisting of an amino acid sequence of SEQ ID NO: 65, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 65; and (ii) an HBV small surface antigen (sAg) polypeptide comprising or consisting of an amino acid sequence of SEQ ID NO: 3, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 3.

In some embodiments, the core-sAg fusion protein comprises in sequential order, from the N-terminus to the C-terminus, (i) an HBV core polypeptide comprising or consisting of an amino acid sequence of SEQ ID NO: 66, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 66; and (ii) an HBV small surface antigen (sAg) polypeptide comprising or consisting of an amino acid sequence of SEQ ID NO: 4, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 4.

In various embodiments, the core-sAg fusion proteins described herein comprise an HBV small surface antigen isoform but do not comprise an HBV medium surface antigen isoform or an HBV large surface antigen isoform. Accordingly, in some embodiments, the core-sAg fusion proteins described herein do not comprise an HBV pre-S1 polypeptide. In some embodiments, the core-sAg fusion proteins described herein do not comprise an HBVpre-S2 polypeptide. In some embodiments, the core-sAg fusion proteins described herein do not comprise both of an HBV pre-S1 polypeptide and an HBV pre-S2 polypeptide.

An illustrative HBV pre-S2 polypeptide not included in the herein described core-sAg fusion protein is provided below:

```
                                        (SEQ ID NO: 79)
MQWNST[A/T]FHQ[T/A]LQDPRVR[A/G]LYFP[A/G]GGSS[L/S]G

[A/T][V/I]NPV[L/P]TT[A/V]S[P/H][L/I]SSIF[S/A]RIGDP

[A/V][L/M/P/T]N.
```

An illustrative HBV pre-S2 consensus polypeptide from HBV genotype A not included in the herein described core-sAg fusion protein is provided below:

```
                                        (SEQ ID NO: 80)
MQWNSTAFHQALQDPRVRGLYFPAGGSSSGTVNPAPNIASHISSISARTG

DPVTN.
```

An illustrative HBV pre-S2 consensus polypeptide from HBV genotype B not included in the herein described core-sAg fusion protein is provided below:

```
                                        (SEQ ID NO: 81)
MQWNSTTEHQTLQDPRVRALYFPAGGSSSGTVSPAQNTVSAISSILSKTG

DPVPN.
```

An illustrative HBV pre-S2 consensus polypeptide from HBV genotype C not included in the herein described core-sAg fusion protein is provided below:

```
                                        (SEQ ID NO: 82)
MQWNSTTFHQALLDPRVRGLYFPAGGSSSGTVNPVPTTASPISSIFSRTG

DPAPN.
```

An illustrative HBV pre-S2 consensus polypeptide from HBV genotype D not included in the herein described core-sAg fusion protein is provided below:

```
                                        (SEQ ID NO: 83)
MQWNSTTFHQTLQDPRVRGLYFPAGGSSSGTVNPVPTTASPISSIFSRIG

DPALN.
```

In some embodiments, the core-sAg fusion proteins described herein do not comprise an HBV pre-S2 polypeptide comprising or consisting of an amino acid sequence of any one of SEQ ID NOs: 79-83, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 79-83.

An illustrative HBV pre-S1-pre-S2 polypeptide not included in the herein described core-sAg fusion protein is provided below:

```
                                        (SEQ ID NO: 84)
MGQNLSTSNPLGFFPDHQL[D/A]PAFRANT[A/G/R]NPDWDFNPNKD

TWPDANKVGAGAFGLGFTPPHGGLLGWSPQAQGI[I/L]QT[L/V]PAN

PPPAS[T/A]NRQ[S/T]GRQPTPLSPPLR[N/D]THPQAMQWNST

[A/T]FHQ[T/A]LQDPRVR[A/G]LYFP[A/G]GGSS[L/S]G[A/T]

[V/I]NPV[L/P]TT[A/V]S[P/H][L/I]SSIF[S/A]RIGDP[A/V]

[L/M/P/T]N.
```

An illustrative HBV pre-S1-pre-S2 consensus polypeptide from HBV genotype A not included in the herein described core-sAg fusion protein is provided below:

```
                                        (SEQ ID NO: 85)
MGGWSSKPRKGMGTNLSVPNPLGEEPDHQLDPAFGANSNNPDWDFNPIKD

HWPAANQVGVGAFGPGLTPPHGGILGWSPQAQGILTTVSTIPPPASTNRQ

SGRQPTPISPPLRDSHPQAMQWNSTAFHQALQDPRVRGLYFPAGGSSSGT

VNPAPNIASHISSISARTGDPVTN.
```

An illustrative HBV pre-S1-pre-S2 consensus polypeptide from HBV genotype B not included in the herein (SEQ ID NO: 86)
MGGWSSKPRKGMGTNLSVPNPLGEEPDHQLDPAFKANSENPDWDLNPHKD

NWPDANKVGVGAFGPGFTPPHGGLLGWSPQAQGLLTTVPAAPPPASTNRQ

SGRQPTPLSPPLRDTHPQAMQWNSTTFHQTLQDPRVRALYFPAGGSSSGT

VSPAQNTVSAISSILSKTGDPVPN.

An illustrative HBV pre-S1-pre-S2 consensus polypeptide from HBV genotype C not included in the herein described core-sAg fusion protein is provided below:

(SEQ ID NO: 87)
MGGWSSKPRQGMGTNLSVPNPLGEEPDHQLDPAFGANSNNPDWDFNPNKD

HWPEANQVGAGAFGPGFTPPHGGLLGWSPQAQGILTTVPAAPPPASTNRQ

SGRQPTPISPPLRDSHPQAMQWNSTTFHQALLDPRVRGLYFPAGGSSSGT

VNPVPTTASPISSIFSRTGDPAPN.

An illustrative HBV pre-S1-pre-S2 consensus polypeptide from HBV genotype D not included in the herein described core-sAg fusion protein is provided below:

(SEQ ID NO: 88)
MGQNLSTSNPLGEEPDHQLDPAFRANTANPDWDENPNKDTWPDANKVGAG

AFGLGETPPHGGLLGWSPQAQGILQTLPANPPPASTNRQSGRQPTPLSPP

LRNTHPQAMQWNSTTFHQTLQDPRVRGLYFPAGGSSSGTVNPVPTTASPI

SSIFSRIGDPALN.

In some embodiments, the core-sAg fusion proteins described herein do not comprise an HBV pre-S1-pre-S2 polypeptide comprising or consisting of an amino acid sequence of any one of SEQ ID NOs: 84-88, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84-88.

Optional Polypeptide Linker

As appropriate, the HBV core polypeptide and the HBV sAg polypeptide in the core-sAg fusion protein can be directly abutted or fused, or can be joined, connected or linked by one or more peptide linkers. In various embodiments, the one or more peptide linkers is selected from one or more of a polyalanine linker, a polyglycine linker, a cleavable linker, a flexible linker, a rigid linker, and combinations thereof, e.g., within a linker or within a full-length fusion polypeptide. Illustrative fusion protein linkers that can be used in the present fusion polypeptides to connect the HBV core polypeptide and the HBV sAg polypeptide are described, e.g., in Chen, et al., Adv Drug Deliv Rev. (2013) 65(10): 1357-1369. In some embodiments, the polyalanine linker comprises or consists of 2 or 3 contiguous alanine residues, e.g. AA, AAA, AAY or AAX, wherein X is any amino acid (e.g., A, C, D, E, F, G, H, I, K, L, M, N, P, Q, R, S, T, V, Y). In some embodiments, a polyglycine linker is used, e.g., GG, GGG, GGS, GSG or GGGS (SEQ ID NO:63). In some embodiments, the cleavable linker is selected from a 2A cleavable peptide. Illustrative 2A cleavable peptides that can be used to connect the HBV core polypeptide and the HBV sAg polypeptide are described, e.g., in Donnelly, et al., J. Gen. Virol (2001), 82, 1027-1041 and Chng, et al., mAbs (2015) 7:2, 403-412. Illustrative 2A cleavable peptides that can be used to link the HBV core polypeptide and the HBV sAg polypeptide include without limitation 2A cleavage sequences (e.g., foot-and-mouth disease virus (F2A), equine rhinitis A virus (E2A), porcine teschovirus-1 (P2A) and Thosea asigna virus (T2A)), optionally in combination with a furin recognition/cleavage sequences (e.g. RAKR (SEQ ID NO: 60), REKR (SEQ ID NO: 61) and RRKR (SEQ ID NO: 62)). In certain embodiments, a furin recognition/cleavage sequence (e.g., RAKR (SEQ ID NO: 60), REKR (SEQ ID NO: 61) and RRKR (SEQ ID NO: 62)) is combined or fused with a 2A cleavable peptide (e.g., foot-and-mouth disease virus (F2A), equine rhinitis A virus (E2A), porcine teschovirus-1 (P2A) and Thosea asigna virus (T2A)) in a single linker. See, e.g., Chng, et al., mAbs (2015) 7:2, 403-412. In some embodiments, the linker comprises a porcine teschovirus-1 (P2A) linker. In various embodiments, the 2A cleavable linker comprises or consists of an amino acid sequence of ATNFSLLKQAGDVEENPGP (SEQ ID NO: 56), APVKQTLNFDLLKLAGDVESNPGP (SEQ ID NO: 57), QCTNYALLKLAGDVESNPGP (SEQ ID NO: 58), or EGRGSLLTCGDVEENPGP (SEQ ID NO: 59), or an amino acid sequence that is at least 90%, 91%, 92%, 93%, 94%, 95%, 96%, 97%, 98% or at least 99% identical to ATNFSLLKQAGDVEENPGP (SEQ ID NO: 56), APVKQTLNFDLLKLAGDVESNPGP (SEQ ID NO: 57), QCTNYALLKLAGDVESNPGP (SEQ ID NO: 58), or EGRGSLLTCGDVEENPGP (SEQ ID NO: 59). In various embodiments, the 2A cleavable linker comprises or consists of an amino acid sequence of ATNFSLLKQAGDVEENPGP (SEQ ID NO: 56), or an amino acid sequence that is at least 90%, 91%, 92%, 93%, 94%, 95%, 96%, 97%, 98% or at least 99% identical to ATNFSLLKQAGDVEENPGP (SEQ ID NO: 56). As appropriate, in certain embodiments, a furin recognition/cleavage sequence can be positioned either at the N-terminus or the C-terminus of a 2A linker. In some embodiments, the cleavable linker comprises or consists of a furin recognition/cleavage site selected from RAKR (SEQ ID NO: 60), REKR (SEQ ID NO: 61) and RRKR (SEQ ID NO: 62). Illustrative linkers that can be used to link or connect the HBV core polypeptide and the HBV sAg polypeptide are provided in Table J.

TABLE J illustrative linkers for connecting HBV core and HBV sAg polypeptides in the core-sAg fusion protein

| SEQ ID NO: | NAME | SEQUENCE |
|---|---|---|
| | poly-alanine (2) | AA |
| | poly-alanine (3) | AAA |
| | poly-alanine-Tyr | AAY |
| | poly-alanine-XXX | AAX (X = any amino acid) |
| | poly-glycine (2) | GG |
| | poly-glycine (3) | GGG |
| | poly-glycine/serine (3) | GGS |
| | poly-glycine/serine (3) | GSG |
| 63 | Gly3Ser | GGGS |
| 60 | furin recognition site | RAKR |
| 61 | furin recognition site | REKR |

TABLE J-continued illustrative linkers for connecting
HBV core and HBV sAg polypeptides
in the core Signal or Leader Sequences In various embodiments, the immunogenic polypeptides described herein comprise a signal sequence or signal peptide, e.g., to direct intracellular trafficking of the polypeptide to a proteasomal or lysosomal compartment. In various embodiments, the immunogenic polypeptide comprises a signal sequence at the N-terminus and/or the C-terminus. In some embodiments, the immunogenic polypeptide comprises an N-terminal signal peptide or leader sequence. In various embodiments, the signal peptide or leader sequence is from a source protein selected from a serum protein, a cytokine, a chemokine, a chaperone protein, an invariant protein, and a protein that directs proteins to the lysosomal compartment. In some embodiments, the signal peptide or leader sequence is from a source protein selected from colony stimulating factor 2 (CSF2, GM-CSF), tissue type plasminogen activator (PLAT, t-PA), C-C motif chemokine ligand 7 (CCL7, MCP-3), C-X-C motif chemokine ligand 10 (CXCL10, IP-10), catenin beta 1 (CTNNB1), CD74 (p33; DHLAG; HLADG; Ia-GAMMA, invariant chain), serum albumin (ALB), polyubiquitin B/C (UBB/UBC), calreticulin (CALR), vesicular stomatitis virus G protein (VSV-G), lysosomal associated membrane protein 1 (LAMP-1) and lysosomal associated membrane protein 2 (LAMP-2). In various embodiments, the signal peptide or leader sequence is selected from an amino acid sequence of any one of SEQ ID NOs: 67-76, or a sequence that is at least 95%, 96%, 97%, 98%, or 99% identical to any one of SEQ ID NOs: 67-76. In certain embodiments, the immunogenic polypeptide comprises N-terminal and C-terminal signal sequences from LAMP-1, e.g, SEQ ID NOs: 77 and 78, respectively. Illustrative signal sequences that can be used in the present immunogenic polypeptides are provided in Table L.

TABLE L illustrative signal sequences

| SEQ ID NO: | source protein name | SEQUENCE |
|---|---|---|
| 67 | CSF2, GM-CSF | MWLQSLLLLGTVACSISV |
| 68 | PLAT, t-PA | MDAMKRGLCCVLLLCGAVFVSAR |
| 69 | CD74 | MHRRRSRSCREDQKPV |
| 70 | albumin | KWVTFISLLFLFSSAYS |
| 71 | β-catenin | MRKAAVSHWQQQSYLDSGIHSGATTTAPSLS |
| 72 | CCL7, MCP-3 | MNPSAAVIFCLILLGLSGTQGILDMAQPVGINTSTTCCYRFI NKKIPKQRLESYRRTTSSHCPREAVIFKTKLDKEICADPTQK WVQDFMKHLDKKTQTPKLASAGA |
| 73 | ubiquitin | MQIFVKTLTGKTITLEVEPSDTIENVKAKIQDKEGIPPDQQR LIFAGKQLEDGRTLSDYNIQKESTLHLVLRLRGG |
| 74 | calreticulin | MLLSVPLLLGLLGLAVA |
| 75 | VSV-G | MKCLLYLAFLFIGVNC |
| 76 | CXCL10, IP-10 | MNQTAILICCLIFLTLSGIQG |
| 77 | LAMP-1 N-terminal | MAPRSARRPLLLLLLLLLLGLMHCASAAMFMVKNGNGTACIM ANFSAAFSVNYDTKSGPKNMTLDLPSDATVVLNRSSCGKENT SDPSLVIAFGRGHTLTLNFTRNATRYSVQLMSFVYNLSDTHL FPNASSKEIKTVESITDIRADIDKKYRCVSGTQVHMNNVTVT LHDATIQAYLSNSSFSRGETRCEQDRPSPTTAPPAPPSPSPS PVPKSPSVDKYNVSGTNGTCLLASMGLQLNLTYERKDNTTVT RLLNINPNKTSASGSCGAHLVTLELHSEGTTVLLFQFGMNAS SSRFFLQGIQLNT1LPDARDPAFKAANGSLRALQATVGNSYK CNAEEHVRVTKAFSVNIFKVWVQAFKVEGGQFGSVEECLLDE NSLEDI |
| 78 | LAMP-1 C-terminal | GSEFTLIPIAVGGALAGLVIVLIAYLVGRKRSHAGYQTI |

Further provided are methods for making the immunogenic polypeptides described herein. In some implementations, the methods comprise constructing the immunogenic polypeptides using peptide synthesis. In some implementations, the methods comprise constructing, using synthetic or recombinant DNA technology, polynucleotides encoding each of the polypeptides of the bivalent antigen and expressing the polypeptides from an expression vector. In some implementations, the methods may further comprise inserting the polynucleotides into one or more vectors and expressing the encoded polypeptides in a cell. This can be done employing known recombinant techniques.

3. Polynucleotides Encoding Immunogenic Polypeptides

Provided are polynucleotides encoding the immunogenic polypeptides, described herein, vectors comprising such polynucleotides, and host cells (e.g., human cells, mammalian cells, yeast cells, plant cells, insect cells, bacterial cells, e.g., *E. coli*) comprising such polynucleotides or expression vectors. Provided herein are polynucleotides comprising nucleotide sequence(s) encoding any of the immunogenic polypeptides provided herein, as well as expression cassettes and vector(s) comprising such polynucleotide sequences, e.g., expression vectors for their efficient expression in host cells, e.g., mammalian cells. In various embodiments, the polynucleotide is a DNA, a cDNA, an mRNA, a self-amplifying RNA (SAM), a self-replicating RNA, or a self-amplifying replicon RNA (RepRNA). In some embodiments, the polynucleotide comprises or is expressed from an alphavirus self-replicating or self-amplifying replicon RNA (RepRNA). Self-replicating RNA and self-amplifying replicon RNA as modes of vaccine delivery are described, e.g., by Tews, et al., *Methods Mol Biol.* (2017) 1499:15-35; Démoulins, et al., *Methods Mol Biol.* (2017) 1499:37-75; Englezou, et al., *Mol Ther Nucleic Acids.* (2018) 12:118-134; McCollough, et al., *Vaccines* (Basel). (2014) 2(4):735-54; and McCollough, et al., *Mol Ther Nucleic Acids.* (2014) 3:e173.

The terms "polynucleotide" and "nucleic acid molecule" interchangeably refer to a polymeric form of nucleotides and includes both sense and anti-sense strands of RNA, cDNA, genomic DNA, and synthetic forms and mixed polymers of the above. As used herein, the term nucleic acid molecule may be interchangeable with the term polynucleotide. In some embodiments, a nucleotide refers to a ribonucleotide, deoxynucleotide or a modified form of either type of nucleotide, and combinations thereof. The terms also include without limitation, single- and double-stranded forms of DNA. In addition, a polynucleotide, e.g., a cDNA or mRNA, may include either or both naturally occurring and modified nucleotides linked together by naturally occurring and/or non-naturally occurring nucleotide linkages. The nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analogue, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). The above term is also intended to include any topological conformation, including single-stranded, double-stranded, partially duplexed, triplex, hairpinned, circular and padlocked conformations. A reference to a nucleic acid sequence encompasses its complement unless otherwise specified. Thus, a reference to a nucleic acid molecule having a particular sequence should be understood to encompass its complementary strand, with its complementary sequence. The term also includes codon-biased polynucleotides for improved expression in a desired viral expression vector or host cell.

A "substitution," as used herein, denotes the replacement of one or more amino acids or nucleotides by different amino acids or nucleotides, respectively.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location. "Isolated nucleic acid encoding an immunogenic polypeptide" refers to one or more nucleic acid molecules encoding such immunogenic polypeptides, including such nucleic acid molecule(s) in a single vector or multiple separate vectors, and such nucleic acid molecule(s) present at one or more locations in a host cell.

A "polynucleotide variant," as the term is used herein, is a polynucleotide that typically differs from a polynucleotide specifically disclosed herein in one or more substitutions, deletions, additions and/or insertions. Such variants may be naturally occurring or may be synthetically generated, for example, by modifying one or more of the polynucleotide sequences described herein and evaluating one or more biological activities of the encoded polypeptide as described herein and/or using any of a number of techniques well known in the art.

In some embodiments, the nucleic acid molecule is codon-biased to enhance expression in a desired host cell, e.g., in human cells, mammalian cells, yeast cells, plant cells, insect cells, or bacterial cells, e.g., *E. coli* cells. Accordingly, provided are polynucleotides encoding an immunogenic polypeptide, described herein, wherein the polynucleotides are codon-biased, comprise replacement heterologous signal sequences, and/or have mRNA instability elements eliminated. Methods to generate codon-biased nucleic acids can be carried out by adapting the methods described in, e.g., U.S. Pat. Nos. 5,965,726; 6,174,666; 6,291,664; 6,414,132; and 6,794,498. Preferred codon usage for expression of the immunogenic polypeptides from desired viral expression vectors and/or in desired host cells is provided, e.g., at kazusa.or.jp/codon/; and genscript.com/tools/codon-frequency-table.

In some embodiments, the polynucleotide encoding an immunogenic polypeptide, as described herein, has at least 80%, at least 85%, at least 90%, at least 91%, at least 92%, at least 93%, at least 94%, at least 95%, at least 96%, at least 97%, at least 98%, at least 99% identical, or 100% identical to a nucleic acid sequence selected from the group consisting of SEQ ID NOs: 27-37 and 89-94, as provided in Table M.

As appropriate, in certain embodiments, the 3'-end of a polynucleotide encoding one or more of the immunogenic polypeptides described herein comprises one or multiple tandem stop codons, e.g., two or more tandem TAG ("amber"), TAA ("ochre") or TGA ("opal" or "umber") stop codons. The multiple tandem stop codons can be the same or different.

Further provided are expression cassettes, comprising a polynucleotide encoding an immunogenic polypeptide, as described herein, operably linked to one or more regulatory sequences. In some embodiments, the polynucleotide is operably linked to and under the control of a constitutive promoter. In some embodiments, the promoter is selected from cytomegalovirus major immediate-early (CMV), the CMV enhancer fused to the chicken beta-actin promoter (CAG), human elongation factor-1α (HEF-1α), mouse cytomegalovirus (mouse CMV), Chinese hamster elongation factor-1α (CHEF-1α), and phosphoglycerate kinase (PGK).

TABLE M

Polynucleotides encoding immunogenic polypeptides

| SEQ ID NO: | HBV genotype | name | Polynucleotide sequence |
|---|---|---|---|
| 27 | B | Pol^A1 | ATGCCCCTGAGCTACCAGCACTTCAGGAAGCTGCTGCTGCTGGATGATGAGGCTGGCCCTCTGGAGGAGGAGC<br>TGCCCAGGCTGGCAGATGAGGGCCTCAACAGGAGAGTGGCAGAGGACCTGAACCTGGGCAACCTGAATGTGAG<br>CATCCCCTGGACCCACAAAGTGGGGAACTTCACTGGCCTCTACAGCAGCACAGTGCCAGTGTTCAACCCTGAG<br>TGGCAGACCCCCTCCTTCCCCCACATCCACCTCCAGGAGGACATCATCAACAGATGTCAGCAGTATGTGGGCC<br>CTCTGACAGTCAATGAGAAGAGGAGGCTGAAGCTGATCATGCCTGCCAGGTTCTACCCCAACCTGACCAAGTA<br>CCTCCCACTGGACAAGGGCATCAAGCCATACTATCCTGAGCATGTGGTGAACCACTACTTTCAGACCAGGCAC<br>TACCTGCACACACTGTGGAAGGCTGGCATCCTGTACAAGAGGGAGAGCACCAGATCAGCCTCTTTCTGTGGCT<br>CCCCCCTACAGCTGGGAGCAGGATCTCCAGCATGGCAGACTGGTGTTCCAGACCTCCAAGAGGCATGGGGACAA<br>GTCCTTTTGCCCCCAGAGCCCTGGCATCCTGCCCAGGAGCGAGCTCCACCACTTCCCCCCCTCCTCCAGCAGA<br>AGCCAGTCCCAGGGACCTGTGCTGTCCTGCTGGTGGCTCCAGTTCAGGAACAGTGAGCCCTGCAGTGAGTACT<br>GTCTGTGTCACATTGTGAACCTGATTGAGGACTGGGGGCCCTGCACTGAGCATGGAGAGCACAGGATCAGAAC<br>CCCCAGGACCCCAGCCAGAGTGACTGGAGGTGTGTTCCTGGTGGACAAGAACCCCCACAACACCACAGAGAGC<br>AGACTGGTGGTGGACTTCTCCCAGTTTTCAAGGGGCAACACCAGAGTGTCCTGGCCCAAGTTTGCAGTGCCCA<br>ACCTCCAGAGCCTGACCAACCTGCTGTCATCAAACCTGAGCTGGCTGTCCCTGGATGTGTCTGCTGCCTTCTA<br>CCACCTGCCCCTGCACCCTGCAGCCATGCCTCACCTCCTGGTGGGCAGCTCAGGCCTGAGCAGGTATGTGGCC<br>AGGCTGTCAAGCAACTCCAGAATCATCAACAACCAGCACAGGACCATGCAGAACCTGCATGACTCTTGCAGCA<br>GGAACCTGTATGTGAGCCTGATGCTGCTGTACAAGACCTATGGCAGGAAGCTGCACCTGTACTCCCACCCCAT<br>CATCCTGGGTTTCAGGAAGATCCCCATGGGAGTGGGACTGTCCCCCTTCCTGCTGGCCCAGTTCACCTCTGCC<br>ATCTGCTCTGTGGTGAGGAGAGCCTTCCCCCACTGCCTCGGCCTTCTCCTACATGCATGATGGTGCTGGGGG<br>CCAAGTCAGTGCAGCACCTGGAGTCTCTGTATGCTGCAGTCACCAACTTCCTGCTCAGCCTGGGCATCCACCT<br>GAACCCCCACAAGACCAAGAGGTGGGGCTACTCTCTGAACTTCATGGGCTATGTGATAGGCAGCTGGGGCACC<br>CTGCCACAGGAGCACATAGTGCAGAAGATCAAGATGTGCTTCAGGAAGCTGCCAGTGAACAGGCCCATTGATT<br>GGAAGGTGTGCCAGAGGATTGTGGGCCTGCTGGGCTTTGCAGCACCCTTCACACAGTGTGGCTACCCAGCTCT<br>GATGCCCCTGTATGCCTGCATCCAGGCCAAGCAGGCCTTCACCTTCTCCCCCACTTACAAGGCCTTCCTGTCC<br>AAGCAGTACCTGCACCTGTACCCTGTGGCAAGGCAGAGGCCAGGCCTCTGCCAGGTGTTTGCAGATGCCACCC<br>CCACAGGCTGGGGCCTGGCCATTGGCCACCAGAGGATGAGAGGGGCCTTTGTGAGCCCACTGCCAATCCACAC<br>AGCCCACCTGCTGGCAGCATGCTTTGCCAGGTCTGGTGCAAAGCTGATTGGCACTGACAACAGTGTG<br>GTGCTGTCCAGAAAGTACACCAGCTTCCCCTGGCTGCTGGGATGTGCTGCCAACTGGATTCTGAGGGGCACCA<br>GCTTTGTCTATGTGCCCTCTGCACTGAACCCTGCAGATGACCCCTCCAGGGGCAGACTGGGGCTGTACAGGCC<br>ACTGCTCAGACTGCTGTACAGGCCCACCACTGGCAGAACCTCCCTGTATGCAGACAGCCCCTCAGTGCCCTCT<br>CACCTGCCAGACAGAGTGCACTTTGCCAGCCCCTGCATGTTGCCTGGAGGCCCCCC |
| 28 | B | Pol^A3 | ATGCCCCTGAGCTACCAGCACTTCAGGAAGCTGCTGCTGCTGGATGATGAGGCTGGCCCTCTGGAGGAGGAGC<br>TGCCCAGGCTGGCAGATGAGGGCCTCAACAGGAGAGTGGCAGAGGACCTGAACCTGGGCAACCTGAATGTGAG<br>CATCCCCTGGACCCACAAAGTGGGGAACTTCACTGGCCTCTACAGCAGCACAGTGCCAGTGTTCAACCCTGAG<br>TGGCAGACCCCCTCCTTCCCCCACATCCACCTCCAGGAGGACATCATCAACAGATGTCAGCAGTATGTGGGCC<br>CTCTGACAGTCAATGAGAAGAGGAGGCTGAAGCTGATCATGCCTGCCAGGTTCTACCCCAACCTGACCAAGTA<br>CCTCCCACTGGACAAGGGCATCAAGCCATACTATCCTGAGCATGTGGTGAACCACTACTTTCAGACCAGGCAC<br>TACCTGCACACACTGTGGAAGGCTGGCATCCTGTACAAGAGGGAGAGCACCAGATCAGCCTCTTTCTGTGGCT<br>CCCCCTACAGCTGGGAGCAGGATCTCCAGCATGGCTGGTGGCTCCAGTTCAGGAACAGTGAGCCCTGCAG<br>TGAGTACTGTCTGTGTCACATTGTGAACCTGATTGAGGACTGGGGGCCCTGCACTGAGCATGGAGAGCACAGG<br>ATCAGAACCCCCAGGACCCCAGCCAGAGTGACTGGAGGTGTGTTCCTGGTGGACAAGAACCCCCACAACACCA<br>CAGAGAGCAGACTGGTGGTGGACTTCTCCCAGTTTTCAAGGGGCAACACCAGAGTGTCCTGGCCCAAGTTTGC<br>AGTGCCCAACCTCCAGAGCCTGACCAACCTGCTGTCATCAAACCTGAGCTGGCTGTCCCTGGATGTGTCTGCT<br>GCCTTCTACCACCTGCCCCTGCACCCTGCAGCCATGCCTCACCTCCTGGTGGGCAGCTCAGGCCTGAGCAGGT<br>ATGTGGCCAGGCTGTCAAGCAACTCCAGAATCATCAACAACCAGCACAGGACCATGCAGAACCTGCATGACTC<br>TTGCAGCAGGAACCTGTATGTGAGCCTGATGCTGCTGTACAAGACCTATGGCAGGAAGCTGCACCTGTACTCC<br>CACCCCATCATCCTGGGTTTCAGGAAGATCCCCATGGGAGTGGGACTGTCCCCCTTCCTGCTGGCCCAGTTCA<br>CCTCTGCCATCTGCTCTGTGGTGAGGAGAGCCTTCCCCCACTGCCTGGCCTTCTCCTACATGCATGATGTGGT<br>GCTGGGGGCCAAGTCAGTGCAGCACCTGGAGTCTCTGTATGCTGCAGTCACCAACTTCCTGCTCAGCCTGGGC<br>ATCCACCTGAACCCCCACAAGACCAAGAGGTGGGGCTACTCTCTGAACTTCATGGGCTATGTGATAGGCAGCT<br>GGGGCACCCTGCCACAGGAGCACATAGTGCAGAAGATCAAGATGTGCTTCAGGAAGCTGCCAGTGAACAGGCC<br>CATTGATTGGAAGGTGTGCCAGAGGATTGTGGGCCTGCTGGGCTTTGCAGCACCCTTCACACAGTGTGGCTAC<br>CCAGCTCTGATGCCCCTGTATGCCTGCATCCAGGCCAAGCAGGCCTTCACCTTCTCCCCCACTTACAAGGCCT<br>TCCTGTCCAAGCAGTACCTGCACCTGTACCCTGTGGCAAGGCAGAGGCCAGGCCTCTGCCAGGTGTTTGCAGA<br>TGCCACCCCCACAGGCTGGGGCCTGGCCATTGGCCACCAGAGGATGAGAGGGGCCTTTGTGAGCCCACTGCCA<br>ATCCACACAGCCCACCTGCTGGCAGCATGCTTTGCCAGGTCCAGGTCTGGTGCAAAGCTGATTGGCACTGACA<br>ACAGTGTGGTGCTGTCCAGAAAGTACACCAGCTTCCCCTGGCTGCTGGGATGTGCTGCCAACTGGATTCTGAG<br>GGGCACCAGCTTTGTCTATGTGCCCTCTGCACTGAACCCTGCAGATGACCCCTCCAGGGGCAGACTGGGGCTG<br>TACAGGCCACTGCTCAGACTGCTGTACAGGCCCACCACTGGCAGAACCTCCCTGTATGCAGACAGCCCCTCAG<br>TGCCCTCTCACCTGCCAGACAGAGTGCACTTTGCCAGCCCCTGCATGTTGCCTGGAGGCCCCCC |
| 29 | B | Pol^300 | ATGTCCAGCAGAAGCCAGTCCCAGGGACCTGTGCTGTCCTGCTGGTGGCTCCAGTTCAGGAACAGTGAGCCCT<br>GCAGTGAGTACTGTCTGTGTCACATTGTGAACCTGATTGAGGACTGGGGGCCCTGCACTGAGCATGGAGAGCA<br>CAGGATCAGAACCCCCAGGACCCCAGCCAGAGTGACTGGAGGTGTGTTCCTGGTGGACAAGAACCCCCACAAC<br>ACCACAGAGAGCAGACTGGTGGTGGACTTCTCCCAGTTTTCAAGGGGCAACACCAGAGTGTCCTGGCCCAAGT<br>TTGCAGTGCCCAACCTCCAGAGCCTGACCAACCTGCTGTCATCAAACCTGAGCTGGCTGTCCCTGGATGTGTC<br>TGCTGCCTTCTACCACCTGCCCCTGCACCCTGCAGCCATGCCTCACCTCCTGGTGGGCAGCTCAGGCCTGAGC<br>AGGTATGTGGCCAGGCTGTCAAGCAACTCCAGAATCATCAACAACCAGCACAGGACCATGCAGAACCTGCATG<br>ACTCTTGCAGCAGGAACCTGTATGTGAGCCTGATGCTGCTGTACAAGACCTATGGCAGGAAGCTGCACCTGTA<br>CTCCCACCCCATCATCCTGGGTTTCAGGAAGATCCCCATGGGAGTGGGACTGTCCCCCTTCCTGCTGGCCCAG<br>TTCACCTCTGCCATCTGCTCTGTGGTGAGGAGAGCCTTCCCCCACTGCCTGGCCTTCTCCTACATGCATGATG<br>TGGTGCTGGGGGCCAAGTCAGTGCAGCACCTGGAGTCTCTGTATGCTGCAGTCACCAACTTCCTGCTCAGCCT<br>GGGCATCCACCTGAACCCCCACAAGACCAAGAGGTGGGGCTACTCTCTGAACTTCATGGGCTATGTGATAGGC |

TABLE M-continued

Polynucleotides encoding immunogenic polypeptides

| SEQ ID NO: | HBV geno-type | name | Polynucleotide sequence |
|---|---|---|---|
| | | | AGCTGGGCACCCTGCCACAGGAGCACATAGTGCAGAAGATCAAGATGTGCTTCAGGAAGCTGCCAGTGAACA GGCCCATTGATTGGAAGGTGTGCCAGAGGATTGTGGGCCTGCTGGGCTTTGCAGCACCCTTCACACAGTGTGG CTACCCAGCTCTGATGCCCCTGTATGCCTGCATCCAGGCCAAGCAGGCCTTCACCTTCTCCCCACTTACAAG GCCTTCCTGTCCAAGCAGTACCTGCACCTGTACCCTGTGGCAAGGCAGAGGCCAGGCCTCTGCCAGGTGTTTG CAGATGCCACCCCCACAGGCTGGGGCCTGGCCATTGGCCACCAGAGGATGAGAGGGGCCTTTGTGAGCCCACT GCCAATCCACACAGCCCACCTGCTGGCAGCATGCTTTGCCAGGTCCAGGTCTGGTGCAAAGCTGATTGGCACT GACAACAGTGGTGCTGTCCAGAAAGTACACCAGCTTCCCCTGGCTGCTGGGATGTGCTGCCAACTGGATTC TGAGGGGCACCAGCTTTGTCTATGTGCCCTCTGCACTGAACCCTGCAGATGACCCCTCCAGGGGCAGACTGGG GCTGTACAGGCCACTGCTCAGACTGCTGTACAGGCCCACCACTGGCAGAACCTCCCTGTATGCAGACAGCCCC TCAGTGCCCTCTCACCTGCCAGACAGAGTGCACTTTGCCAGCCCCTGCATGTTGCCTGGAGGCCCCCC |
| 89 | B | Pol<sup>300</sup> ori | ATGTCTTCAAGATCCCAGAGTCAGGGCCCTGTACTTTCCTGCTGGTGGCTCCAGTTCAGGAACAGTGAGCCCT GCTCCGAATACTGTCTCTGCCATATCGTCAATCTTATCGAAGACTGGGGACCCTGTACCGAACATGGAGAACA TCGCATCAGGACTCCTAGGACCCCTGCTCGTGTTACAGGCGGGGTTTTTCTTGTTGACAAAAATCCTCACAAT ACCACAGAGTCTAGACTCGTGGTGGACTTCTCTCAATTTTCTAGGGGGAACACCCGTGTGTCTTGGCCAAAAT TCGCAGTCCCAAATCTCCAGTCACTCACCAACCTGTTGTCCTCCAATTTGTCCTGGTTATCGCTGGATGTGTC TGCGGCGTTTTATCATCTTCCTCTGCATCCTGCTGCTATGCCTCATCTTCTTGTTGGTTCTTCTGGACTATCA AGGTATGTTGCCCGTTTGTCCTCTAATTCCAGGATCATCAACAACCAGCACCGGACCATGCAAAACCTGCACG ACTCCTGCTCAAGGAACCTCTATGTTTCCCTCATGTTGCTGTACAAAACCTACGGACGGAAACTGCACTTGTA TTCCCATCCCATCATCTTGGGCTTTCGCAAAATTCCTATGGGAGTGGGCCTCAGTCCGTTTCTCTTGGCTCAG TTTACTAGTGCCATTTGTTCAGTGGTTCGTAGGGCTTTCCCCCACTGTCTGGCTTTCAGTTATATGCATGATG TGGTATTGGGGGCCAAGTCTGTACAACATCTTGAGTCCCTTTATGCCGCTGTTACCAATTTTCTTTTGTCTTT GGGTATACATTTAAACCCTCACAAAACAAAAAGATGGGGATATTCCCTTAACTTCATGGGATATGTAATTGGG AGTTGGGGCACATTGCCGCAGGAACATATTGTACAAAAAATCAAAATGTGTTTTAGGAAACTTCCTGTAAACC GGCCTATTGATTGGAAAGTATGTCAACGAATTGTGGGTCTTTTGGGGTTTGCCGCCCCTTCACGCAATGTGG ATATCCTGCTTTAATGCCTTTATATGCATGTATACAAGCAAAACAGGCTTTTACTTTCTCGCCAACTTACAAG GCCTTCCTAAGTAAACAGTATCTGCACCTTTACCCCGTTGCTCGGCAACGGCCTGGTCTGTGCCAAGTGTTTG CTGACGCAACCCCCACTGGTTGGGGCTTGGCCATAGGCCATCAGCGCATGCGTGGAGCCTTCGTGTCCTCT GCCGATCCATACTGCGCATCTCCTGGCCGCTTGTTTTGCTCGCAGCAGGTCTGGGCAAAACTCATCGGGACT GACAATTCTGTCGTGCTCTCCCGCAAGTATACATCCTTTCCATGGCTGCTAGGCTGTGCTGCCAACTGGATCC TGCGCGGGACGTCCTTTGTTTACGTCCCGTCGGCGCTGAATCCCGCGGACGACCCCTCCCGGGGCCGCTTGGG GCTCTACCGCCCGCTTCTCCGCTTGTTGTACCGACCGACTACGGGGCGCACCTCTCTCTACGGCACTCCCG TCTGTGCCTTCTCATCTGCCGGACCGTGTGCACTTCGCTTCACCTCTGCACGTCGCATGGAGACCACCGT |
| 90 | B | Pol<sup>300</sup> dint | ATGTCATCCAGATCCCAGAGTCAGGGCCCTGTCCTTTCCTGTTGGTGGCTCCAGTTCAGGAACAGTGAGCCCT GTTCTGAGTACTGTCTCTGCCACATTGTCAATCTGATTGAGGACTGGGGACCCCTGCACAGAGCATGGTGAACA CAGGATCAGGACTCCAGGACCCCTGCCAGGGTGACTGGTGGGGTTTTCCTTGTTGACAAAAATCCTCACAAC ACCACAGAGTCAAGGCTTGTGGTGGACTTCTCTCAATTTTCAAGGGGGAACACAAGGGTGTCTTGGCCCAAAT TTGCAGTCCCAAATCTCCAGTCTCTGACCAACCTGTTGTCCTCCAATTTGTCCTGGTTGTCTCTGGATGTCTC TGCTGCCTTTTATCATCTTCCTCTCCATCCTGCTGCTATGCCTCATCTTCTTGTTGGTTCTTCTGGCTCTCT AGGTATGTTGCCAGATTGTCCTCCAATTCCAGGATCATCAACAACCAGCACAGGACCATGCAAAACCTGCATG ACTCCTGCTCCAGAAACCTCTATGTTTCCTCATGTTGCTGTACAAAACCTATGGCAGGAAACTGCATTTGTA TTCCCATCCCATCATCTTGGGCTTCAGGAAAATTCCCATGGGAGTGGGCCTCAGTCCCTTCCTCTTGGCTCAG TTCACCAGTGCCATTTGTTCTGTTGTCAGGAGGGCTTTCCCCCACTGTCTTGCTTTCAGTTACATGCATGATG TGGTCTTGGGGGCCAAGTCTGTCCAACATCTTGAGTCACTTTATGCTGCTGTGACCAACTTTCTTTTGTCTTT GGGCATCCATTTGAACCCTCACAAAACCAAAGATGGGGCTATTCCCTCAATTTCATGGGCTATGTCATTGGG AGTTGGGGCACTTTGCCCCAGGAACACATTGTGCAAAAAATCAAGATGTGTTTCAGGAAACTTCCTGTGAACA GGCCATTGACTGGAAAGTCTGTCAGAATTGTGGGTCTTTTGGGGTTTGCAGCTCCTTTCACCCAATGTGG CTATCCTGCTTTGATGCCCTTGTATGCCTGCATCCAGGCCAAACAGGCTTTCACTTTCTCCCCCACTTACAAG GCCTTCCTCAGCAAACAGTATCTCCACCTTTACCCTGTTGCAAGGCAGAGGCCTGGTCTGTGCCAAGTGTTTG CTGATGCAACCCCCACTGGTTGGGGCTTGGCCATTGGCCATCAGAGAATGAGAGGTGCCTTTGTGTCCTCTCT CCCCATCCACACTGCTGCTCATCTCCTGGCAGCTTGCTTTGCAAGGACAGGTCTGGAGCCAAACTCATAGGGACT GACAATTCTGTGGTGCTCTCCAGAAAGTACACCTCCTTTCCTTGGCTGCTGGGCTGTGCAGCCAACTGGATCC TGAGGGGGACTTCCTTTGTTTATGTCCCCTCTGCCCTGAATCCTGCAGATGACCCCTCCAGGGGCAGGTTGGG GCTCTACAGACCCCTTCTCAGGTTGTTGTACAGACCAACAACAGGGAGGACCTCTCTATGCAGATTCCCCC TCTGTTCCTTCTCATCTTCCAGACAGAGTGCACTTTGCTTCTCCTCTGCATGTGGCTTGGAGACCTCCC |
| 91 | B | Pol<sup>300</sup> huCo low GC | ATGTCTAGCAGAAGCCAGTCCCAGGGACCTGTGCTGTCTTGTTGGTGGCTTCAGTTTCGGAATAGCGAGCCAT GTAGCGAGTATTGCCTGTGTCACATCGTGAATCTGATTGAGGATTGGGGACCATGCACAGAGCACGGAGAGCA CCGGATCAGAACCCCTAGGACACCAGCCCGCGTGACAGGAGGCGTGTTCCTGGTGGATAAGAACCCCCATAAT ACAACAGGAGCAGACTGGTGGTGGATTTTTCTCAGTTTTCGTGGGGCAATACAAGAGTGTCCTGGCCAAAGT TTGCCGTGCCCAATCTCCAGAGCTGACAAACCTGCTGTCTTCTAATCTGAGCTGGCTGTCCCTGGACGTGTC CGCCGCCTTTTACCACCTGCCACTGCACCCTGCCGCCATGCCCCACCTGCTGGGGCAGCTCCGGACTGAGC AGATACGTGGCAAGGCTGTCTAGCAATTCTAGAATTATTAATAATCAGCACAGAACAATGCAGAATCTGCATG ATTCTTGTAGCCGGAATCTGTACGTGAGCCTGATGCTGCTGTATAAACATATGGACAGCAAGCTGCACCTGTA TTCTCACCCTATTATTCTGGGCTTCCGGAAGATCCCTATGGGCGTGGGACTGTCCCCATTCCTGCTGGCCCAG TTTACCTCCGCCATCTGCTCTGTGGTCGGAGAGCCTTCCCACATTGTCTGGCTTTTCTTACATGCACGATG TGGTGCTGGGCGCCAAATCCGTGCAGCACCTGGAGTCTCTGTATGCCGCCGTGACAAACTTCCTGCTGAGCCT GGGCATCCACTGAATCCACATAAGACAAAGGACGGTGGGCTATTCTCTGAATTTTATGGGCTATGTGATCGGC AGCTGGGGAACCCTGCCACAGGAGCACATTGTGCAGAAGATCAAGATGTGCTTTCGCAAGCTGCCCGTGAATC GGCCTATCGATTGGAAGGTGTGCCAGAGGATCGTGGGACTGCTGGGATTCGCAGCACCCTTTACCCAGTGCGG CTACCCAGCCCTGATGCCACTGTATGCCTGTATCCAGGCCAAACAGGCCTTCACCTTTTCCCCTACATATAAG GCTTTCTGTCTAAGCAGTACCTGCATCTGTATCCAGTGGCAAGGCAGAGGCCAGGACTGTGCAGGTGTTTG CAGATGCAACACCAACAGGATGGGGACTGGCAATCGGACACCAGAGGATGAGAGGAGCCTTCGTGAGCCCACT |

TABLE M-continued

Polynucleotides encoding immunogenic polypeptides

| SEQ ID NO: | HBV genotype | name | Polynucleotide sequence |
|---|---|---|---|
| | | | GCCAATTCACACCGCCCACCTGCTGGCAGCATGCTTTGCAAGGTCCCGCTCTGGAGCAAAGCTGATTGGCACC
GATAACAGCGTGGTGCTGTCCAGAAAATACACCAGCTTCCCCTGGCTGCTGGGATGTGCAGCAAATTGGATTC
TGAGGGGCACCAGCTTCGTGTATGTGCCTTCCGCCCTGAATCCTGCCGATGATCCATCTCGAGGCAGACTGGG
ACTGTATAGGCCACTGCTGAGACTGCTGTATAGGCCTACCACAGGCAGAACATCCCTGTATGCCGACAGCCCA
TCCGTGCCCTCTCACCTGCCAGATAGAGTGCATTTCGCAAGCCCACTGCATGTGGCATGGAGGCCACCC |
| 92 | B | Pol300 ori_del CpG | ATGTCTTCAAGATCCCAGAGTCAGGGCCCTGTACTTTCCTGCTGGTGGCTCCAGTTCAGGAACAGTGAGCCCT
GCTCTGAATACTGTCTCTGCCATATTGTCAATCTTATAGAAGACTGGGGACCCTGTACTGAACATGGAGAACA
TAGGATCAGGACTCCTAGGACCCCTGCTAGAGTTACAGGGGGGGTTTTTCTTGTTGACAAAAATCCTCACAAT
ACCACAGAGTCTAGACTTGTGGTGGACTTCTCTCAATTTTCTAGGGGAACACCAGGGTGTCTTGGCCAAAAT
TTGCAGTCCCAAATCTCCAGTCACTCACCAACCTGTTGTCCTCCAATTTGTCCTGGTTATCCCTGGATGTGTC
TGCAGCCTTTTATCATCTTCCTCTGCATCCTGCTGCTATGCCTCATCTTCTTGTTGGTTCTTCTGGACTATCA
AGGTATGTTGCCAGGTTGTCCTCTAATTCCAGGATCATCAACAACCAGCACAGGACCATGCAAAACCTGCATG
ACTCCTGCTCAAGGAACCTCTATGTTTCCCTCATGTTGCTGTACAAAACCTATGGAAGGAAACTGCACTTGTA
TTCCCATCCCATCATCTTGGGCTTTAGAAAAATTCCTATGGGAGTGGGCCTCAGTCCCTTTCTCTTGGCTCAG
TTTACTAGTGCCATTTGTTCAGTGGTTAGAAGGGCTTTCCCCCACTGTCTGGCTTTCAGTTATATGCATGATG
TGGTATTGGGGGCCAAGTCTGTACAACATCTTGAGTCCCTTTATGCTGCTGTTACCAATTTTCTTTTGTCTTT
GGGTATACATTTAAACCCTCACAAAACAAAAGATGGGGATATTCCCTTAACTTCATGGGATATGTAATTGGG
AGTTGGGGCACATTGCCTCAGGAACATATTGTACAAAAAATCAAAATGTGTTTTAGGAAACTTCCTGTAAACA
GGCCTATTGATTGGAAAGTATGTCAAAGAATTGTGGGTCTTTTGGGGTTTGCAGCCCCTTTCACCCAATGTGG
ATATCCTGCTTTAATGCCTTTATATGCATGTATACAAGCAAAACAGGCTTTTACTTTCTCCCAACTTACAAG
GCCTTCCTAAGTAAACAGTATCTGCACCTTTACCCTGTTGCTAGGCAAAGGCCTGGTCTGTGCCAAGTGTTTG
CTGATGCAACCCCCACTGGTTGGGGTTGGCCATAGGCCATCAGAGGATGAGGGGAGCCTTTGTGTCTCCTCT
GCCTATCCATACTGCCCATCTCCTGGCAGCTTGTTTTGCTAGGACAGGTCTGGGGCAAAACTCATTGGGACT
GACAATTCTGTTGTGCTCTCCAGAAAGTATACATCCTTTCCATGGCTGCTAGGCGTGCTGCCAACTGGATCC
TGAGGGGGACATCCTTTGTTTATGTCCCTTCAGCACTGAATCCTGCTGATGACCCCTCCAGGGGCAGATTGGG
GCTCTACAGGCCCCTTCTCAGGTTGTTGTACAGACCCACTACTGGGAGAACCTCTCTCTATGCAGACTCCCCC
TCTGTGCCTTCTCATCTGCCTGACAGGGTGCACTTTGCTTCACCTCTGCATGTTGCATGGAGACCACCT |
| 93 | B | Pol300 IDT | ATGAGTTCCCGATCACAGAGTCAGGGGCCCGTCCTTTCATGTTGGTGGCTTCAGTTTCGAAACTCCGAGCCAT
GTTCTGAGTATTGTCTCTGCCACATTGTGAATCTTATTGAAGACTGGGGCCCTGCACCGAGCACGGCGAGCA
CCGAATACGGACACCTCGAACGCCAGCAAGAGTGACGGCGGAGTGTTCCTCGTCGACAAGAATCCACACAAC
ACGACGGAGAGTAGATTGGTCGTTGATTTCAGTCAATTTTCAAGAGGCAATACACGAGTTCTTGGCCGAAAT
TCGCCGTACCGAATCTGCAATCCTTGACAAATTTGCTTAGTTCTAATTTGTCTTGGCTTTCTCTCGATGTTTC
CGCCGCTTTCTATCACTTGCCCCTTCACCCAGCCGCGATGCCGCATCTCTTGGTGGGCAGCTCTGGACTTAGT
AGATACGTAGCTAGACTCAGTTCTAACTCACGGATAATAAATAACCAACATCGACACTATGCAGAACCTGCATG
ATTCTTGTTCCCGGAACTTGTATGTCTCCTTGATGTTGTTGTATAAAACTTATGGGCGAAAGCTTCATCGTA
TAGCCATCCGATTATATTGGGTTTTAGGAAAATTCCTATGGGTGTTGGCTTGAGCCCTTTTCTGCTGGCGCAA
TTTACTTCAGCTATCTGCTCAGTAGTACGCCGGGCGTTTCCCCATTGTCTTGCTTTCTCATACATGCATGATG
TAGTACTTGGGGCCAAGTCTGTACAACACCTTGAGAGTTTGTATGCCGCCGTAACTAATTTCCTTCTCTCTCT
CGGGATCCATCTTAACCCTCACAAAACGAAGAGGTGGGGTTATTCTCGAATTTCATGGGATATGTTATCGGG
TCTTGGGGAACGCTGCCTCAGGAACACATCGTCCAGAAAATCAAGATGTGTTTCAGAAAGTTGCCAGTGAACA
GACCGATAGATTGGAAGGTTTGCCAAAGAATTGTTGGCTTGTTGGGATTCGCAGCCCCATTCACACAGTGCGG
GTATCCGGCTTTGATGCCCCTTTATGCTTGTATCCAGGCAAAACAGGCATTCACCTTTTCACCGACTTACAAA
GCATTTCTTTCTAAGCAGTATCTCCATCTTTACCCTGTCGCTCGACAGCGGCCGGGGCTTTGCCAGGTTTTCG
CAGACGCAACCCCAACTGGTTGGGGTCTTGCGATCGGCCACCAGAGGATGCGCGGTGCATTCGTGTCCCGCT
CCCAATCCATACGGCCCACTTGCTGGCGGCGTGCTTCGCTCGAAGTAGAAGCGGGGCTAAATTGATCGGCACG
GACAATTCAGTCGTGTTGTCACGCAAATATACCTCCTTTCCTGGTTGCTCGGTTGCGCAGCAAACTGGATAC
TTCGGGGAACTAGTTTCGTTTATGCCCTCTGCTCTCAACCCCGCCGACGATCCTTCACGAGGGAGGCTGGG
TCTTTTACCGCCCATTGCTCAGGCTGCTTTACCGGCCTACCACTGGGAGAACAAGCTTGTACGCCGACAGCCCG
AGCGTCCCGTCTCATCTGCCCGACAGAGTTCACTTTGCGAGTCCATTGCACGTCGCTTGGCGCCCGCCG |
| 94 | B | Pol300_IDT_CpGdel | ATGAGTTCCAGATCACAGAGTCAGGGGCCTGTCCTTTCATGTTGGTGGCTTCAGTTTAGAAACTCAGAGCCAT
GTTCTGAGTATTGTCTCTGCCACATTGTGAATCTTATTGAAGACTGGGCCCCTGCACAGAGCATGGAGAGCA
CAGAATAAGGACACCTAGAACCCCAGCAAGAGTGACAGGTGGAGTGTTCCTGGTAGACAAGAATCCACACAAC
ACAACTGAGAGTAGATTGGTGGTTGATTTCAGTCAATTTTCAAGAGGCAATACAAGAGTTTCTTGGCCAAAAT
TTGCTGTACCCAATCTGCAATCCTTGACAAATTTGCTTAGTTCTAATTTGTCTTGGCTTTCTCTAGATGTTTC
TGCAGCTTTCTATCACTTGCCCCTTCACCCAGCAGCTATGCCTCATCTCTTGGTGGGCAGCTCTGGACTTAGT
AGATATGTAGCTAGACTCAGTTCTAACTCAAGGATAATAAATAACCAACATAGGACTATGCAGAACCTGCATG
ATTCTTGTTCCAGGAACTTGTATGTCTCCTTGATGTTGTTGTATAAAACTTATGGGAGAAAGCTTCATCGTA
TAGCCATCCTATTATATTGGGTTTTAGGAAAATTCCTATGGGTGTTGGCTTGAGCCCTTTTCTGCTGCCCAA
TTTACTTCAGCTATCTGCTCAGTAGTAAGGAGGGCCTTTCCCCATTGTCTTGCTTTCTCATACATGCATGATG
TAGTACTTGGGGCCAAGTCTGTACAACACCTTGAGTTTGTATGCAGCAGTAACTAATTTCCTTCTCTCTCT
TGGGATCCATCTTAACCCTCACAAAACCAAGAGGTGGGGTTATTCTCTGAATTTCATGGGATATGTTATAGGG
TCTTGGGGAACCCTGCCTCAGGAACATTGTCCAGAAAATCAAGATGTGTTTCAGAAAGTTGCCAGTGAACA
GACCAATAGATTGGAAGGTTTGCCAAAGAATTGTTGGCTTGTTGGGATTTGCAGCCCCATTCACACAGTGTGG
GTATCCTGCTTTGATGCCCCTTTATGCTTGTATCCAGGCAAAACAGGCATTCACCTTTTCACCCACTTACAAA
GCATTTCTTTCTAAGCAGTATCTCCATCTTTACCCTGTGGCTAGACAGAGGCCAGGGCTTTGCCAGGTTTTG
CAGATGCAACCCCAACTGGTTGGGGTCTTGCAATTGGCCATCAGAGGATGAGAGGTGCATTGTGTCCCACT
CCCAATCCATACTGCCCACTTGCTGGCAGCTTGCTTTGCTAGAAGTAGAAGTGGGGCTAAATTGATTGGCACA
GACAATTCAGTTGTGTTGTCAAGGAAATATACCTCCTTTCCTGGTTGCTTGGTTGTGCAGCAAACTGGATAC
TTAGGGGAACTAGTTTTGTTTATGCCCTCTGCTCTCAACCCTGCAGATGATCCTTCAAGAGGGAGGCTGGG
TCTTTTACAGGCCATTGCTCAGGCTGCTTTACAGGCCTACCACTGGGAGAACAAGCTTGTATGCAGACAGCCCC
AGTGTCCCCTCTCATCTGCCTGACAGAGTTCACTTTGCAAGTCCATTGCATGTTGCTTGGAGACCTCCA |

TABLE M-continued

Polynucleotides encoding immunogenic polypeptides

| SEQ ID NO: | HBV geno-type | name | Polynucleotide sequence |
|---|---|---|---|
| 30 | D | Pol^A1 | ATGCCCCTGAGCTACCAACACTTCAGGAGACTGCTGCTGCTGGATGATGAGGCAGGCCCTCTGGAGGAGGAGC
TGCCCAGGCTGGCAGATGAGGGCCTGAACAGGAGGGTGGCTGAGGACCTGAACCTGGGCAACCTGAATGTGAG
CATCCCTTGGACCCACAAAGTGGGCAACTTCACAGGCCTGTACAGCAGCACTGTGCCTGTGTTCAACCCCCAC
TGGAAGACACCCAGCTTCCCCAACATCCACCTGCACCAGGACATCATCAAGAAGTGTGAGCAGTTTGTGGGCC
CCCTGACAGTCAATGAGAAGAGGAGGCTCCAGCTGATCATGCCAGCCAGGTTCTACCCCAATGTGACCAAGTA
CCTCCCCCTGGACAAGGGCATCAAGCCTTACTATCCAGAGCACCTGGTGAACCACTACTTCCAGACCAGACAC
TACCTGCACACACTGTGGAAGGCAGGCATCCTGTACAAGAGGGAGACCACACAGTGCCTCCTTCTGTGGCA
GCCCCTACTCCTGGGAGCAGGAGCTGCAACATGGAGCTGAGTCCTTCCACCAGCAGTCCAGTGGCATCCTGAG
CAGGCCCCCTGTGGGCAGCGAGCTGCACAACCTGCCCCCCAACTCTGCCAGATCCCAGTCTGAGAGGCCAGTG
TTCCCTTGCTGGTGGCTCCAGTTCAGGAACAGCAAGCCCTGCCTCAGACTACTGCCTGAGCCACATTGTGAACC
TGCTGGAGGACTGGGGCCCCTGTGCAGAGCATGGGGAGCACCACATCAGAATCCCCAGGACCCCTGCCAGGGT
GACAGGAGGGGTGTTCCTGGTGGACAAGAACCCCCACAACACTGCAGAGTCCAGGCTGGTGGTGGACTTCTCC
CAGTTCAGCAGGGGCAACTACAGAGTCTCCTGGCCAAAGTTTGCTGTGCCCAACCTCCAGAGCCTGACAAACC
TGCTGAGCAGCAACCTGTCCTGGCTCTCCCTGGATGTGAGTGCAGCCTTCTATCACCTGCCCCTGCACCCAGC
AGCCATGCCACACCTGCTGGTGGGCTCCAGTGGCCTGTCCAGGTATGTGGCCAGGCTCTCCTCCAACTCCAGG
ATCTTCAACTATCAGCATGGCACCATGCAGAACCTGCATGACAGCTGCTCCAGGAACCTGTATGTGTCCCTGA
TGCTGCTCTATCAGACCTTTGGCAGGAAGCTGCACCTGTACAGCCACCCCATCATCCTGGGGTTCAGGAAGAT
CCCCATGGGTGTGGGCCTGTCCCCCTTCCTGCTGGCCCAGTTCACCAGTGCCATCTGCTCAGTGGTGAGGAGG
GCCTTCCCACACTGCCTGGCCTTCTCTTACATGCATGATGTGGTCCTGGGTGCCAAGTCTGTGCAGCACCTGG
AGAGCCTGTTCACAGCTGTGACAAACTTTCTCCTGAGCCTGGGCATCCACCTGAACCCCAACAAGACCAAGAG
GTGGGGTTATTCACTGCACTTCATGGGCTATGTGATTGGCTGCTATGGCTCTCTGCCACAGGACCACATCATC
CAGAAGATCAAGGAGTGCTTCAGAAAGCTGCCAGTGAACAGGCCCAATTGACTGGAAGGTGTGCCAGAGGATTG
TGGGCCTGCTGGGCTTTGCAGCCCCCTTCACCCAGTGTGGCTACCCTGCCCTGATGCCCCTGTATGCCTGCAT
CCAGAGCAAGCAGGCCTTCACCTTTTCCCCCACTTACAAGGCCTTCCTGTGCAAGCAGTACCTGAACCTGTAC
CCTGTGGCCAGGCAGAGACCTGGGCTGTGCCAGGTGTTTGCAGATGCCACCCCCACAGGATGGGGACTGGTCA
TGGGACACCAGAGGATGAGGGGCACCTTCAAGGCACCCCTGCCCATCCACACAGCCCACCTGCTGGCTGCCTG
CTTTGCCAGGAGCAGGAGTGGGGCCAACATCCTGGGCACAGACAACTCTGTGGTGCTGAGCAGGAAGTACACA
TCCTTCCCCTGGCTGCTGGGATGTGCAGCCAACTGGATCCTGAGGGGCACCAGCTTTGTGTATGTGCCCTCTG
CCCTCAACCCTGCAGATGATCCAAGCAGGGGCAGGCTGGGACTGTACAGGCCACTGCTCAGACTGCCCTTCAG
GCCCACCACTGGCAGGACCAGCCTGTATGCTGACTCCCCATCTGTGCCCTCCCACCTGCCTGACAGAGTGCAC
TTTGCCTCCCCACTGCATGTGGCCTGGAGGCCCCCA |
| 31 | D | Pol^A3 | ATGCCCCTGAGCTACCAACACTTCAGGAGACTGCTGCTGCTGGATGATGAGGCAGGCCCTCTGGAGGAGGAGC
TGCCCAGGCTGGCAGATGAGGGCCTGAACAGGAGGGTGGCTGAGGACCTGAACCTGGGCAACCTGAATGTGAG
CATCCCTTGGACCCACAAAGTGGGCAACTTCACAGGCCTGTACAGCAGCACTGTGCCTGTGTTCAACCCCCAC
TGGAAGACACCCAGCTTCCCCAACATCCACCTGCACCAGGACATCATCAAGAAGTGTGAGCAGTTTGTGGGCC
CCCTGACAGTCAATGAGAAGAGGAGGCTCCAGCTGATCATGCCAGCCAGGTTCTACCCCAATGTGACCAAGTA
CCTCCCCCTGGACAAGGGCATCAAGCCTTACTATCCAGAGCACCTGGTGAACCACTACTTCCAGACCAGACAC
TACCTGCACACACTGTGGAAGGCAGGCATCCTGTACAAGAGGGAGACCACACAGTGCCTCCTTCTGTGGCA
GCCCCTACTCCTGGGAGCAGGAGCTGCAACATGGATGCTGGTGGCTCCAGTTCAGGACAGCAAGCCCTGCTC
AGACTACTGCCTGAGCCACATTGTGAACCTGCTGGAGGACTGGGGCCCCTGTGCAGAGCATGGGGAGCACCAC
ATCAGAATCCCCAGGACCCCTGCCAGGGTGACAGGAGGGGTGTTCCTGGTGGACAAGAACCCCCACAACACTG
CAGAGTCCAGGCTGGTGGTGGACTTCTCCCAGTTCAGCAGGGGCAACTACAGAGTCTCCTGGCCAAAGTTTGC
TGTGCCCAACCTCCAGAGCCTGACAAACCTGCTGAGCAGCAACCTGTCCTGGCTCTCCCTGGATGTGAGTGCA
GCCTTCTATCACCTGCCCCTGCACCCAGCAGCCATGCCACACCTGCTGGTGGGCTCCAGTGGCCTGTCCAGGT
ATGTGGCCAGGCTCTCCTCCAACTCCAGGATCTTCAACTATCAGCATGGCACCATGCAGAACCTGCATGACAG
CTGCTCCAGGAACCTGTATGTGTCCCTGATGCTGCTCTATCAGACCTTTGGCAGGAAGCTGCACCTGTACAGC
CACCCCATCATCCTGGGGTTCAGGAAGATCCCCATGGGTGTGGGCCTGTCCCCCTTCCTGCTGGCCCAGTTCA
CCAGTGCCATCTGCTCAGTGGTGAGGAGGGCCTTCCCACACTGCCTGGCCTTCTCTTACATGCATGATGTGGT
CCTGGGTGCCAAGTCTGTGCAGCACCTGGAGAGCCTGTTCACAGCTGTGACAAACTTTCTCCTGAGCCTGGGC
ATCCACCTGAACCCCAACAAGACCAAGAGGTGGGGTTATTCACTGCACTTCATGGGCTATGTGATTGGCTGCT
ATGGCTCTCTGCCACAGGACCACATCATCCAGAAGATCAAGGAGTGCTTCAGAAAGCTGCCAGTGAACAGGCC
AATTGACTGGAAGGTGTGCCAGAGGATTGTGGGCCTGCTGGGCTTTGCAGCCCCCTTCACCCAGTGTGGCTAC
CCTGCCCTGATGCCCCTGTATGCCTGCATCCAGAGCAAGCAGGCCTTCACCTTTTCCCCCACTTACAAGGCCT
TCCTGTGCAAGCAGTACCTGAACCTGTACCCTGTGGCCAGGCAGAGACCTGGGCTGTGCCAGGTGTTTGCAGA
TGCCACCCCCACAGGATGGGGACTGGTCATGGGACACCAGAGGATGAGGGGCACCTTCAAGGCACCCCTGCCC
ATCCACACAGCCCACCTGCTGGCTGCCTGCTTTGCCAGGAGCAGGAGTGGGGCCAACATCCTGGGCACAGACA
ACTCTGTGGTGCTGAGCAGGAAGTACACATCCTTCCCCTGGCTGCTGGGATGTGCAGCCAACTGGATCCTGAG
GGGCACCAGCTTTGTGTATGTGCCCTCTGCCCTCAACCCTGCAGATGATCCAAGCAGGGGCAGGCTGGGACTG
TACAGGCCACTGCTGCAGACTGCCCTTCAGGCCCACCACTGGCAGGACCAGCCTGTATGCTGACTCCCCATCTG
TGCCCTCCCACCTGCCTGACAGAGTGCACTTTGCCTCCCCACTGCATGTGGCCTGGAGGCCCCCA |
| 32 | D | Pol^300 | ATGTCTGCCAGATCCCAGTCTGAGAGGCCAGTGTTCCCTTGCTGGTGGCTCCAGTTCAGGAACAGCAAGCCCT
GCTCAGACTACTGCCTGAGCCACATTGTGAACCTGCTGGAGGACTGGGGCCCCTGTGCAGAGCATGGGGAGCA
CCACATCAGAATCCCCAGGACCCCTGCCAGGGTGACAGGAGGGGTGTTCCTGGTGGACAAGAACCCCCACAAC
ACTGCAGAGTCCAGGCTGGTGGTGGACTTCTCCCAGTTCAGCAGGGGCAACTACAGAGTCTCCTGGCCAAAGT
TTGCTGTGCCCAACCTCCAGAGCCTGACAAACCTGCTGAGCAGCAACCTGTCCTGGCTCTCCCTGGATGTGAG
TGCAGCCTTCTATCACCTGCCCCTGCACCCAGCAGCCATGCCACACCTGCTGGTGGGCTCCAGTGGCCTGTCC
AGGTATGTGGCCAGGCTCTCCTCCAACTCCAGGATCTTCAACTATCAGCATGGCACCATGCAGAACCTGCATG
ACAGCTGCTCCAGGAACCTGTATGTGTCCCTGATGCTGCTCTATCAGACCTTTGGCAGGAAGCTGCACCTGTA
CAGCCACCCCATCATCCTGGGGTTCAGGAAGATCCCCATGGGTGTGGGCCTGTCCCCCTTCCTGCTGGCCCAG
TTCACCAGTGCCATCTGCTCAGTGGTGAGGAGGGCCTTCCCACACTGCCTGGCCTTCTCTTACATGCATGATG
TGGTCCTGGGTGCCAAGTCTGTGCAGCACCTGGAGAGCCTGTTCACAGCTGTGACAAACTTTCTCCTGAGCCT |

TABLE M-continued

Polynucleotides encoding immunogenic polypeptides

| SEQ ID NO: | HBV genotype | name | Polynucleotide sequence |
|---|---|---|---|
| | | | GGGCATCCACCTGAACCCCAACAAGACCAAGAGGTGGGGTTATTCACTGCACTTCATGGGCTATGTGATTGGC<br>TGCTATGGCTCTCTGCCACAGGACCACATCATCCAGAAGATCAAGGAGTGCTTCAGAAAGCTGCCAGTGAACA<br>GGCCAATTGACTGGAAGGTGTGCCAGAGGATTGTGGGCCTGCTGGGCTTTGCAGCCCCCTTCACCCAGTGTGG<br>CTACCCTGCCCTGATGCCCCTGTATGCCTGCATCCAGAGCAAGCAGGCCTTCACCTTTTCCCCCACTTACAAG<br>GCCTTCCTGTGCAAGCAGTACCTGAACCTGTACCCTGTGGCCAGGCAGAGACCTGGGCTGTGCCAGGTGTTTG<br>CAGATGCCACCCCCACAGGATGGGGACTGGTCATGGGACACCAGAGGATGAGGGGCACCTTCAAGGCACCCCT<br>GCCCATCCACACAGCCCACCTGCTGGCTGCCTGCTTTGCCAGGAGCAGGAGTGGGGCCAACATCCTGGGCACA<br>GACAACTCTGTGGTGCTGAGCAGGAAGTACACATCCTTCCCCTGGCTGCTGGGATGTGCAGCCAACTGGATCC<br>TGAGGGGCACCAGCTTTGTATGTGCCCTCTGCCCTCAACCCTGCAGATGATCAAGCAGGGGCAGGCTGGG<br>ACTGTACAGGCCACTGCTCAGACTGCCCTTCAGGCCCACCACTGGCAGGACCAGCCTGTATGCTGACTCCCCA<br>TCTGTGCCCTCCCACCTGCCTGACAGAGTGCACTTTGCCTCCCCACTGCATGTGGCCTGGAGGCCCCCA |
| 33 | B/C | Core-<br>sAg | ATGGACATTGACCCCTACAAGGAGTTTGGGGCCAGTGTGGAGCTGCTGTCTTTTCTGCCATCTGACTTCTTCC<br>CCAGTGTGAGGGACCTGCTGGACACTGCCTCAGCACTGTACAGAGAGGCCCTGGAGAGCCCAGAGCACTGCTC<br>CCCCCACACACAGCCCTGAGGCAGGCCATCCTCTGCTGGGGGGAGCTGATGAACCTGGCCACCTGGGTGGGC<br>TCCAACCTGGAGGACCCTGCCTCAAGGGAGCTGGTGGTCAGCTATGTCAATGTGAACATGGGCCTCAAGATCA<br>GGCAGCTGCTGTGGTTCCACATCTCCTGCCTGACCTTTGGCAGGGAGACAGTCCTGGAGTACCTGGTGAGCTT<br>TGGGGTGTGGATCAGGACCCCCCCTGCCTACAGGCCCCCAATGCTCCCATCCTGTCCACCCTGCCAGAGACC<br>ACTGTGGTCAGGAGAAGGGGCAGGTCCCCCAGGAGGAGAACCCCCTCTCCCAGGAGGAGGAGAAGCCAGTCCC<br>CCAGGAGGAGGAGGAGCCAGAGCAGAGAGTCTCAGTGCATGGAGAGCACCACATCAGGCTTCCTGGGCCCCCT<br>GCTGGTGCTCCAGGCAGGCTTCTTTCTGCTGACCAGGATTCTGACCATCCCCAGTCCTGGACAGCTGGTGG<br>ACCTCCCTGAATTTTCTGGGGGGGCCCCTACCTGTCCTGGCCAGAACTCTCAGTCTCCCACCTCGAATCACT<br>CACCAACCAGCTGTCCCCCATCTGTCCTGGCTACAGGTGGATGTGCCTGAGGAGATTCATCATCTTCCTGTG<br>CATCCTGCTGCTGTGCCTGATCTTTCTGCTGGTGCTGCTGGACTACCAGGGCATGCTGCCAGTGTGCCCTCTC<br>ATCCCAGGCAGCTCCACCACATCCACAGGACCTTGCAAGACATGCACCACACCAGCCCAGGGCACCAGCATGT<br>TCCCCTCCTGCTGTTGCACCAAGCCAACAGATGGCAACTGCACATGCATTCCCATCCCCTCCAGCTGGGCCTTT<br>TGCCAGGTTTCTGTGGGAGTGGGCCAGTGTGAGATTTTCCTGGCTGTCTCTTCTGGTGCCCTTTGTGCAGTGG<br>TTTGTGGGCCTGTCCCCTACAGTGTGGCTGAGTGTCATCTGGATGATGTGGTACTGGGGCCCCTCCCTGTACA<br>ACATCCTCTCTCCCTTTCTGCCCTCTGCTGCCAATCTTCTTTTGCCTGTGGGTGTACATC |
| 34 | B/C | Core-<br>P2A-<br>sAg | ATGGACATTGACCCCTACAAGGAGTTTGGGGCCAGTGTGGAGCTGCTGTCTTTTCTGCCATCTGACTTCTTCC<br>CCAGTGTGAGGGACCTGCTGGACACTGCCTCAGCACTGTACAGAGAGGCCCTGGAGAGCCCAGAGCACTGCTC<br>CCCCCACCACACAGCCCTGAGGCAGGCCATCCTCTGCTGGGGGGAGCTGATGAACCTGGCCACCTGGGTGGGC<br>TCCAACCTGGAGGACCCTGCCTCAAGGGAGCTGGTGGTCAGCTATGTCAATGTGAACATGGGCCTCAAGATCA<br>GGCAGCTGCTGTGGTTCCACATCTCCTGCCTGACCTTTGGCAGGGAGACAGTCCTGGAGTACCTGGTGAGCTT<br>TGGGGTGTGGATCAGGACCCCCCCTGCCTACAGGCCCCCAATGCTCCCATCCTGTCCACCCTGCCAGAGACC<br>ACTGTGGTCAGGAGAAGGGGCAGGTCCCCCAGGAGGAGAACCCCCTCTCCCAGGAGGAGGAGAAGCCAGTCCC<br>CCAGGAGGAGGAGGAGCCAGAGCAGAGAGTCTCAGTGCGGCAGTGGGGCAACAACTTCAGCCTCCTGAAACA<br>GGCAGGGGATGTGGAGGAAAACCCAGGCCCCGAGAGCACCACATCAGGCTTCCTGGGCCCCCTGCTGGTGCTC<br>CAGGCAGGCTTCTTTCTGCTGACCAGGATTCTGACCATCCCCCAGTCCTGGACAGCTGGTGGACCTCCCTGA<br>ATTTTCTGGGGGGGCCCCTACCTGTCCTGGCCAGAACTCTCAGTCTCCCACCTCGAATCACTCACCAACCAG<br>CTGTCCCCCATCTGTCCTGGCTACAGGTGGATGTGCCTGAGGAGATTCATCATCTTCCTGTGCATCCTGCTG<br>CTGTGCCTGATCTTTCTGCTGGTGCTGCTGGACTACCAGGGCATGCTGCCAGTGTGCCCTCTCATCCCAGGCA<br>GCTCCACCACATCCACAGGACCTTGCAAGACATGCACCACACCAGCCCAGGGCACCAGCATGTTCCCCTCCTG<br>CTGTTGCACCAAGCCAACAGATGGCAACTGCACATGCATTCCCATCCCCTCCAGCTGGGCCTTTGCCAGGTTT<br>CTGTGGGAGTGGGCCAGTGTGAGATTTTCCTGGCTGTCTCTTCTGGTGCCCTTTGTGCAGTGGTTTGTGGGCC<br>TGTCCCCTACAGTGTGGCTGAGTGTCATCTGGATGATGTGGTACTGGGGCCCCTCCCTGTACAACATCCTCTC<br>TCCCTTTCTGCCCTCTGCTGCCAATCTTCTTTTGCCTGTGGGTGTACATC |
| 35 | D/D | Core-<br>sAg | ATGGACATTGACCCCTACAAGGAGTTTGGGGCCAGTGTGGAGCTGCTCTCCTTCCTGCCCTCAGACTTCTTTC<br>CCAGTGTGAGGGACCTGCTTGACACAGCCTCTGCCCTCTACAGAGAGGCCCTGGAGAGCCCAGAGCATTGCTC<br>CCCCCACCACACAGCACTGAGGCAGGCCATCCTGTGTGGGGGGAGCTGATGACCCTGTGCACCTGGGTGGGT<br>GTCAACCTGGAGGACCCCAGCTTCCAGGGATCTGGTGGTCAGCTATGTGAACACAAACATGGGCCTCAAGTTCA<br>GGCAGCTGCTCTGGTTCCACATCTCCTGCCTGACCTTTGGCAGGGAGACTGTGCTGGAGTACCTGGTGAGCTT<br>TGGAGTGTGGATCAGGACCCCACCTGCCTACAGGCCCCCAATGCCCCCATCCTGTCCACCCTGCCTGAGACC<br>ACAGTGGTGAGGAGGAGGGGAGGTCCCCAGAAGGAGGAGACCCCTTCTCCCAGGAGGAGGAGAGTCAGTCTC<br>CCAGGAGGAGGAGGAGCCAGAGCAGAGAGTCCCAGTGTATGGAACATCACCTCTGGCTTTCTGGGACCCCT<br>GCTGGTGCTCCAGGCAGGCTTTTCCTGCTGACCAGGATCCTGACCATCCCTCAGAGCCTGGATCCTGGTGG<br>ACATCTCTGAATTTTCTTGGGGGCACCACTGTGTGCCTGGACAGAACTCCCAGTCTCCCACCTCCAACCACA<br>GCCCAACATCCTGTCCCCCATCTGCCCAGGCTACAGGTGGATGTGCCTGAGGAGGTTCATCATCTTCCTGTT<br>CATCCTGCTGCTGTGCCTGATCTTTCTGCTGGTGCTCCTGGACTATCAGGGCATGCTGCCAGTGTGCCCACTG<br>ATCCCAGGCAGCTCCACCACAAGCACAGGACCTTGCAGGACATGCACCACACCTGCCCAGGGCACTTCCATGT<br>ACCCATCTTGCTGTTGCACCAAGCCATCTGATGGCAATTGCACCTGCATCCCCATCCCCTCAAGCTGGGCCTT<br>TGGCAAGTTCCTGTGGGAGTGGCAAGTGCCAGATTCTCTTGGCTGAGCCTGCTGGTCCTTTTGTGCAGTGG<br>TTTGTGGGCCTGAGCCCCACTGTGTGGCTGTCTGTGATCTGGATGATGTGGTACTGGGGCCCCTCCCTGTATT<br>CAATCCTGAGCCCTTTTCTGCCACTGCTGCCCATCTTCTTTTGTCTGTGGGTGTACATC |
| 36 | D/D | Core-<br>P2A-<br>sAg | ATGGACATTGACCCCTACAAGGAGTTTGGGGCCAGTGTGGAGCTGCTCTCCTTCCTGCCCTCAGACTTCTTTC<br>CCAGTGTGAGGGACCTGCTTGACACAGCCTCTGCCCTCTACAGAGAGGCCCTGGAGAGCCCAGAGCATTGCTC<br>CCCCCACCACACAGCACTGAGGCAGGCCATCCTGTGTGGGGGGAGCTGATGAACCTGGCCACCTGGGTGGGT<br>GTCAACCTGGAGGACCCAGCTTCCAGGGATCTGGTGGTCAGCTATGTGAACACAAACATGGGCCTCAAGTTCA<br>GGCAGCTGCTCTGGTTCCACATCTCCTGCCTGACCTTTGGCAGGGAGACTGTGCTGGAGTACCTGGTGAGCTT<br>TGGAGTGTGGATCAGGACCCCACCTGCCTACAGGCCCCCAATGCCCCCATCCTGTCCACCCTGCCTGAGACC<br>ACAGTGGTGAGGAGGAGGGGAGGTCCCCCAGAAGGAGGACCCCTTCTCCCAGGAGGAGGAGAGTCAGTCTC |

TABLE M-continued

Polynucleotides encoding immunogenic polypeptides

| SEQ ID NO: | HBV genotype | name | Polynucleotide sequence |
|---|---|---|---|
| | | | CCAGGAGGAGGAGGAGCCAGAGCAGAGAGTCCCAGTGTGGCAGTGGGGCAACCAACTTCAGCCTCCTGAAACA<br>GGCAGGGGATGTGGAGGAAAACCCAGGCCCCGAGAACATCACCTCTGGCTTTCTGGGACCCCTGCTGGTGCTC<br>CAGGCAGGCTTTTTCCTGCTGACCAGGATCCTGACCATCCCTCAGAGCCTGGACTCCTGGTGGACATCTCTGA<br>ATTTTCTTGGGGGCACCACTGTGTGCCTGGGACAGAACTCCCAGTCTCCCACCTCCAACCACAGCCCAACATC<br>CTGTCCCCCCATCTGCCCAGGCTACAGGTGGATGTGCCTGAGGAGGTTCATCATCTTCCTGTTCATCCTGCTG<br>CTGTGCCTGATCTTTCTGCTGGTGCTCCTGGACTATCAGGGCATGCTGCCAGTGTGCCCACTGATCCCAGGCA<br>GCTCCACCACAAGCACAGGACCTTGCAGGACATGCACCACACCTGCCCAGGGCACTTCCATGTACCCATCTTG<br>CTGTTGCACCAAGCCATCTGATGGCAATTGCACCTGCATCCCCATCCCCTCAAGCTGGGCCTTTGGCAAGTTC<br>CTGTGGGAGTGGGCAAGTGCCAGATTCTCTTGCTGAGCCTGCTGGTCCCTTTTGTGCAGTGGTTTGTGGGCC<br>TGAGCCCCACTGTGTGGCTGTCTGTGATCTGGATGATGTGGTACTGGGGCCCCTCCCTGTATTCAATCCTGAG<br>CCCTTTTCTGCCACTGCTGCCCATCTTCTTTTGTCTGTGGGTGTACATC |
| 37 | D/D | iCore-<br>P2A-<br>sAg | ATGGACATTGACCCCTACAAGGAGTTTGGGGCCAGTGTGGAGCTGCTGTCTTTTCTGCCATCTGACTTCTTCC<br>CCAGTGTGAGGGACCTGCTGGACACTGCCTCAGCACTGTACAGAGAGGCCCTGGAGAGCCCAGAGCACTGCTC<br>CCCCCACCACACAGCCCTGAGGCAGGCCATCCTCTGCTGGGGGGAGCTGATGAACCTGGCCACCTGGGTGGGC<br>GTCAACCTGGAGGACCCTGCCTCAAGGGACCTGGTGGTCAGCTATGTCAATACGAACATGGGCCTCAAGTTCA<br>GGCAGCTGCTGTGGTTCCACATCTCCTGCCTGACCTTTGGCAGGGAGACAGTCCTGGAGTACCTGGTGAGCTT<br>TGGGGTGTGGATCAGGACCCCCCCTGCCTACAGGCCCCCAATGCTCCCATCCTGTCCACCCTGCCAGAGACC<br>ACTGTGGTCAGGAGAAGGGGCAGGTCCCCCAGGAGGAGAACCCCCTCTCCCAGGAGGAGGAGAAGCCAGTCCC<br>CCAGGAGGAGGAGGAGCCAGAGCAGAGAGTCTCAGTGCGGCAGTGGGGCAACCAACTTCAGCCTCCTGAAACA<br>GGCAGGGGATGTGGAGGAAAACCCAGGCCCCGAGAACATCACATCAGGCTTCCTGGGCCCCCTGCTGGTGCTC<br>CAGGCAGGCTTCTTTCTGCTGACCAGGATTCTGACCATCCCCCAGTCCCTGGACAGCTGGTGGACCTCCCTGA<br>ATTTTCTGGGGGGGACCACTGTCTGTCTTGGCCAGAACTCTCAGTCTCCCACCTCGAATCACTCACCAACCAG<br>CTGTCCCCCCATCTGTCCTGGCTACAGGTGGATGTGCCTGAGGAGATTCATCATCTTCCTGTTCATCCTGCTG<br>CTGTGCCTGATCTTTCTGCTGGTGCTGCTGGACTACCAGGGCATGCTGCCAGTGTGCCCTCTCATCCCAGGCA<br>GCTCCACCACATCCACAGGACCTTGCAGGACATGCACCACACCAGCCCAGGGCACCAGCATGTACCCCTCCTG<br>CTGTTGCACCAAGCCATCAGATGGCAACTGCACATGCATTCCCATCCCCTCCAGCTGGGCCTTTGGCAAGTTT<br>CTGTGGGAGTGGGCCAGTGCGAGATTTTCCTGGCTGTCTCTTCTGGTGCCCTTTGTGCAGTGGTTTGTGGGCC<br>TGTCCCCTACAGTGTGGCTGAGTGTCATCTGGATGATGTGGTACTGGGGCCCCTCCCTGTACAGCATCCTCTC<br>TCCCTTTCTGCCTCTGCTGCCAATCTTCTTTTGCCTGTGGGTGTACATC |

4. Vectors and Host Cells

Further provided are vectors comprising one or more polynucleotides encoding one or more of the immunogenic polypeptides, described herein, or an expression cassette comprising such polynucleotides. A vector can be of any type, for example, a recombinant vector such as an expression vector. Vectors include without limitation, plasmids, cosmids, bacterial artificial chromosomes (BAC) and yeast artificial chromosomes (YAC) and vectors derived from bacteriophages or plant or animal (including human) viruses. Vectors can comprise an origin of replication recognized by the proposed host cell and in the case of expression vectors, promoter and other regulatory regions recognized by the host cell. In additional embodiments, a vector comprises one or more polynucleotides encoding one or more immunogenic polypeptides of the disclosure operably linked to a promoter and optionally additional regulatory elements. Certain vectors are capable of autonomous replication in a host into which they are introduced (e.g., vectors having a bacterial origin of replication can replicate in bacteria). Other vectors can be integrated into the genome of a host upon introduction into the host, and thereby are replicated along with the host genome. Vectors include without limitation, those suitable for recombinant production of the immunogenic polypeptides disclosed herein.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Some vectors are suitable for delivering the nucleic acid molecule or polynucleotide of the present application. Certain vectors are capable of directing the expression of nucleic acids to which they are operatively linked. Such vectors are referred to herein as expression vectors.

The term "operably linked" refers to two or more nucleic acid sequence or polypeptide sequence elements that are usually physically linked and are in a functional relationship with each other. For instance, in the context of nucleic acid sequence elements, a promoter is operably linked to a coding sequence if the promoter is able to initiate or regulate the transcription or expression of a coding sequence, in which case, the coding sequence should be understood as being "under the control of" the promoter.

The choice of the vector is dependent on the recombinant procedures followed and the host used. Introduction of vectors into host cells can be effected by inter alia calcium phosphate transfection, DEAE-dextran-mediated transfection, lipofectamine transfection, electroporation, virus infection, or via administration to a subject, as described herein. Vectors may be autonomously replicating or may replicate together with the chromosome into which they have been integrated. In certain embodiments, the vectors contain one or more selection markers. The choice of the markers may depend on the host cells of choice. These include without limitation, kanamycin, neomycin, puromycin, hygromycin, zeocin, thymidine kinase gene from Herpes simplex virus (HSV-TK), and dihydrofolate reductase gene from mouse (dhfr). Vectors comprising one or more nucleic acid molecules encoding the immunogenic polypeptides described herein, operably linked to one or more nucleic acid molecules encoding proteins or peptides that can be used to isolate the immunogenic polypeptides, are also covered by the disclosure. These proteins or peptides include without limitation, glutathione-S-transferase, maltose binding protein, metal-binding polyhistidine, green fluorescent protein, luciferase and beta-galactosidase.

In other embodiments, the vector that is used is pcDNA™3.1+ (ThermoFisher, MA).

In some embodiments, the vector is viral vector. As appropriate, the viral vector can be a DNA virus or a RNA virus, including a self-replicating RNA virus. Self-replicating RNA viruses include Alphaviruses, and are described, e.g., in Lundstrom, *Molecules*. (2018) 23(12). pii: E3310 (PMID: 30551668); and Ljungberg, et al., *Expert Rev Vaccines*. (2015) 14(2):177-94). In various embodiments, the viral vector is from a virus selected from the group consisting of adenovirus, adeno-associated virus, arenavirus, alphavirus, self-replicating alphavirus, poxvirus, cytomegalovirus, rhabdovirus, vesicular stomatitis virus, flavivirus, maraba virus and vaccinia virus. In some embodiments, the viral vector is from a viral family selected from the group consisting of: Adenoviridae (e.g., Adenovirus, adeno-associated virus), Arenaviridae (e.g., lymphocytic choriomeningitis mammarenavirus, Cali mammarenavirus (a.k.a., Pichinde mammarenavirus (PICV)), Poxviridae (e.g., Vaccinia virus), Herpesviridae (e.g., Cytomegalovirus, Herpesvirus, e.g., HSV-1), Parvoviridae (e.g., Parvovirus H1), Poxviridae (e.g. Vaccinia virus, e.g. modified vaccinia Ankara (MVA)), Flaviviridae (e.g. Yellow fever virus), Reoviridae (e.g., Reovirus), Retroviridae (e.g., Lentivirus), Picornaviridae (e.g., Coxsackievirus, Seneca Valley Virus, Poliovirus), Paramyxoviridae (e.g., Measles virus, Newcastle disease virus (NDV)), Rhabdoviridae (e.g., Vesiculovirus, including Maraba vesiculovirus and Vesicular stomatitis virus (VSV)), Togaviridae (e.g., Alphavirus, e.g., self-replicating Alphavirus; Sindbis virus), Enteroviridae (e.g., Echovirus). Illustrative modified vaccinia viral vectors of use for expressing the present immunogenic polypeptides are described, e.g., in WO 2019/134049.

In some embodiments, the viral expression vector is an arenavirus vector selected from Lymphocytic choriomeningitis mammarenavirus (LCMV)(NCBI:txid11623), Cali mammarenavirus (a.k.a., Pichinde mammarenavirus or Pichinde arenavirus) (NCBI:txid2169993), Guanarito virus (GTOV) (NCBI:txid45219), Argentinian mammarenavirus (a.k.a., Junin virus (JUNV))(NCBI:txid2169991), Lassa virus (LASV)(NCBI:txid11620), Lujo virus (LUJV)(NCBI:txid649188), Machupo virus (MACV)(NCBI:txid11628), Brazilian mammarenavirus (a.k.a., Sabia virus (SABV)) (NCBI:txid2169992), and Whitewater Arroyo virus (WWAV)(NCBI:txid46919). In some embodiments, the viral expression vector is an arenavirus vector selected from Lymphocytic choriomeningitis mammarenavirus (LCMV) or Cali mammarenavirus (a.k.a., Pichinde mammarenavirus or Pichinde arenavirus (PICV)). Illustrative arenavirus vectors that can be used as delivery and expression vehicles for the herein described immunogenic polypeptides are described, e.g., in WO 2009/083210; WO 2015/183895; WO 2016/075250; WO 2017/198726; and U.S. Pat. Nos. 9,943,585 and 10,342,861, which are hereby incorporated herein by reference in their entireties for all purposes.

In some embodiments, the viral expression vector is an adenovirus vector, e.g., from a human adenovirus or a simian adenovirus (e.g., a chimpanzee adenovirus, a gorilla adenovirus or a rhesus monkey adenovirus). In various embodiments, the adenovirus vector is selected from adenovirus serotype 5 (Ad5), adenovirus serotype 26 (Ad26), adenovirus serotype 34 (Ad34), adenovirus serotype 35 (Ad35), adenovirus serotype 48 (Ad48), chimpanzee adenovirus (e.g. ChAdOx1, ChAdOx2, ChAd3 (AdC3), ChAd5 (AdC5), ChAd6 (AdC6), ChAd7 (AdC7), ChAd8 (AdC8), ChAd9 (AdC9), ChAd10 (AdC10), ChAd11 (AdC11), ChAd17 (AdC17), ChAd16 (AdC16), ChAd19 (AdC19), ChAd20 (AdC20), ChAd22 (AdC22), ChAd24 (AdC24), ChAdY25, ChAd26 (AdC26), ChAd28 (AdC28), ChAd30 (AdC30), ChAd31 (AdC31), ChAd37 (AdC37), ChAd38 (AdC38), ChAd43 (AdC43), ChAd44 (AdC44), ChAd55 (AdC55), ChAd63 (AdC63), ChAdV63, ChAd68 (AdC68), ChAd73 (AdC73), ChAd82 (AdC82), ChAd83 (AdC83), ChAd143 (AdC143), ChAd144 (AdC144), ChAd145 (AdC145), ChAd147 (AdC147)), gorilla adenovirus (e.g. GC44, GC45, GC46) and rhesus adenovirus (e.g., RhAd51, RhAd52, RhAd53, RhAd54, RhAd55, RhAd56, RhAd57, RhAd58, RhAd59, RhAd60, RhAd61, RhAd62, RhAd63, RhAd64, RhAd65, RhAd66). Illustrative Chimpanzee, Gorilla and Rhesus monkey adenovirus vectors that can be used as delivery and expression vehicles for the herein described immunogenic polypeptides are described, e.g., in WO2012/172277 (ChAdOx1), WO2017/221031 (ChAdOx2), WO2019/076880; WO2019/076877; Andrabi et al., (2019) *Cell Reports* 27:2426-2441Guo, et al., *Hum Vaccin Immunother*. (2018) 14(7):1679-1685; Abbink, et al., *J Virol*. (2015) 89(3):1512-22; and Abbink, et al., *J Virol*. (2018) 92(6). pii: e01924-17.

In various embodiments, the viral expression vector is incapable of replication (i.e.., replication-defective or replication-deficient), has reduced or diminished capacity for replication, e.g., in comparison to a wild-type viral vector (i.e., replication-attenuated) or is replication competent. In various embodiments, the viral expression vector is a replication-defective or replication-deficient arenavirus vector having a bi-segmented genome, e.g., as described in WO 2009/083210 and WO 2017/076988. In various embodiments, the viral expression vector is a replication-attenuated arenavirus vector having a tri-segmented genome, e.g., as described in WO 2016/075250, WO 2017/076988 and WO 2017/198726.

Further provided are host cells comprising one or more polynucleotides encoding one or more of the immunogenic polypeptides or one or more vectors expressing the immunogenic polypeptides, as described herein. Any of a variety of host cells can be used. In one embodiment, a host cell is a prokaryotic cell, for example, *E. coli*. In another embodiment, a host cell is a eukaryotic cell, for example, a yeast cell, a plant cell, an insect cell, a mammalian cell, such as a Chinese Hamster Ovary (CHO)-based or CHO-origin cell line (e.g., CHO-S, CHO DG44, ExpiCHO™, CHOZN® ZFN-modified GS−/− CHO cell line, CHO-K1, CHO-K1a), COS cells, BHK cells, NSO cells or Bowes melanoma cells. Examples of human host cells are, inter alia, HeLa, 911, AT1080, A549 and HEK293 (e.g., HEK293E, HEK293F, HEK293H, HEK293T, Expi293™). In addition, the immunogenic polypeptides can be expressed in a yeast cell such as *Pichia* (see, e.g., Powers et al., *J Immunol Methods*. 251:123-35 (2001)), *Hanseula*, or *Saccharomyces*.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As appropriate, the host cells can be stably or transiently transfected with one or more polynucleotides encoding one or more immunogenic polypeptides, as described herein. As appropriate, the host cells can be infected with one or more vectors expressing one or more immunogenic polypeptides, as described herein. In some embodiments, the host cells are capable of being infected with and propagating one or more replication-attenuated or replication competent vectors expressing one or more immunogenic polypeptides, as described herein. Illustrative cells useful for infecting with and/or propagating viral vectors include without limitation BHK-21, A549, Vero and HEK293 (e.g., HEK293E, HEK293F, HEK293H, HEK293T, Expi293™) cells. In certain embodiments, the host cells express the Coxsackievirus and adenovirus receptor (CAR), e.g., MDCK, Caco-2 or Calu-3 host cells. In certain embodiments, the polynucleotides integrate into the genome of the host cell.

5. Pharmaceutical Compositions/Immunogenic Compositions

Provided are pharmaceutical compositions or immunogenic compositions comprising one or more of the immunogenic HBV polypeptides, as described herein, or a polynucleotide encoding one or more of the immunogenic HBV polypeptides, as described herein, or a viral expression vector comprising one or more of such polynucleotides, and a pharmaceutically acceptable diluent, carrier or excipient. "Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

Generally, the pharmaceutical compositions described herein are immunogenic. In certain embodiments, the pharmaceutical composition comprises a therapeutically effective amount of the one or more (e.g., two or more, three or more) immunogenic HBV polypeptides, or one or more (e.g., two or more, three or more) polynucleotides encoding one or more (e.g., two or more, three or more) of the immunogenic HBV polypeptides, or one or more (e.g., two or more, three or more) viral expression vectors containing one or more (e.g., two or more, three or more) of the polynucleotides encoding one or more of the immunogenic HBV polypeptides.

Various pharmaceutically acceptable diluents, carriers, and excipients, and techniques for the preparation and use of pharmaceutical compositions will be known to those of skill in the art in light of the present disclosure. Illustrative pharmaceutical compositions and pharmaceutically acceptable diluents, carriers, and excipients are also described in, e.g., Loyd V. Allen Jr (Editor), "Remington: The Science and Practice of Pharmacy," $22^{nd}$ Edition, 2012, Pharmaceutical Press; Brunton, Knollman and Hilal-Dandan, "Goodman and Gilman's The Pharmacological Basis of Therapeutics," 13th Edition, 2017, McGraw-Hill Education/Medical; McNally and Hastedt (Editors), "Protein Formulation and Delivery, 2nd Edition, 2007, CRC Press; Banga, "Therapeutic Peptides and Proteins: Formulation, Processing, and Delivery Systems," 3rd Edition, 2015, CRC Press; Lars Hovgaard, Frokjaer and van de Weert (Editors), "Pharmaceutical Formulation Development of Peptides and Proteins," 2nd Edition, 2012, CRC Press; Carpenter and Manning (Editors), "Rational Design of Stable Protein Formulations: Theory and Practice," 2002, Springer (Pharmaceutical Biotechnology (Book 13)); Meyer (Editor), "Therapeutic Protein Drug Products: Practical Approaches to Formulation in the Laboratory, Manufacturing, and the Clinic, 2012, Woodhead Publishing.

In certain embodiments, the polynucleotides or vectors are formulated into lipid nanoparticles. For example, in some embodiments where the immunogenic HBV polypeptides are expressed from self-replicating or self-amplifying RNA molecules, the self-replicating or self-amplifying RNA can be formulated into lipid nanoparticles (LNPs). As used herein, the term "lipid nanoparticle" refers to one or more spherical nanoparticles with an average diameter of between about 10 to about 1000 nanometers, and which comprise a solid lipid core matrix that can solubilize lipophilic molecules. In certain embodiments, the lipid core is stabilized by surfactants (e.g., emulsifiers), and can comprise one or more of triglycerides (e.g., tristearin), diglycerides (e.g., glycerol bahenate), monoglycerides (e.g., glycerol monostearate), fatty acids (e.g., stearic acid), steroids (e.g., cholesterol), and waxes (e.g., cetyl palmitate), including combinations thereof. Lipid nanoparticles are described, for example, in Petrilli et al., Curr Pharm Biotechnol. 15:847-55, 2014; and U.S. Pat. Nos. 6,217,912; 6,881,421; 7,402,573; 7,404,969; 7,550,441; 7,727,969; 8,003,621; 8,691,750; 8,871,509; 9,017,726; 9,173,853; 9,220,779; 9,227,917; and 9,278,130, each of which is incorporated by reference in its entirety. In one embodiment, a self-replicating or self-amplifying RNA molecule encoding one or more of the immunogenic HBV polypeptides described herein is formulated or condensed into polyethylenimine (PEI)-polyplex delivery vehicles, e.g., as described in Démoulins, et al., *Nanomedicine*. (2016) April; 12(3):711-722 and Démoulins, et al., *J Control Release*. (2017) Nov. 28; 266:256-271, which can be nanoparticulate.

In embodiments where the immunogenic HBV polypeptides are expressed from a viral expression vector, the viral expression vector can be formulated for the desired route of administration, e.g., as an isotonic pharmaceutically acceptable aqueous solution or suspension suitable for intravenous, intramuscular, subcutaneous or intradermal administration. In some embodiments, the viral expression vector can be formulated for mucosal, e.g., buccal, intranasal, intravaginal or intra-rectal delivery. Illustrative formulations for viral expression vectors that can be used in the herein described pharmaceutical compositions and methods are described, e.g., in Manfredsson and Benskey, editors, "Viral Vectors for Gene Therapy: Methods and Protocols (Methods in Molecular Biology)," 2019, Book 1937 in Methods in Molecular Biology Series, Humana Press; WO 2017/013169 (formulation of Adenoviral vectors in an aqueous mixture or freeze dried composition in the presence of amorphous sugar and low salt concentration); and Kumru, et al., *J Pharm Sci.* (2018) November; 107(11):2764-2774 (aqueous formulations buffered in Tris and containing proline, lactose, and mannitol as stabilizing additives). Formulation of arenavirus vectors is described, e.g., in WO 2009/083210; WO 2016075250 and WO 2017/198726. In certain embodiments, the viral expression vectors are delivered via microneedle-mediated delivery, e.g., as described in Zaric, et al., *Expert Opin Drug Deliv*. (2017) October; 14(10): 1177-1187.

In some embodiments, each carrier, diluent or excipient is "acceptable" in the sense of being compatible with the other ingredients of the pharmaceutical composition and not injurious to the subject. Often, the pharmaceutically acceptable carrier is an aqueous pH-buffered solution. Some examples of materials which can serve as pharmaceutically-acceptable carriers, diluents or excipients include: water; buffers, e.g., a buffer having a pKa in the range of about 6.0 to about 8.0, e.g., a physiologically acceptable buffer, e.g., selected from phosphate, carbonate, bicarbonate, citrate, maleate, glycine-glycine, HEPES, HEPPSO, HEPPS, imidazole, BICINE, TRICINE, Tris, and BIS-Tris; sugars, such as lactose, trehalose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Hank's solution, Ringer's solution; ethyl alcohol; phosphate buffer solutions; amino acids (e.g., charged amino acids, including without limitation, aspartate, asparagine, glutamate, glutamine, histidine, arginine, lysine); and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

In one particular formulation, an arenavirus vector (e.g., a LCMV or Pichinde mammarenavirus vector (PICV)) described herein is formulated in an isotonic aqueous solution comprising a biologically compatible buffer having a pKa in the range of about 6.0 to about 8.0 (e.g., HEPES and NaCl), at a neutral or near-neutral pH and a non-ionic surfactant (e.g., PLURONIC® F68 (a.k.a., poloxamer 188)). In one particular formulation, an arenavirus vector (e.g., a LCMV or Pichinde mammarenavirus vector) described herein is formulated in an isotonic aqueous solution comprising HEPES buffer at pH 7.4, NaCl, and PLURONIC® F68 (a.k.a., poloxamer 188). Schleiss, et al. (*Clin Vaccine Immunol.* 2017 Jan. 5; 24(1):e00300-16) describes an LCMV formulating LCMV vectors in a diluent of 25 mM HEPES, 150 mM NaCl, 0.01% PLURONIC® F68; pH 7.4), which can be used to formulate the herein described arenavirus vectors. A final concentration of 10% sorbitol was added before freezing below −60° C.

The formulation of and delivery methods of pharmaceutical compositions will generally be adapted according to the site and the disease to be treated. Exemplary formulations include without limitation, those suitable for parenteral administration, e.g., intravenous, intra-arterial, intramuscular, or subcutaneous administration, including formulations encapsulated in micelles, liposomes or drug-release capsules (active agents incorporated within a biocompatible coating designed for slow-release); ingestible formulations; formulations for topical use, such as creams, ointments and gels; and other formulations such as inhalants, aerosols and sprays. In some embodiments, the pharmaceutical compositions are formulated for parenteral, e.g., intravenous, subcutaneous, or oral administration. In some embodiments, the pharmaceutical compositions are formulated for mucosal, e.g., buccal, intranasal, intrarectal and/or intravaginal administration.

In certain embodiments, pharmaceutical compositions are sterile. In certain embodiments, the pharmaceutical composition has a pH in the range of 4.5 to 8.5, 4.5 to 6.5, 6.5 to 8.5, 6.0 to 8.0, 6.5 to 8.5, or a pH of about 5.0, about 5.5, about 6.0, about 6.5, about 6.6, about 6.7, about 6.8, about 6.9, about 7.0, about 7.1, about 7.2, about 7.3, about 7.5, about 8.0 or about 8.5. In one embodiment, the pharmaceutical composition has an osmolarity in the range of 240-260 or 250-330 mOsmol/L. In certain embodiments, the pharmaceutical composition is isotonic or near isotonic.

In some embodiments, the pharmaceutical compositions are liquids or solids. In some embodiments, the pharmaceutical composition comprises an aqueous solution or suspension. In some embodiments, the pharmaceutical composition is lyophilized or is a frozen liquid.

In some embodiments, the pharmaceutical composition further comprises one or more additional therapeutic agents, e.g., a second therapeutic agent, or second and third therapeutic agents, for use in combination therapies, as described herein.

In certain embodiments, the pharmaceutical composition further comprises an adjuvant. Illustrative adjuvants that can be co-formulated or co-administered with the herein described immunogenic HBV polypeptides, polynucleotides encoding such immunogenic HBV polypeptides and vectors expressing such immunogenic HBV polypeptides include without limitation cytokines, chemokines, immune co-stimulatory molecules, toll-like receptor agonists or inhibitors of immune suppressive pathways, as described herein, and in Li, et al., *Curr Issues Mol Biol.* (2017) 22:17-40. Other adjuvants that can be co-formulated or co-administered with the herein described immunogenic HBV polypeptides, polynucleotides encoding such immunogenic HBV polypeptides and vectors expressing such immunogenic HBV polypeptides include without limitation mineral salts (e.g., aluminum salts (e.g., alum), calcium phosphate, incomplete Freunds's adjuvant), lipid particles (e.g., MF59, cochleates, virus-like particles), microparticles (e.g., virosomes, polylactic acid (PLA), poly[lactide-coglycolide] (PLG)), immune potentiators (e.g., dsRNA:Poly(I:C), Poly-IC:LC, Monophosphoryl lipid A (MPL), LPS, Flagellin, Imidazoquinolines: imiquimod (R837), resiquimod (848), CpG oligodeoxynucleotides (ODN), Muramyl dipeptide (MDP), Saponins (QS-21)), and mucosal adjuvants (e.g., Cholera toxin (CT), Heat-labile enterotoxin (LTK3 and LTR72), Chitosan). Adjuvants that can be co-formulated or co-administered with the herein described immunogenic HBV polypeptides, polynucleotides encoding such immunogenic HBV polypeptides and vectors expressing such immunogenic HBV polypeptides are summarized in Apostólico, et al., *J Immunol Res.* (2016) 2016:1459394.

In some embodiments, the pharmaceutical compositions or immunogenic compositions comprise mixtures of two or more immunogenic HBV polypeptides, two or more polynucleotides encoding such immunogenic HBV polypeptides, or two or more vectors expressing such immunogenic HBV polypeptides. In some embodiments, the pharmaceutical composition comprises two or more immunogenic HBV polypeptides, two or more polynucleotides encoding such immunogenic HBV polypeptides, or two or more vectors expressing such immunogenic HBV polypeptides.

In various embodiments, the immunogenic composition comprises one or more polynucleotides encoding, or one or more vectors capable of expressing, two immunogenic polypeptides, the immunogenic polypeptides comprising: (a) an HBV polymerase polypeptide mutant comprising or consisting of an amino acid sequence of any one of SEQ ID NOs: 5-14, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 5-14; and (b) an HBV core-sAg fusion protein comprising or consisting of an amino acid sequence of any one of SEQ ID NOs: 38-41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 38-41.

In various embodiments, the immunogenic composition comprises one or more polynucleotides encoding, or one or more vectors capable of expressing, two immunogenic polypeptides, the immunogenic polypeptides comprising: (a) an HBV polymerase polypeptide mutant comprising or consisting of an amino acid sequence of any one of SEQ ID NOs: 13-14, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 13-14; and (b) an HBV core-sAg fusion protein comprising or consisting of an amino acid sequence of any one of SEQ ID NOs: 38-41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 38-41.

In various embodiments, the immunogenic composition comprises one or more polynucleotides encoding, or one or more vectors capable of expressing, two immunogenic polypeptides, the immunogenic polypeptides comprising: (a) an HBV polymerase polypeptide mutant comprising or consisting of an amino acid sequence of SEQ ID NO: 13, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 13; and (b) an HBV core-sAg fusion protein comprising or consisting of an amino acid sequence of SEQ ID NO: 41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 41.

With respect to the core-sAg fusion polypeptide in the immunogenic composition, in some embodiments, the core polypeptide comprises a serine (S) residue at the amino acid position corresponding to position 12, and an asparagine (N) residue at the amino acid position corresponding to position 67, wherein the position numbers are with reference to SEQ ID NO:65 or SEQ ID NO:66. In some embodiments, the sAg polypeptide comprises an isoleucine (I) residue at the amino acid position corresponding to position 68, wherein the position numbers are with reference to SEQ ID NO:3 or SEQ ID NO:4. In some embodiments, the sAg polypeptide comprises one or more of a serine (S) residue at the amino acid position corresponding to position 53, an isoleucine (I) residue at the amino acid position corresponding to position 68, a threonine (T) residue at the amino acid position corresponding to position 125, a proline (P) residue at the amino acid position corresponding to position 127, an phenylalanine (F) residue at the amino acid position corresponding to position 161, a tyrosine (Y) residue at the amino acid position corresponding to position 200, a serine (S) residue at the amino acid position corresponding to position 210, and a leucine (L) residue at the amino acid position corresponding to position 213, wherein the position numbers are with reference to SEQ ID NO:3 or SEQ ID NO:4. In some embodiments, the core-sAg fusion polypeptide comprises one or more of a serine (S) residue at the amino acid position corresponding to position 12, an asparagine (N) residue at the amino acid position corresponding to position 67, a valine (V) residue at the amino acid position corresponding to position 74, a phenylalanine (F) residue at the amino acid position corresponding to position 97, a threonine (T) residue at the amino acid position corresponding to position 249, a threonine (T) residue at the amino acid position corresponding to position 250, a serine (S) residue at the amino acid position corresponding to position 317, a serine (S) residue at the amino acid position corresponding to position 318, an arginine (R) residue at the amino acid position corresponding to position 326, a tyrosine (Y) residue at the amino acid position corresponding to position 338, a glycine (G) residue at the amino acid position corresponding to position 363, and an alanine (A) residue at the amino acid position corresponding to position 372, wherein the position numbers are with reference to SEQ ID NO:41.

In some embodiments, the immunogenic composition comprises a first viral expression vector and a second viral expression vector, wherein: (a) the first viral expression vector comprises a polynucleotide comprising or consisting of a nucleic acid sequence of any one of SEQ ID NOs: 27-32 and 89-94, e.g., SEQ ID NOs: 29, 89, 90 and 92, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 27-32 and 89-94, e.g., SEQ ID NOs: 29, 89, 90 and 92; and (b) the second viral expression vector comprises a polynucleotide comprising or consisting of a nucleic acid sequence of any one of SEQ ID NOs: 33-37 or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 33-37.

In some embodiments, the immunogenic composition comprises a first viral expression vector and a second viral expression vector, wherein: (a) the first viral expression vector comprises a polynucleotide comprising or consisting of a nucleic acid sequence of SEQ ID NO: 29 or 90, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 29, 89, 90 or 92; and (b) the second viral expression vector comprises a polynucleotide comprising or consisting of a nucleic acid sequence of SEQ ID NO: 37 or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NO: 37.

In some embodiments, the immunogenic composition comprises a first LCMV arenavirus expression vector and a second LCMV arenavirus expression vector, wherein: (a) the first LCMV arenavirus expression vector comprises a polynucleotide comprising or consisting of a nucleic acid sequence of SEQ ID NO: 29, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 29; and (b) the second LCMV arenavirus expression vector comprises a polynucleotide comprising or consisting of a nucleic acid sequence of SEQ ID NO: 37 or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NO: 37.

In some embodiments, the immunogenic composition comprises a first Pichinde arenavirus expression vector and a second Pichinde arenavirus expression vector, wherein: (a) the first Pichinde arenavirus expression vector comprises a polynucleotide comprising or consisting of a nucleic acid sequence of SEQ ID NO: 90, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 90; and (b) the second Pichinde arenavirus expression vector comprises a polynucleotide comprising or consisting of a nucleic acid sequence of SEQ ID NO: 37 or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to anyone of SEQ ID NO: 37.

As appropriate or desired, the HBV polymerase polypeptide mutant and the HBV core-sAg fusion protein can be provided in the immunogenic composition in a ratio in the range of from 1:10 to 10:1, e.g., in the range of 1:9 to 9:1, 1:8 to 8:1, 1:7 to 7:1, 1:6 to 6:1, 1:5 to 5:1, 1:4 to 4:1, 1:3 to 3:1, 1:2 to 2:1 or 1:1. In various embodiments, ratios can be measured be measured in units of plaque forming units (PFU), focus forming units (FFU), infectious units (IU), or viral particles (vp).

In various embodiments, the one or more polynucleotides are DNA, cDNA, mRNA, or self-replicating RNA.

In some embodiments, the immunogenic composition comprises a first viral expression vector and a second viral expression vector, wherein: (a) the first viral expression vector comprises a polynucleotide encoding a truncated HBV polymerase polypeptide or an HBV polymerase deletion mutant polypeptide, as described herein; and (b) the second viral expression vector comprises a polynucleotide encoding the core-sAg fusion protein, as described herein. As appropriate or desired, the first viral expression vector and the second viral expression vector can be provided in a ratio in the range of from 1:10 to 10:1, e.g., in the range of 1:9 to 9:1, 1:8 to 8:1, 1:7 to 7:1, 1:6 to 6:1, 1:5 to 5:1, 1:4 to 4:1, 1:3 to 3:1, 1:2 to 2:1 or 1:1.

In some embodiments, the immunogenic composition comprise in the range of about $10^3$ to about $10^{12}$ viral focus forming units (FFU) or plaque forming units (PFU) or infectious units (IU) or viral particles (vp), e.g. from about $10^4$ to about $10^7$ viral FFU or PFU, e.g. from about $10^3$ to about $10^4$, $10^5$, $10^6$, $10^7$, $10^8$, $10^9$, $10^{10}$, $10^{11}$ or $10^{12}$ viral FFU or PFU or IU or vp per milliliter, of each of the first viral expression vector and the second viral expression vector.

In various embodiments, the first viral expression vector and the second viral expression vector in the immunogenic composition independently are from a taxonomic family selected from Adenoviridae, Arenaviridae, Herpesviridae (e.g. Cytomegalovirus), Poxviridae (e.g. Vaccinia virus, e.g. modified vaccinia Ankara (MVA)), Flaviviridae (e.g. Yellow fever virus), Rhabdoviridae (e.g. Vesiculovirus, e.g. Maraba vesiculovirus), Togaviridae (e.g., Alphavirus). In various embodiments, the first viral expression vector and the second viral expression vector can be from the same taxonomic family or from different taxonomic families. For example, in some embodiments, both the first viral expression vector and the second viral expression vector in the immunogenic composition are from Adenoviridae, Arenaviridae, or Poxviridae (e.g. Vaccinia virus, e.g. modified vaccinia Ankara (MVA)).

In some embodiments, the first viral expression vector and the second viral expression vector in the immunogenic composition are from Arenaviridae. In some embodiments, the first viral expression vector and the second viral expression vector are from an arenavirus vector selected from Lymphocytic choriomeningitis mammarenavirus (LCMV), Cali mammarenavirus (a.k.a., Pichinde mammarenavirus or Pichinde arenavirus (PICV)), Guanarito virus (GTOV), Junin virus (JUNV), Lassa virus (LASV), Lujo virus (LUJV), Machupo virus (MACV), Sabia virus (SABV), and Whitewater Arroyo virus (WWAV). In some embodiments, the first viral expression vector and the second viral expression vector are from an arenavirus vector selected from Lymphocytic choriomeningitis mammarenavirus (LCMV) or Cali mammarenavirus (a.k.a., Pichinde mammarenavirus or Pichinde arenavirus (PICV)).

In various embodiments, the first viral expression vector and the second viral expression vector in the immunogenic composition are replication-defective or replication-deficient. In some embodiments, the first viral expression vector and the second viral expression vector in the immunogenic composition are replication-attenuated.

6. Methods of Treatment

Further provided are methods for eliciting an immune response to human hepatitis B virus (HBV) in a subject in need thereof. Also provided are methods of treating or preventing human hepatitis B virus (HBV) in a subject in need thereof. Also provided are methods of inhibiting HBV replication in an infected individual. Further provided are methods for reducing the viral load associated with HBV infection. In various embodiments, the methods comprise administering to the subject an effective amount of an immunogenic composition, as described herein. In various embodiments, the "subject" or the "individual" is a human, a woodchuck, a Peking duck, a mouse or a non-human primate (e.g., a chimpanzee).

"Treatment" or "treat" or "treating" as used herein refers to an approach for obtaining beneficial or desired results. For purposes of the present disclosure, beneficial or desired results include, but are not limited to, alleviation of a symptom and/or diminishment of the extent of a symptom, delaying of progression and/or preventing a worsening of a symptom associated with a disease or condition. "Treatment" or "treating" can include one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and c) relieving the disease or condition, e.g., causing the regression of clinical symptoms, ameliorating the disease state, delaying the progression of the disease, increasing the quality of life, and/or prolonging survival.

"Delaying" as used herein refers to development of a disease or condition means to defer, hinder, slow, retard, stabilize and/or postpone development of the disease or condition. This delay can be of varying lengths of time, depending on the history of the disease and/or individual being treated. As is evident to one skilled in the art, a sufficient or significant delay can, in effect, encompass prevention, in that the individual does not develop the disease or condition.

"Prevent" or "prevention" or "preventing" as used herein refers to a regimen that protects against the onset of the disease or disorder such that the clinical symptoms of the disease do not develop. Thus, "prevention" relates to administration of a therapy (e.g., administration of a therapeutic substance) to a subject before signs of the disease are detectable in the subject (e.g., administration of a therapeutic substance to a subject in the absence of detectable infectious agent (e.g., virus) in the subject). The subject may be an individual at risk of developing the disease or disorder, such as an individual who has one or more risk factors known to be associated with development or onset of the disease or disorder. Thus, in certain embodiments, the term "preventing HBV infection" refers to administering to a subject who does not have a detectable HBV infection an anti-HBV therapeutic substance. It is understood that the subject for anti-HBV preventative therapy may be an individual at risk of contracting the HBV virus. It is also understood that prevention does not require a 100% success rate. In some instances, prevention may be understood as a reduction of the risk of infection, but not a complete elimination the occurrence of an infection.

"Therapeutically effective amount" or "effective amount" as used herein refers to an amount that is effective to elicit the desired biological or medical response, including the amount of an immunogenic composition that, when administered to a subject for treating a disease, is sufficient to effect such treatment for the disease. The effective amount will vary depending on the immunogenic composition, the disease, and its severity and the age, weight, etc., of the subject to be treated. The effective amount can include a range of amounts. An effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

In various embodiments, the administered immunogenic composition comprises a mixture comprising a first viral expression vector and a second viral expression vector, wherein: (a) the first viral expression vector comprises a polynucleotide encoding the truncated HBV polymerase polypeptide, as described herein, or the HBV polymerase deletion mutant polypeptide as described herein; and (b) the second viral expression vector comprises a polynucleotide encoding the core-sAg fusion protein, as described herein.

In various embodiments, the administered immunogenic composition comprises a mixture comprising a first viral expression vector and a second viral expression vector, wherein: (a) the first viral expression vector comprises a polynucleotide encoding an HBV polymerase polypeptide mutant comprising or consisting of an amino acid sequence of any one of SEQ ID NOs: 5-14, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 5-14; and (b) the second viral expression vector comprises a polynucleotide encoding the core-sAg fusion protein comprising or consisting of an amino acid sequence of any one of SEQ ID NOs: 38-41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 38-41. Such an immunogenic composition can be administered in a priming composition and/or in a boosting composition.

In various embodiments, the administered immunogenic composition comprises a first viral expression vector and a second viral expression vector, wherein: (a) the first viral expression vector comprises a polynucleotide encoding an HBV polymerase polypeptide mutant comprising or consisting of an amino acid sequence of any one of SEQ ID NOs: 13-14, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 13-14; and (b) the second viral expression vector comprises a polynucleotide encoding the core-sAg fusion protein comprising or consisting of an amino acid sequence of any one of SEQ ID NOs: 38-41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 38-41. Such an immunogenic composition can be administered in a priming composition and/or in a boosting composition.

With respect to the core-sAg fusion polypeptide in the administered immunogenic composition, in some embodiments, the core polypeptide comprises a serine (S) residue at the amino acid position corresponding to position 12, and an asparagine (N) residue at the amino acid position corresponding to position 67, wherein the position numbers are with reference to SEQ ID NO:65 or SEQ ID NO:66. In some embodiments, the sAg polypeptide comprises an isoleucine (I) residue at the amino acid position corresponding to position 68, wherein the position numbers are with reference to SEQ ID NO:3 or SEQ ID NO:4. In some embodiments, the sAg polypeptide comprises one or more of a serine (S) residue at the amino acid position corresponding to position 53, an isoleucine (I) residue at the amino acid position corresponding to position 68, a threonine (T) residue at the amino acid position corresponding to position 125, a proline (P) residue at the amino acid position corresponding to position 127, an phenylalanine (F) residue at the amino acid position corresponding to position 161, a tyrosine (Y) residue at the amino acid position corresponding to position 200, a serine (S) residue at the amino acid position corresponding to position 210, and a leucine (L) residue at the amino acid position corresponding to position 213, wherein the position numbers are with reference to SEQ ID NO:3 or SEQ ID NO:4. In some embodiments, the core-sAg fusion polypeptide comprises one or more of a serine (S) residue at the amino acid position corresponding to position 12, an asparagine (N) residue at the amino acid position corresponding to position 67, a valine (V) residue at the amino acid position corresponding to position 74, a phenylalanine (F) residue at the amino acid position corresponding to position 97, a threonine (T) residue at the amino acid position corresponding to position 249, a threonine (T) residue at the amino acid position corresponding to position 250, a serine (S) residue at the amino acid position corresponding to position 317, a serine (S) residue at the amino acid position corresponding to position 318, an arginine (R) residue at the amino acid position corresponding to position 326, a tyrosine (Y) residue at the amino acid position corresponding to position 338, a glycine (G) residue at the amino acid position corresponding to position 363, and an alanine (A) residue at the amino acid position corresponding to position 372, wherein the position numbers are with reference to SEQ ID NO:41.

In various embodiments, the administered immunogenic composition comprises a mixture comprising a first viral expression vector and a second viral expression vector, wherein: (a) the first viral expression vector comprises a polynucleotide encoding an HBV polymerase polypeptide mutant comprising or consisting of an amino acid sequence of SEQ ID NO: 13, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 13; and (b) the second viral expression vector comprises a polynucleotide encoding the core-sAg fusion protein comprising or consisting of an amino acid sequence of SEQ ID NO: 41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 41. Such an immunogenic composition can be administered in a priming composition and/or in a boosting composition.

In various embodiments, the administered immunogenic composition comprises a mixture comprising a first viral expression vector and a second viral expression vector, wherein: (a) the first viral expression vector comprises a polynucleotide comprising or consisting of a nucleic acid sequence of any one of SEQ ID NOs: 27-32 and 89-94, e.g., SEQ ID NOs: 29, 89, 90 and 92, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 27-32 and 89-94, e.g., SEQ ID NOs: 29, 89, 90 and 92; and (b) the second viral expression vector comprises a polynucleotide comprising or consisting of a nucleic acid sequence of any one of SEQ ID NOs: 33-37, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 33-37. Such an immunogenic composition can be administered in a priming composition and/or in a boosting composition.

In various embodiments, the administered immunogenic composition comprises a mixture comprising a first viral expression vector and a second viral expression vector, wherein: (a) the first viral expression vector comprises a polynucleotide comprising or consisting of a nucleic acid sequence of SEQ ID NOs: 29, 89, 90 or 92, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 29, 89, 90 or 92; and (b) the second viral expression vector comprises a polynucleotide comprising or consisting of a nucleic acid sequence of SEQ ID NO: 37, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 37. Such an immunogenic composition can be administered in a priming composition and/or in a boosting composition.

In various embodiments, the first viral expression vector and the second viral expression vector in the administered immunogenic composition independently are from a taxonomic family selected from Adenoviridae, Arenaviridae, Herpesviridae (e.g. Cytomegalovirus), Poxviridae (e.g. Vaccinia virus, e.g. modified vaccinia Ankara (MVA)), Flaviviridae (e.g. Yellow fever virus), Rhabdoviridae (e.g. Vesiculovirus, e.g. Maraba vesiculovirus), Togaviridae (e.g., Alphavirus), as described above and herein. In various embodiments, the first viral expression vector and the second viral expression vector can be from the same taxonomic family or from different taxonomic families. For example, in some embodiments, both the first viral expression vector and the second viral expression vector in the administered immunogenic composition are from Adenoviridae, Arenaviridae, or Poxviridae (e.g. Vaccinia virus, e.g. modified vaccinia Ankara (MVA)).

In some embodiments, the first viral expression vector and the second viral expression vector are from Arenaviridae. In some embodiments, the first viral expression vector and the second viral expression vector in the administered immunogenic composition are from an arenavirus vector selected from Lymphocytic choriomeningitis mammarenavirus (LCMV), Cali mammarenavirus (a.k.a., Pichinde mammarenavirus or Pichinde arenavirus (PICV)), Guanarito virus (GTOV), Junin virus (JUNV), Lassa virus (LASV), Lujo virus (LUJV), Machupo virus (MACV), Sabia virus (SABV), and Whitewater Arroyo virus (WWAV). In some embodiments, the first viral expression vector and the second viral expression vector in the administered immunogenic composition are from an arenavirus vector selected from Lymphocytic choriomeningitis mammarenavirus (LCMV) or Cali mammarenavirus (a.k.a., Pichinde mammarenavirus or Pichinde arenavirus (PICV)).

In various embodiments, the first viral expression vector and the second viral expression vector in the administered immunogenic composition are replication-defective or replication-deficient. In some embodiments, the first viral expression vector and the second viral expression vector in the administered immunogenic composition are replication-attenuated.

In various embodiments, the administered immunogenic composition comprises a mixture comprising a first LCMV arenavirus expression vector and a second LCMV arenavirus expression vector, wherein: (a) the first LCMV arenavirus expression vector comprises a polynucleotide comprising or consisting of a nucleic sequence of SEQ ID NO: 29, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 29; and (b) the second LCMV arenavirus expression vector comprises a polynucleotide comprising or consisting of a nucleic acid sequence of SEQ ID NO: 37, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 37. Such an immunogenic composition can be administered in a priming composition and/or in a boosting composition.

In various embodiments, the administered immunogenic composition comprises a mixture comprising a first Pichinde arenavirus expression vector and a second Pichinde arenavirus expression vector, wherein: (a) the first Pichinde arenavirus expression vector comprises a polynucleotide comprising or consisting of a nucleic sequence of SEQ ID NO: 90, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 90; and (b) the second Pichinde arenavirus expression vector comprises a polynucleotide comprising or consisting of a nucleic acid sequence of SEQ ID NO: 37, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 37. Such an immunogenic composition can be administered in a priming composition and/or in a boosting composition.

In various embodiments, the subject is infected with HBV, is suspected of being infected with HBV, or is at risk of being infected with HBV. "At risk individual" as used herein refers to an individual who is at risk of developing a condition to be treated. An individual "at risk" may or may not have detectable disease or condition, and may or may not have displayed detectable disease prior to the treatment of methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s). In various embodiments, the subject is chronically infected with HBV, e.g., infected with HBV for longer than 6 months. Typically, the individual is suffering from a chronic hepatitis B infection, although it is within the scope of the present disclosure to treat people who are acutely infected with HBV. Accordingly, in some embodiments, the subject is acutely infected with HBV. In some embodiments, the subject is co-infected with hepatitis D virus (HDV).

In various embodiments, the subject may be asymptomatic. In some embodiments, the subject is experiencing or exhibiting symptoms associated with HBV infection. Symptoms of HBV can include, e.g., jaundice, visible webs of swollen blood vessels in the skin, dark-colored (e.g., orange or brown) urine, light-colored feces, fever, persistent fatigue, malaise, abdominal pain, abdominal fluid, loss of appetite, nausea, and vomiting. Chronic infection with HBV can lead to one or more symptoms including, e.g., hepatic failure, hepatic cancer, hepatic fibrosis and hepatic cirrhosis. One or more administrations of the immunogenic polypeptides, polynucleotides encoding such polypeptides, vectors, LNPs and immunogenic compositions comprising such polypeptides or polynucleotides, as described herein, can prevent, delay, alleviate, mitigate, inhibit, reverse or eliminate one or more symptoms associated with or caused by HBV infection.

In some embodiments, the immunogenic composition is administered via a route selected from intravenous, intramuscular, intradermal, subcutaneous and mucosal (e.g. buccal, intranasal, intrarectal, intravaginal).

In some embodiments, the administered dose of the immunogenic composition comprises in the range of about $10^3$ to about $10^{12}$ viral focus forming units (FFU) or plaque forming units (PFU) or infectious units (IU) or viral particles (vp), e.g., from about $10^4$ to about $10^7$ viral FFU or PFU, e.g., from about $10^3$ to about $10^4$, $10^5$, $10^6$, $10^7$, $10^8$, $10^9$, $10^{10}$, $10^{11}$ or $10^{12}$ viral FFU or PFU or IU or vp per milliliter, of each of the first viral expression vector and the second viral expression vector. In some embodiments, the methods entail administering intravenously or intramuscularly from about $10^6$ to about $10^8$ viral FFU or PFU or IU or vp per administration every other week (Q2W) or monthly (Q4W).

In various embodiments, the methods comprise a prime-boost regimen. In some embodiments, the prime-boost regimen entails administering a priming composition at a first time point and administering one or more boosting compositions at one or more subsequent time points. As appropriate, the methods can entail repeating the prime-boost regimen one or more iterations. In various embodiments, the administrations of the priming composition and the one or more boosting compositions are spaced at least 1 week and up to at least 2 weeks, 3 weeks, 1 month, 2 months, 3 months, 4 months, 5 months or 6 months apart. As appropriate, the dosage or dosing frequency of the immunogenic composition may be adjusted over the course of the treatment, based on the judgment of the administering physician. As appropriate, a subject can be treated with multiple administrations over a time period of at least about 2 weeks to 3 weeks, 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, or longer, or until sAg is no longer detectable in the serum or plasma of the subject.

In some embodiments, after one or more administrations of the one or more immunogenic polypeptides, as described herein, or one or more polynucleotides encoding one or more immunogenic polypeptides, as described herein, or one or more vectors expressing one or more immunogenic polypeptides, as described herein, optionally with one or more additional therapeutic agents, described herein, the subject does not exhibit symptoms of HBV in the absence of antiviral treatment for at least 6 months, at least 1 year, at least 2 years, at least 3 years, or more. In some embodiments, after one or more administrations of the one or more immunogenic polypeptides, as described herein, or one or more polynucleotides encoding one or more immunogenic polypeptides, as described herein, or one or more vectors expressing one or more immunogenic polypeptides, as described herein, optionally with one or more additional therapeutic agents, described herein, sAg is no longer detectable in the serum or plasma of the subject, in the absence of antiviral treatment for at least 6 months, e.g., at least 1 year, at least 2 years, at least 3 years, or more.

As appropriate or desired, the priming composition and the boosting composition can comprise the same immunogenic composition or different immunogenic compositions. In various embodiments, the priming composition and the boosting composition comprise the same one or more polypeptides and same expression vector (e.g., viral expression vector). In some embodiments, the priming composition and the boosting composition comprise different polypeptides and/or different expression vectors (e.g., viral expression vectors). For example, in some embodiments, the priming composition and the boosting composition comprise the same one or more polypeptides and different expression vectors (e.g., viral vectors from different virus species within a taxonomic family, viral vectors from different taxonomic families, viral vectors with different replication competencies). In some embodiments, the priming composition and the boosting composition comprise different immunogenic polypeptides and the same expression vector (e.g., viral expression vector).

In some embodiments, the methods comprise priming with a priming composition comprising one or more viral expression vectors, and boosting with a boosting composition comprising one or more viral expression vectors. In some embodiments, the prime-boost regimen comprises:
  a) Priming with a priming composition comprising one or more viral expression vectors and boosting with a boosting composition comprising one or more polynucleotides, wherein the one or more polynucleotides comprise DNA, cDNA, mRNA or self-replicating RNA;
  b) Priming with a priming composition comprising one or more polynucleotides, wherein the one or more polynucleotides comprise DNA, cDNA, mRNA or self-replicating RNA, and boosting with a boosting composition comprising one or more viral expression vectors;
  c) Priming with a priming composition comprising one or more viral expression vectors, and boosting with a boosting composition comprising one or more viral expression vectors, wherein the one or more viral expression vectors in the priming composition and the one or more viral expression vectors in the boosting composition are from identical, related or unrelated taxonomical families;
  d) Priming with a priming composition comprising one or more replication-deficient viral expression vectors and boosting with a boosting composition comprising one or more replication-deficient viral expression vectors, wherein the one or more replication-deficient viral expression vectors in the priming composition and the one or more replication-deficient viral expression vectors in the boosting composition are from identical, related or unrelated taxonomical families;
  e) Priming with a priming composition comprising one or more replication-attenuated viral expression vectors and boosting with a boosting composition comprising one or more replication-attenuated viral expression vectors, wherein the one or more replication-attenuated viral expression vectors in the priming composition and the one or more replication-attenuated viral expression vectors in the boosting composition are from identical, related or unrelated taxonomical families;
f) Priming with a priming composition comprising one or more replication-deficient viral expression vectors and boosting with a boosting composition comprising one or more replication-attenuated viral expression vectors;
g) Priming with a priming composition comprising one or more replication-attenuated viral expression vectors and boosting with a boosting composition comprising one or more replication-deficient viral expression vectors;
h) Priming with a priming composition comprising one or more Lymphocytic choriomeningitis mammarenavirus (LCMV) viral expression vectors and boosting with a boosting composition comprising one or more Pichinde mammarenavirus (PICV) viral expression vectors;
i) Priming with a priming composition comprising one or more Pichinde mammarenavirus (PICV) viral expression vectors and boosting with a boosting composition comprising one or more Lymphocytic choriomeningitis mammarenavirus (LCMV) viral expression vectors;
j) Priming with a priming composition comprising one or more replication deficient Pichinde mammarenavirus (PICV) viral expression vectors and boosting with a boosting composition comprising one or more replication deficient Lymphocytic choriomeningitis mammarenavirus (LCMV) viral expression vectors;
k) Priming with a priming composition comprising one or more replication deficient Lymphocytic choriomeningitis mammarenavirus (LCMV) viral expression vectors and boosting with a boosting composition comprising one or more replication deficient Pichinde mammarenavirus (PICV) viral expression vectors;
l) Priming with a priming composition comprising one or more arenavirus viral expression vectors and boosting with a boosting composition comprising one or more adenovirus viral expression vectors;
m) Priming with a priming composition comprising one or more adenovirus viral expression vectors and boosting with boosting composition comprising one or more arenavirus viral expression vectors;
n) Priming with a priming composition comprising one or more poxvirus viral expression vectors and boosting with a boosting composition comprising one or more arenavirus viral expression vectors;
o) Priming with a priming composition comprising one or more arenavirus viral expression vectors and boosting with boosting composition comprising one or more poxvirus viral expression vectors;
p) Priming with a priming composition comprising one or more poxvirus viral expression vectors and boosting with a boosting composition comprising one or more adenovirus viral expression vectors; or
q) Priming with a priming composition comprising one or more adenovirus viral expression vectors and boosting with boosting composition comprising one or more poxvirus viral expression vectors.

In some embodiments, the methods comprise priming with a priming composition comprising one or more viral expression vectors, and boosting with a boosting composition comprising one or more viral expression vectors. In some embodiments, the prime-boost regimen comprises:
a) Priming with a priming composition comprising one or more Lymphocytic choriomeningitis mammarenavirus (LCMV) viral expression vectors and boosting with a boosting composition comprising one or more Pichinde mammarenavirus (PICV) viral expression vectors;
b) Priming with a priming composition comprising one or more Pichinde mammarenavirus (PICV) viral expression vectors and boosting with a boosting composition comprising one or more Lymphocytic choriomeningitis mammarenavirus (LCMV) viral expression vectors;
c) Priming with a priming composition comprising one or more replication deficient Pichinde mammarenavirus (PICV) viral expression vectors and boosting with a boosting composition comprising one or more replication deficient Lymphocytic choriomeningitis mammarenavirus (LCMV) viral expression vectors; or
d) Priming with a priming composition comprising one or more replication deficient Lymphocytic choriomeningitis mammarenavirus (LCMV) viral expression vectors and boosting with a boosting composition comprising one or more replication deficient Pichinde mammarenavirus (PICV) viral expression vectors.

In various embodiments, the priming composition and the boosting composition comprise an immunogenic composition as described herein.

In some embodiments, the subject is not receiving antiviral therapy or antiviral therapy is discontinued prior to administration of the one or more immunogenic compositions. In some embodiments, the antiviral therapy is discontinued after one or more administrations of the compositions.

In some embodiments, the treatment methods activate in the subject CD8+ T cells targeting one or more HBV polypeptide epitopes. In some embodiments, the treatment methods elicit in the subject production of antibodies that bind one or more HBV polypeptides.

7. Combination Therapies

In certain embodiments, the immunogenic polypeptides, polynucleotides encoding such polypeptides, vectors, LNPs and immunogenic compositions comprising such polypeptides or polynucleotides, as described herein, are combined or co-administered with one, two, three, four or more additional therapeutic agents. In certain embodiments, the immunogenic polypeptides, polynucleotides encoding such polypeptides, vectors, LNPs and immunogenic compositions comprising such polypeptides or polynucleotides, as described herein, are combined or co-administered with two additional therapeutic agents. In certain embodiments, the immunogenic polypeptides, polynucleotides encoding such polypeptides, vectors, LNPs and immunogenic compositions comprising such polypeptides or polynucleotides, as described herein, are combined or co-administered with three additional therapeutic agents. In certain embodiments, the immunogenic polypeptides, polynucleotides encoding such polypeptides, vectors, LNPs and immunogenic compositions comprising such polypeptides or polynucleotides, as described herein, are combined or co-administered with four additional therapeutic agents. The one, two, three, four or more additional therapeutic agents can be different therapeutic agents selected from the same class of therapeutic agents, and/or they can be selected from different classes of therapeutic agents.

"Co-administration" as used herein refers to administration of unit dosages of the immunogenic polypeptides, polynucleotides encoding such polypeptides, vectors, LNPs and immunogenic compositions comprising such polypeptides or polynucleotides, as described herein, before or after administration of unit dosages of one or more additional therapeutic agents. For example, administration of the immunogenic composition disclosed herein within seconds, minutes, or hours of the administration of one or more additional therapeutic agents. For example, in some embodiments, a unit dose of an immunogenic composition of the present disclosure is administered first, followed within seconds or minutes by administration of a unit dose of one or more additional therapeutic agents. Alternatively, in other embodiments, a unit dose of one or more additional therapeutic agents is administered first, followed by administration of a unit dose of an immunogenic composition of the present disclosure within seconds or minutes. In some embodiments, a unit dose of the immunogenic polypeptides, polynucleotides encoding such polypeptides, vectors, LNPs and immunogenic compositions comprising such polypeptides or polynucleotides, as described herein, is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of the immunogenic polypeptides, polynucleotides encoding such polypeptides, vectors, LNPs and immunogenic compositions comprising such polypeptides or polynucleotides, as described herein.

Co-administration of the immunogenic polypeptides, polynucleotides encoding such polypeptides, vectors, LNPs and immunogenic compositions comprising such polypeptides or polynucleotides, as described herein, with one or more additional therapeutic agents generally refers to simultaneous or sequential administration of an immunogenic composition disclosed herein and one or more additional therapeutic agents, such that therapeutically effective amounts of each agent are present in the body of the patient.

In various embodiments, the immunogenic polypeptides, polynucleotides encoding such polypeptides, vectors, LNPs and immunogenic compositions comprising such polypeptides or polynucleotides, as described herein, are combined or co-administered with one or more additional therapeutic agents as described herein, the components of the composition are administered as a simultaneous or sequential regimen. When administered sequentially, the combination may be administered in two or more administrations.

In various embodiments, the immunogenic polypeptides, polynucleotides encoding such polypeptides, vectors, LNPs and immunogenic compositions comprising such polypeptides or polynucleotides, as described herein, are combined or co-administered with one, two, three, four or more additional therapeutic agents selected from HBV combination drugs, HBV vaccines, HBV DNA polymerase inhibitors, immunomodulators, toll-like receptor (TLR) modulators, interferon alpha receptor ligands, hyaluronidase inhibitors, HBV antigen inhibitors (e.g., HBV core antigen (HBcAg) inhibitors, HBV surface antigen (HBsAg) inhibitors, HBx inhibitors, HBV E antigen inhibitors), anti-HBV antigen antibodies, inhibitory nucleic acids targeting HBV (e.g., antisense oligonucleotide, short interfering RNA (siRNA), DNA-directed RNA interference (ddRNAi)), HBsAg secretion or assembly inhibitors, HBV viral entry inhibitors, immune checkpoint inhibitor, cytotoxic T-lymphocyte-associated protein 4 (CTLA4) inhibitors, cyclophilin inhibitors, endonuclease modulators, ribonucleotide reductase inhibitors, covalently closed circular DNA (cccDNA) inhibitors, farnesoid X receptor (FXR) agonists, STING agonists, anti-HBV antibodies, CCR2 chemokine antagonists, thymosin agonists, cytokines, nucleoprotein modulators, retinoic acid-inducible gene 1 stimulators, NOD2 stimulators, phosphatidylinositol 3-kinase (PI3K) inhibitors, indoleamine-2, 3-dioxygenase (IDO) pathway inhibitors, ZCCHC14 inhibitors, inducers of tertiary lymphoid aggregates, nucleic acid polymers (e.g., NAPs and STOPS), PD-1 inhibitors, PD-L1 inhibitors, recombinant thymosin alpha-1, Bruton's tyrosine kinase (BTK) inhibitors, lysine demethylase (KDM) inhibitors, HBV replication inhibitors, arginase inhibitors, gene therapy and cell therapy, gene editors, cellular therapy, TCR-T cell therapy, and other HBV drugs.

In certain embodiments, the immunogenic polypeptides, polynucleotides encoding such polypeptides, vectors, LNPs and immunogenic compositions comprising such polypeptides or polynucleotides, as described herein, may be combined or co-administered with one or more of a chemotherapeutic agent, an immunomodulator, an immunotherapeutic agent, a therapeutic antibody, a therapeutic vaccine, a bispecific antibody and "antibody-like" therapeutic protein (such as DARPins®, anti-pMHC TCR-like antibodies, DARTs®, Duobodies®, Bites®, XmAbs®, TandAbs®, Fab derivatives), an antibody-drug conjugate (ADC), gene modifiers or gene editors targeting HBV (e.g., CRISPR-Cas (e.g., Cas9, Casi2, Cascade, Casi3), zinc finger nucleases, homing endonucleases, homing meganucleases (e.g., ARCUS), synthetic nucleases, TALENs), cell therapies (e.g., T-cells, NK cells, macrophages having a chimeric antigen receptor (CAR)), and TCR-T (an engineered T cell receptor) or any combination thereof.

In certain embodiments, the immunogenic polypeptides, polynucleotides encoding such polypeptides, vectors, LNPs and immunogenic compositions comprising such polypeptides or polynucleotides, as described herein, are combined or co-administered with one, two, three, four or more additional therapeutic agents, e.g., as 3-dioxygenase (IDO) inhibitors, apolipoprotein A1 modulator, arginase inhibitors, B- and T-lymphocyte attenuator inhibitors, Bruton's tyrosine kinase (BTK) inhibitors, CCR2 chemokine antagonist, CD137 inhibitors, CD160 inhibitors, CD305 inhibitors, CD4 agonist and modulator, compounds targeting hepatitis B core antigen (HBcAg), core protein allosteric modulators, covalently closed circular DNA (cccDNA) inhibitors, cyclophilin inhibitors, cytotoxic T-lymphocyte-associated protein 4 (CTLA4) inhibitors, DNA polymerase inhibitor, endonuclease modulators, epigenetic modifiers, farnesoid X receptor (FXR) agonists, HBV DNA polymerase inhibitors, HBV replication inhibitors, HBV RNAse inhibitors, HBV viral entry inhibitors, HBx inhibitors, Hepatitis B large envelope protein modulator, Hepatitis B large envelope protein stimulator, Hepatitis B structural protein modulator, hepatitis B surface antigen (HBsAg) inhibitors, hepatitis B surface antigen (HBsAg) secretion or assembly inhibitors, hepatitis B virus E antigen inhibitors, hepatitis B virus replication inhibitors, Hepatitis virus structural protein inhibitor, HIV-1 reverse transcriptase inhibitor, Hyaluronidase inhibitor, inhibitor of apoptosis proteins family proteins (IAPs) inhibitors, IL-2 agonist, IL-7 agonist, immunomodulators, indoleamine-2 inhibitors, inhibitors of ribonucleotide reductase, Interleukin-2 ligand, ipi4 inhibitors, lysine demethylase inhibitors, histone demethylase inhibitors, KDM1 inhibitors, KDM5 inhibitors, killer cell lectin-like receptor subfamily G member 1 inhibitors, lymphocyte-activation gene 3 inhibitors, lymphotoxin beta receptor activators, modulators of Axl, modulators of B7-H3, modulators of B7-H4, modulators of CD160, modulators of CD161, modulators of CD27, modulators of CD47, modulators of CD70, modulators of GITR, modulators of HEVEM, modulators of ICOS, modulators of Mer, modulators of NKG2A, modulators of NKG2D, modulators of OX40, modulators of SIRPalpha, modulators of TIGIT, modulators of Tim-4, modulators of Tyro, Na+-taurocholate cotransporting polypeptide (NTCP) inhibitors, natural killer cell receptor 2B4 inhibitors, NOD2 gene stimulator, Nucleoprotein inhibitor, nucleoprotein modulators, OX-40 receptor agonist, PD-1 inhibitors, PD-L1 inhibitors, peptidylprolyl isomerase inhibitor, phosphatidylinositol-3 kinase (PI3K) inhibitors, Retinoic acid-inducible gene 1 stimulator, Reverse transcriptase inhibitor, Ribonuclease inhibitor, RNA DNA polymerase inhibitor, SLC10A1 gene inhibitor, SMAC mimetics, Src tyrosine kinase inhibitor, stimulator of interferon gene (STING) agonists, stimulators of NOD1, T cell surface glycoprotein CD28 inhibitor, T-cell surface glycoprotein CD8 modulator, Thymosin agonist, Thymosin alpha 1 ligand, Tim-3 inhibitors, TLR-3 agonists, TLR-7 agonists, TLR-9 agonists, TLR9 agonists or gene stimulator, toll-like receptor (TLR) modulators, viral ribonucleotide reductase inhibitors, and combinations thereof.

HBV Inhibiting Antiviral Drugs

In various embodiments, the immunogenic polypeptides, polynucleotides encoding such polypeptides, vectors, LNPs and immunogenic compositions comprising such polypeptides or polynucleotides, as described herein, are combined or co-administered with one or more antiviral agents. In some embodiments, the one or more antiviral agents are selected from the group consisting of lamivudine (LAM), adefovir dipivoxil (ADV), entecavir (ETV), telbivudine (LdT), tenofovir disoproxil fumarate (TDF), tenofovir disoproxil fumarate and emtricitabine (TRUVADA®), tenofovir alafenamide (TAF or VEMLIDY®) and ledipasvir and sofosbuvir (HARVONI®).

Other HBV Drugs

Examples of other drugs for the treatment of HBV that can be combined or co-administered include alpha-hydroxytropolones, amdoxovir, antroquinonol, beta-hydroxycytosine nucleosides, ARB-199, CCC-0975, ccc-R08, elvucitabine, ezetimibe, cyclosporin A, gentiopicrin (gentiopicroside), HH-003, hepalatide, JNJ-56136379, nitazoxanide, birinapant, NJK14047, NOV-205 (molixan, BAM-205), oligotide, mivotilate, feron, GST-HG-131, levamisole, Ka Shu Ning, alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IBPB-0061A, Hepuyinfen, DasKloster 0014-01, ISA-204, Jiangantai (Ganxikang), MIV-210, OB-AI-004, PF-06, picroside, DasKloster-0039, hepulantai, IMB-2613, NCO-48 Fumarate, XTYW-001, SFA-001, TCM-800B, reduced glutathione, RO-6864018, ENOB-HB-01, RG-7834, QL-007sofosbuvir, ledipasvir, UB-551, PA-1010, HPN-BV1, STSG-0002, and ZH-2N, and the compounds disclosed in US20150210682, (Roche), US 2016/0122344 (Roche), WO2015173164, WO2016023877, US2015252057A (Roche), WO16128335A1 (Roche), WO16120186A1 (Roche), US2016237090A (Roche), WO16107833A1 (Roche), WO16107832A1 (Roche), US2016176899A (Roche), WO16102438A1 (Roche), WO16012470A1 (Roche), US2016220586A (Roche), and US2015031687A (Roche).

Examples of combination drugs for the treatment of HBV that can be combined or co-administered include tenofovir disoproxil fumarate and emtricitabine (TRUVADA®), ledipasvir and sofosbuvir (HARVONI®); ABX-203 (NASVAC), lamivudine and PEG-IFNα; adefovir and PEG-IFNα; and INO-1800 (INO-9112 and RG7944).

HBV Vaccines

In various embodiments, the immunogenic polypeptides, polynucleotides encoding such polypeptides, vectors, LNPs and immunogenic compositions comprising such polypeptides or polynucleotides, as described herein, are combined or co-administered with one or more HBV vaccines. HBV vaccines that can be combined or co-administered (e.g., in a prime-boost prevention regimen) include both prophylactic and therapeutic vaccines. Examples of HBV prophylactic vaccines include Vaxelis, Hexaxim, Heplisav, Mosquirix, DTwP-HBV vaccine, Bio-Hep-B, D/T/P/HBV/M (LBVP-0101; LBVW-0101), DTwP-Hepb-Hib-IPV vaccine, Heberpenta L, DTwP-HepB-Hib, V-419, CVI-HBV-001, Tetrabhay, hepatitis B prophylactic vaccine (Advax Super D), Hepatrol-07, GSK-223192A, ENGERIX B®, recombinant hepatitis B vaccine (intramuscular, Kangtai Biological Products), recombinant hepatitis B vaccine (*Hansenula polymorpha* yeast, intramuscular, Hualan Biological Engineering), recombinant hepatitis B surface antigen vaccine, Bimmugen, CARG-101, Euforavac, Eutravac, anrix-DTaP-IPV-Hep B, HBAI-20, Infanrix-DTaP-IPV-Hep B-Hib, Pentabio Vaksin DTP-HB-Hib, Comvac 4, Twinrix, Euvax-B, Tritanrix HB, Infanrix Hep B, Comvax, DTP-Hib-HBV vaccine, DTP-HBV vaccine, Yi Tai, Heberbiovac HB, Trivac HB, GerVax, DTwP-Hep B-Hib vaccine, Bilive, Hepavax-Gene, SUPERVAX, Comvac5, Shanvac-B, Hebsulin, Recombivax HB, Revac B mcf, Revac B+, Fendrix, DTwP-HepB-Hib, DNA-001, Shan5, Shan6, rhHBsAG vaccine, HBI pentavalent vaccine, LBVD, Infanrix HeXa, YS-HBV-001, IR-101H, TVAX-008, and DTaP-rHB-Hib vaccine.

Examples of HBV therapeutic vaccines that can be combined or co-administered (e.g., in a prime-boost treatment regimen) include HBsAG-HBIG complex, ARB-1598, Bio-Hep-B, abi-HB (intravenous), ABX-203 (NASVAC), Tetrabhay, GX-110E, GS-4774, peptide vaccine (epsilonPA-44), Hepatrol-07, NASVAC (NASTERAP), IMP-321, BEVAC, Revac B mcf, Revac B+, MGN-1333, KW-2, CVI-HBV-002, AltraHepB, VGX-6200, FP-02, FP-02.2 (HepTcell), NU-500, HBVax, im/TriGrid/antigen vaccine, Mega-CD40L-adjuvanted vaccine, HepB-v, RG7944 (INO-1800), recombinant VLP-based therapeutic vaccine (HBV infection, VLP Biotech), AdTG-17909, AdTG-17910 AdTG-18202, ChronVac-B, TG-1050, VVX-001, GSK-3528869A (ChAd155-hli-HBV+MVA-HBV+Hbc-HBs/AS01B-4), VBI-2601, VTP-300 (ChAdOx1-SIi-HBV-CPmut-TPA-Ssh prime and MVA-SIi-HBV-CPmut-TPA-Ssh boost), Lm HBV and BM32 (Tulaeva, et al., EBioMedicine (2020) 102953). HBV Arenavirus vaccines are described, e.g., in WO2017076988 and WO2017198726.

HBV DNA Polymerase Inhibitors

In various embodiments, the immunogenic polypeptides, polynucleotides encoding such polypeptides, vectors, LNPs and immunogenic compositions comprising such polypeptides or polynucleotides, as described herein, are combined or co-administered with one or more polymerase inhibitors. Examples of HBV DNA polymerase inhibitors that can be combined or co-administered include adefovir (HEPSERA®), emtricitabine (EMTRIVA®), tenofovir disoproxil fumarate (VIREAD®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, CMX-157, tenofovir exalidex, besifovir, entecavir (BARACLUDE®), entecavir maleate, telbivudine (TYZEKA®), filocilovir, pradefovir, clevudine, ribavirin, lamivudine (EPIVIR-HBV®), phosphazide, famciclovir, fusolin, metacavir, SNC-019754, FMCA, AGX-1009, AR-II-04-26, HIP-1302, tenofovir disoproxil aspartate, tenofovir disoproxil orotate, AiB-001, and HS-10234.

Immunomodulators

In various embodiments, the immunogenic polypeptides, polynucleotides encoding such polypeptides, vectors, LNPs and immunogenic compositions comprising such polypeptides or polynucleotides, as described herein, are combined or co-administered with one or more immunomodulators (e.g., an immune checkpoint inhibitor, a tumor necrosis factor (TNF) receptor superfamily (TNFRSF) agonist, an immune stimulator, e.g., a TLR agonist). Examples of immunomodulators that can be combined or co-administered include rintatolimod, imidol hydrochloride, ingaron, dennaVir, plaquenil (hydroxychloroquine), proleukin, hydroxyurea, mycophenolate mofetil (MPA) and its ester derivative mycophenolate mofetil (MMF), JNJ-440, WF-10, AB-452, ribavirin, IL-12, INO-9112, polymer polyethyleneimine (PEI), Gepon, VGV-1, MOR-22, CRV-431, JNJ-0535, TG-1050, ABI-H2158, BMS-936559, GS-9688, RO-7011785 and corresponding prodrug RO-702053, RG-7854, RO-6871765, AIC-649, and IR-103.

Toll-Like Receptor (TLR) Agonists

In various embodiments, the immunogenic polypeptides, polynucleotides encoding such polypeptides, vectors, LNPs and immunogenic compositions comprising such polypeptides or polynucleotides, as described herein, are combined or co-administered with one or more agonists or stimulators of a toll-like receptor (TLR). In various embodiments, the immunogenic polypeptides, polynucleotides encoding such polypeptides, vectors, LNPs and immunogenic compositions comprising such polypeptides or polynucleotides, as described herein, are combined or co-administered with an agonist of a TLR, e.g., an agonist of TLR1 (NCBI Gene ID: 7096), TLR2 (NCBI Gene ID: 7097), TLR3 (NCBI Gene ID: 7098), TLR4 (NCBI Gene ID: 7099), TLR5 (NCBI Gene ID: 7100), TLR6 (NCBI Gene ID: 10333), TLR7 (NCBI Gene ID: 51284), TLR8 (NCBI Gene ID: 51311), TLR9 (NCBI Gene ID: 54106), and/or TLR10 (NCBI Gene ID: 81793), TLR11, TLR12 and TLR13.

Examples of TLR3 agonists that can be combined or co-administered include rintatolimod, poly-ICLC, RIBOXXON®, Apoxxim, RIBOXXIM®, IPH-33, MCT-465, MCT-475 and ND-1.1.

Examples of TLR4 agonists that can be combined or co-administered include G-100, and GSK-1795091.

Example TLR7 agonists that can be combined or co-administered include without limitation AL-034, DSP-0509, GS-9620 (vesatolimod), LHC-165, TMX-101 (imiquimod), GSK-2245035, resiquimod, DSR-6434, DSP-3025, IMO-4200, MCT-465, telratolimod (MEDI-9197), 3M-051, SB-9922, 3M-052, Limtop, TMX-30X, TMX-202, RG-7863, RG-7854, RG-7795, RO-7011785 and corresponding prodrug RO-702053, and the compounds disclosed in US20100143301 (Gilead Sciences), US20110098248 (Gilead Sciences), and US20090047249 (Gilead Sciences), US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics).

Example dual TLR7/TLR8 agonists that can be combined or co-administered is NKTR-262, telratolimod and BDB-001.

Example TLR8 agonists that can be co-administered include without limitation E-6887, IMO-4200, IMO-8400, IMO-9200, MCT-465, telratolimod (MEDI-9197), motolimod, resiquimod, selgantolimod (GS-9688), HRS-9950, VTX-1463, VTX-763, 3M-051, 3M-052, SBT6050, and the compounds disclosed in US2016289229 (Gilead Sciences), US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics), U.S. Pat. No. 9,670,205 (Gilead Sciences, Inc.), US20160289229 (Gilead Sciences, Inc.), WO2017/048727 (Gilead Sciences, Inc.), US20180065938 (Gilead Sciences, Inc.), and US20180086755 (Gilead Sciences, Inc.).

Example TLR9 agonists that can be combined or co-administered include without limitation AST-008, cobitolimod, CMP-001, IMO-2055, IMO-2125, S-540956, litenimod, MGN-1601, BB-001, BB-006, IMO-3100, IMO-8400, IR-103, IMO-9200, agatolimod, DIMS-9054, DV-1079, DV-1179, AZD-1419, lefitolimod (MGN-1703), CYT-003, CYT-003-QbG10, tilsotolimod and PUL-042.

Additional examples of TLR7, TLR8 and TLR9 modulators that can be combined or co-administered include the compounds disclosed in WO2017047769 (Teika Seiyaku), WO2015014815 (Janssen), WO2018045150 (Gilead Sciences Inc), WO2018045144 (Gilead Sciences Inc), WO2015162075 (Roche), WO2017034986 (University of Kansas), WO2018095426 (Jiangsu Hengrui Medicine Co Ltd), WO2016091698 (Roche), WO2016075661 (GlaxoSmithKline Biologicals), WO2016180743 (Roche), WO2018089695 (Dynavax Technologies), WO2016055553 (Roche), WO2015168279 (Novartis), WO2016107536 (Medshine Discovery), WO2018086593 (Livo (Shanghai) Pharmaceutical), WO2017106607 (Merck), WO2017061532 (Sumitomo Dainippon Pharma), WO2016023511 (Chia Tai Tianqing Pharmaceutical), WO2017076346 (Chia Tai Tianqing Pharmaceutical), WO2017046112 (Roche), WO2018078149 (Roche), WO2017040233 (3M Co), WO2016141092 (Gilead Sciences), WO2018049089 (BristolMyers Squibb), WO2015057655 (Eisai Co Ltd), WO2017001307 (Roche), WO2018005586 (BristolMyers Squibb), WO201704023 (3M Co), WO2017163264 (Council of Scientific and Industrial Research (India)), WO2018046460 (GlaxoSmithKline Biologicals), WO2018047081 (Novartis), WO2016142250 (Roche), WO2015168269 (Novartis), WO201804163 (Roche), WO2018038877 (3M Co), WO2015057659 (Eisai Co Ltd), WO2017202704 (Roche), WO2018026620 (BristolMyers Squibb), WO2016029077 (Janus Biotherapeutics), WO201803143 (Merck), WO2016096778 (Roche), WO2017190669 (Shanghai De Novo Pharmatech), U.S. Ser. No. 09/884,866 (University of Minnesota), WO2017219931 (Sichuan KelunBiotech Biopharmaceutical), WO2018002319 (Janssen Sciences), WO2017216054 (Roche), WO2017202703 (Roche), WO2017184735 (IFM Therapeutics), WO2017184746 (IFM Therapeutics), WO2015088045 (Takeda Pharmaceutical), WO2017038909

(Takeda Pharmaceutical), WO2015095780 (University of Kansas), WO2015023958 (University of Kansas).

In certain embodiments, the immunogenic polypeptides, polynucleotides encoding such polypeptides, vectors, LNPs and immunogenic compositions comprising such polypeptides or polynucleotides, as described herein, are combined or co-administered with a TLR7, TLR8 or TLR9 agonist.

Interferon Alpha Receptor Ligands

In various embodiments, the immunogenic polypeptides, polynucleotides encoding such polypeptides, vectors, LNPs and immunogenic compositions comprising such polypeptides or polynucleotides, as described herein, are combined or co-administered with one or more interferon alpha receptor ligands. Examples of interferon alpha receptor ligands that can be combined or co-administered include interferon alpha-2b (INTRON A®), pegylated interferon alpha-2a (PEGASYS®), PEGylated interferon alpha-1b, interferon alpha 1b (HAPGEN®), Veldona, Infradure, Roferon-A, YPEG-interferon alfa-2a (YPEG-rhIFNalpha-2a), P-1101, Algeron, Alfarona, Ingaron (interferon gamma), rSIFN-co (recombinant super compound interferon), Ypeginterferon alfa-2b (YPEG-rhIFNalpha-2b), MOR-22, peginterferon alfa-2b (PEG-INTRON®), Bioferon, Novaferon, Inmutag (Inferon), MULTIFERON®, interferon alfa-n1 (HUMOFERON®), interferon beta-1a (AVONEX®), Shaferon, interferon alfa-2b (Axxo), Alfaferone, interferon alfa-2b (BioGeneric Pharma), interferon-alpha 2 (CJ), Laferonum, VIPEG, BLAUFERON-A, BLAUFERON-B, Intermax Alpha, Realdiron, Lanstion, Pegaferon, PDferon-B, interferon alfa-2b (IFN, Laboratorios Bioprofarma), alfainterferona 2b, Kalferon, Pegnano, Feronsure, PegiHep, interferon alfa 2b (Zydus-Cadila), interferon alfa 2a, Optipeg A, Realfa 2B, Reliferon, interferon alfa-2b (Amega), interferon alfa-2b (Virchow), ropeginterferon alfa-2b, rHSA-IFN alpha-2a (recombinant human serum albumin intereferon alpha 2a fusion protein), PEG-IFN-alpha, rHSA-IFN alpha 2b, recombinant human interferon alpha-(1b, 2a, 2b), peginterferon alfa-2b (Amega), peginterferon alfa-2a, Reaferon-EC, Proquiferon, Uniferon, Urifron, interferon alfa-2b (Changchun Institute of Biological Products), Anterferon, Shanferon, Layfferon, Shang Sheng Lei Tai, INTEFEN, SINOGEN, Fukangtai, Pegstat, rHSA-IFN alpha-2b, SFR-9216, and Interapo (Interapa).

Hyaluronidase Inhibitors

In various embodiments, the immunogenic polypeptides, polynucleotides encoding such polypeptides, vectors, LNPs and immunogenic compositions comprising such polypeptides or polynucleotides, as described herein, are combined or co-administered with one or more hyaluronidase inhibitors. Examples of hyaluronidase inhibitors that can be combined or co-administered include astodrimer.

Hepatitis B Surface Antigen (HBsAg) Inhibitors

In various embodiments, the immunogenic polypeptides, polynucleotides encoding such polypeptides, vectors, LNPs and immunogenic compositions comprising such polypeptides or polynucleotides, as described herein, are combined or co-administered with one or more HBsAg inhibitors. Examples of HBsAg inhibitors that can be combined or co-administered include AK-074, HBF-0259, GP-605, PBHBV-001, PBHBV-2-15, PBHBV-2-1, REP-9AC, REP-9C, REP-9, REP-2139, REP-2139-Ca, REP-2055, REP-2163, REP-2165, REP-2053, REP-2031 and REP-006, and REP-9AC'. Examples of HBsAg secretion inhibitors that can be combined or co-administered include BM601, GST-HG-131, AB-452 and ALG-010093.

Cyclophilin Inhibitors

In various embodiments, the immunogenic polypeptides, polynucleotides encoding such polypeptides, vectors, LNPs and immunogenic compositions comprising such polypeptides or polynucleotides, as described herein, are combined or co-administered with one or more cyclophilin inhibitors. Examples of cyclophilin inhibitors that can be combined or co-administered include CPI-431-32, EDP-494, OCB-030, SCY-635, NVP-015, NVP-018, NVP-019, STG-175, and the compounds disclosed in U.S. Pat. No. 8,513,184 (Gilead Sciences), US20140030221 (Gilead Sciences), US20130344030 (Gilead Sciences), and US20130344029 (Gilead Sciences).

HBV Viral Entry Inhibitors

In various embodiments, the immunogenic polypeptides, polynucleotides encoding such polypeptides, vectors, LNPs and immunogenic compositions comprising such polypeptides or polynucleotides, as described herein, are combined or co-administered with one or more HBV viral entry inhibitors. Examples of HBV viral entry inhibitors that can be combined or co-administered include bulevirtide (Hepcludex; Myrcludex B).

Inhibitory Nucleic Acids

In various embodiments, the immunogenic polypeptides, polynucleotides encoding such polypeptides, vectors, LNPs and immunogenic compositions comprising such polypeptides or polynucleotides, as described herein, are combined or co-administered with one or more inhibitory nucleic acids (e.g., antisense oligonucleotide, short interfering RNA (siRNA), DNA-directed RNA interference (ddRNAi)) specifically targeting an HBV polynucleotide. In some embodiments, the HBV polynucleotide encodes and HBV protein (i.e., is in a coding region within the HBV genome).

Antisense Oligonucleotide Targeting Viral mRNA

In various embodiments, the immunogenic polypeptides, polynucleotides encoding such polypeptides, vectors, LNPs and immunogenic compositions comprising such polypeptides or polynucleotides, as described herein, are combined or co-administered with one or more antisense oligonucleotides. Examples of antisense oligonucleotide targeting viral mRNA that can be combined or co-administered include ISIS-HBVRx, IONIS-HBVRx, IONIS-HBV-LRx, IONIS-GSK6-LRx, GSK-3389404, BNC-1701 and RG-6004.

Short Interfering RNAs (siRNA)

In various embodiments, the immunogenic polypeptides, polynucleotides encoding such polypeptides, vectors, LNPs and immunogenic compositions comprising such polypeptides or polynucleotides, as described herein, are combined or co-administered with one or more siRNAs specifically targeting an HBV polynucleotide. Examples of siRNA specifically targeting an HBV polynucleotide that can be combine or co-administered include TKM-HBV (TKM-HepB), ALN-HBV, SR-008, HepB-nRNA, ARC-520, ARC-521, ARB-1740, ARB-1467, AB-729, DCR-HBVS, RG-6084 (PD-L1), RG-6217, ALN-HBV-02, JNJ-3989 (ARO-HBV), STSG-0002, LUNAR-HBV and DCR-HBVS (DCR-S219).

DNA-Directed RNA Interference (ddRNAi)

In various embodiments, the immunogenic polypeptides, polynucleotides encoding such polypeptides, vectors, LNPs and immunogenic compositions comprising such polypeptides or polynucleotides, as described herein, are combined or co-administered with one or more ddRNAi specifically targeting an HBV polynucleotide. Examples of ddRNAi specifically targeting an HBV polynucleotide that can be combined or co-administered include BB-HB-331.

Endonuclease Modulators

In various embodiments, the immunogenic polypeptides, polynucleotides encoding such polypeptides, vectors, LNPs and immunogenic compositions comprising such polypeptides or polynucleotides, as described herein, are combined or co-administered with one or more endonuclease modulators. Examples of endonuclease modulators that can be combined or co-administered include PGN-514.

Ribonucleotide Reductase Inhibitors

In various embodiments, the immunogenic polypeptides, polynucleotides encoding such polypeptides, vectors, LNPs and immunogenic compositions comprising such polypeptides or polynucleotides, as described herein, are combined or co-administered with one or more ribonucleotide reductase inhibitors. Examples of inhibitors of ribonucleotide reductase that can be combined or co-administered include Trimidox.

Non-Nucleoside Reverse Transcriptase Inhibitors (NNRTIs)

In various embodiments, the immunogenic polypeptides, polynucleotides encoding such polypeptides, vectors, LNPs and immunogenic compositions comprising such polypeptides or polynucleotides, as described herein, are combined or co-administered with one or more NNRTIs. Examples of NNRTIs that can be combined or co-administered include the compounds disclosed in WO2018118826 (Merck), WO2018080903 (Merck), WO2018119013 (Merck), WO2017100108 (Idenix), WO2017027434 (Merck), WO2017007701 (Merck), WO2008005555 (Gilead).

HBV Replication Inhibitors

In various embodiments, the immunogenic polypeptides, polynucleotides encoding such polypeptides, vectors, LNPs and immunogenic compositions comprising such polypeptides or polynucleotides, as described herein, are combined or co-administered with one or more HBV replication inhibitors. Examples of HBV replication inhibitors that can be combined or co-administered include GP-31502, isothiafludine, IQP-HBV, RM-5038, and Xingantie.

Covalently Closed Circular DNA (cccDNA) Inhibitors

In various embodiments, the immunogenic polypeptides, polynucleotides encoding such polypeptides, vectors, LNPs and immunogenic compositions comprising such polypeptides or polynucleotides, as described herein, are combined or co-administered with one or more cccDNA inhibitors. Examples of cccDNA inhibitors that can be combined or co-administered include BSBI-25, ccc-R08, and CHR-101.

Farnesoid X Receptor (FXR) Agonists

In various embodiments, the immunogenic polypeptides, polynucleotides encoding such polypeptides, vectors, LNPs and immunogenic compositions comprising such polypeptides or polynucleotides, as described herein, are combined or co-administered with one or more FXR agonists. Examples of FXR agonists that can be combined or co-administered include EYP-001, cilofexor (GS-9674), EDP-305, MET-409, Tropifexor, AKN-083, RDX-023, BWD-100, LMB-763, INV-3, NTX-023-1, EP-024297 and GS-8670.

Anti-HBV Antibodies

In various embodiments, the immunogenic polypeptides, polynucleotides encoding such polypeptides, vectors, LNPs and immunogenic compositions comprising such polypeptides or polynucleotides, as described herein, are combined or co-administered with one or more antibodies that specifically binds to an HBV antigen, including an HBV peptide presented in a major histocompatibility molecule (MHC) molecule (pMHC). Examples of HBV antibodies targeting the surface antigens of the hepatitis B virus that can be combined or co-administered include lenvervimab (GC-1102), XTL-17, XTL-19, KN-003, IV Hepabulin SN, and fully human monoclonal antibody therapy (hepatitis B virus infection, Humabs BioMed). Antibodies targeting HBV X protein (HBx) that can be combined or co-administered are described, e.g., in Kornyeyev, et al., *J Virol.* 2019 Jul. 30; 93(16). pii: e00248-19.

Examples of HBV antibodies, including monoclonal antibodies and polyclonal antibodies, that can be combined or co-administered include Zutectra, Shang Sheng Gan Di, Uman Big (Hepatitis B Hyperimmune), Omri-Hep-B, Nabi-HB, Hepatect CP, HepaGam B, igantibe, Niuliva, CT-P24, hepatitis B immunoglobulin (intravenous, pH4, HBV infection, Shanghai RAAS Blood Products), and Fovepta (BT-088).

Examples of fully human monoclonal HBV antibodies that can be combined or co-administered include HBC-34.

Antibodies against HBV viral peptide/major histocompatibility complex (MHC) class I (pMHC) complexes that can be combined or co-administered are described, e.g., in Sastry, et al., *J Virol.* 2011 March; 85(5):1935-42 and in WO2011062562.

CCR2 Chemokine Antagonists

In various embodiments, the immunogenic polypeptides, polynucleotides encoding such polypeptides, vectors, LNPs and immunogenic compositions comprising such polypeptides or polynucleotides, as described herein, are combined or co-administered with one or more CCR2 chemokine antagonists. Examples of CCR2 chemokine antagonists that can be combined or co-administered include propagermanium.

Thymosin Agonists

In various embodiments, the immunogenic polypeptides, polynucleotides encoding such polypeptides, vectors, LNPs and immunogenic compositions comprising such polypeptides or polynucleotides, as described herein, are combined or co-administered with one or more thymosin agonists, e.g., a recombinant thymosin alpha-1. Examples of thymosin agonists that can be combined or co-administered include Thymalfasin, and recombinant thymosin alpha 1 (GeneScience). Examples of recombinant thymosin alpha-1 include NL-004 and PEGylated thymosin alpha-1.

Interleukin Receptor Agonists (e.g., Cytokines)

In some embodiments, the immunogenic polypeptides, polynucleotides encoding such polypeptides, vectors, LNPs and immunogenic compositions comprising such polypeptides or polynucleotides, as described herein, are combined or co-administered with one or more interleukin receptor agonists of an interleukin receptor selected from IL-2, IL-7, IL-12 and IL-15. In some embodiments, the immunogenic polypeptides, polynucleotides encoding such polypeptides, vectors, LNPs and immunogenic compositions comprising such polypeptides or polynucleotides, as described herein, are combined or co-administered with one or more cytokines selected from the group consisting of IL-2, IL-7, IL-12, IL-15, IL-21, IL-24, and variants thereof. Examples of IL-2 receptor agonists that can be combined or co-administered include proleukin (aldesleukin, IL-2); celmoleukin; pegylated IL-2 (e.g., NKTR-214); modified variants of IL-2 (e.g., THOR-707), bempegaldesleukin, AIC-284, ALKS-4230, CUI-101 and Neo-2/15. Examples of IL-15 receptor agonists that can be combined or co-administered include ALT-803, NKTR-255, and hetIL-15, interleukin-15/Fc fusion protein, AM-0015, NIZ-985, SO-C101, IL-15 Synthorin (pegylated 11-15), P-22339, and an IL-15-PD-1 fusion protein N-809. Examples of IL-7 receptor agonists that can be combined or co-administered include CYT-107.

Nucleoprotein Modulators

In various embodiments, the immunogenic polypeptides, polynucleotides encoding such polypeptides, vectors, LNPs and immunogenic compositions comprising such polypeptides or polynucleotides, as described herein, are combined or co-administered with one or more nucleoprotein modulators. Nucleoprotein modulators may be either HBV core or capsid protein inhibitors. Examples of nucleoprotein modulators that can be combined or co-administered include GS-4882, AB-423, AB-836, AT-130, ALG-001075, ALG-001024, ALG-000184, EDP-514, GLS4, NVR-1221, NVR-3778, AL-3778, BAY 41-4109, morphothiadine mesilate, ARB-168786, ARB-880, ARB-1820, GST-HG-141, JNJ-379, JNJ-632, RG-7907, GST-HG-141, HEC-72702, KL-060332, AB-506, ABI-H0731, ABI-H3733, JNJ-440, AK-0605, HRS-5091, VNRX-9945, ABI-H2158, CB-HBV-001, AK-0605, SOC-10, SOC-11 and DVR-23.

Examples of capsid inhibitors that can be combined or co-administered include ALG-000184, ABI-H0731, NVR 3-778, and compounds disclosed in US2018161307 (Gilead Sciences), US20140275167 (Novira Therapeutics), US20130251673 (Novira Therapeutics), US20140343032 (Roche), WO2014037480 (Roche), US20130267517 (Roche), WO2014131847 (Janssen), WO2014033176 (Janssen), WO2014033170 (Janssen), WO2014033167 (Janssen), WO2015/059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), WO2017198744 (Roche), US 20170334882 (Novira), US20170334898 (Roche), WO2017202798 (Roche), WO2017214395 (Enanta), WO2018001944 (Roche), WO2018001952 (Roche), WO2018005881 (Novira), WO2018005883 (Novira), WO2018011100 (Roche), WO2018011160 (Roche), WO2018011162 (Roche), WO2018011163 (Roche), WO2018036941 (Roche), WO2018043747 (Kyoto Univ), US20180065929 (Janssen), WO2016168619 (Indiana University), WO2016195982 (The Penn State Foundation), WO2017001655 (Janssen), WO2017048950 (Assembly Biosciences), WO2017048954 (Assembly Biosciences), WO2017048962 (Assembly Biosciences), US20170121328 (Novira), US20170121329 (Novira).

Examples of transcript inhibitors that can be combined or co-administered include compounds disclosed in WO2017013046 (Roche), WO2017016960 (Roche), WO2017017042 (Roche), WO2017017043 (Roche), WO2017061466 (Toyoma chemicals), WO2016177655 (Roche), WO2016161268 (Enanta). WO2017001853 (Redex Pharma), WO2017211791 (Roche), WO2017216685 (Novartis), WO2017216686 (Novartis), WO2018019297 (Ginkgo Pharma), WO2018022282 (Newave Pharma), US20180030053 (Novartis), WO2018045911 (Zhejiang Pharma).

Innate Immune Activators

In some embodiments, the immunogenic polypeptides, polynucleotides encoding such polypeptides, vectors, LNPs and immunogenic compositions comprising such polypeptides or polynucleotides, as described herein, are combined or co-administered with one or more innate immune activators. In various embodiments, the one or more innate immune activators comprises an agonist of a receptor selected from the group consisting of fms related tyrosine kinase 3 (FLT3), stimulator of interferon genes (STING) receptor, DExD/H-box helicase 58 (DDX58; a.k.a., RIG-I), nucleotide binding oligomerization domain containing 2 (NOD2). In some embodiments, the methods entail co-administering GS-3583 and/or GS-9992. In some embodiments, the methods entail combining or co-administering a FLT3 agonist, e.g., GS-3583 or CDX-301.

STING Agonists, RIG-I and NOD2 Modulators

In some embodiments, the immunogenic polypeptides, polynucleotides encoding such polypeptides, vectors, LNPs and immunogenic compositions comprising such polypeptides or polynucleotides, as described herein, are combined or co-administered with a stimulator of interferon response cGAMP interactor 1 (STING or STING1; NCBI Gene ID: 340061) agonist. In some embodiments, the STING/STING1 agonist or activator is selected from the group consisting of ADU-S100 (MIW-815), SB-11285, MK-1454, SR-8291, AdVCA0848, STINGVAX, GSK-532, SYN-STING, MSA-1, SR-8291, 5,6-dimethylxanthenone-4-acetic acid (DMXAA), cyclic-GAMP (cGAMP) and cyclic-di-AMP. Examples of STING agonists that can be combined or co-administered include the compounds disclosed in WO 2018065360 (Biolog Life Science Institute Forschungslabor und Biochemica-Vertrieb GmbH, Germany), WO 2018009466 (Aduro Biotech), WO 2017186711 (InvivoGen), WO 2017161349 (Immune Sensor), WO 2017106740 (Aduro Biotech), US 20170158724 (Glaxo Smithkline), WO 2017075477 (Aduro Biotech), US 20170044206 (Merck), WO 2014179760 (University of California), WO2018098203 (Janssen), WO2018118665 (Merck), WO2018118664 (Merck), WO2018100558 (Takeda), WO2018067423 (Merck), WO2018060323 (Boehringer).

In some embodiments, the immunogenic polypeptides, polynucleotides encoding such polypeptides, vectors, LNPs and immunogenic compositions comprising such polypeptides or polynucleotides, as described herein, are combined or co-administered with a DExD/H-box helicase 58 (DDX58; a.k.a., retinoic acid-inducible gene 1 (RIG-I), RIG1, RIGI, RLR-1, SGMRT2; NCBI Gene ID: 23586). Illustrative RIG-I agonists that can be combined or co-administered include inarigivir soproxil (SB-9200; GS-9992); SB-40, SB-44, ORI-7246, ORI-9350, ORI-7537, ORI-9020, ORI-9198, ORI-7170, and RGT-100.

In some embodiments, the immunogenic polypeptides, polynucleotides encoding such polypeptides, vectors, LNPs and immunogenic compositions comprising such polypeptides or polynucleotides, as described herein, are combined or co-administered with a nucleotide binding oligomerization domain containing 2 (NOD2; NCBI Gene ID: 64127) agonist, such as inarigivir soproxil (SB-9200; GS-9992), and IR-103.

Phosphatidylinositol 3-kinase (PI3K) Inhibitors

In some embodiments, the immunogenic polypeptides, polynucleotides encoding such polypeptides, vectors, LNPs and immunogenic compositions comprising such polypeptides or polynucleotides, as described herein, are combined or co-administered with an inhibitor of a phosphatidylinositol-4,5-bisphosphate 3-kinase catalytic subunit, e.g., phosphatidylinositol-4,5-bisphosphate 3-kinase catalytic subunit alpha (PIK3CA, CLAPO, CLOVE, CWS5, MCAP, MCM, MCMTC, PI3K, PI3K-alpha, p110-alpha; NCBI Gene ID: 5290); phosphatidylinositol-4,5-bisphosphate 3-kinase catalytic subunit beta (PIK3CB, P110BETA, PI3K, PI3KBETA, PIK3C1; NCBI Gene ID: 5291); phosphatidylinositol-4,5-bisphosphate 3-kinase catalytic subunit gamma (PIK3CG, PI3CG, PI3K, PI3Kgamma, PIK3, p110gamma, p120-PI3K; Gene ID: 5494); and/or phosphatidylinositol-4,5-bisphosphate 3-kinase catalytic subunit delta (PIK3CD, APDS, IMD14, P110DELTA, PI3K, p110D, NCBI Gene ID: 5293). In some embodiments, the PI3K inhibitor is a pan-PI3K inhibitor. Examples of PI3K inhibitors include without limitation, ACP-319, AEZA-129, AMG-319, AS252424, AZD8186, BAY 1082439, BEZ235, bimiralisib (PQR309), buparlisib (BKM120), BYL719 (alpelisib), carboxyamidotriazole orotate (CTO), CH5132799, CLR-457, CLR-1401, copanlisib (BAY 80-6946), DS-7423, duvelisib (IPI-145), fimepinostat (CUDC-907), gedatolisib (PF-05212384), GDC-0032, GDC-0084 (RG7666), GDC-0077, pictilisib (GDC-0941), GDC-0980, GSK2636771, GSK2269577, idelalisib (Zydelig®), INCB040093, INCB50465, IPI-443, IPI-549, KAR4141, LY294002, LY3023414, NERLYNX® (neratinib), nemiralisib (GSK2269557), omipalisib (GSK2126458, GSK458), OXY111A, panulisib (P7170, AK151761), PA799, perifosine (KRX-0401), Pilaralisib (SAR245408; XL147), puquitinib mesylate (XC-302), SAR260301, seletalisib (UCB-5857), serabelisib (INK-1117, MLN-1117, TAK-117), SF1126, sonolisib (PX-866), RG7604, rigosertib sodium (ON-01910 sodium), RP5090, tenalisib (RP6530), RV-1729, SRX3177, taselisib, TG100115, umbralisib (TGR-1202), TGX221, voxtalisib (SAR245409), VS-5584, WX-037, X-339, X-414, XL499, XL756, wortmannin, ZSTK474, and the compounds described in WO 2005/113556 (ICOS), WO 2013/052699 (Gilead Calistoga), WO 2013/116562 (Gilead Calistoga), WO 2014/100765 (Gilead Calistoga), WO 2014/100767 (Gilead Calistoga), and WO 2014/201409 (Gilead Sciences).

Immune Checkpoint Modulators

In some embodiments, the immunogenic polypeptides, polynucleotides encoding such polypeptides, vectors, LNPs and immunogenic compositions comprising such polypeptides or polynucleotides, as described herein, are combined or co-administered with one or more blockers or inhibitors of inhibitory immune checkpoint proteins or receptors and/or with one or more stimulators, activators or agonists of one or more stimulatory immune checkpoint proteins or receptors. Blockade or inhibition of inhibitory immune checkpoints can positively regulate T-cell or NK cell activation and prevent immune escape of infected cells. Activation or stimulation of stimulatory immune check points can augment the effect of immune checkpoint inhibitors in infective therapeutics. In various embodiments, the immune checkpoint proteins or receptors regulate T cell responses (e.g., reviewed in Xu, et al., J Exp Clin Cancer Res. (2018) 37:110). In various embodiments, the immune checkpoint proteins or receptors regulate NK cell responses (e.g., reviewed in Davis, et al., Semin Immunol. (2017) 31:64-75 and Chiossone, et al., Nat Rev Immunol. (2018) 18(11):671-688).

Examples of immune checkpoint proteins or receptors include without limitation CD27 (NCBI Gene ID: 939); CD70 (NCBI Gene ID: 970); CD40 (NCBI Gene ID: 958); CD40LG (NCBI Gene ID: 959); CD47 (NCBI Gene ID: 961); CD48 (SLAMF2; NCBI Gene ID: 962); transmembrane and immunoglobulin domain containing 2 (TMIGD2, CD28H; NCBI Gene ID: 126259); CD84 (LY9B, SLAMF5; NCBI Gene ID: 8832); CD96 (NCBI Gene ID: 10225); CD160 (NCBI Gene ID: 11126); MS4A1 (CD20; NCBI Gene ID: 931); CD244 (SLAMF4; NCBI Gene ID: 51744); CD276 (B7H3; NCBI Gene ID: 80381); V-set domain containing T cell activation inhibitor 1 (VTCN1, B7H4; NCBI Gene ID: 79679); V-set immunoregulatory receptor (VSIR, B7H5, VISTA; NCBI Gene ID: 64115); immunoglobulin superfamily member 11 (IGSF11, VSIG3; NCBI Gene ID: 152404); natural killer cell cytotoxicity receptor 3 ligand 1 (NCR3LG1, B7H6; NCBI Gene ID: 374383); HERV-H LTR-associating 2 (HHLA2, B7H7; NCBI Gene ID: 11148); inducible T cell co-stimulator (ICOS, CD278; NCBI Gene ID: 29851); inducible T cell co-stimulator ligand (ICOSLG, B7H2; NCBI Gene ID: 23308); TNF receptor superfamily member 4 (TNFRSF4, OX40; NCBI Gene ID: 7293); TNF superfamily member 4 (TNFSF4, OX40L; NCBI Gene ID: 7292); TNFRSF8 (CD30; NCBI Gene ID: 943); TNFSF8 (CD30L; NCBI Gene ID: 944); TNFRSF10A (CD261, DR4, TRAILR1; NCBI Gene ID: 8797); TNFRSF9 (CD137; NCBI Gene ID: 3604); TNFSF9 (CD137L; NCBI Gene ID: 8744); TNFRSF10B (CD262, DR5, TRAILR2; NCBI Gene ID: 8795); TNFRSF10 (TRAIL; NCBI Gene ID: 8743); TNFRSF14 (HVEM, CD270; NCBI Gene ID: 8764); TNFSF14 (HVEML; NCBI Gene ID: 8740); CD272 (B and T lymphocyte associated (BTLA); NCBI Gene ID: 151888); TNFRSF17 (BCMA, CD269; NCBI Gene ID: 608); TNFSF13B (BAFF; NCBI Gene ID: 10673); TNFRSF18 (GITR; NCBI Gene ID: 8784); TNFSF18 (GITRL; NCBI Gene ID: 8995); MHC class I polypeptide-related sequence A (MICA; NCBI Gene ID: 100507436); MHC class I polypeptide-related sequence B (MICB; NCBI Gene ID: 4277); CD274 (CD274, PDL1, PD-L1; NCBI Gene ID: 29126); programmed cell death 1 (PDCD1, PD1, PD-1; NCBI Gene ID: 5133); cytotoxic T-lymphocyte associated protein 4 (CTLA4, CD152; NCBI Gene ID: 1493); CD80 (B7-1; NCBI Gene ID: 941); CD28 (NCBI Gene ID: 940); nectin cell adhesion molecule 2 (NECTIN2, CD112; NCBI Gene ID: 5819); CD226 (DNAM-1; NCBI Gene ID: 10666); Poliovirus receptor (PVR) cell adhesion molecule (PVR, CD155; NCBI Gene ID: 5817); PVR related immunoglobulin domain containing (PVRIG, CD112R; NCBI Gene ID: 79037); T cell immunoreceptor with Ig and ITIM domains (TIGIT; NCBI Gene ID: 201633); T cell immunoglobulin and mucin domain containing 4 (TIMD4; TIM4; NCBI Gene ID: 91937); hepatitis A virus cellular receptor 2 (HAVCR2, TIMD3, TIM3; NCBI Gene ID: 84868); galectin 9 (LGALS9; NCBI Gene ID: 3965); lymphocyte activating 3 (LAG3, CD223; NCBI Gene ID: 3902); signaling lymphocytic activation molecule family member 1 (SLAMF1, SLAM, CD150; NCBI Gene ID: 6504); lymphocyte antigen 9 (LY9, CD229, SLAMF3; NCBI Gene ID: 4063); SLAM family member 6 (SLAMF6, CD352; NCBI Gene ID: 114836); SLAM family member 7 (SLAMF7, CD319; NCBI Gene ID: 57823); UL16 binding protein 1 (ULBP1; NCBI Gene ID: 80329); UL16 binding protein 2 (ULBP2; NCBI Gene ID: 80328); UL16 binding protein 3 (ULBP3; NCBI Gene ID: 79465); retinoic acid early transcript 1E (RAET1E; ULBP4; NCBI Gene ID: 135250); retinoic acid early transcript 1G (RAET1G; ULBP5; NCBI Gene ID: 353091); retinoic acid early transcript 1L (RAET1L; ULBP6; NCBI Gene ID: 154064); killer cell lectin like receptor C1 (KLRC1, NKG2A, CD159A; NCBI Gene ID: 3821); killer cell lectin like receptor K1 (KLRK1, NKG2D, CD314; NCBI Gene ID: 22914); killer cell lectin like receptor C2 (KLRC2, CD159c, NKG2C; NCBI Gene ID: 3822); killer cell lectin like receptor C3 (KLRC3, NKG2E; NCBI Gene ID: 3823); killer cell lectin like receptor C4 (KLRC4, NKG2F; NCBI Gene ID: 8302); killer cell immunoglobulin like receptor, two Ig domains and long cytoplasmic tail 1 (KIR2DL1; NCBI Gene ID: 3802); killer cell immunoglobulin like receptor, two Ig domains and long cytoplasmic tail 2 (KIR2DL2; NCBI Gene ID: 3803); killer cell immunoglobulin like receptor, two Ig domains and long cytoplasmic tail 3 (KIR2DL3; NCBI Gene ID: 3804); killer cell immunoglobulin like receptor, three Ig domains and long cytoplasmic tail 1 (KIR3DL1, KIR, CD158E1; NCBI Gene ID:

3811) (e.g., Lirilumab (IPH2102/BMS-986015), IPH-4102); and killer cell lectin like receptor D1 (KLRD1; NCBI Gene ID: 3824).

In some embodiments, the immunogenic polypeptides, polynucleotides encoding such polypeptides, vectors, LNPs and immunogenic compositions comprising such polypeptides or polynucleotides, as described herein, are combined or co-administered with one or more blockers or inhibitors of one or more T-cell inhibitory immune checkpoint proteins or receptors. Illustrative T-cell inhibitory immune checkpoint proteins or receptors include without limitation CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In various embodiments, the agents, as described herein, are combined with one or more agonist or activators of one or more T-cell stimulatory immune checkpoint proteins or receptors. Illustrative T-cell stimulatory immune checkpoint proteins or receptors include without limitation CD27, CD70; CD40, CD40LG; inducible T cell co-stimulator (ICOS, CD278); inducible T cell co-stimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); CD244 (2B4, SLAMF4), Poliovirus receptor (PVR) cell adhesion molecule (PVR, CD155). See, e.g., Xu, et al., J Exp Clin Cancer Res. (2018) 37:110.

In some embodiments, the immunogenic polypeptides, polynucleotides encoding such polypeptides, vectors, LNPs and immunogenic compositions comprising such polypeptides or polynucleotides, as described herein, are combined or co-administered with one or more blockers or inhibitors of one or more NK-cell inhibitory immune checkpoint proteins or receptors. Illustrative NK-cell inhibitory immune checkpoint proteins or receptors include without limitation killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); and killer cell lectin like receptor D1 (KLRD1, CD94).

In some embodiments, the immunogenic polypeptides, polynucleotides encoding such polypeptides, vectors, LNPs and immunogenic compositions comprising such polypeptides or polynucleotides, as described herein, are combined or co-administered with one or more agonists or activators of one or more NK-cell stimulatory immune checkpoint proteins or receptors. Illustrative NK-cell stimulatory immune checkpoint proteins or receptors include without limitation CD16, CD226 (DNAM-1); CD244 (2B4, SLAMF4); killer cell lectin like receptor K1 (KLRK1, NKG2D, CD314); SLAM family member 7 (SLAMF7). See, e.g., Davis, et al., Semin Immunol. (2017) 31:64-75; Fang, et al., Semin Immunol. (2017) 31:37-54; and Chiossone, et al., Nat Rev Immunol. (2018) 18(11):671-688.

Inhibitors of Cytotoxic T-Lymphocyte-Associated Protein 4 (CTLA4)

In various embodiments, the immunogenic polypeptides, polynucleotides encoding such polypeptides, vectors, LNPs and immunogenic compositions comprising such polypeptides or polynucleotides, as described herein, are combined or co-administered with one or more Inhibitors of cytotoxic T-lymphocyte-associated protein 4 (CTLA4) (CD152; NCBI Gene ID: 1493). Examples of inhibitors of CTLA4 that can be co-administered include without limitation ipilimumab, tremelimumab, BMS-986218, AGEN1181, AGEN1884, AGEN2041, BMS-986249, MK-1308, REGN-4659, ADU-1604, CS-1002, BCD-145, APL-509, JS-007, BA-3071, ONC-392, JHL-1155, KN-044, CG-0161, ATOR-1144, PBI-5D3H5, BPI-002, belatacept, PSI-001, PRS-010, JHL-1155, as well as multi-specific inhibitors FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4), and AK-104 (CTLA4/PD-1).

Inhibitors of PD-L1 (CD274) or PD-1 (PDCD1; CD279)

In various embodiments, the immunogenic polypeptides, polynucleotides encoding such polypeptides, vectors, LNPs and immunogenic compositions comprising such polypeptides or polynucleotides, as described herein, are combined or co-administered with one or more inhibitors of programmed cell death 1 ligand 1 (PD-L1; CD274; NCBI Gene ID: 29126) or programmed cell death 1 (PD-1; PDCD1; CD279; NCBI Gene ID: 5133). Examples of inhibitors of PD-L1 (CD274) or PD-1 (PDCD1) that can be combined or co-administered include without limitation zimberelimab (AB122), pembrolizumab, nivolumab, cemiplimab, pidilizumab, AMP-224, MEDI0680 (AMP-514), spartalizumab, atezolizumab, avelumab (MSB0010718C), ASC22, durvalumab, ALN-PDL, BMS-936559, CK-301, PF-06801591, BGB-108, BGB-A317 (tislelizumab), GLS-010 (WBP-3055), AK-103 (HX-008), GB-226, AK-105, CS-1003, HLX-10, MGA-012, BI-754091, PDR-001, AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181, PD1-PIK, BAT-1306, RO-6084 (PD-L1 antisense oligonucleotide), STI-1110, GX-P2, RG-7446, mDX-400, CX-072, CBT-502, TSR-042 (dostarlimab), MSB-2311, JTX-4014, BGB-A333, SHR-1316, CS-1001 (WBP-3155), MEDI-0680, envafolimab (KN-035), KD-033, KY-1003, IBI-308 (sintilimab), HLX-20, KL-A167, STI-A1014, STI-A1015 (IMC-001), BCD-135, FAZ-053, TQB-2450, MDX1105-01, MSB-0010718C, GS-4224, GS-4416, INCB086550, MAX10181, as well as multi-specific inhibitors FPT-155 (CTLA4/PD-L1/CD28), PF-06936308 (PD-1/CTLA4), MGD-013 (PD-1/LAG-3), FS-118 (LAG-3/PD-L1) MGD-019 (PD-1/CTLA4), KN-046 (PD-1/CTLA4), MEDI-5752 (CTLA4/

PD-1), RO-7121661 (PD-1/TIM-3), XmAb-20717 (PD-1/CTLA4), AK-104 (CTLA4/PD-1), M7824 (PD-L1/TGFβ-EC domain), CA-170 (PD-L1/VISTA), CDX-527 (CD27/PD-L1), LY-3415244 (TIM3/PDL1), GNS-1480 (Epidermal growth factor receptor antagonist; Programmed cell death ligand 1 inhibitor), M-7824 (PD-L1/TGF-β bifunctional fusion protein), and INBRX-105 (4-1BB/PDL1).

Examples of PD-1 inhibitors that can be combined or co-administered further include the compounds disclosed in WO2017112730 (Incyte Corp), WO2017087777 (Incyte Corp), WO2017017624, WO2014151634 (BristolMyers Squibb Co), WO201317322 (BristolMyers Squibb Co), WO2018119286 (Incyte Corp), WO2018119266 (Incyte Corp), WO2018119263 (Incyte Corp), WO2018119236 (Incyte Corp), WO2018119221 (Incyte Corp), WO2018118848 (BristolMyers Squibb Co), WO20161266460 (BristolMyers Squibb Co), WO2017087678 (BristolMyers Squibb Co), WO2016149351 (BristolMyers Squibb Co), WO2015033299 (Aurigene Discovery Technologies Ltd), WO2015179615 (Eisai Co Ltd; Eisai Research Institute), WO2017066227 (BristolMyers Squibb Co), WO2016142886 (Aurigene Discovery Technologies Ltd), WO2016142852 (Aurigene Discovery Technologies Ltd), WO2016142835 (Aurigene Discovery Technologies Ltd; Individual), WO2016142833 (Aurigene Discovery Technologies Ltd), WO2018085750 (BristolMyers Squibb Co), WO2015033303 (Aurigene Discovery Technologies Ltd), WO2017205464 (Incyte Corp), WO2016019232 (3M Co; Individual; Texas A&M University System), WO2015160641 (BristolMyers Squibb Co), WO2017079669 (Incyte Corp), WO2015033301 (Aurigene Discovery Technologies Ltd), WO2015034820 (BristolMyers Squibb Co), WO2018073754 (Aurigene Discovery Technologies Ltd), WO2016077518 (BristolMyers Squibb Co), WO2016057624 (BristolMyers Squibb Co), WO2018044783 (Incyte Corp), WO2016100608 (BristolMyers Squibb Co), WO2016100285 (BristolMyers Squibb Co), WO2016039749 (BristolMyers Squibb Co), WO2015019284 (Cambridge Enterprise Ltd), WO2016142894 (Aurigene Discovery Technologies Ltd), WO2015134605 (BristolMyers Squibb Co), WO2018051255 (Aurigene Discovery Technologies Ltd), WO2018051254 (Aurigene Discovery Technologies Ltd), WO2017222976 (Incyte Corp), WO2017070089 (Incyte Corp), WO2018044963 (BristolMyers Squibb Co), WO2013144704 (Aurigene Discovery Technologies Ltd), WO2018013789 (Incyte Corp), WO2017176608 (BristolMyers Squibb Co), WO2018009505 (BristolMyers Squibb Co), WO2011161699 (Aurigene Discovery Technologies Ltd), WO2015119944 (Incyte Corp; Merck Sharp & Dohme Corp), WO2017192961 (Incyte Corp), WO2017106634 (Incyte Corp), WO2013132317 (Aurigene Discovery Technologies Ltd), WO2012168944 (Aurigene Discovery Technologies Ltd), WO2015036927 (Aurigene Discovery Technologies Ltd), WO2015044900 (Aurigene Discovery Technologies Ltd), WO2018026971 (Arising International).

In various embodiments, the immunogenic polypeptides, polynucleotides encoding such polypeptides, vectors, LNPs and immunogenic compositions comprising such polypeptides or polynucleotides, as described herein, are combined or co-administered with one or more proteinaceous (e.g., antibody or fragment thereof, or antibody mimetic) inhibitors of PD-L1 (CD274), PD-1 (PDCD1) or CTLA4. In some embodiments, the one or more immune checkpoint inhibitors comprises a small organic molecule inhibitor of PD-L1 (CD274), PD-1 (PDCD1) or CTLA4. In some embodiments, the small molecule inhibitor of CD274 or PDCD1 is selected from the group consisting of GS-4224, GS-4416, INCB086550 and MAX10181. Additional examples of small molecule PD-L1 inhibitors include those disclosed in U.S. Publication No. US2018305315 (Gilead Sciences), US2020017471 (Gilead Sciences) and US2019270727 (Gilead Sciences). In some embodiments, the small molecule inhibitor of CTLA4 comprises BPI-002.

Inhibitors of T Cell Immunoreceptor with Ig and ITIM Domains (TIGIT)

In various embodiments, the immunogenic polypeptides, polynucleotides encoding such polypeptides, vectors, LNPs and immunogenic compositions comprising such polypeptides or polynucleotides, as described herein, are combined or co-administered with one or more inhibitors of T cell immunoreceptor with Ig and ITIM domains (TIGIT) (NCBI Gene ID: 201633). Example anti-TIGIT antibodies, that can be combined or co-administered include etigilimab, BMS-986207, tiragolumab (a.k.a., MTIG-7192A; RG-6058; RO 7092284), AGEN1307, AGEN1327, AGEN1777, COM-902, IBI-939, AB154, MG1131 and EOS884448 (EOS-448).

TNF Receptor Superfamily (TNFRSF) Member Agonists or Activators

In various embodiments, the immunogenic polypeptides, polynucleotides encoding such polypeptides, vectors, LNPs and immunogenic compositions comprising such polypeptides or polynucleotides, as described herein, are combined or co-administered with one or more agonists of one or more TNF receptor superfamily (TNFRSF) members, e.g., an agonist of one or more of TNFRSF1A (NCBI Gene ID: 7132), TNFRSF1B (NCBI Gene ID: 7133), TNFRSF4 (OX40, CD134; NCBI Gene ID: 7293), TNFRSF5 (CD40; NCBI Gene ID: 958), TNFRSF6 (FAS, NCBI Gene ID: 355), TNFRSF7 (CD27, NCBI Gene ID: 939), TNFRSF8 (CD30, NCBI Gene ID: 943), TNFRSF9 (4-1BB, CD137, NCBI Gene ID: 3604), TNFRSF10A (CD261, DR4, TRAILR1, NCBI Gene ID: 8797), TNFRSF10B (CD262, DR5, TRAILR2, NCBI Gene ID: 8795), TNFRSF10C (CD263, TRAILR3, NCBI Gene ID: 8794), TNFRSF10D (CD264, TRAILR4, NCBI Gene ID: 8793), TNFRSF11A (CD265, RANK, NCBI Gene ID: 8792), TNFRSF11B (NCBI Gene ID: 4982), TNFRSF12A (CD266, NCBI Gene ID: 51330), TNFRSF13B (CD267, NCBI Gene ID: 23495), TNFRSF13C (CD268, NCBI Gene ID: 115650), TNFRSF16 (NGFR, CD271, NCBI Gene ID: 4804), TNFRSF17 (BCMA, CD269, NCBI Gene ID: 608), TNFRSF18 (GITR, CD357, NCBI Gene ID: 8784), TNFRSF19 (NCBI Gene ID: 55504), TNFRSF21 (CD358, DR6, NCBI Gene ID: 27242), and TNFRSF25 (DR3, NCBI Gene ID: 8718).

Example anti-TNFRSF4 (OX40) antibodies that can be combined or co-administered include without limitation, MEDI6469, MEDI6383, MEDI0562 (tavolixizumab), MOXR0916, PF-04518600, RG-7888, GSK-3174998, INCAGN1949, BMS-986178, GBR-8383, ABBV-368, and those described in WO2016179517, WO2017096179, WO2017096182, WO2017096281, and WO2018089628.

Example anti-TNFRSF5 (CD40) antibodies that can be combined or co-administered include without limitation RG7876, SEA-CD40, APX-005M and ABBV-428.

In some embodiments, the anti-TNFRSF7 (CD27) antibody varlilumab (CDX-1127) is combined or co-administered.

Example anti-TNFRSF9 (4-1BB, CD137) antibodies that can be combined or co-administered include without limitation urelumab, utomilumab (PF-05082566), AGEN-2373 and ADG-106.

Example anti-TNFRSF18 (GITR) antibodies that can be combined or co-administered include without limitation, MEDI1873, FPA-154, INCAGN-1876, TRX-518, BMS-986156, MK-1248, GWN-323, and those described in WO2017096179, WO2017096276, WO2017096189, and WO2018089628. In some embodiments, an antibody, or fragment thereof, co-targeting TNFRSF4 (OX40) and TNFRSF18 (GITR) is co-administered. Such antibodies are described, e.g., in WO2017096179 and WO2018089628.

Indoleamine-pyrrole-2,3-dioxygenase (IDO1) Inhibitors

In various embodiments, the immunogenic polypeptides, polynucleotides encoding such polypeptides, vectors, LNPs and immunogenic compositions comprising such polypeptides or polynucleotides, as described herein, are combined or co-administered with one or more inhibitors of indoleamine 2,3-dioxygenase 1 (IDO1; NCBI Gene ID: 3620). Examples of IDO1 inhibitors that can be combined or co-administered include without limitation, BLV-0801, epacadostat, resminostat, F-001287, GBV-1012, GBV-1028, GDC-0919, indoximod, NKTR-218, NLG-919-based vaccine, PF-06840003, pyranonaphthoquinone derivatives (SN-35837), SBLK-200802, BMS-986205, and shIDO-ST, EOS-200271, KHK-2455, LY-3381916, and the compounds disclosed in US20100015178 (Incyte), US2016137652 (Flexus Biosciences, Inc.), WO2014073738 (Flexus Biosciences, Inc.), and WO2015188085 (Flexus Biosciences, Inc.).

LAG-3 and TIM-3 Inhibitors

In various embodiments, the immunogenic polypeptides, polynucleotides encoding such polypeptides, vectors, LNPs and immunogenic compositions comprising such polypeptides or polynucleotides, as described herein, are combined or co-administered with an anti-TIM-3 antibody, such as TSR-022, LY-3321367, MBG-453, INCAGN-2390. In various embodiments, the immunogenic polypeptides, polynucleotides encoding such polypeptides, vectors, LNPs and immunogenic compositions comprising such polypeptides or polynucleotides, as described herein, are combined or co-administered with an anti-LAG-3 (Lymphocyte-activation) antibody, such as relatlimab (ONO-4482), LAG-525, MK-4280, REGN-3767, INCAGN2385.

Inhibitors of Apoptosis Proteins Family Proteins (IAPs)

In various embodiments, the immunogenic polypeptides, polynucleotides encoding such polypeptides, vectors, LNPs and immunogenic compositions comprising such polypeptides or polynucleotides, as described herein, are combined or co-administered with an inhibitor of apoptosis proteins family protein (IAP). Examples of IAP inhibitors include APG-1387.

Bruton's Tyrosine Kinase (BTK) Inhibitors

In various embodiments, the immunogenic polypeptides, polynucleotides encoding such polypeptides, vectors, LNPs and immunogenic compositions comprising such polypeptides or polynucleotides, as described herein, are combined or co-administered with an inhibitor of Bruton tyrosine kinase (BTK, AGMX1, AT, ATK, BPK, IGHD3, IMD1, PSCTK1, XLA; NCBI Gene ID: 695). Examples of BTK inhibitors include without limitation, (S)-6-amino-9-(1-(but-2-ynoyl)pyrrolidin-3-yl)-7-(4-phenoxyphenyl)-7H-purin-8 (9H)-one, ABBV-105, acalabrutinib (ACP-196), AC-058, AC-0025, ARQ-531, BMS-986142, dasatinib, ibrutinib (PCI-32765, CRA-032765), GDC-0853, PRN-1008, SNS-062, BGB-3111, CB988, HM71224, KBP-7536, M-2951 (evobrutinib), M7583, tirabrutinib (ONO-4059), ML-319, MSC-2364447, PRN-1008, RDX-022, RG-7845, spebrutinib (CC-292), TAK-020, TAS-5315, TP-0158, TP-4207, vecabrutinib (SNS-062), ARQ-531, SHR-1459, DTRMWXHS-12, and the compounds disclosed in US20140330015 (Ono Pharmaceutical), US20130079327 (Ono Pharmaceutical), and US20130217880 (Ono Pharmaceutical).

Lysine Demethylase (KDM) Inhibitors

In various embodiments, the immunogenic polypeptides, polynucleotides encoding such polypeptides, vectors, LNPs and immunogenic compositions comprising such polypeptides or polynucleotides, as described herein, are combined or co-administered with an inhibitor of a lysine demethylase (KDM). Examples of KDM5 inhibitors that can be combined or co-adminstered include the compounds disclosed in WO2016057924 (Genentech/Constellation Pharmaceuticals), US20140275092 (Genentech/Constellation Pharmaceuticals), US20140371195 (Epitherapeutics), US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), and WO2014164708 (Quanticel).

Examples of KDM1 inhibitors that can be combined or co-administered include the compounds disclosed in U.S. Pat. No. 9,186,337B2 (Oryzon Genomics), GSK-2879552, RG-6016, and ORY-2001.

Arginase Inhibitors

In various embodiments, the immunogenic polypeptides, polynucleotides encoding such polypeptides, vectors, LNPs and immunogenic compositions comprising such polypeptides or polynucleotides, as described herein, are combined or co-administered with an arginase inhibitor. Examples of Arginase inhibitors include CB-1158, C-201, and resminostat.

Bi- and Tri-Specific Natural Killer (NK)-Cell Engagers

In various embodiments, the immunogenic polypeptides, polynucleotides encoding such polypeptides, vectors, LNPs and immunogenic compositions comprising such polypeptides or polynucleotides, as described herein, are combined or co-administered with a bi-specific NK-cell engager (BiKE) or a tri-specific NK-cell engager (TriKE) (e.g., not having an Fc) or bi-specific antibody (e.g., having an Fc) against an NK cell activating receptor, e.g., CD16A, C-type lectin receptors (CD94/NKG2C, NKG2D, NKG2E/H and NKG2F), natural cytotoxicity receptors (NKp30, NKp44 and NKp46), killer cell C-type lectin-like receptor (NKp65, NKp80), Fc receptor FcγR (which mediates antibody-dependent cell cytotoxicity), SLAM family receptors (e.g., 2B4, SLAM6 and SLAM7), killer cell immunoglobulin-like receptors (KIR) (KIR-2DS and KIR-3DS), DNAM-1 and CD137 (41BB). As appropriate, the anti-CD16 binding bi-specific molecules may or may not have an Fc. Illustrative bi-specific NK-cell engagers that can be co-administered target CD16 and one or more HBV-associated antigens as described herein. BiKEs and TriKEs are described, e.g., in Felices, et al., *Methods Mol Biol.* (2016) 1441:333-346; Fang, et al., Semin Immunol. (2017) 31:37-54.

Long Acting Treatments

In various embodiments, the immunogenic polypeptides, polynucleotides encoding such polypeptides, vectors, LNPs and immunogenic compositions comprising such polypeptides or polynucleotides, as described herein, are combined or co-administered with a long acting treatment. Long acting entecavir (subcutaneous depot), long acting tenofovir (TFD and TAF) implants (devices) or subcutaneous depot. An example of long acting entecavir is described in Henry, et al., *Eur J Pharm Sci.* (2019) 136:104958.

Gene Therapy and Cell Therapy

In various embodiments, the immunogenic polypeptides, polynucleotides encoding such polypeptides, vectors, LNPs and immunogenic compositions comprising such polypeptides or polynucleotides, as described herein, are combined or co-administered with a gene or cell therapy regimen. Gene therapy and cell therapy include without limitation the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; genetic approaches to modify cellular activity to further alter endogenous immune responsiveness against the infection.

Gene Editors

The genome editing system can be selected from the group consisting of: a CRISPR/Cas9 system, a zinc finger nuclease system, a TALEN system, a homing endonucleases system, and a meganuclease system (e.g., an ARCUS system); e.g., cccDNA elimination via targeted cleavage, and altering one or more of the hepatitis B virus (HBV) viral genes. Altering (e.g., knocking out and/or knocking down) the PreC, C, X, PreS1, PreS2, S, P or SP gene refers to (1) reducing or eliminating PreC, C, X, PreS1, PreS2, S, P or SP gene expression, (2) interfering with Precore, Core, X protein, Long surface protein, middle surface protein, S protein (also known as HBs antigen and HBsAg), polymerase protein, and/or Hepatitis B spliced protein function (HBe, HBc, HBx, PreS1, PreS2, S, Pol, and/or HBSP or (3) reducing or eliminating the intracellular, serum and/or intraparenchymal levels of HBe, HBc, HBx, LHBs, MHBs, SHBs, Pol, and/or HBSP proteins. Knockdown of one or more of the PreC, C, X, PreS1, PreS2, S, P and/or SP gene(s) is performed by targeting the gene(s) within HBV cccDNA and/or integrated HBV DNA. Additional examples genome editing systems include, but are not limited to those disclosed in US2019284543 (Gilead Sciences), and US2019338263 (Gilead Sciences).

Examples of gene therapy, such as liver targeted anti-HBV gene therapy (using ARCUS technology), or using CRISPR/Cas9 gene editing technology, or EBT-106 (LNP-delivered CRISPR/CasX nuclease.

CAR-T Cell Therapy

CAR-T cell therapy includes a population of immune effector cells engineered to express a chimeric antigen receptor (CAR), wherein the CAR includes an HBV antigen-binding domain. In certain embodiments, the antigen-binding domain is a domain disclosed herein. In certain embodiments, the antigen-binding domain is other than a domain disclosed herein. In certain embodiments, the antigen is HBsAg (i.e. HbsAg-CART). The immune effector cell is a T-cell or an NK cell. In certain embodiments, the T-cell is a CD4+ T-cell, a CD8+ T-cell, a NK cell or a combination thereof. Cells can be autologous or allogeneic. An example of a CART directed to HBV is described in Kruse, et al., *Cytotherapy*. (2018) 20(5):697-705.

TCR-T Cell Therapy

TCR-T cell therapy includes T cells expressing HBV-specific T cell receptors. TCR-T cells are engineered to target HBV derived peptides presented on the surface of virus-infected cells. An example of a TCR directed to HBV is described in Wisskirchen, et al., *J Clin Invest*. (2019) 129(7):2932-2945.

TCR-T cell therapy includes T-Cells expressing HBV surface antigen (HBsAg)-specific TCR, such as IMC-1109V.

TCR-T cell therapy includes TCR-T therapy directed to treatment of HBV, such as LTCR-H2-1.

In another specific embodiment, the immunogenic polypeptides, polynucleotides encoding such polypeptides, vectors, LNPs and immunogenic compositions comprising such polypeptides or polynucleotides, as described herein, are combined or co-administered with an HBV DNA polymerase inhibitor, one or two additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2, and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In another specific embodiment, the immunogenic polypeptides, polynucleotides encoding such polypeptides, vectors, LNPs and immunogenic compositions comprising such polypeptides or polynucleotides, as described herein, are combined or co-administered with at least a second additional therapeutic agent selected from the group consisting of: HBV DNA polymerase inhibitors, immunomodulator, TLR modulators, HBsAg inhibitors, HBV therapeutic vaccines, HBV antibodies including HBV antibodies targeting the surface antigens of the hepatitis B virus and bispecific antibodies and "antibody-like" therapeutic proteins (such as DARPins®, anti-pMHC TCR-like antibodies, DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2.

In another specific embodiment, the immunogenic polypeptides, polynucleotides encoding such polypeptides, vectors, LNPs and immunogenic compositions comprising such polypeptides or polynucleotides, as described herein, are combined or co-administered with at least a second additional therapeutic agent selected from the group consisting of: HBV DNA polymerase inhibitors, HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein inhibitors).

In a particular embodiment the immunogenic polypeptides, polynucleotides encoding such polypeptides, vectors, LNPs and immunogenic compositions comprising such polypeptides or polynucleotides, as described herein, are combined or co-administered with compounds such as those disclosed in U.S. Publication No. 2010/0143301 (Gilead Sciences), U.S. Publication No. 2011/0098248 (Gilead Sciences), U.S. Publication No. 2009/0047249 (Gilead Sciences), U.S. Pat. No. 8,722,054 (Gilead Sciences), U.S. Publication No. 2014/0045849 (Janssen), U.S. Publication No. 2014/0073642 (Janssen), WO2014/056953 (Janssen), WO2014/076221 (Janssen), WO2014/128189 (Janssen), U.S. Publication No. 2014/0350031 (Janssen), WO2014/023813 (Janssen), U.S. Publication No. 2008/0234251 (Array Biopharma), U.S. Publication No. 2008/0306050 (Array Biopharma), U.S. Publication No. 2010/0029585 (Ventirx Pharma), U.S. Publication No. 2011/0092485 (Ventirx Pharma), US2011/0118235 (Ventirx Pharma), U.S. Publication No. 2012/0082658 (Ventirx Pharma), U.S. Publication No. 2012/0219615 (Ventirx Pharma), U.S. Publication No. 2014/0066432 (Ventirx Pharma), U.S. Publication No. 2014/0088085 (Ventirx Pharma), U.S. Publication No. 2014/0275167 (Novira Therapeutics), U.S. Publication No. 2013/0251673 (Novira Therapeutics), U.S. Pat. No. 8,513,184 (Gilead Sciences), U.S. Publication No. 2014/0030221 (Gilead Sciences), U.S. Publication No. 2013/0344030 (Gilead Sciences), U.S. Publication No. 2013/0344029 (Gilead Sciences), US20140275167 (Novira Therapeutics), US20130251673 (Novira Therapeutics), U.S. Publication No. 2014/0343032 (Roche), WO2014037480 (Roche), U.S. Publication No. 2013/0267517 (Roche), WO2014131847 (Janssen), WO2014033176 (Janssen), WO2014033170 (Janssen), WO2014033167 (Janssen), WO2015/059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), US20100015178 (Incyte), US2016137652 (Flexus Biosciences, Inc.), WO2014073738 (Flexus Biosciences, Inc.), WO2015188085 (Flexus Biosciences, Inc.), U.S. Publication No. 2014/0330015 (Ono Pharmaceutical), U.S. Publication No. 2013/0079327 (Ono Pharmaceutical), U.S. Publication No. 2013/0217880 (Ono pharmaceutical), WO2016057924 (Genentech/Constellation Pharmaceuticals), US20140275092 (Genentech/Constellation Pharmaceuticals), US20140371195 (Epitherapeutics) and US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), WO2014164708 (Quanticel), U.S. Pat. No. 9,186,337B2 (Oryzon Genomics), and other drugs for treating HBV, and combinations thereof.

In certain embodiments, the immunogenic polypeptides, polynucleotides encoding such polypeptides, vectors, LNPs and immunogenic compositions comprising such polypeptides or polynucleotides, as described herein, are combined or co-administered with 5-30 mg tenofovir alafenamide fumarate, tenofovir alafenamide hemifumarate, or tenofovir alafenamide. In certain embodiments, the immunogenic polypeptides, polynucleotides encoding such polypeptides, vectors, LNPs and immunogenic compositions comprising such polypeptides or polynucleotides, as described herein, are combined or co-administered with 5-10; 5-15; 5-20; 5-25; 25-30; 20-30; 15-30; or 10-30 mg tenofovir alafenamide fumarate, tenofovir alafenamide hemifumarate, or tenofovir alafenamide. In certain embodiments, the immunogenic polypeptides, polynucleotides encoding such polypeptides, vectors, LNPs and immunogenic compositions comprising such polypeptides or polynucleotides, as described herein, are combined or co-administered with 10 mg tenofovir alafenamide fumarate, tenofovir alafenamide hemifumarate, or tenofovir alafenamide. In certain embodiments, the immunogenic polypeptides, polynucleotides encoding such polypeptides, vectors, LNPs and immunogenic compositions comprising such polypeptides or polynucleotides, as described herein, are combined or co-administered with 25 mg tenofovir alafenamide fumarate, tenofovir alafenamide hemifumarate, or tenofovir alafenamide. An agent as disclosed herein may be combined with the immunogenic polypeptides, polynucleotides encoding such polypeptides, vectors, LNPs and immunogenic compositions comprising such polypeptides or polynucleotides, as described herein, in any dosage amount of the compound (e.g., from 50 mg to 500 mg of compound) the same as if each combination of dosages were specifically and individually listed.

In certain embodiments, the immunogenic polypeptides, polynucleotides encoding such polypeptides, vectors, LNPs and immunogenic compositions comprising such polypeptides or polynucleotides, as described herein, are combined or co-administered with 100-400 mg tenofovir disoproxil fumarate, tenofovir disoproxil hemifumarate, or tenofovir disoproxil. In certain embodiments, an agent disclosed herein, or a pharmaceutically acceptable salt thereof, is combined with 100-150; 100-200, 100-250; 100-300; 100-350; 150-200; 150-250; 150-300; 150-350; 150-400; 200-250; 200-300; 200-350; 200-400; 250-350; 250-400; 350-400 or 300-400 mg tenofovir disoproxil fumarate, tenofovir disoproxil hemifumarate, or tenofovir disoproxil. In certain embodiments, an agent disclosed herein, or a pharmaceutically acceptable salt thereof, is combined with 300 mg tenofovir disoproxil fumarate, tenofovir disoproxil hemifumarate, or tenofovir disoproxil. In certain embodiments, an agent disclosed herein, or a pharmaceutically acceptable salt thereof, is combined with 250 mg tenofovir disoproxil fumarate, tenofovir disoproxil hemifumarate, or tenofovir disoproxil. In certain embodiments, an agent herein, or a pharmaceutically acceptable salt thereof, is combined with 150 mg tenofovir disoproxil fumarate, tenofovir disoproxil hemifumarate, or tenofovir disoproxil. An agent as disclosed herein may be combined with the immunogenic polypeptides, polynucleotides encoding such polypeptides, vectors, LNPs and immunogenic compositions comprising such polypeptides or polynucleotides, as described herein, in any dosage amount of the compound (e.g., from 50 mg to 500 mg of compound) the same as if each combination of dosages were specifically and individually listed.

8. Kits

Further provided is a kit comprising one or more unitary doses of one or more of the truncated HBV polymerase polypeptide, one or more of the HBV polymerase deletion mutant polypeptide, one or more of the core-sAg fusion protein, one or more polynucleotides, one or more vectors, or one or more immunogenic compositions, as described herein. In some embodiments, the kit comprises one or more unitary doses of two or more of the truncated HBV polymerase polypeptide, the HBV polymerase deletion mutant polypeptide, the core-sAg fusion protein, the polynucleotides, the vectors, or the immunogenic compositions, described herein.

In various embodiments, as appropriate or desired, the one or more unitary doses can be in a single container or in two or more separate containers. In various embodiments, the one or more containers can be selected from the group consisting of vials, ampules and pre-loaded syringes.

In some embodiments, the one or more containers comprise the one or more polypeptides, one or more polynucleotides, one or more vectors or one or more immunogenic compositions in an aqueous solution. In some embodiments, the one or more containers comprise the one or more polypeptides, one or more polynucleotides, one or more vectors or one or more immunogenic compositions as a lyophilized preparation.

As appropriate or desired, the one or more unitary doses can be the same or different. In some embodiments, the kit comprises one or more unitary doses of one or more viral vectors capable of expressing the immunogenic polypeptides. In kits comprising viral vectors, the unitary doses can be in the range of about $10^3$ to about $10^{12}$ viral focus forming units (FFU) or plaque forming units (PFU) or infectious units (IU) or viral particles (vp), e.g. from about $10^4$ to about $10^7$ viral FFU or PFU, e.g. from about $10^3$ to about $10^4$, $10^5$, $10^6$, $10^7$, $10^8$, $10^9$, $10^{10}$, $10^{11}$ or $10^{12}$ viral FFU or PFU or IU or vp.

In various embodiments, the kit comprises one or more polynucleotides encoding, or one or more vectors capable of expressing, or an immunogenic composition comprising, two immunogenic polypeptides, the immunogenic polypeptides comprising: (a) an HBV polymerase polypeptide mutant comprising or consisting of an amino acid sequence of any one of SEQ ID NOs: 5-14, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 5-14; and (b) an HBV core-sAg fusion protein comprising or consisting of an amino acid sequence of any one of SEQ ID NOs: 38-41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 38-41.

In various embodiments, the kit comprises one or more polynucleotides encoding, or one or more vectors capable of expressing, or an immunogenic composition comprising, two immunogenic polypeptides, the immunogenic polypeptides comprising: (a) an HBV polymerase polypeptide mutant comprising or consisting of an amino acid sequence of any one of SEQ ID NOs: 13-14, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 13-14; and (b) an HBV core-sAg fusion protein comprising or consisting of an amino acid sequence of any one of SEQ ID NOs: 38-41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 38-41.

In various embodiments, the kit comprises one or more polynucleotides encoding, or one or more vectors capable of expressing, or an immunogenic composition comprising, two immunogenic polypeptides, the immunogenic polypeptides comprising: (a) an HBV polymerase polypeptide mutant comprising or consisting of an amino acid sequence of SEQ ID NO: 13, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 13; and (b) an HBV core-sAg fusion protein comprising or consisting of an amino acid sequence of SEQ ID NO: 41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 41.

With respect to the core-sAg fusion polypeptide in the kit (e.g., expressible from a vector; in an immunogenic composition), in some embodiments, the core polypeptide comprises a serine (S) residue at the amino acid position corresponding to position 12, and an asparagine (N) residue at the amino acid position corresponding to position 67, wherein the position numbers are with reference to SEQ ID NO:65 or SEQ ID NO:66. In some embodiments, the sAg polypeptide comprises an isoleucine (I) residue at the amino acid position corresponding to position 68, wherein the position numbers are with reference to SEQ ID NO:3 or SEQ ID NO:4. In some embodiments, the sAg polypeptide comprises one or more of a serine (S) residue at the amino acid position corresponding to position 53, an isoleucine (I) residue at the amino acid position corresponding to position 68, a threonine (T) residue at the amino acid position corresponding to position 125, a proline (P) residue at the amino acid position corresponding to position 127, an phenylalanine (F) residue at the amino acid position corresponding to position 161, a tyrosine (Y) residue at the amino acid position corresponding to position 200, a serine (S) residue at the amino acid position corresponding to position 210, and a leucine (L) residue at the amino acid position corresponding to position 213, wherein the position numbers are with reference to SEQ ID NO:3 or SEQ ID NO:4. In some embodiments, the core-sAg fusion polypeptide comprises one or more of a serine (S) residue at the amino acid position corresponding to position 12, an asparagine (N) residue at the amino acid position corresponding to position 67, a valine (V) residue at the amino acid position corresponding to position 74, a phenylalanine (F) residue at the amino acid position corresponding to position 97, a threonine (T) residue at the amino acid position corresponding to position 249, a threonine (T) residue at the amino acid position corresponding to position 250, a serine (S) residue at the amino acid position corresponding to position 317, a serine (S) residue at the amino acid position corresponding to position 318, an arginine (R) residue at the amino acid position corresponding to position 326, a tyrosine (Y) residue at the amino acid position corresponding to position 338, a glycine (G) residue at the amino acid position corresponding to position 363, and an alanine (A) residue at the amino acid position corresponding to position 372, wherein the position numbers are with reference to SEQ ID NO:41.

In some embodiments, the kit comprises a first viral expression vector and a second viral expression vector, wherein: (a) the first viral expression vector comprises a polynucleotide comprising or consisting of a nucleic acid sequence of any one of SEQ ID NOs: 27-32 and 89-94, e.g., SEQ ID NOs: 29, 89, 90 and 92, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 27-32 and 89-94, e.g., SEQ ID NOs: 29, 89, 90 and 92; and (b) the second viral expression vector comprises a polynucleotide comprising or consisting of a nucleic acid sequence of any one of SEQ ID NOs: 33-37, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 33-37.

In some embodiments, the kit comprises a first viral expression vector and a second viral expression vector, wherein: (a) the first viral expression vector comprises a polynucleotide comprising or consisting of a nucleic acid sequence of SEQ ID NOs: 29, 89, 90 or 92, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 29, 89, 90 or 92; and (b) the second viral expression vector comprises a polynucleotide comprising or consisting of a nucleic acid sequence of SEQ ID NO: 37, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 37.

In some embodiments, the kit comprises: (a) one or more unitary doses of an immunogenic composition as described above and herein, wherein the first and second viral expression vectors comprise a replication-deficient or replication-defective Cali mammarenavirus (a.k.a., Pichinde mammarenavirus or Pichinde arenavirus (PICV)); and (b) one or more unitary doses of an immunogenic composition as described above and herein, wherein the first and second viral expression vectors comprise a replication-deficient or replication-defective Lymphocytic choriomeningitis mammarenavirus (LCMV).

In some embodiments, the kit comprises: (a) one or more unitary doses of an immunogenic composition as described above and herein, wherein the first and second viral expression vectors are from Adenoviridae; and (b) one or more unitary doses of an immunogenic composition as described above and herein, wherein the first and second viral expression vectors are from Poxviridae (e.g., Vaccinia virus, e.g., modified vaccinia Ankara (MVA)).

In some embodiments, the kit comprises: (a) one or more unitary doses of an immunogenic composition as described above and herein, wherein the first and second viral expression vectors are from Arenaviridae; and (b) one or more unitary doses of an immunogenic composition as described above and herein, wherein the first and second viral expression vectors are from Adenoviridae.

In some embodiments, the kit comprises: (a) one or more unitary doses of an immunogenic composition as described above and herein, wherein the first and second viral expression vectors are from Arenaviridae; and (b) one or more unitary doses of an immunogenic composition as described above and herein, wherein the first and second viral expression vectors are from Poxviridae (e.g., Vaccinia virus, e.g., modified vaccinia Ankara (MVA)).

In some embodiments, the kit comprises a first LCMV arenavirus expression vector and a second LCMV arenavirus expression vector, wherein: (a) the first LCMV arenavirus expression vector comprises a polynucleotide comprising or consisting of a nucleic acid sequence of SEQ ID NO: 29, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 29; and (b) the second LCMV arenavirus expression vector comprises a polynucleotide comprising or consisting of a nucleic acid sequence of SEQ ID NO: 37, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 37.

In some embodiments, the kit comprises a first Pichinde arenavirus expression vector and a second Pichinde arenavirus expression vector, wherein: (a) the first Pichinde arenavirus expression vector comprises a polynucleotide comprising or consisting of a nucleic acid sequence of SEQ ID NO: 90, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 90; and (b) the second Pichinde arenavirus expression vector comprises a polynucleotide comprising or consisting of a nucleic acid sequence of SEQ ID NO: 37, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 37.

In various embodiments, the kit comprises one or more unitary doses of one or more additional therapeutic agents.

For example, in some embodiments, the kit comprises one or more agonists or activators of one or more toll-like receptors (TLRs). In various embodiments, the TLR agonist or activator is selected from the group consisting of a TLR2 agonist, a TLR3 agonist, a TLR4 agonist, a TLR5 agonist, a TLR7 agonist, a TLR8 agonist and a TLR9 agonist. In some embodiments, the TLR7 agonist is selected from the group consisting of GS 9620 (vesatolimod), R848 (Resiquimod), DS-0509, LHC-165 and TMX-101 (imiquimod), and/or wherein the TLR8 agonist is selected from the group consisting of GS-9688, R848 (Resiquimod) and NKTR-262 (dual TLR7/TLR8 agonist).

In some embodiments, the kit comprises one or more interleukin receptor agonists of an interleukin receptor selected from IL-2, IL-7, IL-12 and IL-15. In some embodiments, the kit comprises one or more cytokines selected from the group consisting of IL-2, IL-7, IL-12, IL-15, and variants thereof.

In some embodiments, the kit comprises one or more innate immune activators. In various embodiments, the one or more innate immune activators comprises an agonist of a receptor selected from the group consisting of fms related tyrosine kinase 3 (FLT3), stimulator of interferon genes (STING) receptor, DExD/H-box helicase 58 (DDX58; a.k.a., RIG-I), nucleotide binding oligomerization domain containing 2 (NOD2). In some embodiments, the kit comprises one or more unitary doses of GS-3583 and/or GS-9992.

In some embodiments, the kit comprises one or more antagonists or inhibitors of an inhibitory immune checkpoint protein or receptor and/or one or more activators or agonists of a stimulatory immune checkpoint protein or receptor. In various embodiments, the one or more immune checkpoint proteins or receptors are selected from the group consisting of: CD27, CD70; CD40, CD40LG; CD47, CD48 (SLAMF2), transmembrane and immunoglobulin domain containing 2 (TMIGD2, CD28H), CD84 (LY9B, SLAMF5), CD96, CD160, MS4A1 (CD20), CD244 (SLAMF4); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); natural killer cell cytotoxicity receptor 3 ligand 1 (NCR3LG1, B7H6); HERV-H LTR-associating 2 (HHLA2, B7H7); inducible T cell co-stimulator (ICOS, CD278); inducible T cell co-stimulator ligand (ICOSLG, B7H2); TNF receptor superfamily member 4 (TNFRSF4, OX40); TNF superfamily member 4 (TNFSF4, OX40L); TNFRSF8 (CD30), TNFSF8 (CD30L); TNFRSF10A (CD261, DR4, TRAILR1), TNFRSF9 (CD137), TNFSF9 (CD137L); TNFRSF10B (CD262, DR5, TRAILR2), TNFRSF10 (TRAIL); TNFRSF14 (HVEM, CD270), TNFSF14 (HVEML); CD272 (B and T lymphocyte associated (BTLA)); TNFRSF17 (BCMA, CD269), TNFSF13B (BAFF); TNFRSF18 (GITR), TNFSF18 (GITRL); MHC class I polypeptide-related sequence A (MICA); MHC class I polypeptide-related sequence B (MICB); CD274 (CD274, PDL1, PD-L1); programmed cell death 1 (PDCD1, PD1, PD-1); cytotoxic T-lymphocyte associated protein 4 (CTLA4, CD152); CD80 (B7-1), CD28; nectin cell adhesion molecule 2 (NECTIN2, CD112); CD226 (DNAM-1); Poliovirus receptor (PVR) cell adhesion molecule (PVR, CD155); PVR related immunoglobulin domain containing (PVRIG, CD112R); T cell immunoreceptor with Ig and ITIM domains (TIGIT); T cell immunoglobulin and mucin domain containing 4 (TIMD4; TIM4); hepatitis A virus cellular receptor 2 (HAVCR2, TIMD3, TIM3); galectin 9 (LGALS9); lymphocyte activating 3

(LAG3, CD223); signaling lymphocytic activation molecule family member 1 (SLAMF1, SLAM, CD150); lymphocyte antigen 9 (LY9, CD229, SLAMF3); SLAM family member 6 (SLAMF6, CD352); SLAM family member 7 (SLAMF7, CD319); UL16 binding protein 1 (ULBP1); UL16 binding protein 2 (ULBP2); UL16 binding protein 3 (ULBP3); retinoic acid early transcript 1E (RAET1E; ULBP4); retinoic acid early transcript 1G (RAET1G; ULBP5); retinoic acid early transcript 1L (RAET1L; ULBP6); lymphocyte activating 3 (CD223); killer cell immunoglobulin like receptor, three Ig domains and long cytoplasmic tail 1 (KIR, CD158E1); killer cell lectin like receptor C1 (KLRC1, NKG2A, CD159A); killer cell lectin like receptor K1 (KLRK1, NKG2D, CD314); killer cell lectin like receptor C2 (KLRC2, CD159c, NKG2C); killer cell lectin like receptor C3 (KLRC3, NKG2E); killer cell lectin like receptor C4 (KLRC4, NKG2F); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor D1 (KLRD1); and SLAM family member 7 (SLAMF7).

In some embodiments, the kit comprises one or more blockers or inhibitors of one or more T-cell inhibitory immune checkpoint proteins or receptors. In various embodiments, the blockers or inhibitors of one or more T-cell inhibitory immune checkpoint proteins or receptors are selected from the group consisting of CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1).

In some embodiments, the kit comprises one or more agonists or activators of one or more T-cell stimulatory immune checkpoint proteins or receptors. In various embodiments, the agonists or activators of one or more T-cell stimulatory immune checkpoint proteins or receptors are selected from the group consisting of CD27, CD70; CD40, CD40LG; inducible T cell co-stimulator (ICOS, CD278); inducible T cell co-stimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); Poliovirus receptor (PVR) cell adhesion molecule (PVR, CD155). In some embodiments, the kit comprises one or more unitary doses of AGEN-2373 and/or AGEN-1223.

In some embodiments, the kit comprises one or more blockers or inhibitors of one or more NK-cell inhibitory immune checkpoint proteins or receptors. In various embodiments, the NK-cell inhibitory immune checkpoint proteins or receptors are selected from the group consisting of killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); and killer cell lectin like receptor D1 (KLRD1, CD94).

In some embodiments, the kit comprises one or more agonists or activators of one or more NK-cell stimulatory immune checkpoint proteins or receptors. In various embodiments, the NK-cell stimulatory immune checkpoint proteins or receptors are selected from CD16, CD226 (DNAM-1); killer cell lectin like receptor K1 (KLRK1, NKG2D, CD314); and SLAM family member 7 (SLAMF7).

In various embodiments of the kits, the one or more immune checkpoint inhibitors comprises a proteinaceous inhibitor of PD-L1 (CD274), PD-1 (PDCD1) or CTLA4. In some embodiments, the proteinaceous inhibitor of CTLA4 is selected from the group consisting of ipilimumab, tremelimumab, BMS-986218, AGEN1181, AGEN1884, BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4) and AK-104 (CTLA4/PD-1). In some embodiments, the proteinaceous inhibitor of PD-L1 (CD274) or PD-1 (PDCD1) is selected from the group consisting of zimberelimab (AB122), pembrolizumab, nivolumab, cemiplimab, pidilizumab, AMP-224, MEDI0680 (AMP-514), spartalizumab, atezolizumab, avelumab, ASC22, durvalumab, BMS-936559, CK-301, PF-06801591, BGB-A317 (tislelizumab), GLS-010 (WBP-3055), AK-103 (HX-008), AK-105, CS-1003, HLX-10, MGA-012, BI-754091, AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181, PD1-PIK, BAT-1306, (MSB0010718C), CX-072, CBT-502, TSR-042 (dostarlimab), MSB-2311, JTX-4014, BGB-A333, SHR-1316, CS-1001 (WBP-3155, KN-035, IBI-308 (sintilimab), HLX-20, KL-A167, STI-A1014, STI-A1015 (IMC-001), BCD-135, FAZ-053, TQB-2450, MDX1105-01, FPT-155 (CTLA4/PD-L1/CD28), PF-06936308 (PD-1/CTLA4), MGD-013 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/TIM-3), XmAb-20717 (PD-1/CTLA4), AK-104 (CTLA4/PD-1), M7824 (PD-L1/TGFβ-EC domain), CA-170 (PD-L1/VISTA), CDX-527 (CD27/PD-L1), LY-3415244 (TIM3/PDL1), and INBRX-105 (4-1BB/PDL1). In some embodiments, the one or more immune checkpoint inhibitors comprises a small molecule inhibitor of CD274 (PDL1, PD-L1), programmed cell death 1 (PDCD1, PD1, PD-1) or CTLA4. In some embodiments, the small molecule inhibitor of CD274 or PDCD1 is selected from the group consisting of GS-4224, GS-4416, INCB086550 and MAX10181. In some embodiments, the small molecule inhibitor of CTLA4 comprises BPI-002.

In various embodiments, the kit comprises one or more anti-viral agents. Illustrative anti-viral agents that can be in the kit include lamivudine (LAM), adefovir dipivoxil (ADV), entecavir (ETV), telbivudine (LdT), tenofovir disoproxil fumarate (TDF), tenofovir alafenamide (TAF or VEMLIDY®) and ledipasvir+sofosbuvir (HARVONI®). In some embodiments, the kit comprises one or more therapeutic agents selected from the group consisting of HBV antigen inhibitors (e.g., HBV core antigen (HBcAg) inhibitors, HBV surface antigen (HBsAg) inhibitors, HBx inhibitors, HBV E antigen inhibitors), anti-HBV antigen antibodies, inhibitory nucleic acids targeting HBV (e.g., antisense oligonucleotide, short interfering RNA (siRNA), DNA-directed RNA interference (ddRNAi)), gene editors targeting HBV (e.g., CRISPR-Cas (e.g., Cas9, Cas12, Cascade, Cas13), zinc finger nucleases, homing endonucleases, homing meganucleases (e.g., ARCUS), synthetic nucleases, TALENs), covalently closed circular DNA (cccDNA) inhibitors and HBsAg secretion or assembly inhibitors and HBV viral entry inhibitors.

Optionally associated with such container(s) can be a notice in the form prescribed by a governmental agency regulating the manufacture, use or sale of pharmaceuticals or biological products, which notice reflects approval by the agency of manufacture, use or sale for human administration.

EXAMPLES

The following examples are offered to illustrate, but not to limit the claimed invention.

Example 1

Identification of HBV sAg Sequences that Induce Robust, Genotype Cross-Reactive T Cell Responses In this example, we identified near-consensus, naturally occurring sequences of HBV sAg in genotypes A, B, C, and D, generated adenovirus type 5 vectors encoding each antigen, and tested the magnitude and genotype cross-reactivity of the T cells induced by each of these vectors in outbred mice.

Selection of near-consensus, naturally occurring HBV sAg sequences. In selecting the specific amino acid sequence of an HBV sAg to be used for therapeutic vaccination, we sought an sAg sequence that was both efficiently expressed and processed for antigen presentation, while also inducing T cell responses that react broadly across a range of HBV genotypes. Although consensus sequences or mosaic antigens can be designed to attempt to improve T cell genotype reactivity, such sequences do not occur in nature and have a risk of being inefficiently expressed or poorly processed into T-cell epitopes. Consequently, we identified near-consensus, naturally occurring HBV sAg sequences from genotypes (GT) A, B, C and D. Using a database of sAg sequences from 14207 individuals infected with these HBV genotypes, we constructed consensus sequences for each genotype, then identified the naturally occurring sAg sequence closest to the consensus for each genotype. The naturally occurring, near-consensus sAg sequences for HBV genotypes A, B, C and D are provided in Table 1 as SEQ ID NOs: 1-4, respectively.

TABLE 1

Naturally-occurring, near-consensus sAg polypeptide sequences

| SEQ ID NO: | HBV genotype | Polypeptide sequence |
|---|---|---|
| 1 | A | MENITSGFLGPLLVLQAGFFLLTRILTIPQSLDSWWTSLNFLGGTPVC LGQNSQSPTSNHSPTSCPPICPGYRWMCLRRFIIFLFILLLCLIFLLV LLDYQGMLPVCPLIPGSTTTSTGPCKTCTTPAQGNSMFPSCCCTKPTD GNCTCIPIPSSWAFAKYLWEWASVRFSWLSLLVPFVQWFVGLSPTVWL SVIWMMWYWGPSLYNILSPFIPLLPIFFCLWVYI |
| 2 | B | MESTTSGFLGPLLVLQAGFFLLTRILTIPQSLDSWWTSLNFLGGAPTC PGQNLQSPTSNHSPTSCPPICPGYRWMCLRRFIIFLFILLLCLIFLLV LLDYQGMLPVCPLIPGSSTTSTGPCRTCTTPAQGTSMFPSCCCTKPTD GNCTCIPIPSSWAFAKYLWEWASVRFSWLSLLVPFVQWFVGLSPTVWL SVIWMMWYWGPSLYNILSPFMPLLPIFFCLWVYI |
| 3 | C | MESTTSGFLGPLLVLQAGFFLLTRILTIPQSLDSWWTSLNFLGGAPTC PGQNSQSPTSNHSPTSCPPICPGYRWMCLRRFIIFLCILLLCLIFLLV LLDYQGMLPVCPLIPGSSTTSTGPCKTCTTPAQGTSMFPSCCCTKPTD GNCTCIPIPSSWAFARFLWEWASVRFSWLSLLVPFVQWFVGLSPTVWL SVIWMMWYWGPSLYNILSPFLPLLPIFFCLWVYI |
| 4 | D | MENITSGFLGPLLVLQAGFFLLTRILTIPQSLDSWWTSLNFLGGTTVC LGQNSQSPTSNHSPTSCPPICPGYRWMCLRRFIIFLFILLLCLIFLLV LLDYQGMLPVCPLIPGSSTTSTGPCRTCTTPAQGTSMYPSCCCTKPSD GNCTCIPIPSSWAFGKFLWEWASARFSWLSLLVPFVQWFVGLSPTVWL SVIWMMWYWGPSLYSILSPFLPLLPIFFCLWVYI |

Methods

To evaluate the immunogenicity of each antigen and assess the genotype cross-reactivity of induced T cells across a broad range of epitopes in vivo, Diversity Outbred mice (DO mice) from Jackson Laboratories were used for vaccination. DO mice were developed by random outcross matings of 160 Collaborative Cross recombinant inbred mouse lines, and the colony is maintained by continued random matings that avoid crosses between siblings. The DO parental lines, the Collaborative Cross strains, were developed by crossing eight unique and genetically diverse inbred mouse strains (A/J, C57BL/6J, 129S1/SvImJ, NOD/ShiLtJ, NZO/HlLtJ, CAST/EiJ, PWK/PhJ, and WSB/EiJ). Therefore, DO mice capture the diversity of epitope selection and magnitude of T cell responses present in a highly genetically diverse population.

Results

All four naturally occurring, near-consensus sequences of HBV sAg were robustly immunogenic in DO mice (FIG. 1). Induced T cells reacted to GT-A, B, C, and D HBV sAg peptides with approximately equal magnitude, demonstrating excellent genotype cross-reactivity of the T cell response. Geometric mean response magnitude was largest for GT-C and GT-D sAg.

Example 2

Identification of HBV Core and Pol Sequences that Induce Robust, Genotype Cross-Reactive T Cell Responses In this example, we identified near-consensus, naturally occurring sequences of HBV core and HBV polymerase (Pol) in genotypes A, B, C, and D, generated Adenovirus type 5 expression vectors encoding Pol antigens or core-Pol fusion proteins, and tested the magnitude and genotype cross-reactivity of the T cells induced in inbred and outbred animals.

Selection of near-consensus, naturally occurring HBV core and Pol sequences. In selecting the specific amino acid sequence of an HBV core and Pol antigens to be used for therapeutic vaccination, we sought core and Pol sequences that were both efficiently expressed and processed for antigen presentation, while also inducing T cell responses that react broadly across a range of HBV genotypes. Although consensus sequences or mosaic antigens can be designed to attempt to improve T cell genotype reactivity, such sequences do not occur in nature and have a risk of being inefficiently expressed or poorly processed into T cell epitopes. Consequently, we identified near-consensus, naturally occurring HBV core and Pol sequences from genotypes A, B, C and D. Using a database of core sequences from 5528 individuals infected with HBV genotypes A-D, and Pol sequences from 4713 individuals infected with HBV genotypes A-D, we constructed consensus sequences for core and Pol for each genotype, then identified the naturally occurring core and Pol sequences closest to the consensus for each genotype.

GT-A, B, C, and D Pol sequences were then modified to improve antigen performance. The enzymatic activity of polymerases can induce toxicity when overexpressed, so the enzymatic activity of the reverse transcriptase (RT) and RNase H (RNH) domains was ablated by mutations in the catalytic domains. The YMDD motif in RT was mutated to YMHD, and the AELL motif in RNH was mutated to AHLL (Radziwill, et al., J Virol. (1990) 64(2):613-20). The resulting Pol sequences are referred to as Pol$^{mut}$ The Pol$^{mut}$ sequences for HBV genotypes A, B, C and D are provided in Table 2 as SEQ ID NOs: 52-55, respectively.

TABLE 2

Pol$^{mut}$ polypeptide sequence

| SEQ ID NO: | HBV genotype | Polypeptide sequence - Motifs containing inactivating mutations in Pol are underlined (YMDD mutated to YMHD, AELL mutated to AHLL) |
|---|---|---|
| 52 | A | MPLSYQHFRKLLLLDDETEAGPLEEELPRLADEDLNRRVAEDLNLGNLNV SIPWTHKVGNFTGLYSSTVPIFNPEWQTPSFPKIHLHEDIANRCQQFVGP LTVNEKRRLRLIMPARFYPNSTKYLPLDKGIKPYYPDHVVNHYFQTRHYL HTLWKAGILYKRETTRSASFCGSPYSWEQELHHGRLVIKTSQRHGDEPFC SQPSGILSRSSVGPCIRSQFKQSRLGLQPHQGPLATSQSGRSGSIRARVH SPTRRCFGVEPSGSGHIGHSASSSSSCLHQSAVRKAAYSHLSTSKRQSSS GHAVEFHSFPPSSARSQSQGPVFSCWWLQFRNTQPCSKYCLSHLVNLLED WGPCDEHGEHHIRIPRTPARVTGGVFLVDKNPHNTAESRLVVDFSQFSRG ITRVSWPKFAVPNLQSLTNLLSSNLSWLSLDVSAAFYHIPLHPAAMPHLL VGSSGLSRYVARLSSNSRIHNNQHGTLQNLHDSCSRQLYVSLMLLYKTYG RKLHLYSHPIILGFRKIPMGVGLSPFLLAQFTSAICSVVRRAFPHCLAFS <u>YMHD</u>VVLGAKSVQHLESLYTAVTNFLLSLGIHLNPNKTKRWGYSLNFMGY VIGSWGTLPQDHIVQKIKHCFRKLPINRPIDWKVCQRIVGLLGFAAPFTQ CGYPALMPLYACIQAKQAFTFSPTYKAFLSKQYLNLYPVARQRPGLCQVF ADATPTGWGLAIGHQRMRGTFVAPLPIHT<u>AHLL</u>AACFARSRSGAKLIGTD NSVVLSRKYTSFPWLLGCTANWILRGTSFVYVPSALNPADDPSRGRLGLY RPLLRLPYRPTTGRTSLYAVSPSVPSHLPVRVHFASPLHVAWRPP |
| 53 | B | MPLSYQHFRKLLLLDDEAGPLEEELPRLADEGLNRRVAEDLNLGNLNVSI PWTHKVGNFTGLYSSTVPVFNPEWQTPSFPHIHLQEDIINRCQQYVGPLT VNEKRRLKLIMPARFYPNLTKYLPLDKGIKPYYPEHVVNHYFQTRHYLHT LWKAGILYKRESTRSASFCGSPYSWEQDLQHGRLVFQTSKRHGDKSFCPQ SPGILPRSSVGPCIQNQLRKSRLGPQPAQGQLAGRQQGGSGSIRARVHPS PWGTVGVEPSGSGHIHNCASNSSSCLHQSAVRKAAYSHISTSKGHSSSGH AVELHHFPPSSSRSQSQGPVLSCWWLQFRNSEPCSEYCLCHIVNLIEDWG PCTEHGEHRIRTPRTPARVTGGVFLVDKNPHNTTESRLVVDFSQFSRGNT RVSWPKFAVPNLQSLTNLLSSNLSWLSLDVSAAFYHLPLHPAAMPHLLVG SSGLSRYVARLSSNSRIINNQHRTMQNLHDSCSRNLYVSLMLLYKTYGRK LHLYSHPIILGFRKIPMGVGLSPFLLAQFTSAICSVVRRAFPHCLAFS<u>YM HD</u>VVLGAKSVQHLESLYAAVTNFLLSLGIHLNPHKTKRWGYSLNFMGYVI GSWGTLPQEHIVQKIKMCFRKLPVNRPIDWKVCQRIVGLLGFAAPFTQCG |

TABLE 2-continued

Pol$^{mut}$ polypeptide sequence

| SEQ ID NO: | HBV genotype | Polypeptide sequence - Motifs containing inactivating mutations in Pol are underlined (YMDD mutated to YMHD, AELL mutated to AHLL) |
|---|---|---|
| | | YPALMPLYACIQAKQAFTFSPTYKAFLSKQYLHLYPVARQRPGLCQVFAD<br>ATPTGWGLAIGHQRMRGAFVSPLPIHT<u>AHLL</u>AACFARSRSGAKLIGTDNS<br>VVLSRKYTSFPWLLGCAANWILRGTSF<u>VYV</u>PSALNPADDPSRGRLGLYRP<br>LLRLLYRPTTGRTSLYADSPSVPSHLPDRVHFASPLHVAWRPP |
| 54 | C | MPLSYQHFRKLLLLDDEAGPLEEELPRLADEDLNRRVAEDLNLGNLNVSI<br>PWTHKVGNFTGLYSSTVPVFNPEWQTPSFPHIHLQEDIINRCQQYVGPLT<br>VNEKRRLKLIMPARFYPNLTKYLPLDKGIKPYYPEHTVNHYFKTRHYLHT<br>LWKAGILYKRETTRSASFCGSPYSWEQELQHGRLVFQTSTRHGDESFCSQ<br>SSGILSRSPVGPCIRSQLKQSRLGLQPQQGSLARSKSGRSGSIRARVHPT<br>TRQSFGVEPSGSGHIDNSASSASSCLHQSAVRKTAYSHLSTSKRQSSSGH<br>AVELHNFPPSSARSQSEGPLLSCWWLQFRNSKPCSDYCLSHIVNLLEDWG<br>PCTEHGEHNIRIPRTPARVTGGVFLVDKNPHNTTESRLVVDFSQFSRGST<br>HVSWPKFAVPNLQSLTNLLSSNLSWLSLDVSAAFYHLPLHPAAMPHLLVG<br>SSGLSRYVARLSSTSRNINYQHGAMQDLHDSCSRNLYVSLLLLYKTFGRK<br>LHLYSHPIILGFRKIPMGVGLSPFLLAQFTSAICSVVRRAFPHCLAFSYM<br><u>HDVVLGAKSVQHLESLFTAVTNFLLSLGIHLNPNKTKRWGYSLNFMGYVI</u><br>GSWGTLPQEHIVLKIKQCFRKLPVNRPIDWKVCQRIVGLLGFAAPFTQCG<br>YPALMPLYACIQAKQAFTFSPTYKAFLCKQYLNLYPVARQRSGLCQVFAD<br>ATPTGWGLAVGHQRMRGTFVSPLPIHT<u>AHLL</u>AACFARSRSGAKLIGTDNS<br>VVLSRKYTSFPWLLGCAANWILRGTSF<u>VYV</u>PSALNPADDPSRGRLGLYRP<br>LLRLPFRPTTGRTSLYAVSPSVPSHLPVRVHFASPLHVAWRPP |
| 55 | D | MPLSYQHFRRLLLLDDEAGPLEEELPRLADEGLNRRVAEDLNLGNLNVSI<br>PWTHKVGNFTGLYSSTVPVFNPHWKTPSFPNIHLHQDIIKKCEQFVGPLT<br>VNEKRRLQLIMPARFYPNVTKYLPLDKGIKPYYPEHLVNHYFQTRHYLHT<br>LWKAGILYKRETTHSASFCGSPYSWEQELQHGAESFHQQSSGILSRPPVG<br>SSLQSKHRKSRLGLQSQQGHLARRQQGRGWSIRAGIHPTARRPFGVEPSG<br>SGHTANLASKSASCLYQSAVRKAAYPVVSTFKKHSSSGHAVELHNLPPNS<br>ARSQSERPVFPCWWLQFRNSKPCSDYCLSHIVNLLEDWGPCAEHGEHHIR<br>IPRTPARVTGGVFLVDKNPHNTAESRLVVDFSQFSRGNYRVSWPKFAVPN<br>LQSLTNLLSSNLSWLSLDVSAAFYHLPLHPAAMPHLLVGSSGLSRYVARL<br>SSNSRIFNYQHGTMQNLHDSCSRNLYVSLMLLYQTFGRKLHLYSHPIILG<br>FRKIPMGVGLSPFLLAQFTSAICSVVRRAFPHCLAFS<u>YMHDVVLGAKSVQ</u><br>HLESLFTAVTNFLLSLGIHLNPNKTKRWGYSLHFMGY<u>VI</u>GCYGSLPQDHI<br>IQKIKECFRKLPVNRPIDWKVCQRIVGLLGFAAPFTQCGYPALMPLYACI<br>QSKQAFTFSPTYKAFLCKQYLNLYPVARQRPGLCQVFADATPTGWGLVMG<br>HQRMRGTFKAPLPIHT<u>AHLL</u>AACFARSRSGANILGTDNSVVLSRKYTSFP<br>WLLGCAANWILRGTSF<u>VYV</u>PSALNPADDPSRGRLGLYRPLLRLPFRPTTG<br>RTSLYADSPSVPSHLPDRVHFASPLHVAWRPP |

Figure 2:
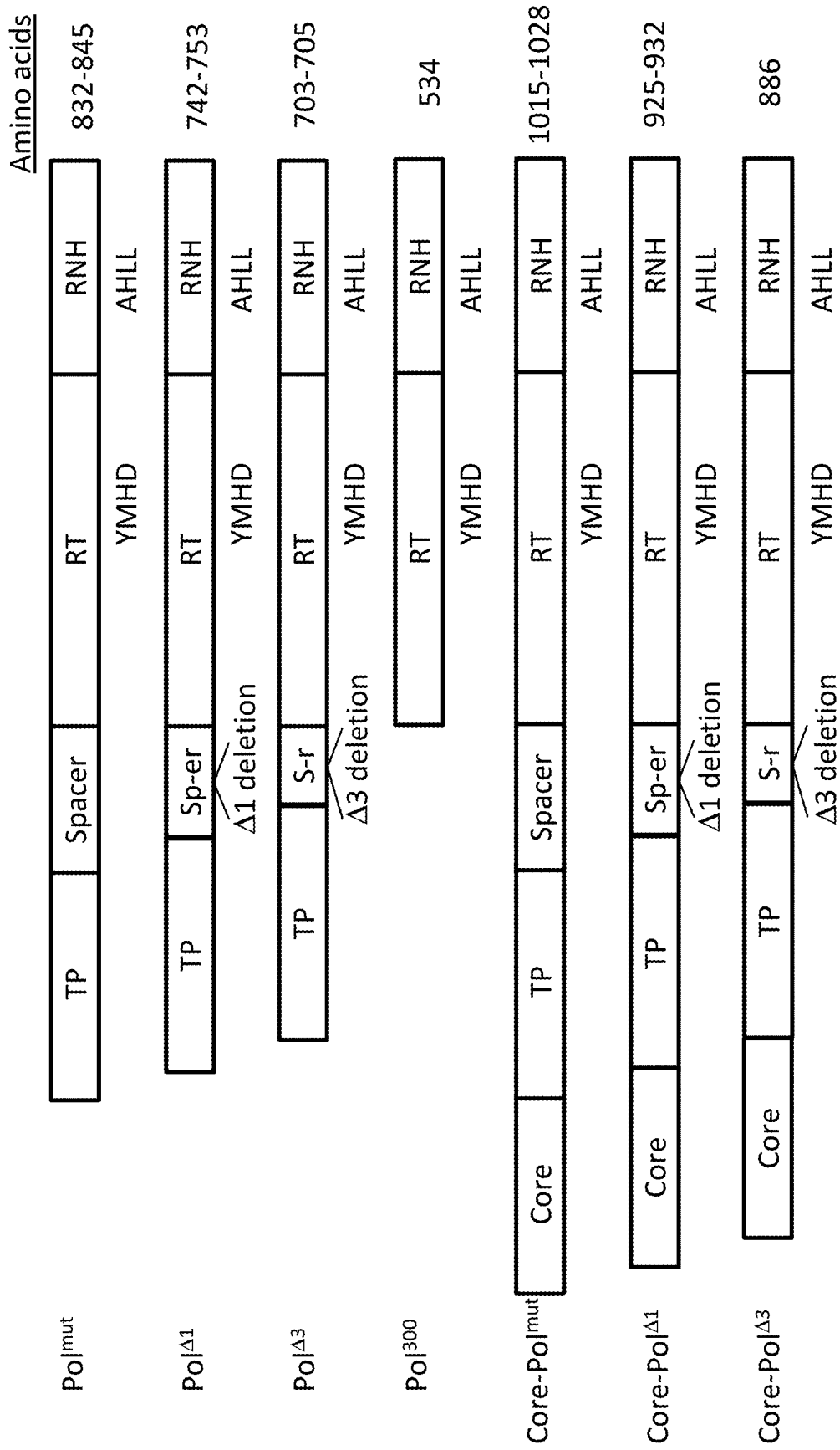
FIG. 2 illustrates schematics of each Pol-containing antigen design. Each Pol domain is indicated separately (TP, terminal protein; RT, Reverse Transcriptase; RNH, RNase H). Approximate location of the D to H mutation in the YMDD motif (SEQ ID NO: 97) in RT and of the E to H mutation in the AELL motif (SEQ ID NO: 98) in RNH are indicated below the RT and RNH domains. Designation of each construct is shown at left, and the amino acid size range of the GT-A, B, C, and D constructs is shown at right. "YMHD" and "AHLL" disclosed as SEQ ID NOS 99 and 100, respectively.

Pol$^{mut}$ sequences were then further modified to remove amino acid regions that are poorly conserved among HBV strains and genotypes, to generate Pol sequences of varying length to accommodate viral vectors with differing constraints on encoded antigen size, and to create core-Pol fusions in order to encode two antigens with a single open reading frame. Pol consists of four functional domains, Terminal Protein (TP), Spacer, RT, and RNH. Of these three, TP, RT, and RNH are highly conserved amongst HBV strains and genotypes and so are likely to induce strain- and genotype-cross-reactive T cells, whereas the Spacer domain is highly variable. We generated GT-A, B, C, and D Pol sequences with deletions in the Spacer region. In one set of sequences, designated pNO$^{\Delta 1}$ the deletion was based on a previously reported deletion mutant that retains enzymatic function in vitro, indicating that the deletion is not disruptive to the expression, structure and folding of the remaining protein (Radziwill, et at., J Virol. (1990) 64(2):613-20). In a second set of vectors designated Pol$^{\Delta 3}$, the entire poorly conserved region was identified by sequence alignment and deleted. Core-Pol fusions were generated by fusing the near-consensus core sequences to the Pol$^{mut}$, Pol$^{\Delta 1}$ and Pol$^{\Delta 3}$ sequences for GT-A, B, C, and D. Lastly, to accommodate viral vectors with smaller packaging limits, we constructed shorter versions of each near-consensus inactivated Pol sequence, designated as Pol$^{300}$. The Pol$^{300}$ variants have large N-terminal deletions in which the entire TP and most of the Spacer domain is removed, but the RT and RNaseH domains are maintained (Lanford et al., J Virol. (1999); 73(3):1885-93). A listing of Pol-containing antigen sequences tested in adenovirus or arenavirus vectors is shown in Table 3 and FIG. 2. Sequences of the amino acids removed from each Pol deletion constructs are provided in SEQ ID NOs: 42-51.

TABLE 3

Sequences of Pol-containing antigens

| Polypeptide SEQ ID NOs | Polypeptide |
|---|---|
| 5-8 for Genotype A-D, respectively | Pol$^{\Delta 1}$ |
| 9-12 for Genotype A-D, respectively | Pol$^{\Delta 3}$ |
| 13-14 for Genotype B and D, respectively | Pol$^{300}$ |
| 15-18 for Genotype A-D, respectively | Core-Pol$^{mut}$ |
| 19-22 for Genotype A-D, respectively | Core-Pol$^{\Delta 1}$ |
| 23-26 for Genotype A-D, respectively | Core-Pol$^{\Delta 3}$ |

Methods

Figure 3:
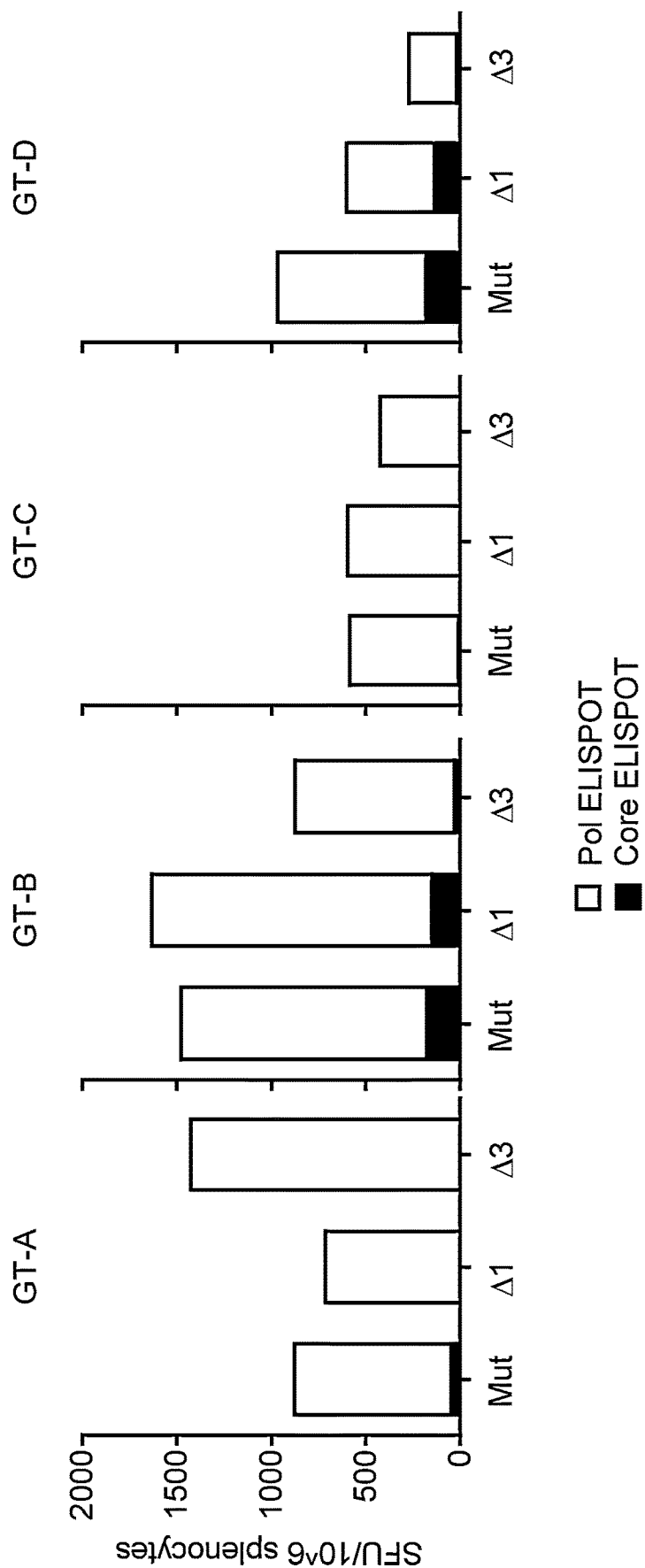
FIG. 3 illustrates the immunogenicity of Core-Pol fusion protein-expressing adenovirus vectors in C57BL/6 mice. Six- to eight-week-old C57BL/6 mice (n=5 per group) were injected with $1\times10^8$ viral particles (vp) of adenovirus encoding core-Pol fusion variants of SEQ ID NOs: 15-26. The genotype of each antigen is shown above each graph, while the antigen designations are shown on the horizontal axis (Mut: core-Pol$^{mut}$, Δ1: core-Pol$^{Δ1}$, Δ3: core-Pol$^{Δ3}$). On day 14 after injection, splenocytes were harvested and T cell responses evaluated by IFN-γ ELISPOT (BD mouse IFN-γ ELISPOT kit, catalog #551083) using overlapping peptide pools corresponding to GT-D core and Pol. Bars show stacked geometric mean responses for each group. SFU, spot forming units.

The immunogenicity of each GT-A, B, C, and D core-Pol fusion construct was initially tested in C57BL/6 mice for induction of T cell responses reactive with GT-D core and Pol peptide pools, to identify the variant within each genotype inducing the largest immunogenic response (FIG. 3). In all genotypes, a robust Pol response was detected but core responses were weaker or absent. The weak or absent core responses likely resulted from the fact that C57BL/6 mice are known to only respond to a single peptide from GT-D HBV core, namely, MGLKFRQL (Chiale, et al., Antiviral Res. 2019 August; 168:156-167). Responses to this peptide in C57BL/6 mice are often weak or absent, and the peptide has an alternate sequence in the GT-A, B, and C core sequences of MGLKIRQL.

Results

All antigen genotypes showed little change in immunogenicity between core-Pol$^{mut}$ and core-Pol$^{\Delta 1}$. GT-A antigen had an increased response to core-Pol$^{\Delta 3}$ vs core-Pol$^{mut}$ and core-Pol$^{\Delta 1}$, whereas GT-B, C, and D all demonstrated reduced immunogenicity with core-Pol$^{\Delta 3}$.

T cell responses in inbred mouse strains are not ideal for comparing antigen immunogenicity across different genotypes because responses can be dominated by one or a few epitopes, which could vary in sequence among the antigens. To better compare the immunogenicity of core-Pol antigens across genotypes, immunogenicity was tested in DO mice to capture responses across a wide range of epitopes. DO mice were immunized with GT-A core-Pol$^{\Delta 3}$ or GT-B, C, or D core-Pol$^{\Delta 1}$, and T cell responses were assessed for IFN-γ ELISPOT response using GT-A and GT-D peptide pools (FIG. 4). GT-B core-Pol$^{\Delta 1}$ gave the best overall responses to Pol, with equally robust ELISPOT responses to GT-A and GT-D peptide pools (FIG. 4A). Pol responses to GT-B core-Pol$^{\Delta 1}$ were statistically significantly higher than responses to GT-A core-Pol$^{\Delta 3}$ using GT-D peptides, and to GT-C core-Pol$^{\Delta 1}$ using both peptide genotypes. The geometric mean Pol ELISPOT responses to GT-D core-Pol$^{\Delta 1}$ were numerically lower than GT-B core-Pol$^{\Delta 1}$, but the difference was not statistically significant. Responses to core were clearly detectable in the DO mice for all four antigen genotypes (FIG. 4B). The pattern of core responses was similar to the Pol responses with GT-B core-Pol$^{\Delta 1}$ yielding the overall best results, although for core no comparisons between antigen genotypes reached statistical significance.

Example 3

Identification of Smaller Immunogenic Pol Antigens

Different viral vector systems have differing limits on the maximum size of encoded antigens.

Methods

Figure 5:
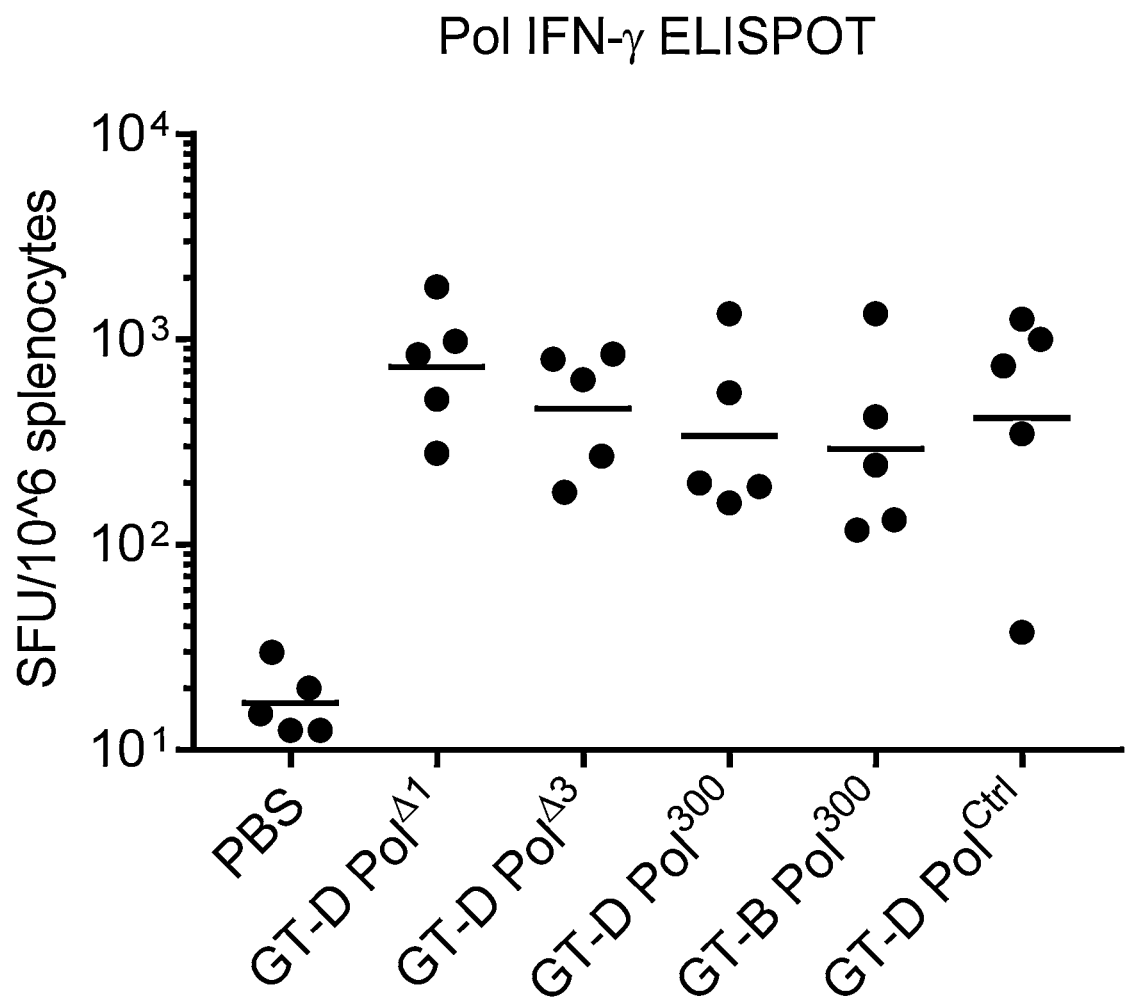
FIG. 5 illustrates the immunogenicity of Pol-expressing adenovirus vectors. Six- to eight-week-old C57BL/6 mice (n=5 per group) were injected with $1\times10^8$ viral particles (vp) of adenovirus expressing Pol antigen variants of SEQ ID NOs: 8, 12, 13, 14, or a full-length, unmodified GT-D Pol sequence (GT-D Pol$^{Ctrl}$). On day 14 after injection, splenocytes were harvested and T cell responses evaluated by IFN-γ ELISPOT (BD mouse IFN-γ ELISPOT kit, catalog #551083) using overlapping peptide pools corresponding to GT-D Pol. SFU: spot forming units.

To identify additional Pol variants that are smaller in size, and thus could be used in a wider range of vector systems, we evaluated the immunogenicity of Pol variants expressed without fusion to core. C57BL/6 mice were immunized with Adenovirus type 5 vectors encoding GT-D Pol$^{\Delta 1}$, Pol$^{\Delta 3}$, and Pol$^{300}$, and GT-B Pol$^{300}$, and compared to a control vector encoding a full-length, unmodified GT-D Polymerase (GT-D Pol$^{Ctrl}$) and mock vaccination with phosphate buffered saline (PBS) as a negative control. IFN-γ ELISPOT responses were measured 14 days after immunization with GT-D Pol peptide pools (FIG. 5).

Results

All tested Pol antigen designs were immunogenic, with no statistically significant differences between groups.

Example 4

Efficacy of Vaccination with Near-Consensus Antigens in Combination with Anti-PD-1 in Adeno-Associated Virus (AAV)-HBV Mice We used an Adeno-Associated Virus (AAV)-HBV model (Dion, et al., J Virol. (2013) 87(10):5554-63; and Yang, et al., Cell Mol Immunol. (2014) 11(1):71-8) to determine if our near-consensus antigen designs could have antiviral effects in a model of chronic HBV infection.

Methods

Figure 6:
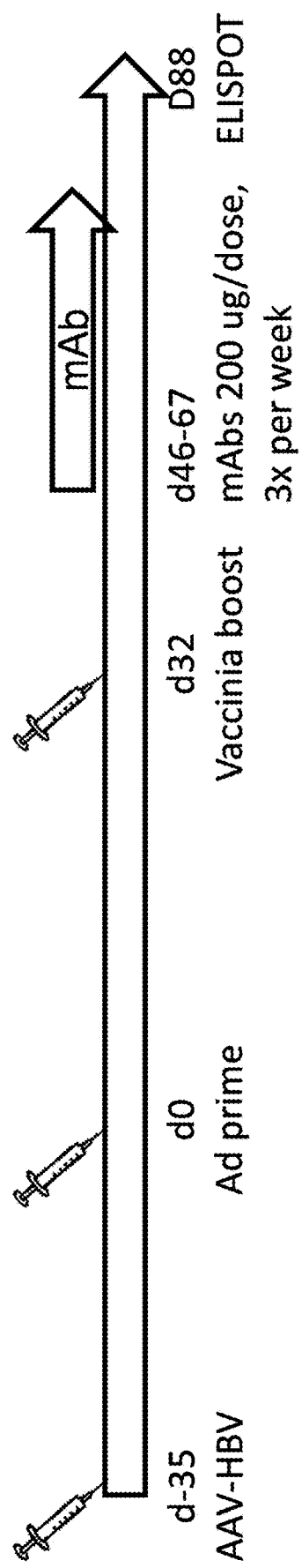
FIG. 6 illustrates the study design assessing the efficacy of HBV-expressing Ad5 and vaccinia vectors in the AAV mouse model of CHB (AAV-HBV). Six- to eight-week-old C57BL/6 mice were transduced with $10^{12}$ genome copies of AAV-HBV on day −35. Mice were randomized to treatment groups based on serum HBsAg levels at day −7. Adenovirus type 5 priming vaccines expressing HBV antigens were administered intramuscularly (i.m.) in 50 μl on day 0, and vaccinia boost vaccines expressing the same HBV antigens were administered i.m. in 50 μl on day 32. From days 46-67, mice were given either anti-PD-1 (anti-CD279) monoclonal antibody RMP1-14 or isotype control mAb. Blood samples were collected for viral antigen testing on days −7, 14, 27, 46, 60, 67, and 88. Splenocytes were harvested on day 88 and assessed for IFN-γ ELISPOT.

In this model, C57BL/6 mice were transduced with AAV vectors encoding a 1.2× length GT-D HBV genome, resulting in persistent HBV protein and virion production in hepatocytes, accompanied by antigenemia and viremia in serum. Heterologous viral vector prime-boost regimens consisting of an adenovirus (Ad) prime and poxvirus boost have yielded strong T cell responses in humans (see, e.g., Barnes, et al., Sci Transl Med. (2012) 4(115):115ra1; Ewer, et al., N Engl J Med. (2016) 374(17):1635-46; Ewer, et al. Nat Commun. (2013) 4:2836; Green, et al., Sci Transl Med. (2015) 7(300):300ra126; Swadling, et al., Sci Transl Med. (2014) 6(261):261ra153), so we generated vaccinia vectors based on the Western Reserve strain (NCBI:txid696871) expressing GT-C sAg and GT-B core-Pol$^{\Delta 1}$. AAV-HBV mice were vaccinated with Ad5 prime and vaccinia boost vectors encoding GT-C sAg and GT-B core-Pol$^{\Delta 1}$ or irrelevant control antigens beta-galactosidase and green fluorescent protein. Mice were further treated with either anti-mouse PD-1 monoclonal antibody or an isotype control antibody after the boost vaccination. A diagram of the AAV-HBV efficacy study is shown in FIG. 6, and treatment groups are shown in Table 4. A control group received HBV vaccine but no AAV-HBV to determine if vaccine responses were reduced in the presence of persistent HBV.

TABLE 4

Study Groups in AAV-HBV Efficacy Study

| Group | N | AAV-HBV | Prime | Boost | Antibody |
|---|---|---|---|---|---|
| 1 | 12 | Y | Ad-β-gal | Vac-GFP | Isotype ctrl |
| 2 | 12 | Y | Ad-sAg GT-C Ad-core-pol$^{\Delta 1}$ GT-B | Vac-sAg GT-C Vac-core-pol$^{\Delta 1}$ GT-B | Isotype ctrl |
| 3 | 12 | Y | Ad-β-gal | Vac-GFP | α-PD-1 |
| 4 | 12 | Y | Ad-sAg GT-C Ad-core-pol$^{\Delta 1}$ GT-B | Vac-sAg GT-C Vac-core-pol$^{\Delta 1}$ GT-B | α-PD-1 |
| 5 | 12 | N | Ad-sAg GT-C Ad-core-pol$^{\Delta 1}$ GT-B | Vac-sAg GT-C Vac-core-pol$^{\Delta 1}$ GT-B | None |

Ad: Adenovirus 5 vector.
Vac: vaccinia vector.
β-gal: beta-galactosidase.
GFP: green fluorescent protein.

Results

Figure 7:
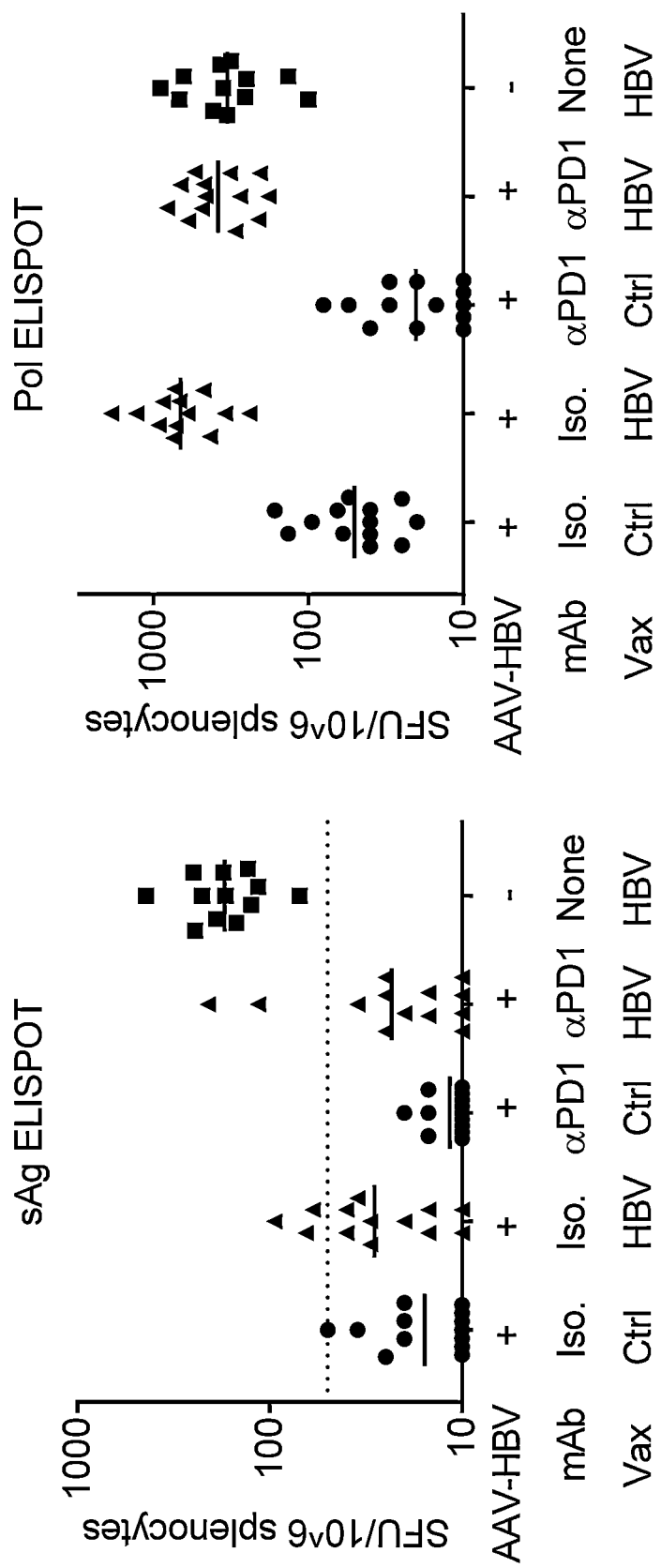
FIG. 7 illustrates the immunogenicity of Ad5 prime-vaccinia boost vaccination in AAV-HBV mice. Splenocytes were harvested on day 88 in the study shown in FIG. 6. T cell responses to HBsAg and Pol were evaluated by IFN-γ ELISPOT (BD mouse IFN-γ ELISPOT kit, catalog #551083) using overlapping peptide pools corresponding to GT-D sAg and Pol. Dashed line indicates the highest signal in HBsAg ELISPOT observed in mice receiving control vaccine. mAb: monoclonal antibody administered. Iso: isotype control. αPD-1: anti-PD-1. Vax: indicates whether the vaccine contained HBV antigens or control (Ctrl) antigens. SFU, spot forming units.

FIG. 7 shows the IFN-γ ELISPOT responses in each group. Note that responses were evaluated using GT-D peptide pools matched to the HBV strain in the AAV-HBV vector, so T cell responses are detected only if they react with the virus present in the AAV-HBV mice. Responses to core were tested but none were detected in any group, consistent with the poor immunogenicity of core in C57BL/6 mice (Chiale, et al., supra). Robust Pol ELISPOT responses were detected in all groups receiving Ad prime and vaccinia boost vectors encoding HBV antigens. Pol ELISPOT magnitude was similar in AAV-HBV mice and in control mice that did not receive AAV-HBV, indicating that the AAV-HBV does not result in T-cell tolerance to Pol. In contrast, ELISPOT responses to sAg were greatly reduced in AAV-HBV mice compared to control mice, demonstrating that AAV-HBV induces T cell tolerance to sAg. Nevertheless, in mice that received AAV-HBV and Adenovirus prime-vaccinia boost HBV vaccine, 2-3 mice per group demonstrated sAg ELISPOT responses above those detected in control-vaccinated mice. ELISPOT response magnitudes were not changed by anti-PD-1 treatment.

Figure 8:
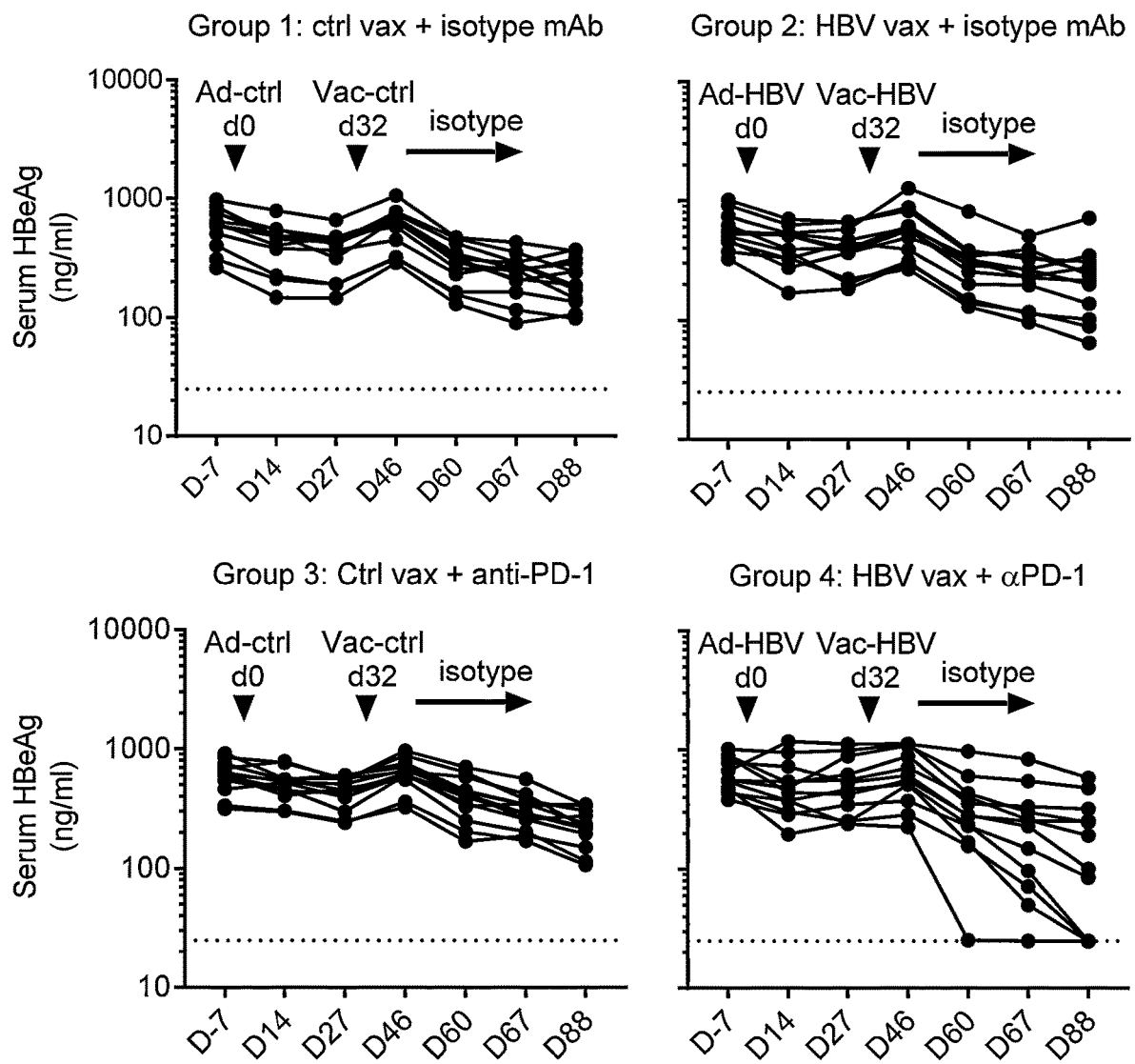
FIG. 8 illustrates the effects of HBV-expressing Ad5 prime-vaccinia boost vaccination in combination with PD-1 blockade in AAV-HBV mice. Serum HBeAg levels in the study shown in FIG. 6 were determined by ELISA (International Immunodiagnostics) at the indicated timepoints. Dashed line indicates the lower limit of detection. Ad: adenovirus 5 vector. Vac: vaccinia vector. Ctrl: control antigen. Isotype: isotype control antibody. αPD-1: anti-mouse PD-1 antibody.

To evaluate any antiviral effects of the HBV-specific T cells induced by vaccination, we measured serum e antigen (HBeAg). Serum HBeAg is a better marker of T-cell mediated antiviral efficacy than serum HBsAg, since the latter may be reduced by the action of anti-HBsAg antibodies induced by vaccination. Neither HBV vaccine alone nor anti-PD-1 alone caused any reduction in serum HBeAg compared to mice receiving control vaccine and isotype control antibody. However, the combination of HBV vaccine+anti-PD-1 resulted in loss of detectable HBeAg in serum in 4 of 12 mice (FIG. 8). These data demonstrate that vaccination with viral vectors encoding our improved antigen sequences contributed to HBV clearance as part of a combination therapy strategy.

Example 5

Immunogenicity of Pol Antigens in Arenavirus Vectors

Figure 9A:
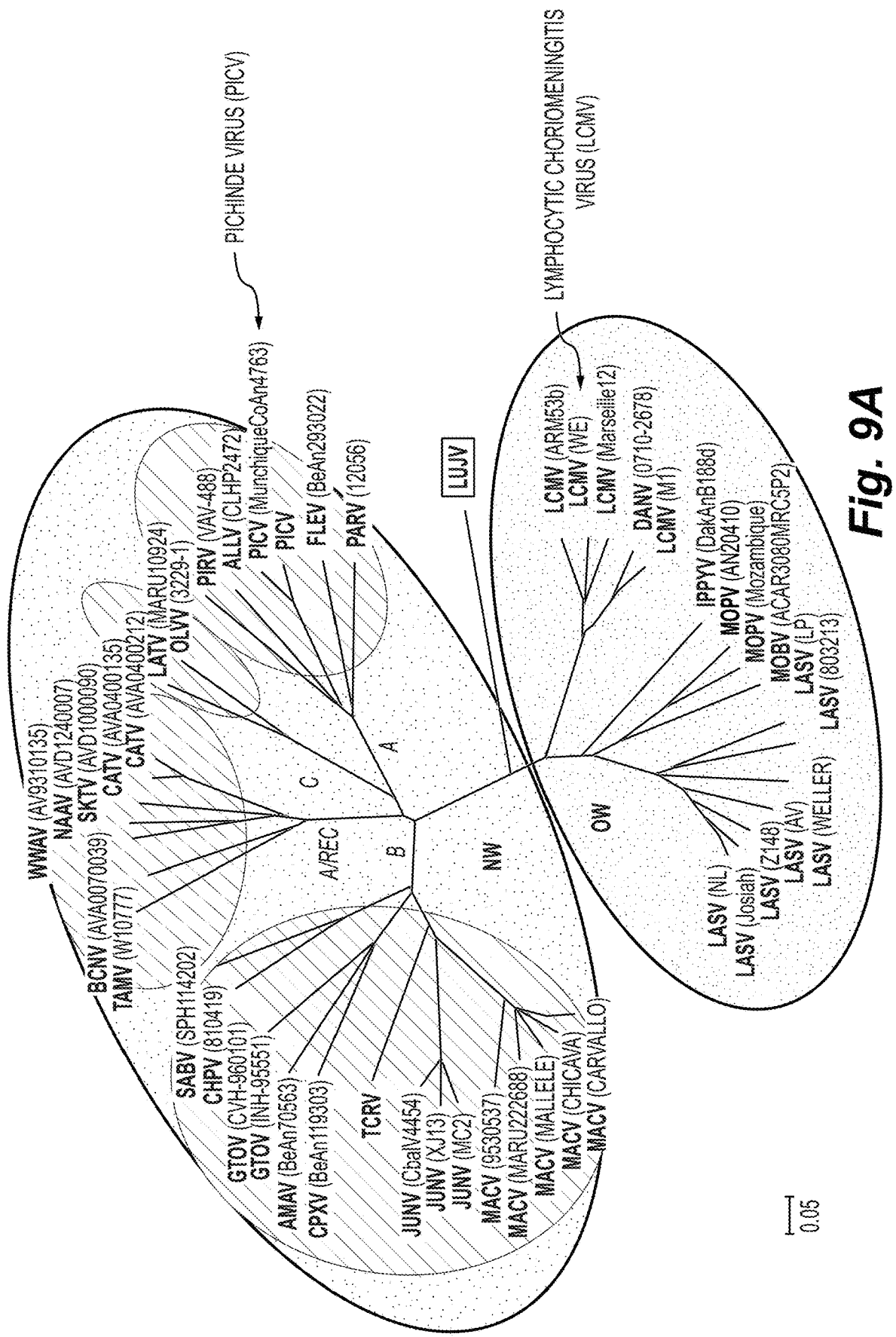

We further improved our HBV antigen designs for use in arenavirus vectors. Unlike adenovirus vectors and most other viral vector systems, arenavirus vectors can be repeatedly administered without inducing neutralizing anti-vector antibodies. Additionally, arenavirus vectors can be produced in several variants differing in the source virus used to generate the vector, e.g., replication-incompetent with a two-segment (i.e., bi-segmented) genome (Flatz, et al., Nat Med. (2010) 16(3):339-45), or replication-attenuated with a three-segment (i.e., tri-segmented) genome (Kallert, et al., Nat Commun. (2017) 8:15327) (FIG. 9). Certain HBV antigens were expressed in tri-segmented replication-attenuated or bi-segmented replication-defective arenavirus platforms with either a Lymphocytic choriomeningitis mammarenavirus (LCMV) or Cali mammarenavirus (a.k.a., Pichinde mammarenavirus or Pichinde arenavirus (PICV)) vector backbone. Replication-defective arenavirus vectors used are described in WO 2009/083210. Replication-attenuated arenavirus vectors used are described in WO 2016075250 (LCMV) and WO 2017/198726 (Pichinde).

Figure 10:
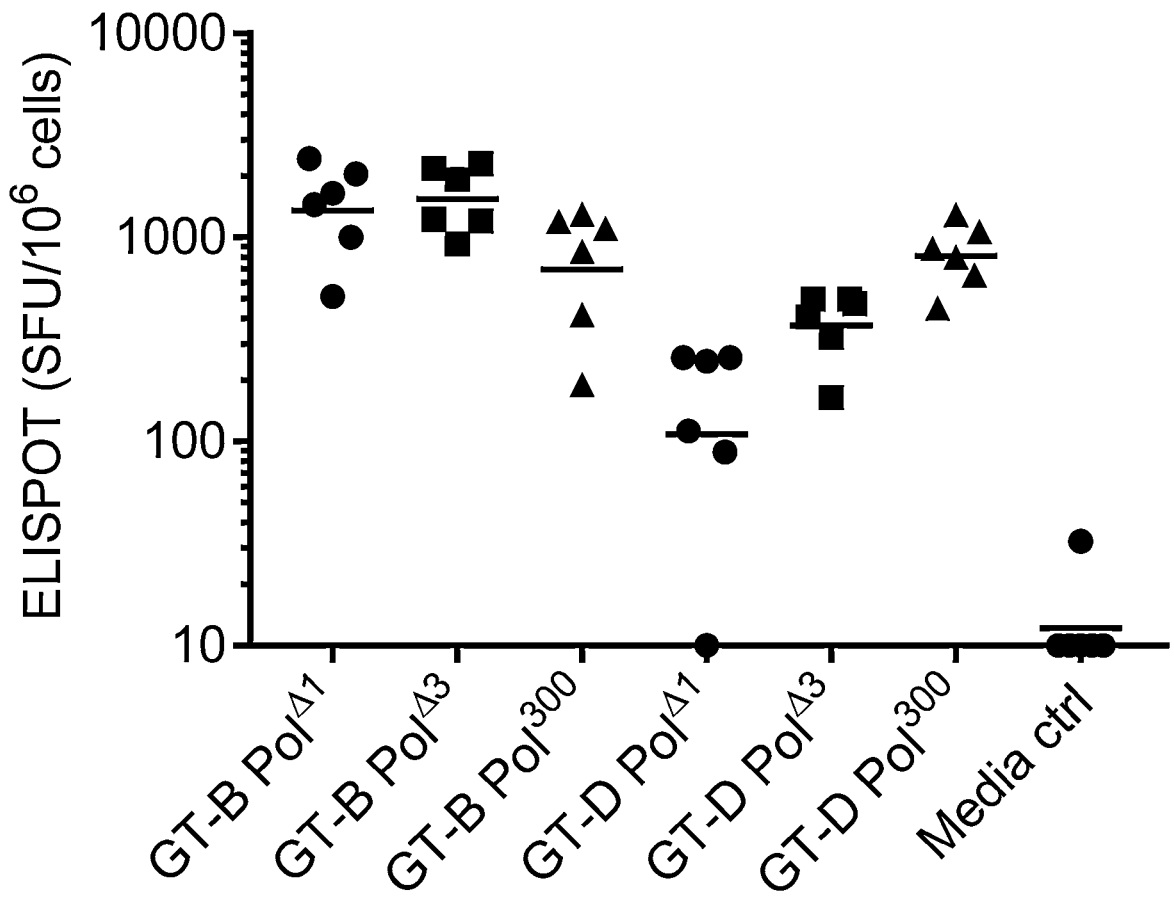
FIG. 10 illustrates the immunogenicity of Pol antigens in replication-incompetent lymphocytic choriomeningitis mammarenavirus (LCMV) vectors. Six- to eight-week-old C57BL/6 mice (n=6 per group) were injected intravenously with 1×10$^6$ focus forming units (FFU) of replication-incompetent LCMV vectors expressing Pol antigen variants GT-D and GT-B Pol$^{A1}$ (SEQ ID NOs: 6 and 8), Pol$^{A3}$ (SEQ ID NOs: 10 and 12), and Pol$^{300}$ (SEQ ID NOs: 13 and 14), or with media as a negative control. On day 7 after injection, splenocytes were harvested and T cell responses evaluated by IFN-γ ELISPOT (BD mouse IFN-γ ELISPOT kit, catalog #551083) using Pol overlapping peptide pools corresponding to the immunization antigen genotype in each group. SFU, spot forming units.

Arenavirus vectors can accommodate antigens of approximately 500-800 amino acids per open reading frame. Therefore, we tested GT-D and GT-B Pol$^{\Delta1}$ (SEQ ID NOs: 6 and 8), Pol$^{\Delta3}$ (SEQ ID NOs: 10 and 12), and Pol$^{300}$ (SEQ ID NOs: 13 and 14) for immunogenicity in replication-incompetent LCMV vectors. C57BL/6 mice were immunized intravenously with 10$^6$ focus forming units (FFU) of replication-incompetent LCMV vectors and IFN-γ ELISPOT responses were measured at day 7 post-immunization. All GT-B antigens and GT-D Pol$^{300}$ induced robust T cell responses, while GT-D Pol$^{\Delta1}$ and Pol$^{\Delta3}$ elicited reduced ELISPOT responses compared to the other antigen designs (FIG. 10).

Example 6

Identification of Genetically Stable Replication-Incompetent LCMV Vectors Encoding Immunogenic Pol Antigens The stability of various immunogenic Pol transgenes within replication-incompetent LCMV vectors (VV1) was evaluated by polymerase chain reaction (PCR) after serial passaging of vector containing supernatant. Genetic stability was defined by the major band showing at the correct size of the full-length transgene (TG). Results are shown in Table 6.

TABLE 6

Overview Table for Assessment of Genetic Stability of Pol Transgenes

| Genotype | Vector | Stable TG insertion until |
|---|---|---|
| GT-B | VV1*-Pol$^{\Delta1}$ | P1 |
| GT-B | VV1-Pol$^{\Delta3}$ | P1 |
| GT-B | VV1-Pol$^{300}$ | P5 |
| GT-D | VV1-Pol$^{\Delta1}$ | P1 |
| GT-D | VV1-Pol$^{\Delta3}$ | P1 |
| GT-D | VV1-Pol$^{300}$ | P2 |

*VV1 refers to replication-incompetent LCMV vectors.
"P#" indicates the number of passages (e.g., P1 equals 1 passage).

Example 7

Immunogenicity of Core-sAg Fusion Proteins in Replication-Incompetent LCMV Vectors Having identified stable, immunogenic Arenavirus vectors encoding HBV Pol, we additionally tested a series of core-sAg fusion proteins for immunogenicity in replication-incompetent LCMV vectors. Core-sAg fusions were generated by fusing near-consensus GT-B core and GT-C sAg, or GT-D core and GT-D sAg, with core at the N-terminus and sAg at the C-terminus. Direct fusions are expected to elicit T cell responses, but may not induce anti-sAg antibodies since the fusion protein will not secrete sAg. Therefore, additional antigen designs were tested with the core and sAg separated by a GSG linker followed by a 2A translational skip site derived from Porcine teschovirus-1 (P2A) (Kim, et al., PLoS ONE. (2011) 6: e18556). This orientation will yield a 21 amino acid extension on the C-terminus of core, while enabling normal sAg secretion to elicit antibody responses. Sequence identification numbers for the amino acid sequences of antigens tested in Arenavirus vectors, and the nucleotide sequences used to encode antigens in Arenavirus vectors, is shown in Table 7.

TABLE 7

Sequences vector antigens and antigen-encoding genes used in LCMV vectors

| Polynucleotide SEQ ID NO: | Polypeptide SEQ ID NO: | Polypeptide |
|---|---|---|
| 27 | 6 | GT-B Pol$^{\Delta1}$ |
| 28 | 10 | GT-B Pol$^{\Delta3}$ |
| 29 | 13 | GT-B Pol$^{300}$ |
| 30 | 8 | GT-D Pol$^{\Delta1}$ |
| 31 | 12 | GT-D Pol$^{\Delta3}$ |
| 32 | 14 | GT-D Pol$^{300}$ |
| 33 | 38 | GT-B/C core-sAg |
| 34 | 39 | GT-B/C core-P2A-sAg |
| 35 | 40 | GT-D core-sAg |
| 36 | 41 | GT-D core-P2A-sAg |
| 37 | 41 | GT-D iCore-P2A-sAg |

Figure 11:
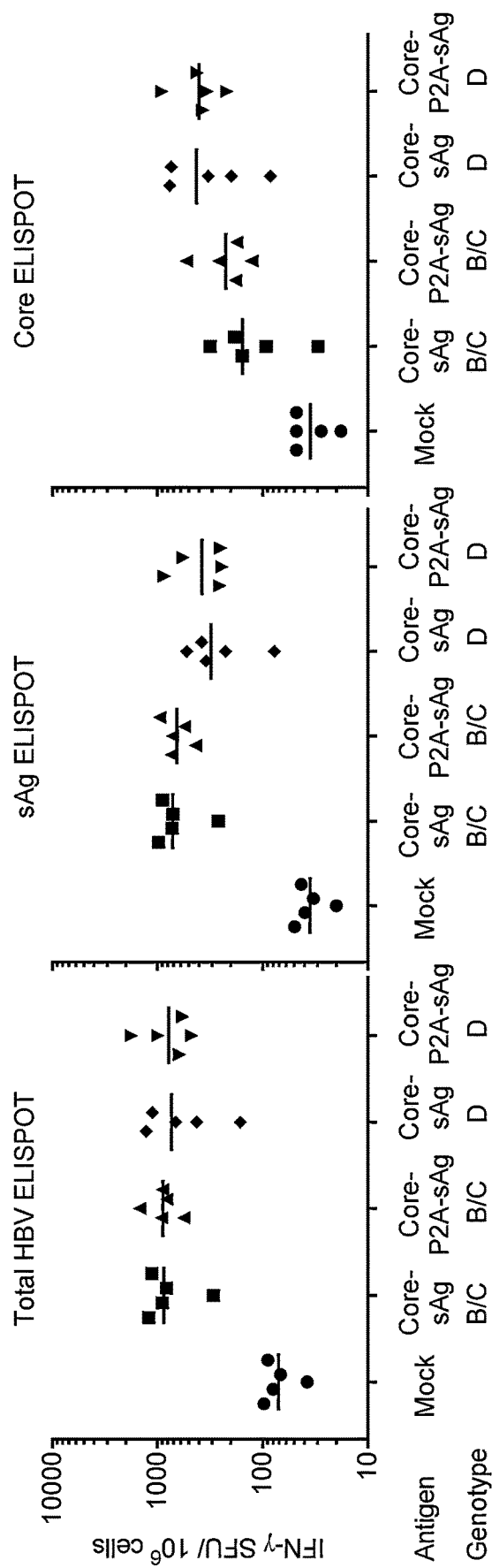
FIG. 11 illustrates the immunogenicity of Core-HBsAg fusion protein-expressing LCMV vectors in C57BL/6 mice. Six- to eight-week-old C57BL/6 mice (n=6 per group) were injected with 1×10$^6$ focus forming units (FFU) of replication-incompetent LCMV vectors expressing core-HBsAg fusion variants of SEQ ID NOs: 38-41 or mock immunized as a negative control. On day 7 after injection, splenocytes were harvested and T cell responses evaluated by IFN-γ ELISPOT (BD mouse IFN-γ ELISPOT kit, catalog #551083) using core and HBsAg overlapping peptide pools corresponding to the immunization antigen genotype in each group. SFU, spot forming units.

Replication-incompetent LCMV vectors encoding core-sAg variants were tested for immunogenicity by immunizing C57BL/6 mice (FIG. 11). The total HBV-specific IFN-γ ELISPOT responses were indistinguishable for all tested vectors, and inclusion of a P2A site had no impact on ELISPOT responses for either GT-B/C or GT-D antigens. Responses to both core and sAg were observed for all tested vectors. Detection of core responses was notable, as core T cell responses tend to be weak and difficult to detect in this mouse strain (Chiale, et al., supra). Similar results were seen in Balb/c mice immunized with the same vectors.

Figure 12:
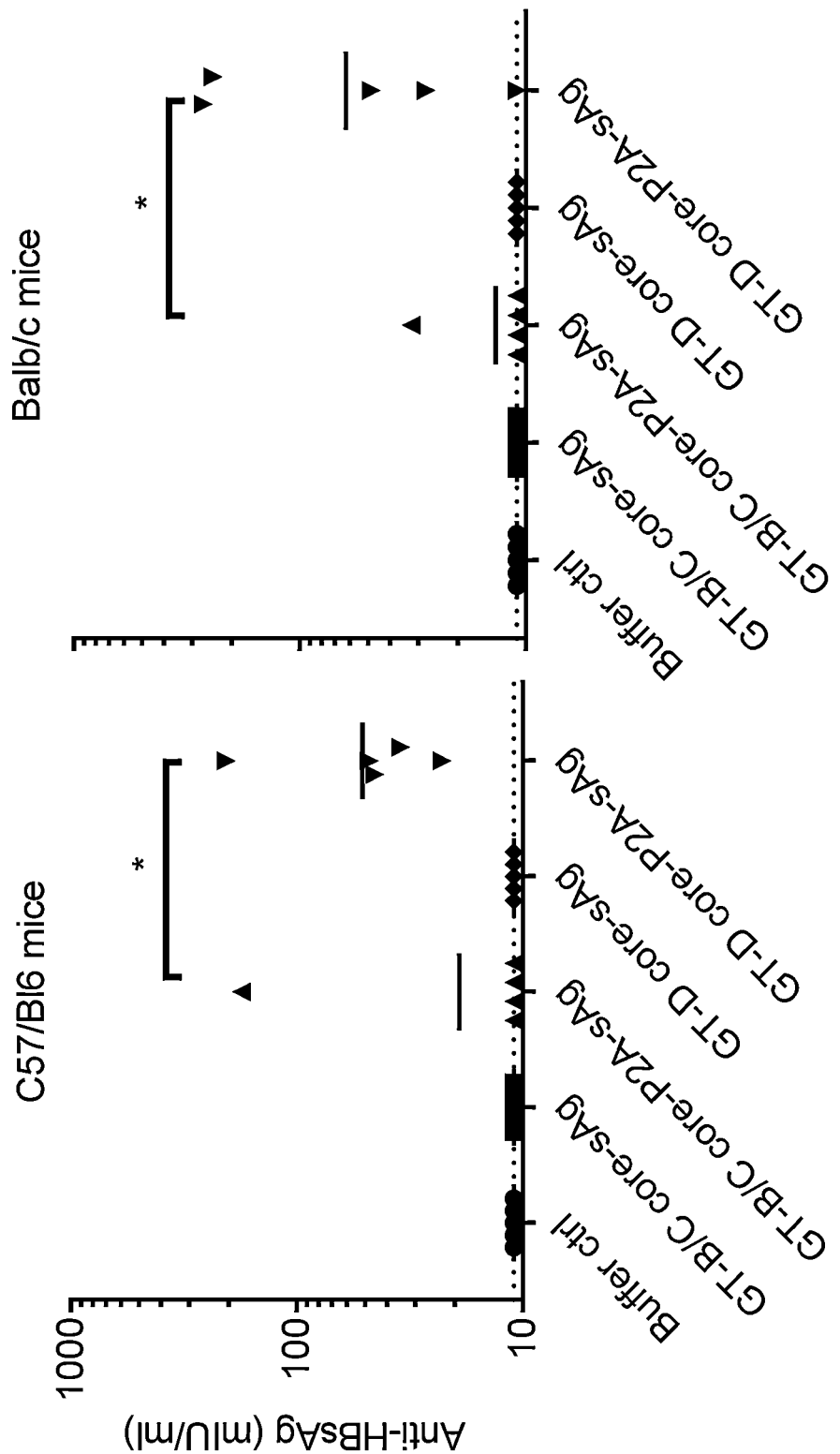
FIG. 12 illustrates the antibody response to HBsAg obtained in mice administered with core-sAg fusion protein-expressing replication-incompetent LCMV vectors. Six- to eight-week-old C57BL/6 (left) or Balb/c (right) mice (n=5 per group) were injected with 1×10$^6$ focus forming units (FFU) of replication-incompetent LCMV vectors expressing core-sAg fusion variants of SEQ ID NOs: 38-41 or with media as a negative control. On day 17 after injection, serum was collected and tested for anti-HBsAg antibody by ELISA (International Immunodiagnostics). Dashed line indicates the lower limit of detection of 11 mIU/ml. *p<0.05 by Mann-Whitney test.
Figure 13:
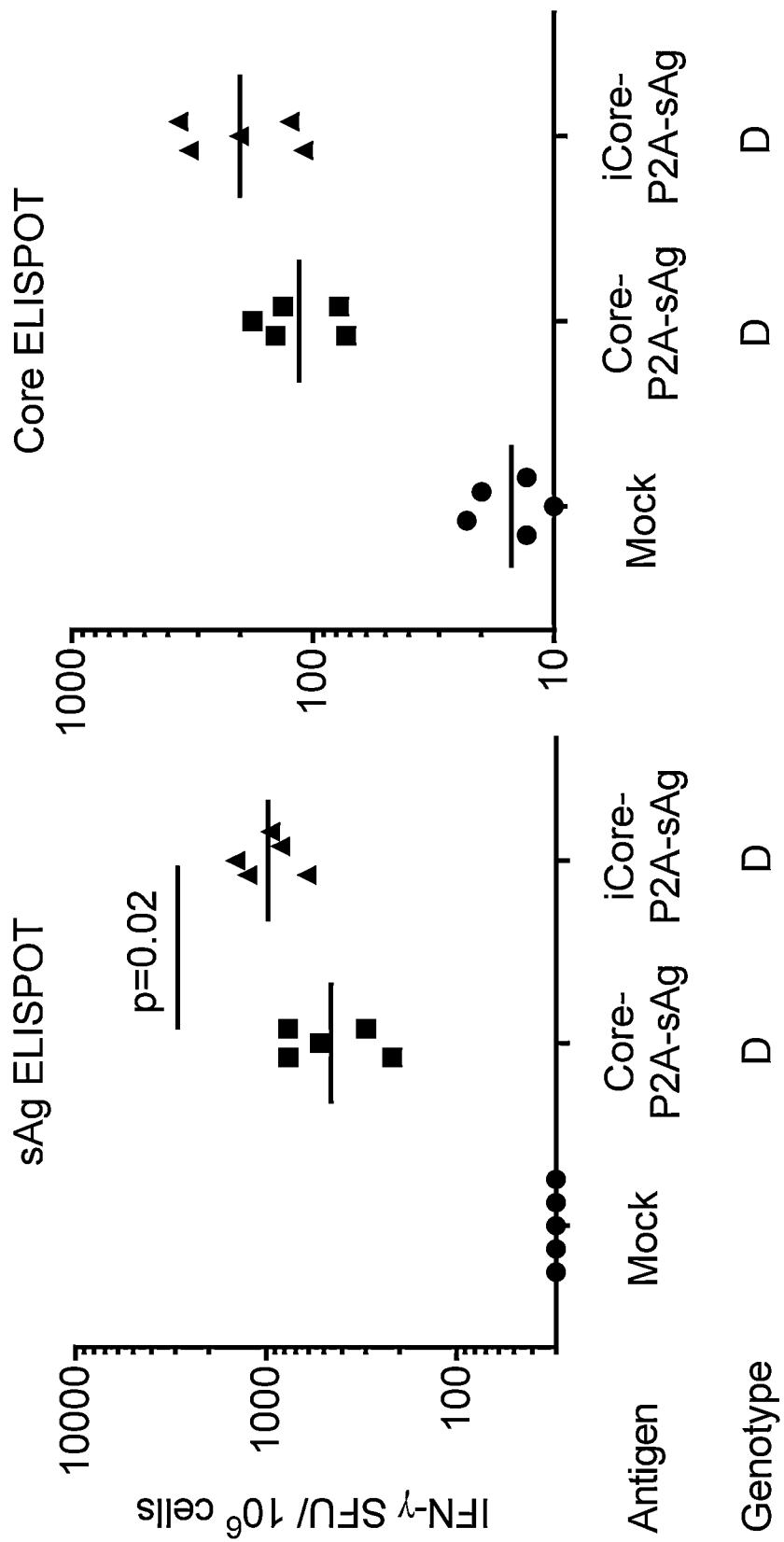
FIG. 13 illustrates the effect of nucleotide sequence modification on T-cell immunogenicity of core-P2A-sAg fusion proteins. Six- to eight-week old C57BL/6 mice (n=6 per group) were injected with 1×10$^6$ focus forming units (FFU) of replication-incompetent LCMV vectors with GT-D core-P2A-sAg (SEQ ID NO:36) or GT-D iCore-P2A-sAg (SEQ ID NO: 37), or mock immunized as a negative control. On day 7 after injection, splenocytes were harvested and T cell responses evaluated by IFN-γ ELISPOT (BD mouse IFN-γ ELISPOT kit, catalog #551083) using core and sAg overlapping peptide pools. Statistical analyses were performed with Mann-Whitney Tests.
Figure 14A:
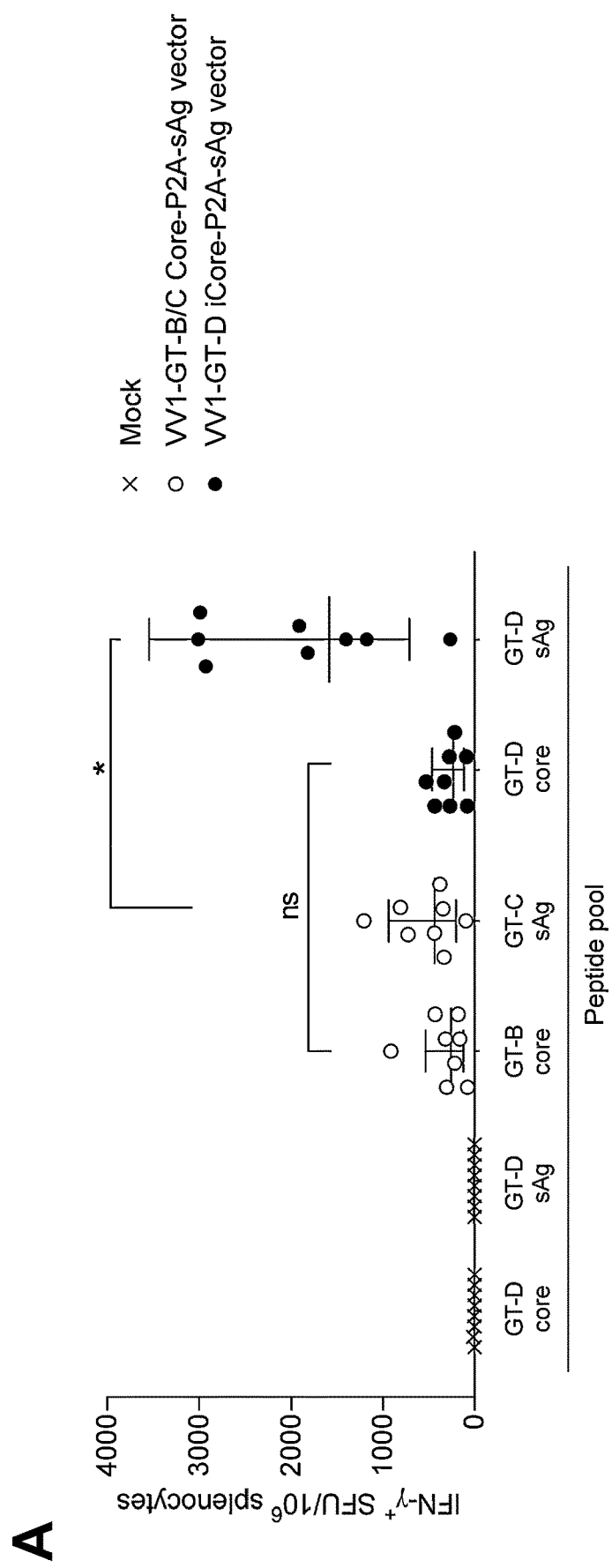
FIGS. 14A-14B illustrate the immunogenicity of prime/boost vaccination with replication-incompetent LCMV vectors (VV1) encoding GT-B/C Core-P2A-sAg or GT-D iCore-P2A-sAg (FIG. 14A) and GT-B Pol$^{A3}$ or GT-B Pol$^{300}$ (FIG. 14B) in diversity outbred mice. Animals were administered with 2 doses of each vaccine at day 0 and day 28 as described in Table 9. Splenocytes were harvested at day 42 and T cell responses to HBV antigens were measured by IFN-γ ELISPOT using sAg, core and polymerase peptide pools from various viral genotypes as indicated. Data are expressed as background (no peptide)-subtracted values. Statistical analyses were performed with Mann-Whitney tests. ns: not statistically significant; *p<0.0332.
Figure 14B:
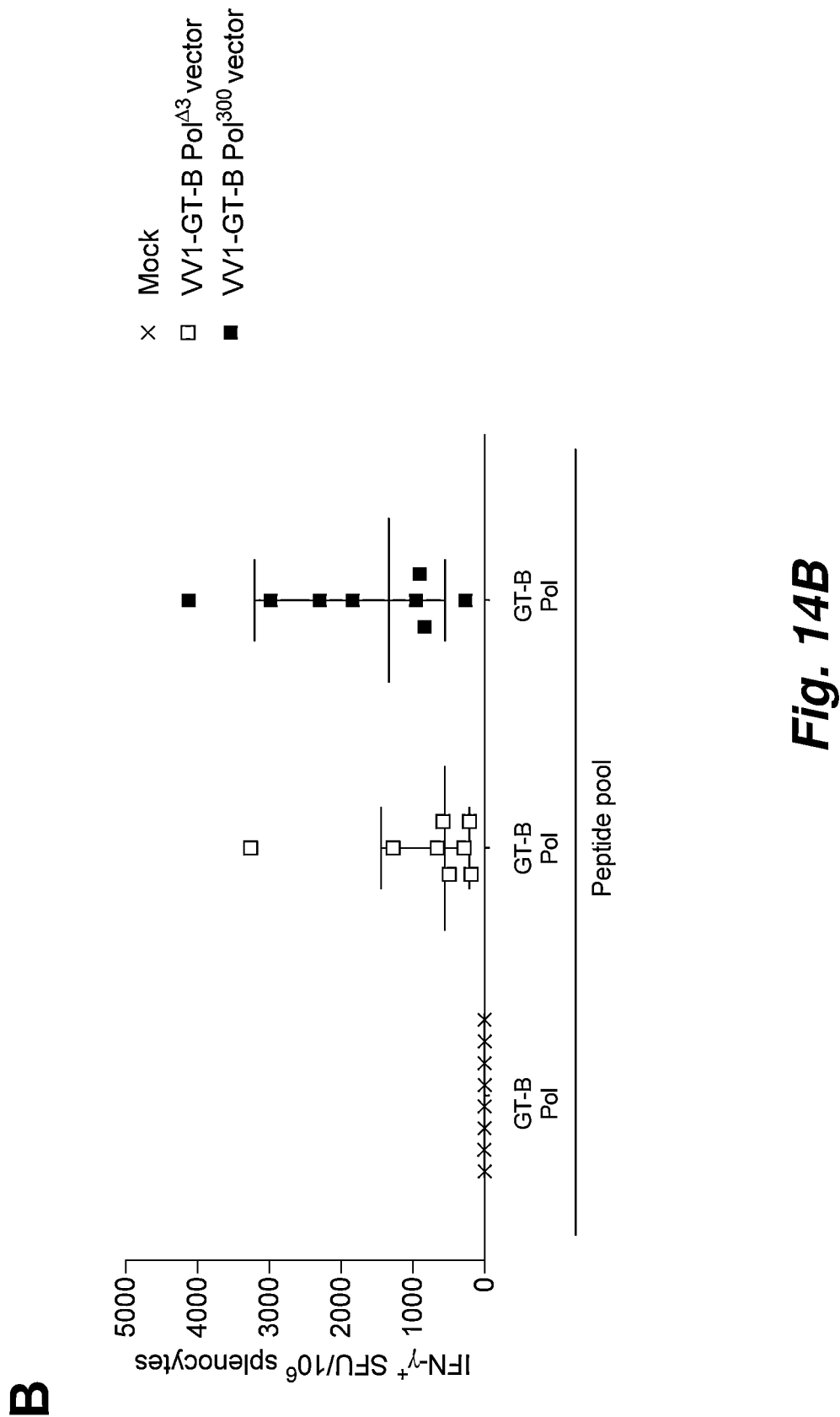
Figure 15A:
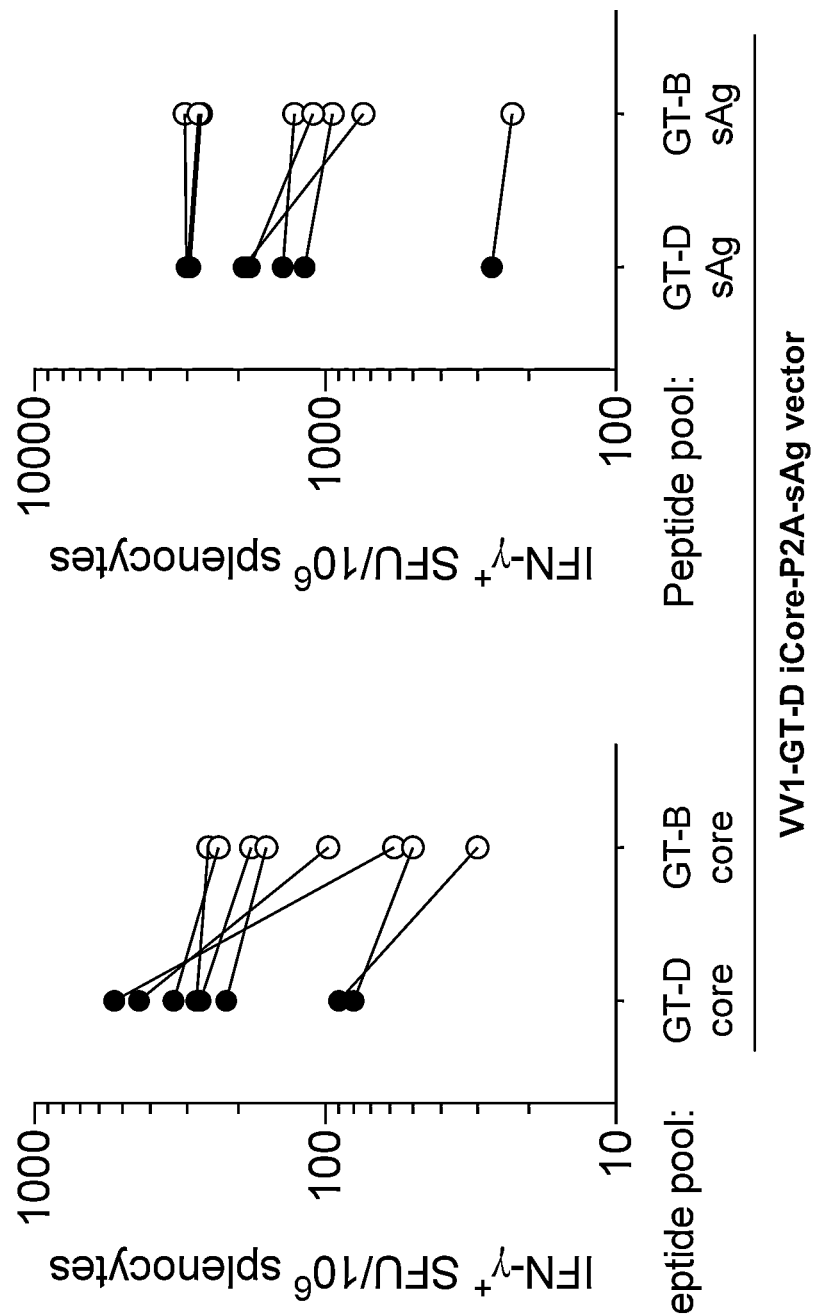
FIGS. 15A-15B illustrate the breadth of HBV-specific T cell responses generated upon prime/boost vaccination with replication-incompetent LCMV (VV1) vectors encoding GT-D iCore-P2A-sAg (FIG. 15A) or GT-B Pol$^{300}$ (FIG. 15B) in diversity outbred mice. IFN-γ ELISPOT was performed using peptides from the same viral genotype (filled circles) or from a different viral genotype (open circles).
Figure 15B:
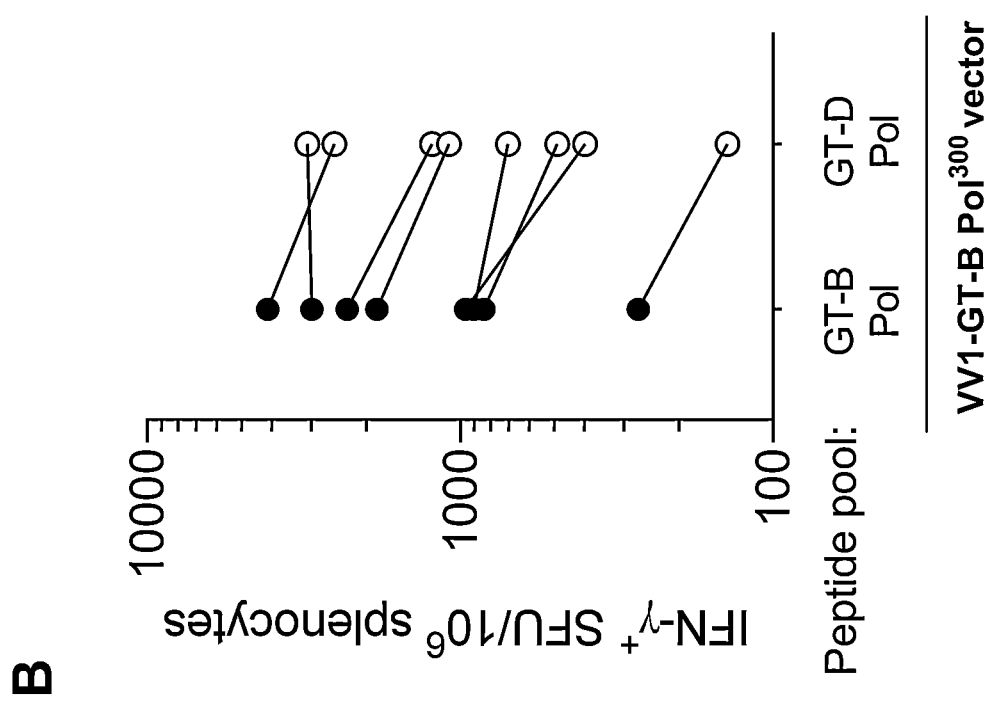

Antibody responses develop more slowly than T-cell responses after replication-incompetent LCMV vector vaccination, so an additional set of C57BL/6 mice was immunized and antibody responses were measured at day 17 post-immunization (FIG. 12). As expected, direct core-sAg fusions did not elicit anti-sAg antibody responses. Among the P2A-containing constructs, only the GT-D core-P2A-sAg vector consistently induced anti-sAg antibodies, while anti-sAg antibodies were observed in only one of five mice immunized with GT-B/C core-P2A-sAg. This result was unexpected, since Western Blots showed efficient separation of core and sAg in both the GT-D and GT-B/C core-P2A-sAg vectors. To confirm that the difference in anti-sAg antibody responses was not an artifact of the mouse strain selected, the same experiment was run in Balb/c mice. Results in the Balb/c mice were similar to the results in C57BL/6 mice: anti-sAg antibodies were detected in 4 of 5

Balb/c mice immunized with GT-D core-P2A-sAg, but only 1 of 5 mice immunized with GT-B/C core-P2A-sAg (FIG. 12).

Example 8

Identification of Genetically Stable Replication-Incompetent LCMV Vectors Encoding Immunogenic Core-sAg Fusion Proteins The stability of various immunogenic core-sAg fusion transgenes within replication-incompetent LCMV vectors (VV1) was evaluated by PCR after serial passaging of vector containing supernatant. Genetic stability was defined by the major band showing at the correct size of the full-length transgene (TG). Results are shown in Table 8.

TABLE 8

Overview Table for Assessment of Genetic Stability of Core-sAg Transgenes

| Genotype | Vector | Stable TG insertion until |
|---|---|---|
| GT-B/C | VV1-Core-sAg | P6 |
| GT-B/C | VV1-Core-P2A-sAg | P7 |
| GT-D | VV1-Core-sAg | P4 |
| GT-D | VV1-Core-P2A-sAg | P2 |
| GT-D | VV1-iCore-P2A-sAg | P6 |

*VV1 refers to replication-incompetent LCMV vectors.
"P#" indicates the number of passages (e.g., P1 equals 1 passage).

GT-D core-P2A sAg induced robust T cell responses and the highest anti-sAg antibody responses of the tested core-sAg fusion designs, but did not have favorable genetic stability in this analysis. However, the modified transgene GT-D iCore-P2A-sAg (polynucleotide SEQ ID NO:37, encoding polypeptide SEQ ID NO:41) showed improved genetic stability in a replication-incompetent LCMV vector (Table 8).

To confirm that the modified transgene did not impair T-cell immunogenicity of GT-D iCore-P2A-sAg, C57BL/6 mice were immunized using replication-incompetent LCMV vectors with the GT-D core-P2A-sAg and GT-D iCore-P2A-sAg designs, or mock immunized, and T cell responses were measured 7 days later by IFN-γ ELISPOT (FIG. 13). sAg ELISPOT responses were significantly higher with GT-D iCore-P2A-sAg, and core ELISPOT responses were numerically higher as well. Thus, the modified transgene of GT-D iCore-P2A-sAg resulted in both improved genetic stability and improved immunogenicity.

Example 9

Immunogenicity of Replication-Incompetent LCMV Vectors in Outbred Mice

The immunogenicity of the replication-incompetent LCMV (VV1) vectors encoding various HBV antigens were evaluated in Diversity Outbred (DO) mice. These mice have more diverse MHC alleles than inbred C57BL/6 mice, so are better for evaluating genotype cross-reactivity of the T cell responses induced by vaccination.

Methods

DO mice were immunized twice at day 0 and day 28 with replication-incompetent LCMV vectors as indicated in Table 9. HBV-specific T cell responses were measured at day 42 by IFN-γ ELISPOT using splenocytes.

TABLE 9

Study Groups in Immunogenicity Study

| Group | N | Prime vector-Day 0 | Boost vector-Day 28 | Harvest Day | Dose/ vector |
|---|---|---|---|---|---|
| 1 | 8 | Mock | Mock | 42 | — |
| 2 | 8 | VV1-GT-B/C Core-P2A-sAg | VV1-GT-B/C Core-P2A-sAg | 42 | $10^6$ FFU |
| 3 | 8 | VV1-GT-D iCore-P2A-sAg | VV1-GT-D iCore-P2A-sAg | 42 | $10^6$ FFU |
| 4 | 8 | VV1-GT-B $Pol^{\Delta3}$ | VV1-GT-B $Pol^{\Delta3}$ | 42 | $10^6$ FFU |
| 5 | 8 | VV1-GT-B $Pol^{300}$ | VV1-GT-B $Pol^{300}$ | 42 | $10^6$ FFU |

Results

Replication-incompetent LCMV vectors encoding GT-B/C Core-P2A-sAg and GT-D iCore-P2A-sAg induced comparable T cell responses specific for their respective core antigen (FIG. 14A). The vector encoding GT-D iCore-P2A-sAg induced a higher frequency of T cells specific for its respective sAg antigen when compared to the vector encoding GT-B/C Core-P2A-sAg (FIG. 14A). The vector encoding GT-B $Pol^{300}$ induced a numerically superior T cell response specific to pol antigens than the vector encoding GT-B $Pol^{\Delta3}$ (FIG. 14B). Thus, the vectors encoding for GT-D iCore-P2A-sAg and GT-B $Pol^{300}$ are more immunogenic than the vectors encoding for GT-B/C Core-P2A-sAg and GT-B $Pol^{\Delta3}$ in outbred mice.

In addition to inducing T cells responses specific to their cognate antigens (i.e., GT-D core, GT-D sAg, GT-B Pol antigens), the GT-D iCore-sAg and GT-B $Pol^{300}$ vectors were also able to generate T cells responses specific for antigens obtained from different viral genotypes of HBV (i.e., GT-B core, GT-B sAg, GT-D Pol antigens) (FIGS. 15A and 15B). Thus, the vectors coding for GT-D iCore-sAg and GT-B $Pol^{300}$ produce T cells which are cross-reactive for different genotypes of HBV.

Example 10

Immunogenicity of Replication-Incompetent LCMV Vectors Administered as Single Vector or Co-Formulated in C57BL/6 Mice Replication-incompetent LCMV vectors encoding GT-D iCore-P2A-sAg and GT-B Pol300 are immunogenic in mice. We next compared their immunogenicity of both vectors when delivered either as single vectors or as a co-formulated mixture in C57BL/6 mice.

Methods

C57BL/6 mice were immunized twice at day 0 and day 21 with replication-incompetent LCMV vectors as indicated in Table 10. HBV-specific T cell responses were measured at day 28 by IFN-γ ELISPOT using splenocytes.

TABLE 10

Study Groups in Immunogenicity Study

| Group | N | Vector Format | Prime vector D0 | Boost vector D21 | Harvest Day | Dose/vector |
|---|---|---|---|---|---|---|
| 1 | 5 | — | Mock | Mock | 28 | $10^6$ FFU |
| 2 | 5 | Single vector | VV1-GT-D iCore_P2A_sAg | VV1-GT-D iCore_P2A_sAg | 28 | $10^6$ FFU |
| 3 | 5 | Single vector | VV1-GT-B Pol$^{300}$ | VV1-GT-B Pol$^{300}$ | 28 | $10^6$ FFU |
| 4 | 5 | Co-formulated | VV1-GT-D iCore_P2A_sAg + VV1-GT-B Pol$^{300}$ | VV1-GT-D iCore_P2A_sAg + VV1-GT-B Pol$^{300}$ | 28 | $10^6$ FFU |

Results

Figure 16A:
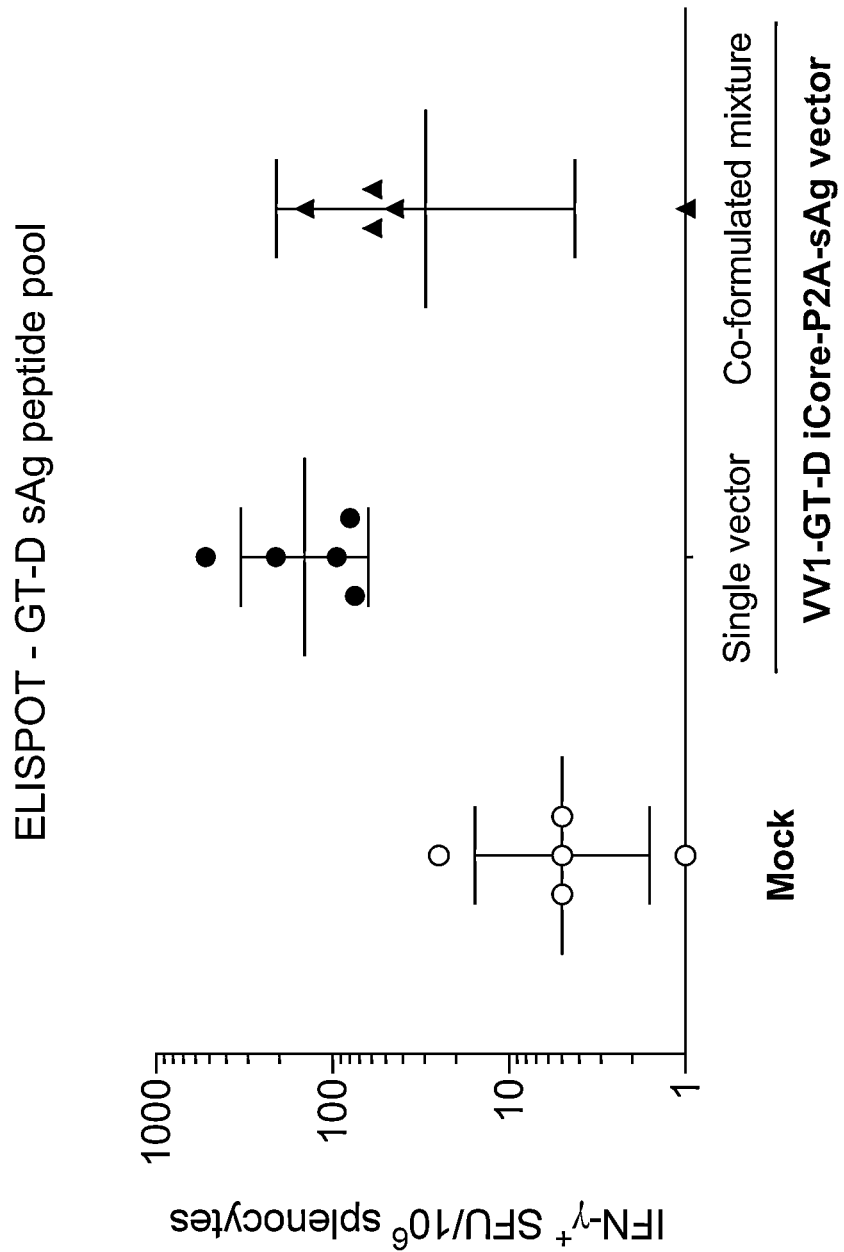
FIGS. 16A-16C illustrate the immunogenicity of prime/boost vaccination with replication-incompetent LCMV (VV1) vectors encoding GT-D iCore-P2A-sAg and GT-B Pol$^{300}$ when delivered either as single vectors or as a co-formulated mixture in C57BL/6 mice. Animals were administered with 2 doses of the vectors at day 0 and day 21 as described in Table 10. Splenocytes were harvested at day 28 and HBV-specific T cell responses were measured by IFN-γ ELISPOT using core (16A), sAg (16B) and Pol (16C) peptide pools.
Figure 16B:
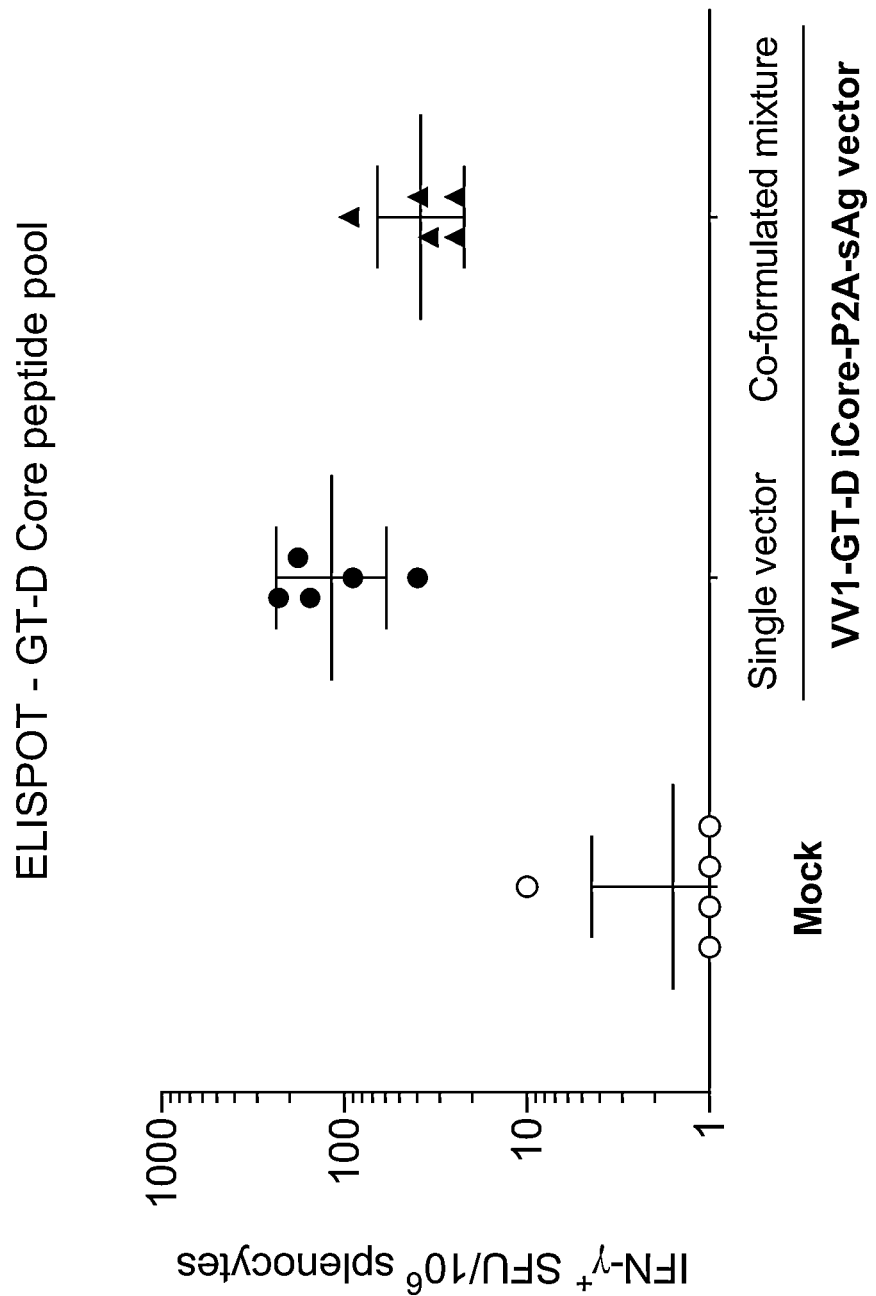
Figure 16C:
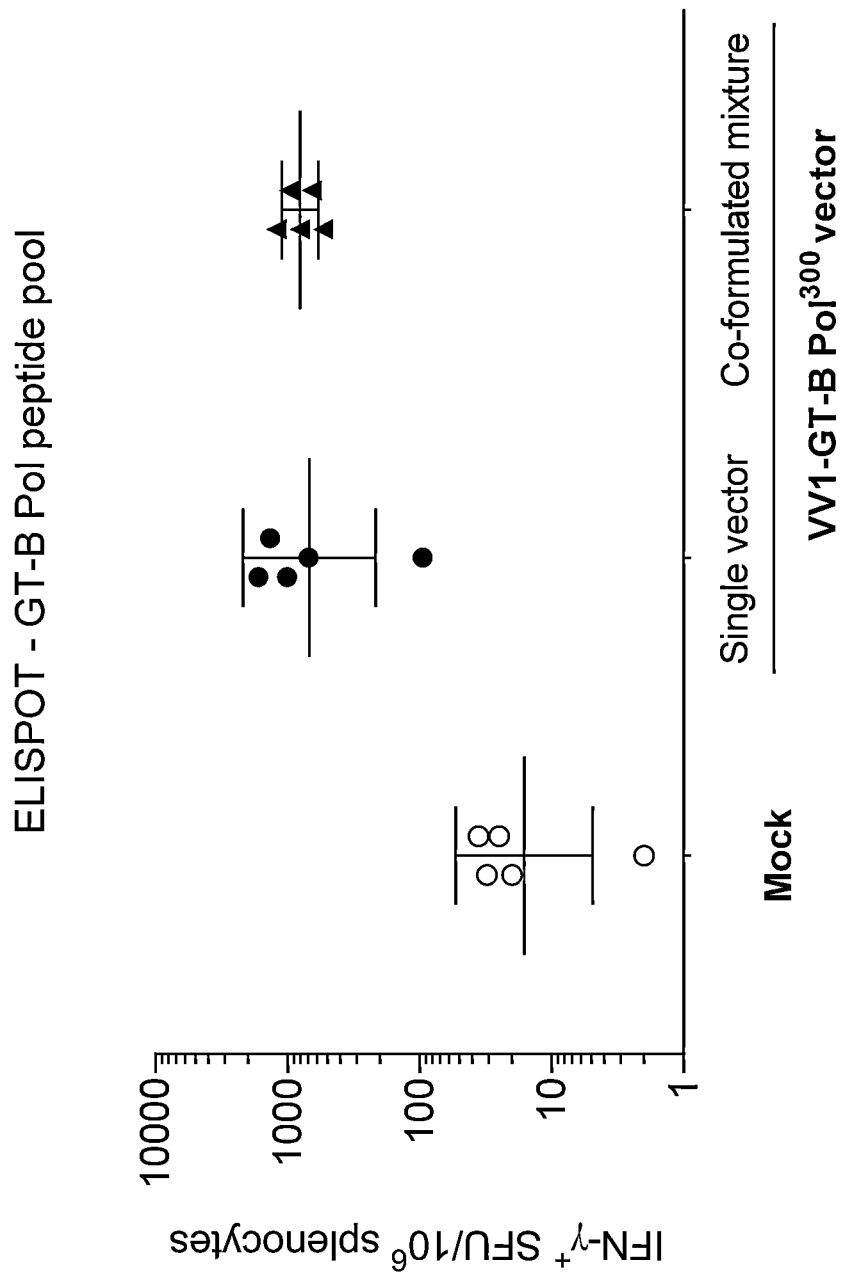
Figure 17A:
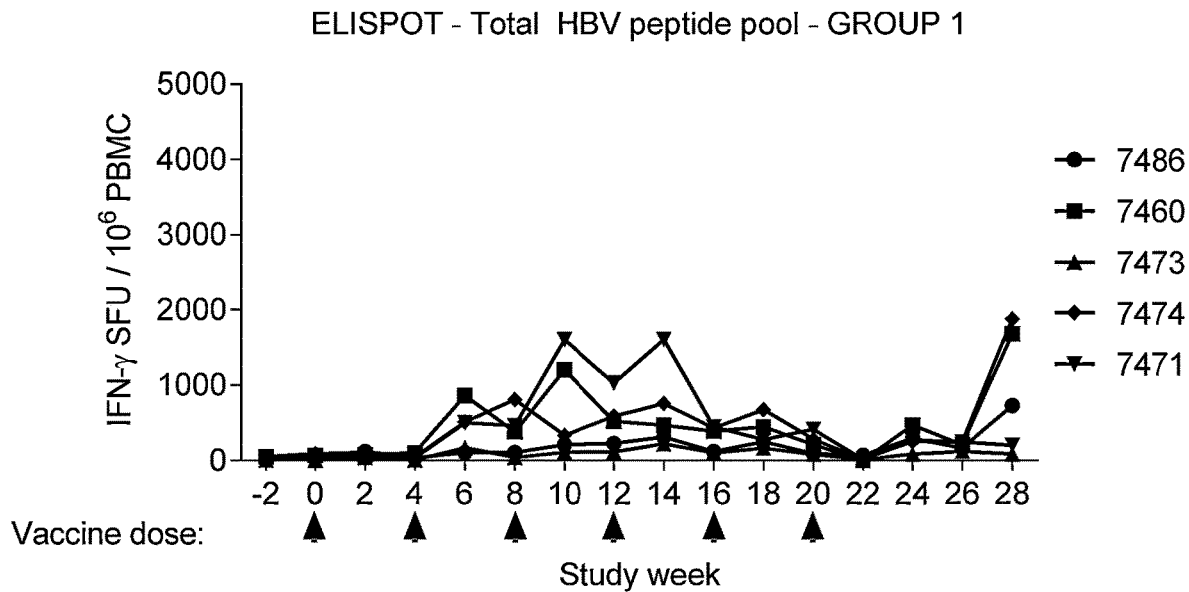
FIGS. 17A-17F illustrate the immunogenicity of repeat vaccinations with replication-incompetent LCMV vectors encoding GT-D iCore-P2A-sAg and GT-B Pol$^{300}$ in cynomolgus macaques. A group of animals was also vaccinated with Ad5 and vaccinia vectors encoding the same HBV antigens. Animals were administered with the vectors as described Table 11. 17A: Group 1; 17B: Group 2; 17C: Group 3; 17D: Group 4; 17E: Group 5; 17F: Group 6. T cell responses to HBV antigens were assessed by performing IFN-γ ELISPOT using sAg, core and Pol peptide pools at the indicated timepoints. Data are expressed at total HBV-specific T cell responses defined as the sum of IFN-γ
Figure 17B:
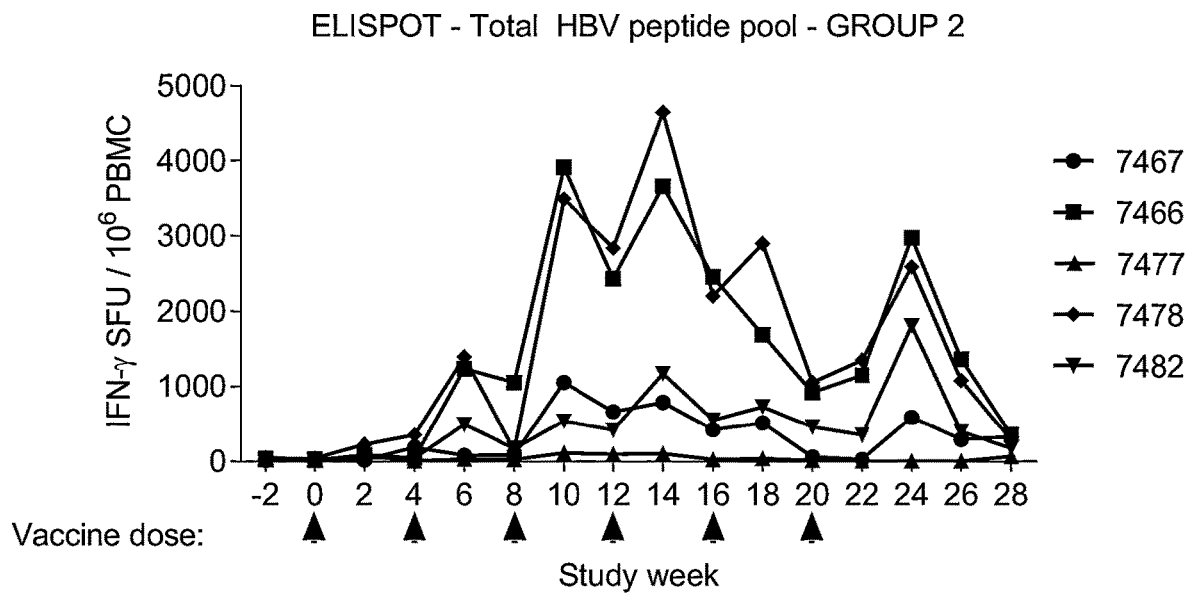
Figure 17C:
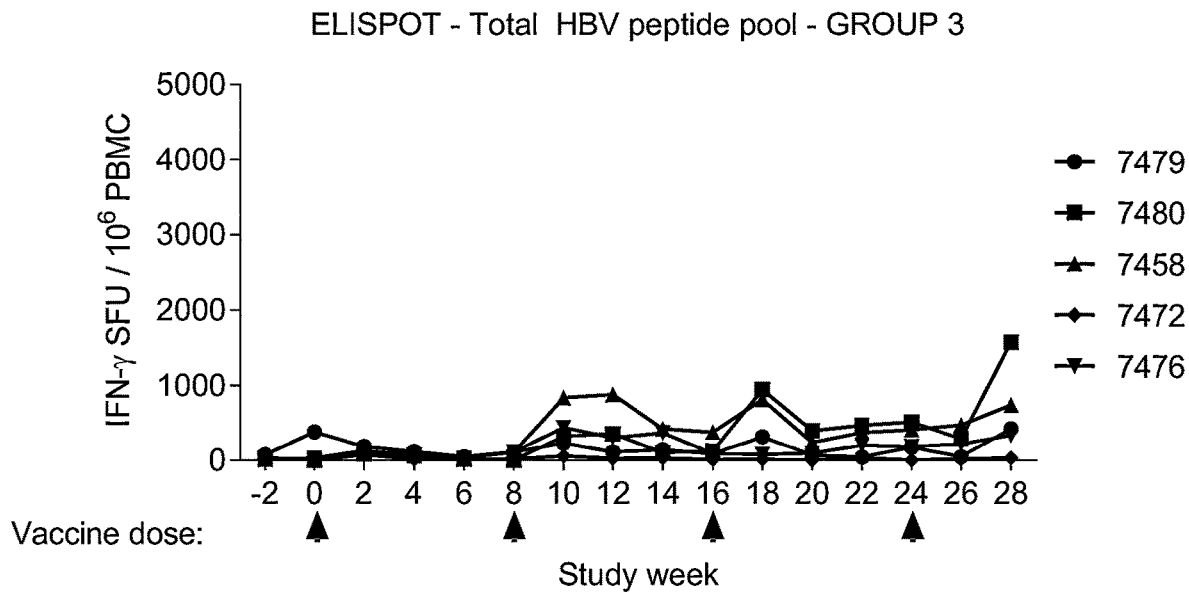
Figure 17D:
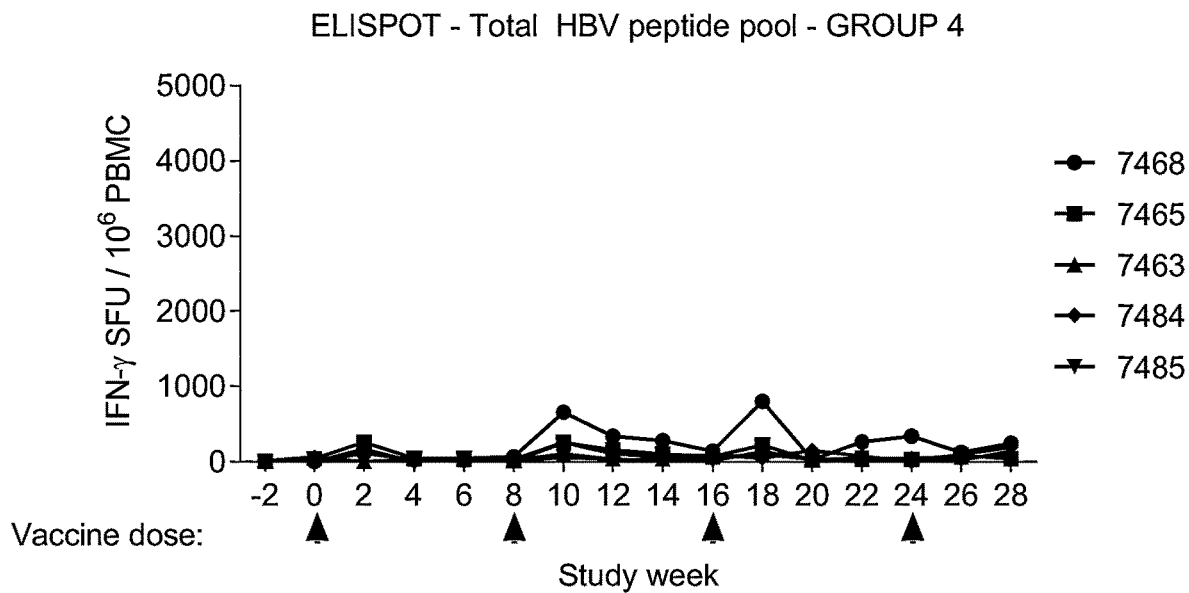
Figure 17E:
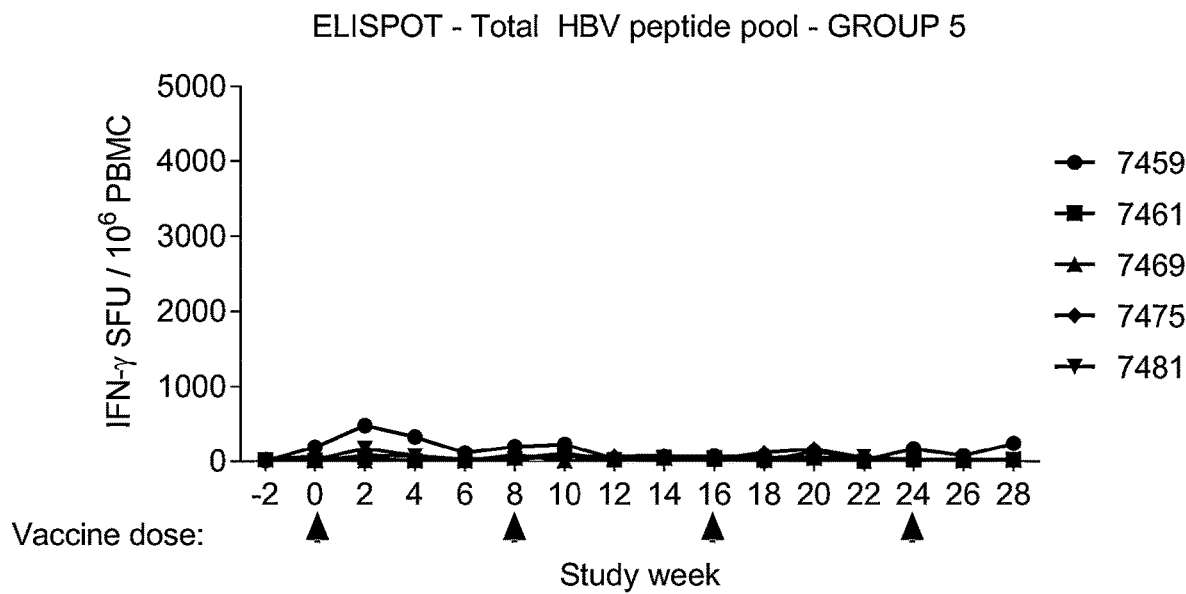
Figure 17F:
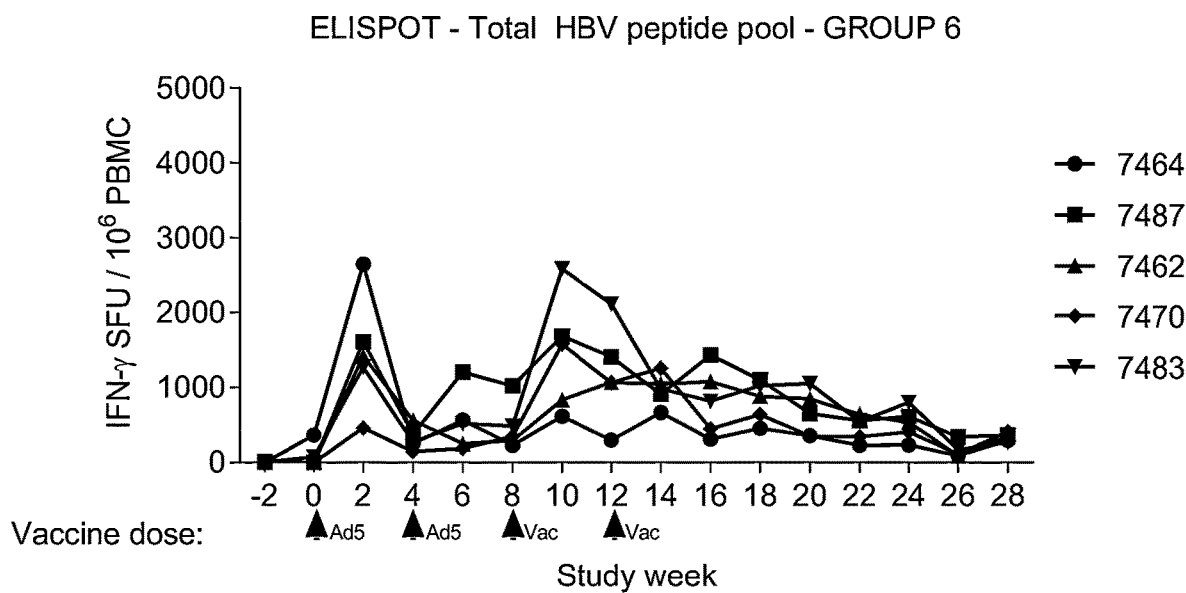
Figure 18A:
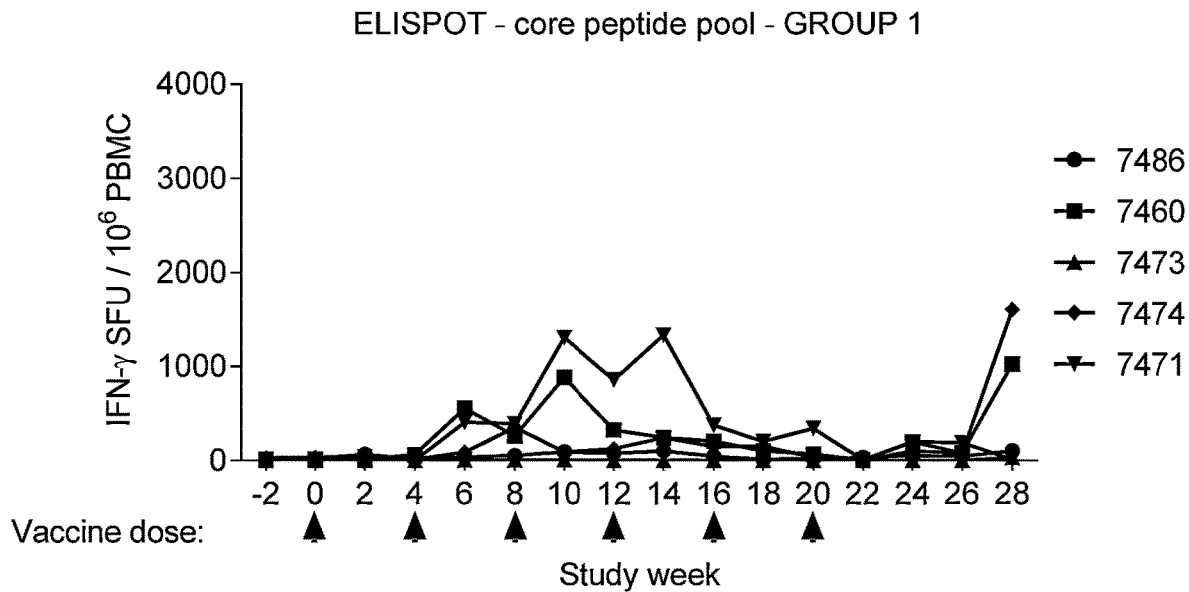
Figure 18B:
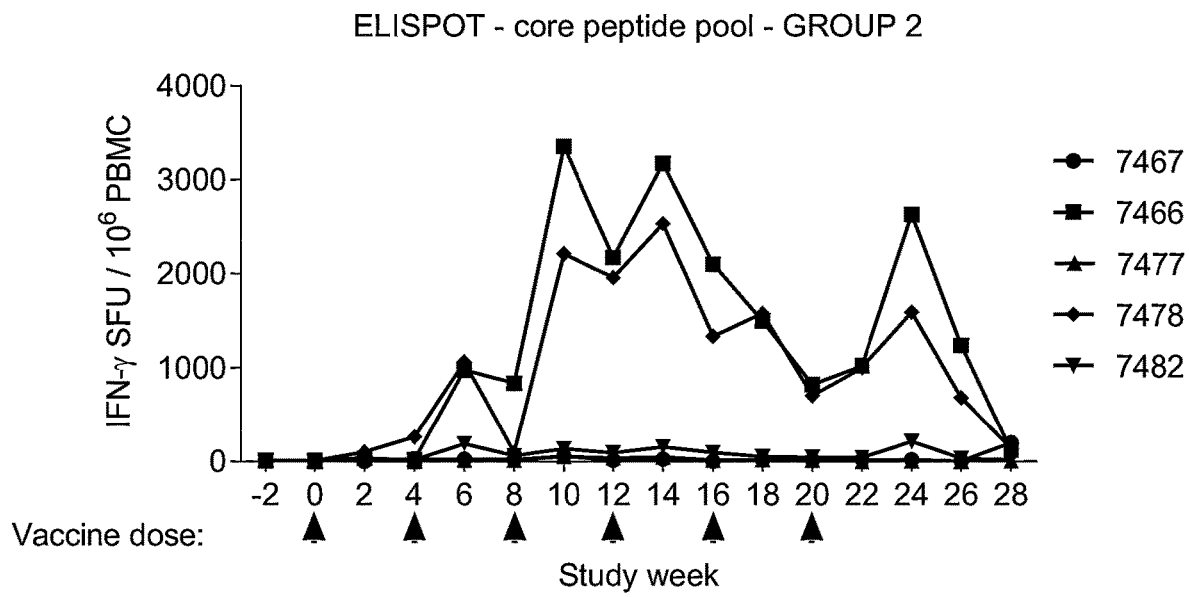
Figure 18C:
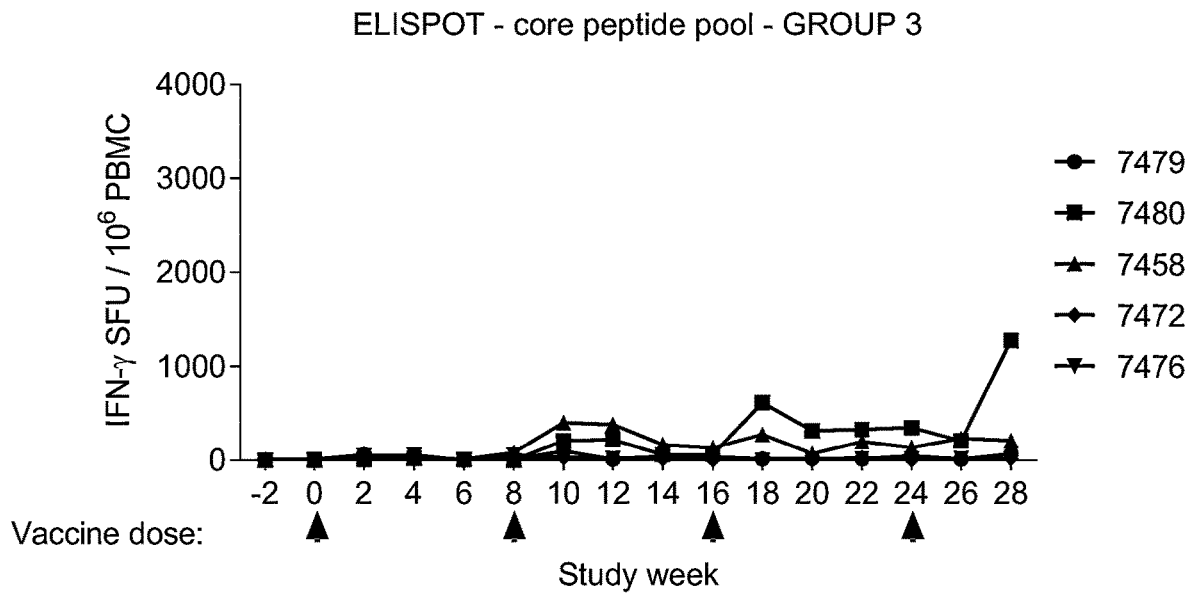
Figure 18D:
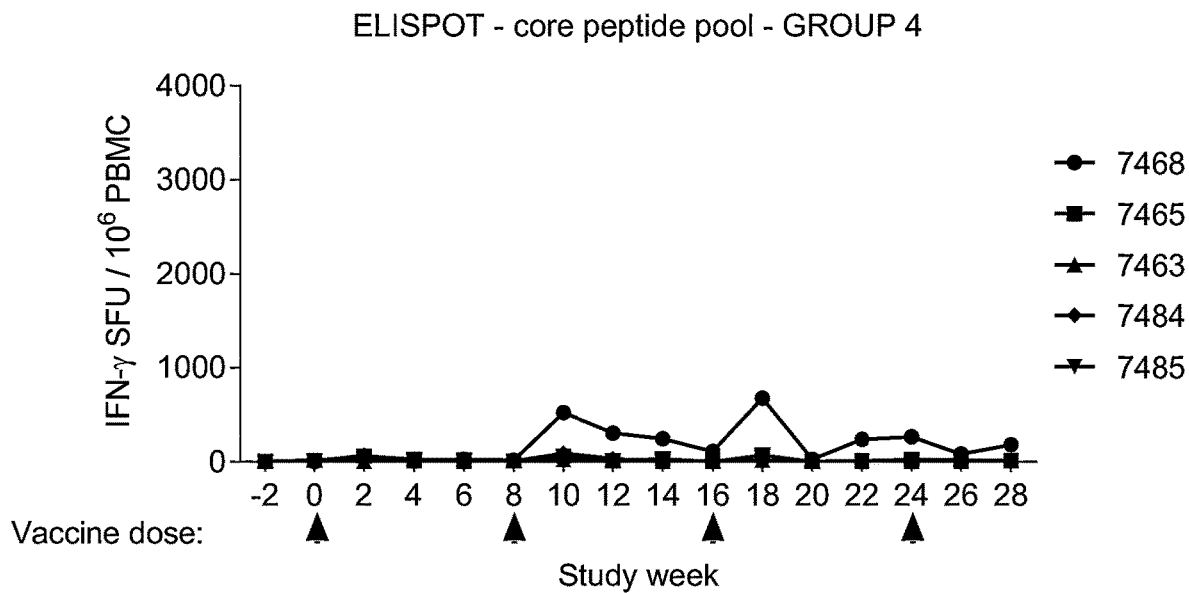
Figure 18E:
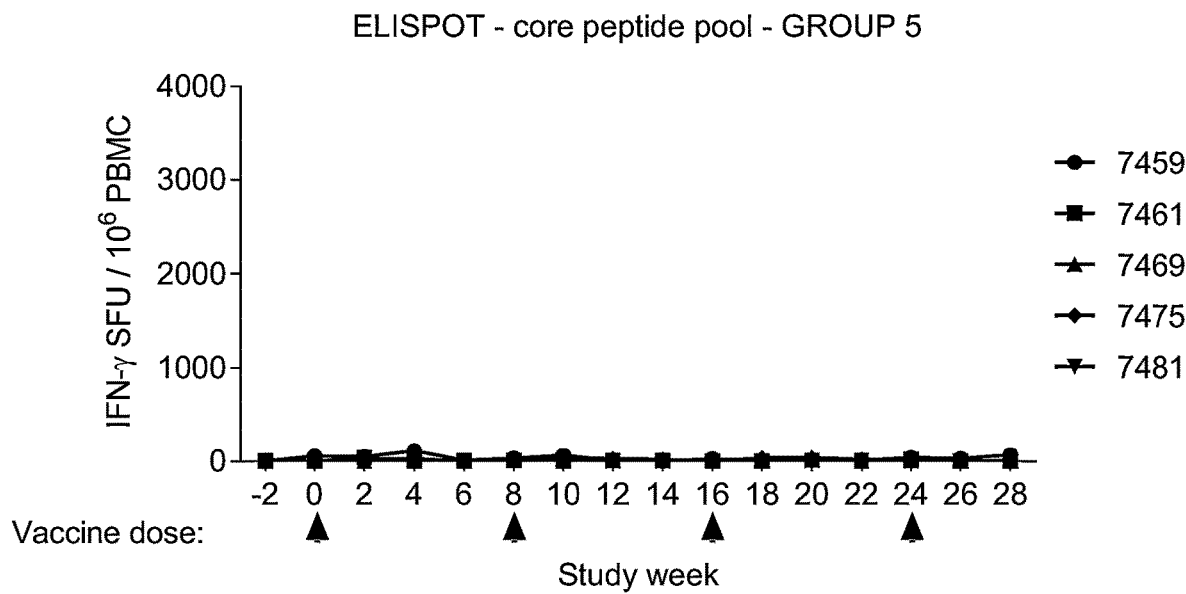
Figure 18F:
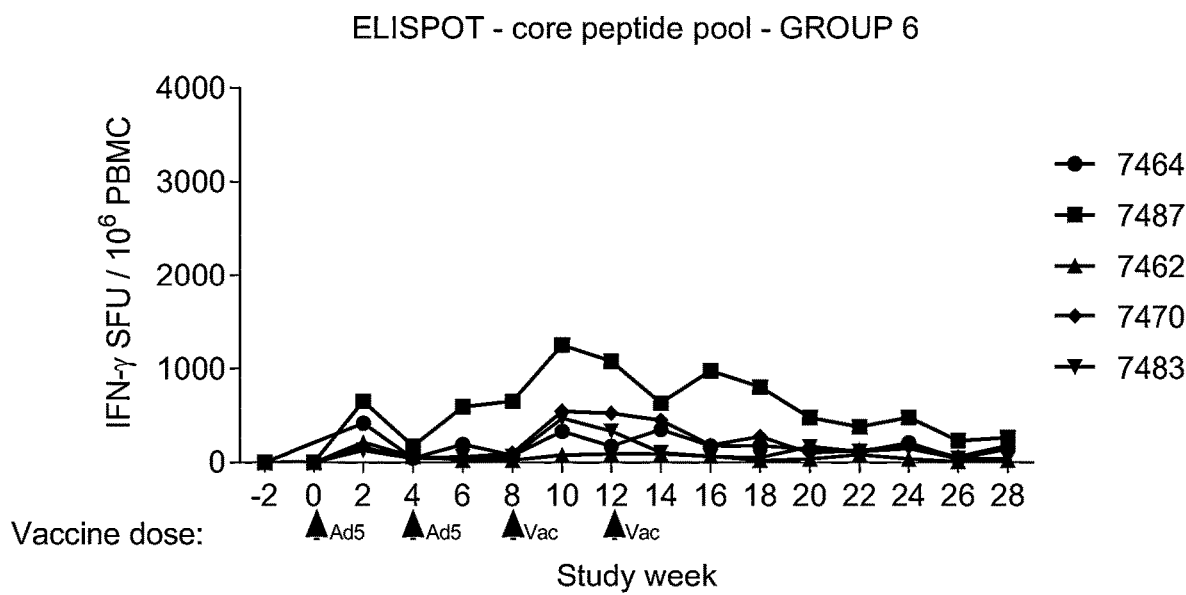
Figure 19A:
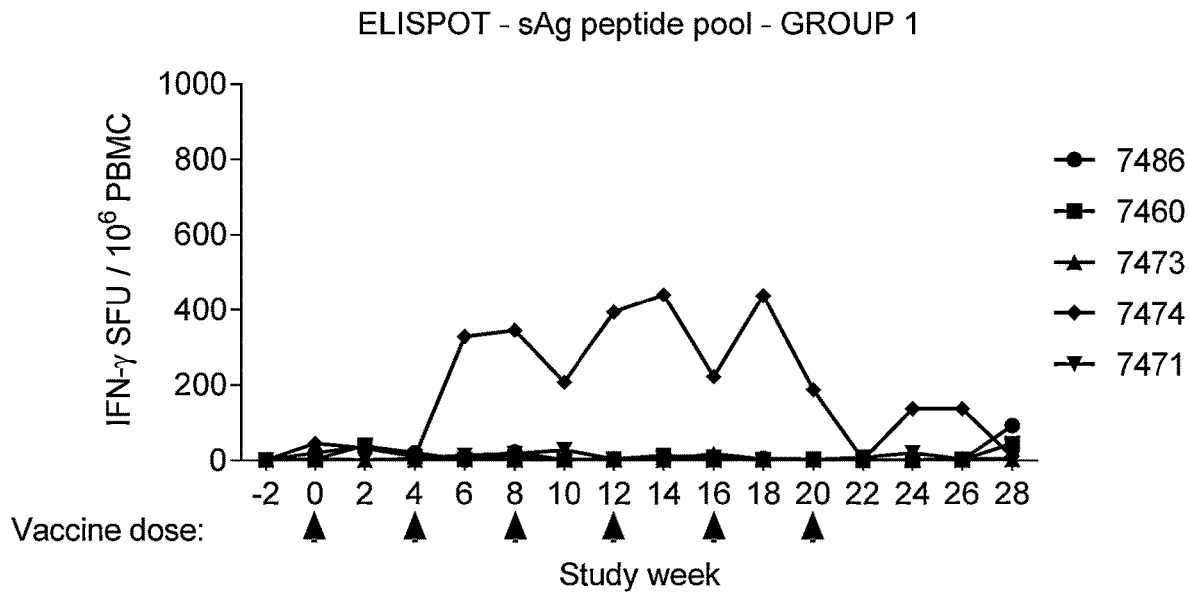
Figure 19B:
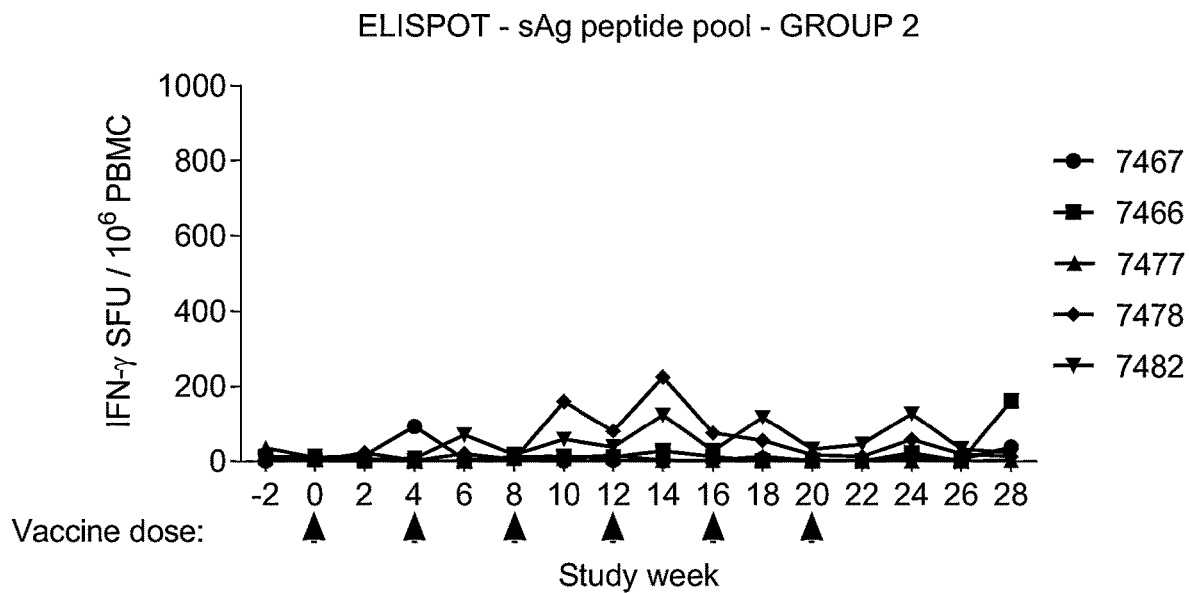
Figure 19C:
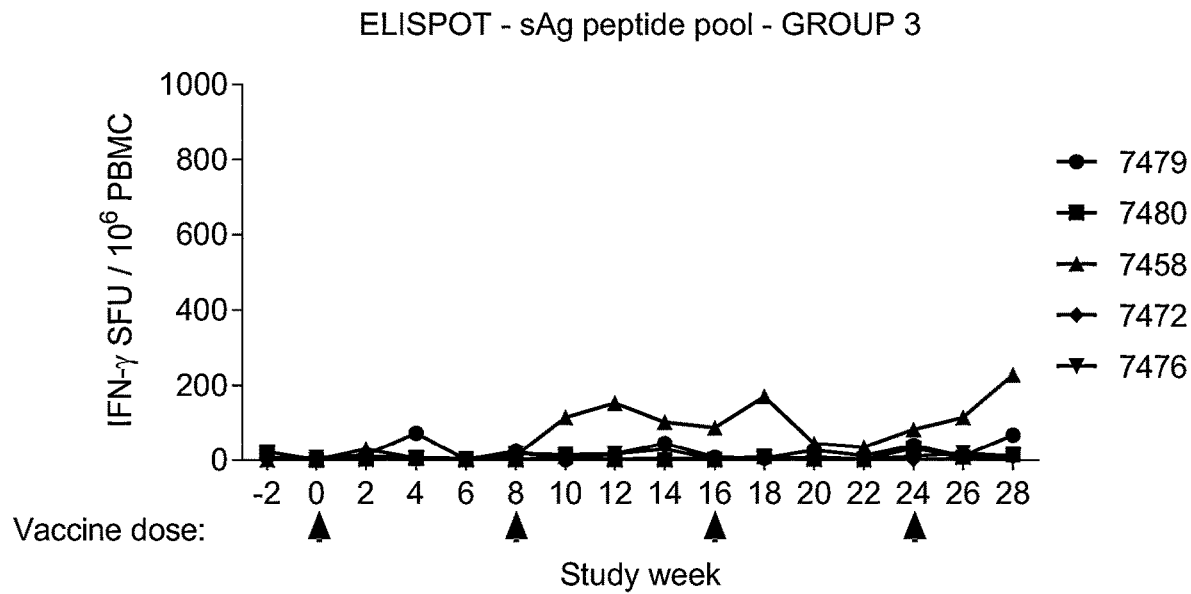
Figure 19D:
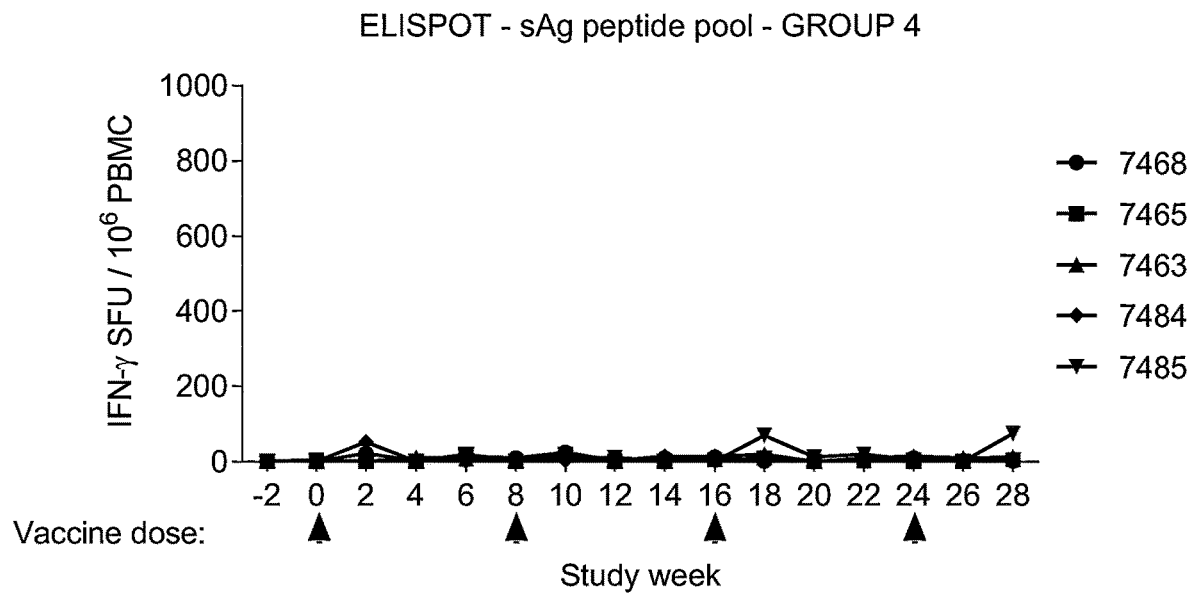
Figure 19E:
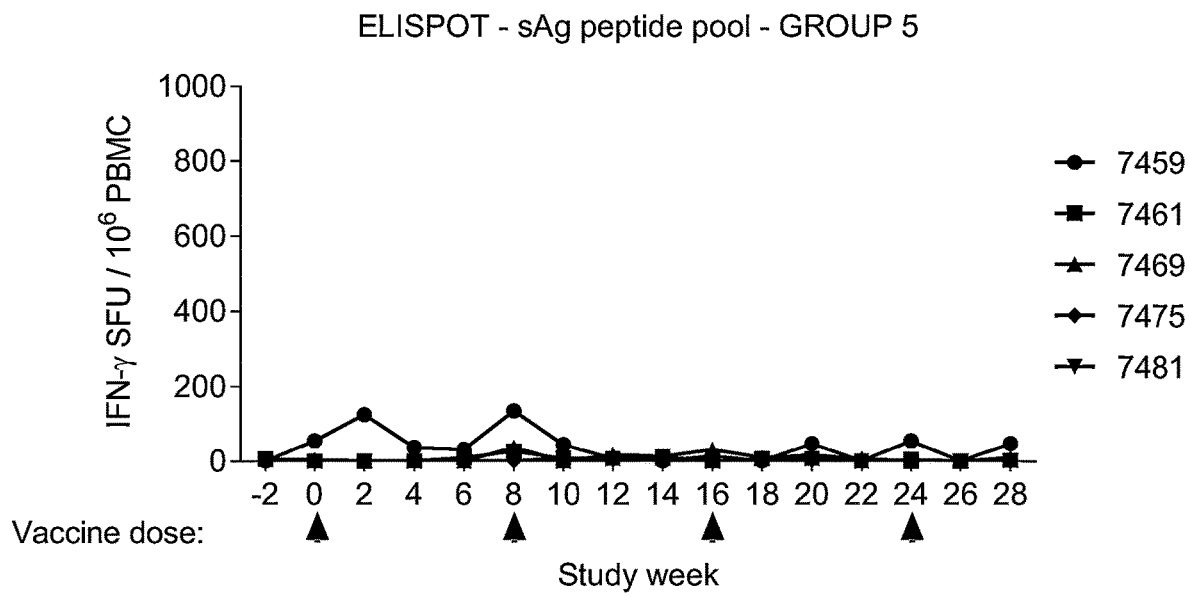
Figure 19F:
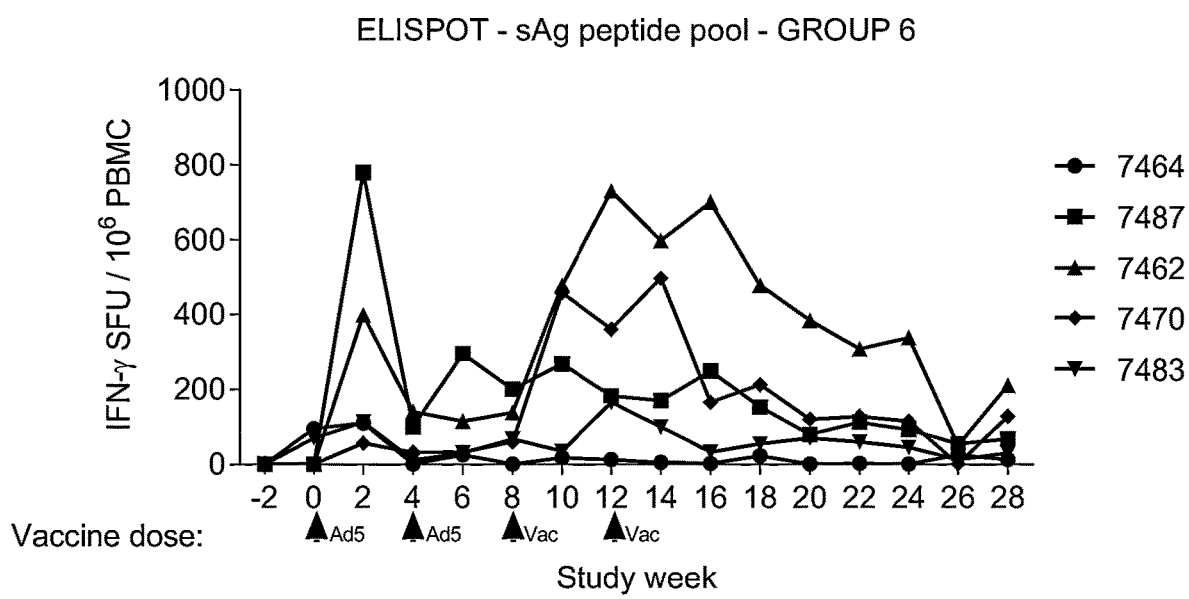
Figure 20A:
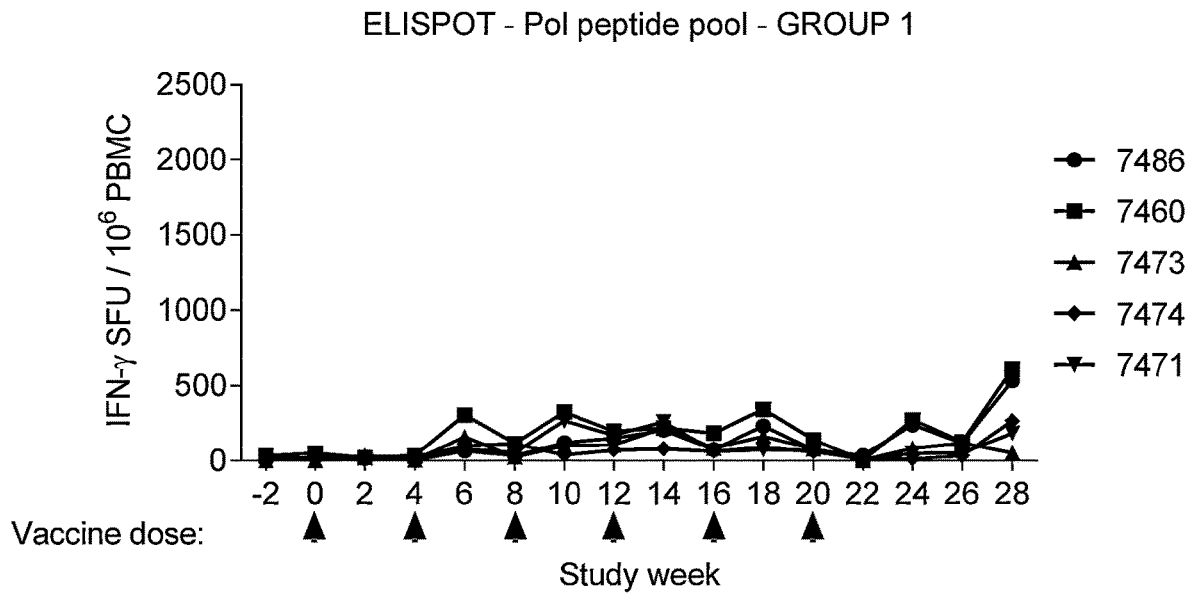
Figure 20B:
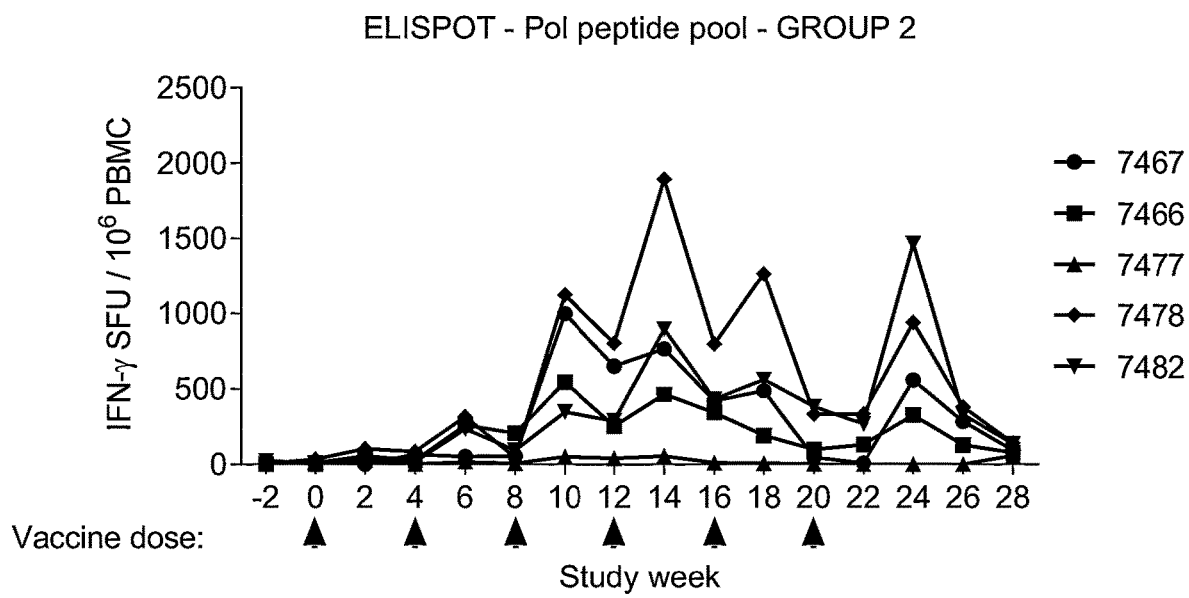
Figure 20C:
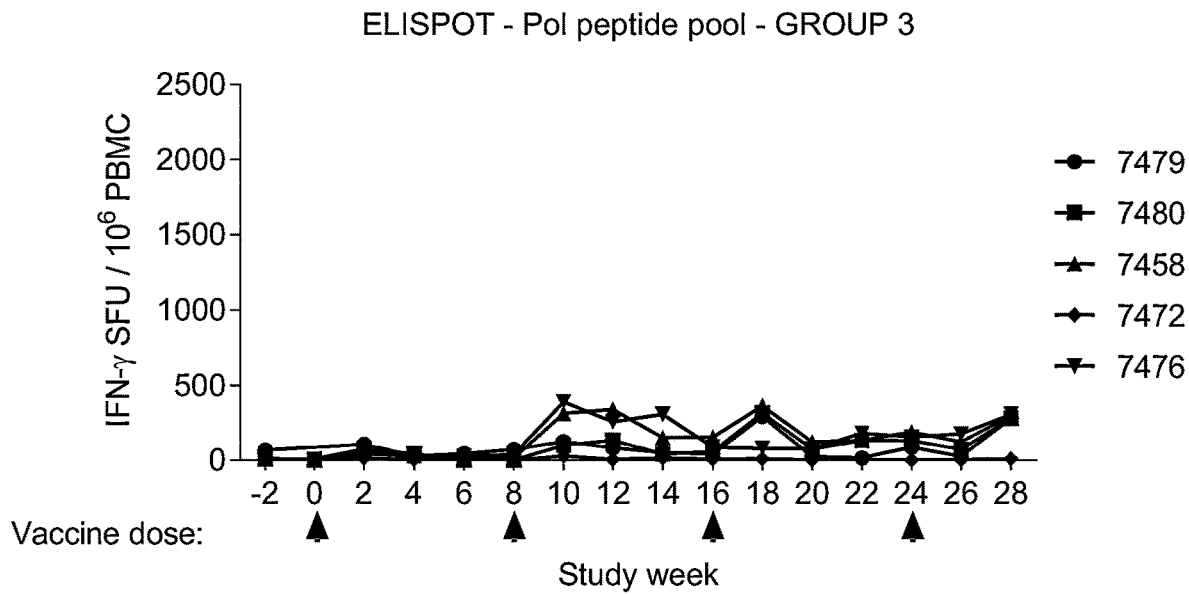
Figure 20D:
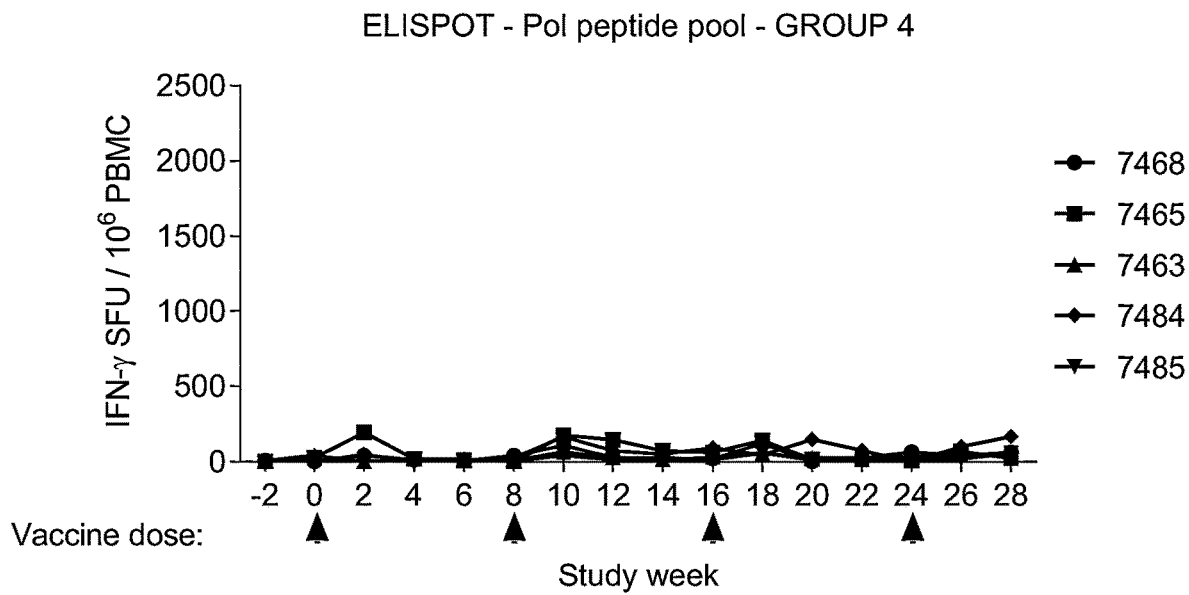
Figure 20E:
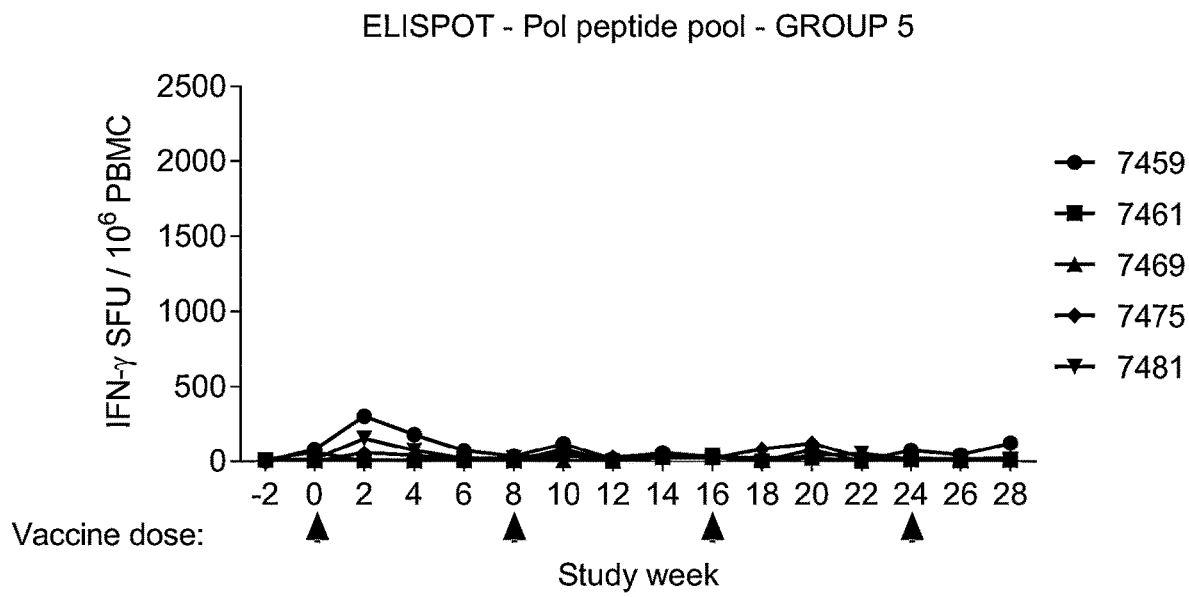
Figure 20F:
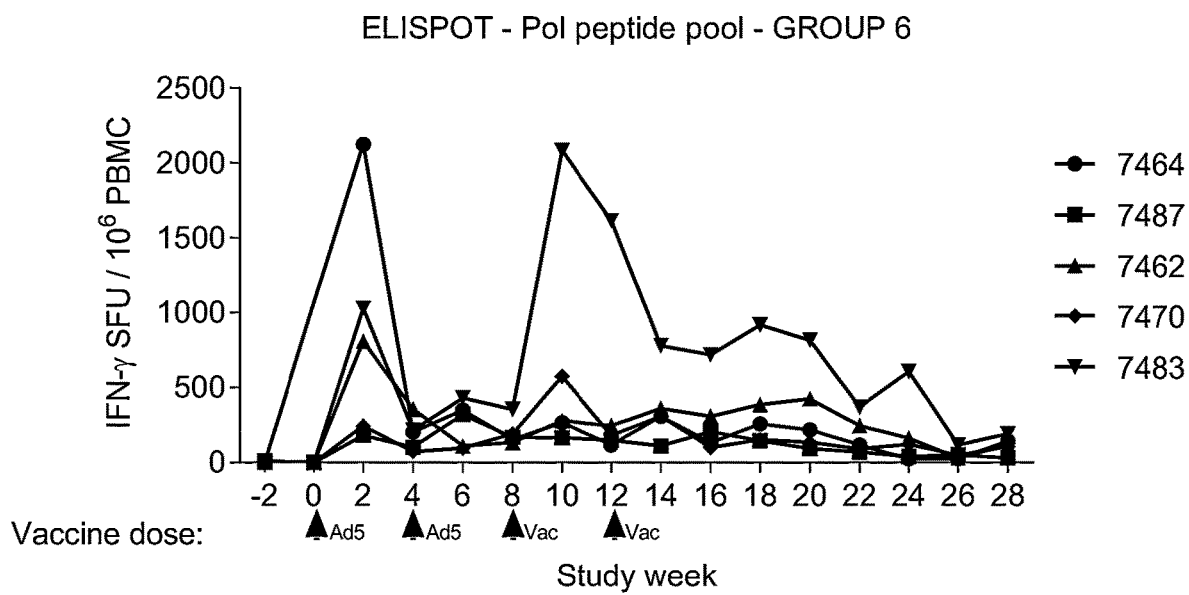
Figure 21A:
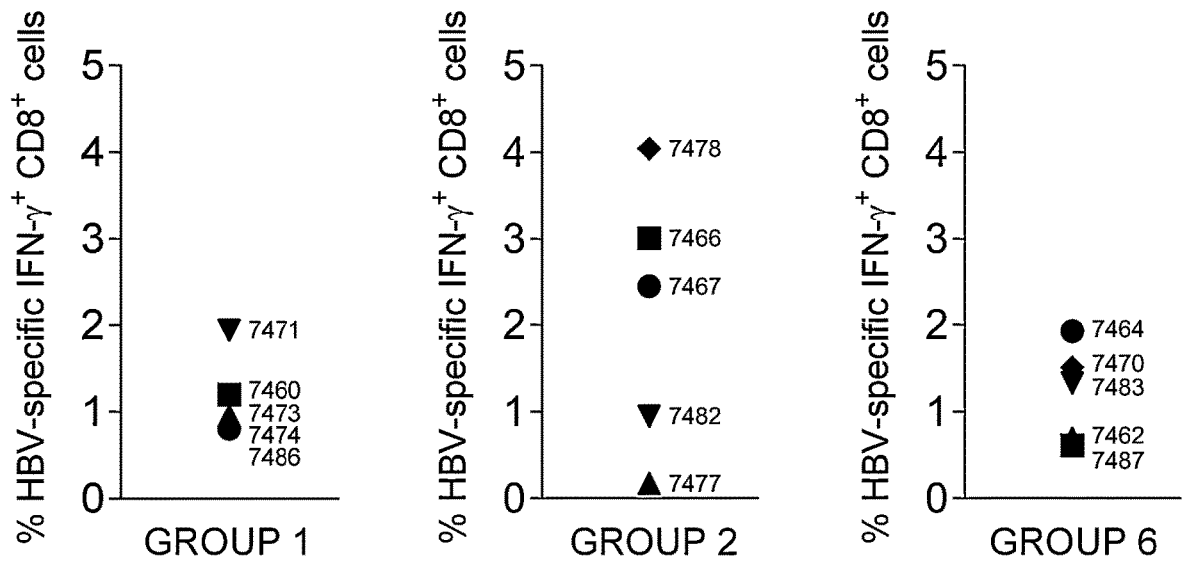
Figure 21B:
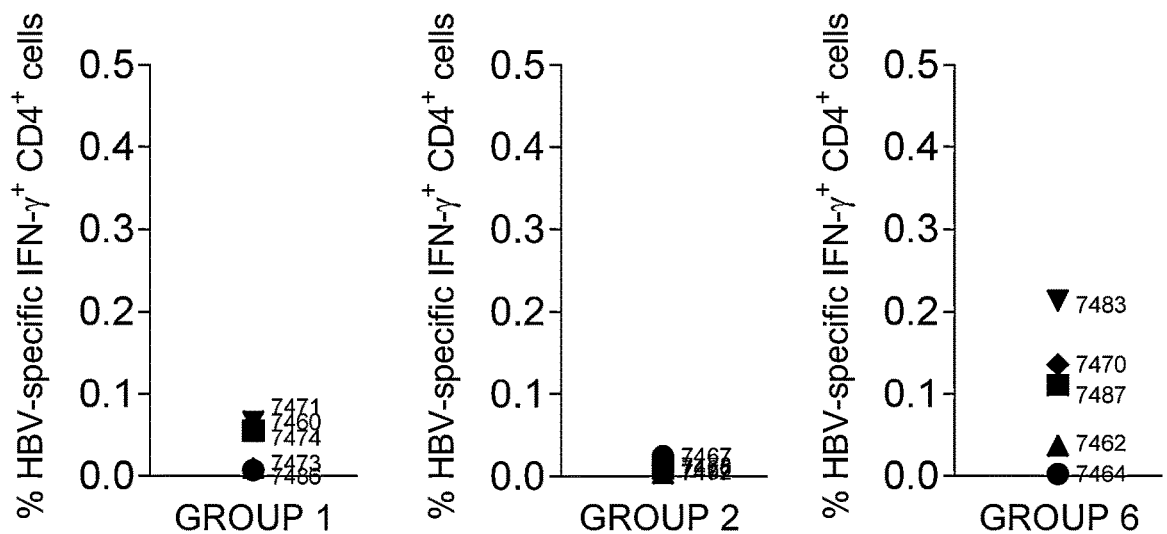

Consistent with data described above, vectors encoding GT-D iCore-P2A-sAg and GT-B Pol$^{300}$ induced T cells responses specific for sAg, core and Pol when administered as single vectors (FIGS. 16A-16C). Administration of the same vectors as a co-formulated mixture induced comparable T cell responses (FIGS. 16A-C). Thus, co-formulation of the LCMV vectors encoding GT-D iCore-P2A-sAg and GT-B $Pol^{300}$ does not interfere with their immunogenicity in C57BL/6 mice.

Example 11

Immunogenicity of Replication-Incompetent LCMV Vectors in Cynomolgus Macaques

We evaluated the immunogenicity of the replication-incompetent LCMV (VV1) vectors GT-D iCore-P2A-sAg and GT-B $Pol^{300}$ vectors in cynomolgus macaques. Ad5 and vaccinia vectors encoding for the core, sAg, and $Pol^{300}$ antigens were also tested.

Methods

Cynomolgus macaques were immunized using different routes, different doses and different immunization schedules as indicated in Table 11. HBV-specific T cell responses were measured using PBMC every 2 weeks by IFN-γ ELISPOT. Intracellular cytokine staining was also performed on CD4+ and CD8+ T cells at week 14 by flow cytometry. Anti-sAg antibody responses were quantified every 4 weeks by ELISA.

TABLE 11

Study Groups in Immunogenicity Study

| Group | N | Vaccine | Dose | Route | Immunization schedule (week) |
|---|---|---|---|---|---|
| 1 | 5 | VV1-GT-D iCore-P2A-sAg + VV1-GT-B $Pol^{300}$ | $5 \times 10^6$ FFU/vector | i.m. | Every 4 weeks: 0, 4, 8, 12, 16, 20 |
| 2 | 5 | | $10^8$ FFU/vector | i.m. | Every 4 weeks: 0, 4, 8, 12, 16, 20 |
| 3 | 5 | | $5 \times 10^6$ FFU/vector | i.m. | Every 8 weeks: 0, 8, 16, 24 |
| 4 | 5 | | $10^8$ FFU/vector | i.m. | Every 8 weeks: 0, 8, 16, 24 |
| 5 | 5 | | $10^8$ FFU/vector | i.v. | Every 8 weeks: 0, 8, 16, 24 |
| 6 | 5 | 1. Ad5-GT-D core-sAg + Ad5-GT-B $Pol^{300}$ (days 0 and 5)<br>2. Vaccinia GT-D core-sAg + Vaccinia GT-B $Pol^{300}$ (days 8 and 12) | $10^{11}$ vp/vector<br>$10^8$ PFU/vector | i.m. | 0 (Ad5), 4 (Ad5), 8 (Vac), 12 (Vac) |

Results

Total HBV-specific T cell responses (defined as the sum of core, sAg and polymerase-specific responses shown in FIGS. 18A-18F to 20A-20F) to the VV1 GT-D iCore-P2A-sAg and GT-B $Pol^{300}$ vectors were highest when administered via the intramuscular route (i.m.) and every 4 weeks (groups 1 and 2) (FIGS. 17A-B). Ad5 and vaccinia vectors encoding for the same antigens also induced comparable T cell responses. HBV-specific immune responses were detected after the first dose of VV1 GT-D iCore-P2A-sAg and GT-B $Pol^{300}$ vectors, and doses two through four induced progressive increases in the HBV-specific ELISPOT magnitude. The fifth and sixth doses did not further increase responses, indicating that the peak response to our vectors was reached after the fourth dose. The geometric mean response by week 14 was 1206 SFU/$10^6$ PBMC in animals administered the full human dose ($10^8$ FFU, Group 2), and approximately 2-fold lower at the lower dose $5\times10^6$ FFU (group 1) indicating dose-responsiveness.

To quantify the contribution of CD4+ and CD8+ T cells to the total T cell response, PBMCs from animals from group 1, 2 and 6 were analyzed by intracellular cytokine staining (ICS) on study week 14, when T cell responses were the highest. Both groups 1 and 2 had increased levels of IFN-γ+CD8+ T cells in response to stimulation with HBV peptides. The background-corrected frequency of these cells ranged from 0.8% to 1.9% in Group 1 and from 0.2% to 4% in Group 2 (FIG. 21A). In contrast, IFN-γ+CD4+ T cells specific for HBV were detectable but at less than 0.1% of total CD4+ T cells (FIG. 21B). Thus, the T cell response induced by our vectors in non-human primates is predominantly composed of CD8+ T cells.

Anti-HBsAg antibodies were also induced by dosing with our vectors. Anti-sAg responses increased with dose level and with repeated administration of the vectors (FIG. 22).

Example 12

Immunogenicity of Replication-Incompetent LCMV Vectors in Combination with Immunomodulators in C57BL/6 Mice We evaluated the immunogenicity of replication-incompetent LCMV (VV1) vectors GT-D iCore-P2A-sAg and GT-B Pol300 alone or in combination with various immunomodulators (anti-PD-1, anti-CTLA-4 and anti-CD137 and FLT3 ligand) in the AAV-HBV mouse model.

Methods

Figure 23:
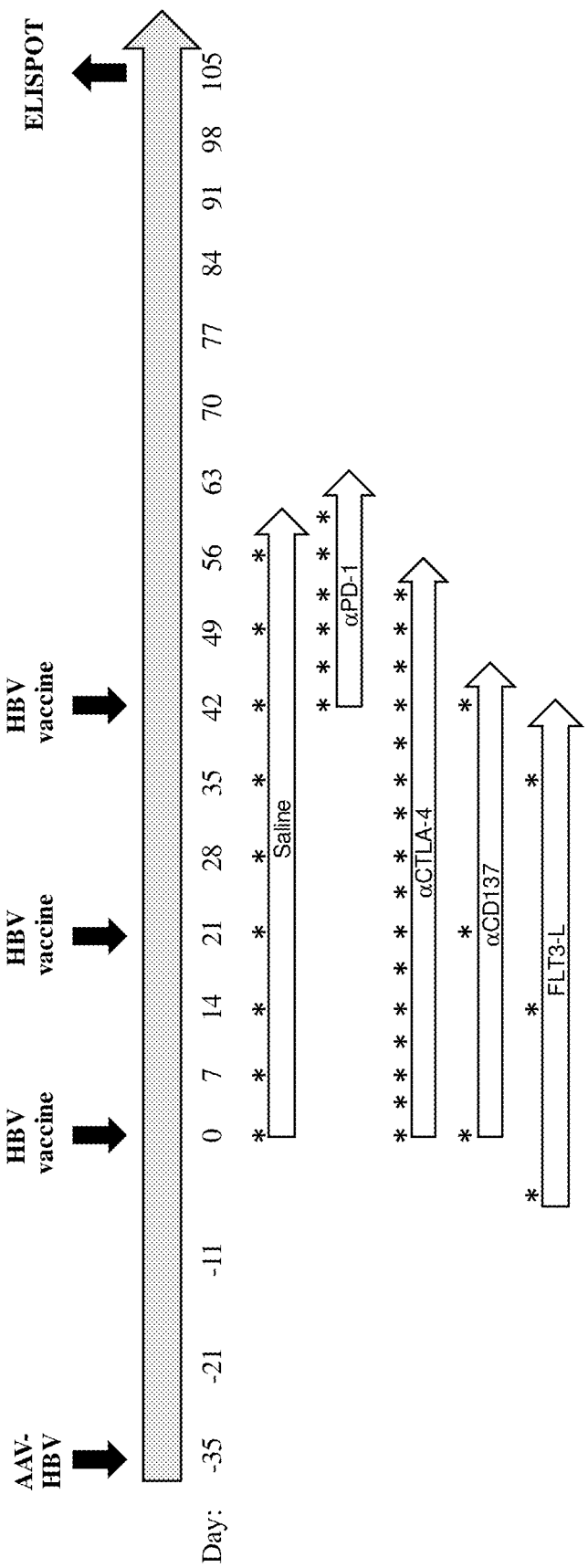

AAV-HBV C57BL/6 mice were administered 3 doses of VV1-GT-D iCore-P2A-sAg and GT-B Pol300 vectors at day 0, day 21 and day 42. Mice were also treated with saline, anti-mouse inhibitory PD-1 antibody, anti-mouse inhibitory CTLA-4 antibody, anti-mouse stimulatory CD137 antibody and mouse FLT3-L as indicated in Table 12 and FIG. 23. A control group of mice received the HBV vaccine alone but no AAV-HBV to determine how the immunogenicity of the HBV vaccine was affected in the context of chronic HBV. HBV-specific T cell responses were measured at day 105 post first vaccination by IFN-γ ELISPOT using splenocytes. Data are expressed after subtraction of background signal in no-peptide control wells. Serum levels of HBeAg were measured at day −11 and day 105 by ELISA.

TABLE 12

Study Groups in AAV-HBV Immunogenicity Study

| Group | N | AAV-HBV | HBV Vaccine | Immuno-modulator | Molecule and Dose |
|---|---|---|---|---|---|
| 1 | 11 | Yes | VV1-GT-D iCore-P2A-sAg + VV1-GT-B Pol300 | Vehicle | Saline |
| 2 | 12 | Yes | | α-PD-1 | Clone RMP1-14 8 mg/kg/dose |
| 3 | 12 | Yes | | α-CTLA4 | Clone 9D9 10 mg/kg/dose |
| 4 | 12 | Yes | | α-CD137 | Clone mAb8 2.5 mg/kg/dose |
| 5 | 12 | Yes | | FLT3L | Murine FLT3L-Fc 1 mg/kg/dose |
| 6 | 5 | No | | Vehicle | Saline |

Figure 24A:
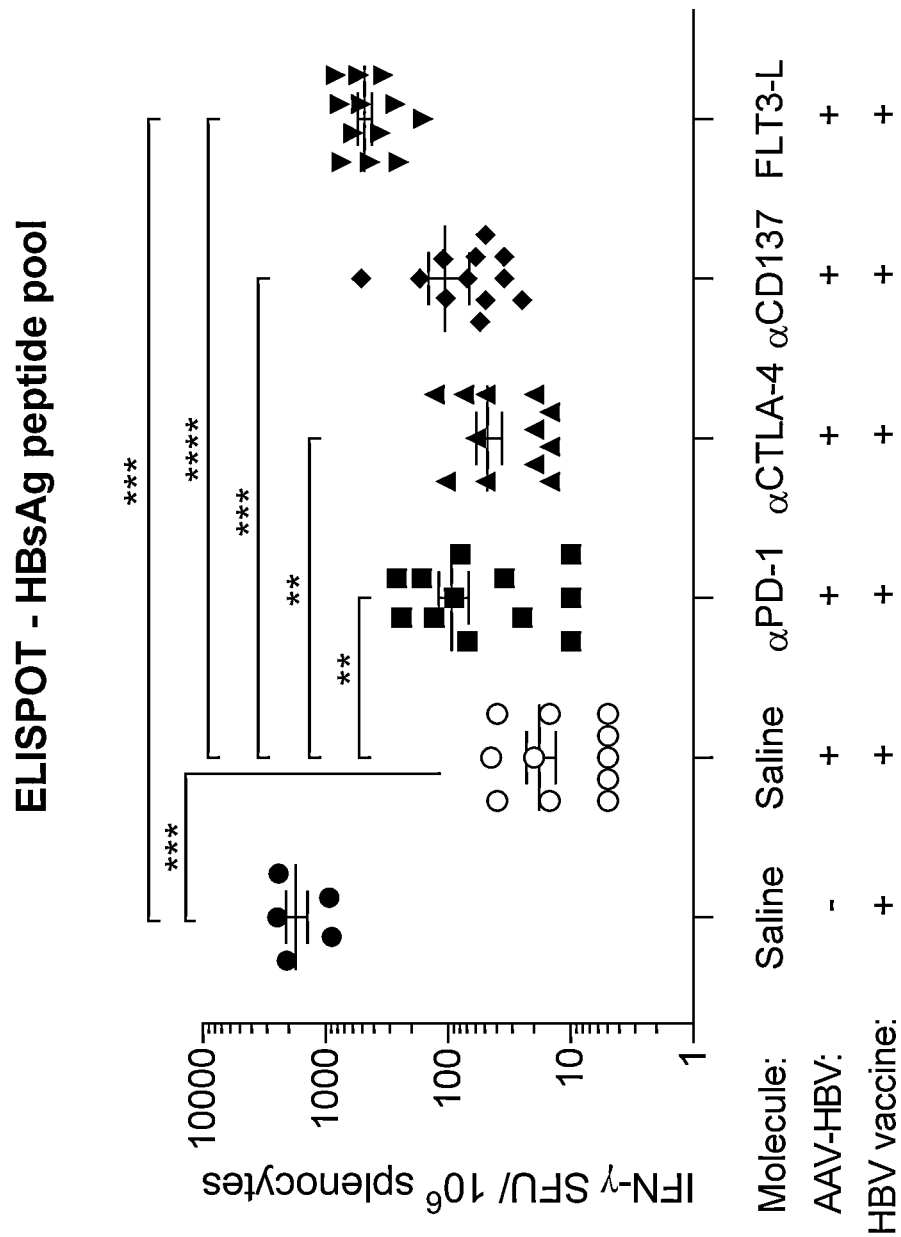
Figure 24B:
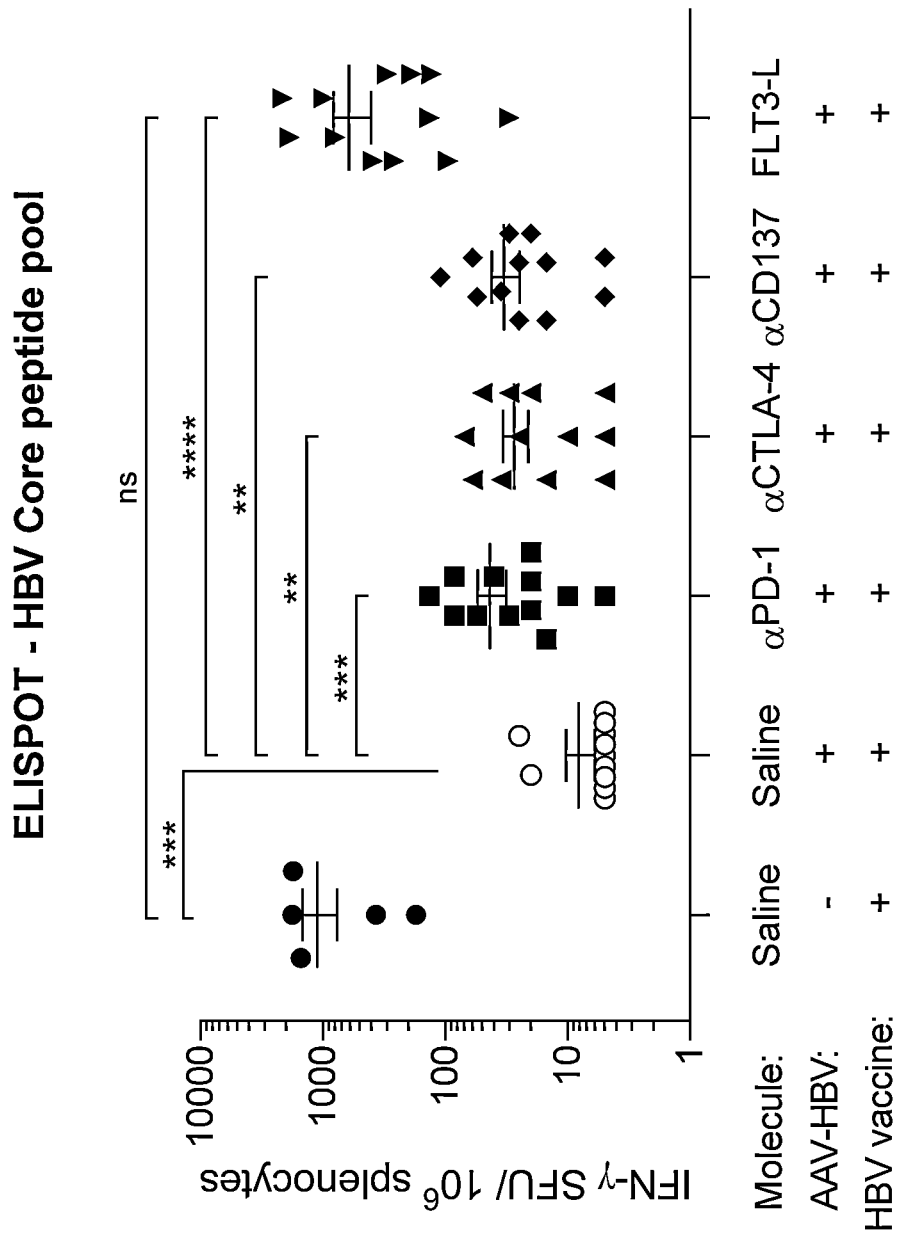
Figure 24C:
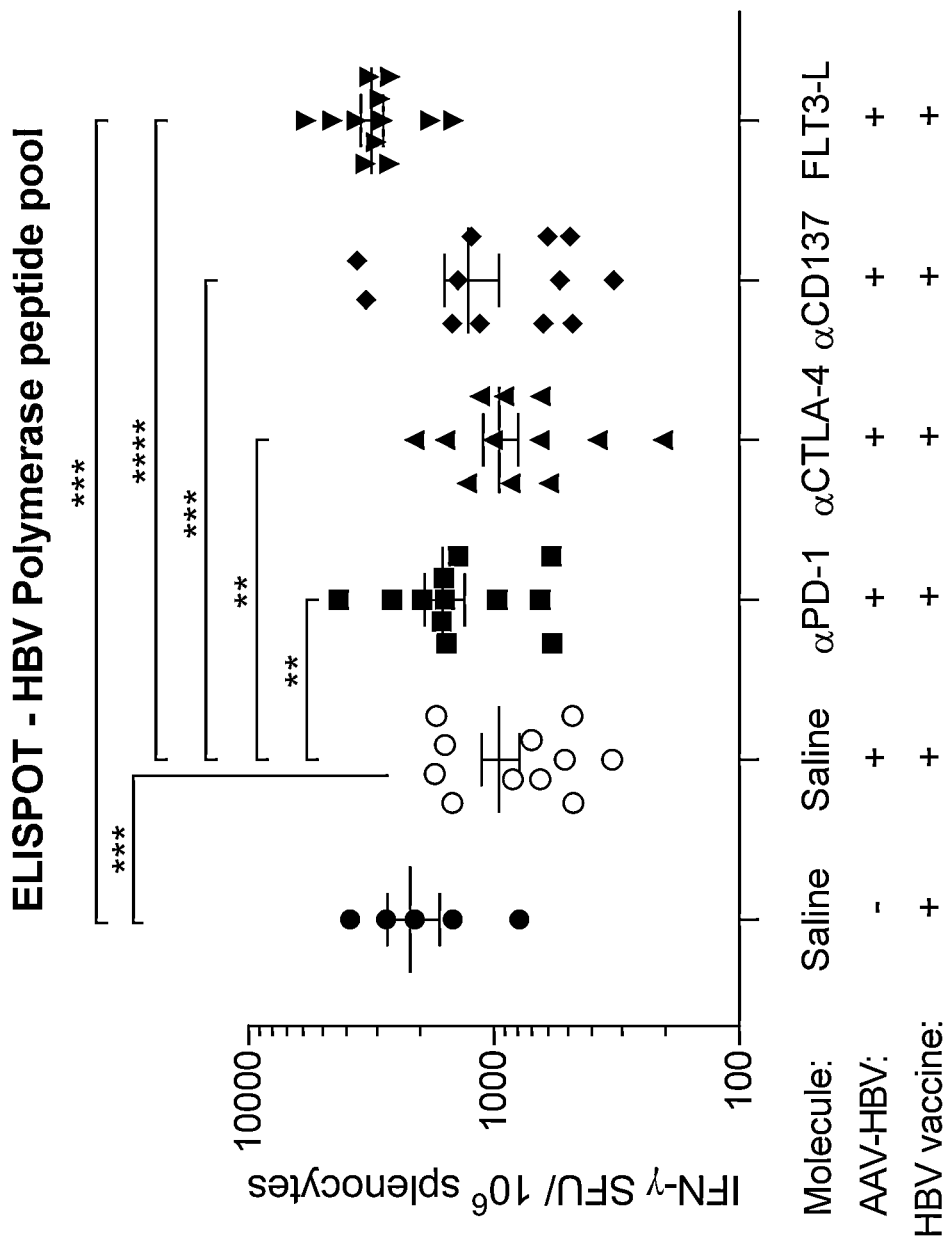

Robust IFN-γ ELISPOT responses were observed for all 3 HBV antigens in mice in the absence of persistent HBV (FIG. 24). The IFN-γ ELISPOT responses obtained from AAV-HBV mice that received the HBV vaccine alone were reduced but still present, demonstrating that VV1 GT-D iCore-P2A-sAg and GT-B Pol300 were immunogenic even in the context of an immune system tolerized to HBV. Combined administration of VV1 GT-D iCore-P2A-sAg and GT-B Pol300 with anti-PD-1, anti-CTLA-4 or anti-CD137 antibodies further improved the HBV-specific IFN-γ ELISPOT responses to core and sAg, while combination of VV1 GT-D iCore-P2A-sAg and GT-B Pol300 with FLT3-L gave the highest ELISPOT magnitude for all 3 HBV antigens.

In addition, administration of VV1 GT-D iCore-P2A-sAg and GT-B Pol300 reduced the serum levels of HBeAg in those AAV-HBV mice as measured at baseline day −11 and at day 105 (Table 13). Importantly, combined administration of VV1 GT-D iCore-P2A-sAg and GT-B Pol300 vectors with anti-PD-1, anti-CTLA-4, anti-CD137 antibodies or FTL3-L further reduced the serum levels of HBeAg (Table 13). Thus, VV1 GT-D iCore-P2A-sAg and GT-B Pol300 vectors show antiviral efficacy in the AAV-HBV mouse model which can be enhanced in combination with some immunomodulators.

TABLE 13

Overview Table of Serum HBeAg Levels in AAV-HBV Mice

| Group | Serum HBeAg Level (geometric mean, ng/mL) Day −11 | Serum HBeAg Level (geometric mean, ng/mL) Day 105 | Animals with serum HBeAg <100 ng/mL at day 105 |
|---|---|---|---|
| HBV vaccine + saline | 868 | 528 | 0/11 |
| HBV vaccine + α-PD-1 | 879 | 337 | 3/12 |
| HBV vaccine + α-CTLA4 | 661 | 341 | 2/12 |
| HBV vaccine + α-CD137 | 1069 | 500 | 1/12 |
| HBV vaccine + FLT3L-Fc | 773 | 315 | 3/12 |

Example 13

Identification of Replication-Incompetent Pichinde (PICV) Vectors Encoding Immunogenic Nucleotide-optimized HBV Antigens We generated replication-incompetent PICV (VV2) vectors encoding the GT-D core-P2A-sAg antigen (SEQ ID NO: 41) and the GT-B Pol300 antigen (SEQ ID NO: 13), initially using the same nucleotide sequences identified to be stable and immunogenic in the replication-incompetent LCMV (VV1) vectors. The stability of the iCore-P2A-sAg transgene in VV2 vectors (SEQ ID NO: 37) was evaluated by PCR after serial passaging of vector containing supernatant and found to be sufficiently stable for manufacture (Table 13). Genetic stability was defined by the major band showing at the correct size of the full-length transgene (TG).

In contrast, when the same GT-B $Pol^{300}$ transgene used in the VV1 vectors (SEQ ID NO: 29) was used in VV2 vectors, the transgene rapidly became unstable during serial passage (Table 14). To identify VV2 vectors with sufficient genetic stability for manufacturing, we generated three additional VV2 vectors encoding the same GT-B $Pol^{300}$ antigen using different nucleotide sequences, designated VV2-Pol300_IDT_CpGdel (SEQ ID NO: 94), $Pol^{300}$ ori (SEQ ID NO: 89), and $Pol^{300}$ dint (SEQ ID NO: 90), Pol300 huCo low GC (SEQ ID NO: 91), and Pol300 oridel CpG (SEQ ID NO: 92). Each vector was evaluated for transgene stability by PCR after serial passaging of vector containing supernatant, with genetic stability defined by the major band showing at the correct size of the full-length transgene (TG). Results are shown in Table 14. Surprisingly, major differences in the stability of $Pol^{300}$ transgenes in VV2 vectors were evident between the different nucleotide sequences despite encoding the identical polypeptide antigen, with $Pol^{300}$ dint, $Pol^{300}$ ori, and $Pol^{300}$ oridel CpG polynucleotide sequences demonstrating the greatest stability, e.g., at least through five passages.

TABLE 14

Overview Table for Assessment of Genetic Stability of
VV2-Core-P2A-sAg and Pol300 Transgenes

| Genotype | Nucleic acid SEQ ID NO: | Vector | Stable TG insertion until |
|---|---|---|---|
| GT-D | 37 | VV2-iCore-P2A-sAg | P5 |
| GT-B | 29 | VV2-Pol$^{300}$ | P1 |
| GT-B | 94 | VV2-Pol300_IDT_CpGdel | P3 |
| GT-B | 91 | VV2-Pol$^{300}$ huCo lowGC | P4 |
| GT-B | 89 | VV2-Pol$^{300}$ ori | P5 |
| GT-B | 92 | VV2-Pol$^{300}$ oridel CpG | P5 |
| GT-B | 90 | VV2-Pol$^{300}$ dint | P5 |

*VV2 refers to replication-incompetent PICV vectors.
"P#" indicates the number of passages (e.g., P1 equals 1 passage).

Figure 25:
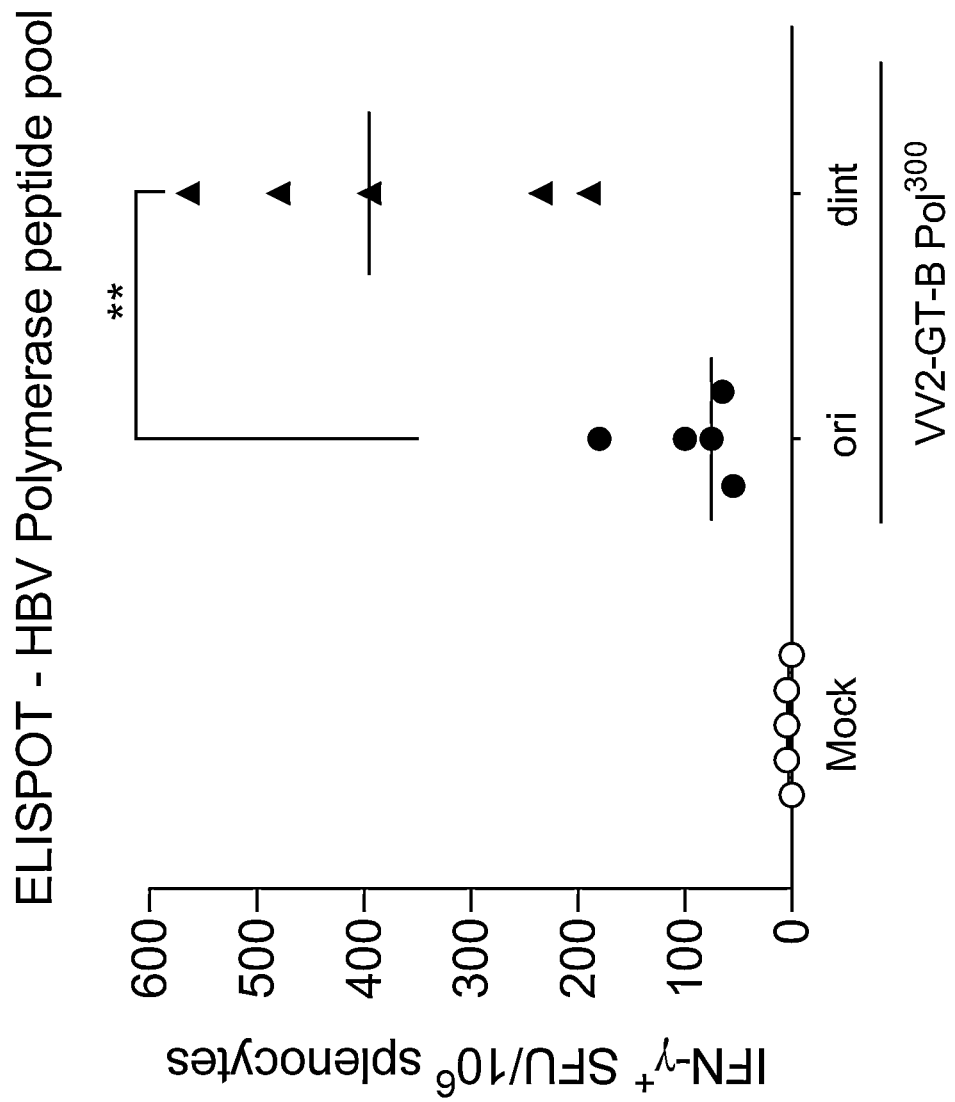

Next, to assess potential differences in immunogenicity between vectors carrying the Pol$^{300}$ dint and Pol$^{300}$ oi transgenes, C57BL/6 mice were immunized twice at day 0 and day 21 with replication-incompetent PICV (VV2) vectors encoding GT-B Pol$^{300}$ oi or GT-B Pol$^{300}$ dint. HBV-specific T cell responses were then measured from splenocytes by IFN-γ ELISPOT using Pol peptide pools. Surprisingly, VV2-GT-B Pol$^{300}$ dint induced a much stronger T cell response than VV2-GT-B Pol$^{300}$ oi despite encoding identical amino acid sequences (FIG. 25). Thus, VV2-GT-B Pol$^{300}$ dint is more immunogenic than VV2-GT-B Pol$^{300}$ oi in C57BL/6 mice.

Example 14

Immunogenicity of Replication-Incompetent LCMV and PICV Arenavirus Vectors Using Homologous or Heterologous Prime-Boost Immunization Regimens in C57BL/6 Mice We evaluated the immunogenicity of replication-incompetent LCMV (VV1) and PICV (VV2) vectors encoding GT-D iCore-P2A-sAg and GT-B Pol$^{300}$ using homologous prime/boost (VV1 vector followed by VV1 vector) or heterologous prime-boost (VV2 vector followed by VV1 vector) immunization regimens in C57BL/6 mice.
Methods
C57BL/6 mice were immunized twice with replication-incompetent LCMV and PICV vectors encoding GT-D iCore-P2A-sAg and GT-B Pol$^{300}$ as indicated in Table 15. HBV-specific T cell responses were measured at day 28 by IFN-γ ELISPOT using splenocytes. Anti-sAg antibody responses were quantified at day 28 by ELISA.

TABLE 15

Study Groups in Immunogenicity Study

| Group | N | Immunization Regimen | Prime vector Day 0 | Boost vector Day 21 | Harvest Day | Dose/ vector |
|---|---|---|---|---|---|---|
| 1 | 5 | — | Mock | Mock | 28 | 10$^6$ FFU |
| 2 | 5 | Homologous Prime/Boost | VV1-GT-D iCore-P2A-sAg | VV1-GT-D iCore-P2A-sAg | 28 | 10$^6$ FFU |
| 3 | 5 | Heterologous Prime/Boost | VV2-GT-D iCore-P2A-sAg | VV1-GT-D iCore-P2A-sAg | 28 | 10$^6$ FFU |
| 4 | 5 | Homologous Prime/Boost | VV1-GT-B Pol$^{300}$ | VV1-GT-B Pol$^{300}$ | 28 | 10$^6$ FFU |
| 5 | 5 | Heterologous Prime/Boost | VV2-GT-B Pol$^{300}$ dint | VV1-GT-B Pol$^{300}$ | 28 | 10$^6$ FFU |

Figure 26A:
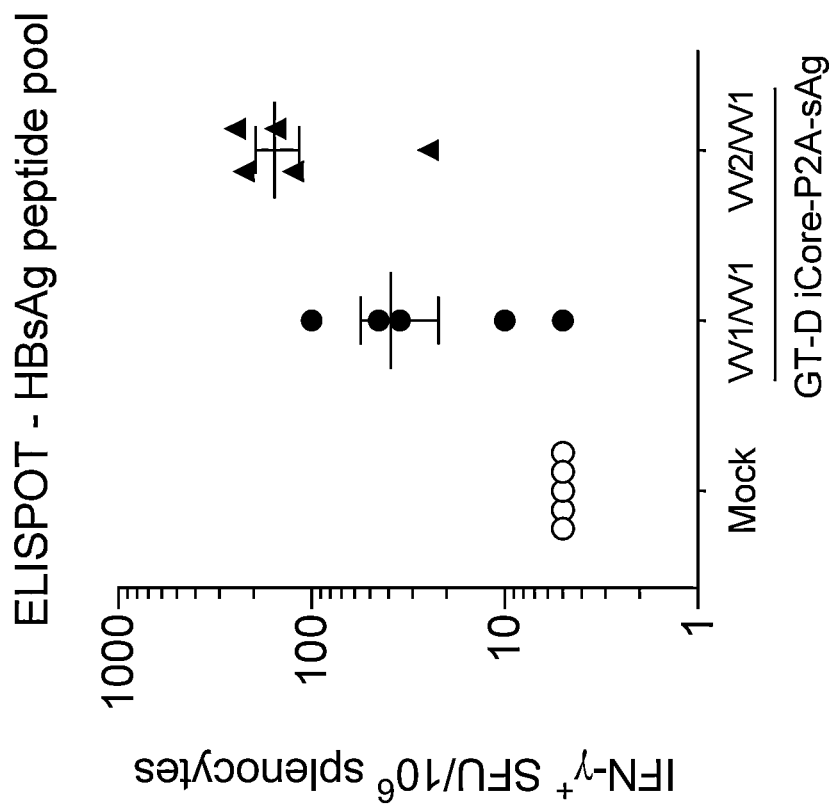
Figure 26B:
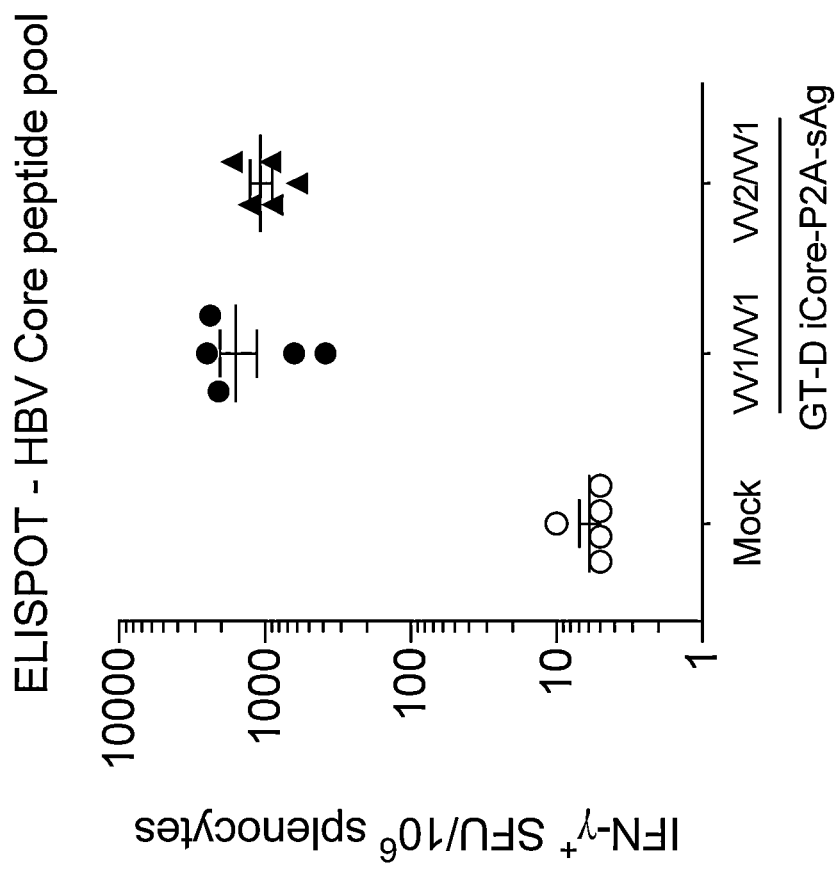
Figure 26C:
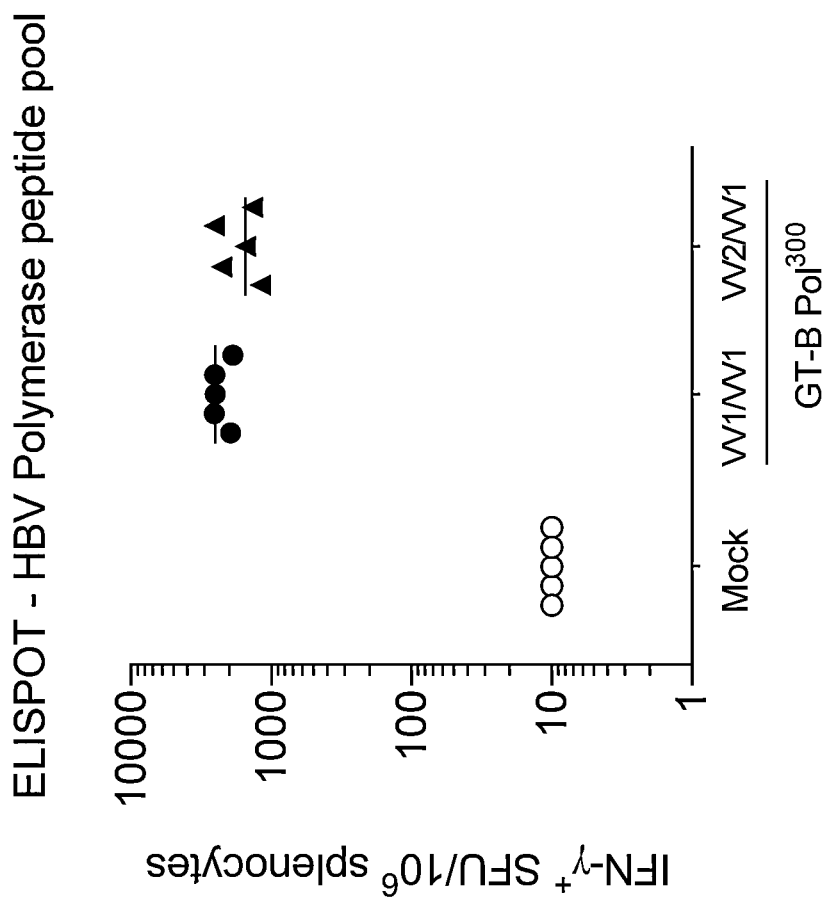
Figure 27:
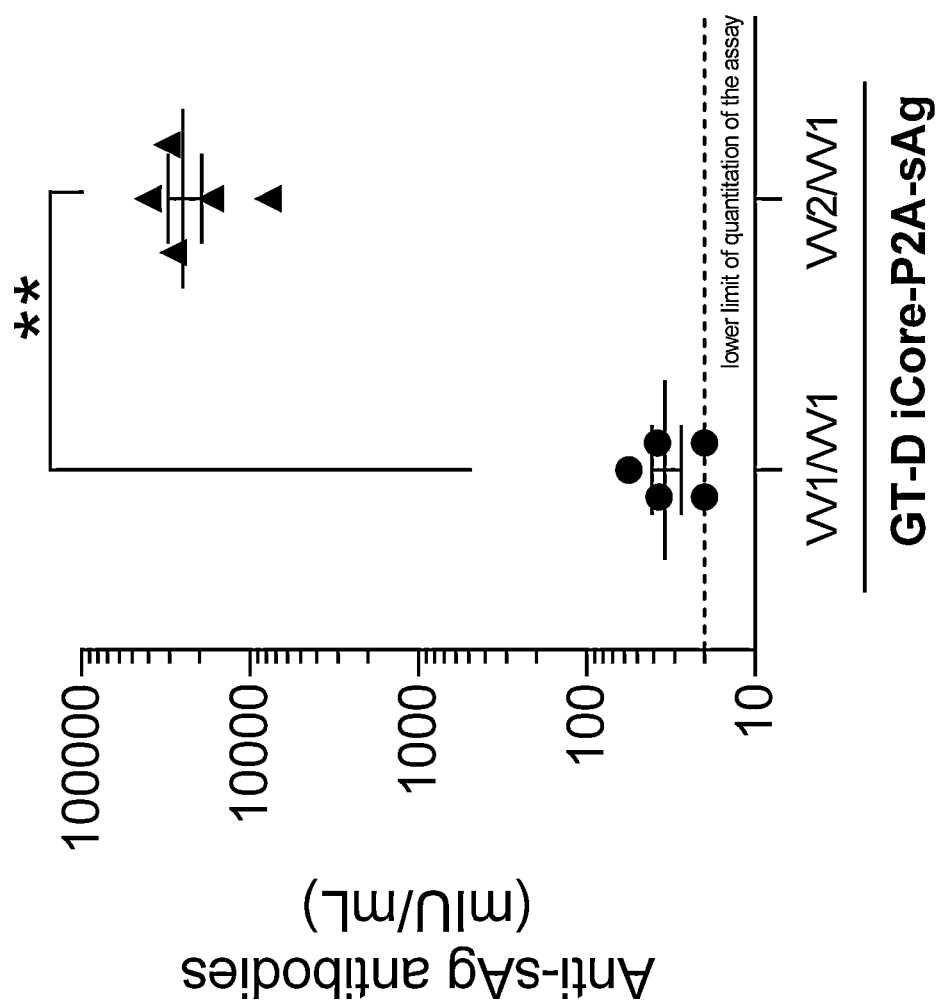
Figure 28A:
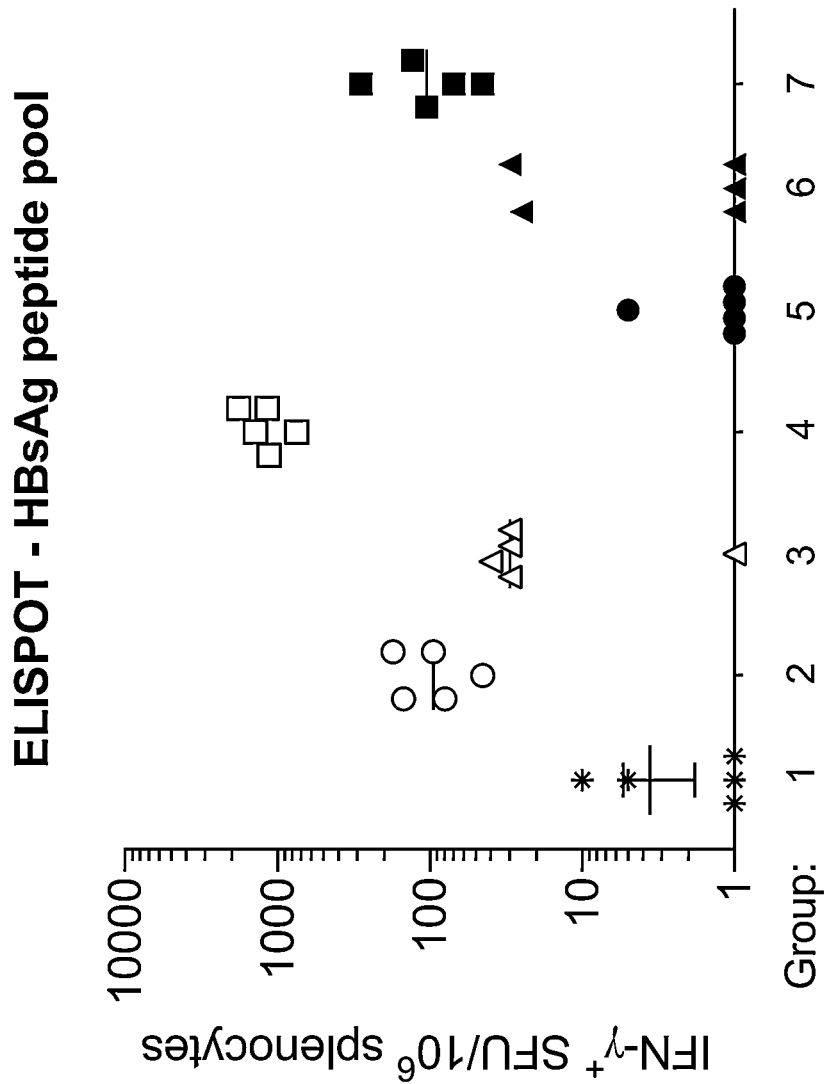
Figure 28B:
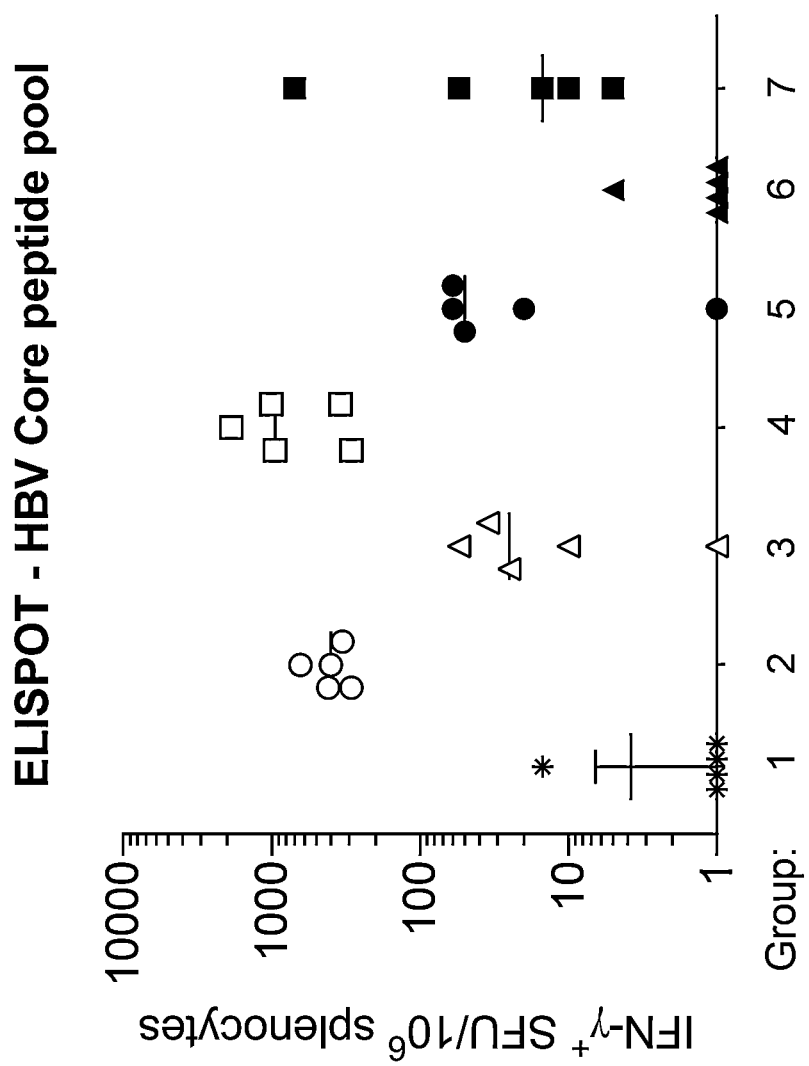
Figure 28C:
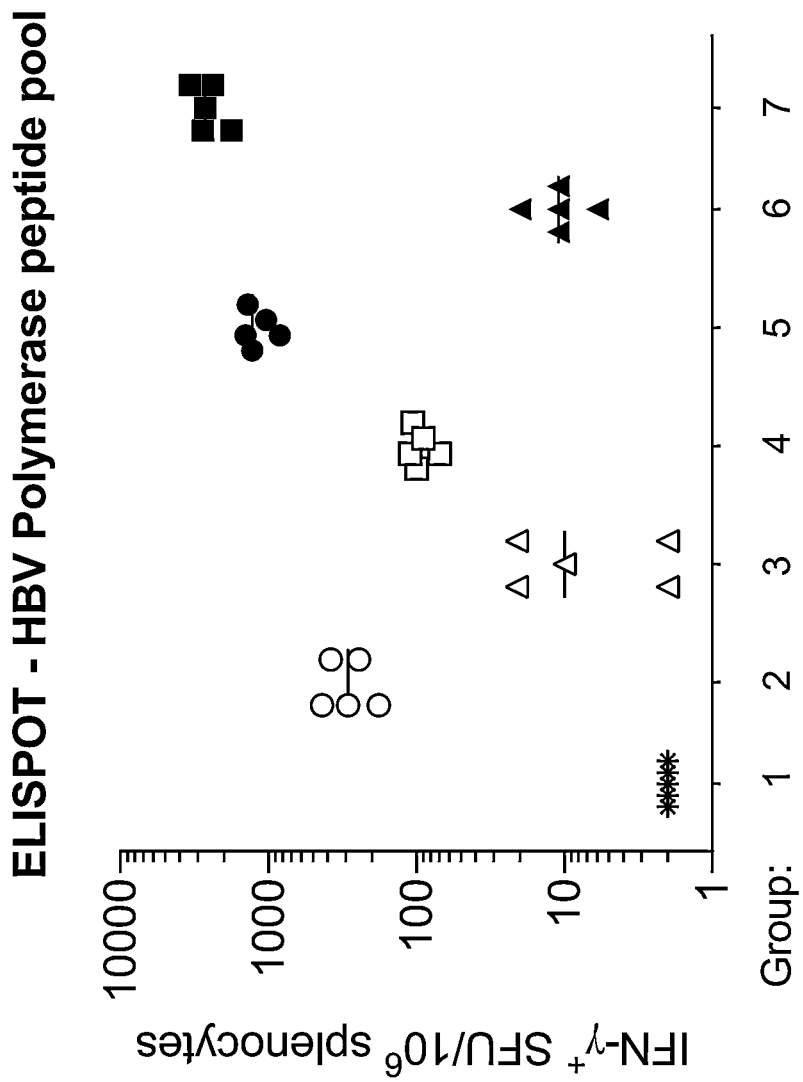
Figure 29:
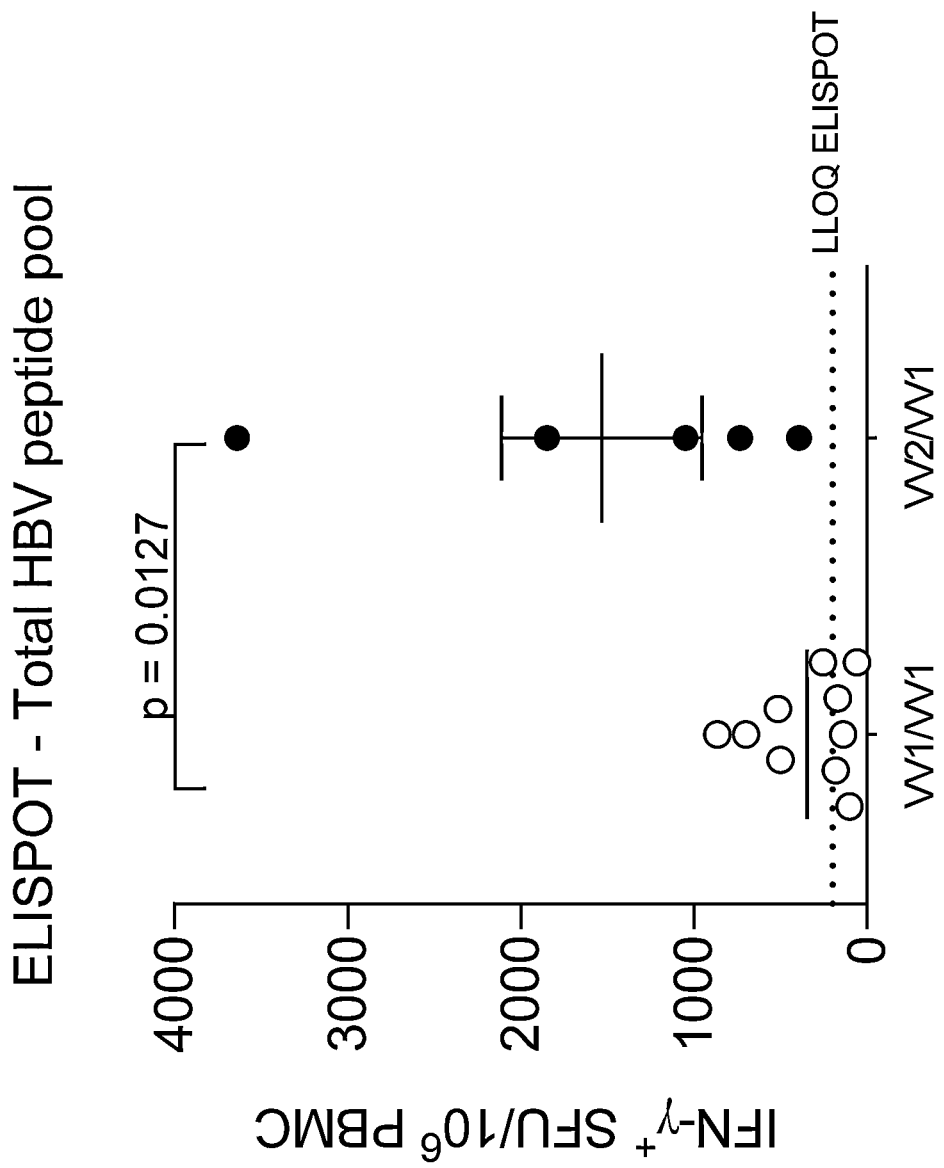

Results
Administration of the replication-incompetent LCMV vector (VV1) encoding GT-D iCore-P2A-sAg or encoding GT-B Pol$^{300}$ using a homologous prime/boost regimen (VV1/VV1) induced robust T cell responses in C57BL/6 mice (FIGS. 26A-C). Administration of the replication-incompetent PICV vector (VV2) followed by the administration of VV1 (heterologous prime-boost regimen VV2/VV1) yielded greater sAg-specific T cell response (FIG. 26A) and similar core and Pol-specific T cell responses (FIGS. 26B-26C) compared to the VV1/VV1 regimen. Furthermore, while administration of the replication-incompetent LCMV vector using a homologous prime/boost regimen (VV1/VV1) inconsistently induced anti-sAg antibodies at low levels, immunization using the heterologous prime/boost regimen (VV2/VV1) unexpectedly led to robust and consistent induction of anti-sAg antibodies in all animals and an approximately 1000-fold increase in the average anti-sAg antibody titer (FIG. 27).

Example 15

Immunogenicity of Replication-Attenuated LCMV and PICV Arenavirus Vectors Using Homologous or Heterologous Prime-Boost Immunization Regimens in C57BL/6 Mice In addition to the replication-incompetent arenavirus vectors LCMV (VV1) and PICV (VV2), replication-competent but attenuated vectors LCMV (TT1) and PICV (TT2) encoding HBV antigens can also be engineered. Unlike VV1 and VV2 vectors, TT1 and TT2 vectors contain three genomic segments allowing genomic space to insert the two HBV antigens (the fusion protein GT-D core-P2A-sAg and the protein GT-B Pol$^{300}$) into the same vector. Because each antigen can be inserted into two different genomic segments, vectors covering the different combinations of insertion within both arenavirus vectors were generated as follows: i) GT-D core-P2A-sAg inserted into segment 1 and GT-B Pol$^{300}$ inserted into segment 2 into the LCMV backbone (TT1-GT-D core-P2A-sAg/GT-B Pol$^{300}$), ii) GT-D core-P2A-sAg inserted into segment 1 and GT-B Pol$^{300}$ inserted into segment 2 into the PICV backbone (TT2-GT-D core-P2A-sAg/GT-B Pol$^{300}$), iii) GT-D core-P2A-sAg inserted into segment 2 and GT-B Pol$^{300}$ inserted into segment 1 into the LCMV backbone (TT1-GT-B Pol$^{300}$/GT-D core-P2A-sAg) and iv) GT-D core-P2A-sAg inserted into segment 2 and GT-B Pol$^{300}$ inserted into segment 1 into the PICV backbone (TT2-GT-B Pol$^{300}$/GT-D core-P2A-sAg). We next evaluated the immunogenicity of these 4 vectors using homologous or heterologous prime-boost immunization regimens in C57BL/6 mice.

Methods

C57BL/6 mice were immunized twice with replication-attenuated LCMV and PICV vectors encoding GT-D Core-P2A-sAg and GT-B $Pol^{300}$ as indicated in Table 16. HBV-specific T cell responses were measured at day 28 by IFN-γ ELISPOT using splenocytes.

TABLE 16

Study Groups in Immunogenicity Study

Figure 30:
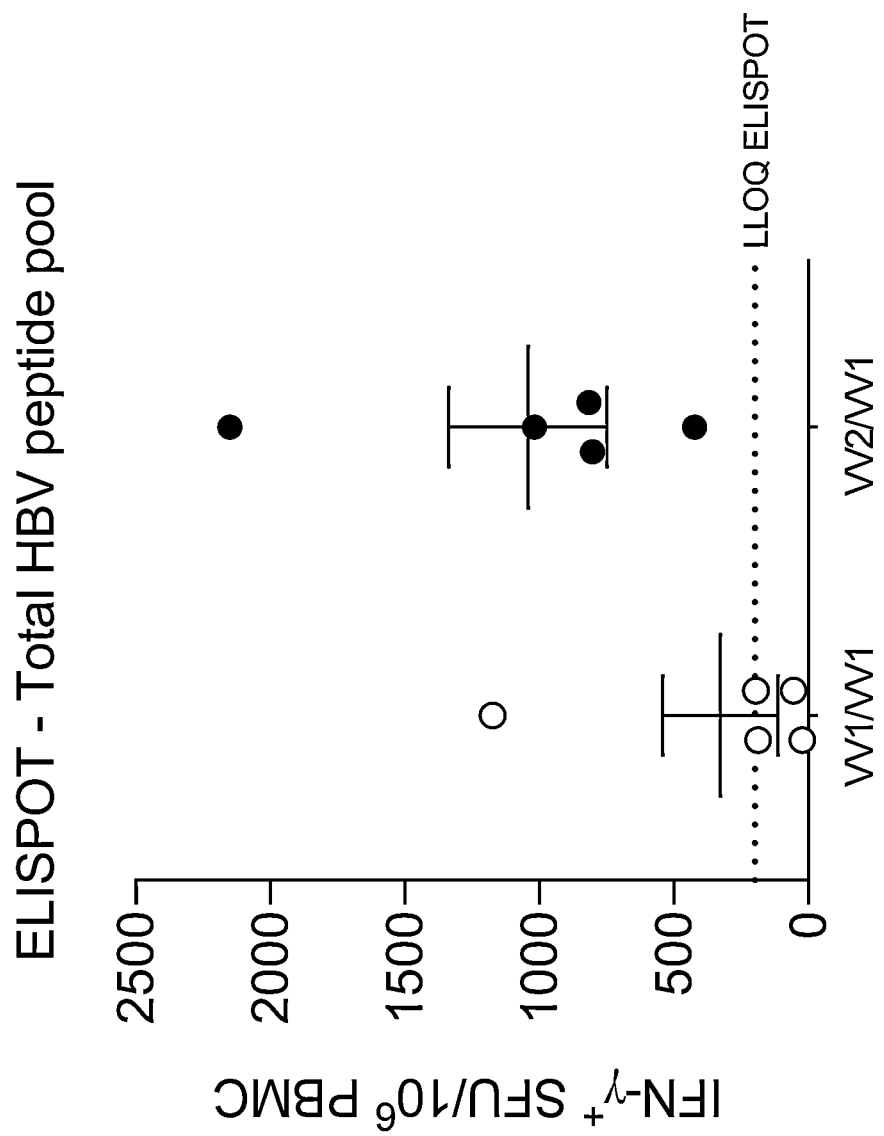

| Group | N | Prime vector Day 0 | Boost vector Day 21 | Harvest Day | Dose/vector (RCV/FFU) |
|---|---|---|---|---|---|
| 1 | 5 | Mock | Mock | 28 | — |
| 2 | 5 | TT1-GT-D core-P2A-sAg/ GT-B $Pol^{300}$ | TT1-GT-D core-P2A-sAg/ GT-B $Pol^{300}$ | 28 | $5 \times 10^4$ |
| 3 | 5 | TT2-GT-D core-P2A-sAg/ GT-B $Pol^{300}$ | TT2-GT-D core-P2A-sAg/ GT-B $Pol^{300}$ | 28 | $5 \times 10^4$ |
| 4 | 5 | TT2-GT-D core-P2A-sAg/ GT-B $Pol^{300}$ | TT1-GT-D core-P2A-sAg/ GT-B $Pol^{300}$ | 28 | $5 \times 10^4$ |
| 5 | 5 | TT1-GT-B $Pol^{300}$/ GT-D core-P2A-sAg | TT1-GT-B $Pol^{300}$/ GT-D core-P2A-sAg | 28 | $5 \times 10^4$ |
| 6 | 5 | TT2-GT-B $Pol^{300}$/ GT-D core-P2A-sAg | TT2-GT-B $Pol^{300}$/ GT-D core-P2A-sAg | 28 | $5 \times 10^4$ |
| 7 | 5 | TT2-GT-B $Pol^{300}$/ GT-D core-P2A-sAg | TT1-GT-B $Pol^{300}$/ GT-D core-P2A-sAg | 28 | $5 \times 10^4$ |

Results

Administration of all replication-competent vectors resulted in robust T cells responses specific for the 3 HBV antigens sAg, core and Pol (FIGS. 28A-28C). Thus, TT1 and TT2 vectors expressing HBV antigens are strongly immunogenic in C57BL/6 mice.

Example 16

Immunogenicity of Replication-Incompetent LCMV and PICV Arenavirus Vectors Using Homologous or Heterologous Prime-Boost Immunization Regimens in Cynomolgus Macaques We evaluated the immunogenicity of replication-incompetent LCMV (VV1) and PICV (VV2) vectors encoding GT-D iCore-P2A-sAg and GT-B Pol300 using homologous prime/boost (VV1 vector followed by VV1 vector) or heterologous prime-boost (VV2 vector followed by VV1 vector) immunization regimens in cynomolgus macaques.

Methods

Cynomolgus macaques (n=5) were immunized with VV2 vectors ($5\times10^6$ FFU/vector) at week 0 and then immunized with VV1 vectors ($5\times10^6$ FFU/vector) at week 4, and HBV-specific T cell responses were measured using PBMC by IFN-γ ELISPOT at week 6. Data were compared to ELISPOTs from 10 cynomolgus macaques immunized with VV1 vectors only ($5\times10^6$ FFU/vector) at both week 0 and week 4 (homologous prime boost regimen).

Results

Administration of the replication-incompetent LCMV vectors (VV1) encoding GT-D iCore-P2A-sAg and GT-B Pol300 using a homologous prime/boost regimen (VV1/VV1) induced HBV-specific T cell responses in 5 out of 10 cynomolgus macaques (FIG. 29). In contrast, administration of the replication-incompetent PICV vector (VV2) followed by VV1 (heterologous prime/boost regimen VV2/VV1) yielded statistically greater HBV-specific T cell responses in all 5 animals compared to the VV1/VV1 homologous prime boot regimen (FIG. 29).

Example 17

Immunogenicity of Replication-Incompetent LCMV and PICV Arenavirus Vectors Using Homologous or Heterologous Prime-Boost Immunization Regimens with 1-Week Dosing Intervals in Cynomolgus Macaques We evaluated the immunogenicity of replication-incompetent LCMV (VV1) and PICV (VV2) vectors encoding GT-D iCore-P2A-sAg and GT-B Pol300 using homologous prime/boost (VV1 vector followed by VV1 vector) or heterologous prime-boost (VV2 vector followed by VV1 vector) immunization regimens administered with a 1-week dosing interval in cynomolgus macaques.

Methods

Cynomolgus macaques were immunized as described in Table 17. HBV-specific T cell responses were measured using PBMC by IFN-γ ELISPOT at week 4.

TABLE 17

Study Groups in Immunogenicity Study

| Group | N | Vaccine Prime | Vaccine Boost | Dose/ vector | Immunization schedule (week) | ELISPOT analysis |
|---|---|---|---|---|---|---|
| 1 | 5 | VV1 | VV1 | $10^8$ FFU | 0 (VV1)<br>1 (VV1)<br>2 (VV1)<br>3 (VV1) | Week 4 |
| 2 | 5 | VV2 | VV1 | $10^8$ FFU | 0 (VV2)<br>1 (VV1)<br>2 (VV2)<br>3 (VV1) | Week 4 |

Results

Administration of the replication-incompetent PICV vector (VV2) followed by VV1 (heterologous prime/boost regimen VV2/VV1) yielded greater HBV-specific T cell responses compared to vaccination with VV1 vector alone (FIG. 30).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

```
                             SEQUENCE LISTING

Sequence total quantity: 102
SEQ ID NO: 1            moltype = AA  length = 226
FEATURE                 Location/Qualifiers
source                  1..226
                        mol_type = protein
                        organism = Hepatitis B virus
SEQUENCE: 1
MENITSGFLG PLLVLQAGFF LLTRILTIPQ SLDSWWTSLN FLGGTPVCLG QNSQSPTSNH   60
SPTSCPPICP GYRWMCLRRF IIFLFILLLC LIFLLVLLDY QGMLPVCPLI PGSTTTSTGP  120
CKTCTTPAQG NSMFPSCCCT KPTDGNCTCI PIPSSWAFAK YLWEWASVRF SWLSLLVPFV  180
QWFVGLSPTV WLSVIWMMWY WGPSLYNILS PFIPLLPIFF CLWVYI                 226

SEQ ID NO: 2            moltype = AA  length = 226
FEATURE                 Location/Qualifiers
source                  1..226
                        mol_type = protein
                        organism = Hepatitis B virus
SEQUENCE: 2
MESTTSGFLG PLLVLQAGFF LLTRILTIPQ SLDSWWTSLN FLGGAPTCPG QNLQSPTSNH   60
SPTSCPPICP GYRWMCLRRF IIFLFILLLC LIFLLVLLDY QGMLPVCPLI PGSSTTSTGP  120
CRTCTTPAQG TSMFPSCCCT KPTDGNCTCI PIPSSWAFAK YLWEWASVRF SWLSLLVPFV  180
QWFVGLSPTV WLSVIWMMWY WGPSLYNILS PFMPLLPIFF CLWVYI                 226

SEQ ID NO: 3            moltype = AA  length = 226
FEATURE                 Location/Qualifiers
source                  1..226
                        mol_type = protein
                        organism = Hepatitis B virus
SEQUENCE: 3
MESTTSGFLG PLLVLQAGFF LLTRILTIPQ SLDSWWTSLN FLGGAPTCPG QNSQSPTSNH   60
SPTSCPPICP GYRWMCLRRF IIFLCILLLC LIFLLVLLDY QGMLPVCPLI PGSSTTSTGP  120
CKTCTTPAQG TSMFPSCCCT KPTDGNCTCI PIPSSWAFAR FLWEWASVRF SWLSLLVPFV  180
QWFVGLSPTV WLSVIWMMWY WGPSLYNILS PFLPLLPIFF CLWVYI                 226

SEQ ID NO: 4            moltype = AA  length = 226
FEATURE                 Location/Qualifiers
source                  1..226
                        mol_type = protein
                        organism = Hepatitis B virus
SEQUENCE: 4
MENITSGFLG PLLVLQAGFF LLTRILTIPQ SLDSWWTSLN FLGGTTVCLG QNSQSPTSNH   60
SPTSCPPICP GYRWMCLRRF IIFLFILLLC LIFLLVLLDY QGMLPVCPLI PGSSTTSTGP  120
CRTCTTPAQG TSMYPSCCCT KPSDGNCTCI PIPSSWAFGK FLWEWASARF SWLSLLVPFV  180
QWFVGLSPTV WLSVIWMMWY WGPSLYSILS PFLPLLPIFF CLWVYI                 226

SEQ ID NO: 5            moltype = AA  length = 755
FEATURE                 Location/Qualifiers
REGION                  1..755
                        note = Description of Artificial Sequence:
                        Syntheticpolypeptide
source                  1..755
                        mol_type = protein
                        organism = synthetic construct
SEQUENCE: 5
MPLSYQHFRK LLLLDDETEA GPLEEELPRL ADEDLNRRVA EDLNLGNLNV SIPWTHKVGN   60
FTGLYSSTVP IFNPEWQTPS FPKIHLHEDI ANRCQQFVGP LTVNEKRRLR LIMPARFYPN  120
STKYLPLDKG IKPYYPDHVV NHYFQTRHYL HTLWKAGILY KRETTRSASF CGSPYSWEQE  180
LHHGRLVIKT SQRHGDEPFC SQPSGILSRS SVGPEFHSFP PSSARSQSQG PVFSCWWLQF  240
RNTQPCSKYC LSHLVNLLED WGPCDEHGEH HIRIPRTPAR VTGGVFLVDK NPHNTAESRL  300
VVDFSQFSRG ITRVSWPKFA VPNLQSLTNL LSSNLSWLSL DVSAAFYHIP LHPAAMPHLL  360
VGSSGLSRYV ARLSSNSRIH NNQHGTLQNL HDSCSRQLYV SLMLLYKTYG RKLHLYSHPI  420
ILGFRKIPMG VGLSPFLLAQ FTSAICSVVR RAFPHCLAFS YMHDVVLGAK SVQHLESLYT  480
AVTNFLLSLG IHLNPNKTKR WGYSLNFMGY VIGSWGTLPQ DHIVQKIKHC FRKLPINRPI  540
DWKVCQRIVG LLGFAAPFTQ CGYPALMPLY ACIQAKQAFT FSPTYKAFLS KQYLNLYPVA  600
RQRPGLCQVF ADATPTGWGL AIGHQRMRGT FVAPLPIHTA HLLAACFARS RSGAKLIGTD  660
NSVVLSRKYT SFPWLLGCTA NWILRGTSFV YVPSALNPAD DPSRGRLGLY RPLLRLPYRP  720
TTGRTSLYAV SPSVPSHLPV RVHFASPLHV AWRPP                             755

SEQ ID NO: 6            moltype = AA  length = 749
FEATURE                 Location/Qualifiers
REGION                  1..749
```

```
                            note = Description of Artificial Sequence:
                                   Syntheticpolypeptide
source                      1..749
                            mol_type = protein
                            organism = synthetic construct
SEQUENCE: 6
MPLSYQHFRK LLLLDDEAGP LEEELPRLAD EGLNRRVAED LNLGNLNVSI PWTHKVGNFT    60
GLYSSTVPVF NPEWQTPSFP HIHLQEDIIN RCQQYVGPLT VNEKRRLKLI MPARFYPNLT   120
KYLPLDKGIK PYYPEHVVNH YFQTRHYLHT LWKAGILYKR ESTRSASFCG SPYSWEQELQ   180
HGRLVFQTSK RHGDKSFCPQ SPGILPRSEL HHFPPSSSRS QSQGPVLSCW WLQFRNSEPC   240
SEYCLCHIVN LIEDWGPCTE HGEHRIRTPR TPARVTGGVF LVDKNPHNTT ESRLVVDFSQ   300
FSRGNTRVSW PKFAVPNLQS LTNLLSSNLS WLSLDVSAAF YHLPLHPAAM PHLLVGSSGL   360
SRYVARLSSN SRIINNQHRT MQNLHDSCSR NLYVSLMLLY KTYGRKLHLY SHPIILGFRK   420
IPMGVGLSPF LLAQFTSAIC SVVRRAFPHC LAFSYMHDVV LGAKSVQHLE SLYAAVTNFL   480
LSLGIHLNPH KTKRWGYSLN FMGYVIGSWG TLPQEHIVQK IKMCFRKLPV NRPIDWKVCQ   540
RIVGLLGFAA PFTQCGYPAL MPLYACIQAK QAFTFSPTYK AFLSKQYLHL YPVARQRPGL   600
CQVFADATPT GWGLAIGHQR MRGAFVSPLP IHTAHLLAAC FARSRSGAKL IGTDNSVVLS   660
RKYTSFPWLL GCAANWILRG TSFVYVPSAL NPADDPSRGR LGLYRPLLRL LYRPTTGRTS   720
LYADSPSVPS HLPDRVHFAS PLHVAWRPP                                    749

SEQ ID NO: 7                moltype = AA   length = 753
FEATURE                     Location/Qualifiers
REGION                      1..753
                            note = Description of Artificial Sequence:
                                   Syntheticpolypeptide
source                      1..753
                            mol_type = protein
                            organism = synthetic construct
SEQUENCE: 7
MPLSYQHFRK LLLLDDEAGP LEEELPRLAD EDLNRRVAED LNLGNLNVSI PWTHKVGNFT    60
GLYSSTVPVF NPEWQTPSFP HIHLQEDIIN RCQQYVGPLT VNEKRRLKLI MPARFYPNLT   120
KYLPLDKGIK PYYPEHTVNH YFKTRHYLHT LWKAGILYKR ETTRSASFCG SPYSWEQELQ   180
HGRLVFQTST RHGDESFCSQ SSGILSRSPV GPELHNFPPS SARSQSEGPL LSCWWLQFRN   240
SKPCSDYCLS HIVNLLEDWG PCTEHGEHNI RIPRTPARVT GGVFLVDKNP HNTTESRLVV   300
DFSQFSRGST HVSWPKFAVP NLQSLTNLLS SNLSWLSLDV SAAFYHLPLH PAAMPHLLVG   360
SSGLSRYVAR LSSTSRNINY QHGAMQDLHD SCSRNLYVSL LLLYKTFGRK LHLYSHPIIL   420
GFRKIPMGVG LSPFLLAQFT SAICSVVRRA FPHCLAFSYM HDVVLGAKSV QHLESLFTAV   480
TNFLLSLGIH LNPNKTKRWG YSLNFMGYVI GSWGTLPQEH IVLKIKQCFR KLPVNRPIDW   540
KVCQRIVGLL GFAAPFTQCG YPALMPLYAC IQAKQAFTFS PTYKAFLCKQ YLNLYPVARQ   600
RSGLCQVFAD ATPTGWGLAV GHQRMRGTFV SPLPIHTAHL LAACFARSRS GAKLIGTDNS   660
VVLSRKYTSF PWLLGCAANW ILRGTSFVYV PSALNPADDP SRGRLGLYRP LLRLPFRPTT   720
GRTSLYAVSP SVPSHLPVRV HFASPLHVAW RPP                               753

SEQ ID NO: 8                moltype = AA   length = 742
FEATURE                     Location/Qualifiers
REGION                      1..742
                            note = Description of Artificial Sequence:
                                   Syntheticpolypeptide
source                      1..742
                            mol_type = protein
                            organism = synthetic construct
SEQUENCE: 8
MPLSYQHFRR LLLLDDEAGP LEEELPRLAD EGLNRRVAED LNLGNLNVSI PWTHKVGNFT    60
GLYSSTVPVF NPHWKTPSFP NIHLQDIIK KCEQFVGPLT VNEKRRLQLI MPARFYPNVT   120
KYLPLDKGIK PYYPEHLVNH YFQTRHYLHT LWKAGILYKR ETTHSASFCG SPYSWEQELQ   180
HGAESFHQQS SGILSRPPVG SELHNLPPNS ARSQSERPVF PCWWLQFRNS KPCSDYCLSH   240
IVNLLEDWGP CAEHGEHHIR IPRTPARVTG GVFLVDKNPH NTAESRLVVD FSQFSRGNYR   300
VSWPKFAVPN LQSLTNLLSS NLSWLSLDVS AAFYHLPLHP AAMPHLLVGS SGLSRYVARL   360
SSNSRIFNYQ HGTMQNLHDS CSRNLYVSLM LLYQTFGRKL HLYSHPIILG FRKIPMGVGL   420
SPFLLAQFTS AICSVVRRAF PHCLAFSYMH DVVLGAKSVQ HLESLFTAVT NFLLSLGIHL   480
NPNKTKRWGY SLHFMGYVIG CYGSLPQDHI IQKIKECFRK LPVNRPIDWK VCQRIVGLLG   540
FAAPFTQCGY PALMPLYACI QSKQAFTFSP TYKAFLCKQY LNLYPVARQR PGLCQVFADA   600
TPTGWGLVMG HQRMRGTFKA PLPIHTAHLL AACFARSRSG ANILGTDNSV VLSRKYTSFP   660
WLLGCAANWI LRGTSFVYVP SALNPADDPS RGRLGLYRPL LRLPFRPTTG RTSLYADSPS   720
VPSHLPDRVH FASPLHVAWR PP                                           742

SEQ ID NO: 9                moltype = AA   length = 705
FEATURE                     Location/Qualifiers
REGION                      1..705
                            note = Description of Artificial Sequence:
                                   Syntheticpolypeptide
source                      1..705
                            mol_type = protein
                            organism = synthetic construct
SEQUENCE: 9
MPLSYQHFRK LLLLDDETEA GPLEEELPRL ADEDLNRRVA EDLNLGNLNV SIPWTHKVGN    60
FTGLYSSTVP IFNPEWQTPS FPKIHLHEDI ANRCQQFVGP LTVNEKRRLR LIMPARFYPN   120
STKYLPLDKG IKPYYPDHVV NHYFQTRHYL HTLWKAGILY KRETTRSASF CGSPYSWEQE   180
LHHGCWWLQF RNTQPCSKYC LSHLVNLLED WGPCDEHGEH HIRIPRTPAR VTGGVFLVDK   240
```

```
NPHNTAESRL VVDFSQFSRG ITRVSWPKFA VPNLQSLTNL LSSNSWLSL  DVSAAFYHIP  300
LHPAAMPHLL VGSSGLSRYV ARLSSNSRIH NNQHGTLQNL HDSCSRQLYV SLMLLYKTYG  360
RKLHLYSHPI ILGFRKIPMG VGLSPFLLAQ FTSAICSVVR RAFPHCLAFS YMHDVVLGAK  420
SVQHLESLYT AVTNFLLSLG IHLNPNKTKR WGYSLNFMGY VIGSWGTLPQ DHIVQKIKHC  480
FRKLPINRPI DWKVCQRIVG LLGFAAPFTQ CGYPALMPLY ACIQAKQAFT FSPTYKAFLS  540
KQYLNLYPVA RQRPGLCQVF ADATPTGWGL AIGHQRMRGT FVAPLPIHTA HLLAACFARS  600
RSGAKLIGTD NSVVLSRKYT SFPWLLGCTA NWILRGTSFV YVPSALNPAD DPSRGRLGLY  660
RPLLRLPYRP TTGRTSLYAV SPSVPSHLPV RVHFASPLHV AWRPP              705

SEQ ID NO: 10          moltype = AA  length = 703
FEATURE                Location/Qualifiers
REGION                 1..703
                       note = Description of Artificial Sequence:
                         Syntheticpolypeptide
source                 1..703
                       mol_type = protein
                       organism = synthetic construct
SEQUENCE: 10
MPLSYQHFRK LLLLDDEAGP LEEELPRLAD EGLNRRVAED LNLGNLNVSI PWTHKVGNFT  60
GLYSSTVPVF NPEWQTPSFP HIHLQEDIIN RCQQYVGPLT VNEKRRLKLI MPARFYPNLT  120
KYLPLDKGIK PYYPEHVVNH YFQTRHYLHT LWKAGILYKR ESTRSASFCG SPYSWEQDLQ  180
HGCWWLQFRN SEPCSEYCLC HIVNLIEDWG PCTEHGEHRI RTPRTPARVT             240
HNTTESRLVV DFSQFSRGNT RVSWPKFAVP NLQSLTNLLS SNLSWLSLDV SAAFYHLPLH  300
PAAMPHLLVG SSGLSRYVAR LSSNSRIINN QHRTMQNLHD SCSRNLYVSL MLLYKTYGRK  360
LHLYSHPIIL GFRKIPMGVG LSPFLLAQFT SAICSVVRRA FPHCLAFSYM HDVVLGAKSV  420
QHLESLYAAV TNFLLSLGIH LNPHKTKRWG YSLNFMGYVI GSWGTLPQEH VIQKIKMCFR  480
KLPVNRPIDW KVCQRIVGLL GFAAPFTQCG YPALMPLYAC IQAKQAFTFS PTYKAFLSKQ  540
YLHLYPVARQ RPGLCQVFAD ATPTGWGLAI GHQRMRGAFV SPLPIHTAHL LAACFARSRS  600
GAKLIGTDNS VVLSRKYTSF PWLLGCAANW ILRGTSFVYV PSALNPADDP SRGRLGLYRP  660
LLRLLYRPTT GRTSLYADSP SVPSHLPDRV HFASPLHVAW RPP              703

SEQ ID NO: 11          moltype = AA  length = 703
FEATURE                Location/Qualifiers
REGION                 1..703
                       note = Description of Artificial Sequence:
                         Syntheticpolypeptide
source                 1..703
                       mol_type = protein
                       organism = synthetic construct
SEQUENCE: 11
MPLSYQHFRK LLLLDDEAGP LEEELPRLAD EDLNRRVAED LNLGNLNVSI PWTHKVGNFT  60
GLYSSTVPVF NPEWQTPSFP HIHLQEDIIN RCQQYVGPLT VNEKRRLKLI MPARFYPNLT  120
KYLPLDKGIK PYYPEHTVNH YFKTRHYLHT LWKAGILYKR ETTRSASFCG SPYSWEQELQ  180
HGCWWLQFRN SKPCSDYCLS HIVNLLEDWG PCTEHGEHNI RIPRTPARVT GGVFLVDKNP  240
HNTTESRLVV DFSQFSRGST HVSWPKFAVP NLQSLTNLLS SNLSWLSLDV SAAFYHLPLH  300
PAAMPHLLVG SSGLSRYVAR LSSTSRNINY QHGAMQDLHD SCSRNLYVSL LLLYKTFGRK  360
LHLYSHPIIL GFRKIPMGVG LSPFLLAQFT SAICSVVRRA FPHCLAFSYM HDVVLGAKSV  420
QHLESLFTAV TNFLLSLGIH LNPNKTKRWG YSLNFMGYVI GSWGTLPQEH IVLKIKQCFR  480
KLPVNRPIDW KVCQRIVGLL GFAAPFTQCG YPALMPLYAC IQAKQAFTFS PTYKAFLCKQ  540
YLNLYPVARQ RSGLCQVFAD ATPTGWGLAV GHQRMRGTFV SPLPIHTAHL LAACFARSRS  600
GAKLIGTDNS VVLSRKYTSF PWLLGCAANW ILRGTSFVYV PSALNPADDP SRGRLGLYRP  660
LLRLPFRPTT GRTSLYAVSP SVPSHLPVRV HFASPLHVAW RPP              703

SEQ ID NO: 12          moltype = AA  length = 703
FEATURE                Location/Qualifiers
REGION                 1..703
                       note = Description of Artificial Sequence:
                         Syntheticpolypeptide
source                 1..703
                       mol_type = protein
                       organism = synthetic construct
SEQUENCE: 12
MPLSYQHFRR LLLLDDEAGP LEEELPRLAD EGLNRRVAED LNLGNLNVSI PWTHKVGNFT  60
GLYSSTVPVF NPHWKTPSFP NIHLHQDIIK KCEQFVGPLT VNEKRRLQLI MPARFYPNVT  120
KYLPLDKGIK PYYPEHLVNH YFQTRHYLHT LWKAGILYKR ETTHSASFCG SPYSWEQELQ  180
HGCWWLQFRN SKPCSDYCLS HIVNLLEDWG PCAEHGEHHI RIPRTPARVT GGVFLVDKNP  240
HNTAESRLVV DFSQFSRGNY RVSWPKFAVP NLQSLTNLLS SNLSWLSLDV SAAFYHLPLH  300
PAAMPHLLVG SSGLSRYVAR LSSNSRIFNY QHGTMQNLHD SCSRNLYVSL MLLYQTFGRK  360
LHLYSHPIIL GFRKIPMGVG LSPFLLAQFT SAICSVVRRA FPHCLAFSYM HDVVLGAKSV  420
QHLESLFTAV TNFLLSLGIH LNPNKTKRWG YSLHFMGYVI GCYGSLPQDH IIQKIKECFR  480
KLPVNRPIDW KVCQRIVGLL GFAAPFTQCG YPALMPLYAC IQSKQAFTFS PTYKAFLCKQ  540
YLNLYPVARQ RPGLCQVFAD ATPTGWGLVM GHQRMRGTFK APLPIHTAHL LAACFARSRS  600
GANILGTDNS VVLSRKYTSF PWLLGCAANW ILRGTSFVYV PSALNPADDP SRGRLGLYRP  660
LLRLPFRPTT GRTSLYADSP SVPSHLPDRV HFASPLHVAW RPP              703

SEQ ID NO: 13          moltype = AA  length = 534
FEATURE                Location/Qualifiers
REGION                 1..534
                       note = Description of Artificial Sequence:
```

```
                        Syntheticpolypeptide
source                  1..534
                        mol_type = protein
                        organism = synthetic construct
SEQUENCE: 13
MSSRSQSQGP VLSCWWLQFR NSEPCSEYCL CHIVNLIEDW GPCTEHGEHR IRTPRTPARV    60
TGGVFLVDKN PHNTTESRLV VDFSQFSRGN TRVSWPKFAV PNLQSLTNLL SSNLSWLSLD   120
VSAAFYHLPL HPAAMPHLLV GSSGLSRYVA RLSSNSRIIN NQHRTMQNLH DSCSRNLYVS   180
LMLLYKTYGR KLHLYSHPII LGFRKIPMGV GLSPFLLAQF TSAICSVVRR APPHCLAFSY   240
MHDVVLGAKS VQHLESLYAA VTNFLLSLGI HLNPHKTKRW GYSLNFMGYV IGSWGTLPQE   300
HIVQKIKMCF RKLPVNRPID WKVCQRIVGL LGFAAPFTQC GYPALMPLYA CIQAKQAFTF   360
SPTYKAFLSK QYLHLYPVAR QRPGLCQVFA DATPTGWGLA IGHQRMRGAF VSPLPIHTAH   420
LLAACFARSR SGAKLIGTDN SVVLSRKYTS FPWLLGCAAN WILRGTSFVY VPSALNPADD   480
PSRGRLGLYR PLLRLLYRPT TGRTSLYADS PSVPSHLPDR VHFASPLHVA WRPP         534

SEQ ID NO: 14           moltype = AA  length = 534
FEATURE                 Location/Qualifiers
REGION                  1..534
                        note = Description of Artificial Sequence:
                        Syntheticpolypeptide
source                  1..534
                        mol_type = protein
                        organism = synthetic construct
SEQUENCE: 14
MSARSQSERP VFPCWWLQFR NSKPCSDYCL SHIVNLLEDW GPCAEHGEHH IRIPRTPARV    60
TGGVFLVDKN PHNTAESRLV VDFSQFSRGN YRVSWPKFAV PNLQSLTNLL SSNLSWLSLD   120
VSAAFYHLPL HPAAMPHLLV GSSGLSRYVA RLSSNSRIFN YQHGTMQNLH DSCSRNLYVS   180
LMLLYQTFGR KLHLYSHPII LGFRKIPMGV GLSPFLLAQF TSAICSVVRR APPHCLAFSY   240
MHDVVLGAKS VQHLESLFTA VTNFLLSLGI HLNPNKTKRW GYSLHFMGYV IGCYGSLPQD   300
HIIQKIKECF RKLPVNRPID WKVCQRIVGL LGFAAPFTQC GYPALMPLYA CIQSKQAFTF   360
SPTYKAFLCK QYLNLYPVAR QRPGLCQVFA DATPTGWGLV MGHQRMRGTF KAPLPIHTAH   420
LLAACFARSR SGANILGTDN SVVLSRKYTS FPWLLGCAAN WILRGTSFVY VPSALNPADD   480
PSRGRLGLYR PLLRLPFRPT TGRTSLYADS PSVPSHLPDR VHFASPLHVA WRPP         534

SEQ ID NO: 15           moltype = AA  length = 1030
FEATURE                 Location/Qualifiers
REGION                  1..1030
                        note = Description of Artificial Sequence:
                        Syntheticpolypeptide
source                  1..1030
                        mol_type = protein
                        organism = synthetic construct
SEQUENCE: 15
MDIDPYKEFG ASVELLSFLP SDFFPSVRDL LDTASALYRE ALESPEHCSP HHTALRQAIL    60
CWGELMTLAT WVGNNLEDPA SRDLVVNYVN TNMGLKIRQL LWFHISCLTF GRETVLEYLV   120
SFGVWIRTPP AYRPPNAPIL STLPETTVVR RRDRGRSPRR RTPSPRRRRS QSPRRRRSQS   180
RESQCMPLSY QHFRKLLLLD DETEAGPLEE ELPRLADEDL NRRVAEDLNL GNLNVSIPWT   240
HKVGNFTGLY SSTVPIFNPE WQTPSFPKIH LHEDIANRCQ QFVGPLTVNE KRRLRLIMPA   300
RFYPNSTKYL PLDKGIKPYY PDHVVNHYFQ TRHYLHTLWK AGILYKRETT RSASFCGSPY   360
SWEQELHHGR LVIKTSQRHG DEPFCSQPSG ILSRSSVGPC IRSQFKQSRL GLQPHQGPLA   420
TSQSGRSGSI RARVHSPTRR CFGVEPSGSG HIGHSASSSS SCLHQSAVRK AAYSHLSTSK   480
RQSSSGHAVE FHSFPPSSAR SQSQGPVFSC WWLQFRNTQP CSKYCLSHLV NLLEDWGPCD   540
EHGEHHIRIP RTPARVTGGV FLVDKNPHNT AESRLVVDFS QFSRGITRVS WPKFAVPNLQ   600
SLTNLLSSNL SWLSLDVSAA FYHIPLHPAA MPHLLVGSSG LSRYVARLSS NSRIHNNQHG   660
TLQNLHDSCS RQLYVSLMLL YKTYGRKLHL YSHPIILGFR KIPMGVGLSP FLLAQFTSAI   720
CSVVRRAFPH CLAFSYMHDV VLGAKSVQHL ESLYTAVTNF LLSLGIHLNP NKTKRWGYSL   780
NFMGYVIGSW GTLPQDHIVQ KIKHCFRKLP INRPIDWKVC QRIVGLLGFA APFTQCGYPA   840
LMPLYACIQA KQAFTFSPTY KAFLSKQYLN LYPVARQRPG LCQVFADATP TGWGLAIGHQ   900
RMRGTFVAPL PIHTAHLLAA CFARSRSGAK LIGTDNSVVL SRKYTSFPWL LGCTANWILR   960
GTSFVYVPSA LNPADDPSRG RLGLYRPLLR LPYRPTTGRT SLYAVSPSVP SHLPVRVHFA  1020
SPLHVAWRPP                                                        1030

SEQ ID NO: 16           moltype = AA  length = 1026
FEATURE                 Location/Qualifiers
REGION                  1..1026
                        note = Description of Artificial Sequence:
                        Syntheticpolypeptide
source                  1..1026
                        mol_type = protein
                        organism = synthetic construct
SEQUENCE: 16
MDIDPYKEFG ASVELLSFLP SDFFPSVRDL LDTASALYRE ALESPEHCSP HHTALRQAIL    60
CWGELMNLAT WVGSNLEDPA SRELVVSYVN VNMGLKIRQL LWFHISCLTF GRETVLEYLV   120
SFGVWIRTPP AYRPPNAPIL STLPETTVVR RRGRSPRRRT PSPRRRRSQS PRRRRSQSRE   180
SQCMPLSYQH FRKLLLLLDDE AGPLEEELPR LADEGLNRRV AEDLNLGNLN VSIPWTHKVG   240
NFTGLYSSTV PVFNPEWQTP SFPHIHLQED IINRCQQYVG PLTVNEKRRL KLIMPARFYP   300
NLTKYLPLDK GIKPYYPEHV VNHYFQTRHY LHTLWKAGIL YKRESTRSAS FCGSPYSWEQ   360
DLQHGRLVFQ TSKRHGDKSF CPQSPGILPR SSVGPCIQNQ LRKSRLGPQP AQGQLAGRQQ   420
GGSGSIRARV HPSPWGTVGV EPSGSGHIHN CASNSSSCLH QSAVRKAAYS HISTSKGHSS   480
```

```
SGHAVELHHF PPSSSRSQSQ GPVLSCWWLQ FRNSEPCSEY CLCHIVNLIE DWGPCTEHGE    540
HRIRTPRTPA RVTGGVFLVD KNPHNTTESR LVVDFSQFSR GNTRVSWPKF AVPNLQSLTN    600
LLSSNLSWLS LDVSAAFYHL PLHPAAMPHL LVGSSGLSRY VARLSSNSRI INNQHRTMQN    660
LHDSCSRNLY VSLMLLYKTY GRKLHLYSHP IILGFRKIPM GVGLSPFLLA QFTSAICSVV    720
RRAFPHCLAF SYMHDVVLGA KSVQHLESLY AAVTNFLLSL GIHLNPHKTK RWGYSLNFMG    780
YVIGSWGTLP QEHIVQKIKM CFRKLPVNRP IDWKVCQRIV GLLGFAAPFT QCGYPALMPL    840
YACIQAKQAF TFSPTYKAFL SKQYLHLYPV ARQRPGLCQV FADATPTGWG LAIGHQRMRG    900
AFVSPLPIHT AHLLAACFAR SRSGAKLIGT DNSVVLSRKY TSFPWLLGCA ANWILRGTSF    960
VYVPSALNPA DDPSRGRLGL YRPLLRLLYR PTTGRTSLYA DSPSVPSHLP DRVHFASPLH    1020
VAWRPP                                                               1026

SEQ ID NO: 17           moltype = AA length = 1026
FEATURE                 Location/Qualifiers
REGION                  1..1026
                        note = Description of Artificial Sequence:
                        Syntheticpolypeptide
source                  1..1026
                        mol_type = protein
                        organism = synthetic construct
SEQUENCE: 17
MDIDPYKEFG ASVELLSFLP SDFFPSVRDL LDTASALYRE ALESPEHCSP HHTALRQAIL    60
CWGELMNLAT WVGSNLEDPA SRELVVSYVN VNMGLKIRQL LWFHISCLTF GRETVLEYLV    120
SFGVWIRTPP AYRPPNAPIL STLPETTVVR RRGRSPRRRT PSPRRRRSQS PRRRRSQSRE    180
SQCMPLSYQH FRKLLLLDDE AGPLEEELPR LADEDLNRRV AEDLNLGNLN VSIPWTHKVG    240
NFTGLYSSTV PVFNPEWQTP SFPHIHLQED IINRCQQYVG PLTVNEKRRL KLIMPARFYP    300
NLTKYLPLDK GIKPYYPEHT VNHYFKTRHY LHTLWKAGIL YKRETTRSAS FCGSPYSWEQ    360
ELQHGRLVFQ TSTRHGDESF CSQSSGILSR SPVGPCIRSQ LKQSRLGLQP QQGSLARSKS    420
GRSGSIRARV HPTTRQSFGV EPSGSGHIDN SASSASSCLH QSAVRKTAYS HLSTSKRQSS    480
SGHAVELHNF PPSSARSQSE GPLLSCWWLQ FRNSKPCSDY CLSHIVNLLE DWGPCTEHGE    540
HNIRIPRTPA RVTGGVFLVD KNPHNTTESR LVVDFSQFSR GSTHVSWPKF AVPNLQSLTN    600
LLSSNLSWLS LDVSAAFYHL PLHPAAMPHL LVGSSGLSRY VARLSSTSRN INYQHGAMQD    660
LHDSCSRNLY VSLLLLYKTF GRKLHLYSHP IILGFRKIPM GVGLSPFLLA QFTSAICSVV    720
RRAFPHCLAF SYMHDVVLGA KSVQHLESLF TAVTNFLLSL GIHLNPNKTK RWGYSLNFMG    780
YVIGSWGTLP QEHIVQKIKQ CFRKLPVNRP IDWKVCQRIV GLLGFAAPFT QCGYPALMPL    840
YACIQAKQAF TFSPTYKAFL CKQYLNLYPV ARQRSGLCQV FADATPTGWG LAVGHQRMRG    900
TFVSPLPIHT AHLLAACFAR SRSGAKLIGT DNSVVLSRKY TSFPWLLGCA ANWILRGTSF    960
VYVPSALNPA DDPSRGRLGL YRPLLRLPFR PTTGRTSLYA VSPSVPSHLP VRVHFASPLH    1020
VAWRPP                                                               1026

SEQ ID NO: 18           moltype = AA length = 1015
FEATURE                 Location/Qualifiers
REGION                  1..1015
                        note = Description of Artificial Sequence:
                        Syntheticpolypeptide
source                  1..1015
                        mol_type = protein
                        organism = synthetic construct
SEQUENCE: 18
MDIDPYKEFG ASVELLSFLP SDFFPSVRDL LDTASALYRE ALESPEHCSP HHTALRQAIL    60
CWGELMNLAT WVGVNLEDPA SRDLVVSYVN TNMGLKFRQL LWFHISCLTF GRETVLEYLV    120
SFGVWIRTPP AYRPPNAPIL STLPETTVVR RRGRSPRRRT PSPRRRRSQS PRRRRSQSRE    180
SQCMPLSYQH FRRLLLLDDE AGPLEEELPR LADEGLNRRV AEDLNLGNLN VSIPWTHKVG    240
NFTGLYSSTV PVFNPHWKTP SFPNIHLHQD IIKKCEQFVG PLTVNEKRRL QLIMPARFYP    300
NVTKYLPLDK GIKPYYPEHL VNHYFQTRHY LHTLWKAGIL YKRETTHSAS FCGSPYSWEQ    360
ELQHGAESFH QQSSGILSRP PVGSSLQSKH RKSRLGLQSQ QGHLARRQQG RGWSIRAGIH    420
PTARRPFGVE PSGSGHTANL ASKSASCLYQ SAVRKAAYPV VSTFKKHSSS GHAVELHNLP    480
PNSARSQSER PVFPCWWLQF RNSKPCSDYC LSHIVNLLED WGPCAEHGEH HIRIPRTPAR    540
VTGGVFLVDK NPHNTAESRL VVDFSQFSRG NYRVSWPKFA VPNLQSLTNL LSSNLSWLSL    600
DVSAAFYHLP LHPAAMPHLL VGSSGLSRYV ARLSSNSRIF NYQHGTMQNL HDSCSRNLYV    660
SLMLLYQTFG RKLHYSHPI ILGFRKIPMG VGLSPFLLAQ FTSAICSVVR RAFPHCLAFS     720
YMHDVVLGAK SVQHLESLFT AVTNFLLSLG IHLNPNKTKR WGYSLHFMGY VIGCYGSLPQ    780
DHIIQKIKEC FRKLPVNRPI DWKVCQRIVG LLGFAAPFTQ CGYPALMPLY ACIQSKQAFT    840
FSPTYKAFLC KQYLNLYPVA RQRPGLCQVF ADATPTGWGL VMGHQRMRGT FKAPLPIHTA    900
HLLAACFARS RSGANILGTD NSVVLSRKYT SFPWLLGCAA NWILRGTSFV YVPSALNPAD    960
DPSRGRLGLY RPLLRLPFRP TTGRTSLYAD SPSVPSHLPD RVHFASPLHV AWRPP         1015

SEQ ID NO: 19           moltype = AA length = 940
FEATURE                 Location/Qualifiers
REGION                  1..940
                        note = Description of Artificial Sequence:
                        Syntheticpolypeptide
source                  1..940
                        mol_type = protein
                        organism = synthetic construct
SEQUENCE: 19
MDIDPYKEFG ASVELLSFLP SDFFPSVRDL LDTASALYRE ALESPEHCSP HHTALRQAIL    60
CWGELMTLAT WVGNNLEDPA SRDLVVNYVN TNMGLKIRQL LWFHISCLTF GRETVLEYLV    120
SFGVWIRTPP AYRPPNAPIL STLPETTVVR RRDRGRSPRR RTPSPRRRRS QSPRRRRSQS    180
RESQCMPLSY QHFRKLLLLD DETEAGPLEE ELPRLADEDL NRRVAEDLNL GNLNVSIPWT    240
```

```
HKVGNFTGLY SSTVPIFNPE WQTPSFPKIH LHEDIANRCQ QFVGPLTVNE KRRLRLIMPA   300
RFYPNSTKYL PLDKGIKPYY PDHVVNHYFQ TRHYLHTLWK AGILYKRETT RSASFCGSPY   360
SWEQELHHGR LVIKTSQRHG DEPFCSQPSG ILSRSSVGPE FHSFPPSSAR SQSQGPVFSC   420
WWLQFRNTQP CSKYCLSHLV NLLEDWGPCD EHGEHHIRIP RTPARVTGGV FLVDKNPHNT   480
AESRLVVDFS QFSRGITRVS WPKFAVPNLQ SLTNLLSSNL SWLSLDVSAA FYHIPLHPAA   540
MPHLLVGSSG LSRYVARLSS NSRIHNNQHG TLQNLHDSCS RQLYVSLMLL YKTYGRKLHL   600
YSHPIILGFR KIPMGVGLSP FLLAQFTSAI CSVVRRAFPH CLAFSYMHDV VLGAKSVQHL   660
ESLYTAVTNF LLSLGIHLNP NKTKRWGYSL NFMGYVIGSW GTLPQDHIVQ KIKHCFRKLP   720
INRPIDWKVC QRIVGLLGFA APFTQCGYPA LMPLYACIQA KQAFTFSPTY KAFLSKQYLN   780
LYPVARQRPG LCQVFADATP TGWGLAIGHQ RMRGTFVAPL PIHTAHLLAA CFARSRSGAK   840
LIGTDNSVVL SRKYTSFPWL LGCTANWILR GTSFVYVPSA LNPADDPSRG RLGLYRPLLR   900
LPYRPTTGRT SLYAVSPSVP SHLPVRVHFA SPLHVAWRPP                         940

SEQ ID NO: 20           moltype = AA   length = 932
FEATURE                 Location/Qualifiers
REGION                  1..932
                        note = Description of Artificial Sequence:
                        Syntheticpolypeptide
source                  1..932
                        mol_type = protein
                        organism = synthetic construct
SEQUENCE: 20
MDIDPYKEFG ASVELLSFLP SDFFPSVRDL LDTASALYRE ALESPEHCSP HHTALRQAIL    60
CWGELMNLAT WVGSNLEDPA SRELVVSYVN VNMGLKIRQL LWFHISCLTF GRETVLEYLV   120
SFGVWIRTPP AYRPPNAPIL STLPETTVVR RRGRSPRRRT PSPRRRRSQS PRRRRSQSRE   180
SQCMPLSYQH FRKLLLLDDE AGPLEEELPR LADEGLNRRV AEDLNLGNLN VSIPWTHKVG   240
NFTGLYSSTV PVFNPEWQTP SFPHIHLQED IINRCQQYVG PLTVNEKRRL KLIMPARFYP   300
NLTKYLPLDK GIKPYYPEHV VNHYFQTRHY LHTLWKAGIL YKRESTRSAS FCGSPYSWEQ   360
DLQHGRLVFQ TSKRHGDKSF CPQSPGILPR SELHHFPPSS SRSQSQGPVL SCWWLQFRNS   420
EPCSEYCLCH IVNLIEDWGP CTEHGEHRIR TPRTPARVTG GVFLVDKNPH NTTESRLVVD   480
FSQFSRGNTR VSWPKFAVPN LQSLTNLLSS NLSWLSLDVS AAFYHLPLHP AAMPHLLVGS   540
SGLSRYVARL SSNSRIINNQ HRTMQNLHDS CSRNLYVSLM LLYKTYGRKL HLYSHPIILG   600
FRKIPMGVGL SPFLLAQFTS AICSVVRRAF PHCLAFSYMH DVVLGAKSVQ HLESLYAAVT   660
NFLLSLGIHL NPHKTKRWGY SLNFMGYVIG SWGTLPQEHI VQKIKMCFRK LPVNRPIDWK   720
VCQRIVGLLG FAAPFTQCGY PALMPLYACI QAKQAFTFSP TYKAFLSKQY LHLYPVARQR   780
PGLCQVFADA TPTGWGLAIG HQRMRGAFVS PLPIHTAHLL AACFARSRSG AKLIGTDNSV   840
VLSRKYTSFP WLLGCAANWI LRGTSFVYVP SALNPADDPS RGRLGLYRPL LRLLYRPTTG   900
RTSLYADSPS VPSHLPDRVH FASPLHVAWR PP                                 932

SEQ ID NO: 21           moltype = AA   length = 936
FEATURE                 Location/Qualifiers
REGION                  1..936
                        note = Description of Artificial Sequence:
                        Syntheticpolypeptide
source                  1..936
                        mol_type = protein
                        organism = synthetic construct
SEQUENCE: 21
MDIDPYKEFG ASVELLSFLP SDFFPSVRDL LDTASALYRE ALESPEHCSP HHTALRQAIL    60
CWGELMNLAT WVGSNLEDPA SRELVVSYVN VNMGLKIRQL LWFHISCLTF GRETVLEYLV   120
SFGVWIRTPP AYRPPNAPIL STLPETTVVR RRGRSPRRRT PSPRRRRSQS PRRRRSQSRE   180
SQCMPLSYQH FRKLLLLDDE AGPLEEELPR LADEDLNRRV AEDLNLGNLN VSIPWTHKVG   240
NFTGLYSSTV PVFNPEWQTP SFPHIHLQED IINRCQQYVG PLTVNEKRRL KLIMPARFYP   300
NLTKYLPLDK GIKPYYPEHT VNHYFKTRHY LHTLWKAGIL YKRETTRSAS FCGSPYSWEQ   360
ELQHGRLVFQ TSTRHGDESF CSQSSGILSR SPVGPELHNF PPSSARSQSE GPLLSCWWLQ   420
FRNSKPCSDY CLSHIVNLLE DWGPCTEHGE HNIRIPRTPA RVTGGVFLVD KNPHNTTESR   480
LVVDFSQFSR GSTHVSWPKF AVPNLQSLTN LLSSNLSWLS LDVSAAFYHL PLHPAAMPHL   540
LVGSSGLSRY VARLSSTSRN INYQHGAMQD LHDSCSRNLY VSLLLLYKTF GRKLHLYSHP   600
IILGFRKIPM GVGLSPFLLA QFTSAICSVV RRAFPHCLAF SYMHDVVLGA KSVQHLESLF   660
TAVTNFLLSL GIHLNPNKTK RWGYSLNFMG YVIGSWGTLP QEHIVLKIKQ CFRKLPVNRP   720
IDWKVCQRIV GLLGFAAPFT QCGYPALMPL YACIQAKQAF TFSPTYKAFL CKQYLNLYPV   780
ARQRSGLCQV FADATPTGWG LAVGHQRMRG TFVSPLPIHT AHLLAACFAR SRSGAKLIGT   840
DNSVVLSRKY TSFPWLLGCA ANWILRGTSF VYVPSALNPA DDPSRGRLGL YRPLLRLPFR   900
PTTGRTSLYA VSPSVPSHLP VRVHFASPLH VAWRPP                             936

SEQ ID NO: 22           moltype = AA   length = 925
FEATURE                 Location/Qualifiers
REGION                  1..925
                        note = Description of Artificial Sequence:
                        Syntheticpolypeptide
source                  1..925
                        mol_type = protein
                        organism = synthetic construct
SEQUENCE: 22
MDIDPYKEFG ASVELLSFLP SDFFPSVRDL LDTASALYRE ALESPEHCSP HHTALRQAIL    60
CWGELMNLAT WVGVNLEDPA SRDLVVSYVN TNMGLKFRQL LWFHISCLTF GRETVLEYLV   120
SFGVWIRTPP AYRPPNAPIL STLPETTVVR RRGRSPRRRT PSPRRRRSQS PRRRRSQSRE   180
SQCMPLSYQH FRRLLLLDDE AGPLEEELPR LADEGLNRRV AEDLNLGNLN VSIPWTHKVG   240
NFTGLYSSTV PVFNPHWKTP SFPNIHLHQD IIKKCEQFVG PLTVNEKRRL QLIMPARFYP   300
```

```
NVTKYLPLDK GIKPYYPEHL VNHYFQTRHY LHTLWKAGIL YKRETTHSAS FCGSPYSWEQ    360
ELQHGAESFH QQSSGILSRP PVGSELHNLP PNSARSQSER PVFPCWWLQF RNSKPCSDYC    420
LSHIVNLLED WGPCAEHGEH HIRIPRTPAR VTGGVFLVDK NPHNTAESRL VVDFSQFSRG    480
NYRVSWPKFA VPNLQSLTNL LSSNLSWLSL DVSAAFYHLP LHPAAMPHLL VGSSGLSRYV    540
ARLSSNSRIF NYQHGTMQNL HDSCSRNLYV SLMLLYQTFG RKLHLYSHPI ILGFRKIPMG    600
VGLSPFLLAQ FTSAICSVVR RAFPHCLAFS YMHDVVLGAK SVQHLESLFT AVTNFLLSLG    660
IHLNPNKTKR WGYSLHFMGY VIGCYGSLPQ DHIIQKIKEC FRKLPVNRPI DWKVCQRIVG    720
LLGFAAPFTQ CGYPALMPLY ACIQSKQAFT FSPTYKAFLC KQYLNLYPVA RQRPGLCQVF    780
ADATPTGWGL VMGHQRMRGT FKAPLPIHTA HLLAACFARS RSGANILGTD NSVVLSRKYT    840
SFPWLLGCAA NWILRGTSFV YVPSALNPAD DPSRGRLGLY RPLLRLPFRP TTGRTSLYAD    900
SPSVPSHLPD RVHFASPLHV AWRPP                                         925

SEQ ID NO: 23            moltype = AA   length = 890
FEATURE                  Location/Qualifiers
REGION                   1..890
                         note = Description of Artificial Sequence:
                         Syntheticpolypeptide
source                   1..890
                         mol_type = protein
                         organism = synthetic construct
SEQUENCE: 23
MDIDPYKEFG ASVELLSFLP SDFFPSVRDL LDTASALYRE ALESPEHCSP HHTALRQAIL    60
CWGELMTLAT WVGNNLEDPA SRDLVVNYVN TNMGLKIRQL LWFHISCLTF GRETVLEYLV    120
SFGVWIRTPP AYRPPNAPIL STLPETTVVR RRDRGRSPRR RTPSPRRRRS QSPRRRRSQS    180
RESQCMPLSY QHFRKLLLLD DETEAGPLEE ELPRLADEDL NRRVAEDLNL GNLNVSIPWT    240
HKVGNFTGLY SSTVPIFNPE WQTPSFPKIH LHEDIANRCQ QFVGPLTVNE KRRLRLIMPA    300
RFYPNSTKYL PLDKGIKPYY PDHVVNHYFQ TRHYLHTLWK AGILYKRETT RSASFCGSPY    360
SWEQELHHGC WWLQFRNTQP CSKYCLSHLV NLLEDWGPCD EHGEHHIRIP RTPARVTGGV    420
FLVDKNPHNT AESRLVVDFS QFSRGITRVS WPKFAVPNLQ SLTNLLSSNL SWLSLDVSAA    480
FYHIPLHPAA MPHLLVGSSG LSRYVARLSS NSRIHNNQHG TLQNLHDSCS RQLYVSLMLL    540
YKTYGRKLHL YSHPIILGFR KIPMGVGLSP FLLAQFTSAI CSVVRRAFPH CLAFSYMHDV    600
VLGAKSVQHL ESLYTAVTNF LLSLGIHLNP NKTKRWGYSL NFMGYVIGSW GTLPQDHIVQ    660
KIKHCFRKLP INRPIDWKVC QRIVGLLGFA APFTQCGYPA LMPLYACIQA KQAFTFSPTY    720
KAFLSKQYLN LYPVARQRPG LCQVFADATP TGWGLAIGHQ RMRGTFVAPL PIHTAHLLAA    780
CFARSRSGAK LIGTDNSVVL SRKYTSFPWL LGCTANWILR GTSFVYVPSA LNPADDPSRG    840
RLGLYRPLLR LPYRPTTGRT SLYAVSPSVP SHLPVRVHFA SPLHVAWRPP              890

SEQ ID NO: 24            moltype = AA   length = 886
FEATURE                  Location/Qualifiers
REGION                   1..886
                         note = Description of Artificial Sequence:
                         Syntheticpolypeptide
source                   1..886
                         mol_type = protein
                         organism = synthetic construct
SEQUENCE: 24
MDIDPYKEFG ASVELLSFLP SDFFPSVRDL LDTASALYRE ALESPEHCSP HHTALRQAIL    60
CWGELMNLAT WVGSNLEDPA SRELVVSYVN VNMGLKIRQL LWFHISCLTF GRETVLEYLV    120
SFGVWIRTPP AYRPPNAPIL STLPETTVVR RRGRSPRRRT PSPRRRRSQS PRRRRSQSRE    180
SQCMPLSYQH FRKLLLLDDE AGPLEEELPR LADEGLNRRV AEDLNLGNLN VSIPWTHKVG    240
NFTGLYSSTV PVFNPEWQTP SFPHIHLQED IINRCQQYVG PLTVNEKRRL KLIMPARFYP    300
NLTKYLPLDK GIKPYYPEHV VNHYFQTRHY LHTLWKAGIL YKRESTRSAS FCGSPYSWEQ    360
DLQHGCWWLQ FRNSEPCSEY CLCHIVNLIE DWGPCTEHGE HRIRTPRTPA RVTGGVFLVD    420
KNPHNTTESR LVVDFSQFSR GNTRVSWPKF AVPNLQSLTN LLSSNLSWLS LDVSAAFYHL    480
PLHPAAMPHL LVGSSGLSRY VARLSSNSRI INNQHRTMQN LHDSCSRNLY VSLMLLYKTY    540
GRKLHLYSHP IILGFRKIPM GVGLSPFLLA QFTSAICSVV RRAFPHCLAF SYMHDVVLGA    600
KSVQHLESLY AAVTNFLLSL GIHLNPHKTK RWGYSLNFMG YVIGSWGTLP QEHIVQKIKM    660
CFRKLPVNRP IDWKVCQRIV GLLGFAAPFT QCGYPALMPL YACIQAKQAF TFSPTYKAFL    720
SKQYLHLYPV ARQRPGLCQV FADATPTGWG LAIGHQRMRG AFVSPLPIHT AHLLAACFAR    780
SRSGAKLIGT DNSVVLSRKY TSFPWLLGCA ANWILRGTSF VYVPSALNPA DDPSRGRLGL    840
YRPLLRLLYP PTTGRTSLYA DSPSVPSHLP DRVHFASPLH VAWRPP                  886

SEQ ID NO: 25            moltype = AA   length = 886
FEATURE                  Location/Qualifiers
REGION                   1..886
                         note = Description of Artificial Sequence:
                         Syntheticpolypeptide
source                   1..886
                         mol_type = protein
                         organism = synthetic construct
SEQUENCE: 25
MDIDPYKEFG ASVELLSFLP SDFFPSVRDL LDTASALYRE ALESPEHCSP HHTALRQAIL    60
CWGELMNLAT WVGSNLEDPA SRELVVSYVN VNMGLKIRQL LWFHISCLTF GRETVLEYLV    120
SFGVWIRTPP AYRPPNAPIL STLPETTVVR RRGRSPRRRT PSPRRRRSQS PRRRRSQSRE    180
SQCMPLSYQH FRKLLLLDDE AGPLEEELPR LADEDLNRRV AEDLNLGNLN VSIPWTHKVG    240
NFTGLYSSTV PVFNPEWQTP SFPHIHLQED IINRCQQYVG PLTVNEKRRL KLIMPARFYP    300
NLTKYLPLDK GIKPYYPEHT VNHYFKTRHY LHTLWKAGIL YKRETTRSAS FCGSPYSWEQ    360
ELQHGCWWLQ FRNSKPCSDY CLSHIVNLLE DWGPCTEHGE HNIRIPRTPA RVTGGVFLVD    420
KNPHNTTESR LVVDFSQFSR GSTHVSWPKF AVPNLQSLTN LLSSNLSWLS LDVSAAFYHL    480
```

```
PLHPAAMPHL LVGSSGLSRY VARLSSTSRN INYQHGAMQD LHDSCSRNLY VSLLLLYKTF    540
GRKLHLYSHP IILGFRKIPM GVGLSPFLLA QFTSAICSVV RRAFPHCLAF SYMHDVVLGA    600
KSVQHLESLF TAVTNFLLSL GIHLNPNKTK RWGYSLNFMG YVIGSWGTLP QEHIVLKIKQ    660
CFRKLPVNRP IDWKVCQRIV GLLGFAAPFT QCGYPALMPL YACIQAKQAF TFSPTYKAFL    720
CKQYLNLYPV ARQRSGLCQV FADATPTGWG LAVGHQRMRG TFVSPLPIHT AHLLAACFAR    780
SRSGAKLIGT DNSVVLSRKY TSFPWLLGCA ANWILRGTSF VYVPSALNPA DDPSRGRLGL    840
YRPLLRLPFR PTTGRTSLYA VSPSVPSHLP VRVHFASPLH VAWRPP                   886

SEQ ID NO: 26           moltype = AA  length = 886
FEATURE                 Location/Qualifiers
REGION                  1..886
                        note = Description of Artificial Sequence:
                        Syntheticpolypeptide
source                  1..886
                        mol_type = protein
                        organism = synthetic construct
SEQUENCE: 26
MDIDPYKEFG ASVELLSFLP SDFFPSVRDL LDTASALYRE ALESPEHCSP HHTALRQAIL     60
CWGELMNLAT WVGVNLEDPA SRDLVVSYVN TNMGLKFRQL LWFHISCLTF GRETVLEYLV    120
SFGVWIRTPP AYRPPNAPIL STLPETTVVR RRGRSPRRRT PSPRRRRSQS PRRRRSQSRE    180
SQCMPLSYQH FRRLLLLDDE AGPLEEELPR LADEGLNRRV AEDLNLGNLN VSIPWTHKVG    240
NFTGLYSSTV PVFNPHWKTP SFPNIHLHQD IIKKCEQFVG PLTVNEKRRL QLIMPARFYP    300
NVTKYLPLDK GIKPYYPEHL VNHYFQTRHY LHTLWKAGIL YKRETTHSAS FCGSPYSWEQ    360
ELQHGCWWLQ FRNSKPCSDY CLSHIVNLLE DWGPCAEHGE HHIRIPRTPA RVTGGVFLVD    420
KNPHNTAESR LVVDFSQFSR GNYRVSWPKF AVPNLQSLTN LLSSNLSWLS LDVSAAFYHL    480
PLHPAAMPHL LVGSSGLSRY VARLSSNSRI FNYQHGTMQN LHDSCSRNLY VSLMLLYQTF    540
GRKLHLYSHP IILGFRKIPM GVGLSPFLLA QFTSAICSVV RRAFPHCLAF SYMHDVVLGA    600
KSVQHLESLF TAVTNFLLSL GIHLNPNKTK RWGYSLHFMG YVIGCYGSLP QDHIIQKIKE    660
CFRKLPVNRP IDWKVCQRIV GLLGFAAPFT QCGYPALMPL YACIQSKQAF TFSPTYKAFL    720
CKQYLNLYPV ARQRPGLCQV FADATPTGWG LVMGHQRMRG TFKAPLPIHT AHLLAACFAR    780
SRSGANILGT DNSVVLSRKY TSFPWLLGCA ANWILRGTSF VYVPSALNPA DDPSRGRLGL    840
YRPLLRLPFR PTTGRTSLYA DSPSVPSHLP DRVHFASPLH VAWRPP                   886

SEQ ID NO: 27           moltype = DNA  length = 2247
FEATURE                 Location/Qualifiers
misc_feature            1..2247
                        note = Description of Artificial Sequence:
                        Syntheticpolynucleotide
source                  1..2247
                        mol_type = other DNA
                        organism = synthetic construct
SEQUENCE: 27
atgccctga gctaccagca cttcaggaag ctgctgctgc tggatgatga ggctggccct      60
ctggaggagg agctgcccag gctggcagat gagggcctca acaggagagt ggcagaggac    120
ctgaacctgg gcaacctgaa tgtgagcatc cctggacccc acaaagtggg gaacttcact    180
ggcctctaca gcagcacagt gccagtgttc aaccctgagt ggcagacccc ctccttccc     240
cacatccacc tccaggagga catcatcaac agatgtgaac agtatgtggg ccctctgaca    300
gtcaatgaga agaggaggct gaagctgatc atgcctgcca ggttctaccc caacctgacc    360
aagtacctcc cactggacaa gggcatcaag ccatactatc ctgagcatgt ggtgaaccac    420
tactttcaga ccaggcacta cctgcacaca ctgtggaagg ctggcatcct gtacaagagg    480
gagagcacca gatcagcctc tttctgtggc tcccccacag gctgggagca ggatctccag    540
catggcagac tggtgttcca gacctccaag aggcatgggg acaagtcctt ttgccccag    600
agccctggca tcctgcccag gagcgagctc accacttcc cccctcctc cagcagaagc    660
cagtcccagg gacctgtgct gtcctgctgg tggctccagt tcaggaacag tgagccctgc    720
agtgagtact gtctgtgtca catttgtgaac ctgattgagg actgggggcc ctgcactgag    780
catggagagc acaggatcag aacccccagg accccagcca gagtgactgg aggtgtgttc    840
ctggtggaca agaaccccca acaccaca gagagcagac tggtggtgga cttctcccag    900
ttttcaaggg gcaacaccag agtgtcctgg cccaagtttg cagtgcccaa cctccagagc    960
ctgaccaacc tgctgtcatc aaacctgagc tggctgtccc tggatgtgtc tgctgccttc   1020
taccacctgc ccctgcaccc tgcagccatg cctcacctcc tggtgggcag ctcaggcctg   1080
agcaggtatg tggccaggct gtcaagcaac tccagaatca tcaacaacca gcacaggacc   1140
atgcagaacc tgcatgactc ttgcagcagg aacctgtatg tgagcctgat gctgctgtac   1200
aagacctatg gcaggaagct gcacctgtac tcccacccca tcatcctggg tttcaggaag   1260
atcccatgg gagtgggact gtccccttc ctgctggcca agttcacctc tgccatctgc   1320
tctgtggtga ggagagcctt ccccactgc ctggccttct cctacatgca tgatgtggtg   1380
ctgggggcca agtcagtgca gcacctggag tctctgtatg ctgcagtcac caacttcctg   1440
ctcagcctgg gcatccacct gaaccccac aagaccaaga ggtggggcta ctctctgaac   1500
ttcatgggct atgtgatagg cagctggggc acctgccac aggagcacat agtgcagaag   1560
atcaagatgt gcttcaggaa gctgccagtg aacaggccca ttgattggaa ggtgtgccag   1620
aggattgtgg gcctgctggg cttttgcagca cccttcacac agtgtggcta cccagctctg   1680
atgcccctgt atgcctgcat ccaggccaag caggccttca ccttctcccc cacttacaag   1740
gccttcctgt gccaagcagta cctgcacctg taccctgtgg caaggcagag gccaggcctc   1800
tgccaggtgt ttgcagatgc cacccccaca ggctgggcc tggccattgg ccaccagaga   1860
atgagagggg ccttttgtgag cccactgcca atccacacag cccactctgc cgcagcatgc   1920
tttgccaggt ccaggtctgg tgcaaagctg attggcactg acaacagtgt ggtgctgtcc   1980
agaaagtaca ccagcttccc ctggctgctg ggatgtgctg ccaactggat tctgaggggc   2040
accagctttg tctatgtgcc ctctgcactg aaccctgcag atgaccctc caggggcaga   2100
ctggggctgt acaggccact gctcagactg ctgtacaggc ccaccactgg cagaacctcc   2160
ctgtatgcag acagccctc agtgccctct cacctgccag acagagtgca ctttgccagc   2220
```

```
cccctgcatg ttgcctggag gccccc                                                2247

SEQ ID NO: 28            moltype = DNA   length = 2109
FEATURE                  Location/Qualifiers
misc_feature             1..2109
                         note = Description of Artificial Sequence:
                         Syntheticpolynucleotide
source                   1..2109
                         mol_type = other DNA
                         organism = synthetic construct
SEQUENCE: 28
atgcccctga gctaccagca cttcaggaag ctgctgctgc tggatgatga ggctggccct    60
ctggaggagg agctgcccag gctggcagat gagggcctca acaggagagt ggcagaggac    120
ctgaacctgg gcaacctgaa tgtgagcatc ccctggaccc acaaagtggg gaacttcact    180
ggcctctaca gcagcacagt gccagtgttc aaccctgagt ggcagacccc ctccttcccc    240
cacatccacc tccaggagga catcatcaac agatgtcagc agtatgtggg ccctctgaca    300
gtcaatgaga gaggaggct gaagctgatc atgcctgcca ggttctaccc caacctgacc    360
aagtacctcc cactgacaca gggcatcaag ccatactatc ctgagcatgt ggtgaaccac    420
tactttcaga ccaggcacta cctgcacaca ctgtggaagg ctggcatcct gtacaagagg    480
gagagcacca gatcagcctc tttctgtggc tccccctaca gctgggagca ggatctccag    540
catggctgct ggtggctcca gttcaggaac agtgagccct gcagtgagta ctgtctgtgt    600
cacattgtga acctgattga ggactggggg ccctgcactg agcatggaaa gcacaggatc    660
agaaccccca ggaccccagc cagagtgact ggaggtgtgt tcctggtgga caagaacccc    720
cacaacacca cagagagcag actggtggtg gacttctccc agttttcaag gggcaacacc    780
agagtgtcct ggcccaagtt tgcagtgccc aacctccaga gcctgaccaa cctgctgtca    840
tcaaacctga gctggctgtc cctggatgtg tctgctgcct tctaccacct gccccctgac    900
cctgcagcca tgcctcacct cctggtgggc agctcaggcc tgagcaggta tgtggccagg    960
ctgtcaagca actccagaat catcaacaac cagcacagga ccatgcagaa cctgcatgac    1020
tcttgcagca ggaacctgta tgtgagcctg atgctgctgt acaagaccta tggcaggaag    1080
ctgcacctgt actcccaccc catcatcctg ggtttcagga agatccccat gggagtggga    1140
ctgtcccccct tcctgctggc ccagttcacc tctgccatct gctctgtggt gaggagagcc    1200
ttcccccact gcctggcctt ctcctacatg catgatgtgg tgctggggc caagtcagtg    1260
cagcacctgg agtctctgta tgctgcagtc accaacttcc tgctcagcct gggcatccac    1320
ctgaaccccc acaagaccaa gaggtggggc tactctctga acttcatggg ctatgtgata    1380
ggcagctggg gcaaccctgcc acaggagcac atagtgcaga agatccaagat gtgcttcagg    1440
aagctgccag tgaacaggcc cattgattgg aaggtgtgcc agaggattgt gggcctgctg    1500
ggctttgcag caccettcac acagtgtggc tacccagctc tgatgcccct gtatgcctgc    1560
atccaggcca agcaggcctt caccttctcc cccacttaca aggccttcct gtccaagcag    1620
tacctgcacc tgtaccctgt ggcaaggcag aggccagtcc tctgccaggt gtttgcagat    1680
gccacccca caggctgggg cctgccatt ggccaccaga ggatgagagg ggccttttgtg    1740
agcccactgc caatccacac agccaccctg ctggcagcat gctttgccag tccaggtct    1800
ggtgcaaagc tgattggcac tgacaacagt gtggtgctgt ccagaaagta caccagcttc    1860
ccctggctgc tgggatgtgc tgccaactgg atttctgaggg gcaccagctt tgtctatgtg    1920
ccctctgcac tgaaccctgc agatgacccc tccaggggca gactggggct gtacaggcca    1980
ctgctcagac tgctgtacag gcccaccact ggcagaacct ccctgtatgc agacagcccc    2040
tcagtgccct ctcacctgcc agacagagtg cactttgcca gccccctgca tgttgcctgg    2100
aggccccc                                                             2109

SEQ ID NO: 29            moltype = DNA   length = 1602
FEATURE                  Location/Qualifiers
misc_feature             1..1602
                         note = Description of Artificial Sequence:
                         Syntheticpolynucleotide
source                   1..1602
                         mol_type = other DNA
                         organism = synthetic construct
SEQUENCE: 29
atgtccagca gaagccagtc ccagggacct gtgctgtcct gctggtggct ccagttcagg    60
aacagtgagc cctgcagtga gtactgtctg tgtcacattg tgaacctgat tgaggactgg    120
gggccctgca ctgagcatgg agagcacagg atcagaaccc ccaggacccc agccagagtg    180
actggaggtg tgttcctggt ggacaagaac ccccacaaca ccacagagag cagactggtg    240
gtggacttct cccagttttc aaggggcaac accagagtgt cctggcccaa gtttgcagtg    300
cccaacctcc agagcctgac caacctgctg tcatcaaacc tgagctggct gtccctggat    360
gtgtctgctg ccttctacca cctgcccctg caccctgcag cctgcagcca tgcctcacct    420
ggcagctcag gcctgagcag gtatgtggca aggctgtcaa gcaactccag aatcatcaac    480
aaccagcaca ggaccatgca gaacctgcat gactcttgca gcaggaacct gtatgtgagc    540
ctgatgctgc tgtacaagac ctatggcagg aagctgcacc tgtactccca ccccatcatc    600
ctgggtttca ggaagatccc catgggagtg gactgtccc ccttcctgct ggcccagttc    660
acctctgcca tctgctctgt ggtgaggaga gccttctcct actgcatgat gtggtgctgg    720
atgcatgatg tggtgctggg ggccaagtca gtgcagcacc tggagtctct gtatgctgca    780
gtcaccaact tcctgctcag cctgggcatc cacctgaacc cccacaagac caagaggtgg    840
ggctactctc tgaacttcat gggctatgtg ataggcagct ggggcaccct gccacaggag    900
cacatagtgc agaagatcaa gatgtgcttc aggaagctgc cagtgaacag gcccattgat    960
tggaaggtgt gccagaggat tgtgggcctg ctggggcctt tgcagcaccc ttcacacagt gt    1020
ggctaccccag ctctgatgcc cctgtatgcc tgcatccagg ccaagcaggc cttcaccttc    1080
tcccccactt acaaggcctt cctgtccaag cagtacctgc acctgtaccc tgtggcaagg    1140
cagaggccag gcctctgcca ggtgtttgca gatgccaccc ccacaggctg gggcctggcc    1200
attgccacca gaggatgaga gggggccttt gtgagccac tgccaatcca cacagcccac    1260
ctgctggcag catgctttgc caggtccagg tctggtgcaa agctgattgg cactgacaac    1320
```

```
agtgtggtgc tgtccagaaa gtacaccagc ttccctggc tgctgggatg tgctgccaac   1380
tggattctga ggggcaccag ctttgtctat gtgccctctg cactgaaccc tgcagatgac   1440
ccctccaggg gcagactggg gctgtacagg ccactgctca gactgctgta caggcccacc   1500
actggcagaa cctccctgta tgcagacagc ccctcagtgc cctctcacct gccagacaga   1560
gtgcactttg ccagccccct gcatgttgcc tggaggcccc cc                      1602
```

SEQ ID NO: 30          moltype = DNA  length = 2226
FEATURE              Location/Qualifiers
misc_feature       1..2226
                      note = Description of Artificial Sequence:
                      Syntheticpolynucleotide
source               1..2226
                      mol_type = other DNA
                      organism = synthetic construct
SEQUENCE: 30

```
atgcccctga gctaccaaca cttcaggaga ctgctgctgc tggatgatga ggcaggccct   60
ctggaggagg agctgcccag gctggcagat gagggcctga caggagggt ggctgaggac   120
ctgaacctgg gcaacctgaa tgtgaacatc ccttggaccc acaaagtggg caacttcaca   180
ggcctgtaca gcagcactgt gcctgtgttc aaccccact ggaagacacc cagcttcccc    240
aacatccacc tgcaccagga catcatcaag aagtgtgagc agtttgtggg cccctgaca    300
gtcaatgaga agaggaggct ccagctgatc atgccagcca ggttctaccc caatgtgacc   360
aagtacctcc cctggacaa gggcatcaag ccttactatc cagagcacct ggtgaaccac    420
tacttccaga ccagacacta cctgcacaca ctgtggaagg caggcatcct gtacaagagg   480
gagaccacac acagtgcctc cttctgtggc agccctact cctgggagca ggagctgcaa    540
catggagctg agtccttcca ccagcagtcc agtggcatcc tgagcaggcc cctgtgggc    600
agcagagctgc acaacctgcc cccaactct gccagatccc agtctgagag gccagtgttc   660
ccttgctggt ggctccagtt caggaacagc aagcccgct cagactactg cctgagccac    720
attgtgaacc tgctggagga ctggggcccc tgtcagagc atggggagca ccacatcaga    780
atccccagga cccctgccag ggtgacagga ggggtgttcc tggtgacaa gaaccccac     840
aacactgcag agtccaggct ggtggtggac ttctccaagt tcagcaggg caactacaga    900
gtctcctggc caaagtttgc tgtgcccaac ctccagagcc tgacaaacct gctgagcagc   960
aacctgtcct ggctctccct ggatgtgagt gcagccttct atcacctgcc cctgcaccca   1020
gcagccatgc cacacctgct ggtgggctcc agtggcctgt ccaggtatgt ggccaggctc   1080
tcctccaact ccaggatctt caactatcag catggcacca tgcagaacct gcatgacagc   1140
tgctccagga acctgtatgt gtccctgatg ctgctctatc agaccttgg caggaagctg   1200
cacctgtaca gccaccccat catcctgggg ttcaggaaga tccccatggg tgtgggcctg   1260
tccccttcc tgctggccca gttcaccagt gccatctgct cagtggtgag gagggccttc    1320
ccacactgcc tggccttctc ttacatgcat gatgtggtcc tgggtgccaa gtctgtgcag   1380
cacctggaga ggctgttcac agctgtgaca aactttctcc tgagcctggg catccacctg   1440
aacccccaaca agaccaagag gtggggttat tcactgcact tcatgggcta tgtgattggc   1500
tgctatggct ctctgccaca ggaccacatc atccagaaga tcaaggagtg cttcagaaag   1560
ctgccagtga acaggccaat tgactggaag gtgtgccaga ggattgtggg cctgctgggc   1620
tttgcagccc ccttcacccca gtgtggctac cctgccctga tgcctgcatc              1680
cagagcaagc aggccttcac ctttttccccc acttacaagg cctcctgtg caagcagtac   1740
ctgaacctgt accctgtggc caggcagaga cctgggctgt gccaggtgtt tgcagatgcc   1800
acccccacag gatggggact ggtcatggga caccagagga tgaggggcac cttcaaggca   1860
cccctgccca tccacacagc ccacctgctg gctgcctgct ttgccaggag caggagtggg   1920
gccaacatcc tgggcacaga caactctgtg gtgctgagca ggaagtacac atccttcccc   1980
tggctgctgg gatgtgcagc caactggatc ctgaggggca ccagctttgt gtatgtgccc   2040
tctgccctca accctgcaga tgatccaagc aggggcagge tgggactgta caggccactg   2100
ctcagactgc ccttcaggcc caccactggc aggaccagcc tgtatgctga ctccccatct   2160
gtgccctccc acctgcctgc cagagtgcac tttgcctccc cactgcatgt ggcctggagg   2220
ccccca                                                              2226
```

SEQ ID NO: 31          moltype = DNA  length = 2109
FEATURE              Location/Qualifiers
misc_feature       1..2109
                      note = Description of Artificial Sequence:
                      Syntheticpolynucleotide
source               1..2109
                      mol_type = other DNA
                      organism = synthetic construct
SEQUENCE: 31

```
atgcccctga gctaccaaca cttcaggaga ctgctgctgc tggatgatga ggcaggccct   60
ctggaggagg agctgcccag gctggcagat gagggcctga caggagggt ggctgaggac   120
ctgaacctgg gcaacctgaa tgtgagcatc ccttggaccc acaaagtggg caacttcaca   180
ggcctgtaca gcagcactgt gcctgtgttc aaccccact ggaagacacc cagcttcccc    240
aacatccacc tgcaccagga catcatcaag aagtgtgagc agtttgtggg cccctgaca    300
gtcaatgaga agaggaggct ccagctgatc atgccagcca ggttctaccc caatgtgacc   360
aagtacctcc cctggacaa gggcatcaag ccttactatc cagagcacct ggtgaaccac    420
tacttccaga ccagacacta cctgcacaca ctgtggaagg caggcatcct gtacaagagg   480
gagaccacac acagtgcctc cttctgtggc agccctact cctgggagca ggagctgcaa    540
catggatgct ggtggctcca gttcaggaac agcaagccct gctcagacta ctgcctgagc   600
cacattgtga acctgctgga ggactggggc cctgtgcag agcatgggga gcaccacatc   660
agaatcccca ggaccctgc agggtgaca ggagggtgt tcctggtgga caagaacccc      720
cacaacactg cagagtccag gctggtggt gacttctccc agttcagcag ggcaactac     780
agagtctcct ggccaaagtt tgctgtgccc aacctccaga gcctgacaaa cctgctgagc   840
agcaacctgt cctggctctc cctggatgtg agtgcagcct ctatcacct gccctgcac    900
ccagcagcca tgccacacct gctggtgggc tccagtggcc tgtccaggta tgtggccagg   960
```

```
ctctcctcca actccaggat cttcaactat cagcatggca ccatgcagaa ccctgcatga  1020
agctgctcca ggaacctgta tgtgtccctg atgctgctct atcagacctt tggcaggaag  1080
ctgcacctgt acagccaccc catcatcctg gggttcagga gatccccat gggtgtgggc   1140
ctgtcccct tcctgctggc ccagttcacc agtgccatct gctcagtggt gaggagggcc   1200
ttcccacact gcctggcctt ctcttacatg catgatgggt tcctgggtgc caagtctgtg  1260
cagcacctgg agagcctgtt cacagctgtg acaaactttc tcctgagcct gggcatccac  1320
ctgaacccca acaagaccaa gaggtggggt tattcactgc acttcatggg ctatgtgatt  1380
ggctgctatg gctctctgcc acaggaccac atcatccaga gatcaagga gtgcttcaga   1440
aagctgccag tgaacaggcc aattgactgg aaggtgtgcc agaggattgt gggcctgctg  1500
ggctttgcag ccccccttcac ccagtgtggc taccctgcc tgatgcccct gtatgcctgc  1560
atccagagca agcaggcctt caccttttcc cccacttaca aggccttcct gtgcaagcag  1620
tacctgaacc tgtaccctgt ggccaggcag agacctgggc tgtgccaggt gtttgcagat  1680
gccaccccca caggatgggg actggtcatg gacaccaga ggatgagggg caccttcaag   1740
gcaccctgc ccatccacac agcccacctg ctggctgcct gctttgccag gagcaggagt  1800
ggggccaaca tcctgggcac agacaactct gtggtgctga gcaggaagta cacatccttc  1860
ccctggctgc tgggatgtgc agccaactgg atcctgaggg gcaccagctt tgtgtatgtg  1920
ccctctgccc tcaaccctgc agatgatcca agcaggggca ggctgggact gtacaggcca  1980
ctgctcagac tgcccttcag gcccaccact ggcaggacca gcctgtatgc tgactcccca  2040
tctgtgccct cccacctgcc tgacagagtg cactttgcct ccccactgca tgtggcctgg  2100
aggcccccca                                                         2109

SEQ ID NO: 32           moltype = DNA  length = 1602
FEATURE                 Location/Qualifiers
misc_feature            1..1602
                        note = Description of Artificial Sequence:
                        Syntheticpolynucleotide
source                  1..1602
                        mol_type = other DNA
                        organism = synthetic construct
SEQUENCE: 32
atgtctgcca gatcccagtc tgagaggcca gtgttccctt gctggtggct ccagttcagg   60
aacagcaagc cctgctcaga ctactgcctg agccacattg tgaacctgct ggaggactgg  120
ggccctgtg cagagcatgg ggagcaccac atcagaatcc caggacccc tgccagggtg   180
acaggagggg tgttcctggt ggacaagaac ccccacaaca ctgcagagtc caggctggtg  240
gtggacttct cccagttcag caggggcaac tacagagtct cctgccaaa gtttgctgtg  300
cccaacctcc agagcctgac aaacctgctg agcagcaacc tgtcctggct ctccctggat  360
gtgagtgcag ccttctatca cctgcccctg cacccagcag ccatgccaca cctgctggtg  420
ggctccagtg gcctgtccag gtatgtggcc aggctctcct ccaactccag gatcttcaac  480
tatcagcatg gcaccatgca gaactgcat gacagctgct ccaggaacct gtatgtgtcc  540
ctgatgctgc tctatcagac cttttggcagg aagctgcacc tgtacagcca cccatcatc   600
ctgggggttca ggaagatccc catgggtgtg ggcctgtccc ccttcctgct ggcccagttc  660
accagtgcca tctgctcagt ggtgaggagg ccttcccac actgcctggc cttctcttac   720
atgcatgatg tggtcctggg tgccaagtct gtgcagcagc tggagagcct gttcacagct  780
gtgacaaaact ttctcctgag cctgggcatc cacctgaacc caacaagac caagaggtgg  840
ggttattcac tgcacttcat gggctatgtg attggctgct atggctctct gccacaggac  900
cacatcatcc agaagatcaa ggagtgcttc agaaagctgc cagtgaacag gccaattgac  960
tggaaggtgt gccagaggat tgtgggcctg ctgggctttg caccccctt cacccagtgt   1020
ggctaccctg ccctgatgcc cctgtatgcc tgcatccaga gcaagcaggc cttcaccttt  1080
tcccccactt acaaggcctt cctgtgcaag cagtacctga acctgtaccc tgtgccagg   1140
cagagacctg ggctgtgcca ggtgtttgca gatgccaccc ccacaggatg gggactggtc  1200
atgggacacc agaggatgag gggcaccttc aaggcaccct gccatcca cacagcccac   1260
ctgctggctg cctgctttgc caggagcagg agtggggcca acatcctggg cacagacaac  1320
tctgtggtgc tgagcaggaa gtacacatcc ttccccggc tgctgggatg tgcagccaac  1380
tggatcctga ggggcaccag ctttgtgtat gtgccctctg ccctcaaccc tgcagatgat  1440
ccaagcaggg gcaggctggg actgtacagg ccactgctca gactgccctt caggcccacc  1500
actggcagga ccagcctgta tgctgactcc ccatcctgtgc cctccacct gcctgacaga  1560
gtgcactttg cctccccact gcatgtggcc tggaggcccc ca                     1602

SEQ ID NO: 33           moltype = DNA  length = 1227
FEATURE                 Location/Qualifiers
misc_feature            1..1227
                        note = Description of Artificial Sequence:
                        Syntheticpolynucleotide
source                  1..1227
                        mol_type = other DNA
                        organism = synthetic construct
SEQUENCE: 33
atggacattg accctacaa ggagtttggg gccagtgtgg agctgctgtc ttttctgcca   60
tctgacttct tccccagtgt gagggacctg ctggacactg cctcagcact gtacagagag  120
gccctggaga gcccagagca ctgctccccc caccacacag ccctgaggca ggccatcctc  180
tgctgggggg agctgatgaa cctgccacc tgggtgggct ccaacctgga ggaccctgcc  240
tcaagggagc tggtggtcag ctatgtcaat gtgaacatgg gcctcaagat caggcagctg  300
ctgtggttcc acatctcctg cctgacctt ggcaggagga cagtcctgga gtacctggtg   360
agctttgggg tgtggatcag gacccccccct gcctacagge cccccaatgc tccatcctg  420
tccaccctgc cagagaccac tgtggtcagg agaaggggca ggtccccag gaggagaacc  480
ccctctccca ggaggaggag aagccagtcc ccaggagga ggagccca gagcagagag   540
tctcagtgca tggagagcac cacatcaggc ttcctgggcc cctgctggt gctccaggca  600
ggcttctttc tgctgaccag gattctgacc atcccccagt ccctgacag ctggtggacc  660
tccctgaatt ttctgggggg ggcccctacc tgtcctggcc agaactctca gtctcccacc  720
```

```
tcgaatcact caccaaccag ctgtcccccc atctgtcctg gctacaggtg gatgtgcctg  780
aggagattca tcatcttcct gtgcatcctg ctgctgtgcc tgatctttct gctggtgctg  840
ctggactacc agggcatgct gccagtgtgc cctctcatcc caggcagctc caccacatcc  900
acaggacctt gcaagacatg caccacacca gcccagggca ccagcatgtt ccctcctctg  960
tgttgcacca agccaacaga tggcaactgc acatgcatcc ccatccctc cagctgggcc  1020
tttgccaggt ttctgtggga gtgggccagt gtgagatttt cctggctgtc tcttctggtg  1080
cccttttgtgc agtggtttgt gggcctgtcc cctacagtgt ggctgagtgt catctggatg  1140
atgtggtact ggggcccctc cctgtacaac atcctctctc cctttctgcc tctgctgcca  1200
atcttctttt gcctgtgggt gtacatc                                      1227

SEQ ID NO: 34           moltype = DNA  length = 1290
FEATURE                 Location/Qualifiers
misc_feature            1..1290
                        note = Description of Artificial Sequence:
                        Syntheticpolynucleotide
source                  1..1290
                        mol_type = other DNA
                        organism = synthetic construct
SEQUENCE: 34
atggacattg accctacaa ggagtttggg gccagtgtgg agctgctgtc ttttctgcca  60
tctgacttct tccccagtgt gagggacctg ctggacactg cctcagcact gtacagagag  120
gccctggaga gccagagca ctgctccccc caccacacag ccctgaggca gccatcctc  180
tgctgggggg agctgatgaa cctggccacc tgggtgggct ccaacctgga ggaccctgcc  240
tcaagggagc tggtggtcag ctatgtcaat gtgaacatgg gcctcaagat caggcagctg  300
ctgtggttcc acatctcctg cctgaccttt ggcaggaga cagtcctgga gtacctggtg  360
agctttgggg tgtggatcag gaccccccct gcctacagc ccccaatgc tcccatcctg  420
tccaccctgc cagagaccac tgtggtcagg agaaggggca ggtcccccag gaggagaacc  480
ccctctccca ggaggaggag aagccagtcc cccaggagga ggaggagcca gagcagagag  540
tctcagtgcg gcagtgggc aaccaacttc agcctcctga acaggcagg ggatgtggag  600
gaaaacccag gccccgagag caccacatca ggcttcctgc cccctgctg ggtgctccag  660
gcaggcttct ttctgctgac caggattctg accatccccc agtccctgga cagctggtga  720
acctccctga attttctggg gggggcccct acctgtcctg gccagaactc tcagtctccc  780
acctcgaatc actcaccaac cagctgtccc ccatctgtc ctggctacag gtggatgtgc  840
ctgaggagat tcatcatctt cctgtgcatc ctgctgctgt gcctgatctt tctgctggtg  900
ctgctggact accagggcat gctgccagtg tgcctctca tcccaggcag ctccaccaca  960
tccacaggac cttgcaagac atgcaccaca ccagcccagg gcaccagcat gttcccctcc  1020
tgctgttgca ccaagccaac agatggcaac tgcacatgca ttcccatccc ctccagctgg  1080
gccttttgcca ggtttctgtg ggagtgggcc agtgtgagat tttcctggct gtctcttctg  1140
gtgcccttttg tgcagtggtt tgtgggcctg tcccctacag tgtggctgag tgtcatctgg  1200
atgatgtggt actggggccc ctccctgtac aacatcctct cccctttct gcctctgctg  1260
ccaatcttct tttgcctgtg ggtgtacatc                                  1290

SEQ ID NO: 35           moltype = DNA  length = 1227
FEATURE                 Location/Qualifiers
misc_feature            1..1227
                        note = Description of Artificial Sequence:
                        Syntheticpolynucleotide
source                  1..1227
                        mol_type = other DNA
                        organism = synthetic construct
SEQUENCE: 35
atggacattg accctacaa ggagtttggg gccagtgtgg agctgctctc cttcctgccc  60
tcagacttct ttcccagtgt gagggacctg cttgacacag cctctgccct ctacagagag  120
gccctggaga gccagagca ttgctccccc caccacacag cactgaggca ggccatcctg  180
tgctgggggg agctcatgaa cctggccacc tgggtgggtg tcaacctgga ggacccagct  240
tccagggatc tggtggtcag ctatgtgaac acaaacatgg gcctcaagtt caggcagctg  300
ctctggttcc acatctcctg cctgaccttt ggcaggaga ctgtgctgga gtacctggtg  360
agctttggag tgtggatcag gaccccacct gcctacaggc ccccaatgc cccatcctg  420
tccaccctgc ctgagaccac agtggtgagg aggagggga ggtcccccag aaggaggacc  480
ccttctccca ggaggaggag gagtcagtct cccaggagga ggaggagcca gagcagagag  540
tcccagtgta tggagaacat cacctctggc tttctgggac ccctgctggt gctccaggca  600
ggcttttttcc tgctgaccag gatcctgacc atccctcaga gcctggactc ctggtggaca  660
tctctgaatt ttcttggggg caccactgtg tgcctggac agaactccca gtctcccacc  720
tccaaccaga gccaacatc ctgtcccccc atctgccag gctacaggtg gatgtgcctg  780
aggaggttca tcatcttcct gttcatcctg ctgctgtgcc tgatctttct gctggtgctc  840
ctggactatc agggcatgct gccagtgtgc ccactgatcc caggcagctc caccacaagc  900
acaggacctt gcaggacatg caccacacct gcccaggca cttccatgta cccatcttgc  960
tgttgcacca agccatctga tggcaattgc acctgcatcc ccatcccctc aagctgggcc  1020
tttgccaagt tcctgtggga gtgggcaagt gccagattct cttgctgag cccactgtgt  1080
ccttttgtgc agtggtttgt gggcctgagc ccactgtgt ggctgtctgt gatctggatg  1140
atgtggtact ggggccccctc cctgtattca atcctgagcc ttttctgcc actgctgccc  1200
atcttctttt gtctgtgggt gtacatc                                      1227

SEQ ID NO: 36           moltype = DNA  length = 1290
FEATURE                 Location/Qualifiers
misc_feature            1..1290
                        note = Description of Artificial Sequence:
                        Syntheticpolynucleotide
source                  1..1290
```

```
                        mol_type = other DNA
                        organism = synthetic construct
SEQUENCE: 36
atggacattg acccctacaa ggagtttggg gccagtgtgg agctgctctc cttcctgccc    60
tcagacttct ttcccagtgt gagggacctg cttgacacag cctctgccct ctacagagag   120
gccctggaga gcccagagca ttgctccccc caccacacag cactgaggca ggccatcctg   180
tgctgggggg agctcatgaa cctggccacc tgggtgggtg tcaacctgga ggacccagct   240
tccagggatc tggtggtcag ctatgtgaac acaaacatgg gcctcaagtt caggcagctg   300
ctctggttcc acatctcctg cctgaccttt ggcagggaga ctgtgctgga gtacctggtg   360
agctttggag tgtggatcag gacccccacct gcctacaggc cccccatcgt ccccatcctg   420
tccaccctgc ctgagaccac agtggtgagg aggagggga ggtcccccag aaggaggacc   480
ccttctccca ggaggaggag gagtcagtct cccaggagga ggaggagcca gagcagagag   540
tcccagtgtg gcagtgggggc aaccaacttc agcctcctga acaggcagg ggatgtggag   600
gaaaacccag gccccgagaa catcacctct ggctttctgg gacccctgct ggtgctccag   660
gcaggcttttt tcctgctgac caggatcctg accatccctc agagcctgga ctcctggtgg   720
acatctctga attttcttgg gggcaccact gtgtgcctgg acagaactcc cagtctccc    780
acctccaacc acagcccaac atcctgtccc cccatctgcc caggctacag gtggatgtgc   840
ctgaggaggt tcatcatctt cctgttcatc ctgctgctgt gcctgatctt tctgctggtg   900
ctcctggact atcagggcat gctgccagtg tgcccactgt tcccaggcag ctccaccaca   960
agcacaggac cttgcaggac atgcaccaca cctgcccagg gcacttccat gtacccatct  1020
tgctgttgca ccaagccatc tgatggcaat tgcacctgca tccccatccc ctcaagctgg  1080
gcctttggca agttcctgtg ggagtgggca agtgccagat tctcttggct gagcctgtcg  1140
gtcccttttg tgcagtggtt tgtgggcctg agcccactg tgtggctgtc tgtgatctgg  1200
atgatgtggt actggggccc ctccctgtat tcaatcctga gccctttcct gccactgctg  1260
cccatcttct tttgtctgtg ggtgtacatc                                    1290

SEQ ID NO: 37            moltype = DNA  length = 1290
FEATURE                  Location/Qualifiers
misc_feature             1..1290
                         note = Description of Artificial Sequence:
                         Syntheticpolynucleotide
source                   1..1290
                         mol_type = other DNA
                         organism = synthetic construct
SEQUENCE: 37
atggacattg accctacaa ggagtttggg gccagtgtgg agctgctgtc ttttctgcca    60
tctgacttct tccccagtgt gagggacctg ctggacactg cctcagcact gtacagagag   120
gccctggaga gcccagagca ctgctccccc caccacacag ccctgaggca ggccatcctc   180
tgctgggggg agctgatgaa cctggccacc tgggtgggcg tcaacctgga ggaccctgca   240
tcaagggacc tggtggtcag ctatgtcaat acgaacatgg gcctcaagtt caggcagctg   300
ctgtggttcc acatctcctg cctgaccttt ggcagggaga cagtcctgga gtacctggtg   360
agctttgggg tgtggatcag gacccccct gcctacaggc cccccaatgc tcccatcctg   420
tccaccctgc cagagaccac tgtggtcagg agaaggggga ggtccccac gaggagaacc   480
ccctctccca ggaggaggag aagccagtcc cccaggagga ggaggagcca gagcagagag   540
tctcagtgcg gcagtgggggc aaccaacttc agcctcctga acaggcagg ggatgtggag   600
gaaaacccag gccccgagaa catcacatca ggcttcctgg gccccctgct ggtgctccag   660
gcaggcttct ttctgctgac caggattctg accatcccca gtcctggaca cagctggtgg   720
acctccctga attttctggg ggggaccact gtcgtcttg gccagaactc tcagtctccc    780
acctcgaatc actcaccaac cagctgtccc cccatctgtc ctggctacag gtggatgtgc   840
ctgaggagat tcatcatctt cctgttcatc ctgctgctgt gcctgatctt tctgctggtg   900
ctgctggact accagggcat gctgccagtg tgccctctca tccaggcag ctccaccaca   960
tccacaggac cttgcaggac atgcaccaca ccagcccagg gcaccagcat gtaccctctc  1020
tgctgttgca ccaagccatc agatggcaac tgcacatgca ttcccatccc ctccagctgg  1080
gcctttggca agtttctgtg ggagtgggcc agtgcgagat ttcctggct gtctcttctg  1140
gtgcccttttg tgcagtggtt tgtgggcctg tccctacag tgtggctgag tgtcatctgg  1200
atgatgtggt actgggggccc ctccctgtac agcatcctct ccccttttct gcctctgctg  1260
ccaatcttct tttgcctgtg ggtgtacatc                                    1290

SEQ ID NO: 38            moltype = AA  length = 409
FEATURE                  Location/Qualifiers
REGION                   1..409
                         note = Description of Artificial Sequence:
                         Syntheticpolypeptide
source                   1..409
                         mol_type = protein
                         organism = synthetic construct
SEQUENCE: 38
MDIDPYKEFG ASVELLSFLP SDFFPSVRDL LDTASALYRE ALESPEHCSP HHTALRQAIL    60
CWGELMNLAT WVGSNLEDPA SRELVVSYVN VNMGLKIRQL LWFHISCLTF GRETVLEYLV   120
SFGVWIRTPP AYRPPNAPIL STLPETTVVR RRGRSPRRRT PSPRRRSQS PRRRRSQSRE    180
SQCMESTTSG FLGPLLVLQA GFFLLTRILT IPQSLDSWWT SLNFLGGAPT CPGQNSQSPT   240
SNHSPTSCPP ICPGYRWMCL RRFIIFLCIL LLCLIFLLVL LDYQGMLPVC PLIPGSSTTS   300
TGPCKTCTTP AQGTSMFPSC CCTKPTDGNC TCIPIPSSWA FARFLWEWAS VRFSWLSLLV   360
PFVQWFVGLS PTVWLSVIWM MWYWGPSLYN ILSPFLPLLP IFFCLWVYI              409

SEQ ID NO: 39            moltype = AA  length = 430
FEATURE                  Location/Qualifiers
REGION                   1..430
                         note = Description of Artificial Sequence:
```

```
                         Syntheticpolypeptide
source                   1..430
                         mol_type = protein
                         organism = synthetic construct
SEQUENCE: 39
MDIDPYKEFG ASVELLSFLP SDFFPSVRDL LDTASALYRE ALESPEHCSP HHTALRQAIL    60
CWGELMNLAT WVGSNLEDPA SRELVVSYVN VNMGLKIRQL LWFHISCLTF GRETVLEYLV   120
SFGVWIRTPP AYRPPNAPIL STLPETTVVR RRGRSPRRRT PSPRRRRSQS PRRRRSQSRE   180
SQCGSGATNF SLLKQAGDVE ENPGPESTTS GFLGPLLVLQ AGFFLLTRIL TIPQSLDSWW   240
TSLNFLGGAP TCPGQNSQSP TSNHSPTSCP PICPGYRWMC LRRFIIFLCI LLLCLIFLLV   300
LLDYQGMLPV CPLIPGSSTT STGPCKTCTT PAQGTSMFPS CCCTKPTDGN CTCIPIPSSW   360
AFARFLWEWA SVRFSWLSLL VPFVQWFVGL SPTVWLSVIW MMWYWGPSLY NILSPFLPLL   420
PIFFCLWVYI                                                         430

SEQ ID NO: 40            moltype = AA  length = 409
FEATURE                  Location/Qualifiers
REGION                   1..409
                         note = Description of Artificial Sequence:
                         Syntheticpolypeptide
source                   1..409
                         mol_type = protein
                         organism = synthetic construct
SEQUENCE: 40
MDIDPYKEFG ASVELLSFLP SDFFPSVRDL LDTASALYRE ALESPEHCSP HHTALRQAIL    60
CWGELMNLAT WVGVNLEDPA SRDLVVSYVN TNMGLKFRQL LWFHISCLTF GRETVLEYLV   120
SFGVWIRTPP AYRPPNAPIL STLPETTVVR RRGRSPRRRT PSPRRRRSQS PRRRRSQSRE   180
SQCMENITSG FLGPLLVLQA GFFLLTRILT IPQSLDSWWT SLNFLGGTTV CLGQNSQSPT   240
SNHSPTSCPP ICPGYRWMCL RRFIIFLFIL LLCLIFLLVL LDYQGMLPVC PLIPGSSTTS   300
TGPCRTCTTP AQGTSMYPSC CCTKPSDGNC TCIPIPSSWA FGKFLWEWAS ARFSWLSLLV   360
PFVQWFVGLS PTVWLSVIWM MWYWGPSLYS ILSPFLPLLP IFFCLWVYI               409

SEQ ID NO: 41            moltype = AA  length = 430
FEATURE                  Location/Qualifiers
REGION                   1..430
                         note = Description of Artificial Sequence:
                         Syntheticpolypeptide
source                   1..430
                         mol_type = protein
                         organism = synthetic construct
SEQUENCE: 41
MDIDPYKEFG ASVELLSFLP SDFFPSVRDL LDTASALYRE ALESPEHCSP HHTALRQAIL    60
CWGELMNLAT WVGVNLEDPA SRDLVVSYVN TNMGLKFRQL LWFHISCLTF GRETVLEYLV   120
SFGVWIRTPP AYRPPNAPIL STLPETTVVR RRGRSPRRRT PSPRRRRSQS PRRRRSQSRE   180
SQCGSGATNF SLLKQAGDVE ENPGPENITS GFLGPLLVLQ AGFFLLTRIL TIPQSLDSWW   240
TSLNFLGGTT VCLGQNSQSP TSNHSPTSCP PICPGYRWMC LRRFIIFLFI LLLCLIFLLV   300
LLDYQGMLPV CPLIPGSSTT STGPCRTCTT PAQGTSMYPS CCCTKPSDGN CTCIPIPSSW   360
AFGKFLWEWA SARFSWLSLL VPFVQWFVGL SPTVWLSVIW MMWYWGPSLY SILSPFLPLL   420
PIFFCLWVYI                                                         430

SEQ ID NO: 42            moltype = AA  length = 90
FEATURE                  Location/Qualifiers
REGION                   1..90
                         note = Description of Artificial Sequence:
                         Syntheticpolypeptide
source                   1..90
                         mol_type = protein
                         organism = synthetic construct
SEQUENCE: 42
CIRSQFKQSR LGLQPHQGPL ATSQSGRSGS IRARVHSPTR RCFGVEPSGS GHIGHSASSS    60
SSCLHQSAVR KAAYSHLSTS KRQSSSGHAV                                    90

SEQ ID NO: 43            moltype = AA  length = 94
FEATURE                  Location/Qualifiers
REGION                   1..94
                         note = Description of Artificial Sequence:
                         Syntheticpolypeptide
source                   1..94
                         mol_type = protein
                         organism = synthetic construct
SEQUENCE: 43
SVGPCIQNQL RKSRLGPQPA QGQLAGRQQG GSGSIRARVH PSPWGTVGVE PSGSGHIHNC    60
ASNSSSCLHQ SAVRKAAYSH ISTSKGHSSS GHAV                               94

SEQ ID NO: 44            moltype = AA  length = 90
FEATURE                  Location/Qualifiers
REGION                   1..90
                         note = Description of Artificial Sequence:
                         Syntheticpolypeptide
source                   1..90
```

```
                        mol_type = protein
                        organism = synthetic construct
SEQUENCE: 44
CIRSQLKQSR LGLQPQQGSL ARSKSGRSGS IRARVHPTTR QSFGVEPSGS GHIDNSASSA    60
SSCLHQSAVR KTAYSHLSTS KRQSSSGHAV                                     90

SEQ ID NO: 45           moltype = AA   length = 90
FEATURE                 Location/Qualifiers
REGION                  1..90
                        note = Description of Artificial Sequence:
                          Syntheticpolypeptide
source                  1..90
                        mol_type = protein
                        organism = synthetic construct
SEQUENCE: 45
SLQSKHRKSR LGLQSQQGHL ARRQQGRGWS IRAGIHPTAR RPFGVEPSGS GHTANLASKS    60
ASCLYQSAVR KAAYPVVSTF KKHSSSGHAV                                     90

SEQ ID NO: 46           moltype = AA   length = 140
FEATURE                 Location/Qualifiers
REGION                  1..140
                        note = Description of Artificial Sequence:
                          Syntheticpolypeptide
source                  1..140
                        mol_type = protein
                        organism = synthetic construct
SEQUENCE: 46
RLVIKTSQRH GDEPFCSQPS GILSRSSVGP CIRSQFKQSR LGLQPHQGPL ATSQSGRSGS    60
IRARVHSPTR RCFGVEPSGS GHIGHSASSS SSCLHQSAVR KAAYSHLSTS KRQSSSGHAV   120
EFHSFPPSSA RSQSQGPVFS                                               140

SEQ ID NO: 47           moltype = AA   length = 140
FEATURE                 Location/Qualifiers
REGION                  1..140
                        note = Description of Artificial Sequence:
                          Syntheticpolypeptide
source                  1..140
                        mol_type = protein
                        organism = synthetic construct
SEQUENCE: 47
RLVFQTSKRH GDKSFCPQSP GILPRSSVGP CIQNQLRKSR LGPQPAQGQL AGRQQGGSGS    60
IRARVHSPW GTVGVEPSGS GHIHNCASNS SSCLHQSAVR KAAYSHISTS KGHSSSGHAV    120
ELHHFPPSSS RSQSQGPVLS                                               140

SEQ ID NO: 48           moltype = AA   length = 140
FEATURE                 Location/Qualifiers
REGION                  1..140
                        note = Description of Artificial Sequence:
                          Syntheticpolypeptide
source                  1..140
                        mol_type = protein
                        organism = synthetic construct
SEQUENCE: 48
RLVFQTSTRH GDESFCSQSS GILSRSPVGP CIRSQLKQSR LGLQPQQGSL ARSKSGRSGS    60
IRARVHPTTR QSFGVEPSGS GHIDNSASSA SSCLHQSAVR KTAYSHLSTS KRQSSSGHAV   120
ELHNFPPSSA RSQSEGPLLS                                               140

SEQ ID NO: 49           moltype = AA   length = 129
FEATURE                 Location/Qualifiers
REGION                  1..129
                        note = Description of Artificial Sequence:
                          Syntheticpolypeptide
source                  1..129
                        mol_type = protein
                        organism = synthetic construct
SEQUENCE: 49
AESFHQQSSG ILSRPPVGSS LQSKHRKSRL GLQSQQGHLA RRQQGRGWSI RAGIHPTARR    60
PPFGVEPSGS HTANLASKSA SCLYQSAVRK AAYPVVSTFK KHSSSGHAVE LHNLPPNSAR   120
SQSERPVFP                                                           129

SEQ ID NO: 50           moltype = AA   length = 309
FEATURE                 Location/Qualifiers
REGION                  1..309
                        note = Description of Artificial Sequence:
                          Syntheticpolypeptide
source                  1..309
                        mol_type = protein
                        organism = synthetic construct
SEQUENCE: 50
```

```
PLSYQHFRKL LLLDDEAGPL EEELPRLADE GLNRRVAEDL NLGNLNVSIP WTHKVGNFTG    60
LYSSTVPVFN PEWQTPSFPH IHLQEDIINR CQQYVGPLTV NEKRRLKLIM PARFYPNLTK   120
YLPLDKGIKP YYPEHVVNHY FQTRHYLHTL WKAGILYKRE STRSASFCGS PYSWEQDLQH   180
GRLVFQTSKR HGDKSFCPQS PGILPRSSVG PCIQNQLRKS RLGPQPAQGQ LAGRQQGGSG   240
SIRARVHPSP WGTVGVEPSG SGHIHNCASN SSSCLHQSAV RKAAYSHIST SKGHSSSGHA   300
VELHHFPPS                                                          309

SEQ ID NO: 51           moltype = AA  length = 298
FEATURE                 Location/Qualifiers
REGION                  1..298
                        note = Description of Artificial Sequence:
                        Syntheticpolypeptide
source                  1..298
                        mol_type = protein
                        organism = synthetic construct
SEQUENCE: 51
PLSYQHFRRL LLLDDEAGPL EEELPRLADE GLNRRVAEDL NLGNLNVSIP WTHKVGNFTG    60
LYSSTVPVFN PHWKTPSFPN IHLHQDIIKK CEQFVGPLTV NEKRRLQLIM PARFYPNVTK   120
YLPLDKGIKP YYPEHVVNHY FQTRHYLHTL WKAGILYKRE TTHSASFCGS PYSWEQELQH   180
GAESFHQQSS GILSRPPVGS SLQSKHRKSR LGLQSQQGHL ARRQQGRGWS IRAGIHPTAR   240
RPFGVEPSGS GHTANLASKS ASCLYQSAVR KAAYPVVSTF KKHSSSGHAV ELHNLPPN    298

SEQ ID NO: 52           moltype = AA  length = 845
FEATURE                 Location/Qualifiers
REGION                  1..845
                        note = Description of Artificial Sequence:
                        Syntheticpolypeptide
source                  1..845
                        mol_type = protein
                        organism = synthetic construct
SEQUENCE: 52
MPLSYQHFRK LLLLDDETEA GPLEEELPRL ADEDLNRRVA EDLNLGNLNV SIPWTHKVGN    60
FTGLYSSTVP IFNPEWQTPS FPKIHLHEDI ANRCQQFVGP LTVNEKRRLR LIMPARFYPN   120
STKYLPLDKG IKPYYPDHVV NHYFQTRHYL HTLWKAGILY KRETTRSASF CGSPYSWEQE   180
LHHGRLVIKT SQRHGDEPFC SQPSGILSRS SVGPCIRSQF KQSRLGLQPH QGPLATSQSG   240
RSGSIRARVH SPTRRCFGVE PSGSGHIGHS ASSSSSCLHQ SAVRKAAYSH LSTSKRQSSS   300
GHAVEFHSFP PSSARSQSQG PVFSCWWLQF RNTQPCSKYC LSHLVNLLED WGPCDEHGEH   360
HIRIPRTPAR VTGGVFLVDK NPHNTAESRL VVDFSQFSRG ITRVSWPKFA VPNLQSLTNL   420
LSSNLSWLSL DVSAAFYHIP LHPAAMPHLL VGSSGLSRYV ARLSSNSRIH NNQHGTLQNL   480
HDSCSRQLYV SLMLLYKTYG RKLHLYSHPI ILGFRKIPMG VGLSPFLLAQ FTSAICSVVR   540
RAFPHCLAFS YMHDVVLGAK SVQHLESLYT AVTNFLLSLG IHLNPNKTKR WGYSLNFMGY   600
VIGSWGTLPQ DHIVQKIKHC FRKLPINRPI DWKVCQRIVG LLGFAAPFTQ CGYPALMPLY   660
ACIQAKQAFT FSPTYKAFLS KQYLNLYPVA RQRPGLCQVF ADATPTGWGL AIGHQRMRGT   720
FVAPLPIHTA HLLAACFARS RSGAKLIGTD NSVVLSRKYT SFPWLLGCTA NWILRGTSFV   780
YVPSALNPAD DPSRGRLGLY RPLLRLPYRP TTGRTSLYAV SPSVPSHLPV RVHFASPLHV   840
AWRPP                                                              845

SEQ ID NO: 53           moltype = AA  length = 843
FEATURE                 Location/Qualifiers
REGION                  1..843
                        note = Description of Artificial Sequence:
                        Syntheticpolypeptide
source                  1..843
                        mol_type = protein
                        organism = synthetic construct
SEQUENCE: 53
MPLSYQHFRK LLLLDDEAGP LEEELPRLAD EGLNRRVAED LNLGNLNVSI PWTHKVGNFT    60
GLYSSTVPVF NPEWQTPSFP HIHLQEDIIN RCQQYVGPLT VNEKRRLKLI MPARFYPNLT   120
KYLPLDKGIK PYYPEHVVNH YFQTRHYLHT LWKAGILYKR ESTRSASFCG SPYSWEQDLQ   180
HGRLVFQTSK RHGDKSFCPQ SPGILPRSSV GPCIQNQLRK SRLGPQPAQG QLAGRQQGGS   240
GSIRARVHPS PWGTVGVEPS GSGHIHNCAS NSSSCLHQSA VRKAAYSHIS TSKGHSSSGH   300
AVELHHFPPS SSRSQSQGPV LSCWWLQFRN SEPCSEYCLC HIVNLIEDWG PCTEHGEHRI   360
RTPRTPARVT GGVFLVDKNP HNTTESRLVV DFSQFSRGNT RVSWPKFAVP NLQSLTNLLS   420
SNLSWLSLDV SAAFYHLPLH PAAMPHLLVG SSGLSRYVAR LSSNSRIINN QHRTMQNLHD   480
SCSRNLYVSL MLLYKTYGRK LHYSHPIIL GFRKIPMGVG LSPFLLAQFT SAICSVVRRA   540
FPHCLAFSYM HDVVLGAKSV QHLESLYAAV TNFLLSLGIH LNPHKTKRWG YSLNFMGYVI   600
GSWGTLPQEH IVQKIKMCFR KLPVNRPIDW KVCQRIVGLL GFAAPFTQCG YPALMPLYAC   660
IQAKQAFTFS PTYKAFLSKQ YLHLYPVARQ RPGLCQVFAD ATPTGWGLAI GHQRMRGAFV   720
SPLPIHTAHL LAACFARSRS GAKLIGTDNS VVLSRKYTSF PWLLGCAANW ILRGTSFVYV   780
PSALNPADDP SRGRLGLYRP LLRLLYRPTT GRTSLYADSP SVPSHLPDRV HFASPLHVAW   840
RPP                                                                843

SEQ ID NO: 54           moltype = AA  length = 843
FEATURE                 Location/Qualifiers
REGION                  1..843
                        note = Description of Artificial Sequence:
                        Syntheticpolypeptide
source                  1..843
                        mol_type = protein
```

-continued

```
                                    organism = synthetic construct
SEQUENCE: 54
MPLSYQHFRK LLLLDDEAGP LEEELPRLAD EDLNRRVAED LNLGNLNVSI PWTHKVGNFT      60
GLYSSTVPVF NPEWQTPSFP HIHLQEDIIN RCQQYVGPLT VNEKRRLKLI MPARFYPNLT     120
KYLPLDKGIK PYYPEHTVNH YFKTRHYLHT LWKAGILYKR ETTRSASFCG SPYSWEQELQ     180
HGRLVFQTST RHGDESFCSQ SSGILSRSPV GPCIRSQLKQ SRLGLQPQQG SLARSKSGRS     240
GSIRARVHPT TRQSFGVEPS GSGHIDNSAS SASSCLHQSA VRKTAYSHLS TSKRQSSSGH     300
AVELHNFPPS SARSQSEGPL LSCWWLQFRN SKPCSDYCLS HIVNLLEDWG PCTEHGEHNI     360
RIPRTPARVT GGVFLVDKNP HNTTESRLVV DFSQFSRGST HVSWPKFAVP NLQSLTNLLS     420
SNLSWLSLDV SAAFYHLPLH PAAMPHLLVG SSGLSRYVAR LSSTSRNINY QHGAMQDLHD     480
SCSRNLYVSL LLLYKTFGRK LHLYSHPIIL GFRKIPMGVG LSPFLLAQFT SAICSVVRRA     540
FPHCLAFSYM HDVVLGAKSV QHLESLFTAV TNFLLSLGIH LNPNKTKRWG YSLNFMGYVI     600
GSWGTLPQEH IVLKIKQCFR KLPVNRPIDW KVCQRIVGLL GFAAPFTQCG YPALMPLYAC     660
IQAKQAFTFS PTYKAFLCKQ YLNLYPVARQ RSGLCQVFAD ATPTGWGLAV GHQRMRGTFV     720
SPLPIHTAHL LAACFARSRS GAKLIGTDNS VVLSRKYTSF PWLLGCAANW ILRGTSFVYV     780
PSALNPADDP SRGRLGLYRP LLRLPFRPTT GRTSLYAVSP SVPSHLPVRV HFASPLHVAW     840
RPP                                                                  843

SEQ ID NO: 55           moltype = AA   length = 832
FEATURE                 Location/Qualifiers
REGION                  1..832
                        note = Description of Artificial Sequence:
                         Syntheticpolypeptide
source                  1..832
                        mol_type = protein
                        organism = synthetic construct
SEQUENCE: 55
MPLSYQHFRR LLLLDDEAGP LEEELPRLAD EGLNRRVAED LNLGNLNVSI PWTHKVGNFT      60
GLYSSTVPVF NPHWKTPSFP NIHLHQDIIK KCEQFVGPLT VNEKRRLQLI MPARFYPNVT     120
KYLPLDKGIK PYYPEHLVNH YFQTRHYLHT LWKAGILYKR ETTHSASFCG SPYSWEQELQ     180
HGAESFHQQS SGILSRPPVG SSLQSKHRKS RLGLQSQQGH LARRQQGRGW SIRAGIHPTA     240
RRPFGVEPSG SGHTANLASK SASCLYQSAV RKAAYPVVST FKKHSSSGHA VELHNLPPNS     300
ARSQSERPVF PCWWLQFRNS KPCSDYCLSH IVNLLEDWGP CAEHGEHHIR IPRTPARVTG     360
GVFLVDKNPH NTAESRLVVD FSQFSRGNYR VSWPKFAVPN LQSLTNLLSS NLSWLSLDVS     420
AAFYHLPLHP AAMPHLLVGS SGLSRYVARL SSNSRIFNYQ HGTMQNLHDS CSRNLYVSLM     480
LLYQTFGRKL HLYSHPIILG FRKIPMGVGL SPFLLAQFTS AICSVVRRAF PHCLAFSYMH     540
DVVLGAKSVQ HLESLFTAVT NFLLSLGIHL NPNKTKRWGY SLHFMGYVIG CYGSLPQDHI     600
IQKIKECFRK LPVNRPIDWK VCQRIVGLLG FAAPFTQCGY PALMPLYACI QSKQAFTFSP     660
TYKAFLCKQY LNLYPVARQR PGLCQVFADA TPTGWGLVMG HQRMRGTFKA PLPIHTAHLL     720
AACFARSRSG ANILGTDNSV VLSRKYTSFP WLLGCAANWI LRGTSFVYVP SALNPADDPS     780
RGRLGLYRPL LRLPFRPTTG RTSLYADSPS VPSHLPDRVH FASPLHVAWR PP             832

SEQ ID NO: 56           moltype = AA   length = 19
FEATURE                 Location/Qualifiers
REGION                  1..19
                        note = Description of Artificial Sequence: Syntheticpeptide
source                  1..19
                        mol_type = protein
                        organism = synthetic construct
SEQUENCE: 56
ATNFSLLQA GDVEENPGP                                                   19

SEQ ID NO: 57           moltype = AA   length = 24
FEATURE                 Location/Qualifiers
REGION                  1..24
                        note = Description of Artificial Sequence: Syntheticpeptide
source                  1..24
                        mol_type = protein
                        organism = synthetic construct
SEQUENCE: 57
APVKQTLNFD LLKLAGDVES NPGP                                            24

SEQ ID NO: 58           moltype = AA   length = 20
FEATURE                 Location/Qualifiers
REGION                  1..20
                        note = Description of Artificial Sequence: Syntheticpeptide
source                  1..20
                        mol_type = protein
                        organism = synthetic construct
SEQUENCE: 58
QCTNYALLKL AGDVESNPGP                                                 20

SEQ ID NO: 59           moltype = AA   length = 18
FEATURE                 Location/Qualifiers
REGION                  1..18
                        note = Description of Artificial Sequence: Syntheticpeptide
source                  1..18
                        mol_type = protein
                        organism = synthetic construct
```

```
SEQUENCE: 59
EGRGSLLTCG DVEENPGP                                                18

SEQ ID NO: 60           moltype = AA  length = 4
FEATURE                 Location/Qualifiers
REGION                  1..4
                        note = Description of Unknown:furin recognition/cleavage
                         site
source                  1..4
                        mol_type = protein
                        organism = unidentified
SEQUENCE: 60
RAKR                                                               4

SEQ ID NO: 61           moltype = AA  length = 4
FEATURE                 Location/Qualifiers
REGION                  1..4
                        note = Description of Unknown:furin recognition/cleavage
                         site
source                  1..4
                        mol_type = protein
                        organism = unidentified
SEQUENCE: 61
REKR                                                               4

SEQ ID NO: 62           moltype = AA  length = 4
FEATURE                 Location/Qualifiers
REGION                  1..4
                        note = Description of Unknown:furin recognition/cleavage
                         site
source                  1..4
                        mol_type = protein
                        organism = unidentified
SEQUENCE: 62
RRKR                                                               4

SEQ ID NO: 63           moltype = AA  length = 4
FEATURE                 Location/Qualifiers
REGION                  1..4
                        note = Description of Artificial Sequence: Syntheticpeptide
source                  1..4
                        mol_type = protein
                        organism = synthetic construct
SEQUENCE: 63
GGGS                                                               4

SEQ ID NO: 64           moltype = AA  length = 185
FEATURE                 Location/Qualifiers
source                  1..185
                        mol_type = protein
                        organism = Hepatitis B virus
SEQUENCE: 64
MDIDPYKEFG ASVELLSFLP SDFFPSVRDL LDTASALYRE ALESPEHCSP HHTALRQAIL   60
CWGELMTLAT WVGNNLEDPA SRDLVVNYVN TNMGLKIRQL LWFHISCLTF GRETVLEYLV  120
SFGVWIRTPP AYRPPNAPIL STLPETTVVR RRDRGRSPRR RTPSPRRRRS QSPRRRRSQS  180
RESQC                                                             185

SEQ ID NO: 65           moltype = AA  length = 183
FEATURE                 Location/Qualifiers
source                  1..183
                        mol_type = protein
                        organism = Hepatitis B virus
SEQUENCE: 65
MDIDPYKEFG ASVELLSFLP SDFFPSVRDL LDTASALYRE ALESPEHCSP HHTALRQAIL   60
CWGELMNLAT WVGSNLEDPA SRELVVSYVN VNMGLKIRQL LWFHISCLTF GRETVLEYLV  120
SFGVWIRTPP AYRPPNAPIL STLPETTVVR RRGRSPRRRT PSPRRRRSQS PRRRRSQSRE  180
SQC                                                               183

SEQ ID NO: 66           moltype = AA  length = 183
FEATURE                 Location/Qualifiers
source                  1..183
                        mol_type = protein
                        organism = Hepatitis B virus
SEQUENCE: 66
MDIDPYKEFG ASVELLSFLP SDFFPSVRDL LDTASALYRE ALESPEHCSP HHTALRQAIL   60
CWGELMNLAT WVGVNLEDPA SRDLVVSYVN TNMGLKFRQL LWFHISCLTF GRETVLEYLV  120
SFGVWIRTPP AYRPPNAPIL STLPETTVVR RRGRSPRRRT PSPRRRRSQS PRRRRSQSRE  180
SQC                                                               183
```

```
SEQ ID NO: 67            moltype = AA   length = 18
FEATURE                  Location/Qualifiers
REGION                   1..18
                         note = Description of Unknown:CSF2, GM-CSF sequence
source                   1..18
                         mol_type = protein
                         organism = unidentified
SEQUENCE: 67
MWLQSLLLLG TVACSISV                                                    18

SEQ ID NO: 68            moltype = AA   length = 23
FEATURE                  Location/Qualifiers
REGION                   1..23
                         note = Description of Unknown:PLAT, t-PA sequence
source                   1..23
                         mol_type = protein
                         organism = unidentified
SEQUENCE: 68
MDAMKRGLCC VLLLCGAVFV SAR                                              23

SEQ ID NO: 69            moltype = AA   length = 16
FEATURE                  Location/Qualifiers
REGION                   1..16
                         note = Description of Unknown:CD74 sequence
source                   1..16
                         mol_type = protein
                         organism = unidentified
SEQUENCE: 69
MHRRRSRSCR EDQKPV                                                      16

SEQ ID NO: 70            moltype = AA   length = 17
FEATURE                  Location/Qualifiers
REGION                   1..17
                         note = Description of Unknown:serum albumin sequence
source                   1..17
                         mol_type = protein
                         organism = unidentified
SEQUENCE: 70
KWVTFISLLF LFSSAYS                                                     17

SEQ ID NO: 71            moltype = AA   length = 31
FEATURE                  Location/Qualifiers
REGION                   1..31
                         note = Description of Unknown:beta-catenin sequence
source                   1..31
                         mol_type = protein
                         organism = unidentified
SEQUENCE: 71
MRKAAVSHWQ QQSYLDSGIH SGATTTAPSL S                                     31

SEQ ID NO: 72            moltype = AA   length = 107
FEATURE                  Location/Qualifiers
REGION                   1..107
                         note = Description of Unknown:CCL7, MCP-3 sequence
source                   1..107
                         mol_type = protein
                         organism = unidentified
SEQUENCE: 72
MNPSAAVIFC LILLGLSGTQ GILDMAQPVG INTSTTCCYR FINKKIPKQR LESYRRTTSS       60
HCPREAVIFK TKLDKEICAD PTQKWVQDFM KHLDKKTQTP KLASAGA                   107

SEQ ID NO: 73            moltype = AA   length = 76
FEATURE                  Location/Qualifiers
REGION                   1..76
                         note = Description of Unknown:ubiquitin sequence
source                   1..76
                         mol_type = protein
                         organism = unidentified
SEQUENCE: 73
MQIFVKTLTG KTITLEVEPS DTIENVKAKI QDKEGIPPDQ QRLIFAGKQL EDGRTLSDYN       60
IQKESTLHLV LRLRGG                                                      76

SEQ ID NO: 74            moltype = AA   length = 17
FEATURE                  Location/Qualifiers
REGION                   1..17
                         note = Description of Unknown:calreticulin sequence
source                   1..17
                         mol_type = protein
                         organism = unidentified
```

```
SEQUENCE: 74
MLLSVPLLLG LLGLAVA                                                              17

SEQ ID NO: 75           moltype = AA  length = 16
FEATURE                 Location/Qualifiers
source                  1..16
                        mol_type = protein
                        organism = Vesicular stomatitis virus
SEQUENCE: 75
MKCLLYLAFL FIGVNC                                                               16

SEQ ID NO: 76           moltype = AA  length = 21
FEATURE                 Location/Qualifiers
REGION                  1..21
                        note = Description of Unknown:CXCL10, IP-10 sequence
source                  1..21
                        mol_type = protein
                        organism = unidentified
SEQUENCE: 76
MNQTAILICC LIFLTLSGIQ G                                                         21

SEQ ID NO: 77           moltype = AA  length = 384
FEATURE                 Location/Qualifiers
REGION                  1..384
                        note = Description of Unknown:LAMP-1, N-terminal sequence
source                  1..384
                        mol_type = protein
                        organism = unidentified
SEQUENCE: 77
MAPRSARRPL LLLLLLLLG LMHCASAAMF MVKNGNGTAC IMANFSAAFS VNYDTKSGPK                 60
NMTLDLPSDA TVVLNRSSCG KENTSDPSLV IAFGRGHTLT LNFTRNATRY SVQLMSFVYN                120
LSDTHLFPNA SSKEIKTVES ITDIRADIDK KYRCVSGTQV HMNNVTVTLH DATIQAYLSN                180
SSFSRGETRC EQDRPSPTTA PPAPPSPSPS PVPKSPSVDK YNVSGTNGTC LLASMGLQLN                240
LTYERKDNTT VTRLLNINPN KTSASGSCGA HLVTLELHSE GTTVLLFQFG MNASSSRFFL                300
QGIQLNTLLP DARDPAFKAA NGSLRALQAT VGNSYKCNAE EHVRVTKAFS VNIFKVWVQA                360
FKVEGGQFGS VEECLLDENS LEDI                                                      384

SEQ ID NO: 78           moltype = AA  length = 39
FEATURE                 Location/Qualifiers
REGION                  1..39
                        note = Description of Unknown:LAMP-1, C-terminal sequence
source                  1..39
                        mol_type = protein
                        organism = unidentified
SEQUENCE: 78
GSEFTLIPIA VGGALAGLVI VLIAYLVGRK RSHAGYQTI                                       39

SEQ ID NO: 79           moltype = AA  length = 55
FEATURE                 Location/Qualifiers
REGION                  1..55
                        note = Description of Artificial Sequence:
                         Syntheticpolypeptide
MOD_RES                 7
                        note = A or T
MOD_RES                 11
                        note = T or A
MOD_RES                 19
                        note = A or G
MOD_RES                 24
                        note = A or G
MOD_RES                 29
                        note = L or S
MOD_RES                 31
                        note = A or T
MOD_RES                 32
                        note = V or I
MOD_RES                 36
                        note = L or P
MOD_RES                 39
                        note = A or V
MOD_RES                 41
                        note = P or H
MOD_RES                 42
                        note = L or I
MOD_RES                 47
                        note = S or A
MOD_RES                 53
                        note = A or V
MOD_RES                 54
```

```
                        note = L, M, P, or T
source                  1..55
                        mol_type = protein
                        organism = synthetic construct
SEQUENCE: 79
MQWNSTXFHQ XLQDPRVRXL YFPXGGSSXG XXNPVXTTXS XXSSIFXRIG DPXXN      55

SEQ ID NO: 80           moltype = AA  length = 55
FEATURE                 Location/Qualifiers
REGION                  1..55
                        note = Description of Artificial Sequence:
                         Syntheticpolypeptide
source                  1..55
                        mol_type = protein
                        organism = synthetic construct
SEQUENCE: 80
MQWNSTAFHQ ALQDPRVRGL YFPAGGSSSG TVNPAPNIAS HISSISARTG DPVTN      55

SEQ ID NO: 81           moltype = AA  length = 55
FEATURE                 Location/Qualifiers
REGION                  1..55
                        note = Description of Artificial Sequence:
                         Syntheticpolypeptide
source                  1..55
                        mol_type = protein
                        organism = synthetic construct
SEQUENCE: 81
MQWNSTTFHQ TLQDPRVRAL YFPAGGSSSG TVSPAQNTVS AISSILSKTG DPVPN      55

SEQ ID NO: 82           moltype = AA  length = 55
FEATURE                 Location/Qualifiers
REGION                  1..55
                        note = Description of Artificial Sequence:
                         Syntheticpolypeptide
source                  1..55
                        mol_type = protein
                        organism = synthetic construct
SEQUENCE: 82
MQWNSTTFHQ ALLDPRVRGL YFPAGGSSSG TVNPVPTTAS PISSIFSRTG DPAPN      55

SEQ ID NO: 83           moltype = AA  length = 55
FEATURE                 Location/Qualifiers
REGION                  1..55
                        note = Description of Artificial Sequence:
                         Syntheticpolypeptide
source                  1..55
                        mol_type = protein
                        organism = synthetic construct
SEQUENCE: 83
MQWNSTTFHQ TLQDPRVRGL YFPAGGSSSG TVNPVPTTAS PISSIFSRIG DPALN      55

SEQ ID NO: 84           moltype = AA  length = 163
FEATURE                 Location/Qualifiers
REGION                  1..163
                        note = Description of Artificial Sequence:
                         Syntheticpolypeptide
MOD_RES                 20
                        note = D or A
MOD_RES                 28
                        note = A, G, or R
MOD_RES                 74
                        note = I or L
MOD_RES                 77
                        note = L or V
MOD_RES                 86
                        note = T or A
MOD_RES                 90
                        note = S or T
MOD_RES                 103
                        note = N or D
MOD_RES                 115
                        note = A or T
MOD_RES                 119
                        note = T or A
MOD_RES                 127
                        note = A or G
MOD_RES                 132
                        note = A or G
MOD_RES                 137
```

```
                       note = L or S
MOD_RES                139
                       note = A or T
MOD_RES                140
                       note = V or I
MOD_RES                144
                       note = L or P
MOD_RES                147
                       note = A or V
MOD_RES                149
                       note = P or H
MOD_RES                150
                       note = L or I
MOD_RES                155
                       note = S or A
MOD_RES                161
                       note = A or V
MOD_RES                162
                       note = L, M, P, or T
source                 1..163
                       mol_type = protein
                       organism = synthetic construct
SEQUENCE: 84
MGQNLSTSNP LGFFPDHQLX PAFRANTXNP DWDFNPNKDT WPDANKVGAG AFGLGFTPPH    60
GGLLGWSPQA QGIXQTXPAN PPPASXNRQX GRQPTPLSPP LRXTHPQAMQ WNSTXFHQXL   120
QDPRVRXLYF PXGGSSXGXX NPVXTTXSXX SSIFXRIGDP XXN                    163

SEQ ID NO: 85          moltype = AA   length = 174
FEATURE                Location/Qualifiers
REGION                 1..174
                       note = Description of Artificial Sequence:
                       Syntheticpolypeptide
source                 1..174
                       mol_type = protein
                       organism = synthetic construct
SEQUENCE: 85
MGGWSSKPRK GMGTNLSVPN PLGFFPDHQL DPAFGANSNN PDWDFNPIKD HWPAANQVGV    60
GAFGPGLTPP HGGILGWSPQ AQGILTTVST IPPPASTNRQ SGRQPTPISP PLRDSHPQAM   120
QWNSTAFHQA LQDPRVRGLY FPAGGSSSGT VNPAPNIASH ISSISARTGD PVTN         174

SEQ ID NO: 86          moltype = AA   length = 174
FEATURE                Location/Qualifiers
REGION                 1..174
                       note = Description of Artificial Sequence:
                       Syntheticpolypeptide
source                 1..174
                       mol_type = protein
                       organism = synthetic construct
SEQUENCE: 86
MGGWSSKPRK GMGTNLSVPN PLGFFPDHQL DPAFKANSEN PDWDLNPHKD NWPDANKVGV    60
GAFGPGFTPP HGGLLGWSPQ AQGLLTTVPA APPPASTNRQ SGRQPTPLSP PLRDTHPQAM   120
QWNSTTFHQT LQDPRVRALY FPAGGSSSGT VSPAQNTVSA ISSILSKTGD PVPN         174

SEQ ID NO: 87          moltype = AA   length = 174
FEATURE                Location/Qualifiers
REGION                 1..174
                       note = Description of Artificial Sequence:
                       Syntheticpolypeptide
source                 1..174
                       mol_type = protein
                       organism = synthetic construct
SEQUENCE: 87
MGGWSSKPRQ GMGTNLSVPN PLGFFPDHQL DPAFGANSNN PDWDFNPNKD HWPEANQVGA    60
GAFGPGFTPP HGGLLGWSPQ AQGILTTVPA APPPASTNRQ SGRQPTPISP PLRDSHPQAM   120
QWNSTTFHQA LLDPRVRGLY FPAGGSSSGT VNPVPTTASP ISSIFSRTGD PAPN         174

SEQ ID NO: 88          moltype = AA   length = 163
FEATURE                Location/Qualifiers
REGION                 1..163
                       note = Description of Artificial Sequence:
                       Syntheticpolypeptide
source                 1..163
                       mol_type = protein
                       organism = synthetic construct
SEQUENCE: 88
MGQNLSTSNP LGFFPDHQLD PAFRANTANP DWDFNPNKDT WPDANKVGAG AFGLGFTPPH    60
GGLLGWSPQA QGILQTLPAN PPPASTNRQS GRQPTPLSPP LRNTHPQAMQ WNSTTFHQTL   120
QDPRVRGLYF PAGGSSSGTV NPVPTTASPI SSIFSRIGDP ALN                    163
```

```
SEQ ID NO: 89           moltype = DNA   length = 1603
FEATURE                 Location/Qualifiers
misc_feature            1..1603
                        note = Description of Artificial Sequence:
                        Syntheticpolynucleotide
source                  1..1603
                        mol_type = other DNA
                        organism = synthetic construct
SEQUENCE: 89
atgtcttcaa gatcccagag tcagggccct gtactttcct gctggtggct ccagttcagg   60
aacagtgagc cctgctccga atactgtctc tgccatatcg tcaatcttat cgaagactgg  120
ggaccctgta ccgaacatgg agaacatcgc atcaggactc ctaggacccc tgctcgtgtt  180
acaggcgggg ttttcttgt tgacaaaaat cctcacaata ccacagagtc tagactcgtg  240
gtggacttct ctcaatttc taggggaac acccgtgtgt cttggccaaa attcgcagtc  300
ccaaatctcc agtcactcac caacctgttg tcctccaatt tgtcctggtt atcgctggat  360
gtgtctgcgg cgttttatca tcttcctctg catcctgctg ctatgcctca tcttcttgtt  420
ggttcttctg gactatcaag gtatgttgcc cgtttgtcct ctaattccag gatcatcaac  480
aaccagcacc ggaccatgca aaacctgcac gactcctgct caaggaacct ctatgtttcc  540
ctcatgttgc tgtacaaaac ctacggacgg aaactgcact tgtattccca tcccatcatc  600
ttgggctttc gcaaaattcc tatgggagtg ggcctcagtc cgtttctctt ggctcagttt  660
actagtgcca tttgttcagt ggttcgtagg gcttcccccc actgtctggc tttcagttat  720
atgcatgatg tggtattggg ggccaagtct gtacaacatc ttgagtccct ttatgccgct  780
gttaccaatt ttcttttgtc tttgggtata catttaaacc ctcacaaaac aaaaagatgg  840
ggatattccc ttaacttcat gggatatgta attgggagtt ggggcacatt gccgcaggaa  900
catattgtac aaaaaatcaa aatgtgtttt aggaaacttc ctgtaaaccg gcctattgat  960
tggaaagtat gtcaacgaat tgtgggtctt ttggggttg ccgcccttt cacgcaatgt 1020
ggatatcctg ctttaatgcc tttatatgca tgtatacaag caaaacaggc ttttactttc 1080
tcgccaactt acaaggcctt cctaagtaaa cagtatctgc acctttaccc cgttgctcgg 1140
caacggcctg gtctgtgcca agtgtttgct gacgcaaccc ccactggttg gggcttggcc 1200
ataggccatc agcgcatgcg tggagccttc gtgtctcctc tgccgatcca tactgcgcat 1260
ctcctggccg cttgttttgc tcgcagcagg tctggggcaa aactcatcgg gactgacaat 1320
tctgtcgtgc tctcccgcaa gtatacatcc tttcatggc tgctaggctg tgctgccaac 1380
tggatcctgc gcgggacgtc ctttgtttac gtcccgtcgg cgctgaatcc gcggacgac 1440
ccctcccggg gccgcttggg gctctaccgc ccgcttctcc gcttgttgta ccgaccgact 1500
acggggcgca cctctctcta cgcggactcc ccgtctgtgc cttctcatct gccggaccgt 1560
gtgcacttcg cttcacctct gcacgtcgca tggagaccac cgt                  1603

SEQ ID NO: 90           moltype = DNA   length = 1602
FEATURE                 Location/Qualifiers
misc_feature            1..1602
                        note = Description of Artificial Sequence:
                        Syntheticpolynucleotide
source                  1..1602
                        mol_type = other DNA
                        organism = synthetic construct
SEQUENCE: 90
atgtcatcca gatcccagag tcagggccct gtcctttcct gttggtggct ccagttcagg   60
aacagtgagc cctgttctga gtactgtctc tgccacattg tcaatctgat tgaggactgg  120
ggcccctgca cagagcatgg tgaacacagg atcaggactc ccaggacccc tgccagggtg  180
actggtgggg tttccttgt tgacaaaaat cctcacaaca ccacagagtc aaggcttgtg  240
gtggacttct ctcaatttc aaggggaac acaagggtgc cttggcccaa atttgcagtc  300
ccaaatctcc agtctctgac caacctgttg tcctccaatt tgtcctggtt gtctctggat  360
gtctctgctg cctttatca tcttcctctc catcctgctg ccatgcctca tcttcttgtt  420
ggttcttctg gcctctctag gtatgttgcc agattgtcct ccaattccag gatcatcaac  480
aaccagcaca ggaccatgca aaacctgcat gactcctgca cagaaacct ctatgtttct  540
ctcatgttgc tgtacaaaac ctatggcagg aaactgcatt tgtattccca tcccatcatc  600
ttgggcttca ggaaaattcc catgggagtg ggcctcagtc cctcctctt ggctcagttc  660
accagtgcca tttgttctgt tgtcaggagg cttccccc actgtcttgc tttcagttac  720
atgcatgatg tggtgtggg ggccaagtct gtccaacatc ttgagtcact ttatgctgct  780
gtgaccaact ttcttttgtc tttgggcatc catttgaacc ctcacaaaac caaaagatgg  840
ggctattccc tcaatttcat gggctatgtc attgggagtt ggggcacttt gccccaggaa  900
cacattgtgc aaaaaatcaa gatgtgtttc aggaaacttc ctgtgaacag gccaattgac  960
tggaaagtct gtcagagaat tgtgggtctt ttggggtttg cagctccttt cacccaatgt 1020
ggctatcctg ctttgatgcc cttgtatgcc tgcatccagg ccaaacaggc tttcacttc 1080
tcccccactt acaaggcctt cctcagcaaa cagtatctcc acctttaccc tgttgcaagg 1140
cagaggcctg gtctgtgcca agtgtttgct gatgcaaccc ccactggttg gggcttggcc 1200
attgccatc agagaatgag aggtgccttt gtgtctcctc tccccatcca cactgctcat 1260
ctcctggcag cttgctttgc aaggagcagg tctggagcca aactcatagg gactgacaat 1320
tctgtggtgc tctccagaaa gtacacctcc tttccttggc tgctgggctg tgcagccaac 1380
tggatcctga gggggacttc ctttgtttat gtccccctg ccctgaatcc tgcagatgac 1440
ccctccaggg gcaggttggg gctctacaga cccttctca ggttgttgta cagaccaaca 1500
acagggagga cctctctcta tgcagattcc ccctctgttc cttctcatct tccagacaga 1560
gtgcactttg cttctcctct gcatgtggct tggagacctc cc                    1602

SEQ ID NO: 91           moltype = DNA   length = 1602
FEATURE                 Location/Qualifiers
misc_feature            1..1602
                        note = Description of Artificial Sequence:
                        Syntheticpolynucleotide
```

```
source                  1..1602
                        mol_type = other DNA
                        organism = synthetic construct
SEQUENCE: 91
atgtctagca gaagccagtc ccagggacct gtgctgtctt gttggtggct tcagtttcgg    60
aatagcgagc catgtagcga gtattgcctg tgtcacatcg tgaatctgat tgaggattgg   120
ggaccatgca cagagcacgg agagcaccgg atcagaaccc ctaggacacc agcccgcgtg   180
acaggaggcg tgttcctggt ggataagaac ccccataata caacagagag cagactggtg   240
gtggattttt ctcagttttc tcggggcaat acaagagtgt ctggccaaa gtttgccgtg    300
cccaatctcc agagcctgac aaacctgctg tcttctaatc tgagctggct gtccctggac   360
gtgtccgccg cctttaccaa cctgccactg caccctgccg ccatgcccca cctgctggtg   420
ggcagctccg gactgagcag atacgtggca aggctgtcta gcaattctag aattattaat   480
aatcagcaca gaacaatgca gaatctgcat gattcttgta gcaggaatct gtacgtgagc   540
ctgatgctgc tgtataagac atatggacgc aagctgcacc tgtattctca ccctattatt   600
ctgggcttcc ggaagatccc tatgggcgtg ggactgtccc cattcctgct ggcccagttt   660
acctccgcca tctgctctgt ggtgcggaga gccttccac attgtctggc ctttcttac    720
atgcacgatg tggtgctggg cgccaaatcc gtgcagcacc tggagtctct gtatgccgcc   780
gtgacaaact tcctgctgag cctgacatc cacctgaatc cacataagac aaagcggtgg   840
ggctattctc tgaattttat gggctatgtg atcggcagct ggggaaccct gccacaggag   900
cacattgtgc agaagatcaa gatgtgcttt cgcaagctgc ccgtgaatcg gcctatcgat   960
tggaaggtgt gccagaggat cgtgggactg ctgggattcg cagcacccct tacccagtgc  1020
ggctacccag ccctgatgcc actgtatgcc tgtatccagg ccaaacaggc cttcacctt   1080
tccctacat ataaggcttt tctgtctaag cagtacctgc atctgtatcc agtggcaagg   1140
cagaggccag gactgtgcca ggtgtttgca gatgcaacac caacaggatg ggactggca  1200
atcggacacc agaggatgag aggagccttc gtgagcccac tgccaattca caccgcccac   1260
ctgctggcag catgctttgc aaggtcccgc tctggagcaa agctgattgg tgctgcaac  1320
agcgtggtgc tgtccagaaa atacaccagc ttccctggc tgctgggatg tgcagcaaat   1380
tggattctga ggggcaccag cttcgtgtat gtgccttccg ccctgaatcc tgccgatgat   1440
ccatctcgag gcagactggg actgtatagg ccactgctga gactgctgta taggcctacc   1500
acaggcagaa catccctgta tgccgacagc ccatccgtgc cctctcacct gccagataga   1560
gtgcatttcg caagcccact gcatgtggca tggaggccac cc                     1602

SEQ ID NO: 92           moltype = DNA  length = 1602
FEATURE                 Location/Qualifiers
misc_feature            1..1602
                        note = Description of Artificial Sequence:
                        Syntheticpolynucleotide
source                  1..1602
                        mol_type = other DNA
                        organism = synthetic construct
SEQUENCE: 92
atgtcttcaa gatcccagag tcagggccct gtactttcct gctggtggct ccagttcagg    60
aacagtgagc cctgctctga atactgtctc tgccatattg tcaatcttat agaagactgt   120
ggaccctgta ctgaacatgg agaacatagg atcaggacct ctaggacccc tgctagagtt   180
acaggggggg tttttcttgt tgacaaaaat cctcacaata ccacagagtc tagacttgtg   240
gtggacttct ctcaatttc taggggaac accaggtgt cttggccaaa atttgcagtc    300
ccaaatctcc agtcactcac caacctgttg tcctccaatt tgtcctggtt atccctggat   360
gtgtctgcag cctttttatca tcttcctctg catcctgctg ctatgcctca tcttcttgtt   420
ggttcttctg gactatcaag gtatgttgcc aggttgtcct ctaattccag gatcatcaac   480
aaccagcaca ggaccatgca aaacctgcat gactcctgct caaggaacct ctatgttcc   540
ctcatgttgc tgtacaaaac ctatggaagg aaactgcact tgtattccca tcccatcatc   600
ttgggcttta gaaaaattcc tatgggagtg ggcctcagtc cctttctctt ggctcagttt   660
actagtgcca tttgttcagt ggttagaagg gcttccccc actgtctggc tttcagttat   720
atgcatgatg tggtattggg ggccaagtct gtacaacatc ttgagtccct ttatgctgct   780
gttaccaatt ttctttttgtc tttgggtata catttaaacc ctcacaaaac aaaaagatgg   840
ggatattccc ttaacttcat gggatatgta attgggagtt ggggcacatt gcctcaggaa   900
catattgtac aaaaatcaa aatgtgtttt aggaaacttc ctgtaaacag gcctattgat   960
tggaaagtat gtcaaagaat tgtgggtctt tgggggtttg cagccccttt cacccaatgt  1020
ggatatcctg ctttaatgcc tttatatgca tgtatacaag caaaacaggc ttttactttc  1080
tccccaactt acaaggcctt cctaagtaaa cagtatctgc acctttaccc tgttgctagg  1140
caaaggcctg gtctgtgcca agtgtttgct gatgcaaccc ccactggttg gggcttggcc  1200
ataggccatc agaggatgag gggagccttt gtgtctcctc tgcctatcca tactgccat   1260
ctcctggcag cttgttttgc taggagcagg tctgggcaa aactcattgg gactgacaat  1320
tctgttgtgc tctccagaaa gtatacatcc tttccatggc tgctaggctg tgctgccaac  1380
tggatcctga ggggacatc cttttgtttat gtccctttcag cactgaatcc tgctgatgac  1440
ccctccaggg gcagattggg gctctacagg cccttctca ggttgttgta cagacccact   1500
actgggagaa cctctctcta tgcagactcc ccctctgtgc cttctcatct gcctgacagg  1560
gtgcactttg cttcacctct gcatgttgca tggagaccac ct                     1602

SEQ ID NO: 93           moltype = DNA  length = 1602
FEATURE                 Location/Qualifiers
misc_feature            1..1602
                        note = Description of Artificial Sequence:
                        Syntheticpolynucleotide
source                  1..1602
                        mol_type = other DNA
                        organism = synthetic construct
SEQUENCE: 93
atgagttccc gatcacagag tcaggggccc gtcctttcat gttggtggct tcagtttcga    60
```

```
aactccgagc catgttctga gtattgtctc tgccacattg tgaatcttat tgaagactgg    120
ggccctgca ccgagcacgg cgagcaccga atacgacac ctcgaacgcc agcaagagtg     180
acgggcggag tgttcctcgt cgacaagaat ccacacaaca cgacggagag tagattggtc   240
gttgatttca gtcaattttc aagaggcaat acacgagttt cttggccgaa attcgccgta   300
ccgaatctgc aatccttgac aaatttgctt agttctaatt tgtcttggct ttctctcgat   360
gtttccgccg cttctctatca cttgcccctt cacccagccg cgatgccgca tctcttggtg  420
ggcagctctg gacttagtag atacgtagct agactcagtt ctaactcacg gataataaat   480
aaccaacatc gcactatgca gaacctgcat gattcttgtt cccggaactt gtatgtctcc   540
ttgatgttgt tgtataaaac ttatgggcga aagcttcatc tgtatagcca tccgattata   600
ttgggtttta ggaaaattcc tatgggtgtt ggcttgagcc cttttctgct ggcgcaattt   660
acttcagcta tctgctcagt agtacgccgg cgtttcccc attgtcttgc tttctcatac    720
atgcatgatg tagtacttgg ggccaagtct gtacaacacc ttgagagttt gtatgccgcc   780
gtaactaatt tccttctctc tctcgggatc catcttaacc ctcacaaaac gaagaggtgg   840
ggttattctc tgaattttcat gggatatgtt atcgggtctt gggaacgct gcctcaggaa   900
cacatcgtcc agaaaatcaa gatgtgtttc agaaagttgc cagtgaacag accgatagat   960
tggaaggttt gccaaagaat tgttggcttg ttgggattcg cagccccatt cacacagtgc  1020
gggtatccgg ctttgatgcc cctttatgct tgtatccagg caaaacaggc attcacctttc 1080
tcaccgactt acaaagcatt tcttttctaag cagtatctcc atctttaccc tgtcgctcga 1140
cagcggccgg ggctttgcca ggttttttcgca gacgcaaccc caactggttg gggtcttgcg 1200
atcggccacc agaggatgcg cggtgcattc gtgtcccccgc tcccaatcca tacggcccac  1260
ttgctggcgg cgtgcttcgc tcgaagtaga agcggggcta aattgatcgg cacggacaat  1320
tcagtcgtgt tgtcacgcaa atatacctcc tttccctggt tgctcggttg cgcagcaaac  1380
tggatacttc ggggaactag tttcgtttat gtgccctctg ctctcaaccc cgccgacgat  1440
ccttcacgag ggaggctggg tctttaccgc ccattgctca ggctgcttta ccggcctacc  1500
actgggagaa caagcttgta cgccgacagc ccgagcgtcc cgtctcatct gcccgacaga  1560
gttcactttg cgagtccatt gcacgtcgct tggcgccccgc cg                    1602
```

SEQ ID NO: 94  moltype = DNA  length = 1602
FEATURE        Location/Qualifiers
misc_feature   1..1602
               note = Description of Artificial Sequence:
               Syntheticpolynucleotide
source         1..1602
               mol_type = other DNA
               organism = synthetic construct
SEQUENCE: 94

```
atgagttcca gatcacagag tcagggggcct gtcctttcat gttggtggct tcagtttaga   60
aactcagagc catgttctga gtattgtctc tgccacattg tgaatcttat tgaagactgg   120
ggccctgca cagagcatgg agagcacaga ataaggacac ctagaacccc agcaagagtg   180
acaggtggag tgttcctggt agacaagaat ccacacaaca caactgagag tagattggtc   240
gttgatttca gtcaattttc aagaggcaat acaagagttt cttggccaaa atttgctgta   300
cccaatctgc aatccttgac aaatttgctt agttctaatt tgtcttggct ttctctagat   360
gtttctgcag cttctctatca cttgcccctt cacccagccg ctatgcctca tctcttggtg   420
ggcagctctg gacttagtag atatgtagct agactcagtt ctaactcaag gataataaat   480
aaccaacata ggactatgca gaacctgcat gattcttgtt ccaggaactt gtatgtctcc   540
ttgatgttgt tgtataaaac ttatgggaga agcttcatc tgtatagcca tcctattata    600
ttgggtttta ggaaaattcc tatgggtgtt ggcttgagcc cttttctgct ggcccaattt   660
acttcagcta tctgctcagt agtaaggagg gcctttcccc attgtcttgc tttctcatac   720
atgcatgatg tagtacttgg ggccaagtct gtacaacacc ttgagagttt gtatgcagca   780
gtaactaatt tccttctctc tcttgggatc catcttaacc ctcacaaaac caagaggtgg   840
ggttattctc tgaattttcat gggatatgtt atagggtctt ggggaaccct gcctcaggaa   900
cacattgtcc agaaaatcaa gatgtgtttc agaaagttgc cagtgaacag accaatagat   960
tggaaggttt gccaaagaat tgttggcttg ttgggatttg cagccccatt cacacagtgt  1020
gggtatccgg ctttgatgcc cctttatgct tgtatccagg caaaacaggc attcacctttc 1080
tcacccactt acaaagcatt tcttttctaag cagtatctcc atctttaccc tgtggctaga 1140
cagaggccag ggctttgcca ggttttttgca gatgcaaccc caactggttg gggtcttgca 1200
attggccacc agaggatgag aggtgcattt gtgtccccac tcccaatcca tactgcccac  1260
ttgctggcag cttgctttgc tagaagtaga agtggggcta aattgattgg cacagacaat  1320
tcagttgtgt tgtcaaggaa atatacctcc tttccctggt tgcttggttg tgcagcaaac  1380
tggatactta ggggaactag ttttgtttat gtgccctctg ctctcaaccc tgcagatgat  1440
ccttcaagag ggaggctggg tctttacagg ccattgctca ggctgcttta caggcctacc  1500
actgggagaa caagcttgta tgcagacagc cccagtgtcc cctctcatct gcctgacaga  1560
gttcactttg caagtccatt gcatgttgct tggagacctc ca                    1602
```

SEQ ID NO: 95  moltype = AA  length = 6
FEATURE        Location/Qualifiers
source         1..6
               mol_type = protein
               organism = Hepatitis B virus
SEQUENCE: 95
SARSQS                                                                6

SEQ ID NO: 96  moltype = AA  length = 6
FEATURE        Location/Qualifiers
source         1..6
               mol_type = protein
               organism = Hepatitis B virus
SEQUENCE: 96
SSRSQS                                                                6

```
SEQ ID NO: 97          moltype = AA  length = 4
FEATURE                Location/Qualifiers
source                 1..4
                       mol_type = protein
                       organism = Hepatitis B virus
SEQUENCE: 97
YMDD                                                                          4

SEQ ID NO: 98          moltype = AA  length = 4
FEATURE                Location/Qualifiers
source                 1..4
                       mol_type = protein
                       organism = Hepatitis B virus
SEQUENCE: 98
AELL                                                                          4

SEQ ID NO: 99          moltype = AA  length = 4
FEATURE                Location/Qualifiers
REGION                 1..4
                       note = Description of Artificial Sequence: Syntheticpeptide
source                 1..4
                       mol_type = protein
                       organism = synthetic construct
SEQUENCE: 99
YMHD                                                                          4

SEQ ID NO: 100         moltype = AA  length = 4
FEATURE                Location/Qualifiers
REGION                 1..4
                       note = Description of Artificial Sequence: Syntheticpeptide
source                 1..4
                       mol_type = protein
                       organism = synthetic construct
SEQUENCE: 100
AHLL                                                                          4

SEQ ID NO: 101         moltype = AA  length = 8
FEATURE                Location/Qualifiers
source                 1..8
                       mol_type = protein
                       organism = Hepatitis B virus
SEQUENCE: 101
MGLKFRQL                                                                      8

SEQ ID NO: 102         moltype = AA  length = 8
FEATURE                Location/Qualifiers
source                 1..8
                       mol_type = protein
                       organism = Hepatitis B virus
SEQUENCE: 102
MGLKIRQL                                                                      8
```

What is claimed is:

1. A polynucleotide encoding a truncated hepatitis B virus (HBV) polymerase polypeptide, the polypeptide comprising an inactivated reverse transcriptase domain and an inactivated RNase H, wherein the polypeptide is no longer than 600 amino acids in length and does not comprise all of the terminal protein (TP) domain and does not comprise all or part of the Spacer domain, wherein the polypeptide comprises or consists of the amino acid sequence of any one of SEQ ID NOs: 13-14.

2. The polynucleotide of claim 1, comprising or consisting of the nucleic acid sequence of any one of SEQ ID NOs: 29 and 89-94, or the nucleic acid sequence that is at least 99% identical to the full length of any one of SEQ ID NOs: 29 and 89-94.

3. An expression cassette, comprising a polynucleotide of claim 1 operably linked to one or more regulatory sequences.

4. A vector comprising one or more polynucleotides of claim 1.

5. The vector of claim 4, wherein the vector is a viral vector.

6. The vector of claim 5, wherein the viral vector is an arenavirus vector selected from Lymphocytic choriomeningitis mammarenavirus (LCMV), Pichinde mammarenavirus (PICV), Guanarito virus (GTOV), Junin virus (JUNV), Lassa virus (LASV), Lujo virus (LUJV), Machupo virus (MACV), Sabia virus (SABV), and Whitewater Arroyo virus (WWAV).

7. The vector of claim 6, wherein the viral vector is an arenavirus vector selected from Lymphocytic choriomeningitis mammarenavirus (LCMV) or Pichinde mammarenavirus (PICV).

8. The vector of claim 5, wherein the viral vector is a replication-defective arenavirus having a bi-segmented genome.

9. An isolated host cell comprising the vector of claim 5.

10. A kit comprising one or more unitary doses of the vector of claim 5.

11. A polynucleotide encoding a fusion protein comprising or consisting of the amino acid sequence of SEQ ID NO: 41, or the amino acid sequence that is at least 94%, 95%, 96%, 97%, 98% or 99% identical to the full length of SEQ ID NO: 41, the fusion protein comprising in sequential order from the N-terminus to the C-terminus, an HBV core polypeptide and an HBV small surface antigen (sAg) polypeptide, wherein the fusion protein is no longer than 450 amino acids in length, does not comprise an HBV pre-S1 polypeptide and/or an HBV pre-S2 polypeptide, and wherein the core polypeptide is from an HBV genotype D and the sAg polypeptide is from an HBV genotype D, wherein the polynucleotide comprises or consists of the nucleic acid sequence of SEQ ID NO: 37, or the nucleic acid sequence that is at least 85%, 86%, 87%, 88%, 89%, 90%, 91%, 92%, 93%, 94%, 95%, 96%, 97%, 98% or 99% identical to the full length of SEQ ID NO: 37.

12. A truncated hepatitis B virus (HBV) polymerase polypeptide comprising an inactivated reverse transcriptase domain and an inactivated RNase H, wherein the polypeptide is no longer than 600 amino acids in length and does not comprise all of the terminal protein (TP) domain and does not comprise all or part of the Spacer domain, wherein the polypeptide comprises or consists of the amino acid sequence of any one of SEQ ID NOs: 13-14.

13. A fusion protein comprising in sequential order from the N-terminus to the C-terminus, an HBV core polypeptide and an HBV small surface antigen (sAg) polypeptide, wherein the fusion protein is no longer than 450 amino acids in length, does not comprise an HBV pre-S1 polypeptide and/or an HBV pre-S2 polypeptide, and wherein: the core polypeptide is from an HBV genotype D and the sAg polypeptide is from an HBV genotype D, wherein the fusion protein comprises or consists of the amino acid sequence of any one of SEQ ID NOs: 40-41, or the amino acid sequence that is at least 97%, 98% or 99% identical to the full length of any one of SEQ ID NOs: 40-41.

14. A polynucleotide encoding the core-sAg fusion protein of claim 13.

15. An expression cassette, comprising the polynucleotide of claim 14 operably linked to one or more regulatory sequences.

16. A vector comprising one or more polynucleotides of claim 14.

17. The vector of claim 16, wherein the vector is a viral vector.

18. The vector of claim 17, wherein the viral vector is an arenavirus vector selected from Lymphocytic choriomeningitis mammarenavirus (LCMV), Pichinde mammarenavirus (PICV), Guanarito virus (GTOV), Junin virus (JUNV), Lassa virus (LASV), Lujo virus (LUJV), Machupo virus (MACV), Sabia virus (SABV), and Whitewater Arroyo virus (WWAV).

19. The vector of claim 18, wherein the viral vector is an arenavirus vector selected from Lymphocytic choriomeningitis mammarenavirus (LCMV) or Pichinde mammarenavirus (PICV).

20. An arenavirus vector comprising a polynucleotide encoding an HBV core-sAg fusion polypeptide comprising or consisting of the amino acid sequence of any one of SEQ ID NOs: 40-41, or the amino acid sequence that is at least 97%, 98% or 99% identical to the full length of any one of SEQ ID NOs: 40-41, and wherein the sAg polypeptide is no longer than 450 amino acids in length and does not comprise an HBV pre-S1 polypeptide and/or an HBV pre-S2 polypeptide.

21. An arenavirus vector comprising a polynucleotide encoding an HBV core-sAg fusion polypeptide comprising or consisting of the amino acid sequence of any one of SEQ ID NO: 41, or the amino acid sequence that is at least 94%, 95%, 96%, 97%, 98% or 99% identical to the full length of any one of SEQ ID NOs: 41, and wherein the sAg polypeptide does not comprise an HBV pre-S1 polypeptide and/or an HBV pre-S2 polypeptide.

22. The arenavirus vector of claim 20, wherein the polynucleotide comprises or consists of the nucleic acid sequence of any one of SEQ ID NOs: 35-37, or that is at least 85%, 86%, 87%, 88%, 89%, 90%, 91%, 92%, 93%, 94%, 95%, 96%, 97%, 98% or 99% identical to the full length of any one of SEQ ID NOs: 35-37.

23. The arenavirus vector of claim 20, wherein the polynucleotide comprises or consists of the nucleic acid sequence of SEQ ID NO: 37, or that is at least 85%, 86%, 87%, 88%, 89%, 90%, 91%, 92%, 93%, 94%, 95%, 96%, 97%, 98% or 99% identical to the full length of SEQ ID NO: 37.

24. The arenavirus vector of claim 20, wherein the vector has a bisegmented genome and further comprises a polynucleotide encoding a truncated HBV polymerase comprising or consisting of the amino acid sequence of any one of SEQ ID NOs: 13-14 and wherein the truncated HBV polymerase is no longer than 600 amino acids in length and does not comprise all of an HBV polymerase terminal protein (TP) domain and does not comprise all or part of an HBV polymerase Spacer domain.

25. The arenavirus vector of claim 24, wherein the polynucleotide comprises or consists of the nucleic acid sequence of any one of SEQ ID NOs: 29 and 89-94, or that is at least 99% identical to the full length of any one of SEQ ID NOs: 29 and 89-94.

26. The arenavirus vector of claim 24, wherein the arenavirus vector is a Lymphocytic choriomeningitis mammarenavirus (LCMV) vector and the polynucleotide comprises or consists of the nucleic acid sequence of SEQ ID NO: 29, or that is at least 85%, 86%, 87%, 88%, 89%, 90%, 91%, 92%, 93%, 94%, 95%, 96%, 97%, 98% or 99% identical to the full length of SEQ ID NO: 29.

27. The arenavirus vector of claim 24, wherein the arenavirus vector is a Pichinde mammarenavirus (PICV) vector and the polynucleotide comprises or consists of the nucleic acid sequence of SEQ ID NO: 90, or that is at least 88%, 89%, 90%, 91%, 92%, 93%, 94%, 95%, 96%, 97%, 98% or 99% identical to the full length of SEQ ID NO: 90.

28. An arenavirus vector comprising a polynucleotide encoding a truncated HBV polymerase comprising or consisting of the amino acid sequence of any one of SEQ ID NOs: 13-14, and wherein the truncated HBV polymerase is no longer than 600 amino acids in length and does not comprise all of an HBV polymerase terminal protein (TP) domain and does not comprise all or part of an HBV polymerase Spacer domain.

29. The arenavirus vector of claim 28, wherein the polynucleotide comprises or consists of the nucleic acid sequence of any one of SEQ ID NOs: 29 and 89-94, or that is at least 99% identical to the full length of any one of SEQ ID NOs: 29 and 89-94.

30. The arenavirus vector of claim 28, wherein the arenavirus vector is a Lymphocytic choriomeningitis mammarenavirus (LCMV) vector and the polynucleotide comprises or consists of the nucleic acid sequence of SEQ ID NO: 29, or the nucleic acid sequence that is at least 99% identical to the full length of any one of SEQ ID NO: 29.

31. The arenavirus vector of claim 28, wherein the arenavirus vector is a Pichinde mammarenavirus (PICV) vector and the polynucleotide comprises or consists of the nucleic acid sequence of SEQ ID NO: 90, or the nucleic acid sequence that is at least 88%, 89%, 90%, 91%, 92%, 93%, 94%, 95%, 96%, 97%, 98% or 99% identical to the full length of SEQ ID NO: 90.

32. The arenavirus vector of claim 20, wherein the arenavirus vector is replication-defective, replication-deficient, or replication-incompetent.

33. An isolated host cell comprising one or more vectors of claim 20.

34. A kit comprising one or more unitary doses of one or more vectors of claim 20.

35. An immunogenic composition comprising a first viral expression vector and a second viral expression vector, wherein: the first viral expression vector comprises a polynucleotide encoding a truncated HBV polymerase polypeptide mutant, wherein the polypeptide is no longer than 600 amino acids in length, does not comprise all of the terminal protein (TP) domain and does not comprise all or part of the Spacer domain, wherein the polypeptide comprises or consists of the amino acid sequence of any one of SEQ ID NOs: 13-14; and the second viral expression vector comprises a polynucleotide encoding a core-sAg fusion protein comprising in sequential order from the N-terminus to the C terminus, an HBV core polypeptide and an HBV small surface antigen (sAg) polypeptide, wherein the fusion protein is no longer than 450 amino acids in length, and wherein the core polypeptide is from an HBV genotype D and the sAg polypeptide is from an HBV genotype D, wherein the fusion protein comprises or consists of the amino acid sequence of any one of SEQ ID NOs: 40-41, or the amino acid sequence that is at least 97%, 98% or 99% identical to the full length of any one of SEQ ID NOs: 40-41.

36. The immunogenic composition of claim 35, comprising a first viral expression vector and a second viral expression vector, wherein: the first viral expression vector comprises a polynucleotide encoding an HBV polymerase polypeptide mutant comprising or consisting of the amino acid sequence of SEQ ID NO: 13; and the second viral expression vector comprises a polynucleotide encoding the core-sAg fusion protein comprising or consisting of the amino acid sequence of SEQ ID NO: 41, or the amino acid sequence that is at least 97%, 98% or 99% identical to the full length of SEQ ID NO: 41.

37. The immunogenic composition of claim 35, comprising a first viral expression vector and a second viral expression vector, wherein: a) the first viral expression vector comprises a polynucleotide comprising or consisting of the nucleic acid sequence of any one of SEQ ID NOs: 29, 32, 89, 90, 91, 92, 93 and 94, or the nucleic acid sequence that is at least 99% identical to the full length of any one of SEQ ID NOs: 29, 32, 89, 90, 91, 92, 93 and 94; b) the second viral expression vector comprises a polynucleotide comprising or consisting of the nucleic acid sequence of any one of SEQ ID NOs: 33-37 or the nucleic acid sequence that is at least 85%, 86%, 87%, 88%, 89%, 90%, 91%, 92%, 93%, 94%, 95%, 96%, 97%, 98% or 99% identical to the full length of any one of SEQ ID NOs: 33-37.

38. The immunogenic composition of claim 35, comprising a first viral expression vector and a second viral expression vector, wherein: a) the first viral expression vector comprises a polynucleotide comprising or consisting of the nucleic acid sequence of SEQ ID NOs: 29, 89, 90 or 92, or the nucleic acid sequence that is at least 99% identical to the full length of SEQ ID NOs: 29, 89, 90 or 92; and b) the second viral expression vector comprises a polynucleotide comprising or consisting of the nucleic acid sequence of SEQ ID NO: 37 or the nucleic acid sequence that is at least 85%, 86%, 87%, 88%, 89%, 90%, 91%, 92%, 93%, 94%, 95%, 96%, 97%, 98% or 99% identical to the full length of any one of SEQ ID NO: 37.

39. The immunogenic composition of claim 35, wherein the first viral expression vector and the second viral expression vector are independently from a taxonomic family selected from Adenoviridae, Arenaviridae, Herpesviridae, Poxviridae, Flaviviridae, Rhabdoviridae, and Togaviridae.

40. The immunogenic composition of claim 35, wherein the first viral expression vector and the second viral expression vector are from the same taxonomic family.

41. The immunogenic composition of claim 40, wherein the first viral expression vector and the second viral expression vector are from Arenaviridae.

42. The immunogenic composition of claim 40, wherein the first viral expression vector and the second viral expression vector are independently from an arenavirus vector selected from Lymphocytic choriomeningitis mammarenavirus (LCMV), Pichinde mammarenavirus (PICV), Guanarito virus (GTOV), Junin virus (JUNV), Lassa virus (LASV), Lujo virus (LUJV), Machupo virus (MACV), Sabia virus (SABV), and Whitewater Arroyo virus (WWAV).

43. The immunogenic composition of claim 40, wherein the first viral expression vector and the second viral expression vector are from an arenavirus vector selected from Lymphocytic choriomeningitis mammarenavirus (LCMV) or Pichinde mammarenavirus (PICV).

44. The immunogenic composition of claim 40, wherein the first viral expression vector and the second viral expression vector are replication-defective or replication-deficient.

45. The immunogenic composition of claim 40, wherein the first viral expression vector and the second viral expression vector are replication-attenuated.

46. The immunogenic composition of claim 35, wherein the first viral expression vector and the second viral expression vector are from different taxonomic families.

47. The immunogenic composition of claim 35, wherein the first viral expression vector and the second viral expression vector are provided in a ratio in the range of from 1:10 to 10:1.

48. The immunogenic composition of claim 35, comprising in the range of about $10^3$ to about $10^{12}$ viral focus forming units (ffu) or plaque forming units (pfu) or infectious units (iu) or viral particles (vp) per milliliter of each of the first viral expression vector and the second viral expression vector.

49. The immunogenic composition of claim 35, further comprising one or more of an adjuvant, a detergent, a micelle-forming agent, and an oil.

50. The immunogenic composition of claim 35, formulated for administration via a route selected from the group consisting of intravenous, intramuscular, intradermal, subcutaneous and mucosal.

51. The immunogenic composition of claim 35, formulated as a liquid.

52. The immunogenic composition of claim 35, wherein the composition is lyophilized.

53. A kit comprising one or more unitary doses of the immunogenic composition of claim 35.

* * * * *